(12) United States Patent
Yang et al.

(10) Patent No.: US 11,542,500 B2
(45) Date of Patent: Jan. 3, 2023

(54) TRIM11 FOR DEGRADATION OF PROTEIN AGGREGATES

(71) Applicant: The Trustees of the University of Pennsylvania, Philadelphia, PA (US)

(72) Inventors: Xiaolu Yang, Wynnewood, PA (US); Lili Guo, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/577,915

(22) PCT Filed: May 27, 2016

(86) PCT No.: PCT/US2016/034751
§ 371 (c)(1),
(2) Date: Nov. 29, 2017

(87) PCT Pub. No.: WO2016/196328
PCT Pub. Date: Dec. 8, 2016

(65) Prior Publication Data
US 2018/0163202 A1    Jun. 14, 2018

Related U.S. Application Data

(60) Provisional application No. 62/168,309, filed on May 29, 2015.

(51) Int. Cl.
| | |
|---|---|
| A61K 48/00 | (2006.01) |
| C12N 15/113 | (2010.01) |
| A61K 38/17 | (2006.01) |
| G01N 33/50 | (2006.01) |
| G01N 33/68 | (2006.01) |
| A61P 11/12 | (2006.01) |
| A61P 25/28 | (2006.01) |
| C12N 7/00 | (2006.01) |

(52) U.S. Cl.
CPC ........ *C12N 15/113* (2013.01); *A61K 38/1709* (2013.01); *A61P 11/12* (2018.01); *A61P 25/28* (2018.01); *C12N 7/00* (2013.01); *G01N 33/5058* (2013.01); *G01N 33/6896* (2013.01); *A61K 48/00* (2013.01); *C12N 2310/14* (2013.01); *C12N 2710/10043* (2013.01); *G01N 2800/2814* (2013.01)

(58) Field of Classification Search
CPC ............ A61K 2039/53; A61K 31/7105; A61K 48/0066; A61K 31/711; A61P 25/00; A61P 25/16; C12N 15/67; C12N 2840/105
See application file for complete search history.

(56) References Cited

U.S. PATENT DOCUMENTS

| | | | |
|---|---|---|---|
| 2002/0068713 A1 | 6/2002 | Rade | |
| 2004/0235733 A1 | 11/2004 | Steffan | |
| 2005/0215562 A1 | 9/2005 | Tremblay | |
| 2007/0141679 A1* | 6/2007 | Sodroski | C07K 14/705 435/91.1 |
| 2009/0208455 A1 | 8/2009 | Janer | |
| 2010/0087474 A1 | 4/2010 | Kaushal | |
| 2010/0247511 A1 | 9/2010 | Rezaie | |
| 2010/0263062 A1 | 10/2010 | Dillin | |
| 2013/0195801 A1* | 8/2013 | Gao | A61K 38/50 424/93.2 |
| 2013/0202593 A1* | 8/2013 | James | C07K 16/08 424/134.1 |
| 2013/0203041 A1 | 8/2013 | Franklin | |
| 2014/0056873 A1 | 2/2014 | Schwaeble | |
| 2018/0265571 A1* | 9/2018 | Esteves | C07K 7/00 |

FOREIGN PATENT DOCUMENTS

| | | |
|---|---|---|
| WO | 9961043 | 12/1999 |
| WO | 2014086835 A1 | 6/2014 |

OTHER PUBLICATIONS

Bougrini et al., PML positively regulates interferon gamma signaling, Biochimie, vol. 93, pp. 389-398. (Year: 2011).*
Niikura et al., A tripartite motif protein TRIM11 binds and destabilizes Humanin, a neuroprotective peptide against Alzheimer's disease-relevant insults, European Journal of Neuroscience, vol. 17, pp. 1150-1158. (Year: 2003).*
Tydlacka et al., Differential activities of the ubiquitin-proteasome system in neurons versus glia may account for the preferential accumulation of misfolded proteins in neurons, The Journal of Neuroscience, vol. 28, pp. 13285-13295. (Year: 2008).*
Martin-Aparicio et al., Proteasomal-dependent aggregate reversal and absence of cell death in a conditional mouse model of Huntington's disease, The Journal of Neuroscience, vol. 21, pp. 8772-8781. (Year: 2001).*
De Calignon et al., Propagation of Tau pathology in a model of early Alzheimer's disease, Neuron, vol. 73, pp. 685-697. (Year: 2012).*
Tran et al., alpha-synuclein immunotherapy blocks uptake and templated propagation of misfolded alpha-synuclein and neurodegeneration, Cell Reports, vol. 7, pp. 2054-2065. (Year: 2014).*
Rakhit et al., An immunological epitope selective for pathological monomer-misfolded SOD1 in ALS, Nature Medicine, vol. 13, pp. 754-759. (Year: 2007).*
Zhu et al., TRIM11 prevents and reverses protein aggregation and rescues a mouse model of Parkinson's disease, Cell Reports, vol. 33, 108418, pp. 1-18 and e1-e10. (Year: 2020).*

(Continued)

*Primary Examiner* — Dana H Shin
(74) *Attorney, Agent, or Firm* — Riverside Law LLP

(57) ABSTRACT

The present invention relates to compositions and methods for promoting the degradation of misfolded proteins and protein aggregates. The compositions and methods may be used to treat a disorder associated with misfolded proteins or protein aggregates. In certain instances, the compositions and methods relate to modulators of one or more TRIM proteins or one or more STUbLs.

9 Claims, 97 Drawing Sheets
(58 of 97 Drawing Sheet(s) Filed in Color)
Specification includes a Sequence Listing.

(56) References Cited

OTHER PUBLICATIONS

A. Chort et al: "Interferon beta induces clearance of mutant ataxin 7 and improves locomotion in SCAT knock-in mice", BRAIN., vol. 136, No. 6, Mar. 21, 2013 (Mar. 21, 2013), pp. 1732-1745, XP055334156, GB ISSN: 0006-8950, DOI: 10.1093/brain/awt061.
Ahner et al., "Small heat shock proteins target mutant cystic fibrosis transmembrane conductance regulator for degradation via a small ubiquitin-like modifier-dependent pathway", Mol Biol Cell, (Nov. 14, 2012), vol. 24, No. 2, pp. 74-84, XP055334157.
Balch, William E., et al. "Adapting proteostasis for disease intervention." science 319.5865 (2008): 916-919.
Bernardi, Rosa, and Pier Paolo Pandolfi. "Structure, dynamics and functions of promyelocytic leukaemia nuclear bodies." Nature reviews Molecular cell biology 8.12 (2007): 1006.
Buchberger, Alexander, Bernd Bukau, and Thomas Sommer. "Protein quality control in the cytosol and the endoplasmic reticulum: brothers in arms." Molecular cell 40.2 (2010): 238-252.
Burright, Eric N., et al. "SCA1 transgenic mice: a model for neurodegeneration caused by an expanded CAG trinucleotide repeat." Cell 82.6 (1995): 937-948.
Cao, Tongyu, et al. "Ret finger protein is a normal component of PML nuclear bodies and interacts directly with PML." Journal of cell science 111.10 (1998): 1319-1329.
Chort et al., "Interferon beta induces clearance of mutant ataxin 7 and improves locomotion in SCA7 knock-in mice", Brain, (Mar. 21, 2013), vol. 136, pp. 1732-1745, XP055334156.
Chu, Yaya, and Xiaolu Yang. "SUMO E3 ligase activity of TRIM proteins." Oncogene 30.9 (2011): 1108.
Clark, H. Brent, et al. "Purkinje Cell Expression of a Mutant Allele of SCA1in Transgenic Mice Leads to Disparate Effects on Motor Behaviors, Followed by a Progressive Cerebellar Dysfunction and Histological Alterations." Journal of Neuroscience 17.19 (1997): 7385-7395.
Cummings, Christopher J., et al. "Mutation of the E6-AP ubiquitin ligase reduces nuclear inclusion frequency while accelerating polyglutamine-induced pathology in SCA1 mice." Neuron 24.4 (1999): 879-892.
Deng, Min, and Mark Hochstrasser. "Spatially regulated ubiquitin ligation by an ER/nuclear membrane ligase." Nature 443.7113 (2006): 827.
Dobson, Christopher M. "Protein folding and misfolding." Nature 426.6968 (2003): 884.
Dorval, Véronique, and Paul E. Fraser. "Small ubiquitin-like modifier (SUMO) modification of natively unfolded proteins tau and α-synuclein." Journal of Biological Chemistry 281.15 (2006): 9919-9924.
Duda, John E., et al. "Immunohistochemical and biochemical studies demonstrate a distinct profile of α-synuclein permutations in multiple system atrophy." Journal of Neuropathology & Experimental Neurology 59.9 (2000): 830-841.
Emmer, Kristel L., et al. "E46K human α-synuclein transgenic mice develop Lewy-like and tau pathology associated with age-dependent detrimental motor impairments." Journal of Biological Chemistry (2011): jbc-M111.
Fiumara, Ferdinando, et al. "Essential role of coiled coils for aggregation and activity of Q/N-rich prions and PolyQ proteins." Cell 143.7 (2010): 1121-1135.
Fu, Nai Yang, et al. "TRIM39 is a MOAP-1-binding protein that stabilizes MOAP-1 through inhibition of its poly-ubiquitination process." Experimental cell research 315.7 (2009): 1313-1325.
Gardner, Richard G., Zara W. Nelson, and Daniel E. Gottschling. "Degradation-mediated protein quality control in the nucleus." Cell 120.6 (2005): 803-815.
Gehrking, Kristin M., et al. "Partial loss of Tip60 slows mid-stage neurodegeneration in a spinocerebellar ataxia type 1 (SCA1) mouse model." Human molecular genetics 20.11 (2011): 2204-2212.
Glover, John R., and Susan Lindquist. "Hsp104, Hsp70, and Hsp40: a novel chaperone system that rescues previously aggregated proteins." Cell 94.1 (1998): 73-82.

Goldberg, Alfred L. "Protein degradation and protection against misfolded or damaged proteins." Nature 426.6968 (2003): 895.
Golebiewski, Filip, et al. "System-wide changes to SUMO modifications in response to heat shock." Sci. Signal. 2.72 (2009): ra24-ra24.
Guo Lili et al., "A Cellular System that Degrades Misfolded Proteins and Protects against Neurodegeneration", Molecular Cell, vol. 55, No. 1, Jul. 3, 2014 (Jul. 3, 2014), pp. 15-30, XP028862088, ISSN: 1097-2765, DOI: 10.1016/J.MOLCEL.2014.04.030.
Guo, Lili, et al. "A cellular system that degrades misfolded proteins and protects against neurodegeneration." Molecular cell 55.1 (2014): 15-30.
Gupta, Rajat, et al. "Firefly luciferase mutants as sensors of proteome stress." Nature methods 8.10 (2011): 879. 182 Pages.
Häkli, Marika, et al. "The RING finger protein SNURF is a bifunctional protein possessing DNA binding activity." Journal of Biological Chemistry 276.26 (2001): 23653-23660.
Hartl, F. Ulrich, Andreas Bracher, and Manajit Hayer-Hartl. "Molecular chaperones in protein folding and proteostasis." Nature 475.7356 (2011): 324.
Hatakeyama, Shigetsugu. "TRIM proteins and cancer." Nature reviews cancer 11.11 (2011): 792.
Haupt et al., "Loss of PML cooperates with mutant p53 to drive more aggressive cancers in a gender-dependent manner", Cell Cycle, (20130601), vol. 12, No. 11, pp. 1722-1731, XP055334159.
Hu, Xiaoyi V., et al. "Identification of RING finger protein 4 (RNF4) as a modulator of DNA demethylation through a functional genomics screen." Proceedings of the National Academy of Sciences 107.34 (2010): 15087-15092.
Ishikawa, Hideaki, et al. "TRIM11 binds to and destabilizes a key component of the activator☐ mediated cofactor complex (ARC105) through the ubiquitin-proteasome system." FEBS letters 580.20 (2006): 4784-4792.
Iwata, Atsushi, et al. "Intra-nuclear degradation of polyglutamine aggregates by the ubiquitin proteasome system." Journal of Biological Chemistry (2009).
Janer, Alexandre, et al. "PML clastosomes prevent nuclear accumulation of mutant ataxin-7 and other polyglutamine proteins." The Journal of cell biology 174.1 (2006): 65-76.
Krobitsch, Sylvia, and Susan Lindquist. "Aggregation of huntingtin in yeast varies with the length of the polyglutamine expansion and the expression of chaperone proteins." Proceedings of the National Academy of Sciences 97.4 (2000): 1589-1594.
Lukacs et al., "Conformational maturation of CFTR but not its mutant counterpart (delta F508) occurs in the endoplasmic reticulum and requires ATP", EMBO J., (Dec. 15, 1994), vol. 13, No. 24, pp. 6076-6086, XP055334162.
Martin, Stéphane, et al. "Emerging extranuclear roles of protein SUMOylation in neuronal function and dysfunction." Nature Reviews Neuroscience 8.12 (2007): 948.
Meroni, Germana, and Graciana Diez☐Roux. "TRIM/RBCC, a novel class of 'single protein RING finger'E3 ubiquitin ligases." Bioessays 27.11 (2005): 1147-1157.
Mukhopadhyay, Debaditya, et al. "SUSP1 antagonizes formation of highly SUMO2/3-conjugated species." The Journal of cell biology 174.7 (2006): 939-949.
Nisole, Sébastien, et al. "Differential roles of PML isoforms." Frontiers in oncology 3 (2013): 125.
Orr, Harry T., and Huda Y. Zoghbi. "Trinucleotide repeat disorders." Annu. Rev. Neurosci. 30 (2007): 575-621.
Ozato, Keiko, et al. "TRIM family proteins and their emerging roles in innate immunity." Nature reviews immunology 8.11 (2008): 849.
Panavas, Tadas, Carsten Sanders, and Tauseef R. Butt. "SUMO fusion technology for enhanced protein production in prokaryotic and eukaryotic expression systems." SUMO protocols. Humana Press, Totowa, NJ, 2009. 303-317.
Reymond, Alexandre, et al. "The tripartite motif family identifies cell compartments." The EMBO journal 20.9 (2001): 2140-2151.
Riley, Brigit E., Huda Y. Zoghbi, and Harry T. Orr. "SUMOylation of the polyglutamine repeat protein, ataxin-1, is dependent on a functional nuclear localization signal." Journal of Biological Chemistry 280.23 (2005): 21942-21948.

(56) References Cited

OTHER PUBLICATIONS

Rüdiger, Stefan, et al. "Substrate specificity of the DnaK chaperone determined by screening cellulose☐bound peptide libraries." The EMBO journal 16.7 (1997): 1501-1507.
Saitoh, Hisato, and Joseph Hinchey. "Functional heterogeneity of small ubiquitin-related protein modifiers SUMO-1 versus SUMO-2/3." Journal of Biological Chemistry 275.9 (2000): 6252-6258.
Schlieker, Christian, et al. "Substrate recognition by the AAA+ chaperone ClpB." Nature Structural and Molecular Biology 11.7 (2004): 607.
Selkoe, Dennis J. "Folding proteins in fatal ways." Nature 426.6968 (2003): 900.
Sharma, Sandeep K., et al. "The kinetic parameters and energy cost of the Hsp70 chaperone as a polypeptide unfoldase." Nature chemical biology 6.12 (2010): 914.
Skinner, Pamela J., et al. "Ataxin-1 with an expanded glutamine tract alters nuclear matrix-associated structures." Nature 389.6654 (1997): 971.
Steffan, Joan S., et al. "SUMO modification of Huntingtin and Huntington's disease pathology." Science 304.5667 (2004): 100-104.
Sun, Huaiyu, Joel D. Leverson, and Tony Hunter. "Conserved function of RNF4 family proteins in eukaryotes: targeting a ubiquitin ligase to SUMOylated proteins." The EMBO journal 26.18 (2007): 4102-4112.
T. C. Tuoc et al: "Trim11 modulates the function of neurogenic transcription factor Pax6 through ubiquitin-proteosome system", Genes and Development., vol. 22, No. 14, Jul. 15, 2008 (Jul. 15, 2008), pp. 1972-1986, XP055535073, US ISSN: 0890-9369, DOI: 10.1101/gad.471708.
Takahasi et al., 2003, "PML nuclear bodies and neuronal intranuclear inclusion in polyglutamine diseases." Neurobiol Dis 13:230-70.
Takako Niikura et al: "A tripartite motif protein TRIM11 binds and destabilizes Humanin, a neuroprotective peptide against Alzheimer's disease-relevant insults:TRIM11 regulates intracellular level of Humanin", European Journal of Neuroscience., vol. 17, No. 6, Mar. 1, 2003 (Mar. 1, 2003), pp. 1150-1158, XP055535074, GB ISSN: 0953-816X, DOI: 10.1046/j.1460-9568.2003.02553.x.
Tang, Jun, et al. "A novel transcription regulatory complex containing death domain-associated protein and the ATR-X syndrome protein." Journal of Biological Chemistry 279.19 (2004): 20369-20377.
Tang, Jun, et al. "Critical role for Daxx in regulating Mdm2." Nature cell biology 8.8 (2006): 855.
Tatham, Michael H., et al. "RNF4 is a poly-SUMO-specific E3 ubiquitin ligase required for arsenic-induced PML degradation." Nature cell biology 10.5 (2008): 538.
Taylor, J. Paul, John Hardy, and Kenneth H. Fischbeck. "Toxic proteins in neurodegenerative disease." Science 296.5575 (2002): 1991-1995.
Tyedmers, Jens, Axel Mogk, and Bernd Bukau. "Cellular strategies for controlling protein aggregation." Nature reviews Molecular cell biology 11.11 (2010): 777.
Uchil, Pradeep D., et al. "TRIM E3 ligases interfere with early and late stages of the retroviral life cycle." PLoS pathogens 4.2 (2008): e16.
Urano et al., "TRIM44 interacts with and stabilizes terf, a TRIM ubiquitin E3 ligase", Biochem Biophys Res Commun, (Apr. 7, 2009), vol. 383, No. 2, doi:doi:10.1016/j.bbrc.2009.04.010, pp. 263-268, XP026057403.
Verhoef, Lisette GGC, et al. "Aggregate formation inhibits proteasomal degradation of polyglutamine proteins." Human molecular genetics 11.22 (2002): 2689-2700.
Versteeg, Gijs A., et al. "The E3-ligase TRIM family of proteins regulates signaling pathways triggered by innate immune pattern-recognition receptors." Immunity 38.2 (2013): 384-398.
Wang, Zheng, and Gregory Prelich. "Quality control of a transcriptional regulator by SUMO-targeted degradation." Molecular and cellular biology 29.7 (2009): 1694-1706.
Wang, Zhu Gang, et al. "Role of PML in cell growth and the retinoic acid pathway." Science 279.5356 (1998): 1547-1551.
Wanker, Erich E., et al. "[24] Membrane filter assay for detection of amyloid-like polyglutamine-containing protein aggregates." Methods in enzymology. vol. 309. Academic Press, 1999. 375-386.
Wilkinson, Kevin A., and Jeremy M. Henley. "Mechanisms, regulation and consequences of protein SUMOylation." Biochemical Journal 428.2 (2010): 133-145.
Brettschneider, J., Del Tredici, K., Lee, V.M., and Trojanowski, J.Q. (2015). Spreading of pathology in neurodegenerative diseases: a focus on human studies. Nat Rev Neurosci 16, 109-120.
Chiti, F., and Dobson, C.M. (2006). Protein misfolding, functional amyloid, and human disease. Annu Rev Biochem 75, 333-366.
Eisenberg, D., and Jucker, M. (2012). The amyloid state of proteins in human diseases. Cell 148, 1188-1203.
Ge, P., Dawson, V.L., and Dawson, T.M. (2020). PINK1 and Parkin mitochondrial quality control: a source of regional vulnerability in Parkinson's disease. Mol Neurodegener 15, 20, 18 pages.
Guo, L., Kim, H.J., Wang, H., Monaghan, J., Freyermuth, F., Sung, J.C., O'Donovan, K., Fare, C.M., Diaz, Z., Singh, N., et al. (2018). Nuclear-Import Receptors Reverse Aberrant Phase Transitions of RNA-Binding Proteins with Prion-like Domains. Cell 173, 677-692 e620.
Hofweber, M., Hutten, S., Bourgeois, B., Spreitzer, E., Niedner-Boblenz, A., Schifferer, M., Ruepp, M.D., Simons, M., Niessing, D., Madl, T., et al. (2018). Phase Separation of FUS Is Suppressed by Its Nuclear Import Receptor and Arginine Methylation. Cell 173, 706-719 e713.
Jucker, M., and Walker, L.C. (2013). Self-propagation of pathogenic protein aggregates in neurodegenerative diseases. Nature 501, 45-51.
Knowles, T.P., Vendruscolo, M., and Dobson, C.M. (2014). The amyloid state and its association with protein misfolding diseases. Nat Rev Mol Cell Biol 15, 384-396.
Yoshizawa, T., Ali, R., Jiou, J., Fung, H.Y.J., Burke, K.A., Kim, S.J., Lin, Y., Peeples, W.B., Saltzberg, D., Soniat, M., et al. (2018). Nuclear Import Receptor Inhibits Phase Separation of FUS through Binding to Multiple Sites. Cell 173, 693-705 e622.

\* cited by examiner

6His Tag                          TAT peptide        HA tag

MRGSHHHHHHGMASMTGGQQMGRDLYDDDDKDRWGSKLGYGRKKRRQRRRGGSTMSGYPYDVPDYAGS

| | | | | |
|---|---|---|---|---|
| MAAPDLSTNL | QEEATCAICL | DYFTDPVMTD | CGRNFCRECI | RRCWGQPEGP | YACPECRELS |
| PQRNLRPNRF | LAKMARMARR | LHPPSEVPQG | VCPAHREPLA | AFCGDELRLL | CAACERSGEH |
| WAHRVRFLQD | AAEDLKAKLE | KSLEHLRKQM | QDALLFQAQA | DETCVLWQKM | VESQPQNVLG |
| EFERLRRLIA | EEEQLLQRL | EEEELEVLER | LREGAAHLGQ | QSAHLAELIA | ELEGRCQLPA |
| LGLLQDIKDA | LRRVQDVKLQ | FPEVVPMELR | TVCRVPGLVE | TLRRFRGDVT | LDPDTANPEL |
| ILSEDRRSVQ | RGDLRQALPD | SPERFDPGPC | VLGQERFTSG | RHYWEVEVGD | RTSWALGVCR |
| ENVNRKEKGE | LSAGNGFWIL | VFLGSYYNSS | ERALAPLRDP | PRRVGIFLDY | EAGHLSFYSA |
| TDGSLLFIFP | EIPFSGTLRP | LFSPLSSSPT | PMTICRPKGG | SGDTLAPQ | |

TRIM11 (human) (SEQ ID NO: 22)

Figure 22

TRIM11 FOR DEGRADATION OF PROTEIN AGGREGATES

CROSS-REFERENCE TO RELATED APPLICATIONS

This application is the U.S. national phase application filed under 35 U.S.C. § 371 claiming benefit to International Patent Application No. PCT/US2016/034751, filed on May 27, 2016, which is entitled to priority under 35 U.S.C. § 119(e) to U.S. Provisional Application No. 62/168,309, filed May 29, 2015, all of which are incorporated herein by reference in their entireties.

STATEMENT REGARDING FEDERALLY SPONSORED RESEARCH OR DEVELOPMENT

This invention was made with government support under CA088868, GM060911, CA182675, CA184867, and P30 AI045008, awarded by the National Institute of Health. The government has certain rights in the invention.

BACKGROUND OF THE INVENTION

Proteins are the most abundant macromolecules of the cell and are critical to virtually all physiological processes. To perform their biological functions, the majority of proteins need to fold into and maintain their native conformations. Although the native conformation of a protein is determined by its amino acid sequence, the folding process is extraordinarily complex and highly prone to error, and its utility can be further limited in situations of genetic mutations, biogenetic inaccuracies, and posttranslational damages (Dobson, 2003, Nature, 426: 884-890; Goldberg, 2003, Nature, 426: 895-899). Proteins that have adopted aberrant conformations, and the aggregates formed by them, pose a constant threat to cell viability and function. Failure to eliminate these proteins is closely linked to the pathogenesis of various debilitating human diseases (Selkoe, 2003, Nature, 426: 900-904; Taylor et al., 2002, Science, 296: 1991-1995)

To contend with protein misfolding, cells employ two broad sets of protein quality control (PQC) systems: systems that assist proteins in achieving their native conformations, and systems that eliminate misfolded proteins once they are formed. The former consist mainly of a large number of molecular chaperones and their cochaperones, which in an ATP-dependent manner protect proteins in their nonnative state and reduce misfolding and aggregation. Notable examples include (1) heat shock protein 70 (Hsp70), which aids the folding of a wide range of proteins; (2) Hsp60/chaperonin, which forms a macromolecular cage to encapsulate relatively small proteins for uninterrupted folding; and (3) HSP90, which most commonly acts on proteins involved in cell signaling and transcription (Hartl et al., 2011, Nature, 475: 324-332).

Systems that remove misfolded proteins include protein disaggregases. For example, Hsp100 proteins in prokaryotes or lower eukaryotes (e.g., ClpB in bacteria and Hsp104 in yeast) can resolubilize protein aggregates, functioning in concert with Hsp70 and its cochaperone Hsp40 (Glover and Linguist, 1998, Cell, 94: 73-82). Nevertheless, given that protein misfolding is inevitable and often cannot be reversed due to mutations, biogenetic errors, or irreparable damages, cells ultimately rely on degradative systems to maintain protein quality. Yet, these systems are still poorly understood. Although the ubiquitin-proteasome pathway, along with autophagy, must be an important part of these systems, the critical issue of how they selectively recognize misfolded proteins and target them for degradation remains elusive (Goldberg, 2003, Nature, 426: 895-899; Tyedmers et al, 2010, Nat Rev Mol Cell Biol, 11: 777-788).

Furthermore, compared to the other cellular compartments such as the endoplasmic reticulum (Buchberger et al., 2010, Mol Cell, 40: 238-252), the PQC systems in the nucleus are conspicuously unclear. Misfolded proteins in the nucleus can be particularly damaging to postmitotic mammalian cells (e.g., neurons and cardiac myocytes), which are unable to remove these proteins through the breakdown of the nuclear envelope during mitosis. The importance of understanding PQC in this cellular compartment is emphasized by the formation of neuronal intranuclear inclusions that are associated with various dominantly inherited neurodegenerative diseases, including Huntington's disease (HD) and several types of spinocerebellar ataxias (SCAs). These diseases are caused by an expansion within the relevant genes of a CAG repeat, which encodes a polyQ stretch. They are manifested when the polyQ stretch exceeds a threshold length that is disease specific, and become progressively more severe as its length increases (Orr and Zoghbi, 2007, Annu Rev Neurosci, 30: 575-621).

Thus, there is a need in the art for compositions and methods for eliminating misfolded proteins. The present invention satisfies this unmet need.

SUMMARY OF THE INVENTION

In one aspect, the present invention provides a composition for treating or preventing a disease or disorder associated with misfolded protein or protein aggregates, wherein the composition comprises a modulator of one or more TRIM proteins. In one embodiment, the modulator increases the expression or activity of the one or more TRIM proteins. In one embodiment, the modulator is at least one of a chemical compound, a protein, a peptide, a peptidomemetic, an antibody, a ribozyme, a small molecule chemical compound, a nucleic acid, a vector, and an antisense nucleic acid.

In one embodiment, the modulator increases the expression or activity of at least one of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30.

In one embodiment, the composition comprises an isolated peptide comprising one or more TRIM proteins. In one embodiment, the isolated peptide further comprises a cell penetrating peptide (CPP) to allow for entry of the isolated peptide into a cell. In one embodiment, the CPP comprises the protein transduction domain of HIV tat.

In one embodiment, the composition comprises an isolated nucleic acid molecule encoding one or more TRIM proteins.

In one embodiment, the disease or disorder is a polyQ disorder. In one embodiment, the disease or disorder is a neurodegenerative disease or disorder selected from the group consisting of Spinocerebellar ataxia (SCA) Type 1 (SCA1), SCA2, SCA3, SCA6, SCA7, SCA17, Huntington's disease, Dentatorubral-pallidoluysian atrophy (DRPLA), Alzheimer's disease, Parkinson's disease, amyotrophic lateral sclerosis (ALS), a transmissible spongiform encephalopathy (prion disease), a tauopathy, and Frontotemporal lobar degeneration (FTLD). In one embodiment, the disease or disorder is selected from the group consisting of AL amyloidosis, AA amyloidosis, Familial Mediterranean fever, senile systemic amyloidosis, familial amyloidotic polyneuropathy, hemodialysis-related amyloidosis, ApoAI amyloidosis, ApoAII amyloidosis, ApoAIV amyloidosis, Finnish hereditary amyloidosis, lysozyme amyloidosis, fibrinogen amyloidosis, Icelandic hereditary cerebral amyloid angiopathy, type II diabetes, medullary carcinoma of the thyroid, atrial amyloidosis, hereditary cerebral hemorrhage with amyloidosis, pituitary prolactinoma, injection-localized amyloidosis, aortic medial amyloidosis, hereditary lattice corneal dystrophy, corneal amyloidosis associated with trichiasis, cataract, calcifying epithelial odontogenic tumor, pulmonary alveolar proteinosis, inclusion-body myostis, and cuteaneous lichen amyloidosis. In one embodiment, the disease or disorder is cancer associated with p53 mutant aggregates.

In one aspect, the present invention provides a method for treating or preventing a disease or disorder associated with misfolded protein or protein aggregates in a subject in need thereof, where the method comprises administering to the subject a composition comprising a modulator of one or more TRIM proteins. In one embodiment, the modulator increases the expression or activity of the one or more TRIM proteins. In one embodiment, the modulator is at least one of a chemical compound, a protein, a peptide, a peptidomemetic, an antibody, a ribozyme, a small molecule chemical compound, a nucleic acid, a vector, and an antisense nucleic acid.

In one embodiment, the modulator increases the expression or activity of at least one of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30.

In one embodiment, the composition comprises an isolated peptide comprising one or more TRIM proteins. In one embodiment, the isolated peptide further comprises a cell penetrating peptide (CPP) to allow for entry of the isolated peptide into a cell. In one embodiment, the CPP comprises the protein transduction domain of HIV tat.

In one embodiment, the composition comprises an isolated nucleic acid molecule encoding one or more TRIM proteins.

In one embodiment, the disease or disorder is a polyQ disorder. In one embodiment, the disease or disorder is a neurodegenerative disease or disorder selected from the group consisting of Spinocerebellar ataxia (SCA) Type 1 (SCA1), SCA2, SCA3, SCA6, SCA7, SCA17, Huntington's disease, Dentatorubral-pallidoluysian atrophy (DRPLA), Alzheimer's disease, Parkinson's disease, amyotrophic lateral sclerosis (ALS), a transmissible spongiform encephalopathy (prion disease), a tauopathy, and Frontotemporal lobar degeneration (FTLD). In one embodiment, the disease or disorder is selected from the group consisting of AL amyloidosis, AA amyloidosis, Familial Mediterranean fever, senile systemic amyloidosis, familial amyloidotic polyneuropathy, hemodialysis-related amyloidosis, ApoAI amyloidosis, ApoAII amyloidosis, ApoAIV amyloidosis, Finnish hereditary amyloidosis, lysozyme amyloidosis, fibrinogen amyloidosis, Icelandic hereditary cerebral amyloid angiopathy, type II diabetes, medullary carcinoma of the thyroid, atrial amyloidosis, hereditary cerebral hemorrhage with amyloidosis, pituitary prolactinoma, injection-localized amyloidosis, aortic medial amyloidosis, hereditary lattice corneal dystrophy, corneal amyloidosis associated with trichiasis, cataract, calcifying epithelial odontogenic tumor, pulmonary alveolar proteinosis, inclusion-body myostis, and cuteaneous lichen amyloidosis. In one embodiment, the disease or disorder is cancer associated with p53 mutant aggregates.

In one embodiment, the method comprises administering the composition to at least one neural cell of the subject.

In one aspect, the present invention provides a composition for treating or preventing a disease or disorder associated with degradation of functional mutant protein, where the composition comprises a modulator of one or more TRIM proteins. In one embodiment, the modulator increases the expression or activity of the one or more TRIM proteins. In one embodiment, the modulator is at least one of the group consisting of a chemical compound, a protein, a peptide, a peptidomemetic, an antibody, a ribozyme, a small molecule chemical compound, a nucleic acid, a vector, and an antisense nucleic acid. In one embodiment, the disease or disorder is cystic fibrosis.

In one aspect, the present invention provides a method for treating or preventing a disease or disorder associated with degradation of functional mutant protein in a subject in need thereof, where the method comprises administering to the subject a composition comprising a modulator of one or more TRIM proteins. In one embodiment, the modulator increases the expression or activity of the one or more TRIM proteins. In one embodiment, the modulator is at least one of the group consisting of a chemical compound, a protein, a peptide, a peptidomemetic, an antibody, a ribozyme, a small molecule chemical compound, a nucleic acid, a vector, and an antisense nucleic acid. In one embodiment, the disease or disorder is cystic fibrosis.

In one aspect, the present invention provides a composition for treating or preventing a disease or disorder associated with misfolded protein or protein aggregates, where the composition comprises a modulator of one or more SUMO-targeted ubiquitin ligase (STUbl). In one embodiment, the modulator increases the expression or activity of one or more STUbLs. In one embodiment, the modulator is at least one of a chemical compound, a protein, a peptide, a peptidomemetic, an antibody, a ribozyme, a small molecule chemical compound, a nucleic acid, a vector, and an antisense nucleic acid. In one embodiment, the modulator increases the expression or activity of RNF4.

In one aspect, the present invention provides a method for treating or preventing a disease or disorder associated with misfolded protein or protein aggregates in a subject in need thereof, where the method comprises administering to the subject a composition comprising a modulator of one or more STUbLs. In one embodiment, the modulator increases the expression or activity of one or more STUbLs. In one embodiment, the modulator is at least one of a chemical compound, a protein, a peptide, a peptidomemetic, an antibody, a ribozyme, a small molecule chemical compound, a nucleic acid, a vector, and an antisense nucleic acid. In one embodiment, the modulator increases the expression or activity of RNF4.

In one aspect, the present invention provides a method for producing a recombinant protein, where the method comprises administering a modulator of one or more TRIM proteins to cell modified to express a recombinant protein. In one embodiment, the modulator comprises an isolated peptide comprising one or more TRIM proteins. In one embodiment, the modulator comprises an isolated nucleic acid molecule encoding one or more TRIM proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising (FIG. 1A) HeLa cells transfected with Atxn1 82Q-GFP were stained with anti-PML antibody (red) and DAPI (blue). Individual and merged images are shown. Scale bar, 10 (FIG. 1B) Atxn1 82Q-GFP was expressed alone or together with PML in HeLa cells. Left, representative fluorescence images of cells. Scale bar, 20 Right, quantification of cells based on sizes of Atxn1 82Q-GFP inclusions. (FIG. 1C) Atxn1 82Q-GFP was expressed alone or together with PML in HeLa cells (left), or alone in HeLa cells that were previously treated with control (–) or PML siRNA. Cell lysate fractions (when indicated) and whole-cell lysates (WCL) were analyzed by filter retardation assay (for SR fraction) or western blot (WB; for the rest). Molecular weight standards (in kDa) and relative ratios of SS or SR Atxn1 versus actin are indicated. (FIG. 1D) Steady-state levels of FLAG-Atxn1 82Q or 30Q when expressed alone or together with PML in HeLa cells (left), or when expressed alone in HeLa cells that were treated with control or PML siRNA (right), analyzed by WB. (FIG. 1E) Effect of PML on the stability of total FLAG-Atxn1 82Q protein, analyzed by a pulse-chase assay and autoradiography. The relative amounts of $^{35}$S-labeled Atxn1 82Q are indicated. (FIG. 1F and FIG. 1G) Effect of PML overexpression (FIG. 1F) and knockdown (FIG. 1G) on the stability of Atxn1 82Q-GFP, analyzed by CHX treatment and WB. (FIG. 1H) Effect of PML on Atxn1 82Q-GFP levels in the absence or presence of MG132. (FIG. 1I) Top, relative percentages of Httex1p 97QP-expressing cells with cytoplasmic (left) and nuclear (right) inclusions, in the absence or presence of PML (means+SD, n=3). Bottom, representative fluorescence images of transfected cells immunostained with an anti-Htt antibody. Arrowheads indicate Httex1p 97QP aggregates. (FIG. 1J and FIG. 1K) Levels of HA-Httex1p 97QP and HA-Httex1p 97QP(KR) (FIG. 1J) and GFP-TDP-43 (FIG. 1K) in cells with and without PML overexpression. Virtually all Htt aggregates were in the SR fraction. (FIG. 1L) Stability of nFucDM-GFP in control and PML-depleted cells, analyzed by CHX treatment and WB.

FIG. 2, comprising (FIG. 2A) Binding of GST-Htt 25Q and GST-Htt 103Q to immobilized FLAG-PML and FLAG-GFP (negative control), analyzed by an in vitro pull-down assay followed by WB (top and bottom) and Ponceau S staining (middle). *IgG heavy chain. (FIG. 2B) Binding of GST-PML (shown on the right) and the control GST protein to native (N) and urea-denatured (D) luciferase (luc) immobilized on Ni-NTA beads, analyzed as in (FIG. 2A). *Nonspecific proteins from BL21 bacterial lysates that bound to the control beads. (FIG. 2C) Binding of indicated GST-Htt fusions to FLAG-PML CC conjugated on anti-Flag M2 beads or to control beads, analyzed by WB (top and middle) and Coomassie staining (bottom). (FIG. 2D) Binding of PML F12/SRS2 (shown on the right) to a peptide library derived from luciferase. The N-terminal amino acid of the first peptide and the number of the last peptide spotted in each row are indicated. (FIG. 2E) The occurrence of each amino acid in PML SRS2-binding peptides relative to its occurrence in the luciferase peptide array (set at 100%).

FIG. 3, comprising (FIG. 3A) SUMO1 and SUMO2/3 modification of Atxn1 82Q in HeLa cells treated without or with MG132. For better comparison of modified Atxn1 82Q, Denaturing immunoprecipitation (d-IP) products with a similar level of unmodified Atxn1 82Q were analyzed by WB. *Nonspecific bands. (FIG. 3B) Localization of Atxn1 82Q (detected by anti-FLAG antibody, red) in GFP-SUMO2- or GFP-SUMO3-expressing U2OS cells treated with or without MG132. Scale bar, 10 (FIG. 3C) SUMO2/3 modification of Atxn1 82Q and 30Q in HeLa cells, analyzed by d-IP followed by WB (top) and Ponceau S staining (bottom). (FIG. 3D) Atxn1 82Q was expressed alone or together with SUMO1 or HA-SUMO2 KR in HeLa cells that were previously transfected with the indicated siRNA or un-transfected (–). Cells were treated with or without MG132. SUMOylation and ubiquitination of FLAG-Atxn1 82Q was analyzed by d-IP and WB. (FIG. 3E) Levels of Atxn1 82Q-GFP expressed alone or together with increasing amounts of PML in HeLa cells pretreated with the indicated siRNA. (FIG. 3F) Effect of PML on Atxn1 82Q-GFP levels in the presence or absence of SUMO1 or SUMO2 KR.

FIG. 4, comprising (FIG. 4A) SUMOylation of FLAG-Atxn1 82Q in HeLa cells in the absence or presence of HA-PML cells, and without or with MG132 treatment. The amount of Atxn1 82Q DNA used for transfected was adjusted to yield comparable levels of the unmodified protein. (FIG. 4B and FIG. 4C) SUMOylation of FLAG-Atxn1 82Q (FIG. 4B) and FLAG-nFlucDM-GFP (FIG. 4C) in control and PML siRNA-transfected HeLa cells treated without or with MG132. (FIG. 4D and FIG. 4E) SUMOylation of purified HA-Atxn1 82Q-FLAG was performed in the presence of recombinant FLAG-PML, FLAG-PML M6, and SUMO2 as indicated. In (FIG. 4D), the amounts of different d-IP products were adjusted to yield a similar level of unmodified Atxn1 82Q (middle). (FIG. 4F) Levels of Atxn1 82Q-GFP in HeLa cells in the absence or presence of increasing amounts of PML or PML M6.

FIG. 5, comprising (FIG. 5A) Levels of Atxn1 82Q-GFP in HeLa cells without and with RNF4 overexpression. (FIG. 5B and FIG. 5C) Effect of RNF4 overexpression on Atxn1 82Q-GFP stability in control and PML-depleted HeLa cells, analyzed by CHX treatment and WB. Relative SS Atxn1 82Q/actin ratios are shown in (FIG. 5C). (FIG. 5D) Levels of FLAG-Atxn1 82Q in HeLa cells pretreated with a control siRNA (–) or a combination of three RNF4 siRNAs. (FIG. 5E) Representative fluorescent images of Atxn1 82Q-GFP in control and RNF4-knockdown HeLa cells. Scale bar, 20 μm (FIG. 5F) Localization of Atxn1 82Q-GFP and endogenous RNF4 in HeLa cells treated with vehicle (DMSO) or MG132. Scale bar, 10 (FIG. 5G and FIG. 5H) Levels of FLAG-Atxn1 82Q and FLAG-Atxn1 30Q (FIG. 5G) or HA-Httex1p 97QP and HA-Httex1p 97QP(KR) (FIG. 5H) in HeLa cells without and with RNF4 overexpression. (FIG. 5I) Stability of nFlucDM-GFP in HeLa cells stably expressing shCtrl and shRNF4 (left) and the levels of RNF4 in these cells (right).

FIG. 6, comprising (FIG. 6A and FIG. 6B) Levels of SUMOylated FLAG-Atxn1 82Q (FIG. 6A) and FLAG-nFlucDM-GFP (FIG. 6B), in the absence or presence of RNF4, in HeLa cells treated with or without MG132. d-IP products with similar levels of unmodified proteins, as well as WCL, were analyzed. (FIG. 6C) Levels of SUMOylated FLAG-Atxn1 82Q in HeLa cells that were pretreated with a control siRNA or a combination of RNF4 siRNAs, analyzed as in (FIG. 6A). (FIG. 6D and FIG. 6E) Unmodified and SUMO2-modified FLAG-Atxn1 82Q proteins conjugated on M2 beads (+), or control M2 beads (−), were incubated with ubiquitination reaction mixture, in the absence or presence of GST-RNF4. (FIG. 6D) A schematic diagram of the experimental design. (FIG. 6E) WB analysis of FLAG-Atxn1 82Q (left) and GST-RNF4 (right). (FIG. 6F and FIG. 6G) Localization of Atxn1 82Q-GFP and RNF4 proteins (detected by anti-FLAG antibody) in HeLa. Scale bar, 10 μm. (FIG. 6H) Effect of the indicated RNF4 proteins on Atxn1 82Q-GFP levels in HeLa cells. (FIG. 6I) Effect of PML overexpression on Atxn1 82Q-GFP levels in HeLa cells that were pretreated with control or RNF4 siRNA.

FIG. 7, comprising (FIG. 7A and FIG. 7B) Retention times (average+SEM) on accelerating Rotarod at 7 (FIG. 7A) and 11 (FIG. 7B) weeks of age, with the number of animals indicated in parenthesis. (FIG. 7C and FIG. 7D) Cerebellar sections of 12-week-old animals were stained with hematoxylin. (FIG. 7C) Quantification of molecular layer thickness (means±SEM, n=3 mice/genotype). (FIG. 7D) Representative images of the staining. Scale bar, 200 μm. (FIG. 7E and FIG. 7F) Cerebellar sections of 1-year-old animals were stained with an anti-calbindin antibody. (E) Quantitation of Purkinje cells, graphed as the average number of soma per 1 mm length (means±SEM, n=4 mice/genotype). (F) Representative images of the staining. Scale bar, 200 μm. (FIG. 7G and FIG. 7H) Sections of the cerebellar cortex from 12-week-old mice were stained with an anti-ubiquitin antibody and counterstained with hematoxylin. (FIG. 7G) Percentage of Purkinje cells with aggregates (means±SEM, n=3 mice/genotype). (FIG. 7H) Representative images of the immunohistochemistry staining. Arrowheads indicate the ubiquitin positive aggregates in Purkinje cell bodies. Scale bar, 50 μm. No ubiquitin-positive aggregates were observed in Purkinje cells in mice without Atxn1$^{tg/-}$ (see FIG. 14D). (FIG. 7I) A model for PQC by the PML-RNF4 system. PML recognizes misfolded proteins through SRSs and conjugates them with poly-SUMO2/3 chain through its SUMO E3 ligase activity (a). RNF4 ubiquitinates SUMOylated-misfolded proteins (b) and targets them for proteasomal degradation (c).

FIG. 8, comprising (FIG. 8A) Atxn1 82Q-GFP was expressed in PML-deficient (PML$^{-/-}$) mouse embryonic fibroblasts (MEFs) together with each of the indicated PML isoforms. Cells were stained with anti-PML antibody (red) and DAPI (blue). (FIG. 8B) Levels of FLAG-Atxn1 82Q in HeLa cells treated with a control siRNA (−), PML siRNA #4, or PML siRNA #9. Cell lysates were analyzed by Western blot and filter retardation assays. The ratios of Atxn1 82Q in the SS fraction versus actin, normalized to the control, are shown. (FIG. 8C) HeLa cells were transfected with a control siRNA, PML siRNA #4 (which targeted the 5'UTR of the PML mRNA), or PML siRNA #4 plus a plasmid expressing the open reading frame of PML (hence resistant to the siRNA). Levels of Atxn1 82Q-GFP in various fractions were analyzed. (FIG. 8D) HeLa cells were treated with control siRNA, PML siRNA #4, and PML siRNA #9 and then transfected with FLAG-Atxn1 82Q. The levels of the FLAG-Atxn1 82Q transcript were determined by quantitative RT-PCR normalized to levels of 18S rRNA. (FIG. 8E) Atxn1 30Q-GFP was expressed in HeLa cells in the absence or presence of PML. Cells were then treated with CHX for the indicated times. (FIG. 8F) HeLa cells were transfected with nFlucDM-GFP and the corresponding wild-type luciferase (WT) protein. Endogenous PML was detected by an anti-PML antibody (red), and DNA by DAPI (blue). Scale bar: 10 μm. (FIG. 8G) PML knockdown leads to accumulation of insoluble mutant luciferase. HeLa cells were transfected with control or PML siRNA and then with nFluc-GFP or nFlucDM-GFP. The SR fraction contained very small amounts of nFlucDM-GFP.

FIG. 9, comprising (FIG. 9A) PML preferentially interact with pathogenic Htt. Lysates of 293T cells expressing FLAG-GFP or FLAG-PML were incubated with GST-Htt 25Q or GST-Htt 103Q immobilized on glutathione beads (lanes 1-3 and 5-7), or with control glutathione beads (lanes 4 and 8). The input and pull-down fractions were analyzed by Western blot. (FIG. 9B) Schematic representation of wild-type PML isoforms IV (aa 1-633) (called PML in the present work) and various deletion fragments (F1-F10). The RING domain (R), B1 box, B2 box, and coiled-coil region (CC) are labeled. Substrate recognition sites SRS1 and SRS2 are indicated by lines. The interaction of PML with pathogenic Htt proteins (Htt 103Q or 52Q) and denatured luciferase are shown. ND: not done. (FIG. 9C) Interactions of full-length PML and PML deletion mutants with Htt. PML proteins were generated by coupled in vitro transcription/translation in the presence of [$^{35}$S]Met, and were incubated with purified GST-Htt 103Q, GST-Htt 25Q, or GST immobilized on glutathione beads. [$^{35}$S]Met-labeled proteins in the input and pull-down samples were analyzed by autoradiography, and GST proteins in the pull-down samples were analyzed by Coomassie staining. The three pull-down sample sets were analyzed at the same time and in the same way, including the amount of samples and the exposure duration of autoradiography. The input samples were exposed for a shorter period of time. (FIG. 9D) Sequences of Htt 52Q and the CC-destabilizing (cc-) mutant. The amino acids in Htt 52Q that are changed to Pro in Htt 52Q cc- are shown in red. (FIG. 9E) Interaction of purified PML CC region (shown on the right) with cellulose-bound luciferase peptide scans was assayed as in FIG. 2D. * TEV protease.

FIG. 10, comprising (FIG. 10A) Interaction of PML fragments with denatured luciferase. In vitro-translated, [$^{35}$S]-labeled full-length FLAG-PML and FLAG-PML deletion mutants were incubated with native or denatured luciferase immobilized on beads, or control beads. The input and beads-bound PML proteins were analyzed by autoradiography, and luciferase by Coomassie blue staining. *, Non-specific bands. The three pull down sample sets were analyzed at the same time and in the same way, including the amount of samples and the exposure duration of autoradiography. The input samples were exposed for a shorter period of time. (FIG. 10B and FIG. 10C) Identification of the second substrate recognition site (SRS2) on PML. (FIG. 10B) PML deletion mutations encompassing amino acids at the C-terminus and summary of their interaction with denatured luciferase. (FIG. 10C) In vitro-translated, [$^{35}$S]-labeled GST-fusions of PML fragments or GST were tested for interaction with luciferase as described in (FIG. 10A).

FIG. 11, comprising (FIG. 11A) HeLa cells were transfected with FLAG-Atxn1 82Q or FLAG-Atxn1 82Q (5KR) and were treated with or without MG132. FLAG-Atxn1 82Q and FLAG-Atxn1 82Q (5KR) were isolated by d-IP, and their SUMO2/3 modification was analyzed by Western blot. (FIG. 11B) HeLa cells were transfected without or with GFP-TDP-43 and treated with vehicle (DMSO) (−) or MG132 (+). d-IP was performed using an anti-GFP antibody or a control antibody. d-IP products were analyzed by Western blot. (FIG. 11C) HeLa cells were transfected with nFluc-GFP, nFlucSM-GFP, and nFlucSM-GFP (each was also N-terminally tagged with the FLAG epitope) and treated with or without MG132. nFluc proteins were isolated by d-IP. The whole cell lysates (WCL) and IP products were analyzed by Western blot. Note that the difference between the SUMO2/3 modifications of WT luciferase versus SM/DM luciferase (top, lanes 1-3) was not due to a change in the overall SUMO2/3 conjugation in the WCL (bottom). (FIG. 11D) Atxn1 82Q-GFP was expressed in HeLa cells pre-treated with control (Ctrl), SUMO2/3, or SUMO1 siRNA. Cell lysates were analyzed by Western blot. (FIG. 11E and FIG. 11F) HeLa cells were treated with control (Ctrl) siRNA, SUMO2/3 siRNA, or SUMO1 siRNA (FIG. 11E), or treated with these siRNAs and then transfected with GFP (FIG. 11F). Cell lysates were analyzed by Western blot. (FIG. 11G) PML and PML M6 proteins used for in vitro SUMOylation assay. FLAG-PML and FLAG-PML M6 were expressed in 293T cells and purified by anti-FLAG (M2) beads. The proteins were analyzed by Coomassie staining along with BSA standards (left) and by Western blot (right). The two additional bands (arrowheads) presented in both PML and PML M6 lanes (left) were determined to be PML fragments based on both Western blot (right) and by mass spectrometry analysis. A schematic representation of M6 mutant is shown at the bottom. *: Point mutations are described elsewhere herein.

FIG. 12, comprising (FIG. 12A) Representative fluorescence images of HeLa cells expressing Atxn1 82Q-GFP alone or together with RNF4. Scale bar: 20 μm. Images are from the same experiment as that shown in FIG. 1B. (FIG. 12B) The half-life of Atxn1 82Q-GFP in HeLa cells with and without RNF4 overexpression. Samples are from the same experiments as those shown in FIG. 1F. (FIG. 12C) HeLa cells were transfected with control siRNA (−), RNF4 siRNA alone, or RNF4 siRNA plus an siRNA-resistant RNF4. Cell lysates were analyzed by Western blot. (FIG. 12D) FLAG-Atxn1 82Q was expressed in HeLa cells that were pre-treated with control siRNA and the indicated RNF4 siRNA. FLAG-Atxn1 82Q was isolated by d-IP with anti-FLAG M2 beads. WCL and IP products were analyzed by Western blot with indicated antibodies. (FIG. 12E) HeLa cells expressing both Atxn1 82Q-GFP and FLAG-RNF4 were treated with vehicle (DMSO) or MG132. Exogenous (Exo.) RNF4 was detected anti-FLAG antibody. In control cells treated with DMSO, exogenous RNF4 showed partial co-localization with Atxn1 82Q-GFP aggregates. Upon MG132 treatment, complete co-localization of exogenous RNF4 with Atxn1 82Q aggregates was observed in 100% of cells. Scale bar: 10 μm. (FIG. 12F) Western blot analysis of HeLa cells transfected with GFP-TDP-43 alone or together with increasing amounts of RNF4. (FIG. 12G) GFP-TDP-43 was expressed in cells pre-treated with a control siRNA (−) or the indicated RNF4 siRNA. 500 cells were counted in each experiment. Percentages of cells with GFP-TDP-43 foci are shown. (FIG. 12H) HeLa cells treated with RNF4 siRNA were transfected with GFP-TDP-43. Cells were stained with an anti-RNF4 antibody (red) and DAPI (blue). Note that TDP-43 formed aggregates in a cell in which RNF4 was knocked down (filled arrowhead), but was diffused in a control cell (open arrowhead). (FIG. 12I) HeLa cells were transfected with GFP-TDP-43 and treated with MG132. Endogenous RNF4 was immunostained with anti-RNF4 antibody (red). Note that RNF4 also formed nuclear foci in cells with no TDP-43 (FIG. 12E-FIG. 12H).

FIG. 13, comprising (FIG. 13A) Atxn1 82Q-GFP and/or RNF4 were expressed in HeLa cells pre-treated with control siRNA, SUMO2/3 siRNA, and SUMO1 siRNA. Cell lysates were analyzed by Western blot. (FIG. 13B) U2OS cells stably expressing GFP-SUMO2 were transfected first with the indicated RNF4 siRNAs or a control siRNA (−) and then with FLAG-Atxn1 82Q. The percentages of transfected cells with GFP-SUMO2-positive Atxn1 82Q aggregates are shown (mean+SD, n=3). In each experiment, 200 cells were counted. Representative images of the transfected cells are shown on the right. GFP-SUMO2 does not form aggregated structure in cells without Atxn1 82Q expression. (FIG. 13C) Schematic representation of wild-type and mutant RNF4 proteins. The SUMO-interaction motifs (SIMs) 1 to 4 and the RING domain are shown. *: Point mutations are described elsewhere herein. (FIG. 13D and FIG. 13E) Purified recombinant GST fusions of rat (r) RNF4 and RNF4 CS1 (FIG. 13D) or human RNF4 and RNF4 SIMm (FIG. 13E) were incubated with ubiquitin E1, E2 (UbcH5a), and ubiquitin (Ub) as indicated, plus Mg$^{2+}$-ATP. The reaction mixtures were analyzed by Western blot using an anti-GST antibody. (FIG. 13F) Expression of Atxn1 82Q-GFP in cells treated with the indicated combinations of control, PML, and RNF4 siRNAs as indicated. Cell lysates were analyzed by Western blot.

FIG. 14, comprising (FIG. 14A) Midsagittal cerebellar sections of 12-week-old mice were stained with an antibody against the Purkinje cell-specific protein calbindin. Fluorescence intensity was plotted from a rectangular area from the preculminate fissures (n=2 mice for PML$^{+/+}$, and n=3 mice for all the other genotypes). PAIL' mice showed significant loss of dendritic arborization compared to PML$^{+/+}$ mice (ANOVA, p=0.031). (FIG. 14B)

Representative confocal images of calbindin immunofluorescence. Scale bar: 100 (FIG. 14C) Quantitation of Purkinje cell density in 12-week PML$^{+/+}$, PML$^{+/-}$ and PML$^{-/-}$ mice with and without Atxn1$^{tg/-}$, graphed as the average number of soma per 1 mm length (means+SEM, n=3 mice/genotype). (FIG. 14D) Immunohistochemical staining of the cerebellar cortex sections from 12-week-old PML$^{+/+}$ and PML$^{-/-}$ mice without Atxn1$^{tg/-}$. The sections were stained with an anti-ubiquitin antibody and counterstained with hematoxylin. Scale bar: Note that no ubiquitin positive aggregates were detected in those sections. The stained sections of PML$^{+/+}$:Atxn1$^{tg/-}$ and PML$^{-/-}$:Atxn1$^{tg/-}$ mice are shown in FIG. 7G.

FIG. 15, comprising (FIG. 15A) Atxn1 82Q-GFP was expressed in HeLa cells together with the indicated FLAG-tagged TRIM proteins. Cells were stained with anti-FLAG antibody (red) and DAPI (blue). Scale bar: 10 (FIG. 15B and FIG. 15C) Httex1p 97QP was expressed in HeLa cells together with FLAG-tagged TRIM5δ TRIM27 (FIG. 15B), and TRIM32 (FIG. 15C). Cells were immunostained with anti-huntingtin (green) and anti-FLAG (red) antibodies. Note that TRIM32 co-localized with Httex1p 97QP regardless of the cellular localization of Httex1p 97QP. (FIG. 15D) HeLa cells were transfected with Atxn1 82Q-GFP. Endogenous TRIM27 was detected by anti-TRIM27 antibody (red). Arrowheads indicate endogenous TRIM27 bodies that were co-localized with the Atxn1 82Q aggregates. Scale bar: 10 μm.

FIG. 16, comprising (FIG. 16C) Expression levels of Atxn1 82Q in HeLa cells treated with control (-) or TRIM27 siRNA. *, a non-specific band. (FIG. 16D) PIASy does not inhibit the levels of Atxn1 82Q protein. Western blot analysis of HeLa cells transfected with Atxn1 82Q-GFP, PIASy, and PML as indicated.

FIG. 17, comprising (FIG. 17A) Partial co-localization of TRIM27 with PML. HeLa cells transfected with FLAG-TRIM27 were immunostained with anti-FLAG (green) and anti-PML (red) antibodies. (FIG. 17B) Co-localization of TRIM27 with Atxn1 82Q-GFP aggregates in PML$^{+/+}$ and PML$^{-/-}$ MEFs. FLAG-TRIM 27 was stained by anti-FLAG (red) antibody. (FIG. 17C) Atxn1 82Q-GFP was expressed alone or together with the indicated TRIM proteins in PML$^{+/+}$ and PAIL$^{-/-}$ MEFs. Extracts were analyzed by filter retardation assay. To better compare the effects of TRIM proteins on the aggregates, a lighter exposure is shown on the right panel.

FIG. 18, comprising (FIG. 18A-FIG. 18F) Atxn1 82Q-GFP was expressed alone or together with TRIM5δ TRIM27, and TRIM32 in cells treated without or with MG132 (FIG. 18A-FIG. 18C), or in control or SUMO2/3 knockdown cells (FIG. 18D-FIG. 18F). Cell lysates were analyzed by Western blot. (FIG. 18G) SUMOylation of purified HA-Atxn1 82Q-FLAG was performed in the presence of recombinant FLAG-TRIM11 and SUMO2 as indicated. HA-Atxn1 82Q-FLAG was isolated using denaturing immunoprecipitation. The reaction mixtures and IP samples were analyzed by Western blot.

FIG. 19, comprising FIG. 19A through FIG. 19F, depicts the results of example experiments demonstrating the localization of TRIM proteins in relation to Atxn1 82Q. Atxn1 82Q-GFP (green) was expressed in HeLa cells together with the indicated HA-tagged TRIM proteins. Cells were immunostained with anti-HA antibody (red). The representative localization patterns for each TRIM protein are shown. (FIG. 19A) The representative localization patterns of TRIM1-TRIM 16. (FIG. 19B) The representative localization patterns of TRIM17-TRIM32. (FIG. 19C) The representative localization patterns of TRIM33-TRIM41 and TRIM44-TRIM 41. (FIG. 19D) The representative localization patterns of TRIM52, TRIM54-TRIM58, TRIM62-TRIM66, TRIM73-TRIM74, and TRIM76. TRIM proteins that showed co-localization with Atxn1 82Q-GFP in a substantial number of cells are indicated in yellow. Scale bar: 10 μm.

FIG. 20, comprising

FIG. 21, comprising (FIG. 21A) Treatment of HeLa cells with TRIM11 led to strong reduction in the levels of Atxn1 82Q. (FIG. 21B) Treatment of HeLa cells with TRIM11 also led to strong reduction in the levels of Htt 97Q. (FIG. 21C) SUMO2 had minimal effect on the levels of Atxn1 82Q.

FIG. 22 depicts the amino acid sequence of Tat-TRIM11 used in example experiments.

FIG. 23A through FIG. 23F, depicts results of experiments demonstrating RNF4 staining of human brain samples. Anti-RNF4 (green) immunostaining of HD brain tissues. RNF4 showed diffused nuclear localization (FIG. 23A-FIG. 23C) or formed foci (FIG. 23D-FIG. 23F) (indicated by arrowheads). Scale bar: 10 μm.

FIG. 24A through FIG. 24H, depicts results of experiments demonstrating co-localization of RNF4 with neuronal inclusions of SCA1 patients. Immunostaining of SCA1 brain tissues with anti-polyQ (1C2) and anti-RNF4 antibodies. Scale bar: 10 μm.

FIG. 25A through FIG. 25L, depicts results of experiments demonstrating co-localization of RNF4 with neuronal inclusions of SCA1 patients. FIG. 25 depicts immunostaining of HD brain tissues with anti-Htt, anti-ubiquitin and two separate RNF4 antibodies. Note that Htt and ubiquitin form ring-like structures (FIG. 25A-FIG.

25H) or evenly distributed inclusions (FIG. 25I-FIG. 25L) with the RNF4 signal in the center.

Figure 26:
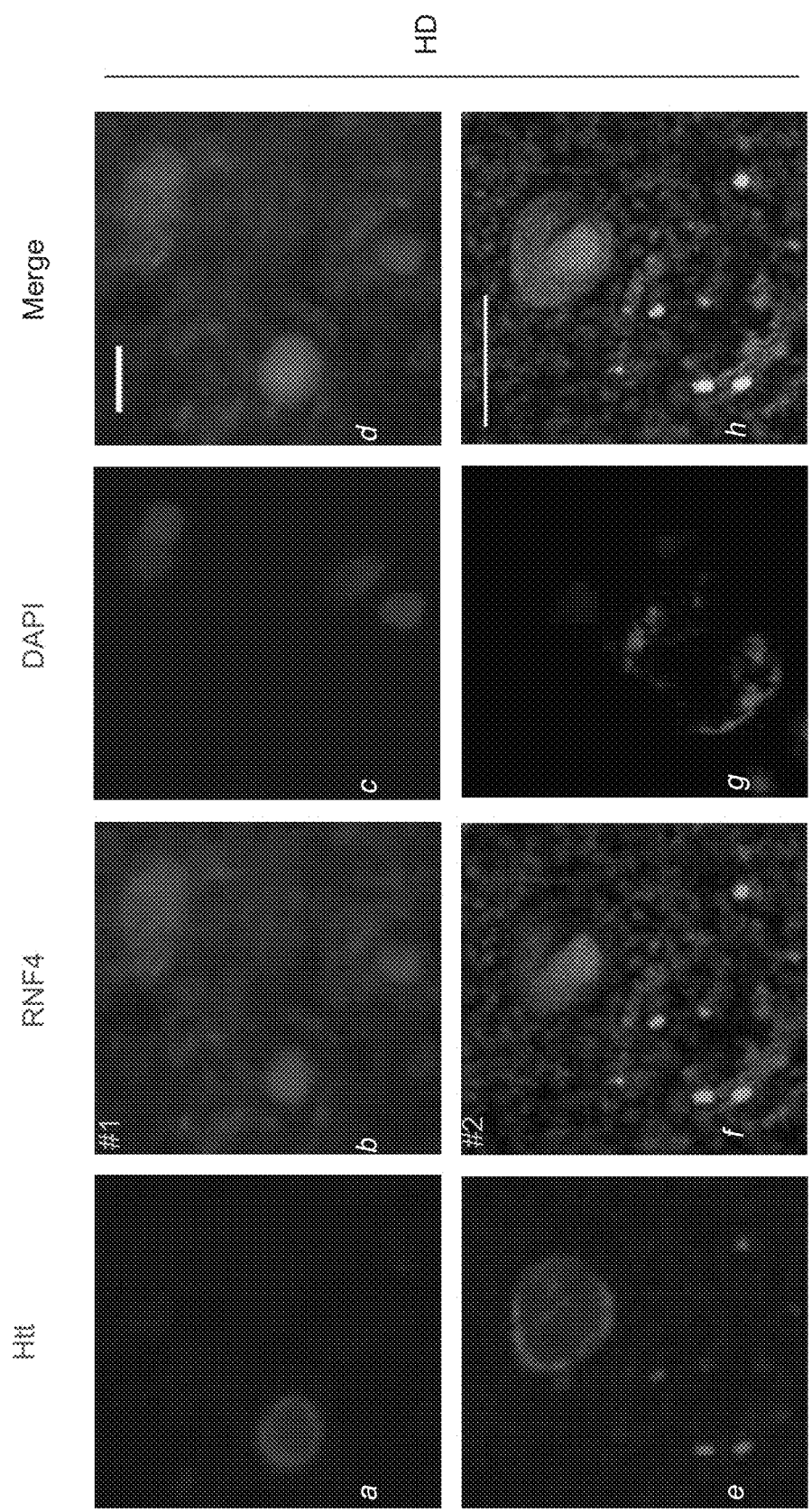

FIG. 26, comprising FIG. 26A through FIG. 26H, depicts results of experiments demonstrating co-localization of RNF4 with inclusions in neurons of HD patients. Shown are Htt and RNF4 immunostaining of HD brain tissues. Two different RNF4 antibodies (#1 and #2) were used. Scale bar: 10 μm.

Figures 27A, 27B:
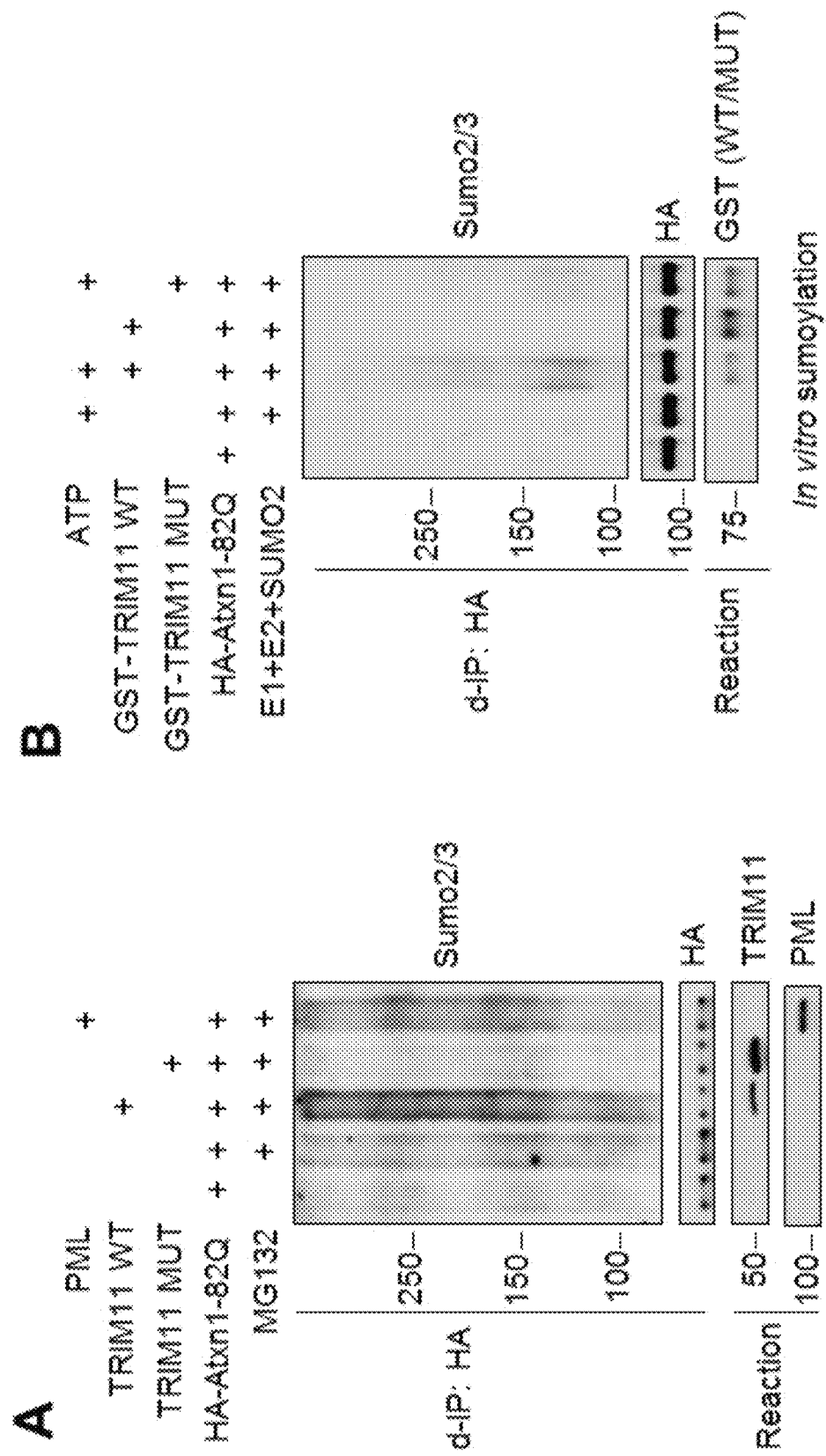
Figures 27C, 27D:
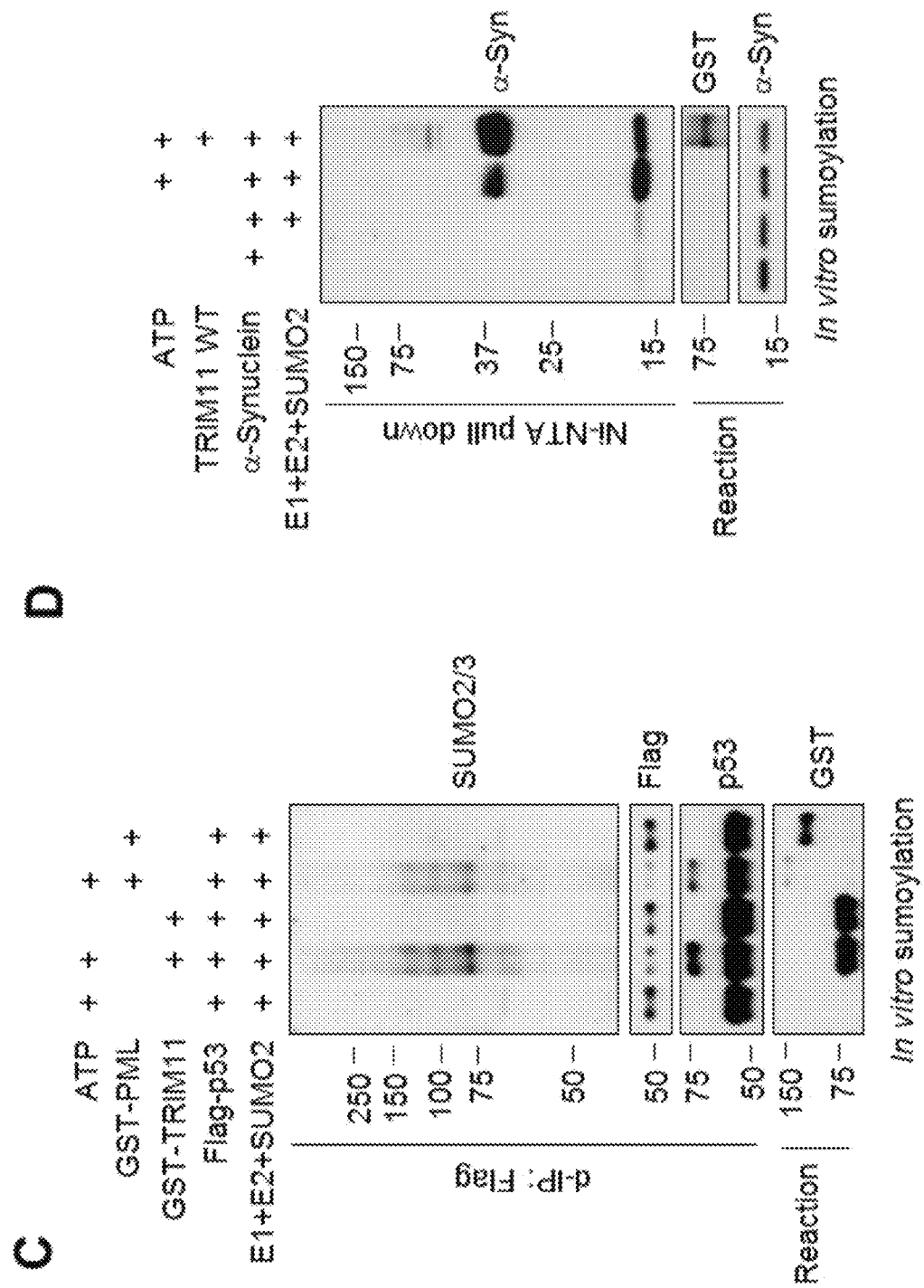

FIG. 27, comprising FIG. 27A through FIG. 27D, depicts results from experiments demonstrating SUMOylation of Atxn1 82Q, p53 and alpha-Synuclein. FIG. 27A depicts experiments where SUMOylation of Atxn1 82Q was analyzed when TRIM11 WT, TRIM11 MUT or PML was co-expressed. Before lysis, 10 μM MG132 was added for 4 hours. FIG. 27B depicts in vitro SUMOylation of purified Atxn1 82Q incubated with TRIM11 WT or TRIM11 MUT in the presence of E1, E2 and SUMO2.

FIG. 27C depicts in vitro SUMOylation of purified Flag-p53 incubated with TRIM11 or PML in the presence of E1, E2 and SUMO2. FIG. 27D depicts in vitro SUMOylation of alpha-Synuclein incubated with TRIM11 WT in the presence or absence of E1, E2 and SUMO2.

Figures 28A, 28B:
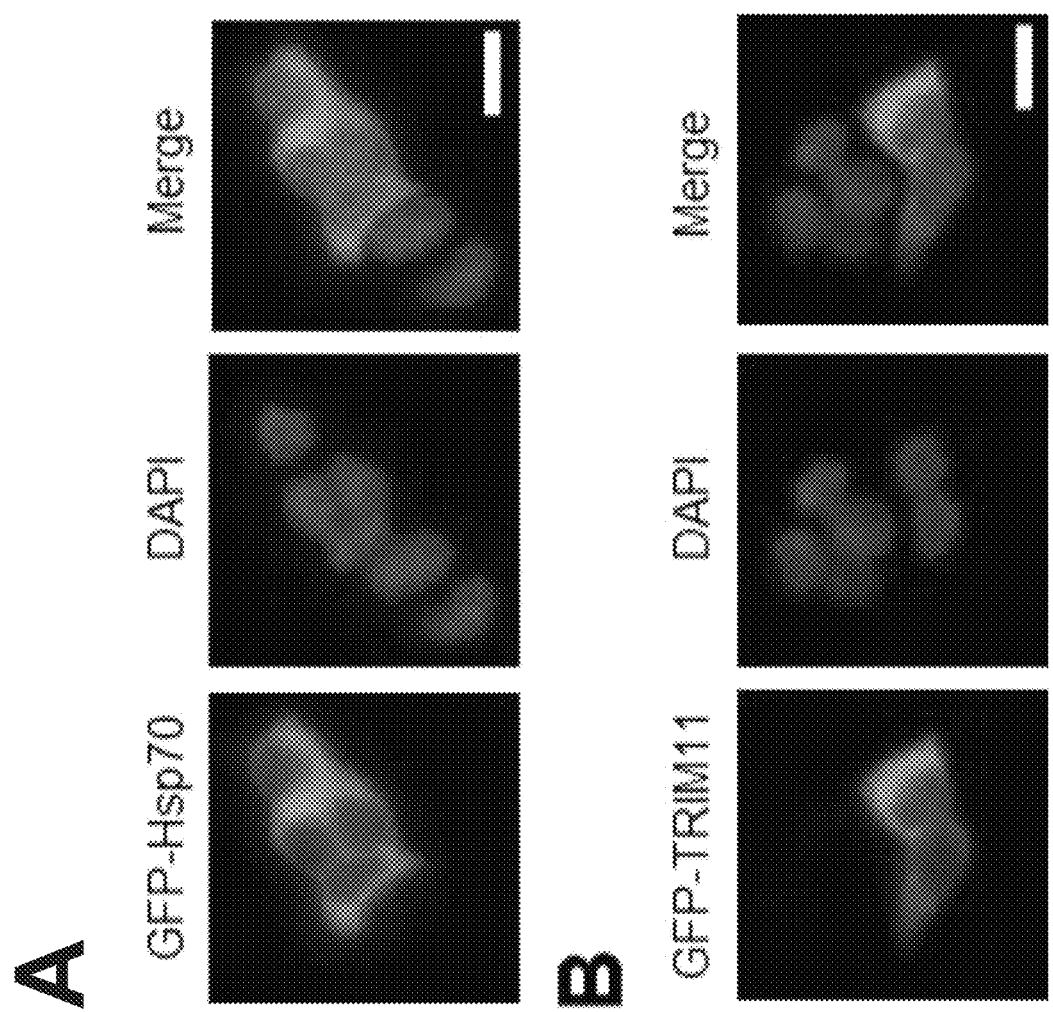
Figures 28C, 28D:
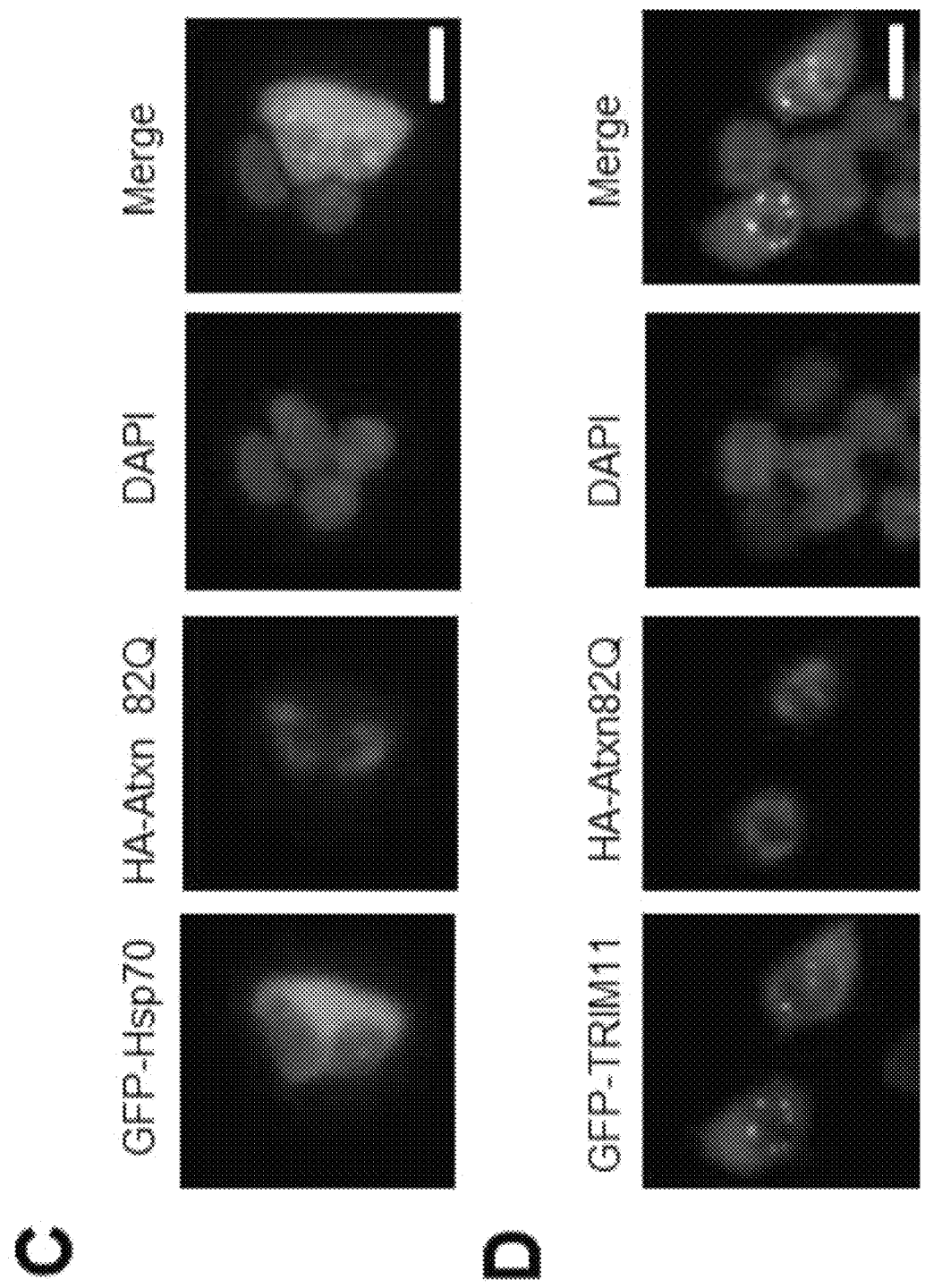
Figures 28E, 28F:
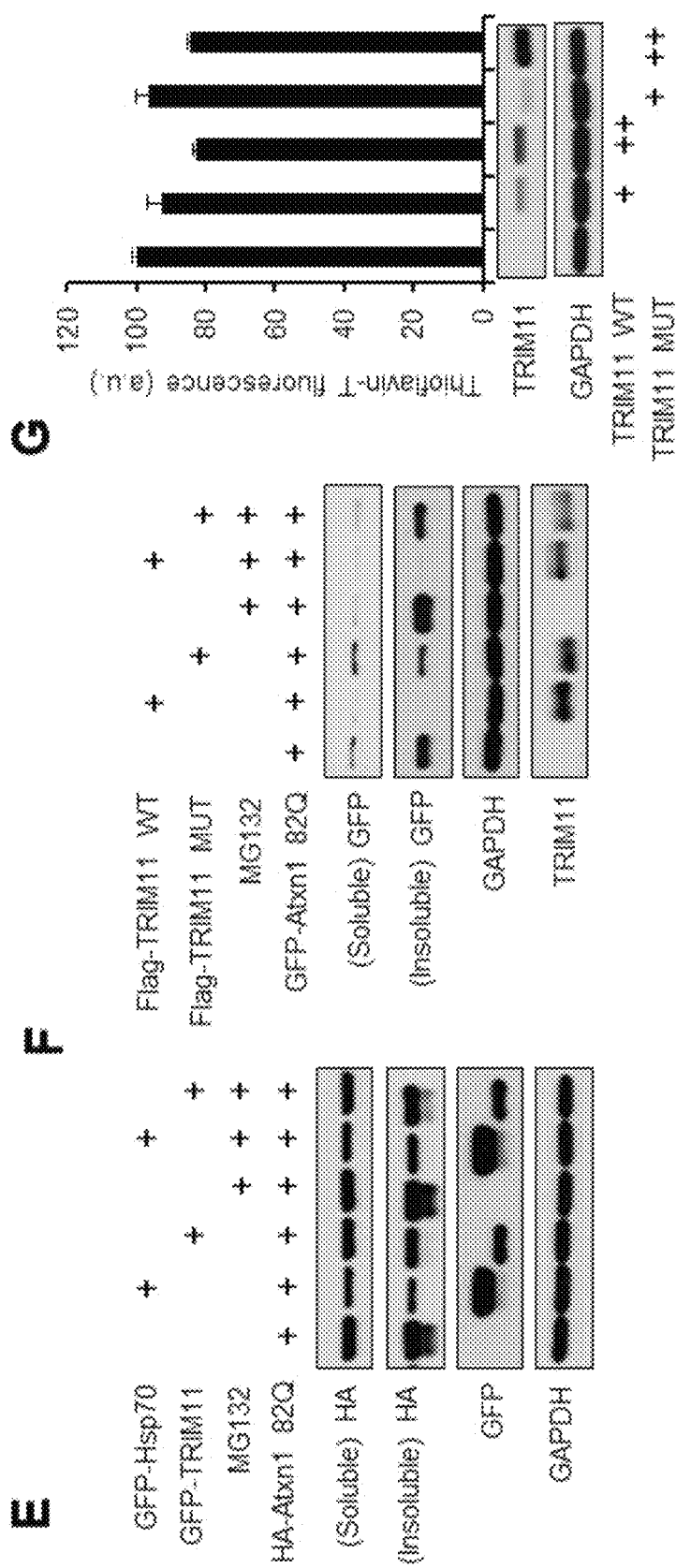

FIG. 28, comprising FIG. 28A through FIG. 28G, depicts results from experiments demonstrating TRIM11 is recruited to Atxn1 82Q aggregates. FIG. 28A depicts immunofluorescence analysis of transfected GFP-Hsp70 in 293T cells.

FIG. 28B depicts immunofluorescence analysis of transfected GFP-TRIM11 in 293T cells. FIG. 28C depicts immunofluorescence analysis showing that Hsp70 can be recruited into the aggregates of Atxn1 82Q. FIG. 28D depicts immunofluorescence analysis showing that TRIM11 can be recruited into the aggregates of Atxn1 82Q. FIG. 28E depicts immunoblotting analysis detergent-soluble and insoluble fractions of cells transfected with Atxn1 82Q, TRIM11 or Hsp70. Where indicated, 10 μM MG132 is added for 3 hours. FIG. 28F depicts immunoblotting analysis of detergent-soluble and insoluble fractions of cells transfected with Atxn1 82Q, TRIM11 WT (wild type) or TRIM11 MUT (mutation). Where indicated, 10 μM MG132 is added for 3 hours. FIG. 28G depicts immunoblotting where HCT116 cells are transfected with the indicated plasmids. After 48 hours, cells were lysed and then stained with 20 μM Thioflavin-T (ThT).

Figures 29A, 29B:
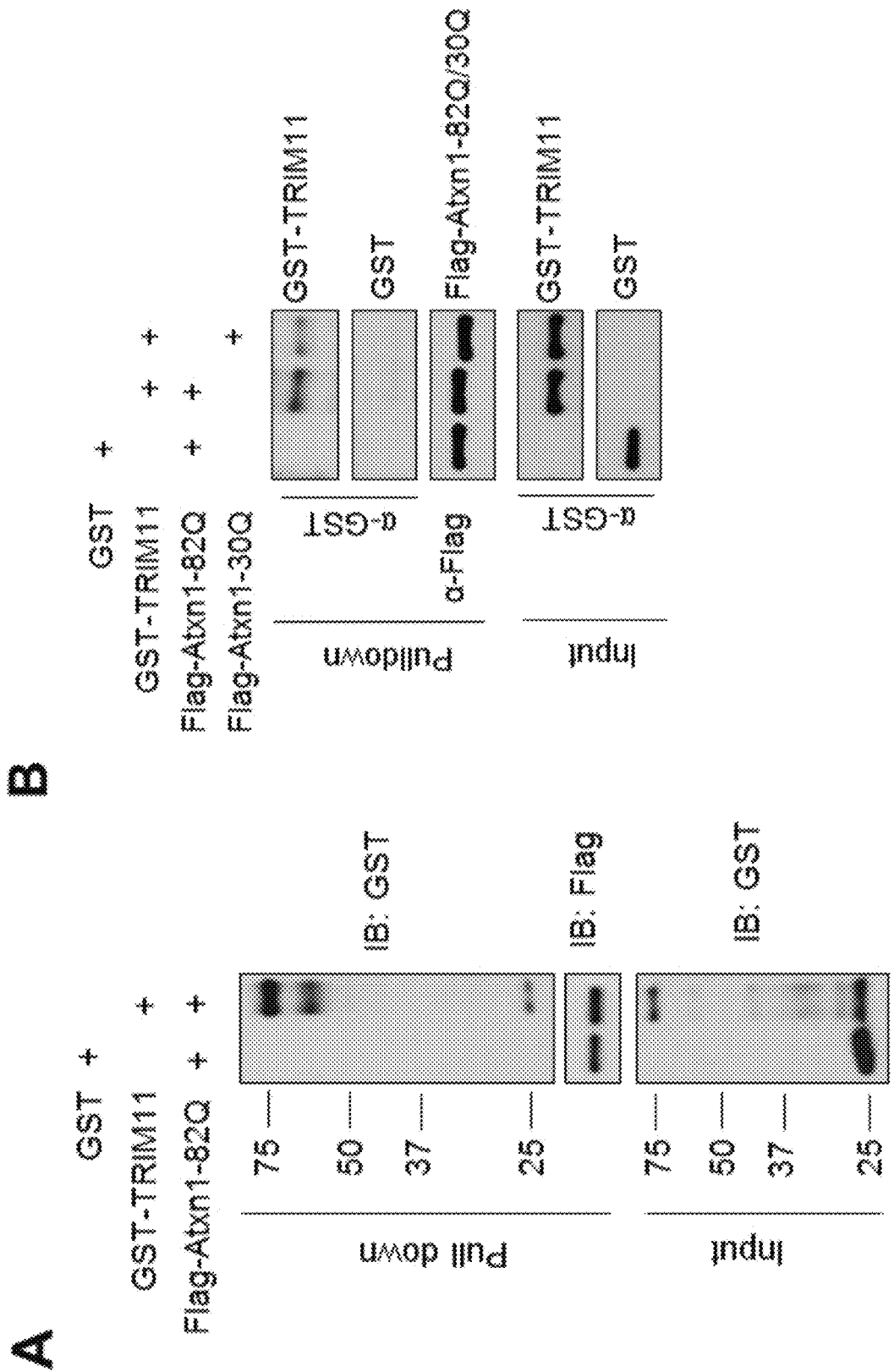
Figure 29C:
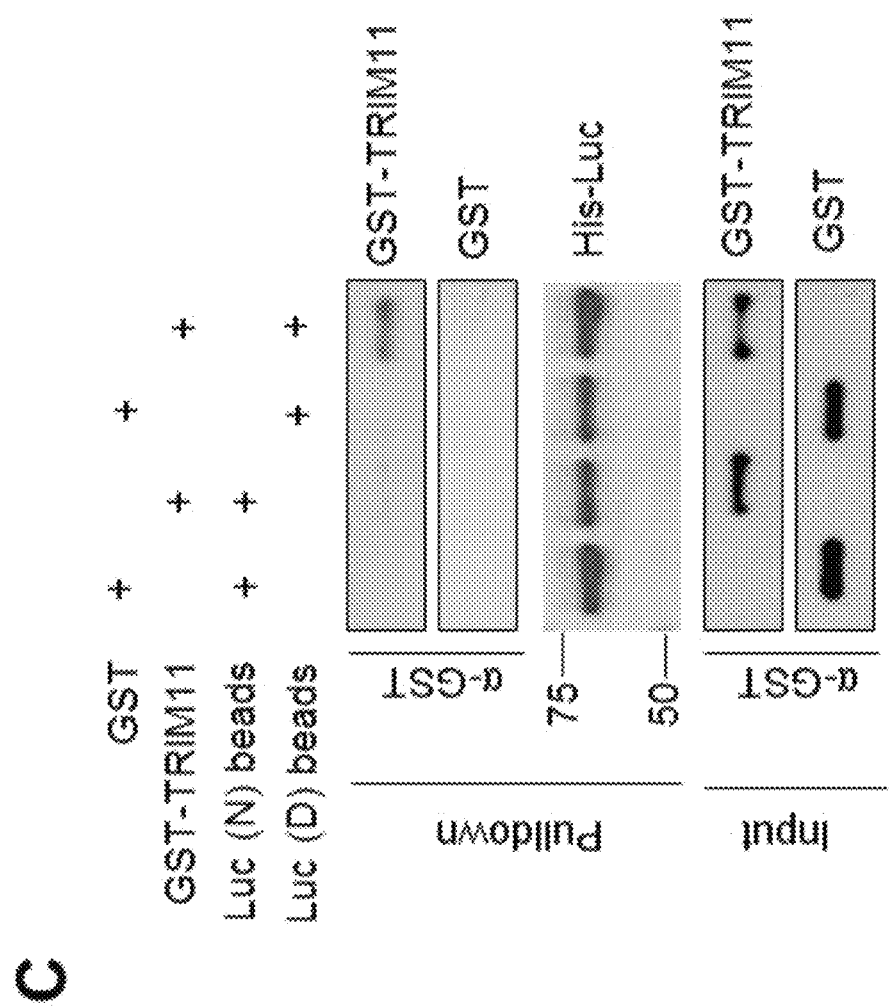

FIG. 29, comprising FIG. 29A through FIG. 29C, depicts results from experiments demonstrating TRIM11 binding to Atxn1 82Q. FIG. 29A depicts purified experiments where Flag-Atxn1 82Q immobilized on beads was incubated with GST or GST-TRIM11. FIG. 29B experiments where depicts purified Flag-Atxn1 82Q or Flag-Atxn1 30Q immobilized on beads was incubated with GST or GST-TRIM11.

FIG. 29C depicts binding of GST-TRIM11 and GST protein to native (N) and urea-denatured (D) luciferase (luc) immobilized on Ni-NTA beads.

Figures 30A, 30B, 30C, 30D:
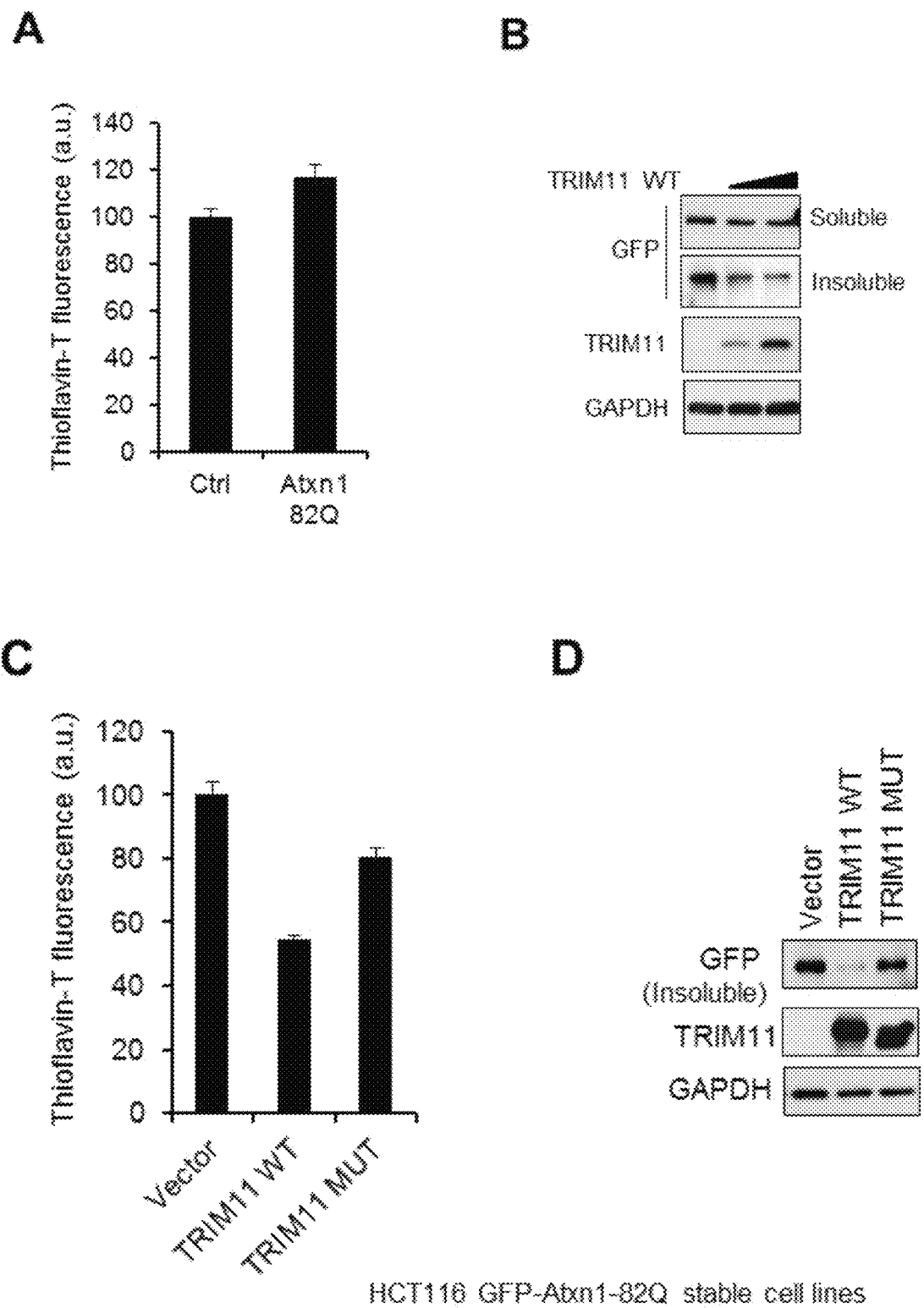

FIG. 30, comprising FIG. 30A through FIG. 30D, depicts results from experiments demonstrating TRIM11 reduces cellular aggregates. FIG. 30A depicts experiments where HCT116 cells stably expressing GFP-Atxn1 82Q were lysed and then stained with 20 μM Thioflavin-T (ThT). FIG. 30B depicts sedimentation analysis of GFP-Atxn1 82Q-HCT116 cells transfected with TRIM11. FIG. 30C depicts experiments where HCT116 cells stably expressing GFP-Atxn1 82Q were transfected with TRIM11 WT or TRIM11 MUT. After 48 hours, cells were lysed and stained with 20 μM ThT. FIG. 30D depicts sedimentation analysis of GFP-Atxn1 82Q-HCT116 cells transfected with TRIM11 WT or TRIM11 MUT.

Figures 31A, 31B, 31C, 31D:
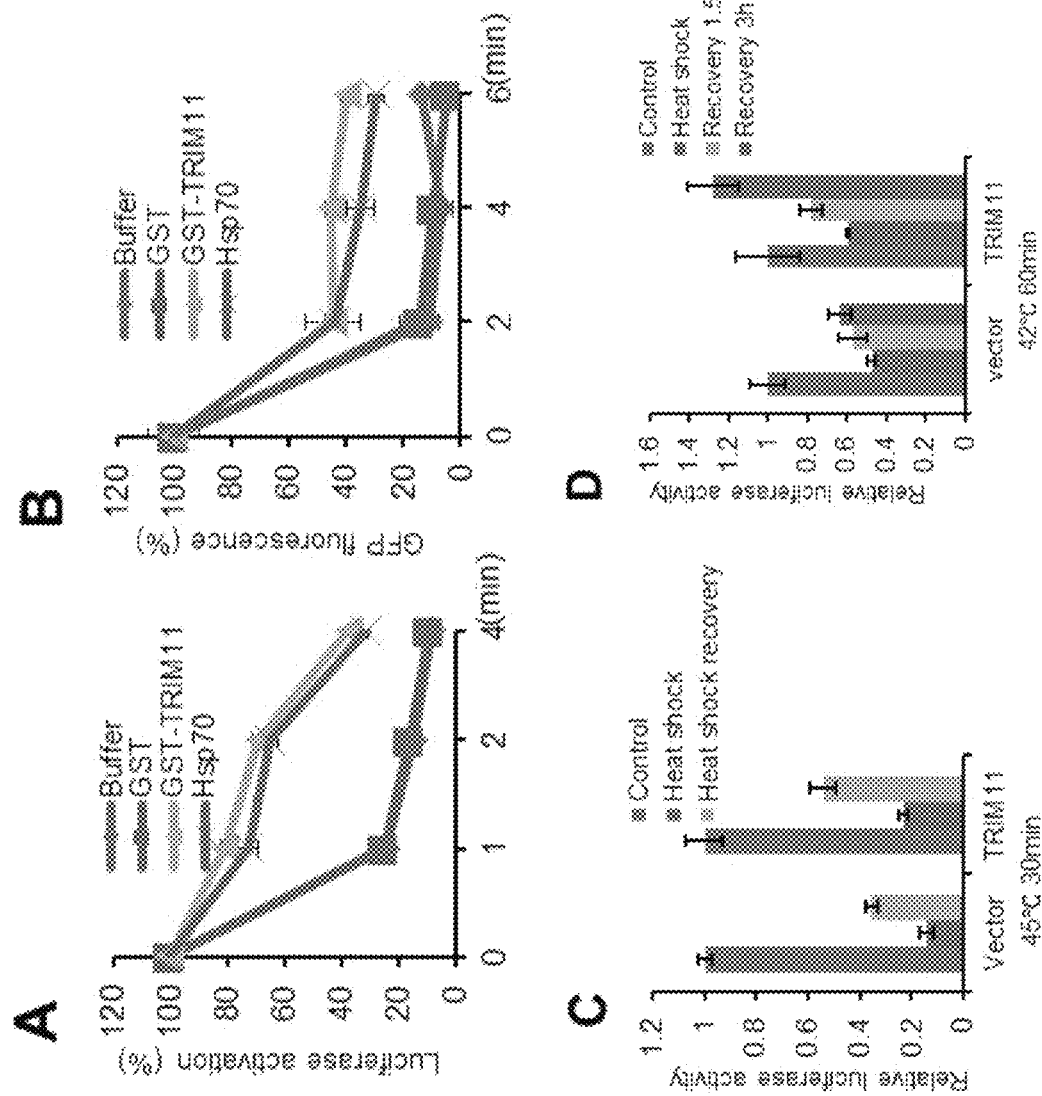
Figures 31E, 31F:
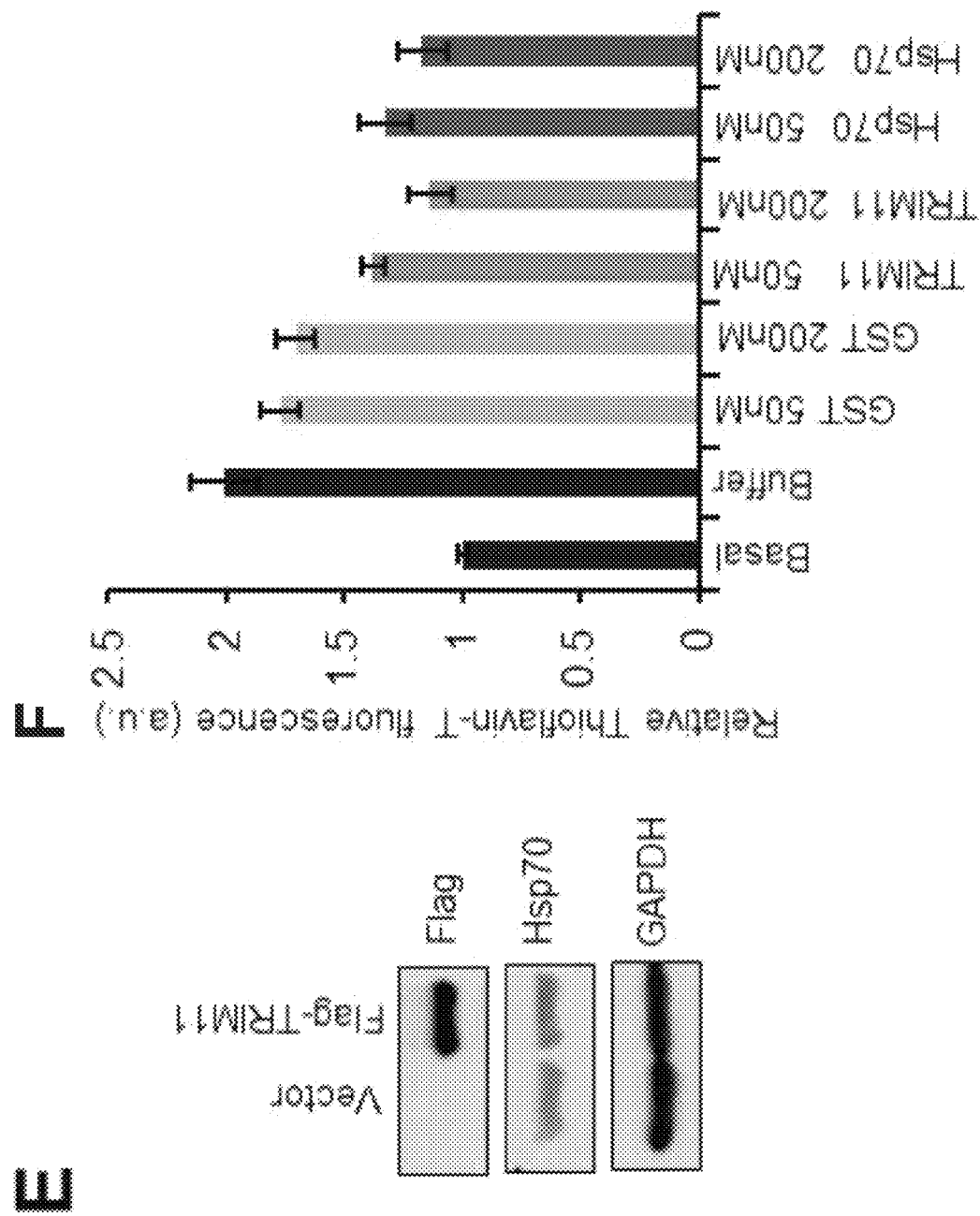
Figures 31G, 31H:
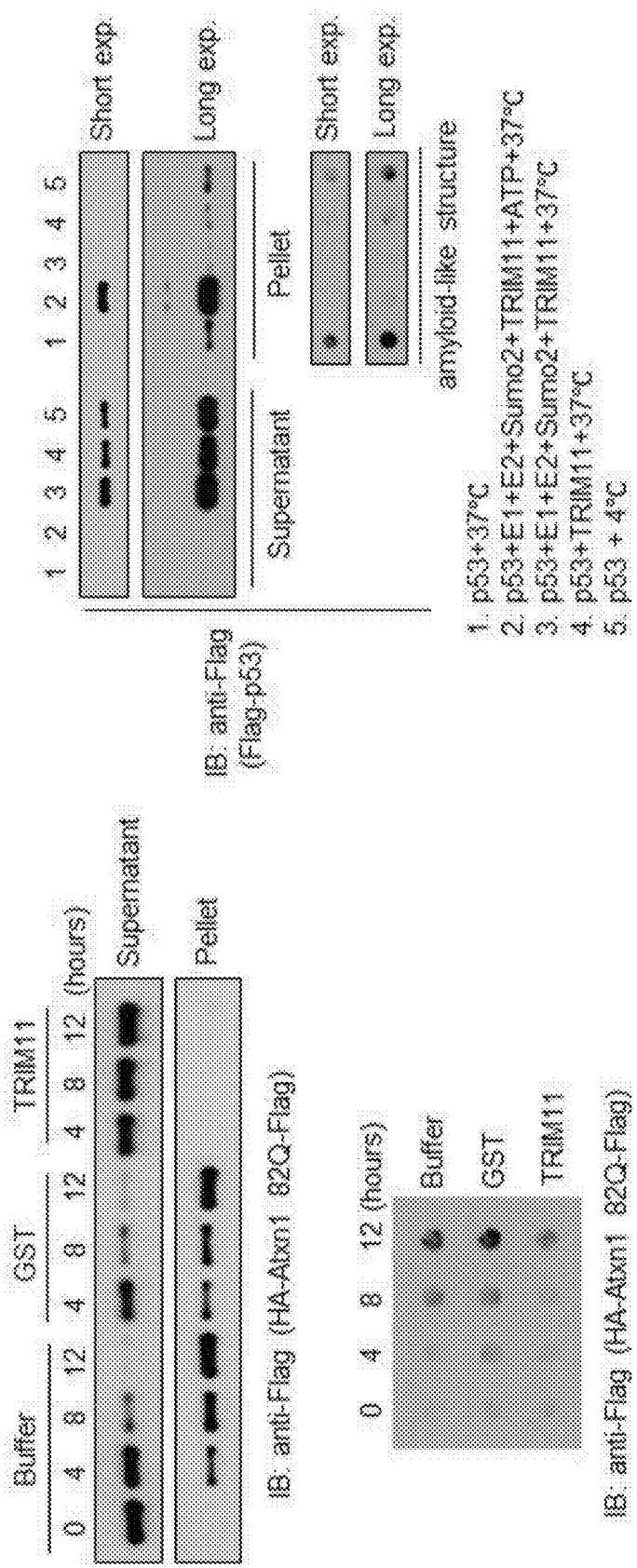

FIG. 31, comprising FIG. 31A through FIG. 31H, depicts results from experiments demonstrating TRIM11 acts as a molecular chaperone to prevent aggregate formation. FIG. 31A depicts experiments where luciferase (10 nM) was incubated with 200 nM GST, 200 nM GST-TRIM11 or 200 nM Hsp70 at 45° C. with the indicated time. Native luciferase activity was set as 100%. N=3. FIG. 31B depicts experiments where GFP (0.45 uM) was incubated with 200 nM GST, 200 nM GST-TRIM11 or 200 nM Hsp70 at 45° C. with the indicated time. Native GFP fluorescence was set as 100%. N=3. FIG. 31C depicts the activity of transfected luciferase in HCT116 measured without heat shock as control. After 30 min heat shock at 45° C. or after 3 hour recovery at incubator, the luciferase activities were relative to the control. FIG. 31D depicts the activity of transfected luciferase in HCT116 measured without heat shock as control. After 60 min heat shock at 45° C. or after 1.5 hour or 3 hour recovery at incubator, the luciferase activities were relative to the control. FIG. 31E depicts immunoblotting analysis of HCT116 cells stably expressing control vector or Flag-TRIM11. FIG. 31F depicts ThT analysis showing the prevention of beta-amyloid fibrils formation by GST, TRIM11 or Hsp70. FIG. 31G depicts a sedimentation assay showing the prevention of Atxn1 82Q aggregates formation by Lysozyme, GST or TRIM11. The results were shown by immunoblotting and dot-blot assay. FIG. 31H depicts a sedimentation assay showing the prevention of p53 aggregates formation by L TRIM11. Where indicated, E1, E2, SUMO2 or ATP was applied. The results were shown by immunoblotting and dot-blot assay.

Figures 32A, 32B, 32C, 32D:
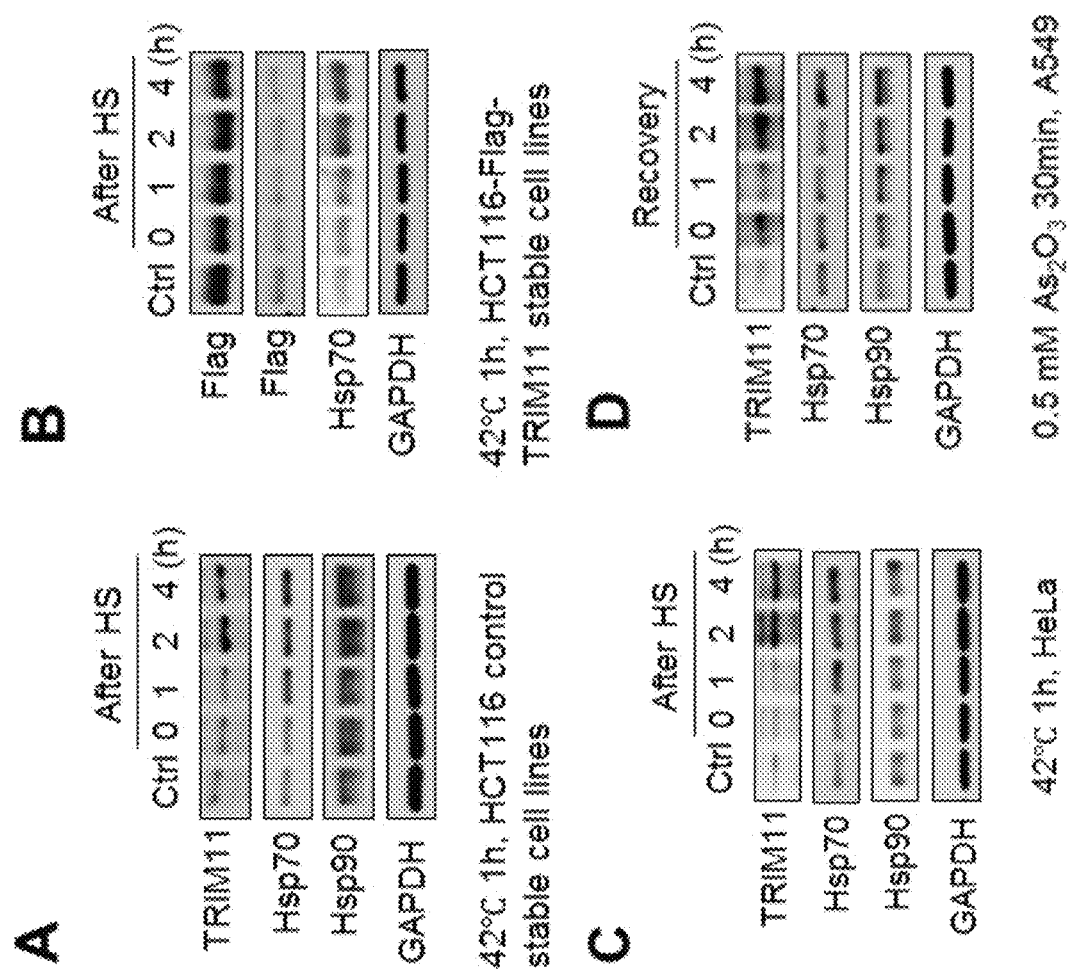
Figures 32E, 32F, 32G:
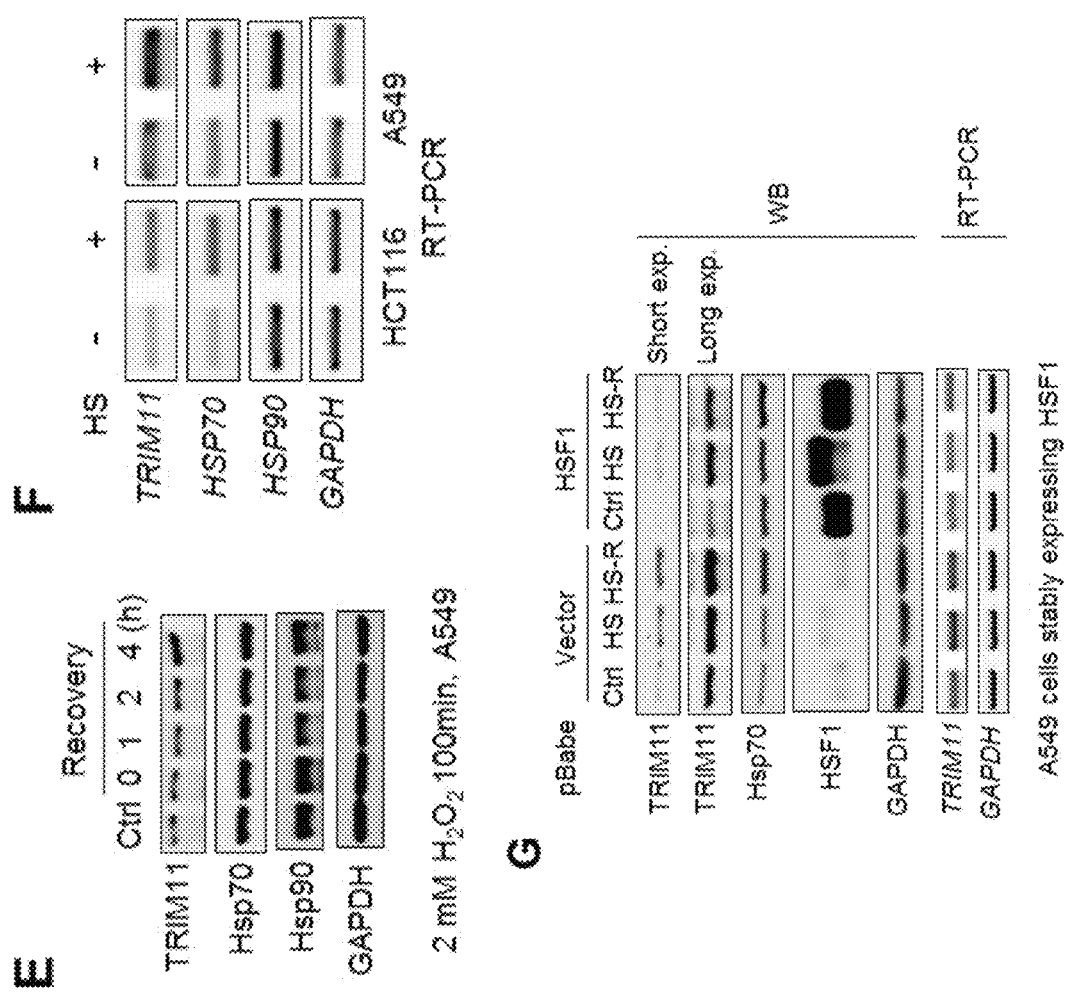

FIG. 32, comprising FIG. 32A through FIG. 32G, depicts results from experiments demonstrating HSF1 is not required for regulating the transcription of TRIM11. FIG. 32A depicts experiments where HCT116 cells were treated with or without heat shock (42° C.) for 1 hour and then recovered for different time. Total cell lysates were subjected to immunoblotting with the indicated antibodies. FIG. 32B depicts experiments where HCT116 cells stably expressing Flag-TRIM11 were treated with or without heat shock (42° C.) for 1 hour and then recovered for different time. Total cell lysates were subjected to immunoblotting with the indicated antibodies. FIG. 32C depicts experiments where HeLa cells were treated with or without heat shock (42° C.) for 1 hour and then recovered for different time. Total cell lysates were subjected to immunoblotting with the indicated antibodies. FIG. 32D depicts experiments where A549 cells were treated with or without $As_2O_3$ for 30 min and then recovered for different time. Total cell lysates were subjected to immunoblotting with the indicated antibodies. FIG. 32E depicts experiments where A549 cells were treated with or without $H_2O_2$ for 100 min and then recovered for different time. Total cell lysates were subjected to immunoblotting with the indicated antibodies. FIG. 32F depicts semi-quantitative PCR analysis of TRIM11, HSP70, HSP90 and GAPDH in response to heat shock. FIG. 32G depicts experiments where A549 cells stably expressing vector or HSF1 were treated with or without heat shock and recovered for 3 hours. Immunoblotting and semi-quantitative PCR were analyzed.

Figures 33A, 33B:
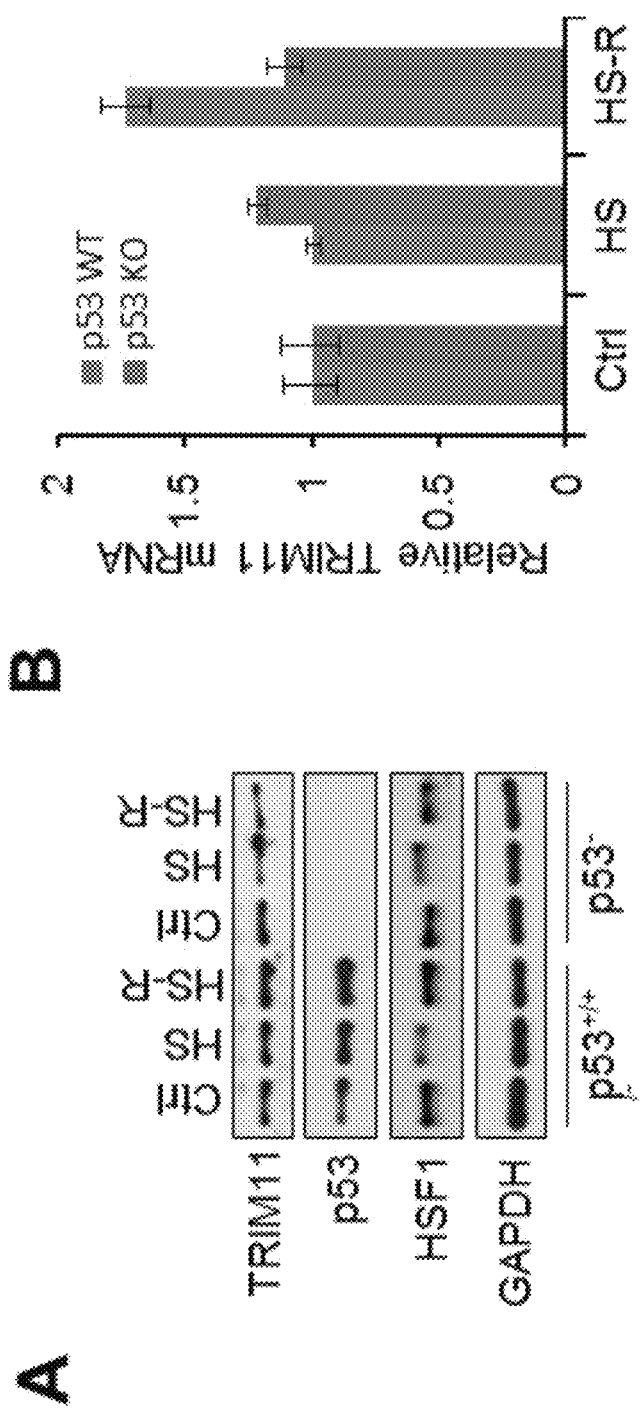
Figures 33C, 33D:
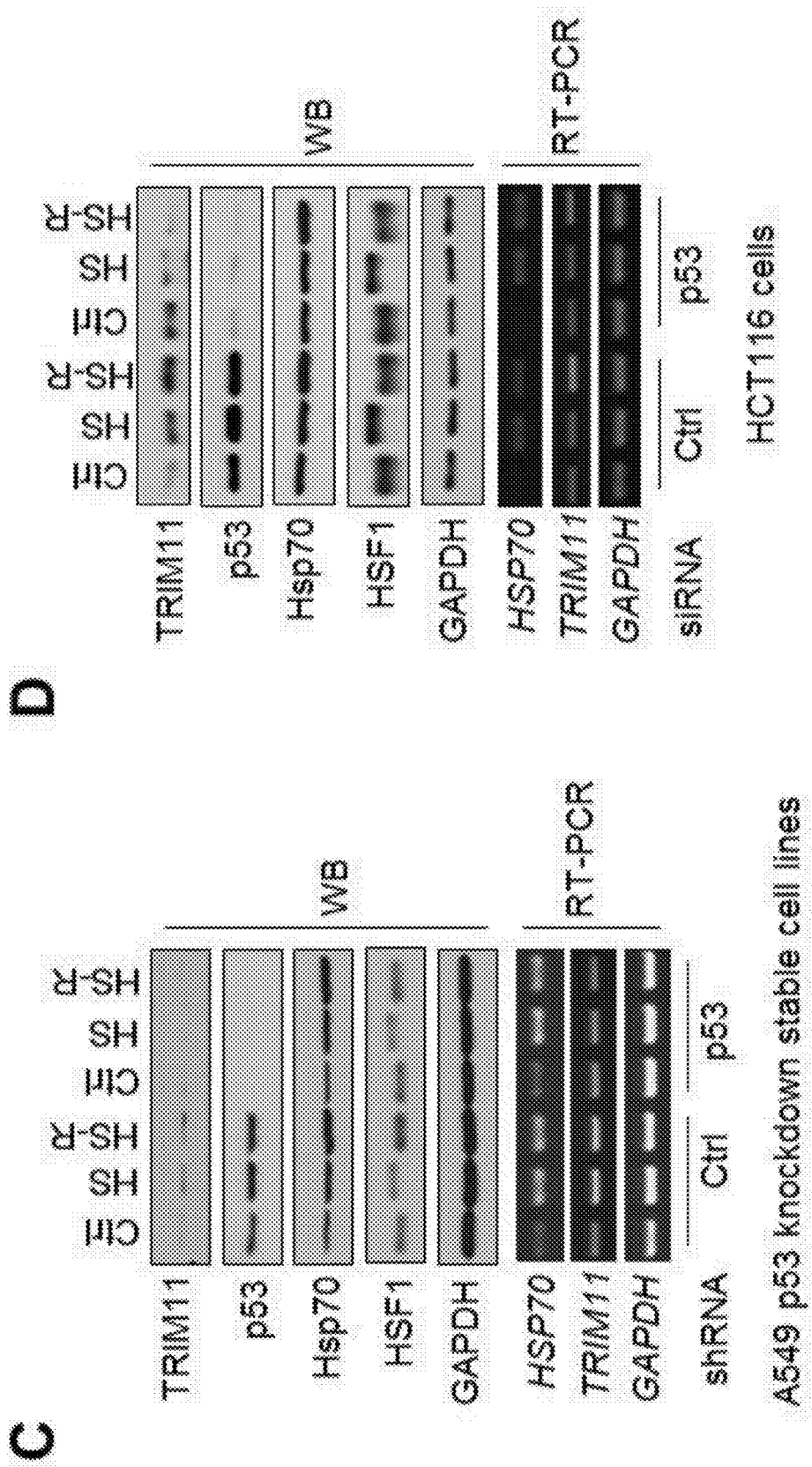
Figures 33E, 33F:
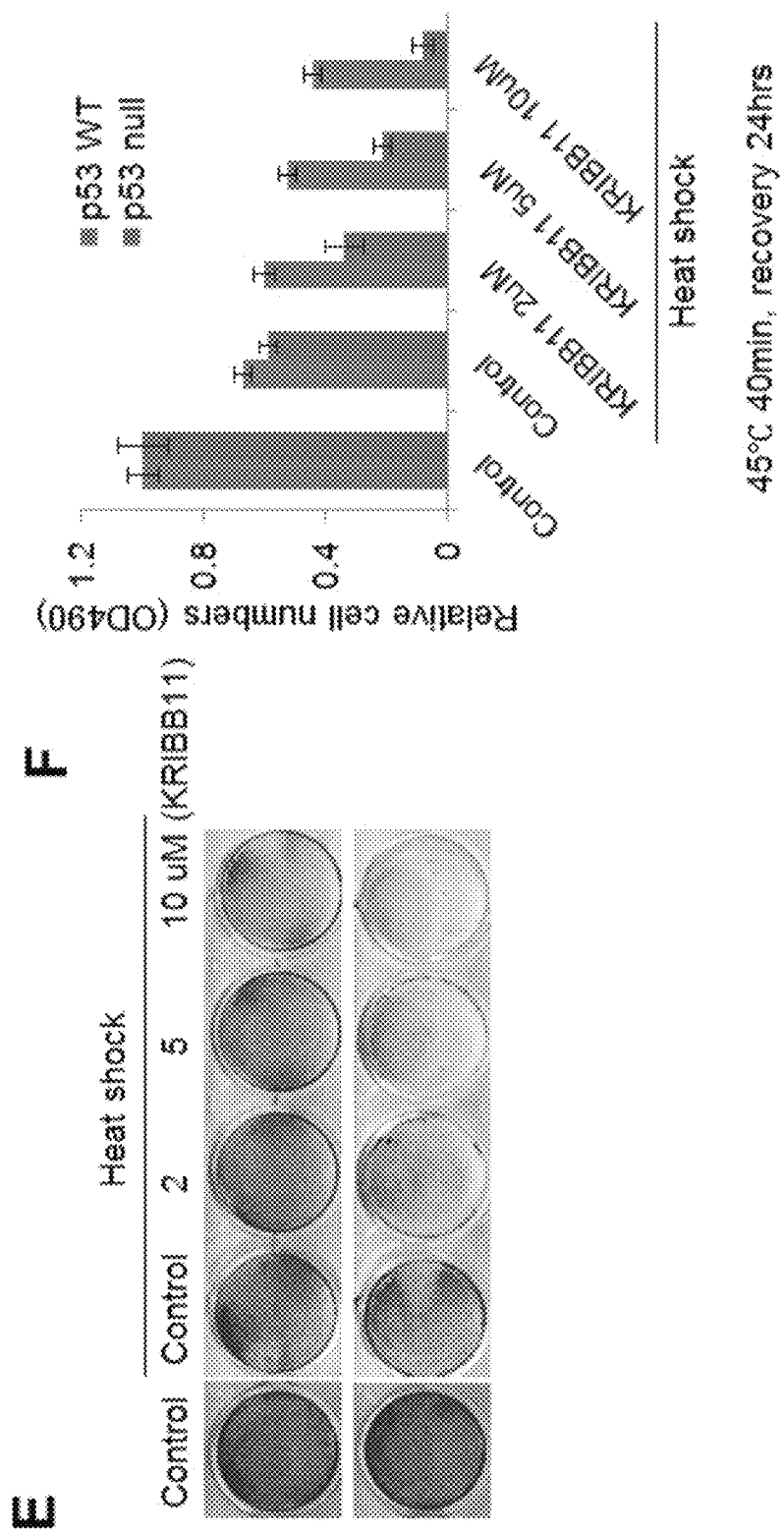

FIG. 33, comprising FIG. 33A through FIG. 33F, depicts results from experiments demonstrating that p53 is a factor in upregulating TRIM11 in heat shock response. FIG. 33A depicts immunoblotting of HCT116 p53 wild type or p53 null cells treated with heat shock and recovered. FIG. 33B depicts qPCR analysis of TRIM11 mRNA level in HCT116 p53 wild type or p53 null cells treated with heat shock and recovered. FIG. 33C depicts immunoblotting and semi-quantitative PCR analysis of A549 cells stably expressing control (Ctrl) or p53 shRNA treated with or without heat shock and recovered for 3 hours. FIG. 33D depicts immunoblotting and semi-quantitative PCR analysis of HCT116 cells transfected with Ctrl or p53 siRNA treated with or without heat shock and recovered for 3 hours. FIG. 33E depicts crystal violet analysis of survival of HCT116 cells which were heated and recovered for 24 hours. Where indicated, KRIBB11 was added. FIG. 33F depicts relative cell numbers of results presented in FIG. 33E analyzed by OD490.

Figures 34A, 34B, 34C, 34D:
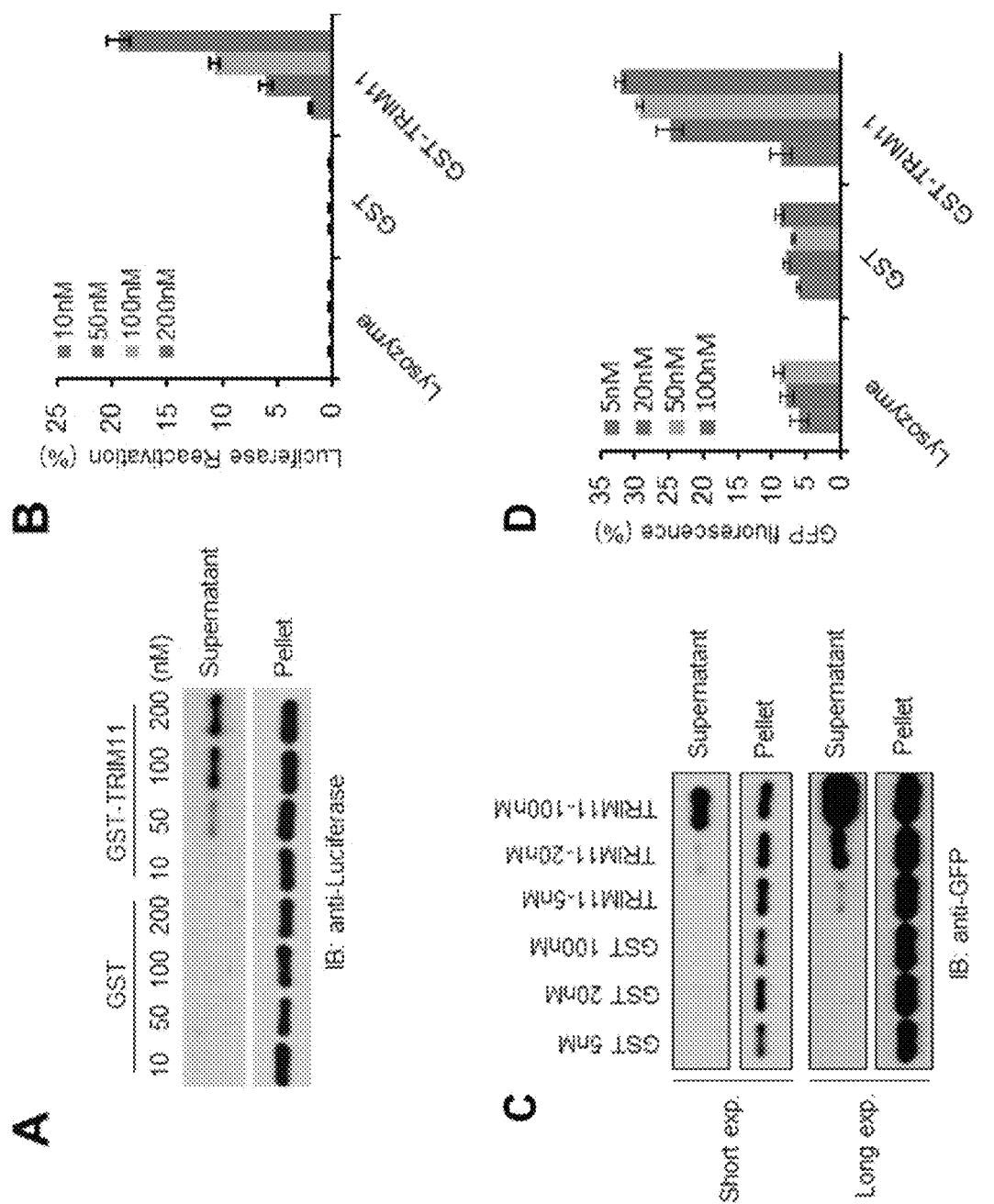
Figures 34E, 34F, 34G:
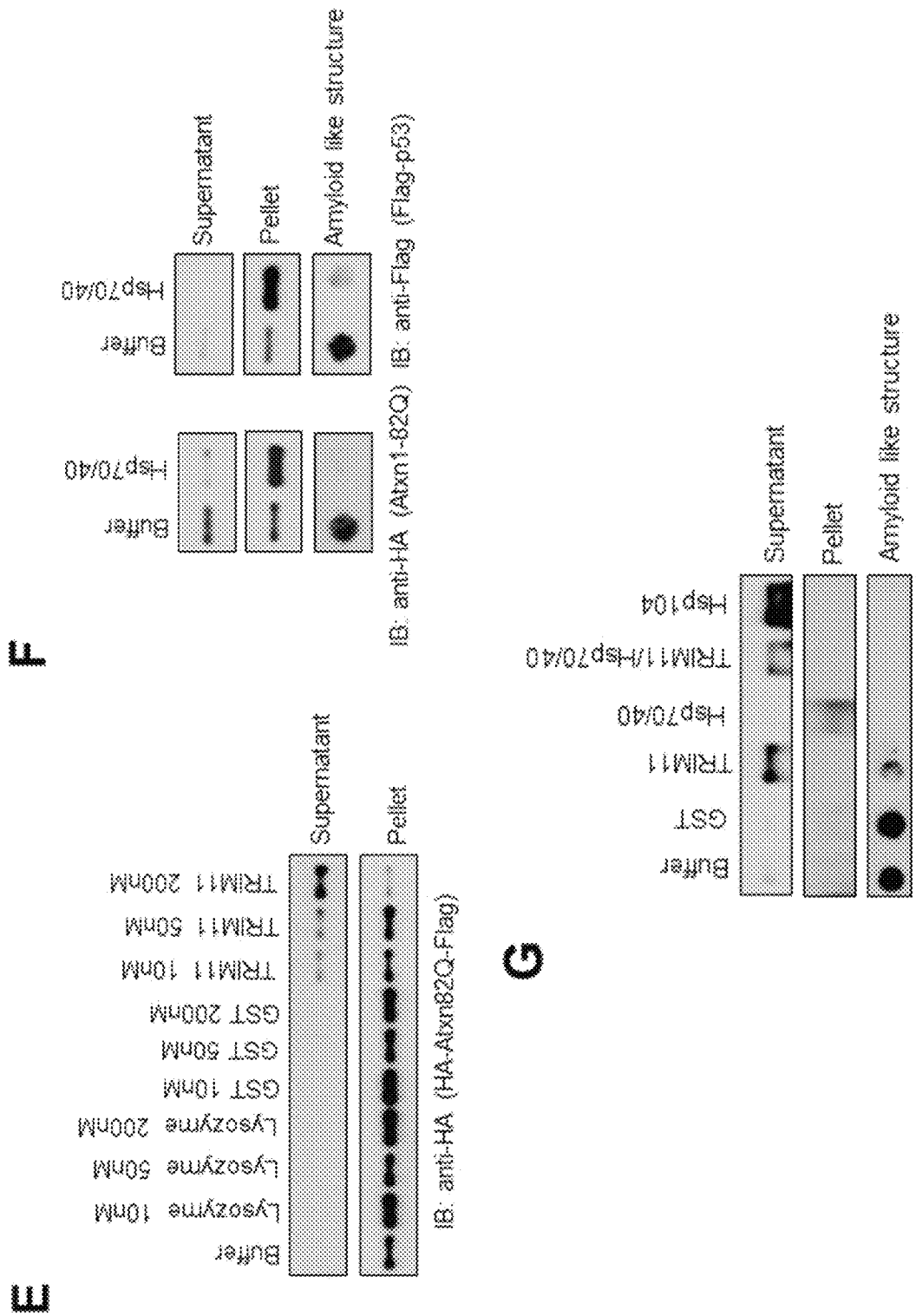

FIG. 34, comprising FIG. 34A through FIG. 34G, depicts results from experiments demonstrating TRIM11 acts as a disaggregase to resolve preformed aggregates. FIG. 34A depicts disaggregation and reactivation of preformed luciferase aggregates using increasing concentrations of Lysozyme, GST or GST-TRIM11 (n=3).

FIG. 34B depicts a sedimentation assay showing that heat-aggregated luciferase resolved by GST or GST-TRIM11. The results were shown by immunoblotting. FIG. 34C depicts disaggregation and reactivation of preformed GFP aggregates using increasing concentrations of Lysozyme, GST or GST-TRIM11 (n=3). FIG. 34D depicts a sedimentation assay showing that heat-aggregated GFP resolved by GST or GST-TRIM11. The results were shown by immunoblotting. FIG. 34E depicts a sedimentation assay showing preformed Atxn1 82Q aggregates resolved by Lysozyme, GST or TRIM11. The results were shown by immunoblotting. FIG. 34F depicts a sedimentation assay showing that preformed Atxn1 82Q aggregates (left) and p53 aggregates (right) disaggregated by 1 µM Hsp70 and 0.5 µM Hsp40. FIG. 34G depicts a sedimentation assay showing that preformed Atxn1 82Q aggregates disaggregated by 0.5 µM GST, 0.5 µM TRIM11, 1 µM Hsp70, 0.5 µM Hsp40 or 1 µM Hsp104.

Figures 35A, 35B:
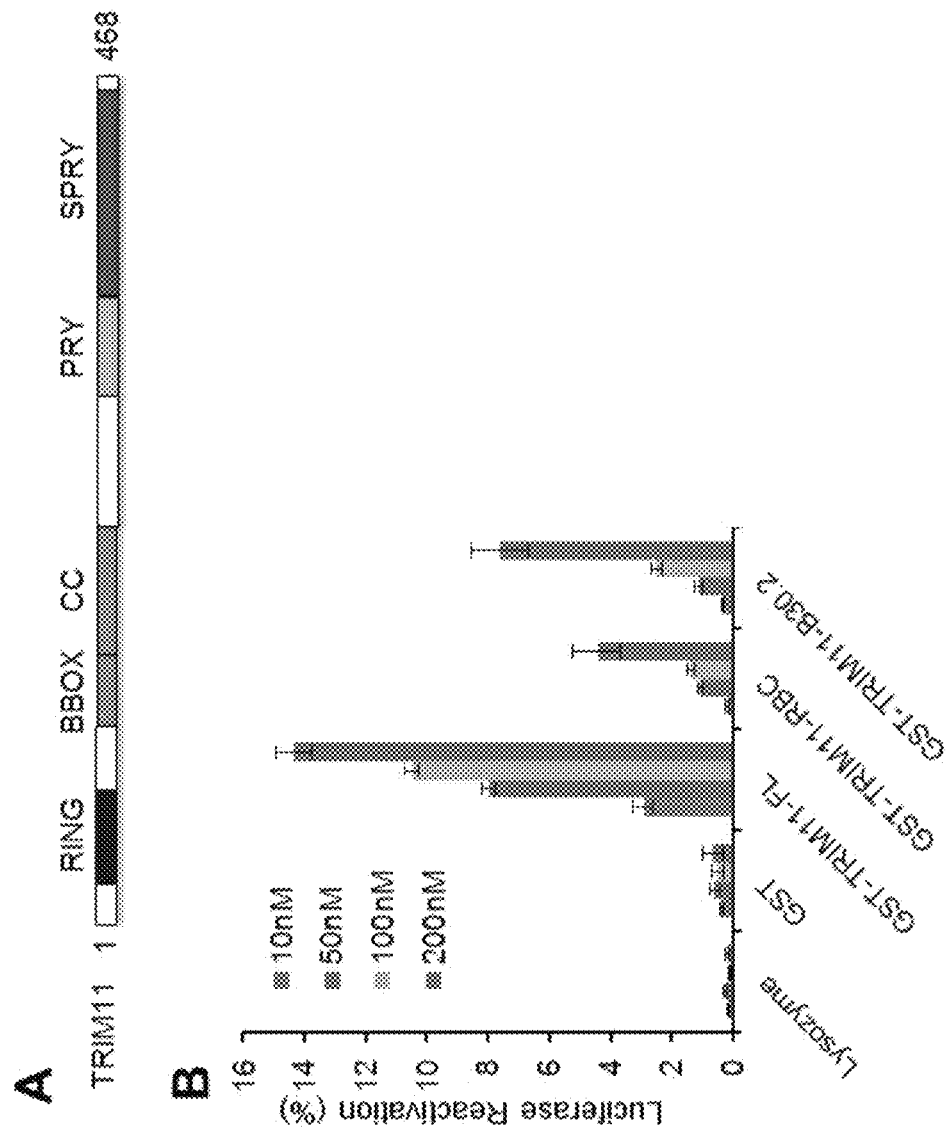
Figures 35C, 35D:
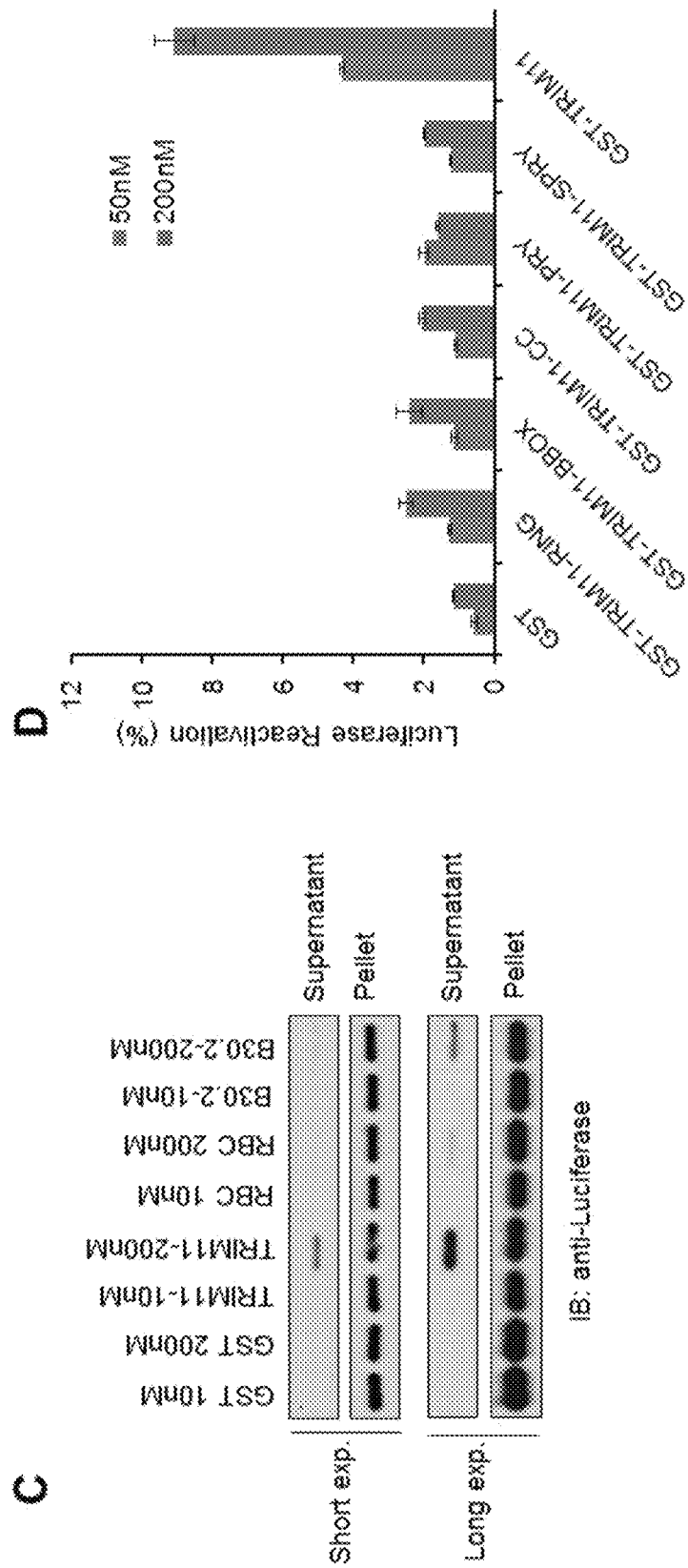

FIG. 35, comprising FIG. 35A through FIG. 35D, depicts results from experiments demonstrating full length TRIM11 is required for refolding activity. FIG. 35A depicts a schematic diagram of TRIM11 structure. FIG. 35B depicts disaggregation and reactivation of preformed luciferase aggregates using increasing concentrations of the indicated proteins (n=3). FIG. 35C depicts a sedimentation assay showing heated luciferase aggregates disaggregated by GST, TRIM11, RBC or B30.2. FIG. 35D depicts disaggregation and reactivation of preformed luciferase aggregates using the indicated proteins (n=3).

Figures 36A, 36B:
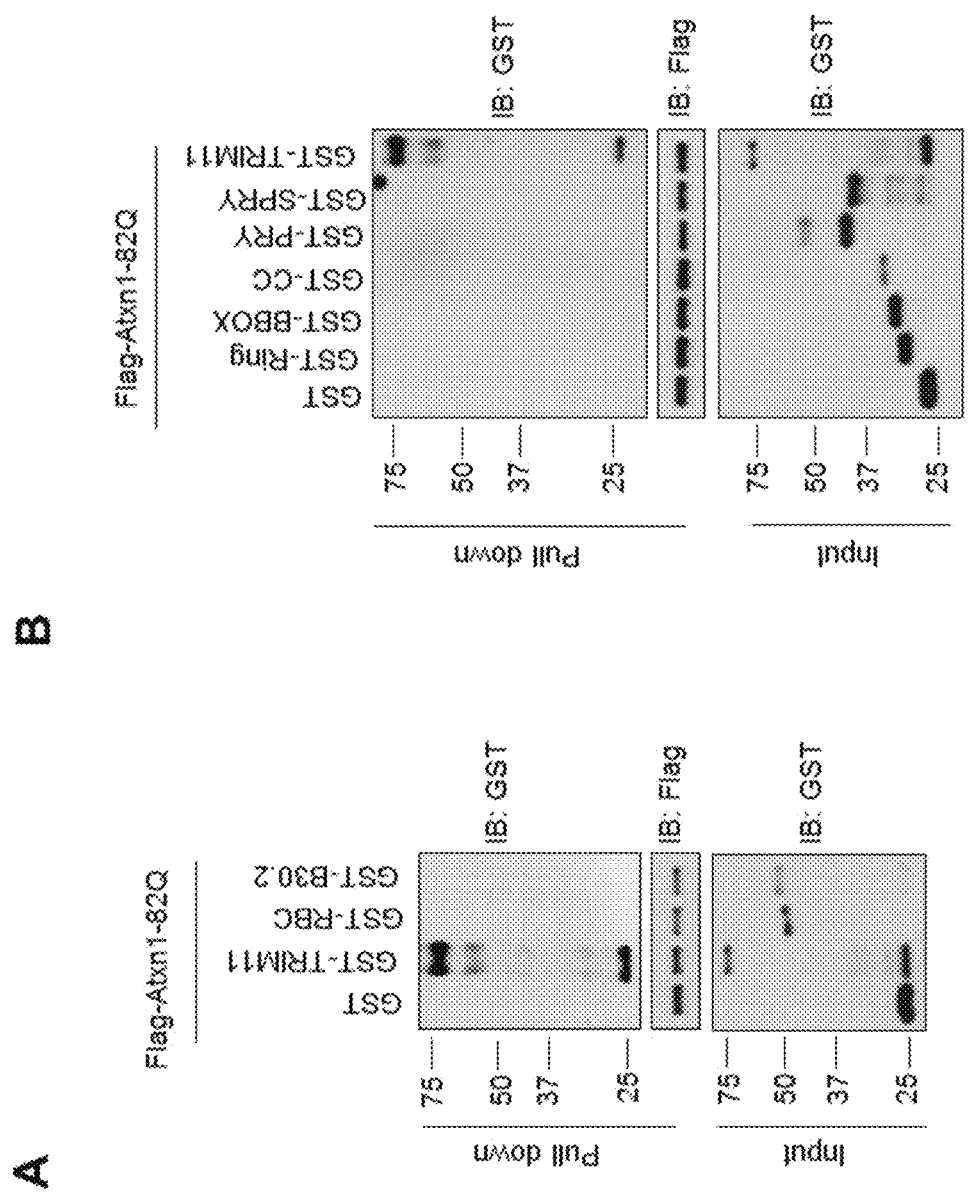

FIG. 36, comprising FIG. 36A and FIG. 36B depicts results from experiments demonstrating TRIM11 binding to substrates is required for TRIM11 disaggregation function. FIG. 36A depicts purified Flag-Atxn1 82Q immobilized on beads was incubated with GST, GST-TRIM11, GST-RBC or GST-B30.2. FIG. 36B depicts purified Flag-Atxn1 82Q immobilized on beads was incubated with GST, GST-TRIM11 or other TRIM11 fragments.

Figures 37A, 37B:
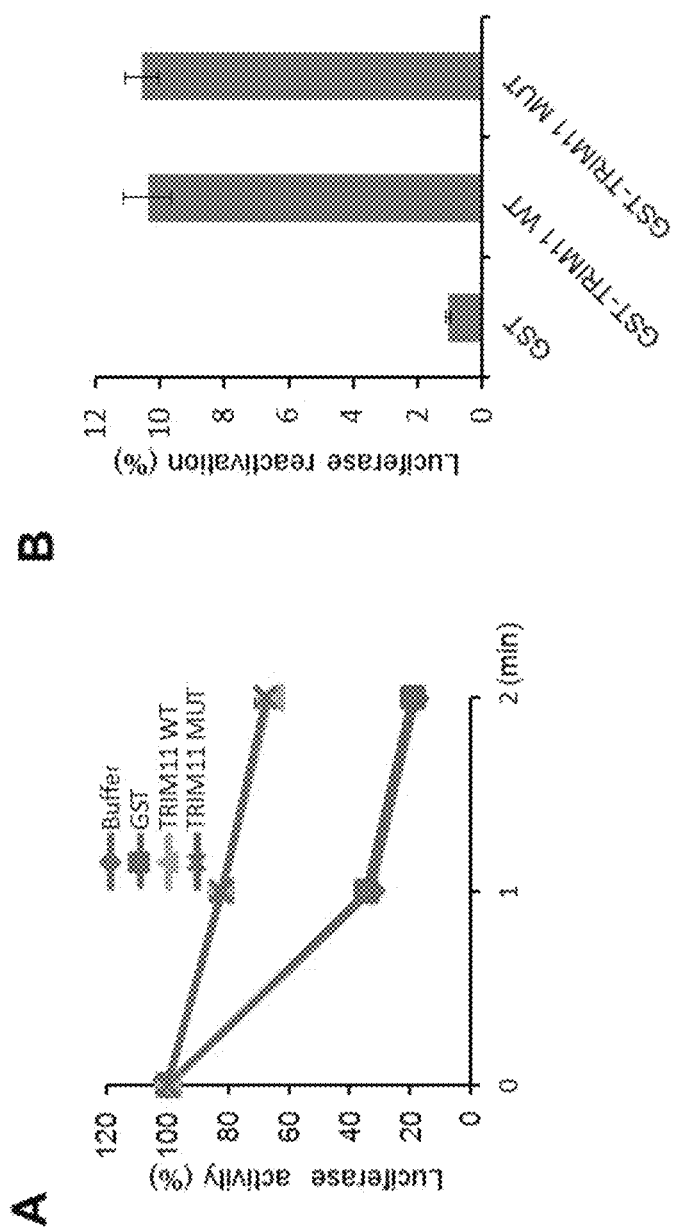
Figures 37C, 37D, 37E:
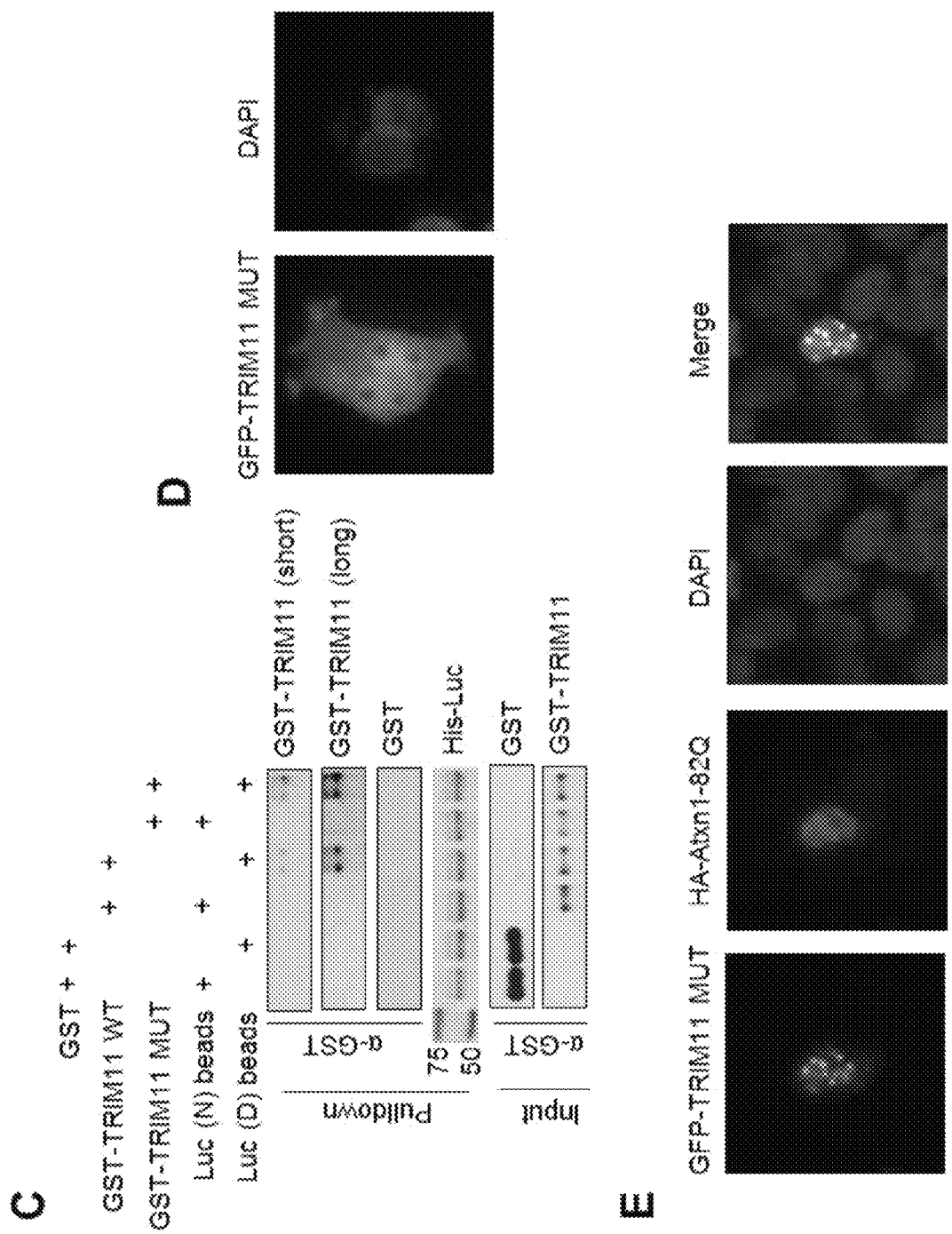

FIG. 37, comprising FIG. 37A through FIG. 37E depicts results from experiments demonstrating TRIM11 performs disaggregation independently of its SUMO E3 ligase activity. FIG. 37A depicts experiments where luciferase (10 nM) was incubated with 200 nM GST, 200 nM GST-TRIM11 WT or MUT at 45° C. with the indicated time. Native luciferase activity was set as 100%. N=3. FIG. 37B depicts disaggregation and reactivation of preformed luciferase aggregates by 200 nM GST, 200 nM GST-TRIM11 WT or MUT. FIG. 37C depicts the binding of GST, GST-TRIM11 WT or MUT to native (N) and urea-denatured (D) luciferase (luc) immobilized on Ni-NTA beads. FIG. 37D depicts immunofluorescence analysis of transfected GFP-TRIM11 MUT in 293T cells. FIG. 37E depicts immunofluorescence analysis show that TRIM11 MUT can be recruited into the aggregates of Atxn1 82Q.

Figures 38A, 38B:
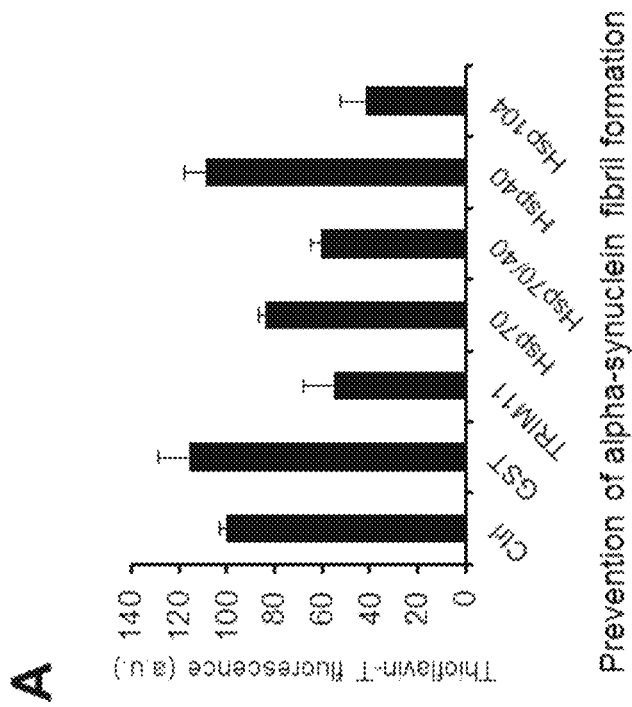
Figures 38C, 38D, 38E:
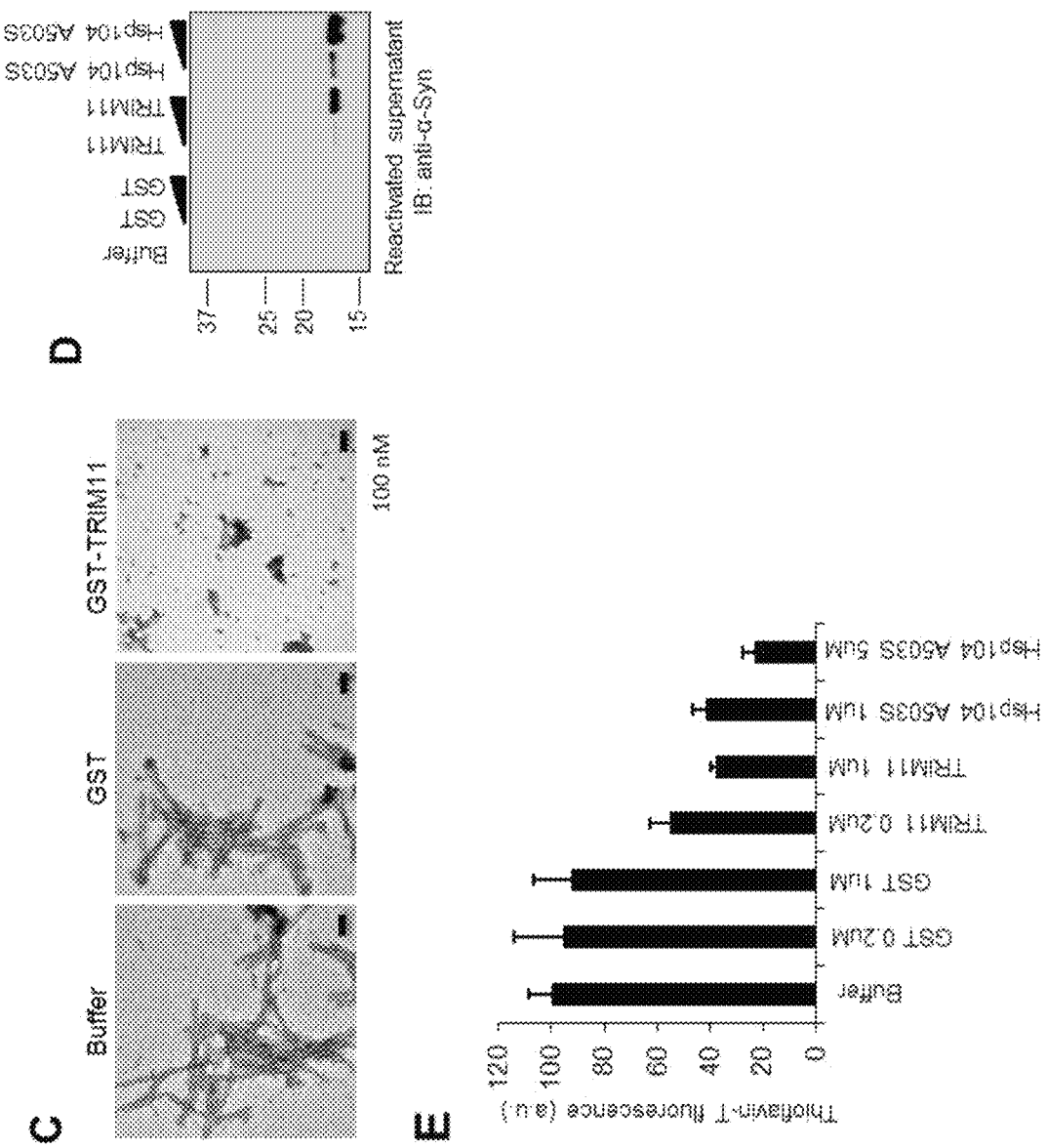

FIG. 38, comprising FIG. 38A through FIG. 38E, depicts results from experiments demonstrating TRIM11 can also preform alpha-Synuclein amyloid fibril formation and disaggregate preformed alpha-Synuclein fibers. FIG. 38A depicts ThT analysis showing prevention of alpha-Syn fibrils formation by GST, TRIM11, Hsp70, Hsp40 or Hsp104. FIG. 38B depicts ThT analysis showing prevention of alpha-Syn fibrils formation by TRIM11 in a dose-dependent manner. FIG. 38C depicts EM images of the fiber formation of alpha-Syn monomer incubated with GST or GST-TRIM11. FIG. 38D depicts a sedimentation assay showing that preformed alpha-Syn fiber disaggregated by TRIM11 and Hsp104 A503S. FIG. 38E depicts ThT analysis showing disaggregation of preformed alpha-Syn fibrils by GST, TRIM11 or Hsp104.

Figures 39A, 39B:
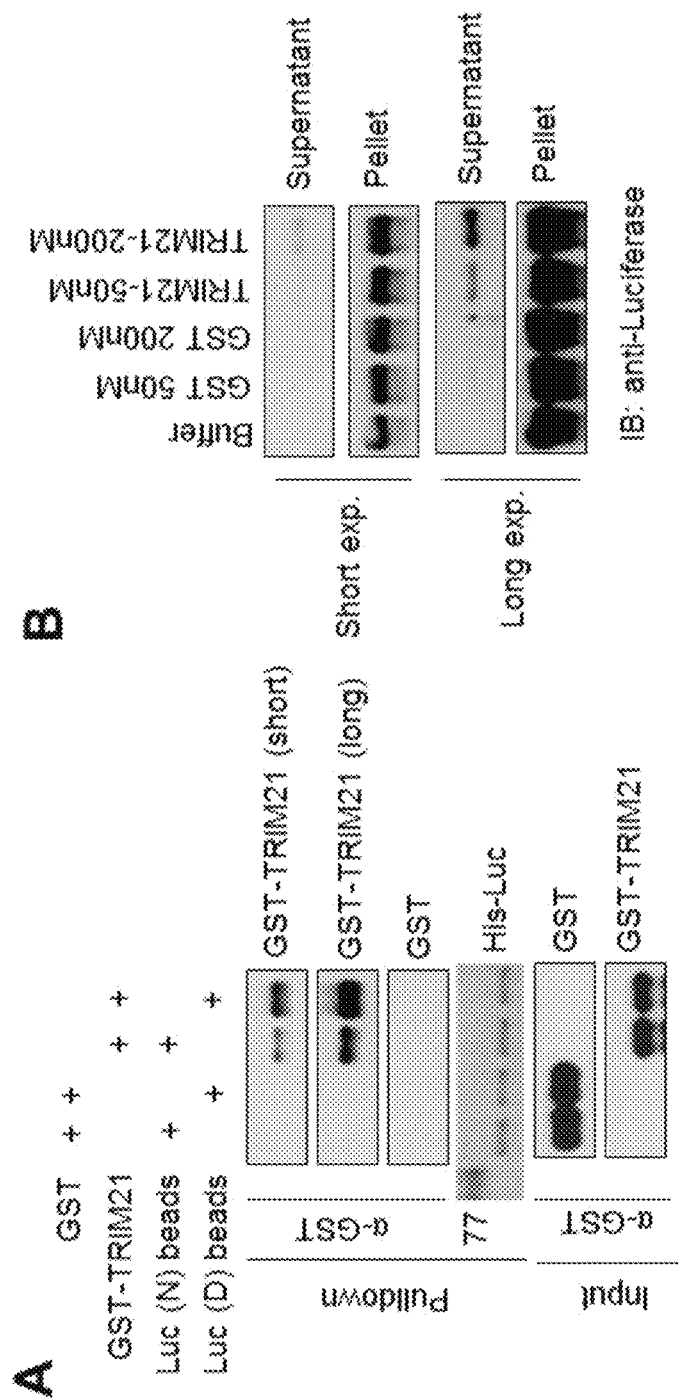
Figures 39C, 39D:
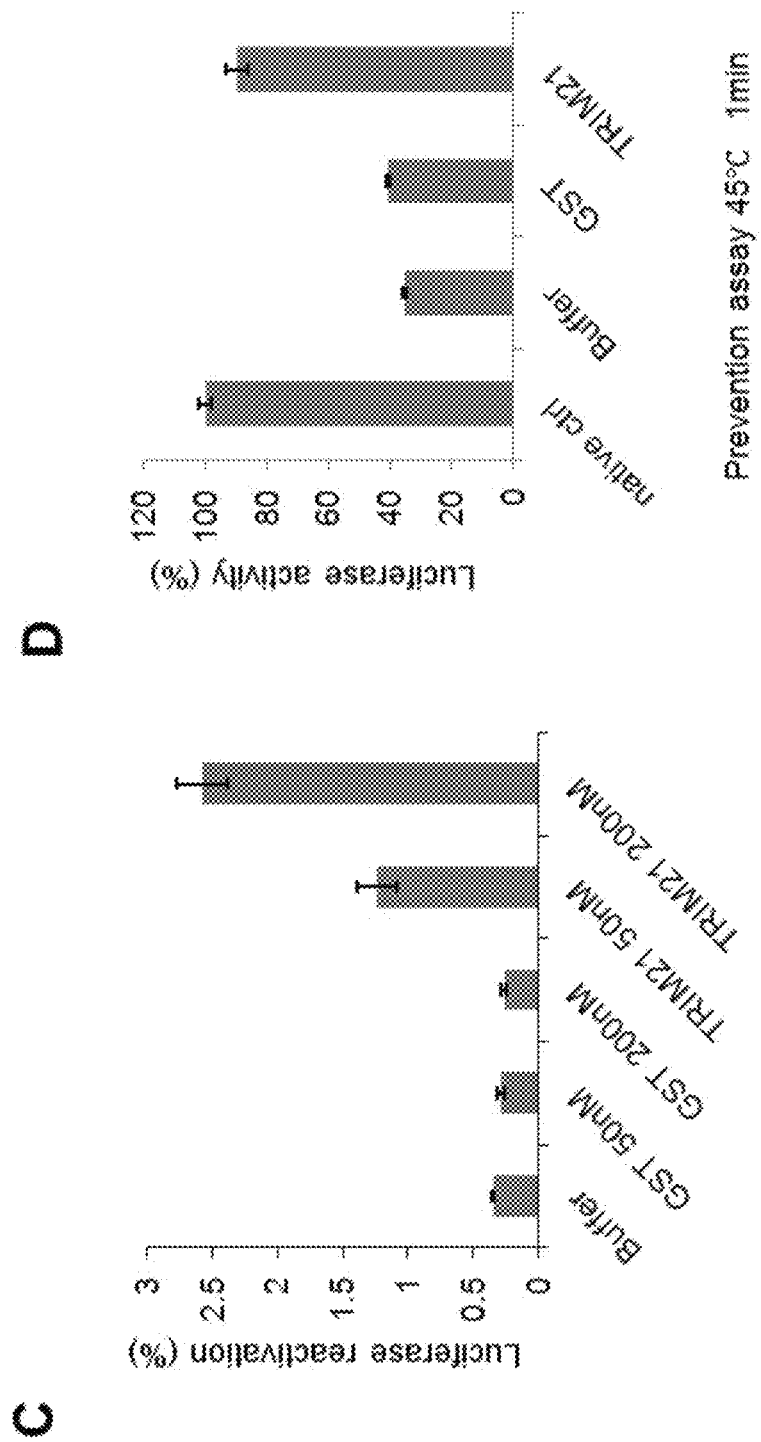

FIG. 39, comprising FIG. 39A through FIG. 39D, depicts results from experiments demonstrating TRIM21 has similar disaggregation functions to TRIM11. FIG. 39A depicts binding of GST, GST-TRIM11 WT or MUT to native (N) and urea-denatured (D) luciferase (luc) immobilized on Ni-NTA beads. FIG. 39B depicts a sedimentation assay showing that heat-aggregated luciferase resolved by GST or GST-TRIM21. FIG. 39C depicts Disaggregation and reactivation of preformed luciferase aggregates using increasing concentrations of GST or GST-TRIM21 (n=3). FIG. 39D depicts a luciferase assay where luciferase (10 nM) was incubated with 200 nM GST or 200 nM GST-TRIM21 at 45° C. for 1 min. Native luciferase activity was set as 100%. N=3.

Figures 40A, 40B:
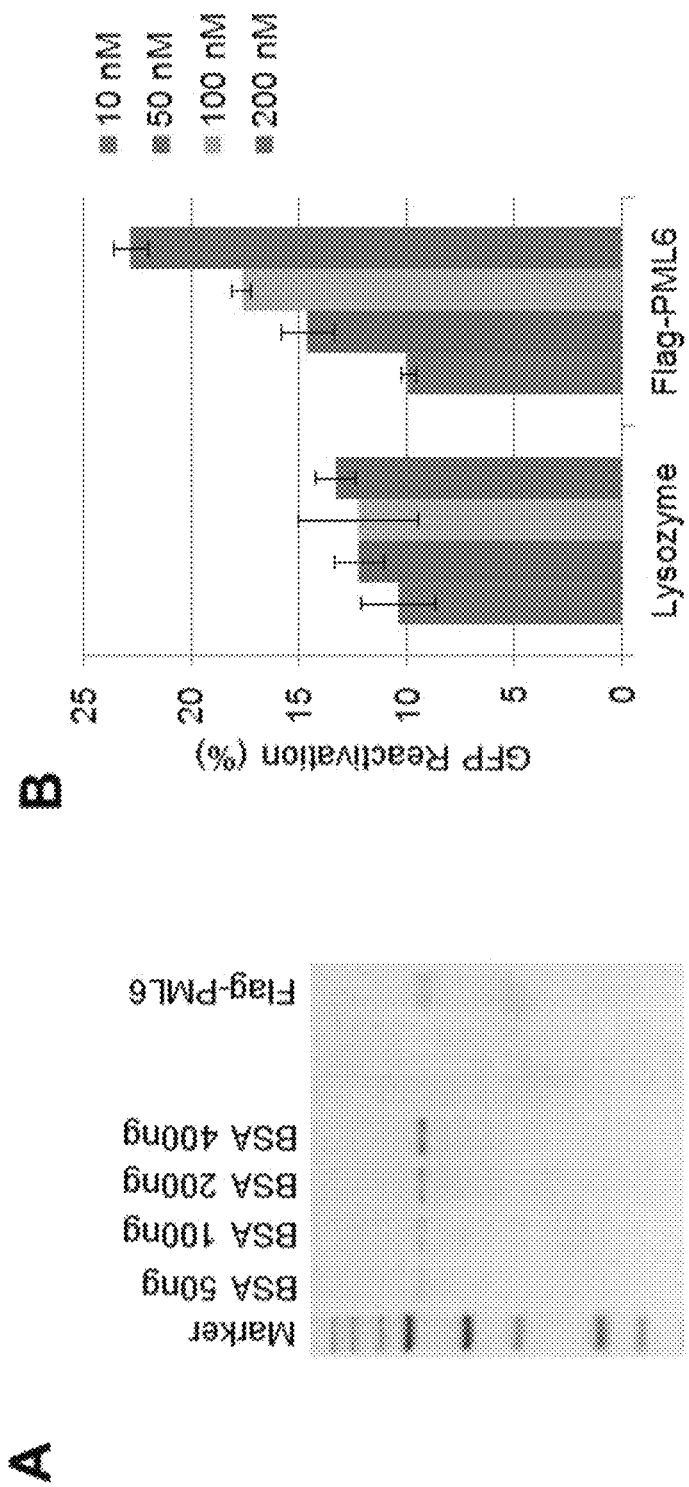
Figures 40C, 40D, 40E:
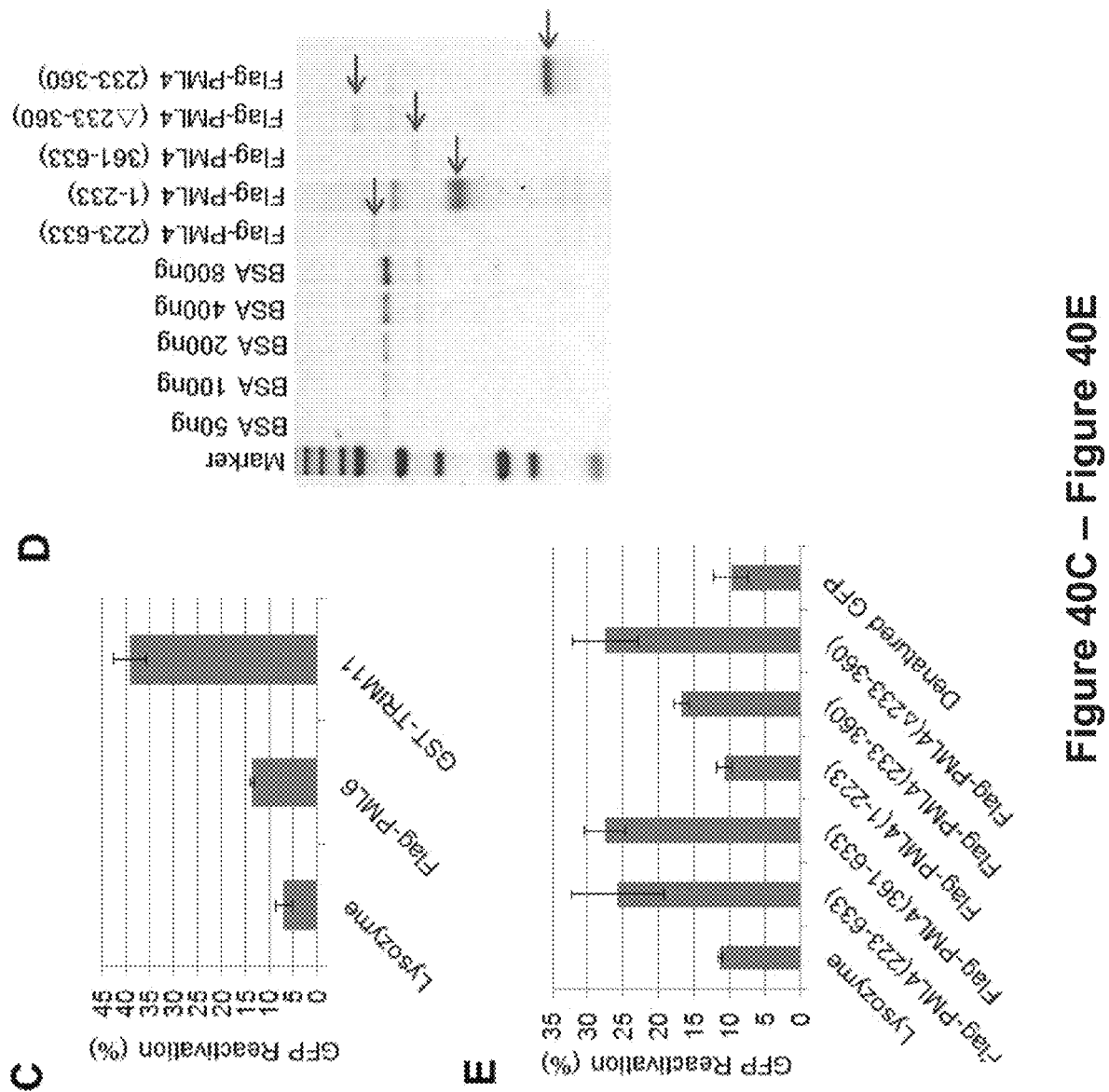

FIG. 40, comprising FIG. 40A through FIG. 40E, depicts results from experiments demonstrating PML and Atxn1 82Q disaggregation. FIG. 40A depicts commassie blue staining of purified Flag-PML6 from 293T cells. FIG. 40B depicts disaggregation and reactivation of preformed GFP aggregates using increasing concentrations of Lysozyme or Flag-PML6 (n=3). FIG. 40C depicts disaggregation and reactivation of preformed GFP aggregates using Lysozyme, Flag-PML6 or GST-TRIM11 (n=3). FIG. 40D depicts commassie blue staining of purified Flag-PML4 fragments from 293T cells. FIG. 40E depicts disaggregation and reactivation of preformed GFP aggregates using different PML4 fragments (n=3).

Figure 41A:
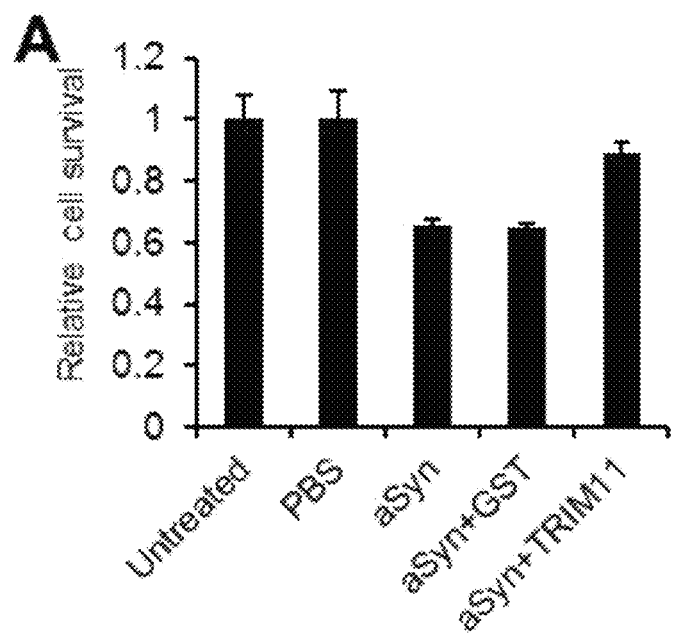
Figure 41B:
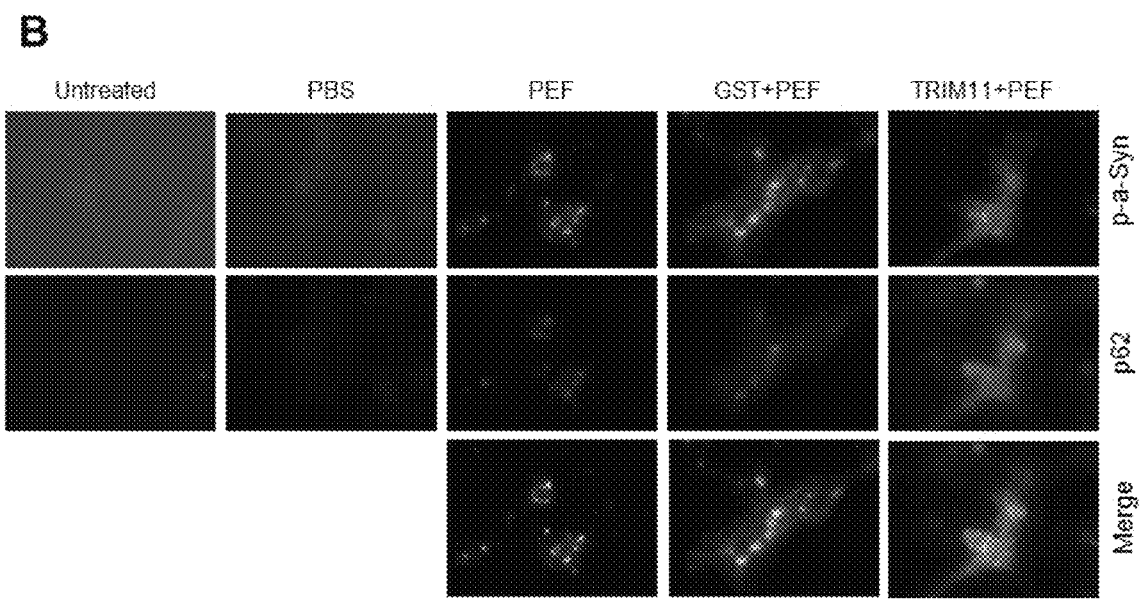

FIG. 41, comprising FIG. 41A and FIG. 41B, depicts results from experiments demonstrating TRIM11 in mouse primary hippocampal neurons. FIG. 41A depicts MTT analysis showing that GST or TRIM11 incubated alpha-Syn-induced cell death. FIG. 41B depicts immunofluorescence analysis of p-alpha-Syn or p62 in alpha-Syn fiber treated Hippocampal neuron cells.

Figures 42A, 42B, 42C:
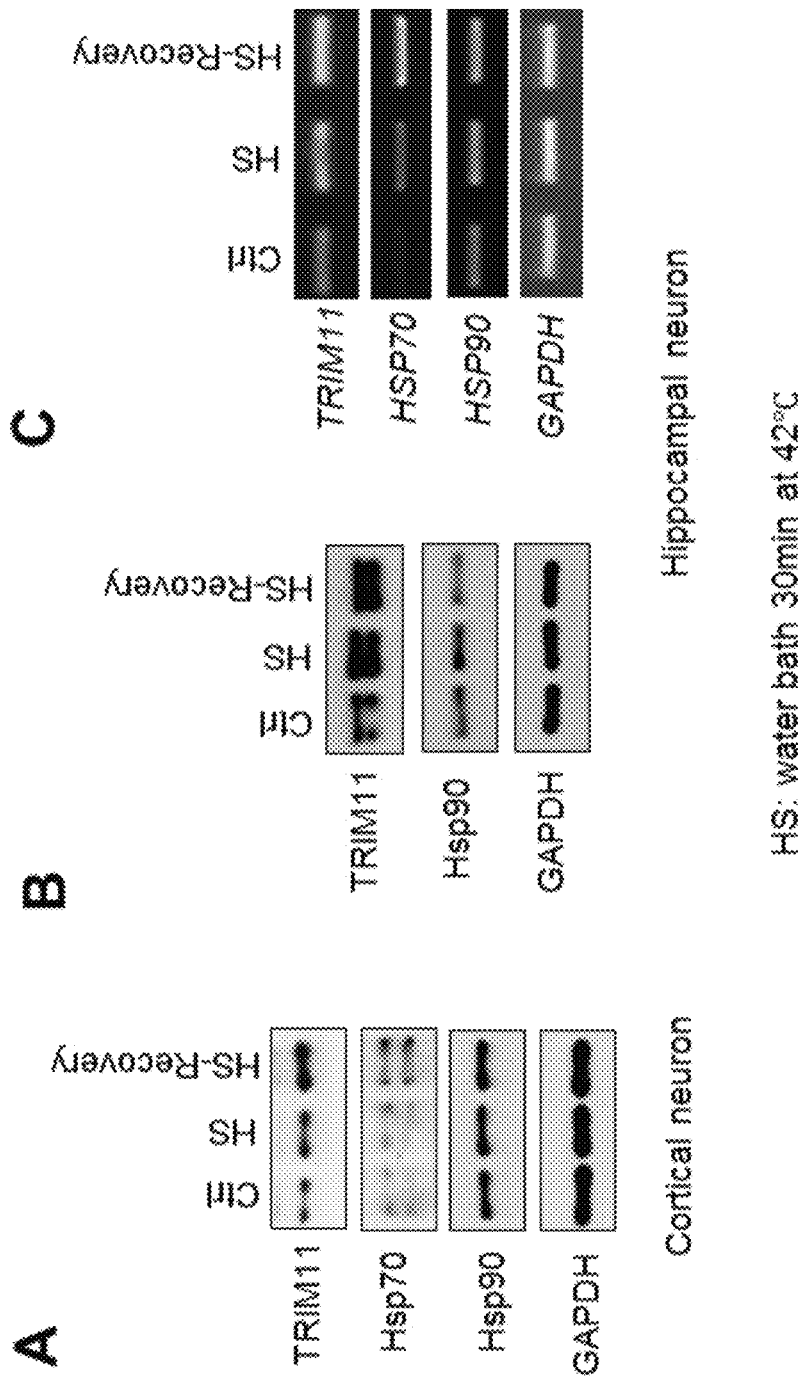

FIG. 42, comprising FIG. 42A through FIG. 42C, depicts results from experiments demonstrating TRIM11 is upregulated in response to heat shock in cortical and hippocampal neurons. FIG. 42A depicts immunoblotting of mouse primary cortical neurons treated with heat shock for 30 minutes at 42° C. and recovered for 3 hours. FIG. 42B depicts immunoblotting of mouse primary hippocampal neurons treated with heat shock for 30 min at 42° C. and recovered for 3 hours. FIG. 42C depicts semi-quantitative PCR analysis of TRIM11, HSP70, HSP90 and GAPDH in response to heat shock in hippocampal neurons.

DETAILED DESCRIPTION

The present invention is related to the discovery of the role of members of the tripartite motif (TRIM) family of proteins and the SUMO-dependent ubiquitin ligase RNF4 in the recognition and degradation of misfolded proteins, which play a role in the pathology of a variety of neurodegenerative disorders.

In one aspect, the present invention provides compositions and methods to treat or prevent a disease or disorder associated with misfolded protein or protein aggregates. It is demonstrated herein that TRIM proteins have roles in targeting misfolded proteins for proteosomal degradation, as chaperone protein, and in disaggregating protein aggregates or inclusions. Thus, in certain aspects, the present invention can be used to eliminate intracellular or extracellular misfolded proteins, protein aggregates, or protein inclusions.

For example, in certain embodiments, the invention provides compositions and methods to treat or prevent a neurodegenerative disorder in a subject in need thereof. For example, in certain embodiments, the invention provides compositions and methods for the treatment or prevention of neurodegenerative disorders that are poly-glutamine (polyQ) disorders, where repeats of the CAG codon encode proteins with polyglutamine tracts that can result in misfolded protein aggregates. Exemplary polyQ disorders include, but are not limited to Spinocerebellar ataxia (SCA) Type 1 (SCA1), SCA2, SCA3, SCA6, SCAT, SCA17, Huntington's disease, and Dentatorubral-pallidoluysian atrophy (DRPLA). In certain embodiments, the invention provides compositions and methods for the treatment of neurodegenerative disorders associated with misfolded proteins or protein aggregates, including, but not limited to, Alzheimer's disease, Parkinson's disease, amyotrophic lateral sclerosis (ALS), transmissible spongiform encephalopathies (prion disease), tauopathies, and Frontotemporal lobar degeneration (FTLD). However, the present invention is not limited to the treatment or prevention of neurodegenerative disorders. Rather, the invention encompasses the treatment or prevention of any disease or disorder associated with a misfolded protein or protein aggregate. Other such diseases and disorders include, but is not limited to AL amyloidosis, AA amyloidosis, Familial Mediterranean fever, senile systemic amyloidosis, familial amyloidotic polyneuropathy, hemodialysis-related amyloidosis, ApoAI amyloidosis, ApoAII amyloidosis, ApoAIV amyloidosis, Finnish hereditary amyloidosis, lysozyme amyloidosis, fibrinogen amyloidosis, Icelandic hereditary cerebral amyloid angiopathy, type II diabetes, medullary carcinoma of the thyroid, atrial amyloidosis, hereditary cerebral hemorrhage with amyloidosis, pituitary prolactinoma, injection-localized amyloidosis, aortic medial amyloidosis, hereditary lattice corneal dystrophy, corneal amyloidosis associated with trichiasis, cataract, calcifying epithelial odontogenic tumor, pulmonary alveolar proteinosis, inclusion-body myostis, and cuteaneous lichen amyloidosis. In certain embodiments, the invention encompasses the treatment or prevention of cancer associated with p53 mutant aggregates, including but not limited to bladder carcinoma, astrocytoma, pharynx carcinoma, lymphoma, and adenocarcinoma.

In one aspect, the invention encompasses the use of one or more TRIM proteins to stabilize a misfolded protein. In certain aspects, stabilization of a functional misfolded protein via one or more TRIM proteins described herein can treat or prevent a disease or disorder associated with the misfolded protein. For example, in one embodiment, stabilization of mutant cystic fibrosis transmembrane conductance regulator (CFTR), via one or more TRIM proteins described herein, would allow mutant CFTR to function instead of being degraded. It is envisioned that using TRIM proteins to stabilize misfolded proteins can be used to treat cystic fibrosis and other diseases associated with degradation of partially functional proteins. Stabilization of proteins, via one or more TRIM proteins described herein, can be used to treat any disease or disorder associated with degradation of functional mutant protein, including but not limited to cystic fibrosis and lysosomal storage diseases such as Gaucher's disease and Fabry's disease.

In one aspect, the present invention provides compositions and methods to increase the expression, activity, or both of a TRIM protein. In certain embodiments, the composition comprises a nucleic acid molecule, expression vector, protein, peptide, small molecule, or the like, which increases the expression, activity, or both of one or more TRIM proteins.

In one aspect, the present invention provides compositions and methods to increase the expression, activity, or both of one or more SUMO-targeted ubiquitin ligases (STUbL). In certain embodiments, the composition comprises a nucleic acid molecule, expression vector, protein, peptide, small molecule, or the like, which increases the expression, activity, or both of one or more STUbLs.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of a compound which is sufficient to provide a beneficial effect to the subject to which the compound is administered. An "effective amount" of a delivery vehicle is that amount sufficient to effectively bind or deliver a compound.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

The phrase "biological sample" as used herein, is intended to include any sample comprising a cell, a tissue, or a bodily fluid in which expression of a nucleic acid or polypeptide is present or can be detected. Samples that are liquid in nature are referred to herein as "bodily fluids." Biological samples may be obtained from a patient by a variety of techniques including, for example, by scraping or swabbing an area of the subject or by using a needle to obtain bodily fluids. Methods for collecting various body samples are well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, a "modulator of one or more TRIM proteins" is a compound that modifies the expression, activity or biological function of the TRIM protein as compared to the expression, activity or biological function of the TRIM protein in the absence of the modulator.

As used herein, a "modulator of RNF4" is a compound that modifies the expression, activity or biological function of RNF4 as compared to the expression, activity or biological function of RNF4 in the absence of the modulator.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one aspect, the present invention provides compositions and methods to treat or prevent a disease or disorder associated with misfolded proteins or protein aggregates. For example, the present invention provides compositions and methods to increase the recognition and elimination of misfolded proteins. In certain embodiments, the invention provides for the SUMO-mediated ubiquitination and eventual degradation of misfolded protein. In certain embodiments, the invention provides for the disaggregation of protein aggregates or inclusions. The present invention can thus be used to eliminate misfolded proteins, protein aggregates, or protein inclusions, both intracellularly or extracellularly.

The present invention is related to the discovery of the role of members of the tripartite motif (TRIM) family of proteins and the SUMO-targeted ubiquitin ligase (STUbL), RNF4, in the recognition and degradation of misfolded proteins, which play a role in the pathology of a variety of diseases and disorders, including many neurodegenerative diseases and disorders.

The data presented herein demonstrates that members of the TRIM protein family co-localize with misfolded proteins and mediate the degradation of misfolded proteins. Further, it is described herein that RNF4 is an ubiquitin ligase which mediates the ubiquitination and degradation of misfolded proteins. Thus, the present invention provides compositions that increase the expression, activity, or both of one or more TRIM proteins, one or more STUbLs, or a combination thereof. For example, it is demonstrated that nucleic acid molecules encoding a TRIM protein and recombinant TRIM proteins promotes the degradation of misfolded protein.

In one embodiment, the composition comprises a modulator of the expression or activity of one or more TRIM proteins. For example, in one embodiment, the modulator increases the expression or activity of one or more TRIM proteins. The one or more TRIM proteins, include, any member of the TRIM protein family, including mammalian and non-mammalian members. In certain embodiments, the modulator increases the expression or activity of one or more of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30.

In one embodiment, the composition comprises a modulator of one or more STUbLs. For example, in one embodiment, the modulator increases the expression or activity of one or more STUbLs. Exemplary STUbLs include, but are not limited to RNF4 and RNF111 (also known as Arkadia).

In one embodiment, the composition comprises a modulator of one or more TRIM proteins and a modulator of one or more STUbLs.

The present invention provides a method for treating or preventing a disease or disorder associated with misfolded proteins or protein aggregates, in a subject in need. It is found herein that increasing the level of expression or activity of a TRIM protein or STUbL, can promote the degradation of misfolded protein, thereby treating the disease or disorder in the subject.

Examples of neurodegenerative diseases or disorders which may be treated or prevented by the compositions and methods of this invention include, but are not limited to polyQ disorders such as SCA1, SCA2, SCA3, SCA6, SCA7, SCA17, Huntington's disease, Dentatorubral-pallidoluysian atrophy (DRPLA), Alzheimer's disease, Parkinson's disease, amyotrophic lateral sclerosis (ALS), transmissible spongiform encephalopathies (prion disease), tauopathies, and Frontotemporal lobar degeneration (FTLD). However, the present invention is not limited to the treatment or prevention of neurodegenerative disorders. Rather, the invention encompasses the treatment or prevention of any disease or disorder associated with a misfolded protein or protein aggregate. Other such diseases and disorders include, but is not limited to AL amyloidosis, AA amyloidosis, Familial Mediterranean fever, senile systemic amyloidosis, familial amyloidotic polyneuropathy, hemodialysis-related amyloidosis, ApoAI amyloidosis, ApoAII amyloidosis, ApoAIV amyloidosis, Finnish hereditary amyloidosis, lysozyme amyloidosis, fibrinogen amyloidosis, Icelandic hereditary cerebral amyloid angiopathy, type II diabetes, medullary carcinoma of the thyroid, atrial amyloidosis, hereditary cerebral hemorrhage with amyloidosis, pituitary prolactinoma, injection-localized amyloidosis, aortic medial amyloidosis, hereditary lattice corneal dystrophy, corneal amyloidosis associated with trichiasis, cataract, calcifying epithelial odontogenic tumor, pulmonary alveolar proteinosis, inclusion-body myostis, and cuteaneous lichen amyloidosis. In certain embodiments, the invention encompasses the treatment or prevention of cancer associated with p53 mutant aggregates, including but not limited to bladder carcinoma, astrocytoma, pharynx carcinoma, lymphoma, and adenocarcinoma.

In one aspect, the invention encompasses the use of one or more TRIM proteins to stabilize a misfolded protein. In certain aspects, stabilization of a functional misfolded protein via one or more TRIM proteins described herein can treat or prevent a disease or disorder associated with the misfolded protein, including but not limited to cystic fibrosis and lysosomal storage diseases such as Gaucher's disease and Fabry's disease.

In one aspect, the present invention provides a method to diagnose a disease or disorder associated with a misfolded protein or protein aggregate. For example, in one embodiment, one or more TRIM proteins or one or more STUbLs are used as diagnostic markers.

In one aspect, the present invention is directed to compositions and methods for manufacture of a recombinant protein of interest. For example, in certain embodiments, the one or more TRIM proteins and one or more STUbLs can be used to disaggregate protein aggregates of recombinant protein of interest.

Compositions

In various embodiments, the present invention includes modulator compositions and methods of preventing and treating a disease or disorder associated with misfolded protein or protein aggregates. In various embodiments, the modulator compositions and methods of preventing or treating of the invention modulate the level or activity of a gene, or gene product. In some embodiments, the modulator composition of the invention is an activator that increases the level or activity of a gene, or gene product.

It will be understood by one skilled in the art, based upon the disclosure provided herein, that modulating a gene, or gene product, encompasses modulating the level or activity of a gene, or gene product, including, but not limited to, modulating the transcription, translation, splicing, degradation, enzymatic activity, binding activity, or combinations thereof. Thus, modulating the level or activity of a gene, or gene product, includes, but is not limited to, modulating transcription, translation, degradation, splicing, or combinations thereof, of a nucleic acid; and it also includes modulating any activity of polypeptide gene product as well.

In one embodiment, the modulator increases the expression or activity of a gene or gene product by increasing production of the gene or gene product, for example by modulating transcription of the gene or translation of the gene product. In one embodiment, the modulator increases the expression or activity of a gene or gene product by providing exogenous gene or gene product. For example, in certain embodiments, the modulator comprises an isolated nucleic acid encoding one or more TRIM proteins or one or more STUbLs. In one embodiment, the modulator comprises an isolated nucleic acid encoding one or more TRIM proteins and one or more STUbLs. In certain embodiments, the modulator comprises an isolated peptide comprising one or more TRIM proteins or one or more STUbLs. In one embodiment, the modulator comprises an isolated peptide comprising one or more TRIM proteins and one or more STUbLs. In one embodiment, the modulator increases the expression or activity of a gene or gene product by inhibiting the degradation of the gene or gene product. For example, in one embodiment, the modulator decreases the ubiquitination, proteosomal degradation, or proteolysis of one or more TRIM proteins or one or more STUbLs. In one embodiment, the modulator increases the stability or half-life of a gene product.

In various embodiments, the modulated gene, or gene product, is one or more TRIM proteins. For example, it is described herein that TRIM proteins recognize misfolded proteins and mediate the degradation of misfolded proteins and protein aggregates. In one embodiment, the gene or gene product is one or more STUbLs. For example, it is described herein that RNF4, a member of the STUbl family of proteins, mediates the degradation of misfolded proteins and protein aggregates.

Modulation of a gene, or gene product, can be assessed using a wide variety of methods, including those disclosed herein, as well as methods known in the art or to be developed in the future. That is, the routineer would appreciate, based upon the disclosure provided herein, that modulating the level or activity of a gene, or gene product, can be readily assessed using methods that assess the level of a nucleic acid encoding a gene product (e.g., mRNA), the level of polypeptide gene product present in a biological sample, the activity of polypeptide gene product present in a biological sample, or combinations thereof.

The modulator compositions and methods of the invention that modulate the level or activity of a gene, or gene product, include, but should not be construed as being limited to, a chemical compound, a protein, a peptide, a peptidomemetic, an antibody, a ribozyme, a small molecule chemical compound, a nucleic acid, a vector, an antisense nucleic acid molecule (e.g., siRNA, miRNA, etc.), or combinations thereof. One of skill in the art would readily appreciate, based on the disclosure provided herein, that a modulator composition encompasses a chemical compound that modulates the level or activity of a gene, or gene product. Additionally, a modulator composition encompasses a chemically modified compound, and derivatives, as is well known to one of skill in the chemical arts.

In one embodiment, the modulator composition of the present invention is an agonist, which increases the expression, activity, or biological function of a gene or gene product. For example, in certain embodiments, the modulator of the present invention is an agonist of one or more TRIM proteins or one or more STUbLs.

Further, one of skill in the art would, when equipped with this disclosure and the methods exemplified herein, appreciate that modulators include such modulators as discovered in the future, as can be identified by well-known criteria in the art of pharmacology, such as the physiological results of modulation of the genes, and gene products, as described in detail herein and/or as known in the art. Therefore, the present invention is not limited in any way to any particular modulator composition as exemplified or disclosed herein; rather, the invention encompasses those modulator compositions that would be understood by the routineer to be useful as are known in the art and as are discovered in the future.

Further methods of identifying and producing modulator compositions are well known to those of ordinary skill in the art. Alternatively, a modulator can be synthesized chemically. Further, the routineer would appreciate, based upon the teachings provided herein, that a modulator composition can be obtained from a recombinant organism. Compositions and methods for chemically synthesizing modulators and for obtaining them from natural sources are well known in the art and are described in the art.

One of skill in the art will appreciate that a modulator can be administered as a small molecule chemical, a polypeptide, a peptide, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a peptide or a nucleic acid encoding a peptide that is modulator of a gene, or gene product. For example, the invention includes a peptide or a nucleic acid encoding a peptide that comprises one or more TRIM proteins, one or more STUbLs, or a combination thereof. (Sambrook et al., 2001, Molecular Cloning: A Laboratory Manual, Cold Spring Harbor Laboratory, New York; Ausubel et al., 1997, Current Protocols in Molecular Biology, John Wiley & Sons, New York).

Peptides

In one embodiment, the composition of the present invention comprises one or more peptides. For example, in one embodiment, a peptide of the composition comprises an amino acid sequence of one or more TRIM proteins. For example, in one embodiment, the peptide comprises one or more of TRIM5δ, TRIM 11, TRIM19, TRIM 21, TRIM27, and TRIM32. In certain embodiments, the peptide comprises an amino acid sequence of one or more STUbLs. For example, in one embodiment, the peptide comprises one or more of RNF4 and RNF111 (Arkadia).

Exemplary amino acid sequences of TRIM proteins, and cDNA nucleotide sequences encoding TRIM proteins is provided in Table 1 below.

TABLE 1

TRIM protein nucleotide and amino acid sequences

| Name | Nucleotide Accession Number | Nucleotide Sequence | Protein Accession Number | Amino Acid Sequence |
|---|---|---|---|---|
| TRIM1 | NM_012216.3 | SEQ ID NO: 1 | NP_036348.2 | SEQ ID NO: 2 |
| TRIM2 | NM_015271.4 | SEQ ID NO: 3 | NP_056086.2 | SEQ ID NO: 4 |
| TRIM3 | NM_006458.3 | SEQ ID NO: 5 | NP_006449.2 | SEQ ID NO: 6 |
| TRIM4 | NM_033017.3 | SEQ ID NO: 7 | NP_148977.2 | SEQ ID NO: 8 |
| TRIM5 | NM_033034.2 | SEQ ID NO: 9 | NP_149023.2 | SEQ ID NO: 10 |
| TRIM6 | NM_001003818.2 | SEQ ID NO: 11 | NP_001003818.1 | SEQ ID NO: 12 |
| TRIM7 | NM_033342.3 | SEQ ID NO: 13 | NP_203128.1 | SEQ ID NO: 14 |
| TRIM8 | NM_030912.2 | SEQ ID NO: 15 | NP_112174.2 | SEQ ID NO: 16 |
| TRIM9 | NM_015163.5 | SEQ ID NO: 17 | NP_055978.4 | SEQ ID NO: 18 |
| TRIM10 | NM_006778.3 | SEQ ID NO: 19 | NP_006769.2 | SEQ ID NO: 20 |
| TRIM11 | NM_145214.2 | SEQ ID NO: 21 | NP_660215.1 | SEQ ID NO: 22 |
| TRIM12 | NM_023835.2 | SEQ ID NO: 23 | NP_076324.2 | SEQ ID NO: 24 |
| TRIM13 | NM_005798.4 | SEQ ID NO: 25 | NP_005789.2 | SEQ ID NO: 26 |
| TRIM14 | NM_014788.3 | SEQ ID NO: 27 | NP_055603.2 | SEQ ID NO: 28 |
| TRIM15 | NM_033229.2 | SEQ ID NO: 29 | NP_150232.2 | SEQ ID NO: 30 |
| TRIM16 | NM_006470.3 | SEQ ID NO: 31 | NP_006461.3 | SEQ ID NO: 32 |
| TRIM17 | NM_016102.3 | SEQ ID NO: 33 | NP_057186.1 | SEQ ID NO: 34 |
| TRIM18 | NM_000381.3 | SEQ ID NO: 35 | NP_000372.1 | SEQ ID NO: 36 |
| TRIM19 | NM_033238.2 | SEQ ID NO: 37 | NP_150241.2 | SEQ ID NO: 38 |
| TRIM20 | NM_000243.2 | SEQ ID NO: 39 | NP_000234.1 | SEQ ID NO: 40 |
| TRIM21 | NM_003141.3 | SEQ ID NO: 41 | NP_003132.2 | SEQ ID NO: 42 |
| TRIM22 | NM_006074.4 | SEQ ID NO: 43 | NP_006065.2 | SEQ ID NO: 44 |
| TRIM23 | NM_001656.3 | SEQ ID NO: 45 | NP_001647.1 | SEQ ID NO: 46 |
| TRIM24 | NM_015905.2 | SEQ ID NO: 47 | NP_056989.2 | SEQ ID NO: 48 |
| TRIM25 | NM_005082.4 | SEQ ID NO: 49 | NP_005073.2 | SEQ ID NO: 50 |
| TRIM26 | NM_003449.4 | SEQ ID NO: 51 | NP_003440.1 | SEQ ID NO: 52 |

TABLE 1-continued

TRIM protein nucleotide and amino acid sequences

| Name | Nucleotide Accession Number | Nucleotide Sequence | Protein Accession Number | Amino Acid Sequence |
|---|---|---|---|---|
| TRIM27 | NM_006510.4 | SEQ ID NO: 53 | NP_006501.1 | SEQ ID NO: 54 |
| TRIM28 | NM_005762.2 | SEQ ID NO: 55 | NP_005753.1 | SEQ ID NO: 56 |
| TRIM29 | NM_012101.3 | SEQ ID NO: 57 | NP_036233.2 | SEQ ID NO: 58 |
| TRIM30 | NM_009099.2 | SEQ ID NO: 59 | NP_033125.2 | SEQ ID NO: 60 |
| TRIM31 | NM_007028.4 | SEQ ID NO: 61 | NP_008959.3 | SEQ ID NO: 62 |
| TRIM32 | NM_012210.3 | SEQ ID NO: 63 | NP_036342.2 | SEQ ID NO: 64 |
| TRIM33 | NM_015906.3 | SEQ ID NO: 65 | NP_056990.3 | SEQ ID NO: 66 |
| TRIM34 | NM_021616.5 | SEQ ID NO: 67 | NP_067629.2 | SEQ ID NO: 68 |
| TRIM35 | NM_171982.4 | SEQ ID NO: 69 | NP_741983.2 | SEQ ID NO: 70 |
| TRIM36 | NM_018700.3 | SEQ ID NO: 71 | NP_061170.2 | SEQ ID NO: 72 |
| TRIM37 | NM_015294.4 | SEQ ID NO: 73 | NP_056109.1 | SEQ ID NO: 74 |
| TRIM38 | NM_006355.4 | SEQ ID NO: 75 | NP_006346.1 | SEQ ID NO: 76 |
| TRIM39 | NM_021253.3 | SEQ ID NO: 77 | NP_067076.2 | SEQ ID NO: 78 |
| TRIM40 | NM_001286633.1 | SEQ ID NO: 79 | NP_001273562.1 | SEQ ID NO: 80 |
| TRIM41 | NM_033549.4 | SEQ ID NO: 81 | NP_291027.3 | SEQ ID NO: 82 |
| TRIM42 | NM_152616.4 | SEQ ID NO: 83 | NP_689829.3 | SEQ ID NO: 84 |
| TRIM43 | NM_138800.1 | SEQ ID NO: 85 | NP_620155.1 | SEQ ID NO: 86 |
| TRIM44 | NM_017583.5 | SEQ ID NO: 87 | NP_060053.2 | SEQ ID NO: 88 |
| TRIM45 | NM_025188.3 | SEQ ID NO: 89 | NP_079464.2 | SEQ ID NO: 90 |
| TRIM46 | NM_025058.4 | SEQ ID NO: 91 | NP_079334.3 | SEQ ID NO: 92 |
| TRIM47 | NM_033452.2 | SEQ ID NO: 93 | NP_258411.2 | SEQ ID NO: 94 |
| TRIM48 | NM_024114.3 | SEQ ID NO: 95 | NP_077019.2 | SEQ ID NO: 96 |
| TRIM49 | NM_020358.2 | SEQ ID NO: 97 | NP_065091.1 | SEQ ID NO: 98 |
| TRIM50 | NM_178125.3 | SEQ ID NO: 99 | NP_835226.2 | SEQ ID NO: 100 |
| TRIM51 | NM_032681.3 | SEQ ID NO: 101 | NP_116070.2 | SEQ ID NO: 102 |
| TRIM52 | NM_032765.2 | SEQ ID NO: 103 | NP_116154.1 | SEQ ID NO: 104 |
| TRIM54 | NM_032546.3 | SEQ ID NO: 105 | NP_115935.3 | SEQ ID NO: 106 |
| TRIM55 | NM_184085.1 | SEQ ID NO: 107 | NP_908973.1 | SEQ ID NO: 108 |
| TRIM56 | NM_030961.2 | SEQ ID NO: 109 | NP_112223.1 | SEQ ID NO: 110 |
| TRIM58 | NM_015431.3 | SEQ ID NO: 111 | NP_056246.3 | SEQ ID NO: 112 |
| TRIM59 | NM_173084.2 | SEQ ID NO: 113 | NP_775107.1 | SEQ ID NO: 114 |
| TRIM60 | NM_152620.2 | SEQ ID NO: 115 | NP_689833.1 | SEQ ID NO: 116 |
| TRIM61 | NM_001012414.2 | SEQ ID NO: 117 | NP_001012414.1 | SEQ ID NO: 118 |
| TRIM62 | NM_018207.2 | SEQ ID NO: 119 | NP_060677.2 | SEQ ID NO: 120 |
| TRIM63 | NM_032588.3 | SEQ ID NO: 121 | NP_115977.2 | SEQ ID NO: 122 |
| TRIM64 | NM_001136486.1 | SEQ ID NO: 123 | NP_001129958.1 | SEQ ID NO: 124 |
| TRIM65 | NM_173547.3 | SEQ ID NO: 125 | NP_775818.2 | SEQ ID NO: 126 |
| TRIM66 | NM_014818.1 | SEQ ID NO: 127 | NP_055633.1 | SEQ ID NO: 128 |
| TRIM67 | NM_001004342.3 | SEQ ID NO: 129 | NP_001004342.3 | SEQ ID NO: 130 |
| TRIM68 | NM_018073.7 | SEQ ID NO: 131 | NP_060543.5 | SEQ ID NO: 132 |
| TRIM69 | NM_080745.4 | SEQ ID NO: 133 | NP_542783.2 | SEQ ID NO: 134 |
| TRIM70 | NM_001037330.1 | SEQ ID NO: 135 | NP_001032407.1 | SEQ ID NO: 136 |
| TRIM71 | NM_001039111.2 | SEQ ID NO: 137 | NP_001034200.1 | SEQ ID NO: 138 |
| TRIM72 | NM_001008274.3 | SEQ ID NO: 139 | NP_001008275.2 | SEQ ID NO: 140 |
| TRIM73 | NM_198924.3 | SEQ ID NO: 141 | NP_944606.2 | SEQ ID NO: 142 |
| TRIM74 | NM_198853.2 | SEQ ID NO: 143 | NP_942150.1 | SEQ ID NO: 144 |
| TRIM75 | NM_001033429.2 | SEQ ID NO: 145 | NP_001028601.1 | SEQ ID NO: 146 |
| TRIM76 | NM_153610.4 | SEQ ID NO: 164 | NP_705838.3 | SEQ ID NO: 165 |
| TRIM77 | NM_001146162.1 | SEQ ID NO: 166 | NP_001139634.1 | SEQ ID NO: 167 |

The invention should also be construed to include any form of a peptide having substantial homology to the peptides disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the peptides disclosed herein.

In one embodiment, the composition of the invention comprises a peptide, a fragment of a peptide, a homolog, a variant, a derivative or a salt of a peptide described herein. For example, in certain embodiments, the composition comprises a peptide comprising one or more TRIM proteins, a fragment of one or more TRIM proteins, a homolog of one or more TRIM proteins, a variant of one or more TRIM proteins, a derivative of one or more TRIM proteins, or a salt of one or more TRIM proteins. In certain embodiments, the composition comprises a peptide comprising one or more STUbLs, a fragment of one or more STUbLs, a homolog of one or more STUbLs, a variant of one or more STUbLs, a derivative of one or more STUbLs, or a salt of one or more STUbLs.

In one embodiment, the composition comprises a combination of the peptides described herein. For example, in certain embodiments, the composition comprises a peptide comprising one or more TRIM proteins and a peptide comprising one or more STUbLs. In one embodiment, the composition comprises a peptide comprising one or more TRIM proteins and one or more STUbLs.

In certain embodiments, the peptide comprises a targeting domain, which targets the peptide to a desired location. For example, in certain embodiments, the targeting domain binds to a targeted cell, protein, or protein aggregate, thereby delivering the therapeutic peptide to a desired location. For example, in one embodiment, the targeting domain is directed to bind to a protein or protein aggregate associated with a disease or disorder, including but not limited to the proteins and protein aggregates of amyloid-beta, alpha-synuclein, tau, prions, SOD1, TDP-43, FUS, p53 mutants, and proteins associated with polyglutamine repeats, such as huntingtin, ataxins.

In certain embodiments, the targeting domain comprises a peptide, nucleic acid, small molecule, or the like, which has the ability to bind to the targeted cell, protein, or protein aggregate. For example, in one embodiment, the targeting domain comprises an antibody or antibody fragment which binds to a targeted cell, protein, or protein aggregate.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

The peptides of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide of the invention.

Cyclic derivatives of the peptides the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Peptides of the invention may also have modifications. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Such variants include those containing residues other than naturally-occurring L-amino acids, e.g., D-amino acids or non-naturally-occurring synthetic amino acids. The peptides of the invention may further be conjugated to non-amino acid moieties that are useful in their therapeutic application. In particular, moieties that improve the stability, biological half-life, water solubility, and/or immunologic characteristics of the peptide are useful. A non-limiting example of such a moiety is polyethylene glycol (PEG).

Covalent attachment of biologically active compounds to water-soluble polymers is one method for alteration and control of biodistribution, pharmacokinetics, and often, toxicity for these compounds (Duncan et al., 1984, Adv. Polym. Sci. 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, 1980, Polyethylene glycol. In R. L. Davidson (Ed.) Handbook of Water Soluble Gums and Resins. McGraw-Hill, New York, chapter 18). PEG possess an ideal set of properties: very low toxicity (Pang, 1993, J. Am. Coll. Toxicol. 12: 429-456) excellent solubility in aqueous solution (Powell, supra), low immunogenicity and antigenicity (Dreborg et al., 1990, Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p 145-154; Olson et al., 1997, Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p 170-181).

A peptide of the invention may be synthesized by conventional techniques. For example, the peptides of the invention may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

The peptides may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the amino acid residues, both which methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g. with DCC, can then proceed by addition of the desired alcohol, followed by deprotection and isolation of the esterified peptide product.

The peptides of the invention may be prepared by standard chemical or biological means of peptide synthesis.

Biological methods include, without limitation, expression of a nucleic acid encoding a peptide in a host cell or in an in vitro translation system.

Included in the invention are nucleic acid sequences that encode the peptide of the invention. In one embodiment, the invention includes nucleic acid sequences encoding the amino acid sequence of one or more TRIM proteins or one or more STUbLs. Accordingly, subclones of a nucleic acid sequence encoding a peptide of the invention can be produced using conventional molecular genetic manipulation for subcloning gene fragments, such as described by Sambrook et al., *Molecular Cloning: A Laboratory Manual*, Cold Springs Laboratory, Cold Springs Harbor, New York (2012), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

Combined with certain formulations, such peptides can be effective intracellular agents. However, in order to increase the efficacy of such peptides, the one or more peptides of the invention can be provided a fusion peptide along with a second peptide which promotes "transcytosis", e.g., uptake of the peptide by cells. For example, in one embodiment, the peptide may comprise a cell-penetrating domain, for example a cell-penetrating peptide (CPP) to allow for the peptide to enter a cell. In one embodiment, the CPP is derived from HIV Tat.

To illustrate, the one or more peptides of the present invention can be provided as part of a fusion polypeptide with all or a fragment of the N-terminal domain of the HIV protein Tat, e.g., residues 1-72 of Tat or a smaller fragment thereof which can promote transcytosis. In one embodiment, the peptide comprises the protein transduction domain of HIV Tat (YGRKKRRQRRR; (SEQ ID NO: 163)). In other embodiments, the one or more peptides can be provided a fusion polypeptide with all or a portion of the antenopedia III protein. Other cell-penetrating domains that mediate uptake of the peptide are known in the art, and are equally applicable for use in a fusion peptide of the present invention.

Nucleic Acids

In one embodiment, the composition of the invention comprises one or isolated nucleic acids. For example, in one embodiment, the one or more isolated nucleic acids encodes one or more TRIM proteins. For example, in one embodiment, the one or more isolated nucleic acids encodes one or more of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30. In certain embodiments, the one or more isolated nucleic acids encodes one or more STUbLs. For example, in one embodiment, the one or more isolated nucleic acids encodes one or more of RNF4 and RNF111 (Arkadia).

Exemplary nucleotide sequences encoding TRIM proteins is found in Table 1.

In certain embodiments, a peptide corresponding to one or more TRIM proteins or one or more STUbLs is expressed from the one or more nucleic acids in a cell in vivo or in vitro using known techniques.

The nucleotide sequence of the isolated nucleic acids include both the DNA sequence that is transcribed into RNA and the RNA sequence that is translated into a polypeptide. According to other embodiments, the nucleotide sequences are inferred from the amino acid sequence of the peptides of the invention. As is known in the art several alternative nucleotide sequences are possible due to redundant codons, while retaining the biological activity of the translated peptides.

Further, the invention encompasses an isolated nucleic acid comprising a nucleotide sequence having substantial homology to a nucleotide sequence encoding a disclosed herein. Preferably, the nucleotide sequence of an isolated nucleic acid is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a peptide of the invention.

In one embodiment, the composition comprises a combination of the nucleic acid molecules described herein. For example, in certain embodiments, the composition comprises an isolated nucleic acid molecule encoding one or more TRIM proteins and an isolated nucleic acid molecule encoding one or more STUbLs. In one embodiment, the composition comprises an isolated nucleic acid molecule encoding one or more TRIM proteins and one or more STUbLs.

Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

The desired nucleic acid encoding one or more one or more TRIM proteins or one or more STUbLs can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In a preferred embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In one embodiment, the encoding sequence is contained within an AAV vector. More than 30 naturally occurring serotypes of AAV are available. Many natural variants in the AAV capsid exist, allowing identification and use of an AAV with properties specifically suited for skeletal muscle. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

Thus, expression of one or more TRIM proteins or one or more STUbLs can be achieved by delivering a recombinantly engineered AAV or artificial AAV that contains one or more encoding sequences. The use of AAVs is a common mode of exogenous delivery of DNA as it is relatively non-toxic, provides efficient gene transfer, and can be easily optimized for specific purposes. Exemplary AAV serotypes include, but is not limited to AAV1, AAV2, AAV3, AAV4, AAV5, AAV6, AAV7, AAV8 and AAV9.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, suitable for expression of one or more TRIM proteins or one or more STUbLs, include AAV2/8 (see U.S. Pat. No. 7,282,199), AAV2/5 (available from the National Institutes of Health), AAV2/9 (International Patent Publication No. WO2005/033321), AAV2/6 (U.S. Pat. No. 6,156,303), and AAVrh8 (International Patent Publication No. WO2003/042397), among others.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In one embodiment, the promoter or enhancer specifically directs expression of the one or more TRIM proteins or one or more STUbLs in the intestinal epithelium in neural tissue. For example, in certain embodiments, the promoter or enhancer specifically directs expression of the one or more TRIM proteins or one or more STUbLs in a neuron, astrocyte, oligodendrocyte, Perkinje cell, pyramidal cell, or the like.

In order to assess the expression of the desired polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

In one embodiment, the composition of the invention comprises in vitro transcribed (IVT) RNA encoding one or more components of the one or more TRIM proteins or one or more STUbLs. In one embodiment, an IVT RNA can be introduced to a cell as a form of transient transfection. The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is one or more TRIM proteins or one or more STUbLs.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

In one embodiment, the composition of the present invention comprises a modified nucleic acid encoding one or more one or more TRIM proteins or RNF4 described herein. For example, in one embodiment, the composition comprises a nucleoside-modified RNA. In one embodiment, the composition comprises a nucleoside-modified mRNA. Nucleoside-modified mRNA have particular advantages over non-modified mRNA, including for example, increased stability, low immunogenicity, and enhanced translation. Nucleoside-modified mRNA useful in the present invention is further described in U.S. Pat. No. 8,278,036, which is incorporated by reference herein in its entirety.

Modified Cell

The present invention includes a composition comprising a cell which comprises one or more TRIM proteins, one or more STUbLs, a nucleic acid encoding a one or more TRIM proteins, a nucleic acid encoding a one or more STUbLs or a combination thereof. In one embodiment, the cell is genetically modified to express a protein and/or nucleic acid of the invention. In certain embodiments, genetically modified cell is autologous to a subject being treated with the composition of the invention. Alternatively, the cells can be allogeneic, syngeneic, or xenogeneic with respect to the subject. In certain embodiment, the cell is able to secrete or release the expressed protein into extracellular space in order to deliver the peptide to one or more other cells.

The genetically modified cell may be modified in vivo or ex vivo, using techniques standard in the art. Genetic modification of the cell may be carried out using an expression vector or using a naked isolated nucleic acid construct.

In one embodiment, the cell is obtained and modified ex vivo, using an isolated nucleic acid encoding one or more proteins described herein. In one embodiment, the cell is obtained from a subject, genetically modified to express the protein and/or nucleic acid, and is re-administered to the subject. In certain embodiments, the cell is expanded ex vivo or in vitro to produce a population of cells, wherein at least a portion of the population is administered to a subject in need.

In one embodiment, the cell is genetically modified to stably express the protein. In another embodiment, the cell is genetically modified to transiently express the protein.

Substrates

The present invention provides a scaffold or substrate composition comprising a protein of the invention, an isolated nucleic acid of the invention, a cell expressing the protein of the invention, or a combination thereof. For example, in one embodiment, a protein of the invention, an isolated nucleic acid of the invention, a cell a cell expressing the protein of the invention, or a combination thereof is incorporated within a scaffold. In another embodiment, a protein of the invention, an isolated nucleic acid of the invention, a cell expressing the protein of the invention, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Therapeutic Methods

The present invention also provides therapeutic methods for a disease or disorder associated with protein misfolding, protein aggregates, or a combination thereof.

In various embodiments, diseases and disorders treatable by the methods of the invention include, but are not limited to: polyQ disorders such as SCA1, SCA2, SCA3, SCA6, SCA7, SCA17, Huntington's disease, Dentatorubral-pallidoluysian atrophy (DRPLA), Alzheimer's disease, Parkinson's disease, amyotrophic lateral sclerosis (ALS), transmissible spongiform encephalopathies (prion disease), tauopathies, Frontotemporal lobar degeneration (FTLD), AL amyloidosis, AA amyloidosis, Familial Mediterranean fever, senile systemic amyloidosis, familial amyloidotic polyneuropathy, hemodialysis-related amyloidosis, ApoAI amyloidosis, ApoAII amyloidosis, ApoAIV amyloidosis, Finnish hereditary amyloidosis, lysozyme amyloidosis, fibrinogen amyloidosis, Icelandic hereditary cerebral amyloid angiopathy, type II diabetes, medullary carcinoma of the thyroid, atrial amyloidosis, hereditary cerebral hemorrhage with amyloidosis, pituitary prolactinoma, injection-localized amyloidosis, aortic medial amyloidosis, hereditary lattice corneal dystrophy, corneal amyloidosis associated with trichiasis, cataract, calcifying epithelial odontogenic tumor, pulmonary alveolar proteinosis, inclusion-body myostis, and cuteaneous lichen amyloidosis. In certain embodiments, the method comprises the treatment or prevention of cancer associated with p53 mutant aggregates, including but not limited to bladder carcinoma, astrocytoma, pharynx carcinoma, lymphoma, and adenocarcinoma.

It will be appreciated by one of skill in the art, when armed with the present disclosure including the methods detailed herein, that the invention is not limited to treatment of a disease associated with protein misfolding or protein aggregates that is already established. Particularly, the disease or disorder need not have manifested to the point of detriment to the subject; indeed, the disease or disorder need not be detected in a subject before treatment is administered. That is, significant signs or symptoms of the disease or disorder do not have to occur before the present invention may provide benefit. Therefore, the present invention includes a method for preventing a disease or disorder associated with protein misfolding or protein aggregates, in that a modulator composition, as discussed previously elsewhere herein, can be administered to a subject prior to the onset of the disease or disorder, thereby preventing the disease or disorder.

One of skill in the art, when armed with the disclosure herein, would appreciate that the prevention of a disease associated with protein misfolding or protein aggregates, encompasses administering to a subject a modulator composition as a preventative measure against the development of, or progression of a disease associated with protein misfolding or protein aggregates. As more fully discussed elsewhere herein, methods of modulating the level or activity of a gene, or gene product, encompass a wide plethora of techniques for modulating not only the level and activity of polypeptide gene products, but also for modulating expression of a nucleic acid, including either transcription, translation, or both.

Additionally, as disclosed elsewhere herein, one skilled in the art would understand, once armed with the teaching provided herein, that the present invention encompasses methods of treating, or preventing, a wide variety of diseases associated with protein misfolding or protein aggregates, where modulating the level or activity of a gene, or gene product treats or prevents the disease. Various methods for assessing whether a disease is associated protein misfolding or protein aggregates are known in the art. Further, the invention encompasses treatment or prevention of such diseases discovered in the future.

In one aspect, the method comprises use of one or more TRIM proteins to stabilize a misfolded protein. In certain aspects, stabilization of a functional misfolded protein via one or more TRIM proteins described herein can treat or prevent a disease or disorder associated with the misfolded protein. For example, in one embodiment, stabilization of mutant cystic fibrosis transmembrane conductance regulator (CFTR), via one or more TRIM proteins described herein, would allow mutant CFTR to function instead of being degraded. It is envisioned that using TRIM proteins to stabilize misfolded proteins can be used to treat cystic fibrosis and other diseases associated with degradation of partially functional proteins. Stabilization of proteins, via one or more TRIM proteins described herein, can be used to treat any disease or disorder associated with degradation of functional mutant protein, including but not limited to cystic fibrosis and lysosomal storage diseases such as Gaucher's disease and Fabry's disease.

The invention encompasses administration of a modulator of a gene, or gene product. To practice the methods of the invention; the skilled artisan would understand, based on the disclosure provided herein, how to formulate and administer the appropriate modulator composition to a subject. The present invention is not limited to any particular method of administration or treatment regimen.

In one embodiment, the method comprises administering to the subject in need an effective amount of a composition that increases the expression or activity of one or more TRIM protein or one or more STUbLs.

For example, in one embodiment, the method comprises administering to the subject in need an effective amount of a composition that increases the expression or activity of one or more of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30.

In one embodiment, the method comprises administering to the subject in need an effective amount of a composition that increases the expression or activity of one or more of RNF4 and RNF111 (Arkadia).

In one embodiment, the method comprises administering to the subject an effective amount of a composition that increases the expression or activity of one or more TRIM proteins and one or more STUbLs.

In one embodiment, the method comprises increasing the expression or activity of the one or more TRIM proteins or one or more STUbLs in at least one neural cell of the subject. For example, in certain embodiments, the method comprises increasing the expression or activity of the one or more TRIM proteins or one or more STUbLs in a at least one neuron, astrocyte, oligodendrocyte, Perkinje cell, pyramidal cell, or the like.

In one embodiment, the method comprises contacting the neural tissue of a subject with an effective amount of a composition that increases the expression or activity of one or more components of the one or more TRIM proteins or one or more STUbLs. For example, in certain embodiments, the method comprises contacting a neuron, astrocyte, oligodendrocyte, Perkinje cell, pyramidal cell, or the like, of a subject with an effective amount of a composition that increases the expression or activity of one or more TRIM proteins or one or more STUbLs.

One of skill in the art will appreciate that the modulators of the invention can be administered singly or in any combination. Further, the modulators of the invention can be administered singly or in any combination in a temporal sense, in that they may be administered concurrently, or before, and/or after each other. One of ordinary skill in the art will appreciate, based on the disclosure provided herein, that the modulator compositions of the invention can be used to prevent or to treat a disease or disorder associated with a misfolded protein or protein aggregate, and that a modulator composition can be used alone or in any combination with another modulator to effect a prophylactic or therapeutic result.

In various embodiments, any of the modulators of the invention described herein can be administered alone or in combination with other modulators of other molecules associated with a disease associated with protein misfolding or protein aggregates. In various embodiments, any of the modulators of the invention described herein can be administered alone or in combination with other therapeutic or preventative agents which may be used to treat or prevent a disease associated with protein misfolding or protein aggregates. Exemplary therapeutic agents which may be used in combination with the modulators of the present invention include, but is not limited to, anti-amyloid-$\beta$ antibodies and anti-tau antibodies.

Gene Therapy

Contacting cells in a subject with a nucleic acid composition that encodes a protein that increases the expression or activity of one or more TRIM proteins or one or more STUbLs can inhibit or delay the onset of one or more symptoms of a disease or disorder associated with protein misfolding or protein aggregates.

In one embodiment, the nucleic acid composition of the present invention encodes one or more peptides. For example, in one embodiment, a nucleic acid composition can encode a peptide that comprises an amino acid sequence of one or more TRIM proteins. For example, in one embodiment, the nucleic acid composition encodes a peptide comprising one or more of human TRIM3, TRIM4, TRIM5, TRIM6, TRIM7, TRIM9, TRIM11, TRIM13, TRIM14, TRIM15, TRIM16, TRIM17, TRIM19 (also referred to herein as "PML"), TRIM20, TRIM21, TRIM24, TRIM25, TRIM27, TRIM28, TRIM29, TRIM32, TRIM34, TRIM39, TRIM43, TRIM44, TRIM45, TRIM46, TRIM49, TRIM50, TRIM52, TRIM58, TRIM59, TRIM65, TRIM67, TRIM69, TRIM70, TRIM74 and TRIM75; and mouse TRIM30. In certain embodiments, the nucleic acid composition encodes a peptide comprising the amino acid sequence of one or more STUbLs. For example, in one embodiment, the nucleic acid composition encodes a peptide comprising one or more of RNF4 and RNF111 (Arkadia).

The invention should also be construed to include any form of a nucleic acid encoding a peptide having substantial homology to the peptides disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the peptides disclosed herein.

In one embodiment, the composition of the invention comprises a nucleic acid encoding a peptide, a fragment of a peptide, a homolog, a variant, a derivative or a salt of a peptide described herein. For example, in certain embodiments, the composition comprises a nucleic acid encoding a peptide comprising one or more TRIM proteins, a fragment of one or more TRIM proteins, a homolog of one or more TRIM proteins, a variant of one or more TRIM proteins, or a derivative of one or more TRIM proteins. In certain embodiments, the composition comprises a nucleic acid encoding a peptide comprising one or more STUbLs, a fragment of one or more STUbLs, a homolog of one or more STUbLs, a variant of one or more STUbLs, or a derivative of one or more STUbLs.

According to the present invention, a method is also provided of supplying protein to a cell which carries a normal, or a mutant gene, associated with diminished or insufficient activity of one or more TRIM proteins or one or more STUbLs. Supplying protein to a cell with a mutant gene should allow normal functioning of the recipient cells. The nucleic acid encoding a peptide may be introduced into the cell in a vector such that the nucleic acid remains extrachromosomal. In such a situation, the nucleic acid will be expressed by the cell from the extrachromosomal location. More preferred is the situation where the nucleic acid or a part thereof is introduced into the cell in such a way that it integrates into the cell's genome or recombines with the endogenous mutant gene present in the cell. Vectors for introduction of genes both for recombination, for integration, and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, a nucleic acid, where applicable, may be employed in gene therapy methods in order to increase the level or activity of the peptides of the invention even in those persons in which the wild type gene is expressed at a "normal" level, but the gene product is insufficiently functional.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g., by substituting their negatively charged phosphodiester groups by uncharged groups. One or more TRIM proteins or one or more STUbLs of the present invention can be delivered using gene therapy methods, for example locally in neural cell or tissue or systemically (e.g., via vectors that selectively target specific tissue types, for example, tissue-specific adeno-associated viral vectors). In some embodiments, primary cells harvested from the individual can be transfected ex vivo with a nucleic acid encoding any of the peptides of the present invention, and then returned the transfected cells to the individual's body.

Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., Circulation 97: 12, 1114-1123 (1998), Fatham, C. G. 'A gene therapy approach to treatment of autoimmune diseases', Immun. Res. 18:15-26 (2007); and U.S. Pat. No. 7,378,089, both incorporated herein by reference. See also Bainbridge J W B et al. "Effect of gene therapy on visual function in Leber's congenital Amaurosis". N Engl J Med 358:2231-2239, 2008; and Maguire A M et al. "Safety and efficacy of gene transfer for Leber's Congenital Amaurosis". N Engl J Med 358:2240-8, 2008.

There are two major approaches for introducing a nucleic acid encoding a peptide or protein (optionally contained in a vector) into a patients cells; in vivo and ex vivo. For in vivo delivery, in certain instances, the nucleic acid is injected directly into the patient, sometimes at the site where the protein is most required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Gene therapy would be carried out according to generally accepted methods, for example, as described by Friedman et al., 1991, Cell 66:799-806 or Culver, 1996, Bone Marrow Transplant 3:S6-9; Culver, 1996, Mol. Med. Today 2:234-236. In one embodiment, cells from a patient would be first analyzed by the diagnostic methods known in the art, to ascertain the expression or activity of one or more TRIM proteins or one or more STUbLs. A virus or plasmid vector, containing a copy of the gene or a functional equivalent thereof linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992, J. Gen. Virol. 73:1533-1536), adenovirus (Berkner, 1992; Curr. Topics Microbiol. Immunol. 158:39-66), vaccinia virus (Moss, 1992, Current Opin. Biotechnol. 3:518-522; Moss, 1996, PNAS 93:11341-11348), adeno-associated virus (Russell and Hirata, 1998, Mol. Genetics 18:325-330), herpesviruses including HSV and EBV (Fink et al., 1996, Ann. Rev. Neurosci. 19:265-287), lentiviruses (Naldini et al., 1996, PNAS 93:11382-11388), Sindbis and Semliki Forest virus (Berglund et al., 1993, Biotechnol. 11:916-920), and retroviruses of avian (Petropoulos et al., 1992, J. Virol. 66:3391-3397), murine (Miller, 1992, Hum. Gene Ther. 3:619-624), and human origin (Shimada et al., 1991; Helseth et al., 1990; Page et al., 1990; Buchschacher and Panganiban, 1992, J. Virol. 66:2731-2739). Most human gene therapy protocols have been based on disabled murine retroviruses, although adenovirus and adeno-associated virus are also being used.

Nonviral gene transfer methods known in the art include chemical techniques such as calcium phosphate coprecipitation; mechanical techniques, for example microinjection; membrane fusion-mediated transfer via liposomes; and direct DNA uptake and receptor-mediated DNA transfer (Curiel et al., 1992, Am. J. Respir. Cell. Mol. Biol 6:247-252). Viral-mediated gene transfer can be combined with direct in vitro gene transfer using liposome delivery, allowing one to direct the viral vectors to the tumor cells and not into the surrounding non-dividing cells. Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration.

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes a protein, expression will produce the protein. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

In certain embodiments, the method comprises the use of gene transfer techniques which target an isolated nucleic acid directly to neural tissue. Receptor-mediated gene transfer, for example, is accomplished by the conjugation of a nucleic acid molecule (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, co-infection with adenovirus can be included to disrupt endosome function.

Pharmaceutical Compositions and Formulations

The invention also encompasses the use of pharmaceutical compositions of the invention or salts thereof to practice the methods of the invention. Such a pharmaceutical composition may consist of at least one modulator composition of the invention or a salt thereof in a form suitable for administration to a subject, or the pharmaceutical composition may comprise at least one modulator composition of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In one embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol or sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intracerebral, epidural, intracerebroventricular, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Diagnostic Methods

The present invention provides a method to diagnose a subject having or at risk for developing a disease or disorder associated with protein misfolding or protein aggregates. For example, in one embodiment, the method comprises using the level of expression or activity of one or more TRIM proteins or one or more STUbLs as diagnostic markers. In one embodiment, the method comprises detecting the presence of a genetic mutation in a nucleic acid encoding one or more TRIM proteins or one or more STUbLs.

In one embodiment, the method is used to diagnose a subject as having a disease or disorder associated with protein misfolding or protein aggregates. In one embodiment, the method is used to diagnose a subject as being at risk for developing a disease or disorder associated with protein misfolding or protein aggregates. In one embodiment, the method is used to evaluate the effectiveness of a therapy for a neurodegenerative disease or disorder associated with protein misfolding or protein aggregates.

In one embodiment, the method comprises collecting a biological sample from a subject. Exemplary samples include, but are not limited to blood, urine, feces, sweat, bile, serum, plasma, tissue biopsy, and the like. For example, in one embodiment, the sample comprises at least one cell of neural tissue. In one embodiment, the sample comprises a neuron, astrocyte, oligodendrocyte, Perkinje cell, pyramidal cell, or the like.

Methods for detecting a reduced expression or activity of one or more TRIM proteins or one or more STUbLs comprise any method that interrogates a gene or its products at either the nucleic acid or protein level. Such methods are well known in the art and include, but are not limited to, nucleic acid hybridization techniques, nucleic acid reverse transcription methods, and nucleic acid amplification methods, western blots, northern blots, southern blots, ELISA, immunoprecipitation, immunofluorescence, flow cytometry, immunocytochemistry. In particular embodiments, disrupted gene transcription is detected on a protein level using, for example, antibodies that are directed against specific proteins. These antibodies can be used in various methods such as Western blot, ELISA, immunoprecipitation, flow cytometry, or immunocytochemistry techniques.

Methods of Manufacturing Recombinant Protein

In certain embodiments, the present invention provides a method of using one or more TRIM proteins, one or more STUbLs, or a combination thereof, in the production of a recombinant protein of interest. For example, the one or more TRIM proteins, one or more STUbLs, or a combination thereof, can be used to disaggregate protein aggregates of the recombinant protein of interest, thereby allowing for the production and collection of the recombinant protein of interest.

In certain embodiments, the method comprises administering to a cell one or more TRIM proteins, one or more STUbLs, a nucleic acid molecule encoding one or more TRIM proteins, a nucleic acid molecule encoding one or more STUbLs, or a combination thereof. In certain embodiments, the cell is modified to express the recombinant protein of interest. The cell may be of any expression system, including, but not limited to a yeast expression system, bacterial expression system, insect expression system, or mammalian expression system.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: A Cellular System that Degrades Misfolded Proteins and Protects Against Neurodegeneration Misfolded proteins compromise cellular function and cause disease. How these proteins are detected and degraded is not well understood. The experiments presented herein show that PML (also known as TRIM19) and the SUMO-dependent ubiquitin ligase RNF4 act together to promote the degradation of misfolded proteins in the mammalian cell nucleus. PML selectively interacts with misfolded proteins through distinct substrate recognition sites and conjugates these proteins with the small ubiquitin-like modifiers (SUMOs) through its SUMO ligase activity. SUMOylated misfolded proteins are then recognized and ubiquitinated by RNF4 and are subsequently targeted for proteasomal degradation. Further, it is demonstrated herein that PML deficiency exacerbates polyglutamine (polyQ) disease in a mouse model of spinocerebellar ataxia 1 (SCA1). These findings reveal a mammalian system that removes misfolded proteins through sequential SUMOylation and ubiquitination and define its role in protection against protein-misfolding diseases.

The promyelocytic leukemia protein (PML; also known as TRIM19) is a member of the tripartite motif (TRIM) family of proteins, which contain an N-terminal TRIM/BRCC region, consisting of a RING domain, one or two B boxes, and a coiled-coil (CC) motif, followed by a variable C-terminal region. PML is predominantly a nuclear protein and is the eponymous component of PML nuclear bodies. It is implicated in a wide variety of cell processes, including apoptosis, transcription, DNA damage signaling, and antiviral responses (Bernardi and Pandolfi, 2007, Nat Rev Mol Cell Biol, 8: 1006-1016). Notably, PML also colocalizes with aggregates formed by polyQ proteins associated with SCAs (Skinner et al., 1997, Nature, 389, 971-974; Takahashi et al., 2003, Neurobiol Dis, 13: 230-237) and, upon overexpression, promotes degradation of at least one of them (mutant ataxin-7) (Janer et al., 2006, J Cell Biol, 174: 65-76). Despite the potential importance of these observations, the role of PML in the removal of misfolded proteins is not well understood. In particular, it is unclear whether PML plays a broad role in the removal of nuclear misfolded proteins. The critical issue of the molecular mechanisms by which PML removes misfolded proteins is unaddressed. Moreover, the physiological relevance of the effect of PML on misfolded proteins is not known.

The materials and methods employed in these experiments are now described.

Plasmids

All proteins are of human origin unless otherwise indicated. Plasmids for expressing the following proteins in mammalian cells were made in pRK5 by PCR, and each was fused with HA, FLAG, or 6xHis tag, or GST or GFP protein at the NH2- or COOH-terminus as indicated: FLAG-PML mutants (isoform IV unless otherwise indicated); GST-PML; Atxn1 82Q-GFP, HA-Atxn1 82Q-FLAG, FLAG-Atxn1 82Q; HA-Httex1p 97QP and HA-Httex1p 97QP(KR); FLAG-nFluc-GFP, FLAG-nFlucSM-GFP, and FLAG-nFlucDM-GFP; HA-RNF4, HA-RNF4 SIMm, HA-RNF4-FLAG, and HA-RNF4 SIMm-FLAG; and HA-SUMO2 KR. Atxn1 82Q plasmids were made based on the FLAG-Atxn1 82Q/pcDNA plasmid provided by H. Orr (Riley et al., 2005, J Biol Chem, 280: 21942-21948); Httex1p 97QP and Httex1p 97QP(KR) (in which K6, K9, and K15 were changed to Arg) are based on Steffan et al., 2004, Science, 304: 100-104; and nFluc plasmids based on Gupta et al., 2011, Nat Methods, 8: 879-884. Each nFluc protein was fused to the SV40 nuclear localization signal (PKKKRKV) (SEQ ID NO: 147) at the NH2-terminus and to GFP at the COOH-terminus. In FlucDM, R188 and R261 were changed to Glu; In FlucSM, R188 was changed to Glu (Gupta et al., 2011, Nat Methods, 8: 879-884). The template for PCR amplification of RNF4 was purchased from Open Biosystems (gene accession number: NM002938). In RNF4 SIMm, the following resides within SIMs were changed to Ala: 136, L38, and V39 (SIM1); 146, V47, and L49 (SIM2); V57, V58, and V59 (SIM3); and V67, V68, 169 and V70 (SIM4). In SUMO2 KR, the internal SUMOylation consensus site Lys11 was mutated to Arg.

For bacterial expression, GST fusions of Htt 25Q, Htt 103Q, Htt 52Q, Htt 52Q cc-, PML CC-FLAG, RNF4, and RNF4 SIMm were constructed in pGEX-1ZT, a derivative of pGEX-1λT with additional cloning sites. Htt 25Q, Htt 52Q and Htt 103Q contained the Htt amino acids 1-17 followed by a polyQ stretch of the indicated length (Krobitsch and Lindquist, 2000, Proc Natl Acad Sci USA, 97: 1589-1594). Htt 52Q and Htt 52Q cc- cDNAs were assembled by joining synthetic oligos. FLAG-PML F12 (571-633)-6xHis was constructed in pET28a. All plasmids generated for this study were confirmed by DNA sequencing.

The following plasmids were previously described: FLAG-PML, FLAG-PML M6 (which had the C57S, C60S, C129A, C132A, C189A, and H194A mutations), 6xHis-SUMO1, and 6xHis-SUMO2 (Chu and Yang, 2011, Oncogene, 30: 1108-1116); FLAG-Atxn1 82Q and FLAGAtxn1 30Q (Riley et al., 2005, J Biol Chem, 280: 21942-21948); luciferase-6xHis (a *Photinus pyralis* luciferase variant) (Sharma et al., 2010, Nat Chem Biol, 6: 914-920); GST-rRNF4 (where "r" denotes rat origin, same below), GSTrRNF4 CS1 (in which C136 and C139 were changed to Ser), FLAG-rRNF4, and FLAGrRNF4 CS (in which C136, C139, C177, and C180 were changed to Ser) (Hakli et al., 2004, FEBS Lett, 560: 56-62); and PML isoforms I, II, III, IV, and VI (used in FIG. 8A) (Xu et al., 2005, Mol Cel, 17: 721-732).

siRNAs

PML and RNF4 siRNAs were purchased from Qiagen, and the sense strand sequences were: PML#4, CTCCAA-GATCTAAACCGAGAA (SEQ ID NO: 148); PML#9, CACCCGCAAGACCAACAACAT (SEQ ID NO: 149); RNF4#5, CCCTGTTTCCTAAGAACGAAA (SEQ ID NO: 150); RNF4#6, TAGGCCGAGCTTTGCGGGAAA (SEQ ID NO: 151); RNF4#8, AAGACTGTTTCGAAACCAACA (SEQ ID NO: 152). RNF4 was knocked down with either siRNAs individually or in combination at an equal molar ratio. SUMO1 siRNA (Thermo Scientific, siGENOME SMARTpool M-016005-03-0005) was a pool of 4 target-specific siRNA duplexes. The sense strand sequences were: TCAAGAAACUCAAAGAAUC (SEQ ID NO: 153), GACAGGGTGTTCCAATGAA (SEQ ID NO: 154), GGTTTCTCTTTGAGGGTCA (SEQ ID NO: 155), and GAATAAATGGGCATGCCAA (SEQ ID NO: 156). SUMO2/3 siRNAs (Santa Cruz sc-37167) was a pool of three different siRNA duplexes, and sense strand sequences were CCCAUUCCUUUAUUGUACA (SEQ ID NO: 157), CAGAGAAUGACCACAUCAA (SEQ ID NO: 158), and CAGUUAUGUUGUCGUGUAU (SEQ ID NO: 159).

Cell Culture and Transfection

HeLa cells (from ATCC) and U2OS cells expressing GFP-SUMO2 or GFP-SUMO3 (Mukhopadhyay et al., 2006, J Cell Biol, 174: 939-949) were maintained in standard culture conditions. DNA plasmids were transfected into cells using Lipofectamine 2000. When PML and Atxn1 were co-transfected, either FLAG-PML plus Atxn1 82Q/30Q-GFP or HA-PML plus FLAG-Atxn1 82Q/30Q was used. HA-RNF4 and HA-RNF4-FLAG plasmids were used for testing protein expression and cellular localization, respectively.

siRNAs using Lipofectamine 2000 or RNAiMAX (Invitrogen), according to the manufacturer's instructions. For knockdown experiments, two rounds of siRNA transfection were performed on consecutive days. When both DNA and siRNA were transfected, DNA was transfected 4-6 hours after treatment with combined RNF4 siRNAs, and a day after treatment with other siRNAs. MG132 (Sigma) was added 24 hours after the last transfection at 7.5-10 µM (final concentration) for 4-5 hours.

Generation of RNF4 shRNA Stable Cell Lines shRNA against human RNF4, cloned into pLKO.1, was obtained from Thermo Scientific. The antisense sequence of shRNF4 is TGGCGTTTCTGGGAGTATGGG (SEQ ID NO: 160) (TRCN0000017054). For lentiviral production, 293T cells were transfected with lentiviral vectors, Gag helper plasmid, Rev helper plasmid, and VSVG helper plasmid. Virus-containing media was collected at 48 hours and 72 hours and spun for 5 minutes at 100 g. HeLa cells were transduced using virus-containing supernatant with polybrene and selected with puromycin. The pLKO.1 vector was used to create control stable cells.

Cell Lysate Fractionation, Filter Retardation Assay, and Western Blot

Cell lysates were made in NP-40-containing buffer and fractionated into supernatant (NS) and pellet by centrifugation. Both fractions were boiled in buffer containing 2% SDS and analyzed by western blot. A portion of the pellet was analyzed by a filter retardation assay for SR species.

Samples were prepared as described with modifications (Janer et al., 2006, J Cell Biol, 174: 65-76). Cells were harvested and lysed for 30 min on ice in buffer containing 50 mM Tris, pH 8.8, 100 mM NaCl, 5 mM $MgCl_2$, 0.5% NP-40, 2 mM DTT, 250 IU/ml benzonase (Sigma), 1 mM PMSF, 1× complete protease cocktail (Roche), and 20 mM N-Ethylmaleimide (NEM; Sigma). Protein concentrations were determined by Bradford assay (Bio-Rad Labs). The whole cell lysates were centrifuged at 13,000 rpm for 15 minutes at 4° C. The supernatant, containing NP-40-soluble (NS) proteins, was analyzed by SDS-PAGE. The pellet was resuspended in the pellet buffer (20 mM Tris, pH 8.0, 15 mM MgCl2, 2 mM DTT, 250 IU/ml benzonase, 1 mM PMSF, 1× complete protease cocktail, and 20 mM NEM) and incubated for 30 minutes on ice. The pellet fraction was boiled in 2% SDS, 50 mM DTT. One portion of the boiled pellet fraction was resolved by SDS-PAGE, and proteins entering the gel (SDS-soluble, SS) were detected by Western blot. The other portion was applied to a membrane filter with 0.2 µm pore size as previously described (Wanker et al., 1999, Methods Enzymol, 309: 375-386), and the SDS-resistant (SR) aggregates retained on the filter was analyzed by immunoblotting.

Primary antibodies against the following proteins were used for Western blot with product information and dilutions indicated: PML (rabbit, H-238, 1:1,000 and goat, N-19, 1:500), ubiquitin (mouse, P4D1, 1:10,000), and HA (rabbit, Y-11, 1:500) (Santa Cruz Biotechnology); FLAG (mouse, M2, 1:7,500), actin (rabbit, 1:10,000), and β-tubulin (mouse, 1:5,000) (Sigma); GFP (mouse, 1:4,000) (Clonetech); GST (goat, 1:1000, GE Healthcare Life Sciences); SUMO1 (mouse, 1:500, Invitrogen); SUMO2/3 (rabbit, 1:250, Abgent); HA (for transfected HA-RNF4) (rat, 3F10, horseradish peroxidase or HRP-conjugated, 1:10,000) (Roche); RNF4 (mouse, 1:500, Abnova, and a mouse monoclonal antibody developed by Abmart using antigen peptide DLTH-NDSVVI (SEQ ID NO: 161), 1:1,000). Transfected FLAG-PML was detected by anti-FLAG antibody, and transfected HA-PML and HA-RNF4 were detected by HA antibody.

The secondary antibodies were either conjugated to HRP (Santa Cruz Biotechnology), or labeled with IRD Fluor 800 or IRD Fluor 680 (LI-COR, Inc.). Western blots were developed using ECL reagents and analyzed using ImageJ, or scanned with the Odyssey infrared imaging system, and analyzed using Image Studio Lite (LI-COR, Inc.).

Immunofluorescence of Cultured Cells

Cells cultured on coverslips were fixed with 4% paraformaldehyde for 15 minutes, permeabilized with 0.2% Triton X-100 for 15 minutes, blocked with 1% BSA, and incubated with antibodies as indicated. Cells were mounted with medium containing DAPI (for DNA detection) (Vector Labs), and the images were acquired with a Nikon Eclipse E800 or Olympus IX81 microscope. The following primary antibodies were used with product information and concentrations indicated: PML (rabbit, H-238 and mouse, PG-M3, 1:100), RNF4 (goat, C-15, 1:25) (Santa Cruz Biotechnology), and FLAG (for transfected FLAG-PML and HA-RNF4-FLAG) (mouse, M2, 1:2,000) (Sigma). Secondary antibodies were FITC-conjugated anti-mouse, anti-rabbit (Zymed), and anti-goat (Invitrogen) IgGs; Texas Red-conjugated anti-mouse and anti-rabbit IgGs (Vector labs); and Rhodamine Red-X conjugated anti-goat (Jackson ImmunoResearch Labs).

For quantification of Atxn1 82Q, Httex1p 97QP, and SUMO2-positive Atxn1 82Q aggregates, approximately 400, 500, and 200 cells, respectively, from ten or more randomly selected fields were examined. The sizes of Atxn1 82Q inclusions were measured using ImageJ, and cells were categorized based on the largest inclusion in cells. P-value for the proportions of cells with aggregates of various sizes in the presence and the absence of PML was calculated using a chi-squared test. For cells transfected with Httex1p 97QP, approximately 30% of them had either cytoplasmic or nuclear aggregates.

Assays of Protein Half-Life

Cells were pulse labeled in Met- and Cys-free DMEM medium supplemented with [$^{35}$S]Met and [$^{35}$S]Cys, and then cultured in regular DMEM. Alternatively, cells were treated with CHX. Immunoprecipitated [$^{35}$S]Atxn1 82Q or unlabeled Atxn1 82Q in cell lysate was analyzed by autoradiography or western blot.

For pulse-chase analysis, HeLa cells were transfected with FLAG-Atxn1 82Q alone or together with a moderate amount of PML. 17 h after transfection, cells were cultured in Met and Cys-free DMEM medium for 30 min, and then pulse labeled for 30 min with [$^{35}$S]Met and [$^{35}$S]Cys (100 µCi/ml each). Afterwards, cells were rinsed twice with PBS and chased in DMEM with 10% FBS for 0-18 h. Cells were lysed in IP-lysis buffer (50 mM HEPES, pH 7.5, 150 mM NaCl, 0.5% NP-40, and 2 mM DTT) containing 2% SDS and 50 mM DTT, and boiled at 95° C. for 10 minutes. The whole cell lysates were centrifuged at 13,000 rpm for 15 minutes. The supernatants were diluted 20-fold in IP-lysis buffer and incubated with anti-FLAG M2 beads at 4° C. overnight. The beads were sequentially washed with IP lysis buffer with additional 0, 0.5 M, and 1 M KCl, and boiled in a 2% SDS sample buffer. Samples were resolved by SDS-PAGE and analyzed by autoradiography. To better compare the half-life of Atxn1 82Q under different conditions, exposures with similar signal intensity at 0 hours were presented.

For cycloheximide (CHX) treatment of Atxn1 82Q-transfected cells, 150 µg/ml CHX was added to cell culture medium 4-5 hours after transfection. Cells were harvested and snap-frozen on dry ice at indicated time points, lysed, and fractioned for Western blot analysis. For CHX treatment of nFlucDM-transfected cells, 50 µg/ml CHX was added to cell culture medium 17 hours after transfection. Cells were harvested at indicated time points, and whole cell lysates were used for Western blot analysis.

Quantitative RT-PCR Analysis

Total RNA was extracted using TRIzol (Invitrogen). cDNA synthesis was carried out by reverse transcription of total RNA using the First Strand cDNA Synthesis Kit (Marligen Biosciences). A Taqman Gene Expression Assay (Applied Biosystems) with human Atxn1 (Hs00165656_m1) and 18s rRNA (4333760F) primers/probe sets were used for qPCR analysis.

Protein Purification

Figures 11A, 11B:
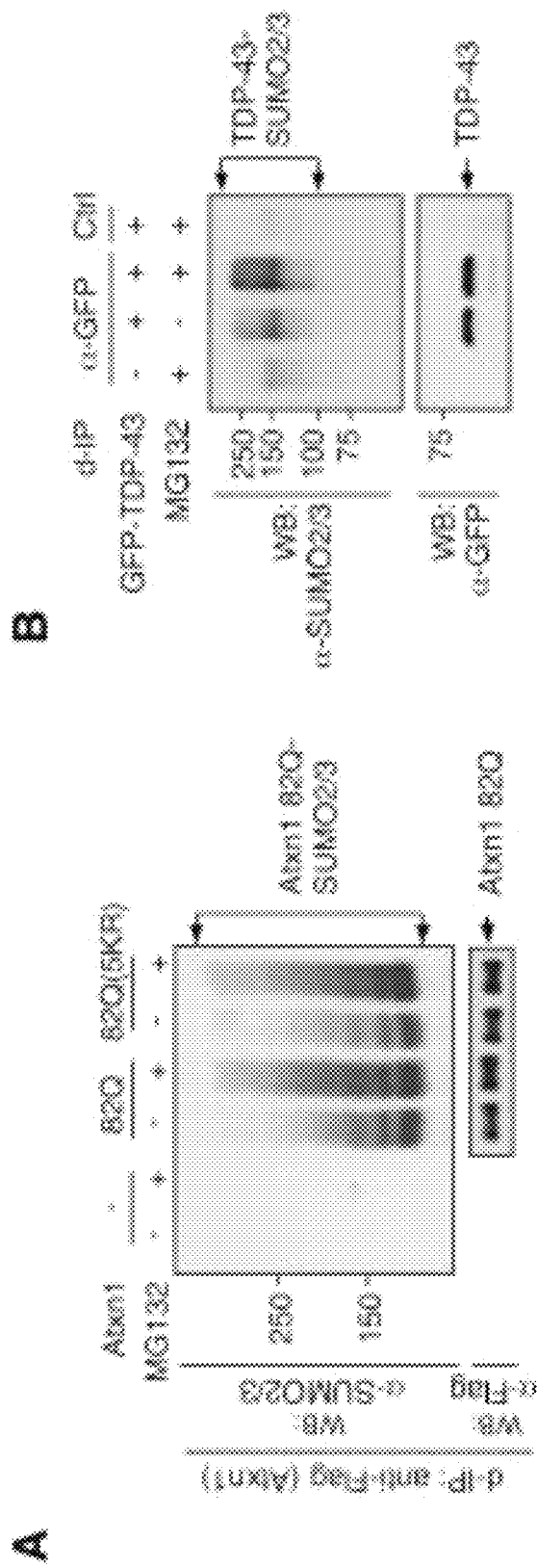
FIG. 11A through FIG. 11G, depicts the results of example experiments demonstrating the modification of misfolded proteins by SUMO2/3.
Figures 11C, 11D:
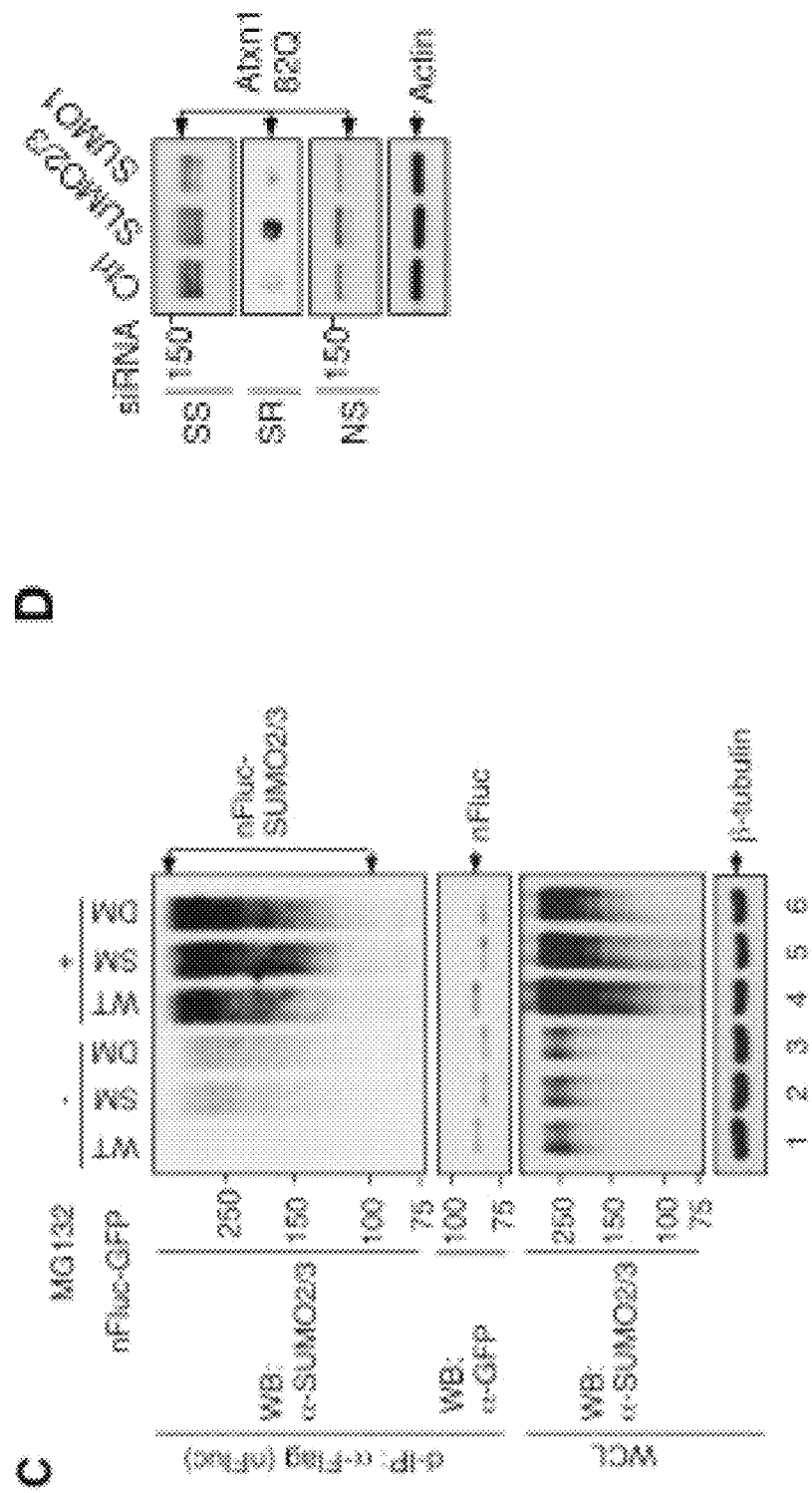
Figures 11E, 11F, 11G:
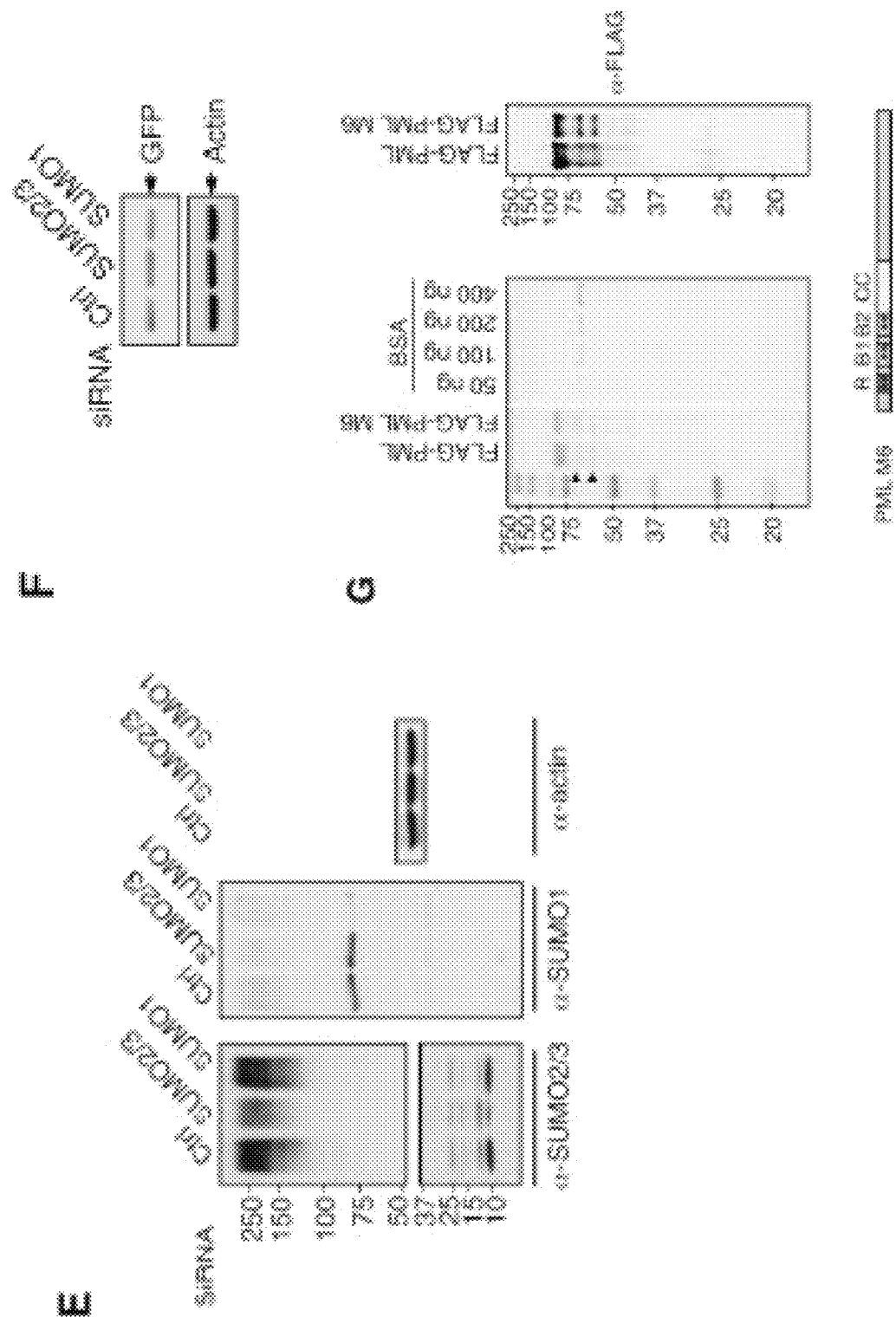

FLAG-PML, FLAG-PML M6, and FLAG-Atxn1 82Q-HA were expressed in 293T cells and purified by anti-FLAG M2 beads (Sigma) as previously described (Tang et al., 2006, Nat Cell Biol, 8: 855-862; Tang et al., 2004, J Biol Chem, 279: 20369-20377) with modifications. Cells were lysed in IP-lysis buffer (50 mM Tris, pH 7.5, 150 mM NaCl, 0.5% Triton X-100, 0.5% NP-40 and 2 mM DTT) supplemented with 1 mM PMSF, and 1× complete protease cocktail. For PML purification, IP-lysis buffer was also supplemented with 20 µM ZnCl2. The lysates were centrifuged at 13,000 rpm for 15 minutes. Supernatants were incubated with anti-FLAG M2 beads at 4° C. for 4 hours to overnight. M2 beads were sequentially washed with IP lysis buffers containing 0, 0.5, and 1 M KCl, and with an elution buffer (50 mM Tris, pH 7.5, 150 mM NaCl, and 2 mM DTT). The bound proteins were eluted in the elution buffer containing 0.1-0.3 mg/ml 3×FLAG peptide (Sigma). The major additional bands observed in the FLAG-PML and FLAG-PML M6 preps were derived from PML based on both Western blot and mass spectrometry analyses (FIG. 11G).

GST fusion of PML was expressed in 293T cells and purified using glutathione-Sepharose™ 4B beads (GE Healthcare Life Sciences) with similar lysis and wash conditions as described above. GST fusions of rRNF4, rRNF4 CS1, RNF4, and RNF4 SIMm were expressed in *Escherichia coli* BL21 DE3 or Rosetta 2 (EMD Chemicals) and purified as previously described (Hakli et al., 2001, J Biol Chem, 276: 23653-23660). The bacteria were grown at 37° C. to A 600 nm=0.6-0.8, and were induced for protein expression with 0.3 mM IPTG for 3 hours at 30° C. GST-tagged proteins were purified with glutathione beads. GST and GST fusions of Htt 25Q, Htt 103Q were purified similarly except that 0.1 mM IPTG was used for inducing protein expression. The bound proteins were eluted in the elution buffer containing 30 mM glutathione (Sigma).

Luciferase-6xHis was expressed in BL21 DE3 as previously described (Sharma et al., 2010, Nat Chem Biol, 6: 914-920). To generate immobilized native luciferase, Luc (N), Ni-NTA beads (Qiagen) were incubated with bacterial lysates and washed according to the manufacturer's instructions. Denatured luciferase, Luc (D), was generated by treating immobilized Luc (N) with 8 M urea for 5 minutes. A luciferase activity assay showed that only 0.2% of enzymatic activity remained after urea treatment. For control beads, lysates from bacteria expressing no luciferase were incubated with Ni-NTA beads in parallel.

To generate PML mutants used for luciferase peptide scans, FLAG-PML F12 (571-633)-6xHis and GST-PML CC-FLAG were expressed in BL21 DE cells at room temperature with 0.1 mM IPTG induction for 3 hours and 1 hour, respectively. Flag-PML F12 (571-633)-6xHis was purified first using M2 beads and the FLAG peptide elution, and was subjected to a second purification using Ni-NTA beads, according to the manufacturer's instructions. To generate the PML CC domain, a TEV protease cleavage site was introduced between GST and PML CC. The GST-PML CC-FLAG conjugated glutathione beads were incubated with TEV protease (Sigma) according to the manufacturer's instructions to release PML CC-FLAG from the GST moiety (and from the beads). PML CC-FLAG used for pull-down assay was generated by incubating the purified PML CC-FLAG proteins with M2 beads and washed as described above.

Pull-Down Assays

For FLAG pull-down assays, FLAG-PML, FLAG-GFP and PML CC-FLAG bound to anti-FLAG M2 beads were prepared as described above. Purified GST-Htt 25Q, GST-Htt 103Q, GST-Htt 52Q or GST-Htt 52Q cc- were centrifuged at 13,000 rpm for 15 minutes to remove any aggregated proteins. FLAG-PML (2.5 µg) or FLAG-GFP (1.1 µg) at comparable molarity was incubated with GST-Htt 25Q or GST-Htt 103Q (2.5 µg each) in the absence or presence of Hsp70 (2.5 µg) and Hsp40 (1.4 µg) (Enzo Life Sciences) in a final volume of 200 µl assay buffer (50 mM Tris, pH 7.5, 150 mM NaCl, and 2 mM DTT, 0.5% NP-40) for 2 hours at 4° C. The beads were washed three times with IP-lysis buffer in Compact Reaction Columns (Affymetrix/USB) and boiled in 2% SDS sample buffer. Samples were analyzed by Western blot. The PML CC pull-down assay was performed similarly, except M2 beads containing 1.6 µg PML CC-FLAG or control M2 beads were incubated with 5 µg GST or GST-Htt proteins.

For GST pull-down assay, 2 µg each of GST, GST-Htt 25Q, and GST-Htt 103Q proteins that bound to glutathione-Sepharose™ 4B beads were incubated with 400 µg lysates from 293T cells expressing FLAG-PML protein at 4° C. for 4 hours. The beads were washed three times with IP-lysis buffer in Compact Reaction Columns and boiled in 2% SDS sample buffer. Samples were analyzed by Western blot. For detecting the interaction between PML mutants and Htt, [$^{35}$S]Met-labeled full-length and mutant PML proteins were generated using the SP6 Coupled Transcription/Translation System (Promega) and incubated with GST, GST-25Q and GST-Htt 103Q that bound to beads in 150 µl IP-lysis buffer at 4° C. overnight. Beads were washed and boiled as described above. Input and pull-down samples were analyzed by autoradiography and Coomassie blue staining. For autoradiography, pull-down samples from the same experiments that were resolved on different gels were subjected to the same exposure time.

For the luciferase pull-down assay, 3 µg of Luc (N) or Luc (D) bound Ni-NTA beads or control beads prepared from an equal amount of bacterial lysate were incubated with purified GST (1 µg), GST-PML (3 µg) in the absence or presence of Hsp70 (3 µg) and Hsp40 (1.7 µg), or [$^{35}$S]Met-labeled full-length and mutant PML proteins in 200 µl PBS containing 15 mM Imidazole, 1 mM DTT, 0.5% Triton X-100 and 0.5% NP-40 at 4° C. for 4 hours. The beads were washed three times with PBS containing 20 mM Imidazole, 1 mM DTT, 0.5% Triton X-100 and 0.5% NP-40 and boiled. The input and pull-down samples were analyzed as described above.

Screening of Cellulose-Bound Peptides for Binding to PML Domains

A peptide library (13-mers overlapping by ten amino acids) for *Photinus pyralis* luciferase was prepared by automated spot synthesis (JPT peptide Technologies). The peptide array membrane was probed with purified PML SRS1 and SRS2 fragments. The peptide array membrane was blocked with Odyssey Blocking buffer (LI-COR, Inc) and incubated with FLAG-PML F12(571-633)-HisX6 or PML F4/CC-FLAG (150 nM each) in TBS-T (50 mM TRIS, pH 8.0, 137 mM NaCl, 2.7 mM KCl, 0.05% Tween and 1 mM DTT) at 4° C. for 2 hours. The membrane was washed and blotted with mouse anti-Flag and anti-mouse-HRP antibodies following the manufacturer's instructions. The blots were developed using ECL reagents. Background signal on blots with anti-Flag and anti-mouse-HRP antibodies alone was minimal even at long exposures. The peptide array membrane was regenerated according to the manufacturer's protocol.

SUMOylation and Ubiquitination Analysis

Cells or in vitro reaction mixtures were boiled in buffer containing 2% SDS and then diluted in buffer without SDS or passed through a Bio-Spin chromatography column to reduce the SDS concentration. Proteins were immunoprecipitated (denaturing IP or d-IP) and analyzed by western blot.

In Vivo SUMOylation and Ubiquitination Assays

Cells were transfected with FLAG-Atxn1, FLAG-nFluc-GFP, and other expression plasmids as indicated. For the experiments shown in FIG. 4A, a SUMO2-expressing plasmid was also used. Twenty four hours after transfection, cells were treated with 7.5 µM MG132 or DMSO for 5 hours or left untreated, and harvested in IP-lysis buffer supplemented with 2% SDS and 50 mM DTT. For denaturing immunoprecipitation (d-IP), cell lysates were boiled at 95° C. for 10 minutes. One aliquot was saved for Western blot analysis. The rest of the lysates were either diluted 20-fold in IP-lysis buffer or passed through a Bio-Spin chromatography column (Bio-Rad) equilibrated with IP-lysis buffer to reduce the SDS concentration. Lysates were then incubated with anti-FLAG (M2) beads at 4° C. for 4 hours or overnight. The beads were washed as described for FLAG-tagged protein purification, and boiled in 2% SDS sample buffer. Proteins from beads were analyzed by Western blot with anti-FLAG, -SUMO2/3, -SUMO1, -ubiquitin, and other antibodies as indicated. To better compare the levels of ubiquitinated or SUMOylated species, d-IP products containing similar levels of unmodified proteins were often used for Western blot analysis.

In Vitro SUMOylation Assays

Components for in vitro ubiquitination and SUMOylation reactions were purchased from Boston Biochem. In vitro SUMOylation assays were performed at 37° C. for 1.5 hours in 30 µl reaction buffer (50 mM Tris pH 7.5, 5.0 mM Mg2+-ATP, and 2.5 mM DTT) containing purified HA-Atxn1 82Q-FLAG (600 ng/200 nM), FLAG-PML (for FIG. 4D, 50 and 200 ng or 22 and 90 nM; for FIG. 4E 100 ng or 45 nM) or FLAG-PML M6 (100 ng or 45 nM), SAE1/SAE2 (125 nM), Ubc9 (1 µM), His-SUMO2 (25 µM), Hsp70 (420 ng/200 nM), Hsp40 (240 ng/200 nM) and BSA (0.1 µg/ml). The reaction mixtures were denatured by the addition of 30 µl IP-lysis buffer containing 2% SDS and 50 mM DTT and heating at 95° C. for 10 minutes. One aliquot of the heated reaction mixes were saved for Western blot analysis, and the rest were diluted 20-fold in IP-lysis buffer without SDS. HA-Atxn1-FLAG was immunoprecipitated by anti-HA beads (Roche) and analyzed for SUMO2/3 modification using anti-SUMO2/3 antibodies.

In Vitro Ubiquitination Assays

In vitro assays for RNF4 self-ubiquitination were performed at 37° C. for 1 hour in 10 µl reaction buffer (50 mM Tris pH 7.5 and 2.5 mM DTT) containing purified GST-RNF4 protein (250 ng/530 nM), UBE1 (125 nM), UbcH5a (625 nM), ubiquitin (2.5 µg/30 µM), and Mg$^{2+}$-ATP (2.5 mM). The reaction mixtures were heated at 95° C. for 10 minutes and analyzed by Western blot.

For in vitro ubiquitination of SUMOylated Atxn1 82Q, a mix of SUMOylated and unmodified Atxn1 82Q proteins was prepared as ubiquitination reaction substrate. M2 beads conjugated with FLAG-Atxn1 82Q-HA (1.5 µg/300 nM) and control M2 beads were mixed with 0.75 μM SAE1/SAE2, 12.5 μM Ubc9, 125 μM His-SUMO2, and 2.5 mM DTT in a total volume of 50 μl of Mg2+-ATP-Energy Regeneration Solution containing 5 mM ATP (Boston Biochem). To achieve sufficient Atxn1 82Q SUMOylation, the reaction was performed at 37° C. for 24 hours, and the reaction buffer was replaced after 12 hours. Beads were then washed sequentially with IP-lysis buffer with additional 0, 0.5, and 1 M KCl and with ubiquitination reaction buffer (50 mM Tris pH 7.5 and 150 mM NaCl) (Tang et al., 2006, Nat Cell Biol, 8: 855-862).

Atxn1 82Q beads and control beads were then incubated at 37° C. for 1 hour with ubiquitination reaction mixes in 20 μl volume containing GST-rRNF4 (0, 40, 160 and 500 ng, or 0, 43, 170, and 530 nM), UBE1 (100 nM), UbcH5a (500 nM), ubiquitin (5 μg/30 μM), and $Mg^{2+}$-ATP (2.5 mM) in reaction buffer (50 mM Tris-HCl pH 7.5, 150 mM NaCl, and 2.5 mM DTT). Afterwards, beads were separated from the supernatant and washed with IP-lysis buffer. Atxn1 82Q was denatured and released from the beads by the addition of IP-lysis buffer containing 2% SDS and 50 mM DTT and heat at 95° C. for 10 minutes. After dilution, Atxn1 82Q was immunoprecipitated with M2 beads. The IP products and the supernatant from the reaction were analyzed by Western blot.

Mouse Breeding and Genotyping

The heterozygous B05 transgenic mice ($Atxn1^{tg/-}$), which harbor the human SCA1-coding region with 82 CAG repeats driven by a Purkinje cell-specific promoter element, were provided (Burright et al., 1995, Cell, 82: 937-948). $PML^{-/-}$ mice were provided (Wang et al., 1998, Science, 279: 1547-1551). $Atxn1^{tg/-}$ mice (on FVB background) were mated with $PML^{-/-}$ (on 129Sv background). $PML^{+/-}$:$Atxn1^{tg/-}$ mice from the F1 generation were mated with $PML^{-/-}$ or $PML^{+/+}$ to generate mice used for Rotarod tests and pathology. The mating scheme did not affect the Rotarod performance, formation of aggregates, molecular layer thickness, or dendritic arborization of the F2 generation of PML+ or $PML^{+/-}$:$Atxn1^{tg/-}$ mice. The mouse genotype was determined by PCR either as described (Burright et al., 1995, Cell, 82: 937-948) (for Atxn1) or according to suggestions by the NCI Mouse Repository (for PML).

Accelerating Rotarod Test

An accelerating Rotarod apparatus (47600, Ugo Basile, Italy) was used to measure motor coordination and balance. Only naïve animals were used. Each animal was given three trials per day for four consecutive days, with a 1 hour rest between trials. For each trial, mice was placed on the Rotarod with increasing speed, from 4-80 rpm, over 10 minutes. Their latency to fall off the Rotarod (in seconds) was recorded.

Immunostaining and Pathological Analysis of Mouse Cerebellum

Paraffin-embedded cerebellar midsagital sections were stained with indicated antibodies and visualized using a Leica SP5 II laser scanning confocal microscope, or stained with hematoxylin and visualized using an Olympus BX51 microscope.

Immunohistochemistry and immunofluorescence were performed as previously described with modifications (Duda et al., 2000, J Neuropathol Exp Neurol, 59: 830-841; Emmer et al., 2011, J Biol Chem 286: 35104-35118). Paraffin-embedded cerebella were cut into 10-μm sections. For molecular layer measurements, three haematoxylin stained midsagittal sections with 100 μm intervals were analyzed per mouse. Twenty measurements at the primary fissure for each section were averaged.

To quantify Purkinje cell dendritic arborization, midsagittal sections of cerebella were stained with an antibody against the Purkinje cell-specific protein calbindin (mouse, CB-955, 1:250; Sigma). Twenty 0.5 μm optical sections were accumulated with Leica SP5 II laser scanning confocal microscope. The brightest continuous 12 sections (6 μm) were projected for maximum intensity. The fluorescence intensity profile from the same region of preculminate fissure was plotted using ImageJ.

To quantify Purkinje cells, midsagittal sections were stained with anti-calbindin antibody and comparable regions were used for cell counting. The length of the Purkinje cell layer was measured by drawing segmented line along Purkinje cell soma center using ImageJ. For each mouse, 350-900 neurons along approximately 30 mm were measured. The Purkinje cell density was determined by dividing the number of cells by the length of Purkinje cell layer.

To determine the number of Purkinje cells with aggregates, midsagittal sections were stained with anti-ubiquitin (mouse, Ubi-1, MAB1510, 1:2,000; Millipore) antibody. Three hundred cells or more were counted from the same brain regions per mouse. Images were taken using an Olympus BX51 microscope mounted with a DP71 Olympus digital camera.

Four mice per genotype were used for counting Purkinje cells of 1-year-old mice, two $PML^{+/+}$ mice per genotype for quantification of dendritic arborization, and three mice per genotype for the rest of the studies.

Statistical Analysis

The numbers of cells with aggregates were analyzed by chi-squared test and Student's t-test when appropriate. The behavioral scores and cerebellar pathology were analyzed by two-way ANOVA with repeated measurements and Student's t-test. All the data were analyzed using Prism5 software or Microsoft Excel 2008.

The results of the experiments are now described

PML Promotes Proteasomal Degradation of Pathogenic Ataxin-1 Protein

SCA1 is a fatal neurological disorder characterized by progressive ataxia and loss of neurons, especially cerebellar Purkinje cells. It is caused by the expansion of a polyQ stretch in the SCA1 gene product, Ataxin-1 (Atxn1) (Orr and Zoghbi, 2007, Annu Rev Neurosci, 30: 575-621). To investigate the role of PML in eliminating nuclear misfolded proteins, a cell culture model was generated in which a pathogenic Atxn1 protein with 82 contiguous glutamines that was C-terminally fused to the enhanced green fluorescent protein, Atxn1 82Q-GFP, was expressed in HeLa cells. Similar to pathogenic Atxn1 proteins in human SCA1 patients and mouse SCA1 transgenic models (Skinner et al., 1997, Nature, 389: 971-974), Atxn1 82Q-GFP was localized to the nucleus, exhibiting a diffuse localization pattern with markedly higher concentration in microscopically visible inclusions (FIG. 1A and FIG. 1B). Atxn1 82Q-GFP also yielded both NP-40-soluble (soluble or NS) and NP-40-insoluble (aggregated) species in cell lysates. The latter could be further divided into SDS-soluble (SS) and SDS-resistant (SR) species (FIG. 1C).

Figures 1A, 1B, 1C:
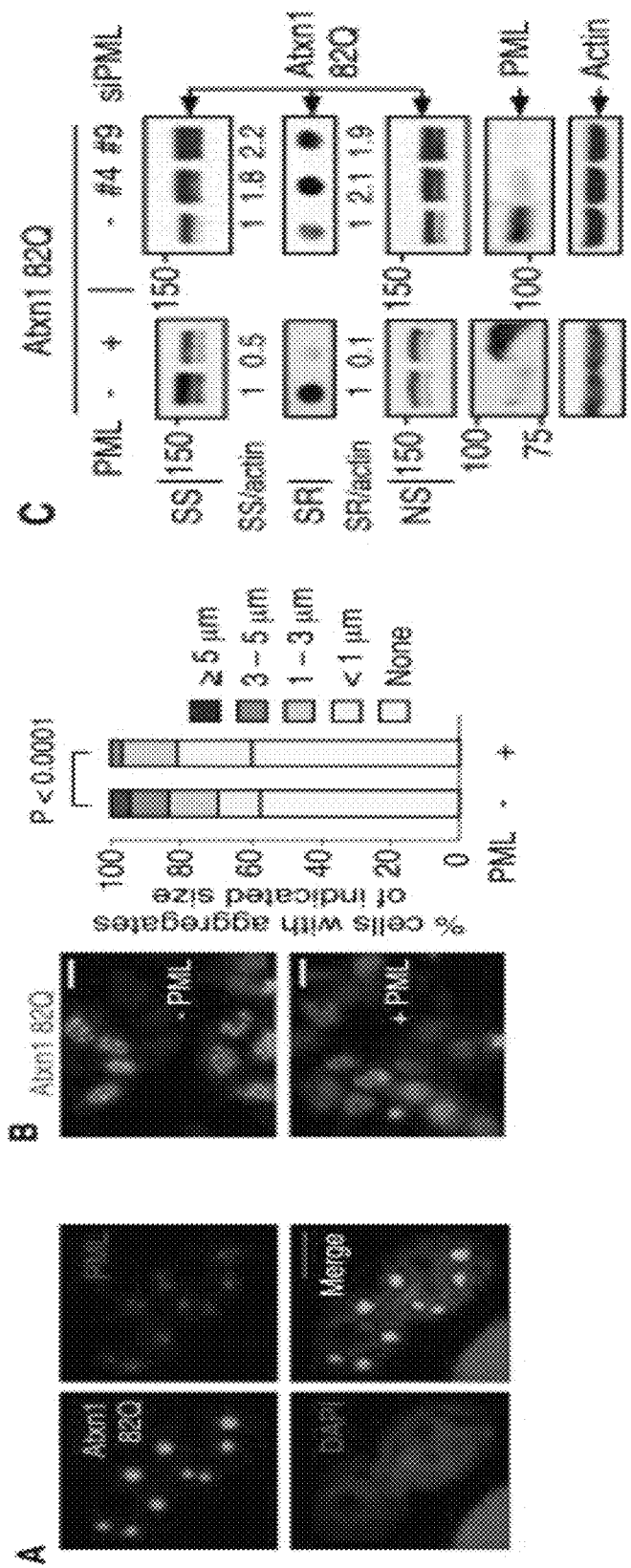
FIG. 1A through FIG. 1L, depicts the results of example experiments demonstrating that PML promotes the degradation of Atxn1 82Q and other nuclear misfolded proteins.
Figures 8A, 8B, 8C:
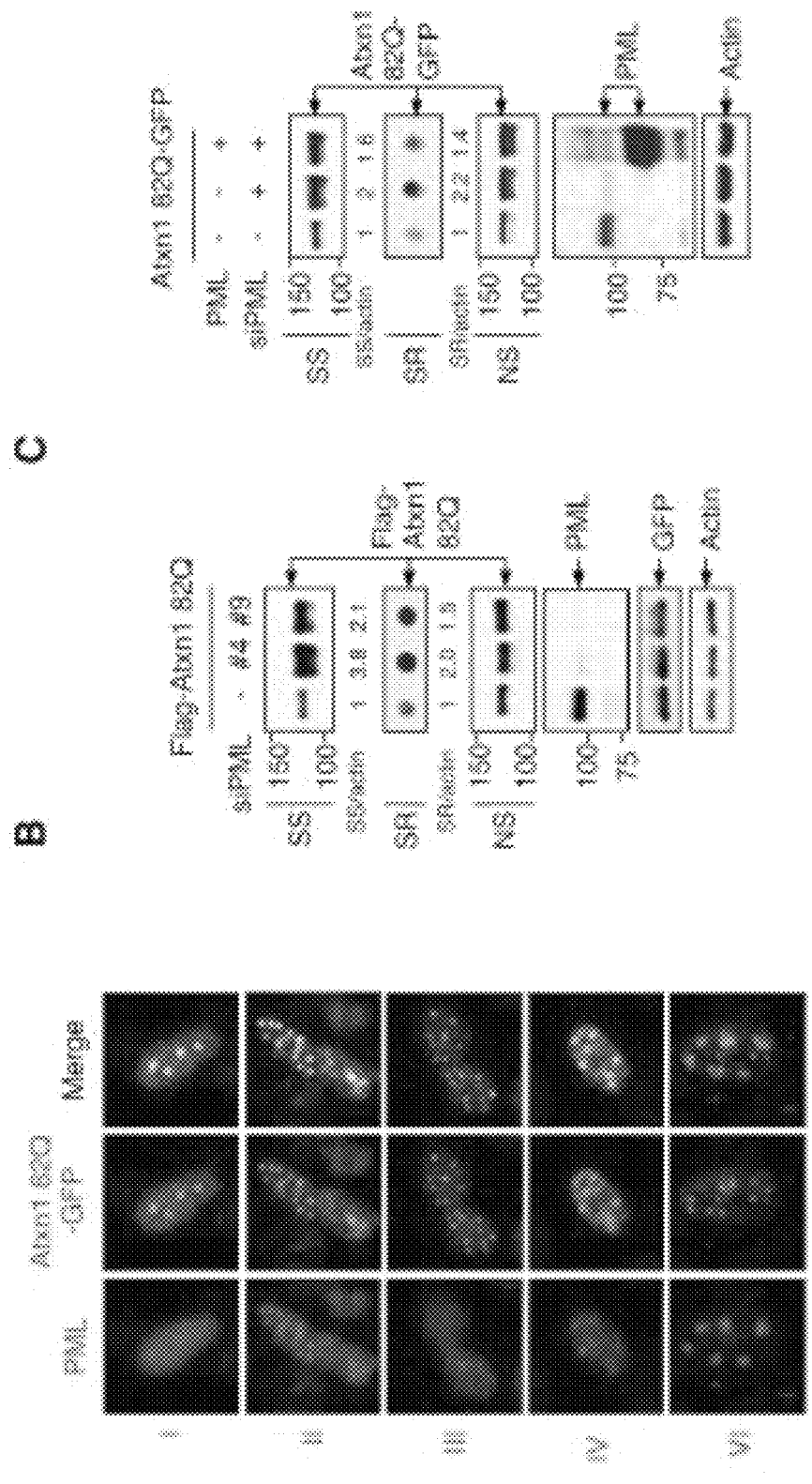
FIG. 8A through FIG. 8G, depicts the results of example experiments demonstrating that PML co-localizes with Atxn1 82Q aggregates and decreases insoluble Atxn1 82Q.

Concordant with previous reports (Skinner et al., 1997, Nature, 389: 971-974), endogenous PML colocalized with Atxn1 82Q-GFP inclusions, accumulating in bodies adjacent to them and also being distributed within (FIG. 1A). PML is expressed as several isoforms (Nisole et al., 2013, Front Oncol, 3: 125). Five major PML isoforms (I, II, III, IV, and VI) were examined and it was found that all five colocalized with Atxn1-GFP inclusions (FIG. 8A). For subsequent analyses, the commonly used isoform IV (hereafter called PML unless otherwise noted) was chosen.

When co-expressed with Atxn1 82Q, PML significantly decreased the size of Atxn1 82Q-GFP nuclear inclusions (FIG. 1B). It also reduced the steady-state levels of the Atxn1 82Q-GFP protein, especially the aggregated SS and SR species (FIG. 1C, left). To evaluate the effect of endogenous PML (all isoforms), it was knocked down using two independent small interfering RNAs (siRNAs). This noticeably raised the levels of Atxn1 82Q-GFP, especially aggregated species (FIG. 1C, right). Silencing PML also increased the steady-state levels of a FLAG-tagged Atxn1 82Q protein (FIG. 8B). The effect of PML siRNA on Atxn1 82Q could be reversed by an siRNA-resistant form of PML (FIG. 8C), ruling out off-target effects of the siRNA.

To evaluate whether PML specifically reduces pathogenic Atxn1 proteins, a nonpathogenic ataxin-1 protein, Atxn1 30Q, was used. Forced expression of PML did not reduce the abundance of Atxn1 30Q-GFP, while knockdown of PML did not significantly augment it either (FIG. 1D), underscoring the selective effect of PML on pathogenic Atxn1 proteins.

Figures 1D, 1E, 1F:
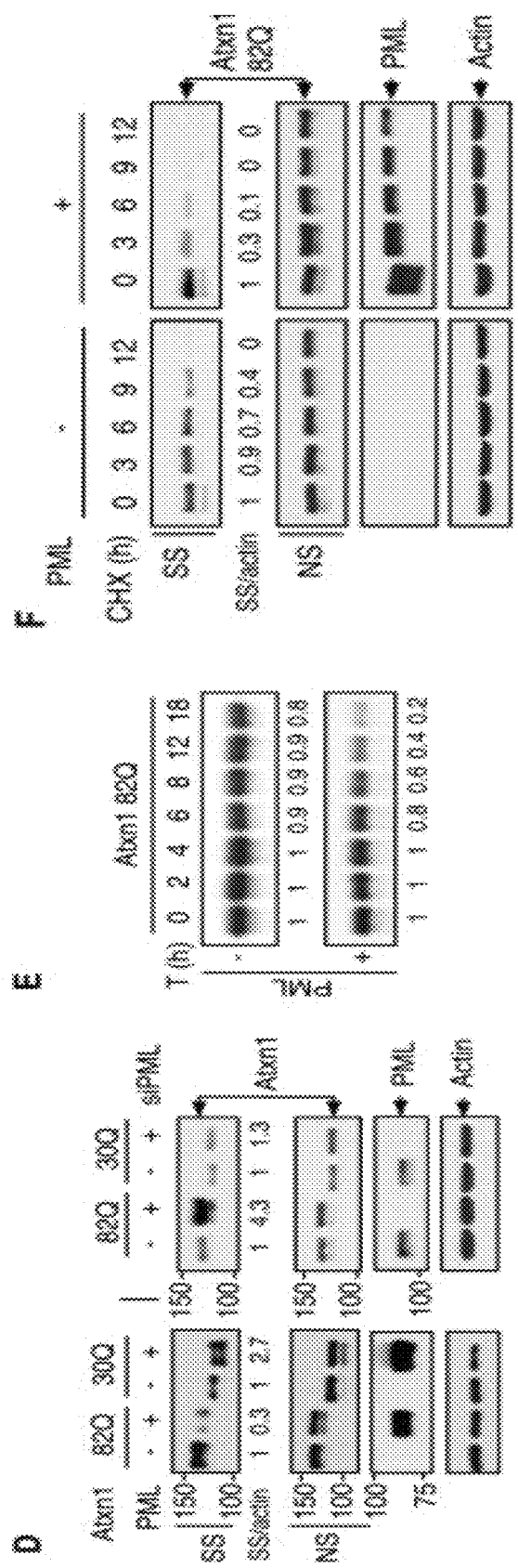
Figures 8D, 8E:
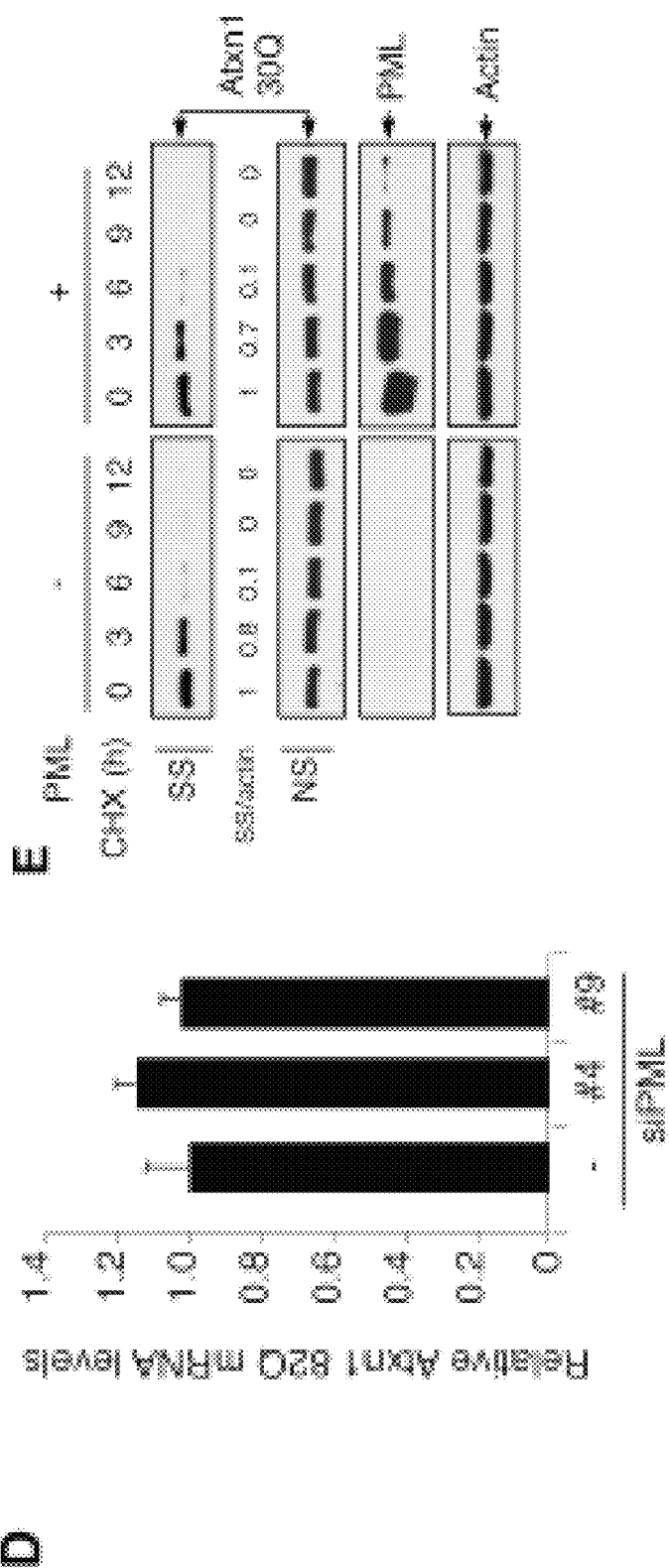

PML did not inhibit the transcription of the Atxn1 82Q gene (FIG. 8D). To determine whether PML promotes the degradation of the Atxn1 82Q protein, a pulse-chase assay was performed. In the absence of co-transfected PML, total [$^{35}$S]-labeled Atxn1 82Q protein was rather stable, and its levels declined only ~20% in 18 hours. By contrast, in the presence of PML, total [$^{35}$S]Atxn1 82Q protein was destabilized, and its levels declined ~80% over the same period of time (FIG. 1E).

Figures 1G, 1H, 1I:
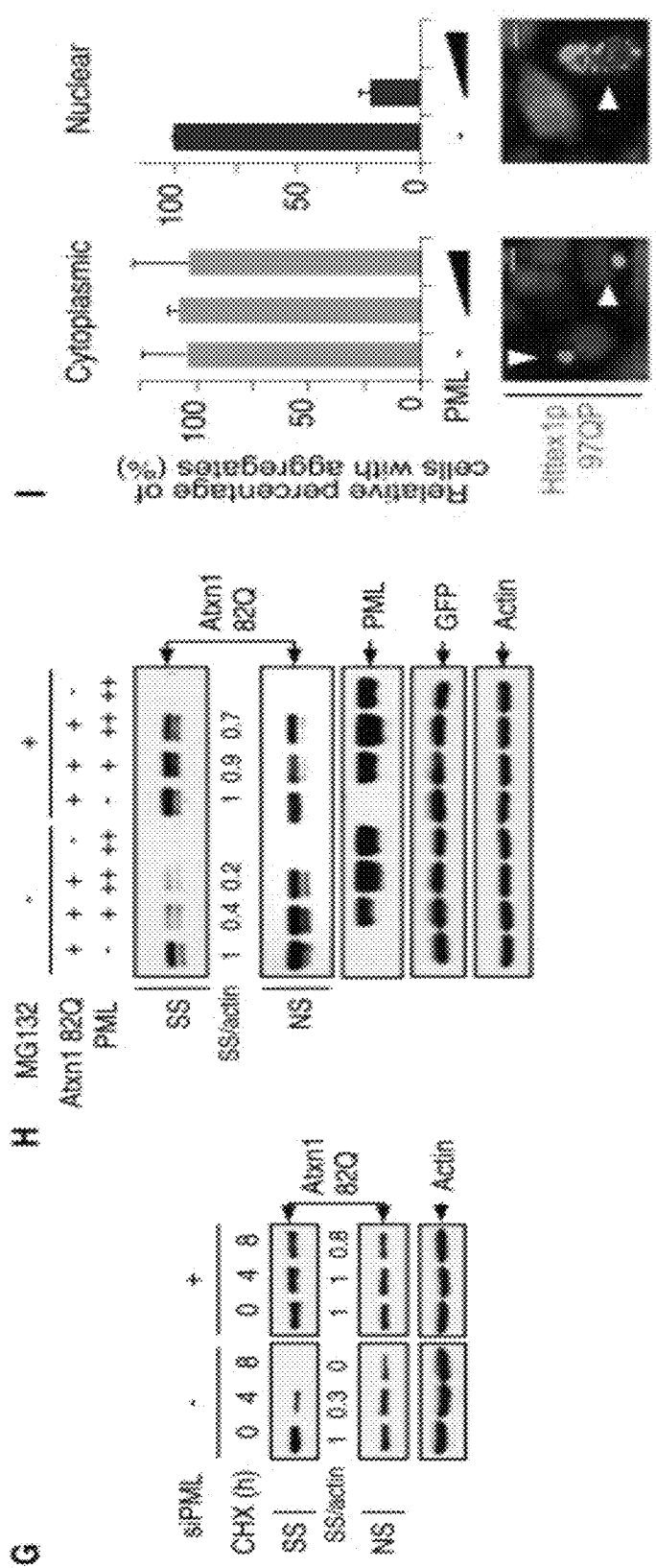

Experiments were conducted using cycloheximide (CHX) to block protein synthesis and to investigate the degradation of the pre-existing Atxn1 82Q protein. Forced expression of PML accelerated the degradation of aggregated Atxn1 82Q, reducing its half-life from ~8 hours to ~2 hours, while having a minimal effect on soluble Atxn1 82Q (FIG. 1F). Conversely, silencing PML prolonged the half-life of aggregated Atxn1 82Q and, to a lesser extent, the half-life of soluble Atxn1 82Q (FIG. 1G). The ability of PML to remove aggregated Atxn1 82Q was markedly diminished by the proteasome inhibitor MG132 (FIG. 1H). In contrast, PML did not alter the half-life of Atxn1 30Q (FIG. 8E). Collectively, these results indicate that PML targets pathogenic, but not normal, Atxn1 protein for proteasomal degradation.

A General Role for PML in Degrading Nuclear Misfolded Proteins

Figures 1J, 1K, 1L:
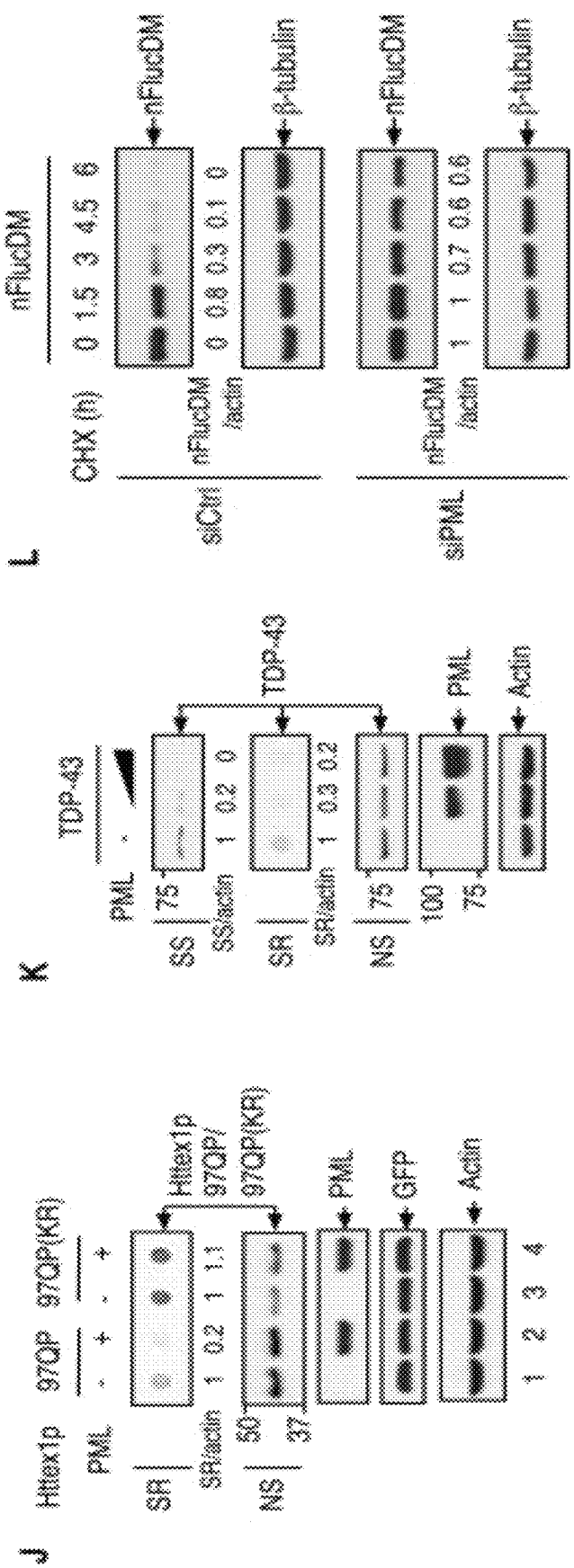

To assess whether PML plays a broad role in degrading misfolded proteins in the nucleus, two additional proteins linked to neurodegeneration were tested: (1) a pathogenic fragment of huntingtin (Htt) encoded by the first exon of the HD gene, Httex1p 97QP (Steffan et al., 2004, Science, 304: 100-104); and (2) TAR DNA-binding protein 43 (TDP-43), which is associated with both amyotrophic lateral sclerosis (ALS, also known as Lou Gehrig's disease) and frontotemporal lobar degeneration with ubiquitinated inclusions (FTLD-U) (Chen-Plotkin et al., 2010, Nat Rev Neurosci, 6: 211-220). Httex1p 97QP formed microscopically visible inclusions in both the nucleus and the cytoplasm (FIG. 1I), while TDP-43 formed inclusions mainly in the nucleus. PML reduced the nuclear, but not the cytoplasmic, Httex1p 97QP inclusions (FIG. 1I), and decreased the amount of aggregated Httex1p 97QP (FIG. 1J, lanes 1 and 2). PML also lowered the amount of aggregated, but not soluble, TDP-43 (FIG. 1K).

Figures 8F, 8G:
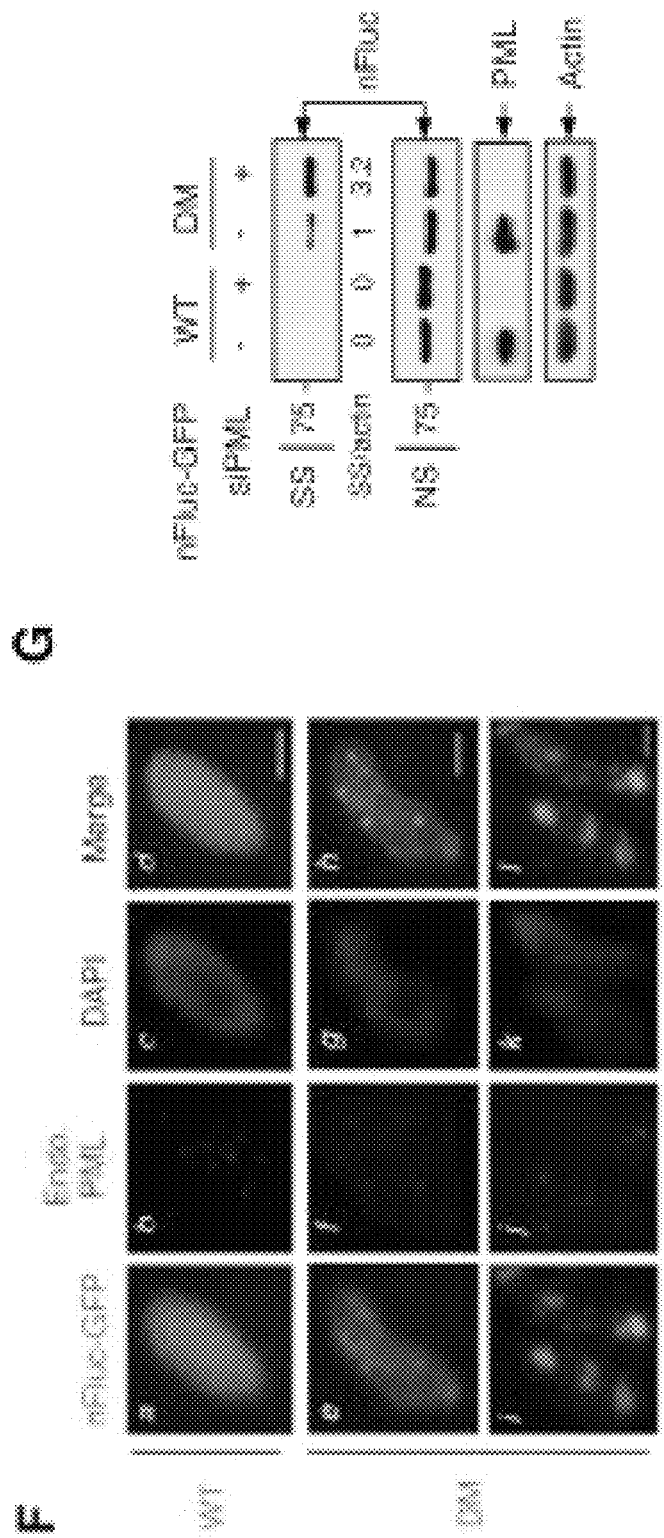

To extend these analyses, a structurally destabilized mutant of the model chaperone substrate firefly luciferase (FlucDM) was used, which was developed as a probe for the capacity of cellular PQC systems (Gupta et al., 2011, Nat Methods, 8: 879-884). Endogenous PML partially co-localized with a nuclear form of FlucDM (nFlucDM-GFP), which formed inclusions, but not with the wild-type counterpart (nFlucWT-GFP), which displayed diffuse localization (FIG. 8F). Silencing PML noticeably elevated the levels of aggregated nFlucDM-GFP (FIG. 8G) and extended the half-life of total nFlucDM-GFP protein (FIG. 1L). Taken together, these results indicate that PML facilitates the removal of multiple misfolded proteins in the mammalian cell nucleus.

Recognition of Misfolded Proteins by Distinct Sites on PML

Figure 2A:
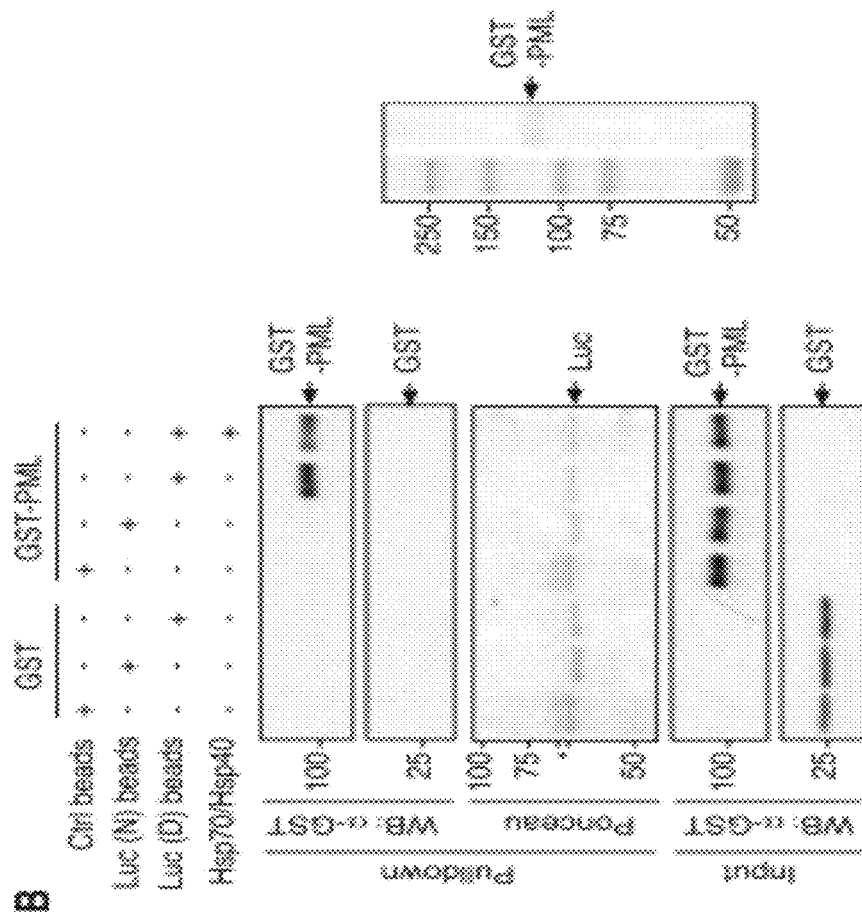
FIG. 2A through FIG. 2E, depicts the results of example experiments demonstrating the recognition of misfolded proteins by PML.
Figure 9A:
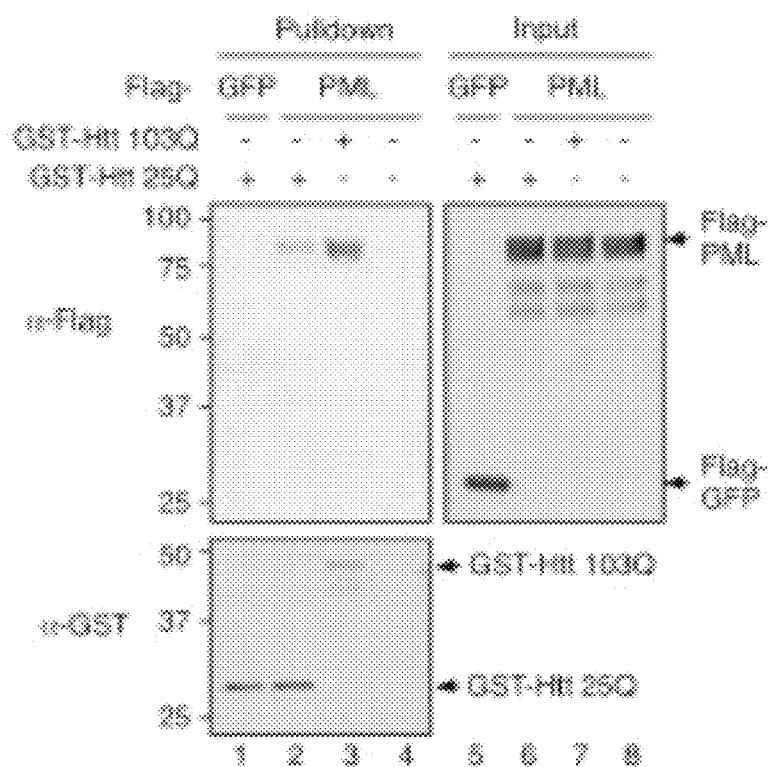
FIG. 9A through FIG. 9E, depicts the results of example experiments demonstrating the interaction of PML with pathogenic Htt proteins.

To investigate the mechanism by which PML degrades misfolded proteins, it was first examined whether PML is able to directly recognize these proteins. For these experiments a pathogenic (103Q) and a nonpathogenic (25Q) Htt fragment, each being fused to glutathione S-transferase (GST), were used. In an in vitro assay with purified recombinant proteins, immobilized FLAG-PML, but not the control protein FLAG-GFP, pulled down GST-Htt 103Q (FIG. 2A), indicating a specific and direct interaction between PML and Htt 103Q. FLAG-PML also pulled down GST-Htt 25Q. However, this interaction was substantially weaker than the PML-Htt 103Q interaction (FIG. 2A). In a reciprocal experiment, immobilized GST-Htt 103Q proteins also interacted more strongly with FLAG-PML than immobilized GST-Htt 25Q did (FIG. 9A). Hsp70 and Hsp40, which recognize a broad range of misfolded proteins, did not enhance the PML-Htt 103Q interaction (FIG. 2A). These results suggest that PML can directly associate with polyQ proteins and preferentially with the pathogenic form.

Figure 2B:
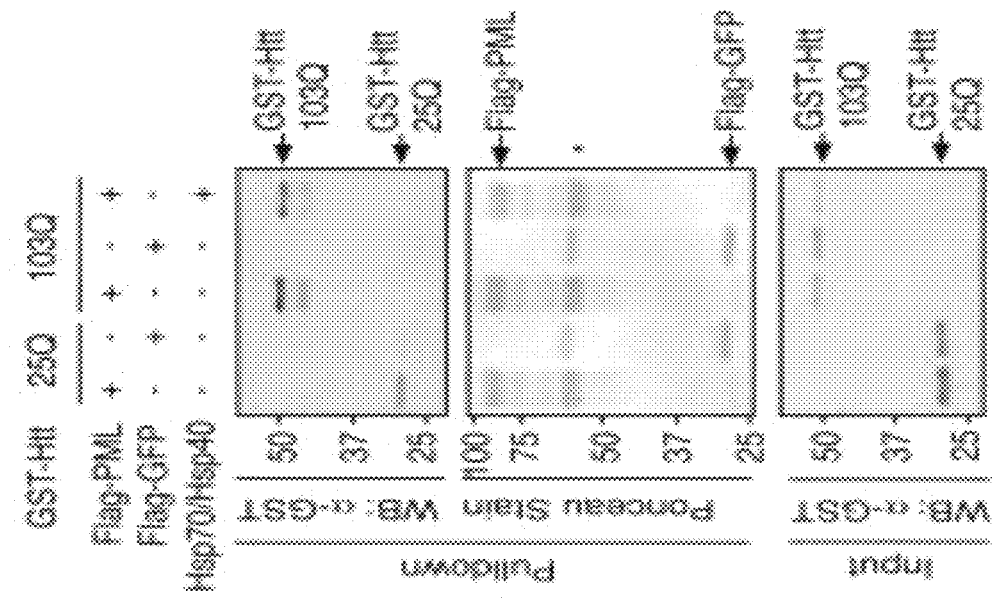

It was also examined whether PML selectively binds to denatured luciferase. 6xHis-tagged luciferase that was immobilized on Ni-NTA beads was either denatured with urea or kept in the native form. Denatured, but not native, luciferase specifically interacted with GST-PML, and the Hsp70/Hsp40 system did not enhance this interaction (FIG. 2B). Thus, PML can directly recognize misfolded, but not native, luciferase.

Figures 2C, 2D:
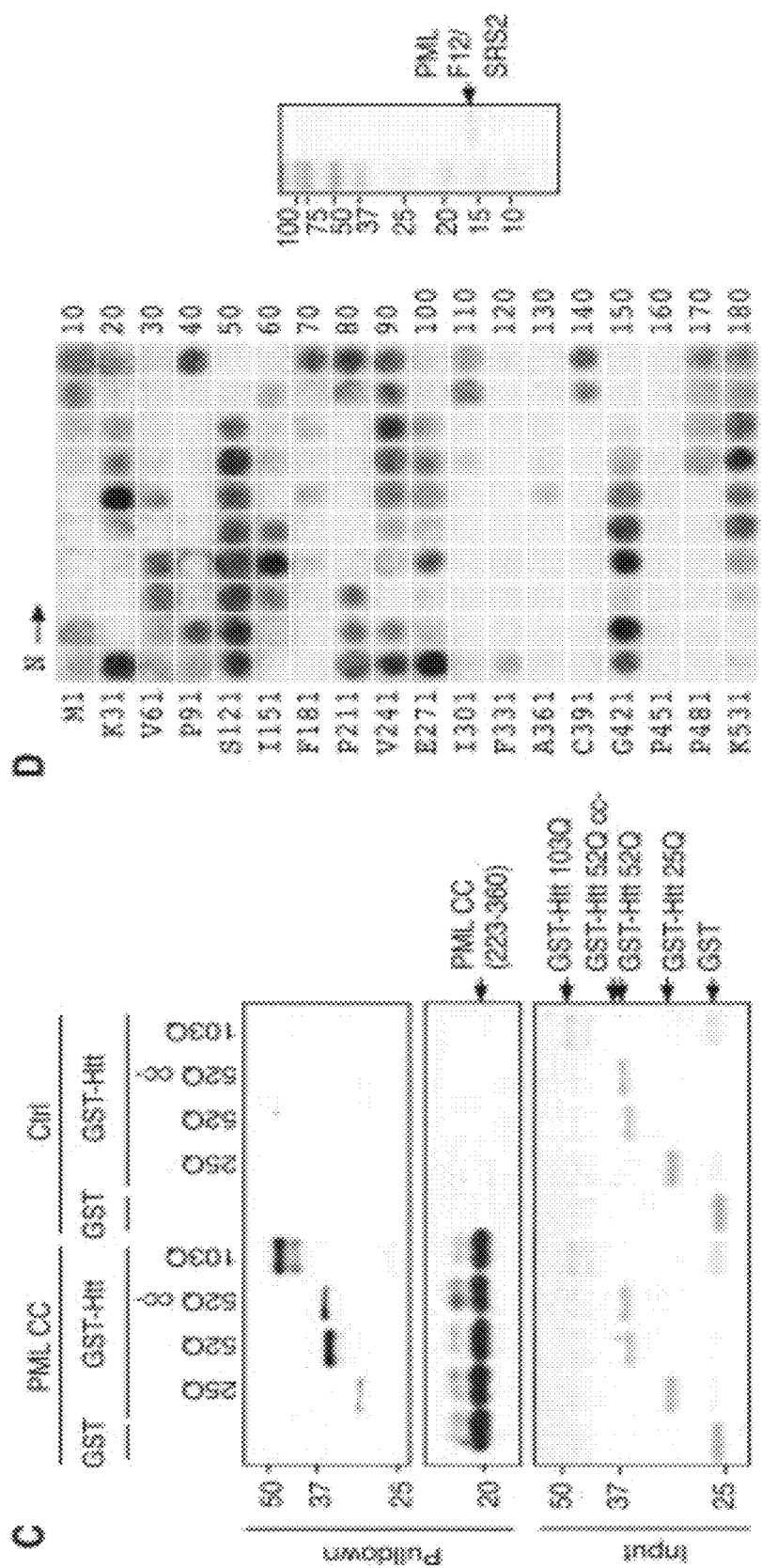
Figure 9B:
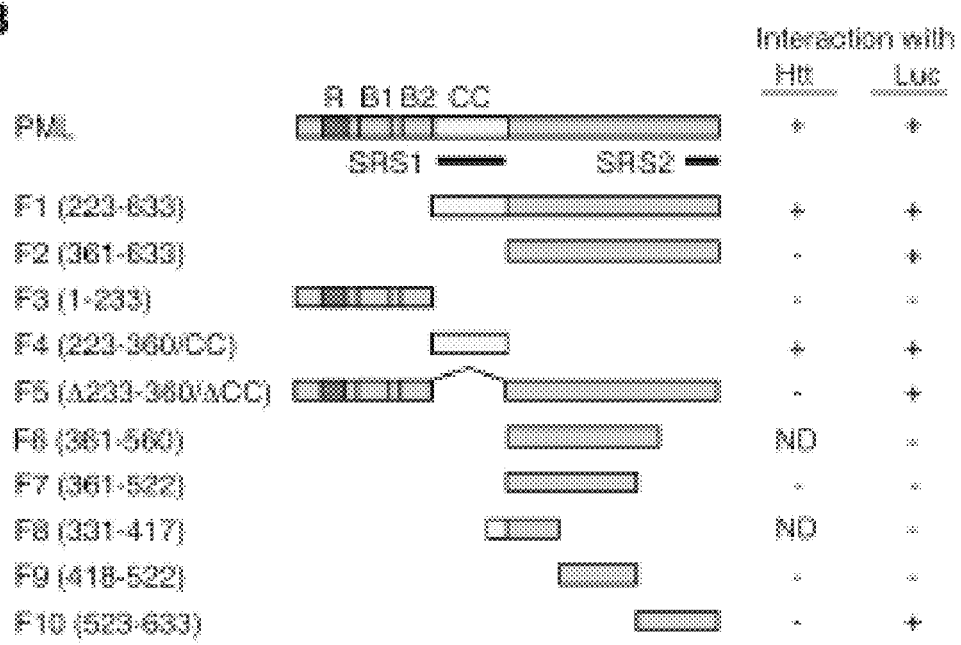
Figure 9C:
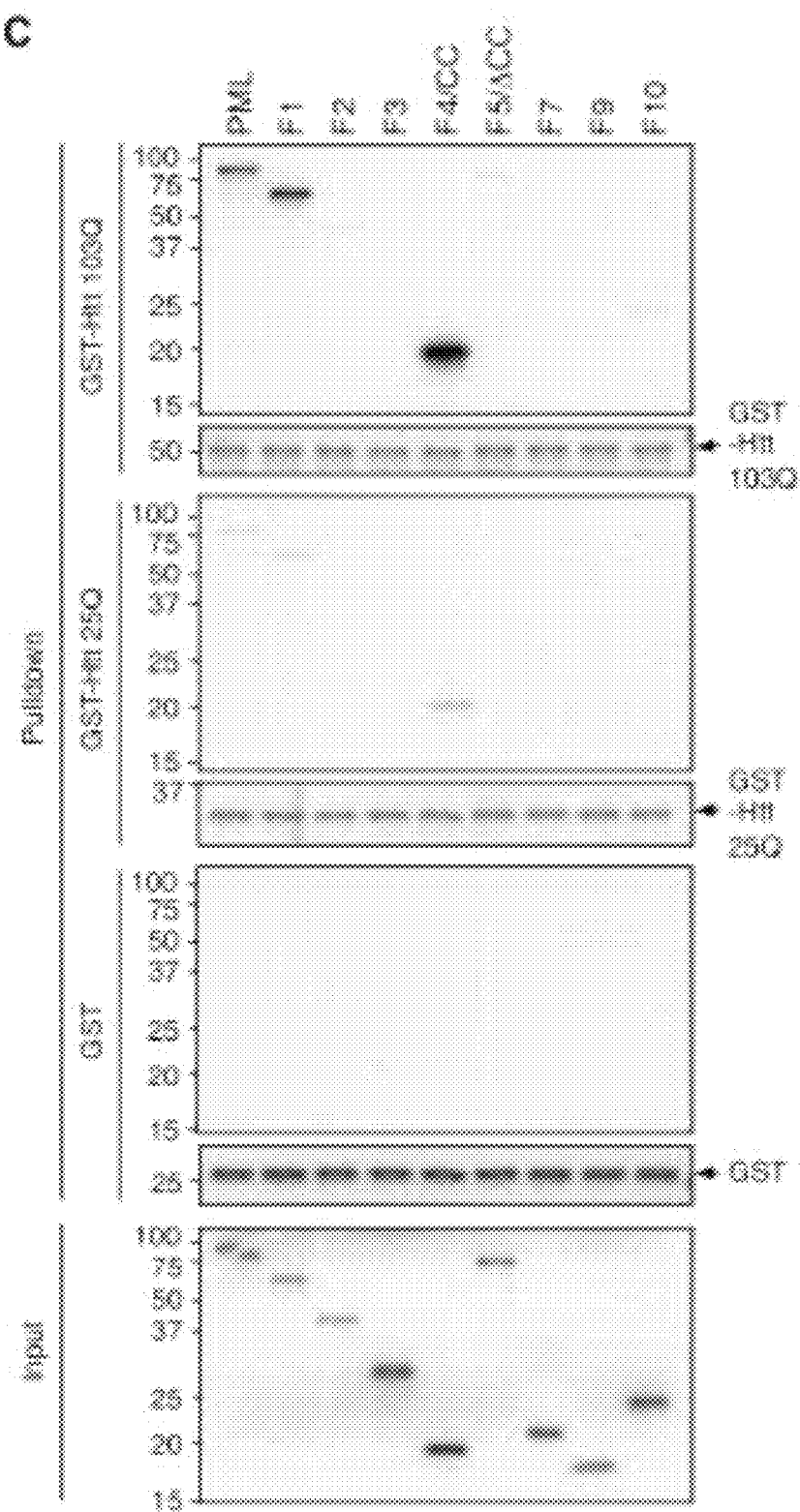

To understand the molecular basis for the interaction of PML with misfolded proteins, it was sought to identify the substrate recognition sites (SRSs) of PML, as well as the structural features on substrates that these SRSs discern. It was previously shown that, in a manner dependent on its length, polyQ and the flanking regions form CC structures, which facilitate the assembly of polyQ proteins into an oligomeric or aggregated state and also mediate the interaction of polyQ proteins with CC-containing proteins (Fiumara et al., 2010, Cell, 143: 1121-1135). Thus, it was hypothesized that PML, via its CC region within the TRIM/RBCC motif, interacts with pathogenic polyQ proteins. A panel of PML fragments (F1-F5) was constructed, where each fragment either contained or lacked the CC region (FIG. 9B). A fragment containing the CC region (F1) interacted with Htt 103Q, while two fragments lacking this region (F2 and F3) did not (FIG. 9B and FIG. 9C). Moreover, the CC region alone (F4) bound to Htt 103Q, while deleting this region from the entire PML protein (F5 or ΔCC) greatly diminished this binding. Thus, PML recognizes Htt 103Q almost exclusively through the CC region. Similar to the full-length PML, PML CC displayed a clear binding preference for the pathogenic Htt 103Q to the nonpathogenic Htt 25Q (FIG. 2C). PML CC also strongly interacted with another pathogenic Htt construct, Htt 52Q (FIG. 2C). Thus, PML CC likely constitutes an SRS (called SRS1).

Figures 9D, 9E:
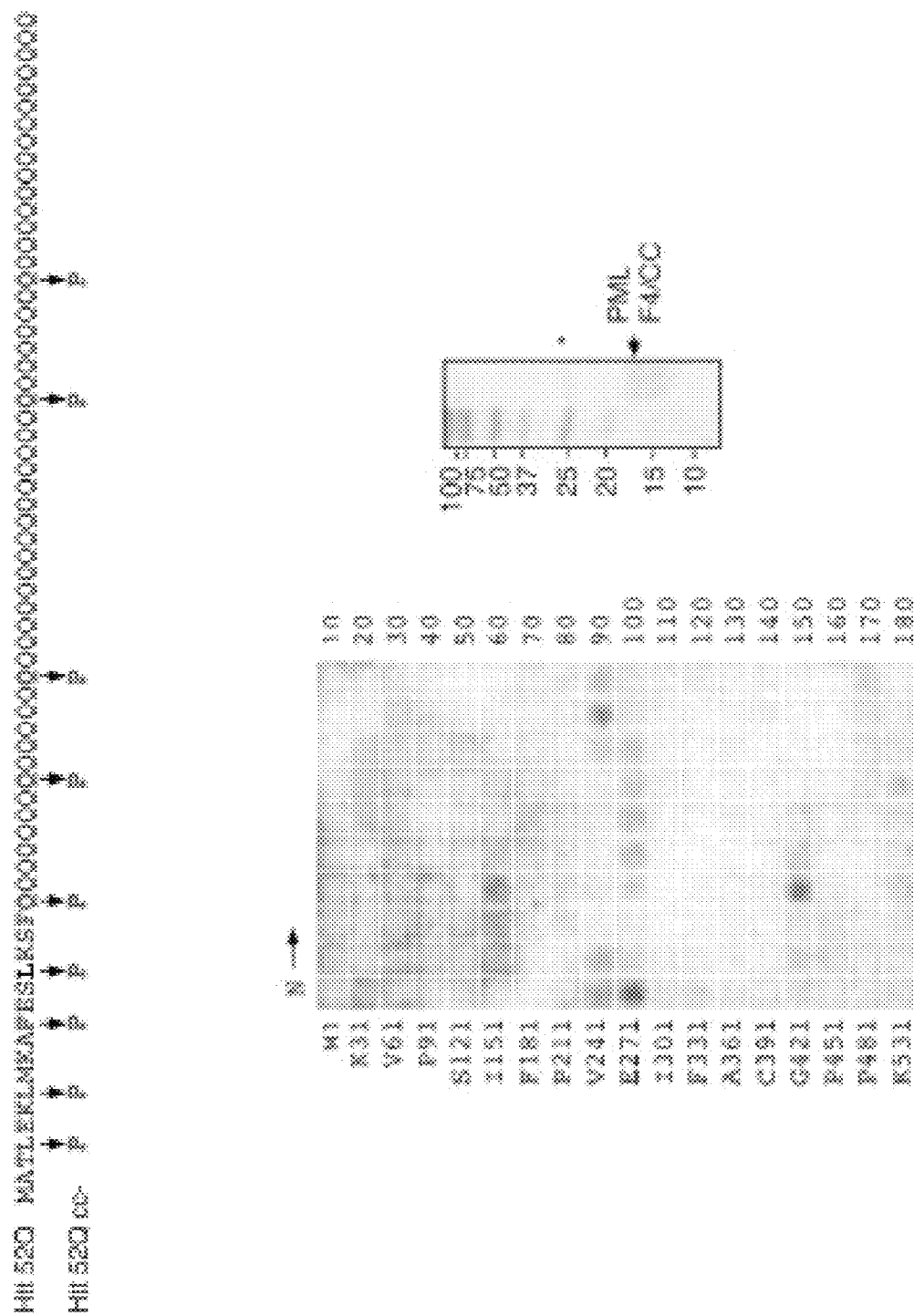

To test whether PML CC recognizes the homologous CC structure in Htt proteins, the residues in Htt 52Q that were predicted to be involved in the CC formation were mutated, yielding Htt 52Q cc- (FIG. 9D). A similar mutation was previously shown to reduce the formation of the CC structure in Htt 72Q (Fiumara et al., 2010, Cell, 143: 1121-1135). Indeed, compared to Htt 52Q, Htt 52Q cc- displayed a noticeably reduced propensity to form aggregates and a substantially weaker interaction with PML CC (FIG. 2C). Therefore, PML CC/SRS1 likely interacts with the CC structure on pathogenic Htt proteins.

Figure 10A:
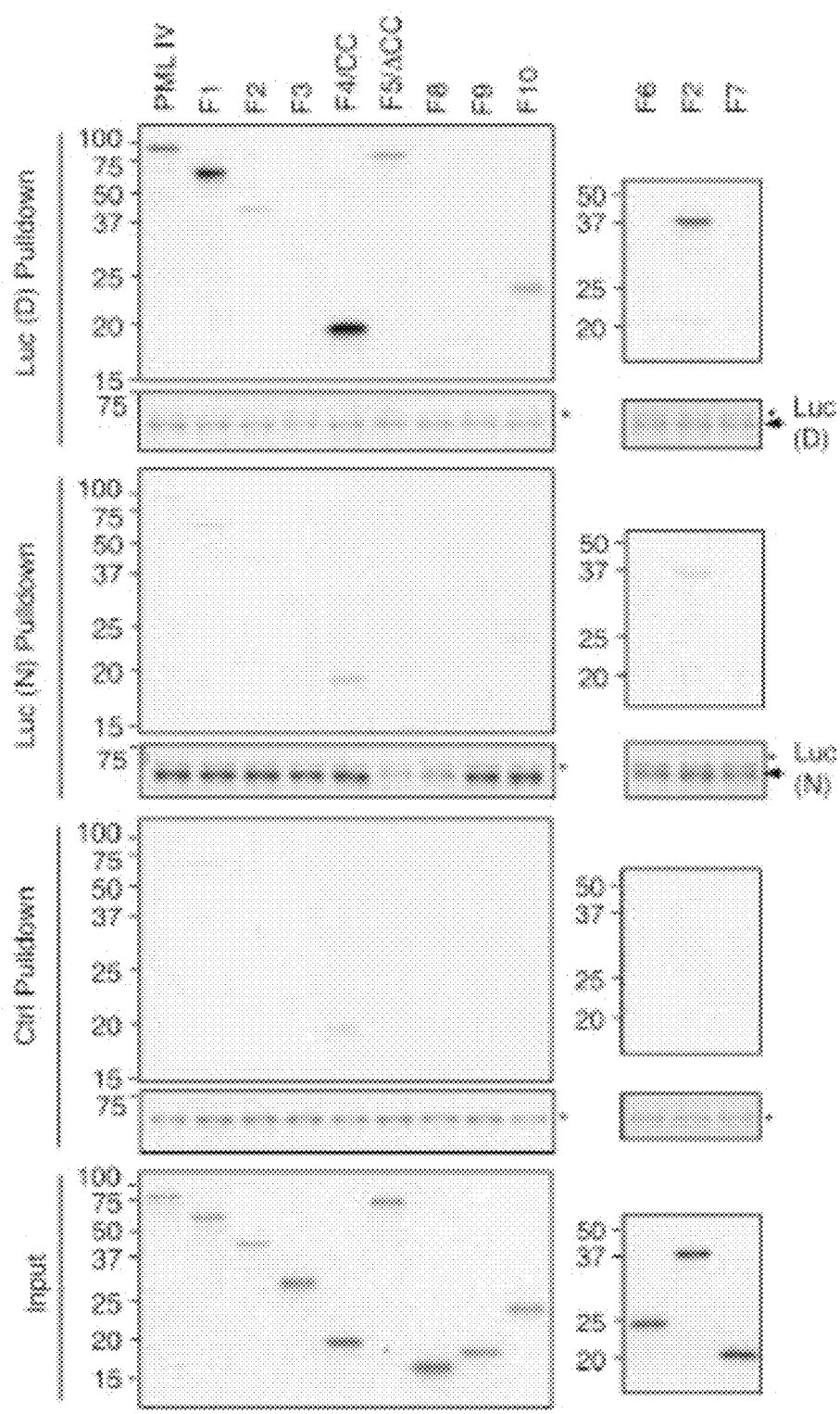
FIG. 10A through FIG. 10C, depicts the results of example experiments demonstrating the interaction of PML with denatured luciferase.
Figure 10B:
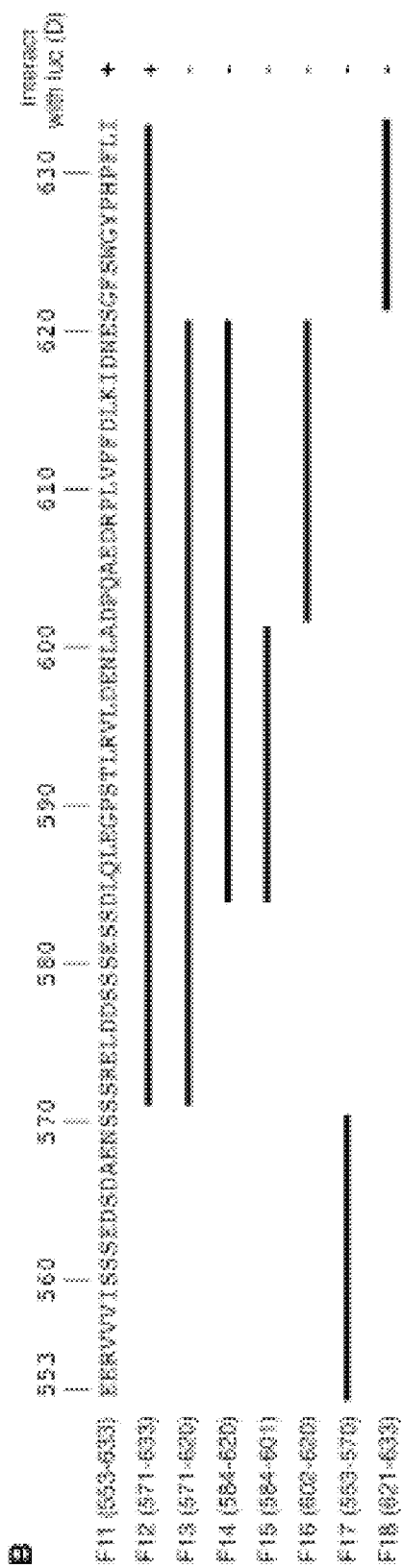
Figure 10C:
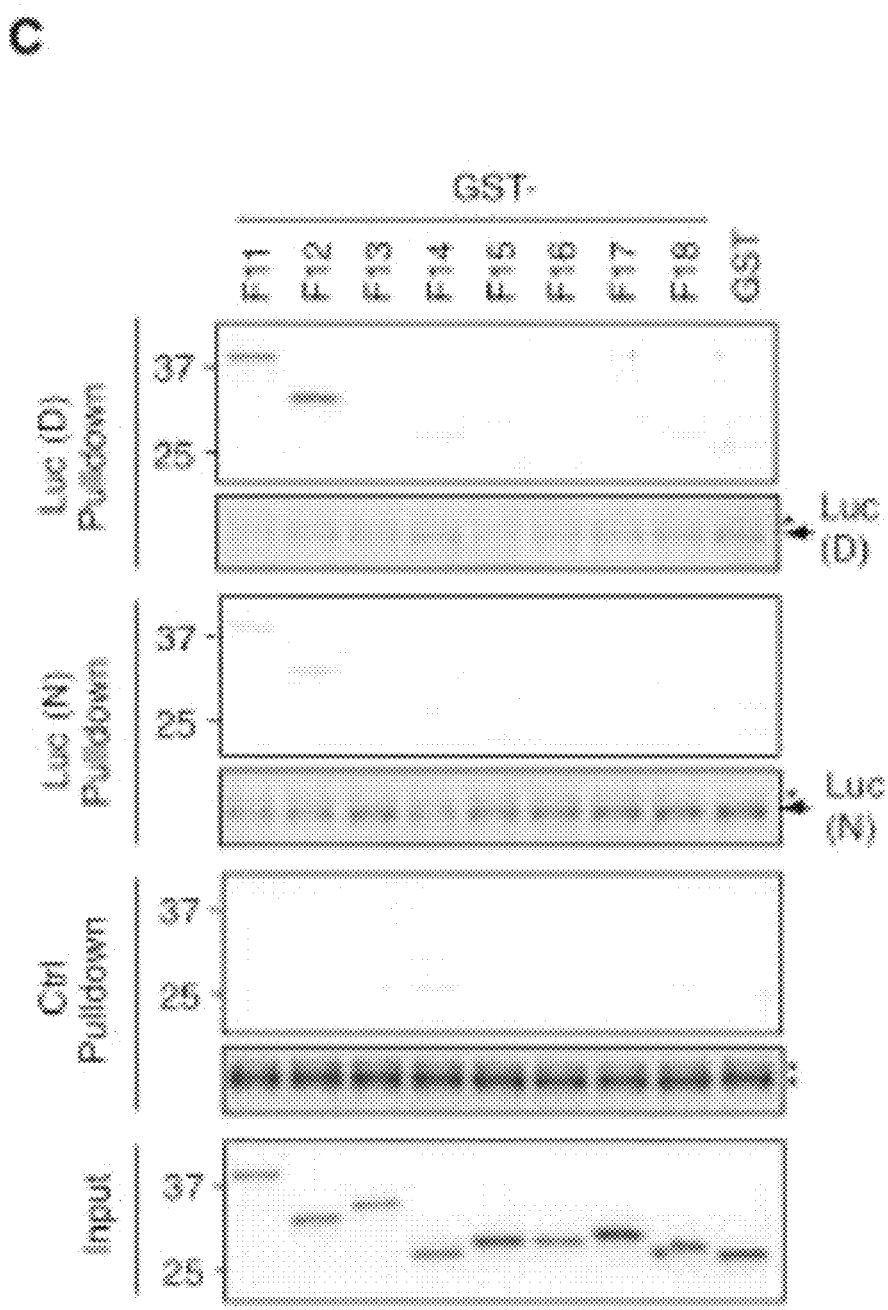

Given that PML also promotes the degradation of non-polyQ proteins such as luciferase and TDP-43 (FIG. 1 and FIG. 8), it was reasoned that PML might contain at least another SRS that could discern non-CC structural features on misfolded proteins. To test this possibility, the panel of PML fragments was examined for interaction with denatured luciferase. Although the CC region alone could interact with denatured luciferase, significant levels of interaction were also observed in two fragments (F2 and F5) that lacked this region but contained the C terminus (aa 361-633) (FIG. 9B and FIG. 10A). Using additional deletion constructs within the C terminus (F6-F18, FIG. 9B and FIG. 10B), it was found that a stretch of 63 amino acids (aa 571-633) was sufficient for binding to denatured luciferase. Either $NH_2$- or COOH-terminal deletions of this stretch abolished the binding (FIG. 10). Thus, the last 63 amino acids of PML likely constitute another SRS (called SRS2).

Figure 2E:
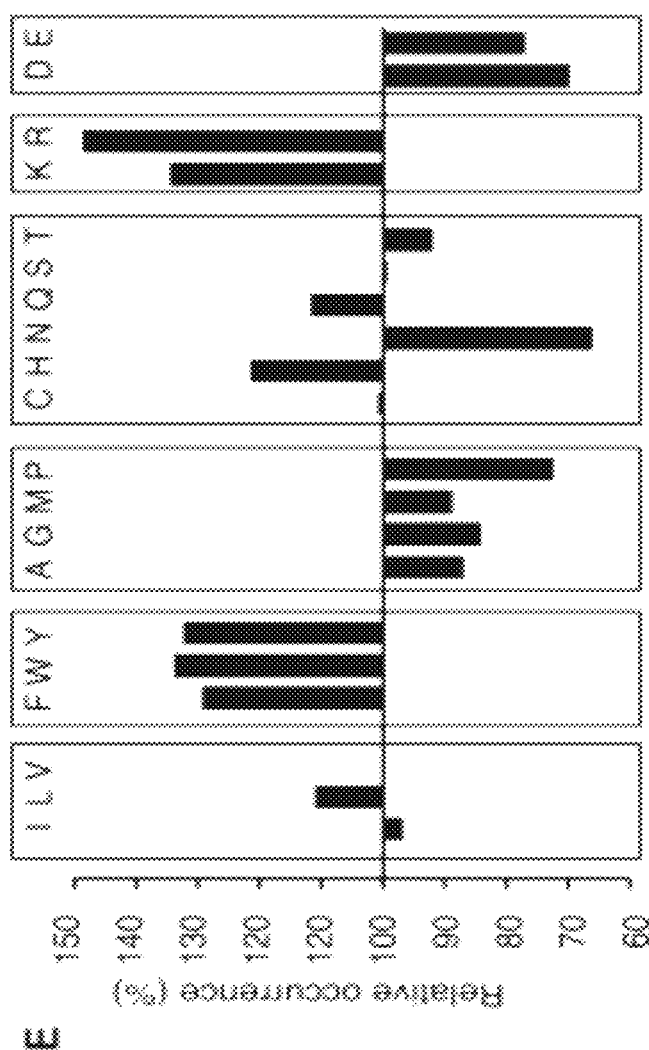

To investigate the linear sequences in luciferase that can be recognized by PML SRS2, purified PML SRS2 was used to screen a cellulose-bound peptide library that represented the complete sequence of luciferase. The library consisted of 180 peptides, each containing 13 amino acid residues that overlapped adjacent peptides by ten. Similar to chaperones such as Hsp70 and ClpB (Rudiger et al., 1997, EMBO J, 16: 1501-1507; Schlieker et al., 2004, Nat Struct Mol Biol, 11: 607-615), PML SRS2 only bound to a subset of these peptides (FIG. 2D), indicating its ability to distinguish peptides with different amino acid compositions. An analysis of the relative occurrence of all 20 amino acids in PML SRs2-interacting peptides versus all peptides in the library showed that PML SRS2 strongly favored aromatic (Phe, Trp, and Tyr) and positively charged (Arg and Lys) residues, and disfavored negatively charged residues (Asp and Glu) (FIG. 2E). This amino acid preference was similar to that of ClpB, except that SRS2 had an additional preference for Leu and His, which are disfavored by ClpB (Schlieker et al., 2004, Nat Struct Mol Biol, 11: 607-615).

For comparison, the binding of PML CC/SRS1 to the peptide library was tested. Consistent with the notion that this region recognizes higher-order structures instead of linear sequences, PML CC/SRS1 weakly bound to only a few peptides (FIG. 9E). Based on these results, it was concluded that PML contains at least two regions that can recognize misfolded proteins: the CC region within the TRIM/RBCC motif (SRS1) and the 63 amino acid stretch at its C terminus (SRS2), which can discern CC structures and exposed peptides enriched in both aromatic and basic amino acids, respectively.

Involvement of SUMOylation in the Degradation of Atxn1 82Q

Experiments were conducted to investigate how PML promotes the degradation of misfolded proteins upon recognition. Misfolded proteins associated with neurodegeneration are frequently modified by SUMO, although the role of this modification remains unclear (Martin et al., 2007, Nat Rev Neurosci, 8: 948-959). Mammalian cells express three major SUMO proteins, SUMO1-SUMO3. SUMO2 and SUMO3 are nearly identical to each other in their sequence (collectively called SUMO2/3) and are approximately 50% identical to SUMO1 (Wilkinson and Henley, 2010, Biochem J, 428: 133-145). The modification of Atxn1 82Q by these SUMO proteins and their involvement in Atxn1 82Q degradation was investigated.

Figures 3A, 3B:
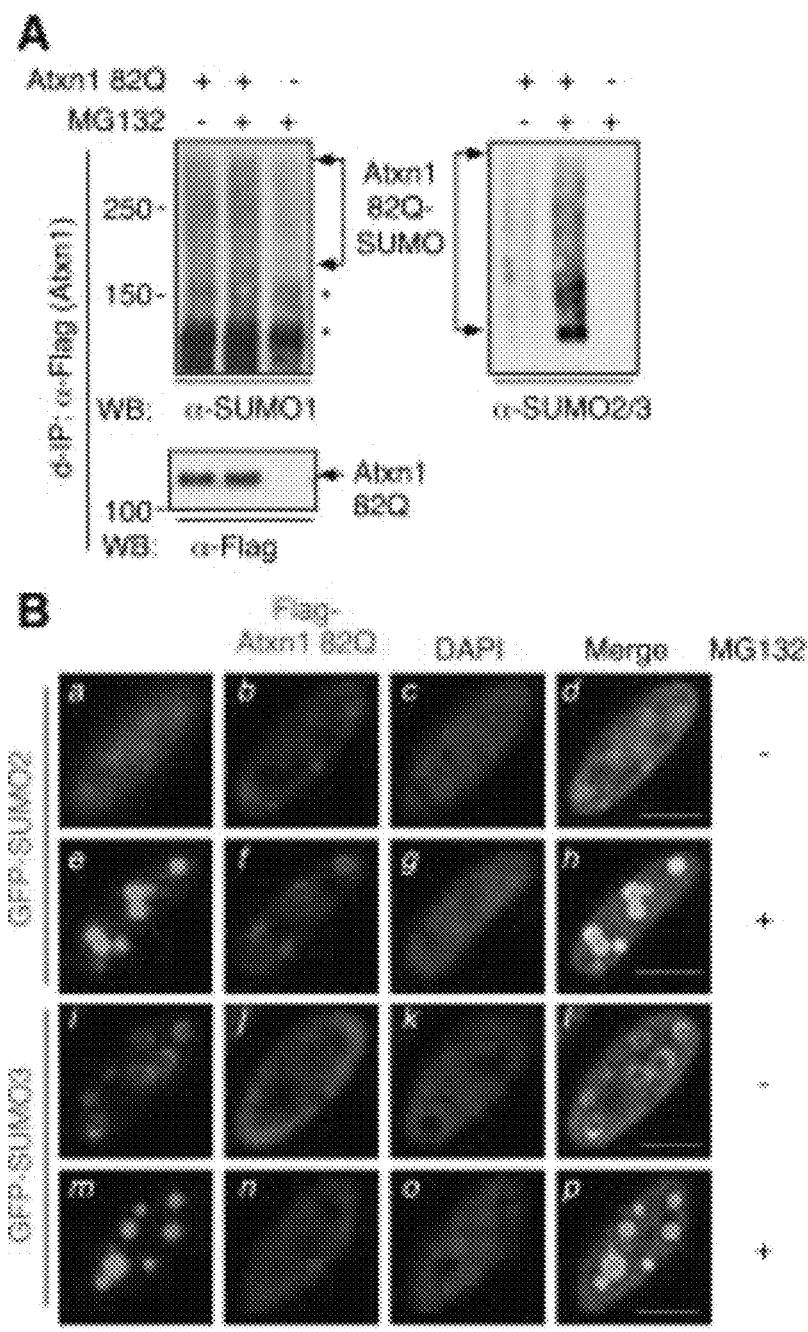
FIG. 3A through FIG. 3F, depicts the results of example experiments demonstrating that SUMO2/3 is involved in the ubiquitination and PML-mediated degradation of Atxn1 82Q.

Atxn1 82Q was modified by both exogenous (Riley et al., 2005, J Biol Chem, 280: 21942-21948) and endogenous (FIG. 3A, left) SUMO1, and this modification was weaker than that of Atxn1 30Q (Riley et al., 2005, J Biol Chem, 280: 21942-21948). Atxn1 82Q was also modified by endogenous SUMO2/3 (FIG. 3A, right), and co-localized with GFP-SUMO2/3 in the nucleus (FIG. 3B). The sites in Atxn1 82Q that were conjugated with SUMO1 and SUMO2/3 might be different, because a mutant Atxn1 82Q with impaired SUMO1 conjugation, Atxn1 82Q (5KR) (Riley et al., 2005, J Biol Chem, 280: 21942-21948), showed no defect in SUMO2/3 conjugation (FIG. 11A).

Of note, Atxn1 82Q was more strongly modified by endogenous SUMO2/3 compared to Atxn1 30Q (FIG. 3C), correlating with the different responses of these Atxn1 proteins to PML-mediated degradation (FIG. 1 and FIG. 8). Similarly, TDP-43 was modified by endogenous SUMO2/3 (FIG. 11B). SUMO 2/3 also modified FlucDM, as well as another structurally destabilized luciferase mutant, FlucSM (Gupta et al., 2011, Nat Methods, 8: 879-884). The SUMO2/3 modification of these luciferase mutants was also stronger than that of wild-type luciferase (FIG. 11C).

Figures 3C, 3D:
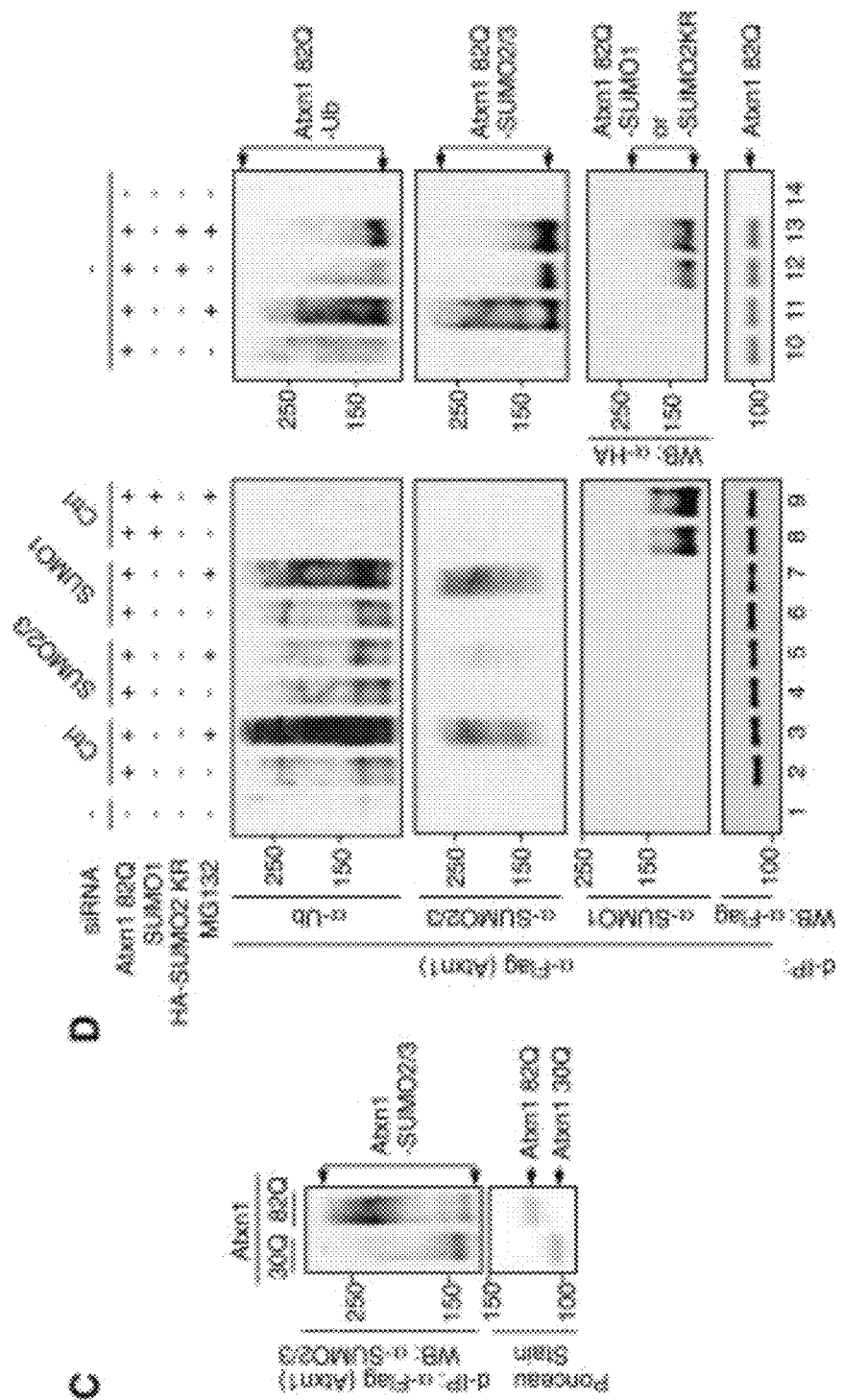

Moreover, proteasome inhibition enhanced the co-localization of Atxn1 82Q with GFP-SUMO2/3 (FIG. 3B). It also increased SUMO2/3-modified Atxn1 82Q concurrently with ubiquitinated Atxn1 82Q, but not SUMO1-modified Atxn1 82Q (FIG. 3A and FIG. 3D, lanes 2 and 3). Likewise, proteasome inhibition increased SUMO2/3-modified TDP-43 and luciferase mutants (FIG. 11B and FIG. 11C).

Figure 3E:
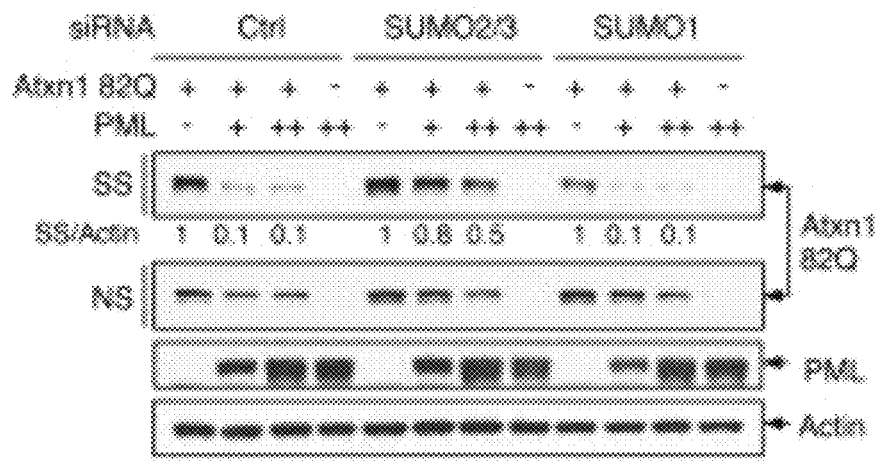

To assess the role of SUMO proteins in the ubiquitination and proteasomal degradation of Atxn1 82Q, SUMO2/3 and SUMO1 were silenced separately using siRNA. Silencing SUMO2/3, but not SUMO1, effectively reduced ubiquitination of Atxn1 82Q (FIG. 3D, lanes 4-7). Silencing SUMO2/3 also raised the levels of Atxn1 82Q, especially the aggregated form, but not the levels of the control protein GFP (FIG. 11D-FIG. 11F), and it diminished the ability of PML to remove aggregated Atxn1 82Q (FIG. 3E).

Figure 3F:
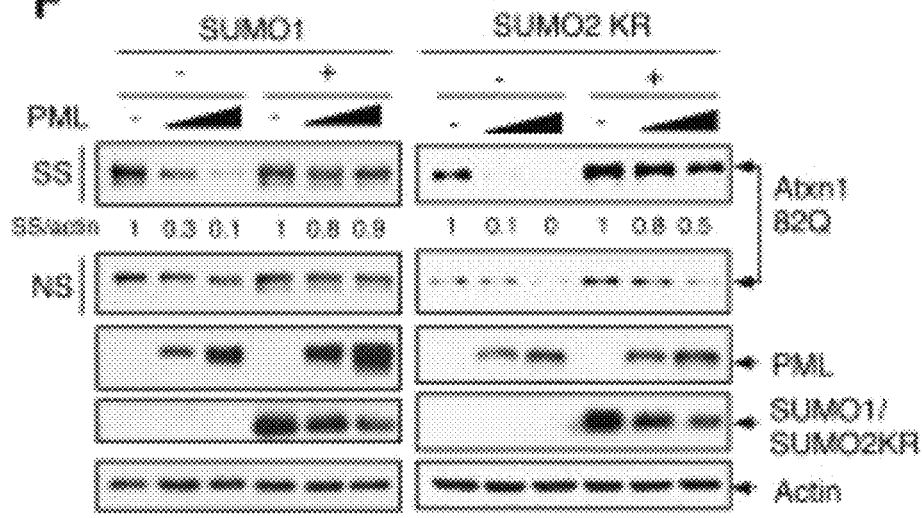

SUMO2 and SUMO3 contain an internal SUMOylation consensus site that enables the formation of polychains. SUMO1 does not contain this site, and when conjugated to the SUMO2/3 chain, it can terminate the chain elongation (Wilkinson and Henley, 2010, Biochem J, 428: 133-145). Therefore, two additional strategies were used to inhibit the modification of Atxn1 82Q by SUMO2/3. First, SUMO1 was overexpressed. This strongly reduced Atxn1 82Q conjugation to SUMO2/3 and, at the same time, impaired conjugation of Atxn1 82Q to ubiquitin (FIG. 3D, lanes 8 and 9) and its degradation by PML (FIG. 3F, left). Second, a SUMO2 mutant that was deficient in chain formation, SUMO2 KR, was used. Overexpression of SUMO2 KR effectively reduced the amount of SUMO2/3-modified Atxn1 82Q species, especially those of high molecular weights. It also reduced ubiquitin-modified Atxn1 82Q species (FIG. 3D, lanes 12 and 13) and blunted the ability of PML to degrade Atxn1 82Q (FIG. 3F, right). Moreover, a SUMOylation-defective Htt mutant, Httex1p 97QP(KR) (Steffan et al., 2004, Science, 304: 100-104), was used, and it was found that it was resistant to the PML-mediated degradation (FIG. 1J). Taken together, these results show that ubiquitination and degradation of Atxn1 82Q and likely other misfolded proteins are dependent on their modification by SUMO2/3.

PML as a SUMO E3 Ligase of Atxn1 82Q

Figures 4A, 4B:
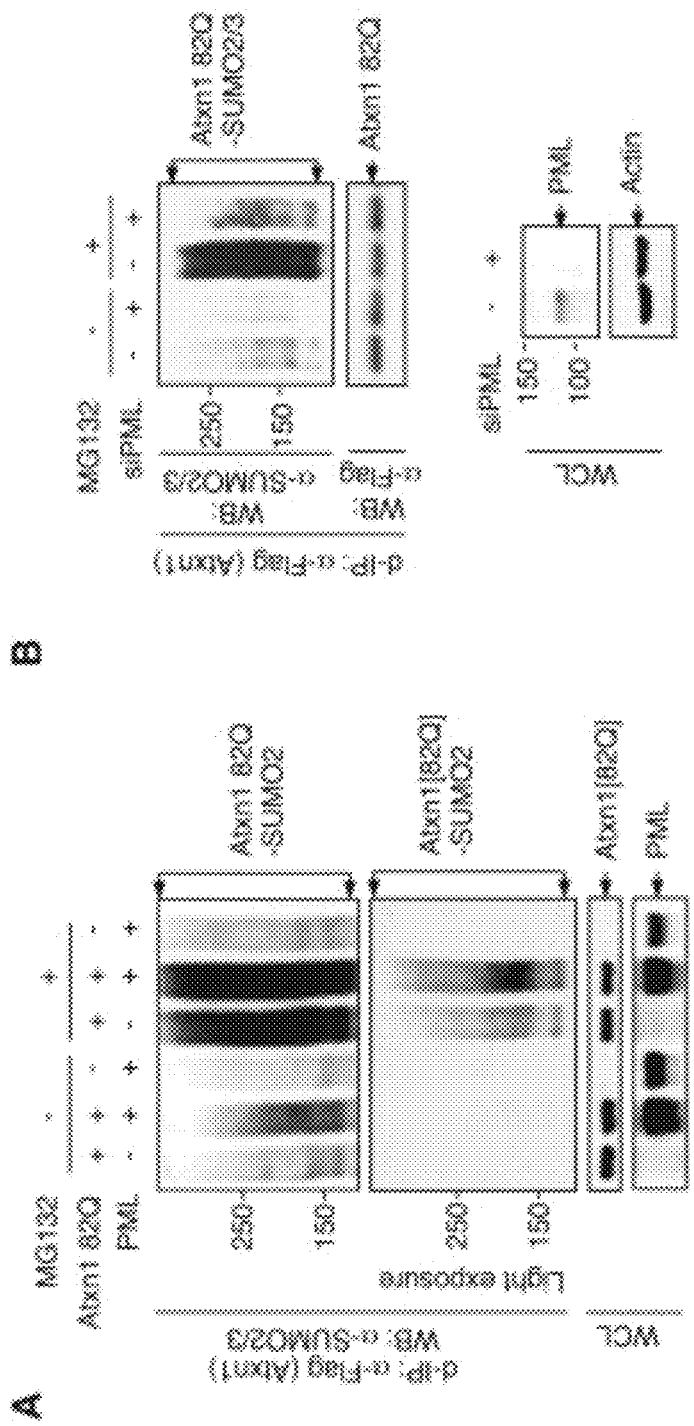
FIG. 4A through FIG. 4F, depicts the results of example experiments demonstrating that PML promotes SUMOylation of Atxn1 82Q.
Figures 4C, 4D:
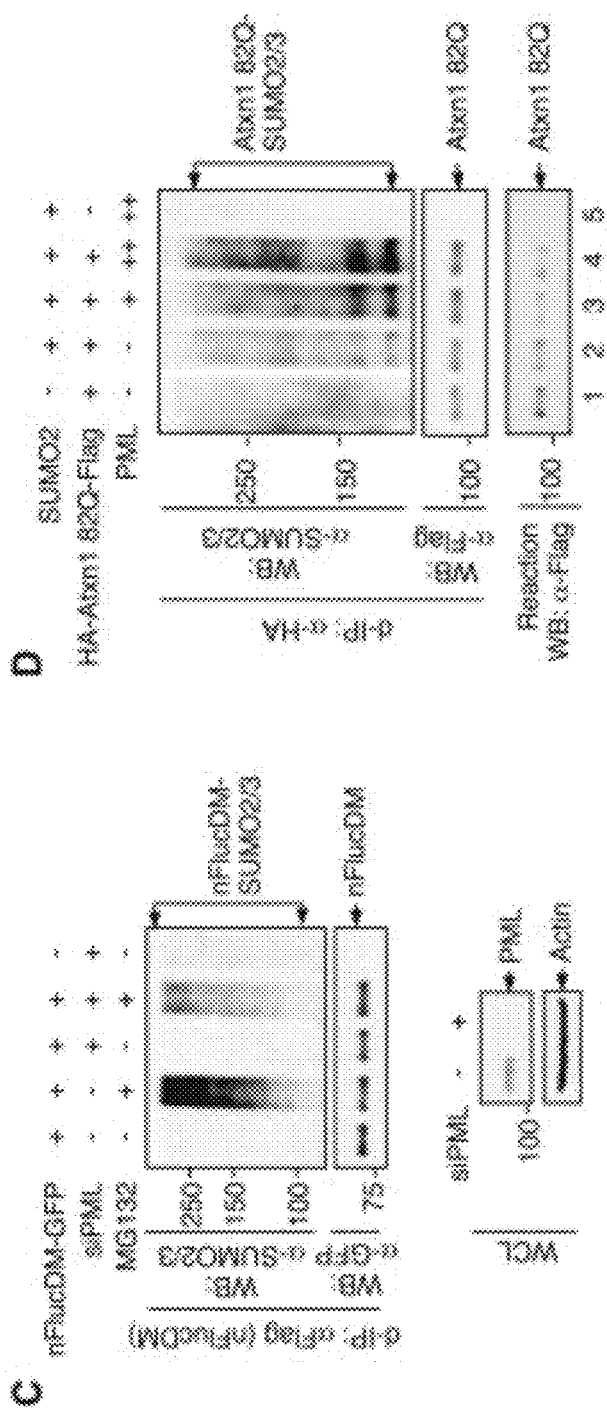

It was previously demonstrated that PML possesses SUMO E3 ligase activity that enhances the efficiency and specificity of SUMOylation (Chu and Yang, 2011, Oncogene, 30: 1108-1116). Hence, it was examined whether PML promotes SUMOylation of Atxn1 82Q. When co-expressed with Atxn1 82Q in cells, PML strongly increased SUMO2/3 modification of Atxn1 82Q, both in the absence and in the presence of the proteasome inhibitor MG132 (FIG. 4A). Conversely, silencing PML markedly reduced SUMO2/3-modified Atxn1 82Q under these conditions (FIG. 4B). Similarly, silencing PML reduced SUMO2/3 modification of nFlucDM (FIG. 4C).

Figures 4E, 4F:
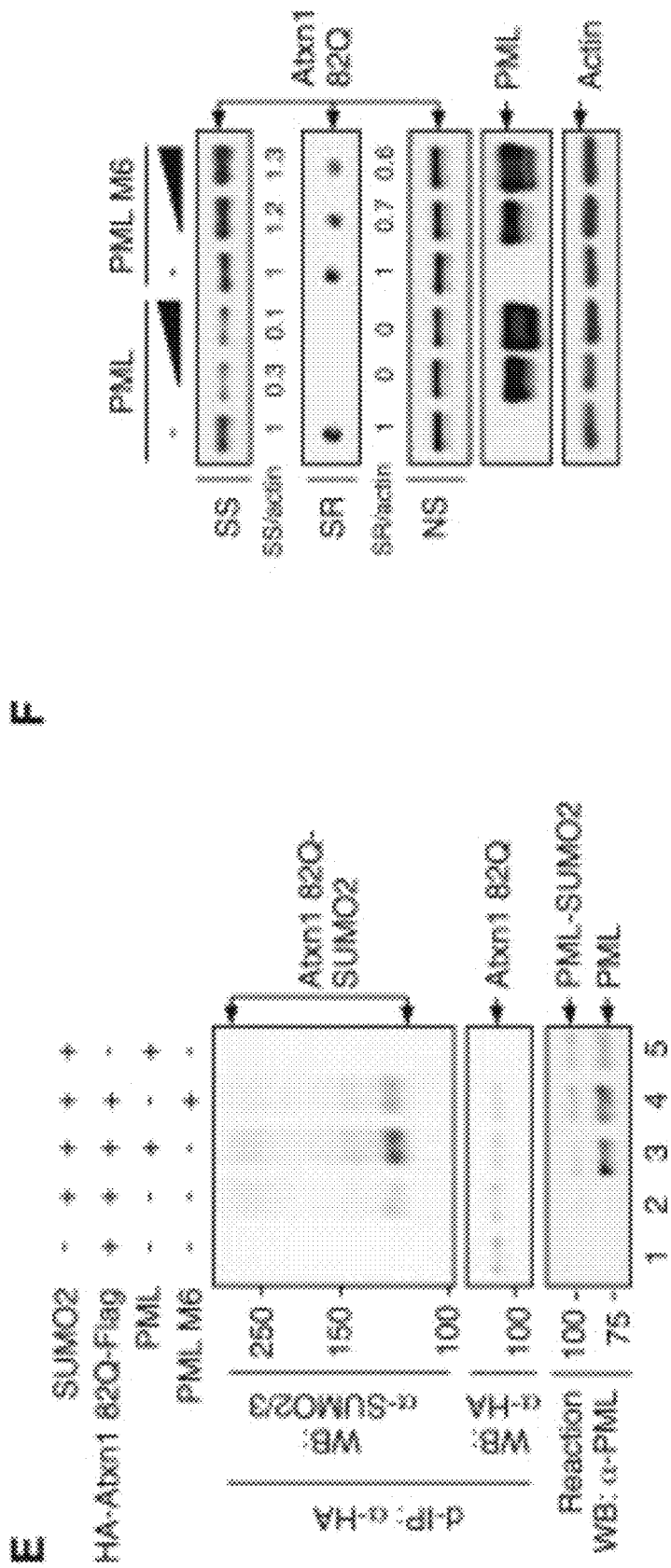

To confirm the SUMO E3 activity of PML toward Atxn1 82Q, in vitro SUMOylation assays were performed with purified recombinant proteins. In the absence of PML, Atxn1 82Q was weakly modified by SUMO2 (FIG. 4D and FIG. 4E), consistent with previous observations that SUMOylation can proceed in vitro without a SUMO E3 ligase (Wilkinson and Henley, 2010, Biochem J, 428: 133-145). Of note, PML augmented Atxn1 82Q SUMOylation in a dose-dependent manner (FIG. 4D and FIG. 4E). In contrast, a SUMO E3-defective mutant, PML M6 (Chu and Yang, 2011, Oncogene, 30: 1108-1116), failed to do so (FIG. 4E and FIG. 11G); PML M6 was also ineffective at reducing aggregated Atxn1 82Q (FIG. 4F). These results suggest that PML is a SUMO E3 ligase of Atxn1 82Q, and that this activity is involved in Atxn1 82Q degradation.

A Role for RNF4 in Degrading Misfolded Proteins

Figures 5A, 5B, 5C:
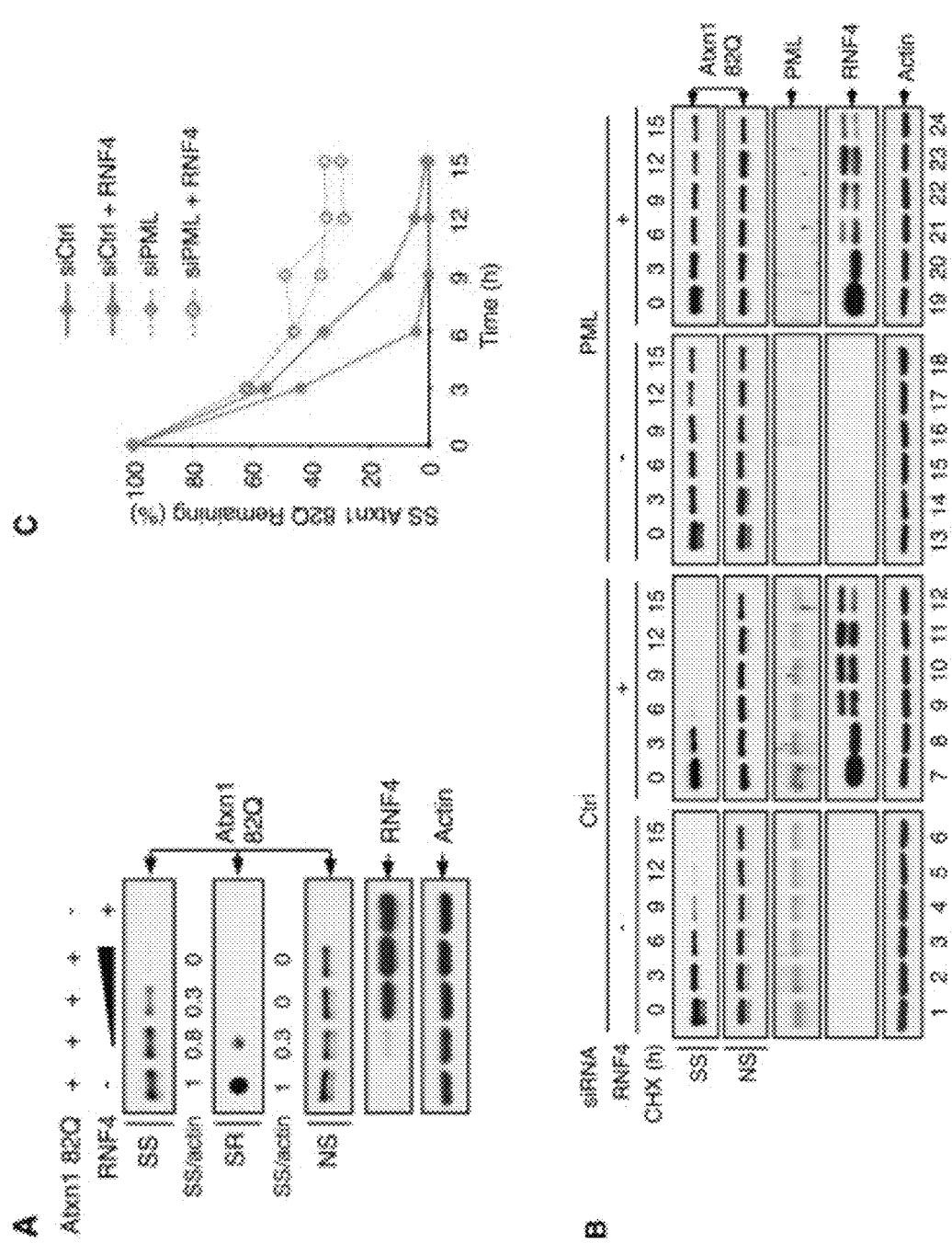
FIG. 5A through FIG. 5I, depicts the results of example experiments demonstrating a role of RNF4 in the degradation of Atxn1 82Q.
Figures 5D, 5E, 5F:
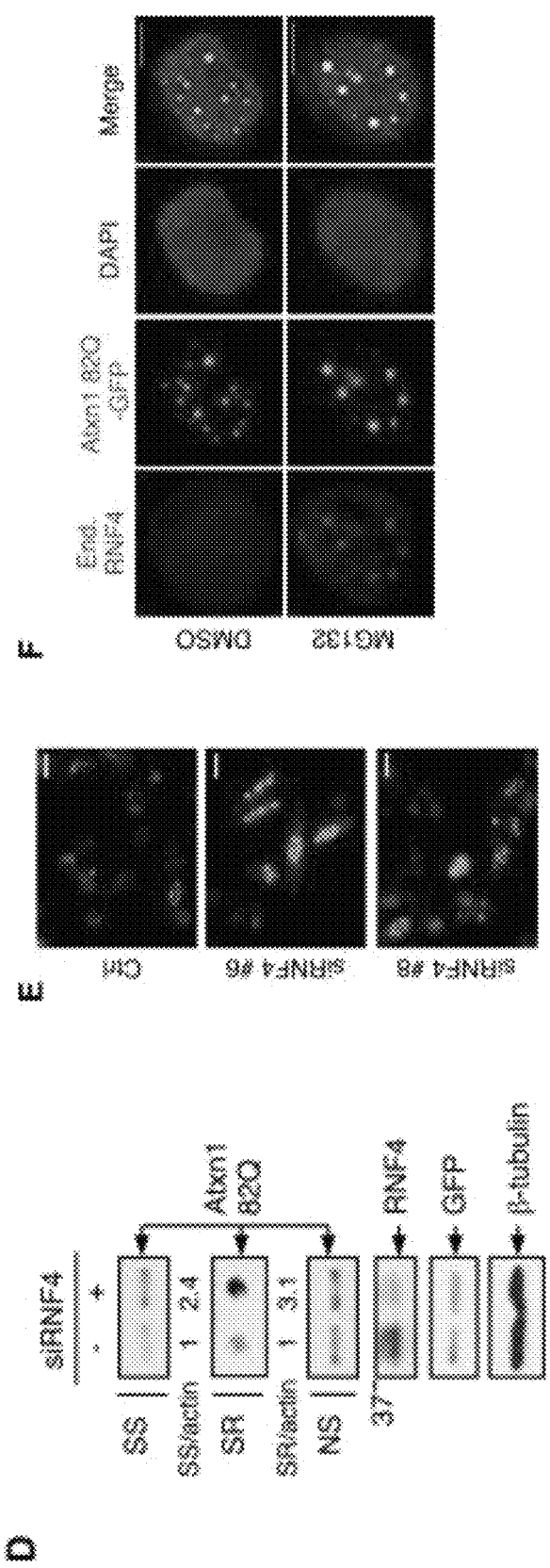
Figures 12A, 12B:
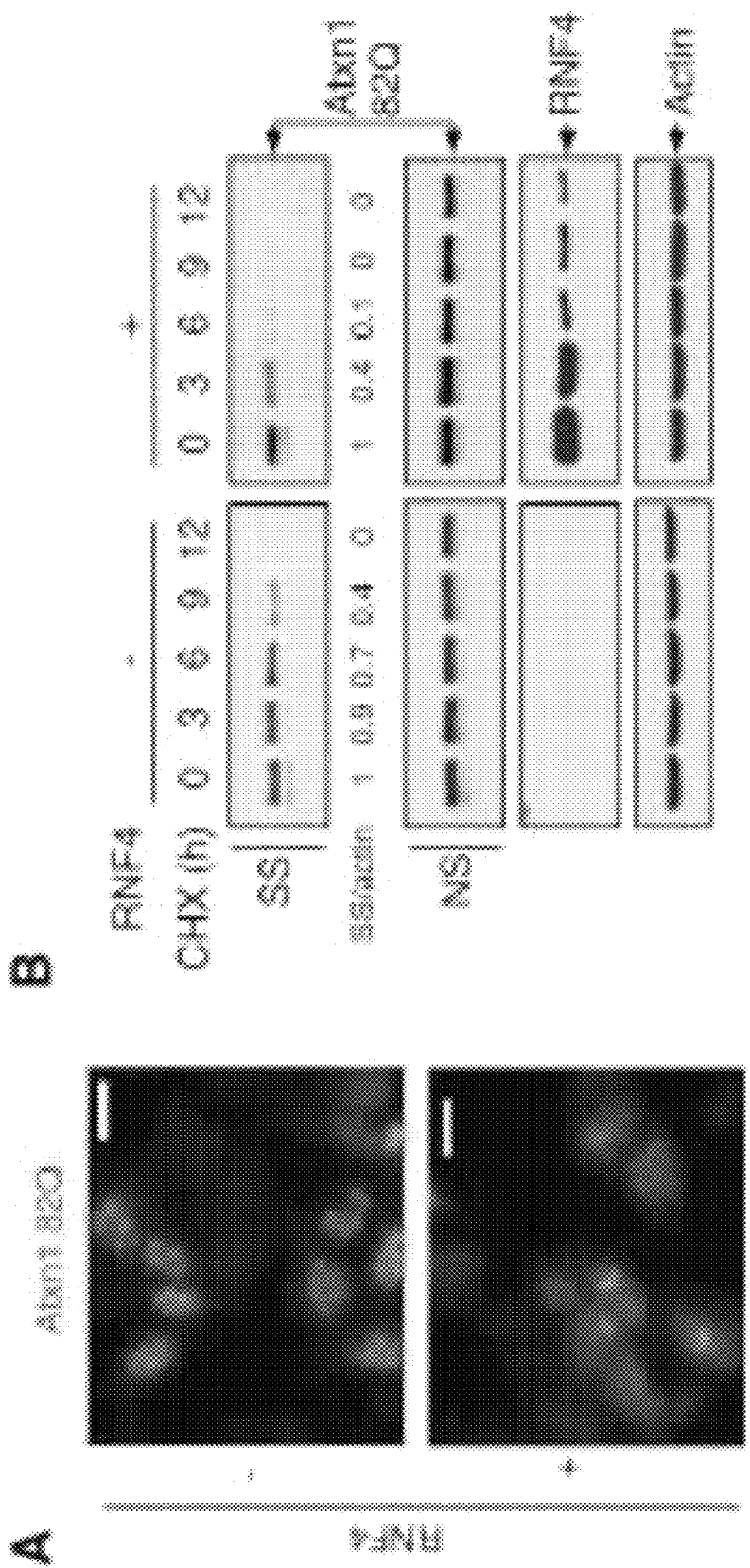
FIG. 12A through FIG. 12I, depicts the results of example experiments demonstrating that RNF4 promotes degradation of misfolded proteins.
Figures 12C, 12D:
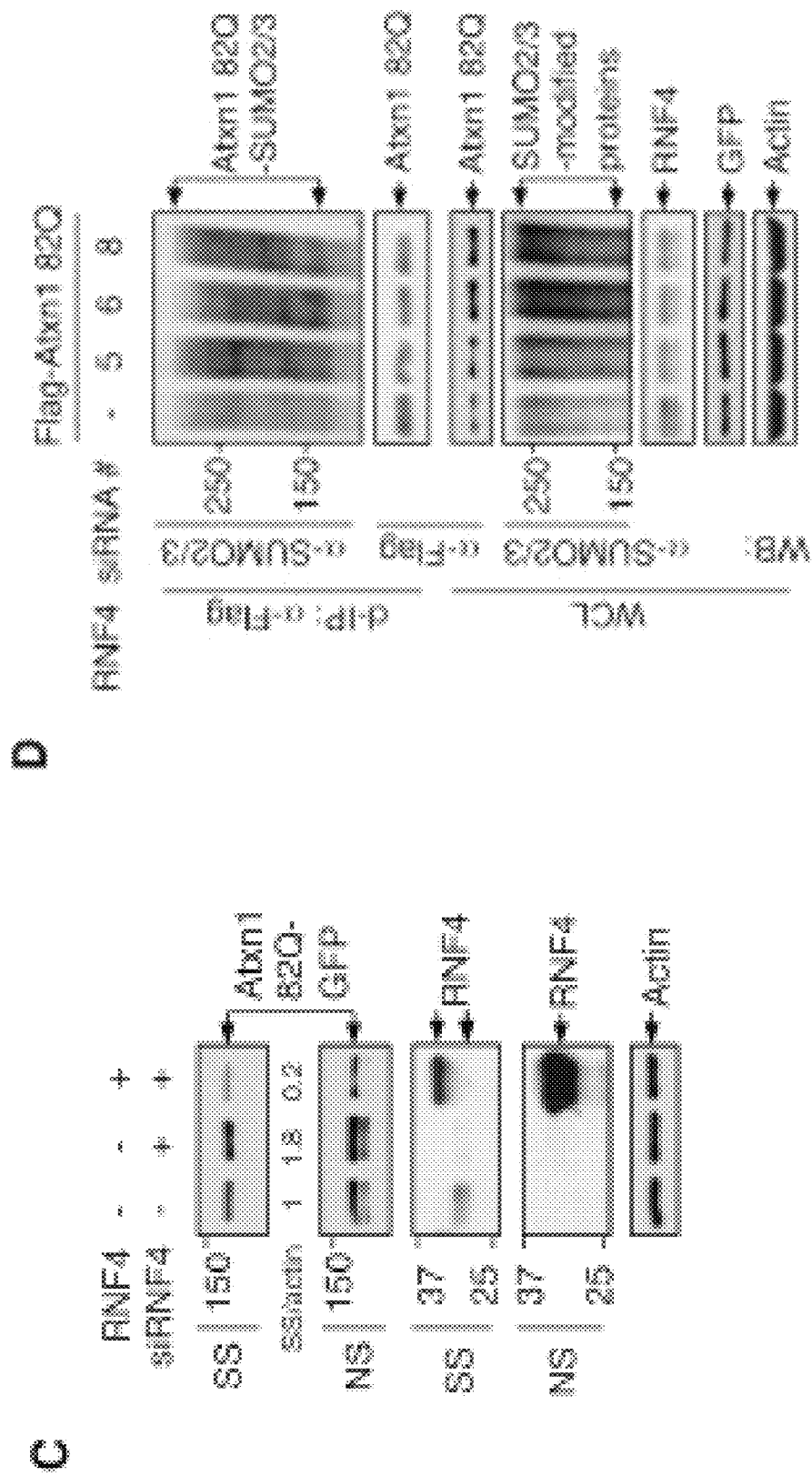

Proteins conjugated with a poly-SUMO2/3 chain can be recognized and ubiquitinated by RNF4, a RING domain ubiquitin ligase with four tandem SUMO-interacting motifs (SIMs) (Sun et al., 2007, EMBO J, 26: 4102-4112). However, the role of RNF4 in degrading misfolded proteins remains undefined. It was found that forced RNF4 expression strongly reduced the steady-state levels of aggregated Atxn1 82Q in cell lysates (FIG. 5A), as well as the number of Atxn1 82Q inclusions in the nucleus (FIG. 12A). RNF4 also shortened the half-life of aggregated, but not soluble, Atxn1 82Q (FIG. 5B, lanes 1-12; FIG. 5C and FIG. 12B). Conversely, knocking down endogenous RNF4 with three siRNAs, individually or in combination, increased total and aggregated Atxn1 82Q proteins in cell lysates (FIG. 5D, FIG. 12C and FIG. 12D), as well as Atxn1 82Q inclusions in the nucleus (FIG. 5E). An siRNA-resistant form of RNF4 could reverse the effect of RNF4 knockdown (FIG. 12C), indicative of the specificity of the siRNA.

Figures 5G, 5H, 5I:
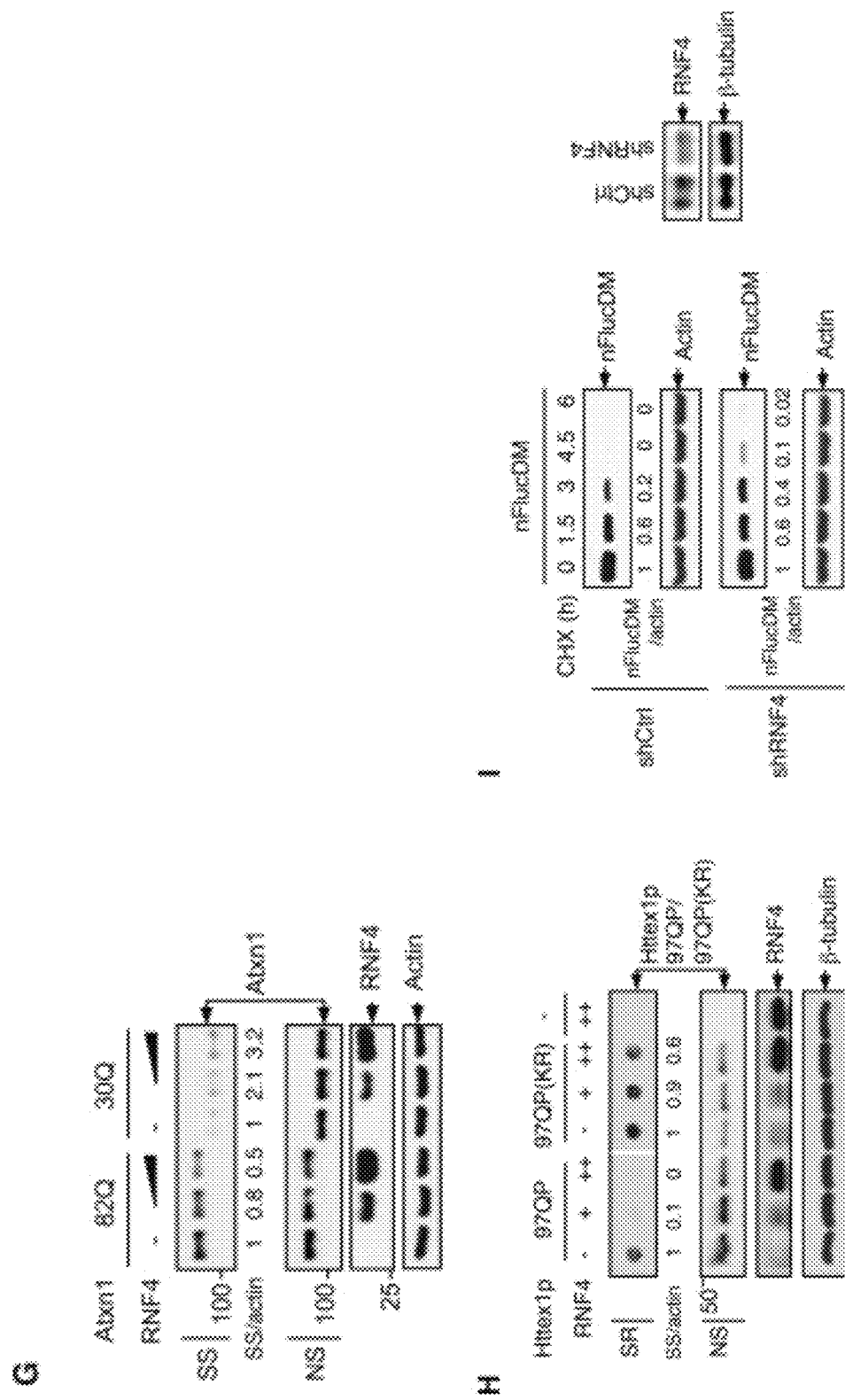

Moreover, both endogenous and exogenous RNF4 proteins normally displayed a diffuse nuclear distribution pattern with minimal or moderate co-localization with Atxn1 82Q inclusions. However, upon proteasome blockage, RNF4 became highly enriched in Atxn1 82Q inclusions (FIG. 5F and FIG. 12E), likely reflecting a stalled attempt of RNF4 in clearing Atxn1 82Q. In contrast to its effect on Atxn1 82Q, RNF4 did not reduce the levels of Atxn1 30Q (FIG. 5G). Collectively, these results demonstrate a role for RNF4 in eliminating pathogenic Atxn1 proteins.

Figures 12E, 12F, 12G:
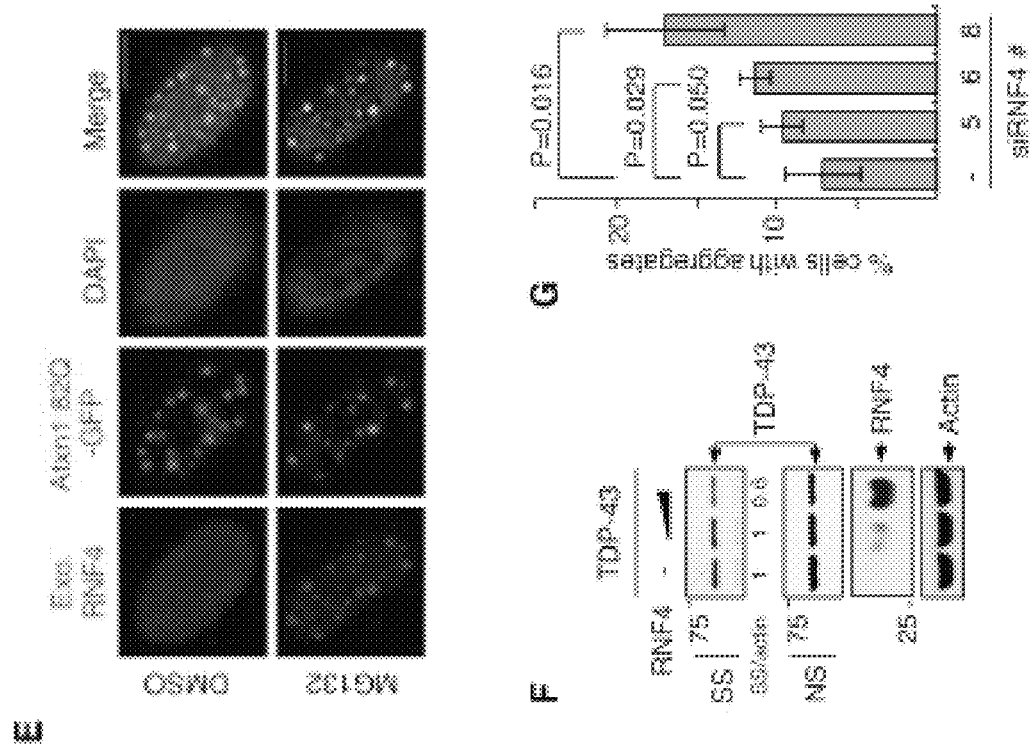
Figures 12H, 12I:
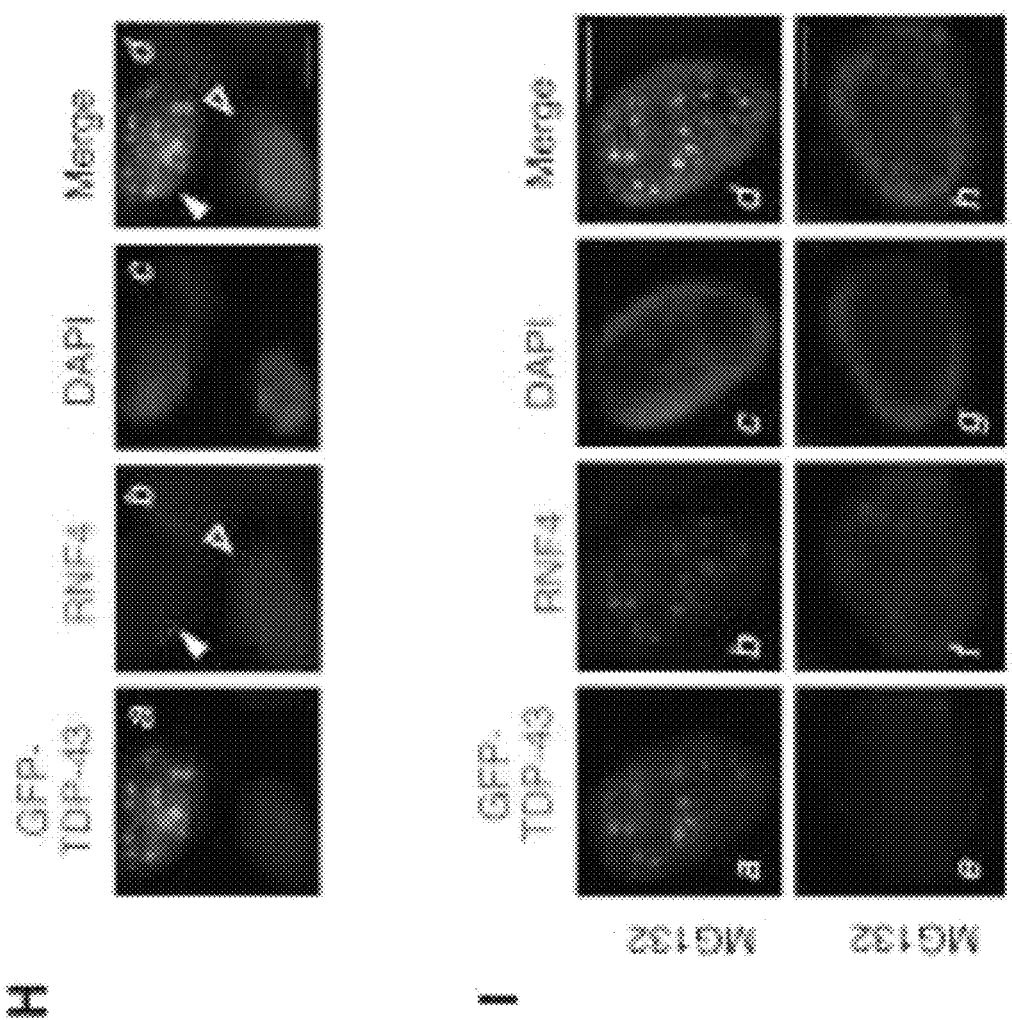

To assess a general effect of RNF4 on misfolded proteins, it was tested on Httex1p 97QP, TDP-43, and nFlucDM. Forced expression of RNF4 markedly reduced Httex1p 97QP, especially the aggregated form, while having a much weaker effect on Httex1p 97QP(KR) (FIG. 5H). Likewise, forced expression of RNF4 decreased the levels of TDP-43 (FIG. 12F), whereas silencing RNF4 augmented the percentage of TDP-43-expressing cells with nuclear inclusions (FIG. 12G and FIG. 12H). Upon proteasome inhibition, endogenous RNF4 became highly enriched in TDP-43 inclusions (FIG. 12I), similar to its accumulation in Atxn1 82Q inclusions under the same conditions (FIG. 5F). Moreover, silencing RNF4 prolonged the half-life of nFlucDM (FIG. 5I). Collectively, these observations suggest that RNF4 plays a critical role in the degradation of diverse misfolded proteins.

RNF4 Mediates Ubiquitination and Degradation of SUMO2/3-Modified Atxn1 82Q

Figure 6A:
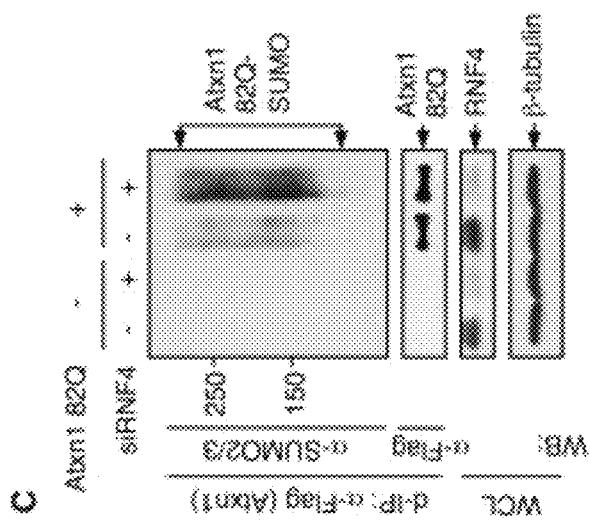
FIG. 6A through FIG. 6I, depicts the results of example experiments demonstrating that RNF4 promotes the ubiquitination and degradation of SUMO2/3-modified Atxn1 82Q.
Figure 6B:
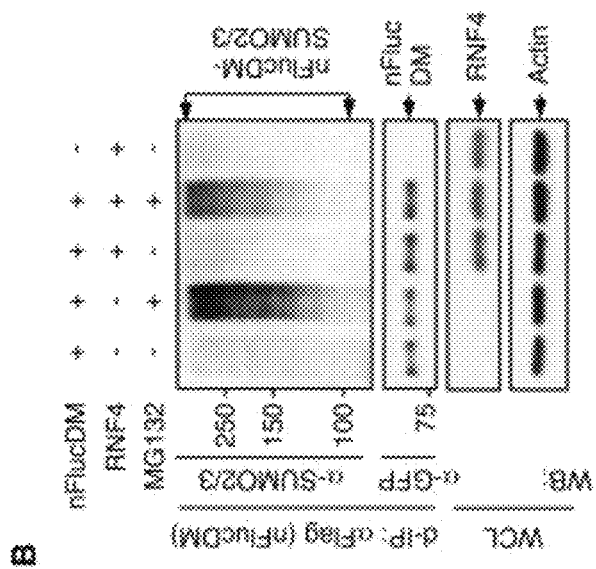
Figure 6C:
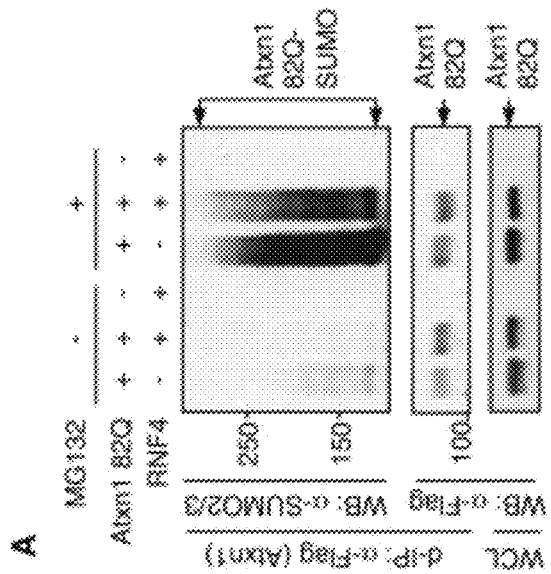
Figure 13A:
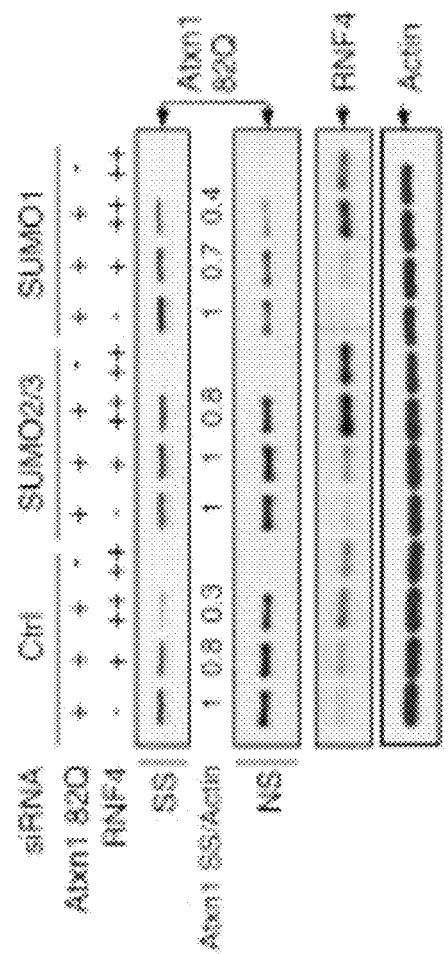
FIG. 13A through FIG. 13F, depicts the results of example experiments demonstrating that SUMO2/3 are involved in RNF4-mediated degradation of Atxn1 82Q.
Figure 13B:
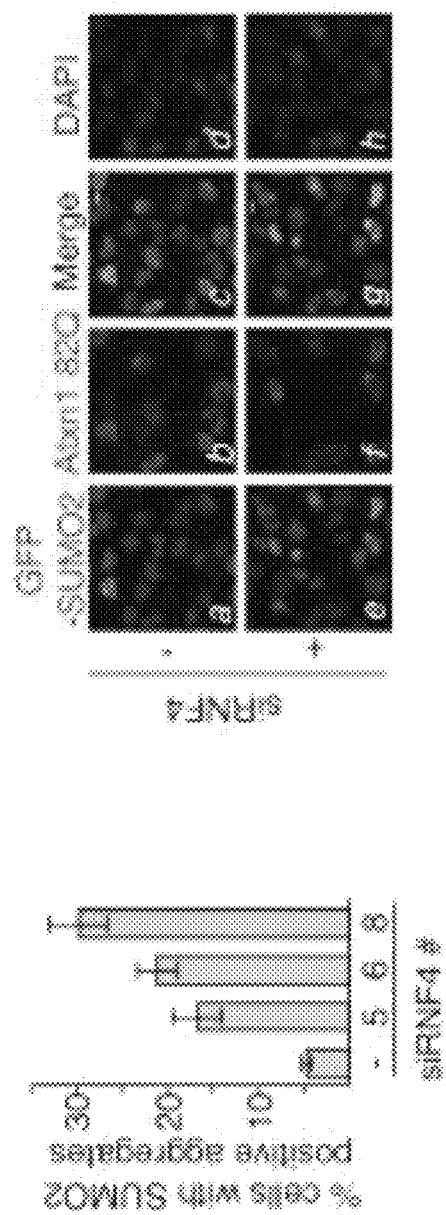

Similar to PML, the ability of RNF4 to eliminate misfolded proteins was dependent on SUMO2/3, as this ability was compromised in cells devoid of SUMO2/3, but not in cells devoid of SUMO1 (FIG. 13A). Of note, forced expression of RNF4 preferentially reduced SUMO2/3-modified Atxn1 82Q and nFlucDM over the unmodified proteins (FIG. 6A and FIG. 6B). Conversely, silencing RNF4 increased SUMO2/3-modified Atxn1 82Q (FIG. 6C) and enhanced the localization of GFP-SUMO2 to the Atxn1 82Q inclusions (FIG. 13B). These results show that RNF4 targets SUMO2/3-modified misfolded proteins for degradation.

Figure 6D:
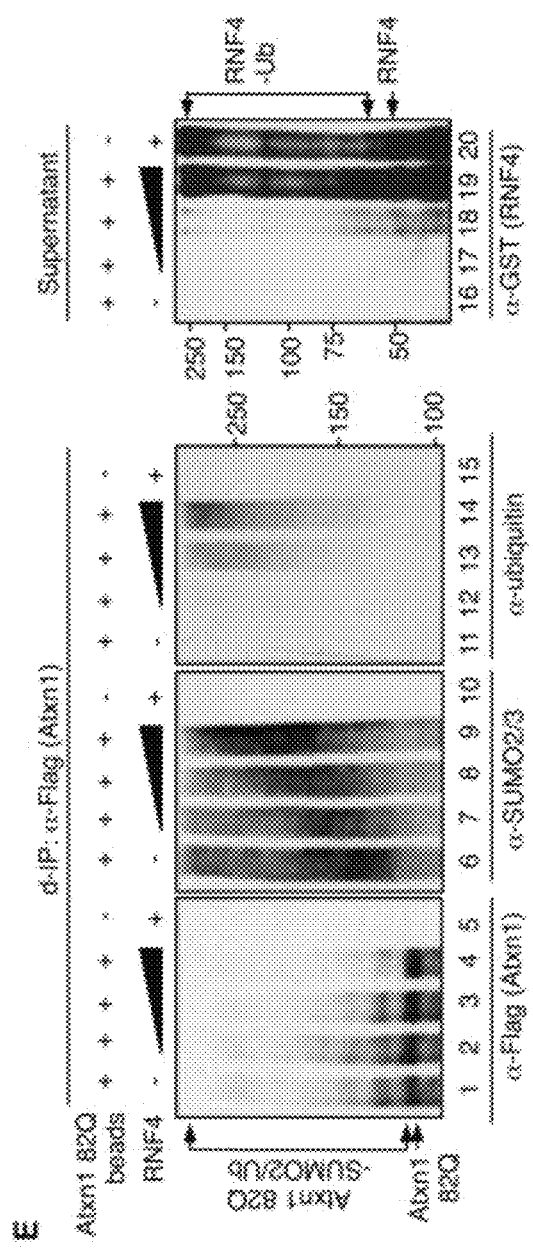
Figure 6E:
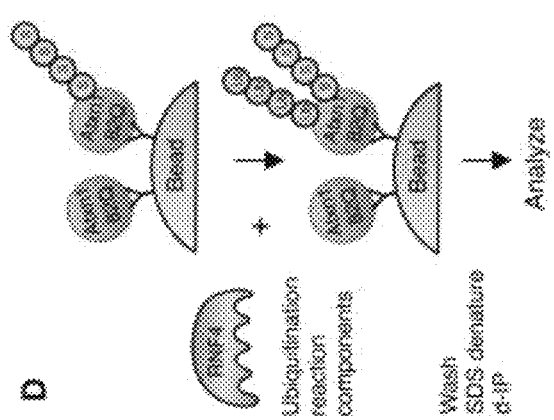

To confirm that RNF4 ubiquitinates SUMO2/3-conjugated misfolded proteins, an in vitro ubiquitination assay was performed using a mixture of unmodified and SUMO2-modified Atxn1 82Q proteins (FIG. 6D). In the presence of increasing doses of RNF4, the SUMO2-modified Atxn1 82Q proteins, which were of relatively low molecular weight (FIG. 6E, lanes 1, 6, and 9), were progressively converted to higher-molecular-weight species that were also modified by ubiquitin (lanes 2-4, 7-9, and 12-14). In contrast, the unmodified Atxn1 82Q protein was not ubiquitinated (lanes 1-4). Therefore, RNF4 is a ubiquitin ligase for SUMO2/3-modified, but not unmodified, Atxn1 82Q protein.

Figure 6F:
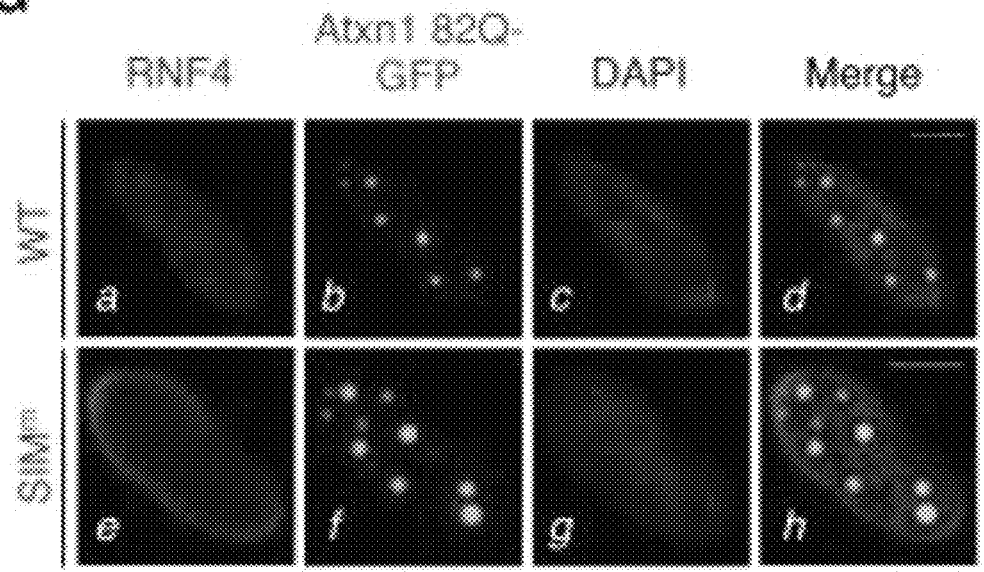
Figure 6G:
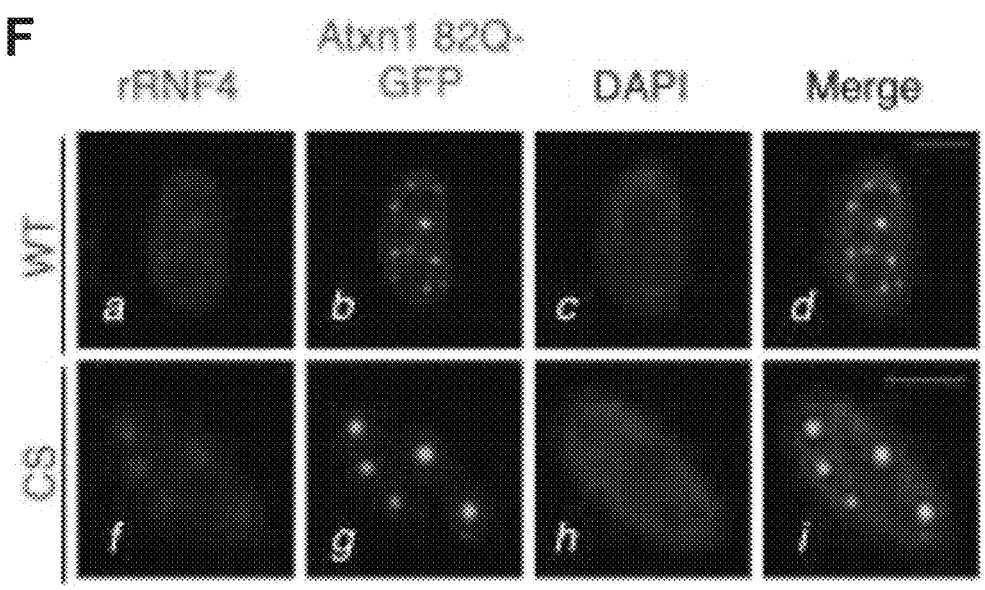
Figures 6H, 6I:
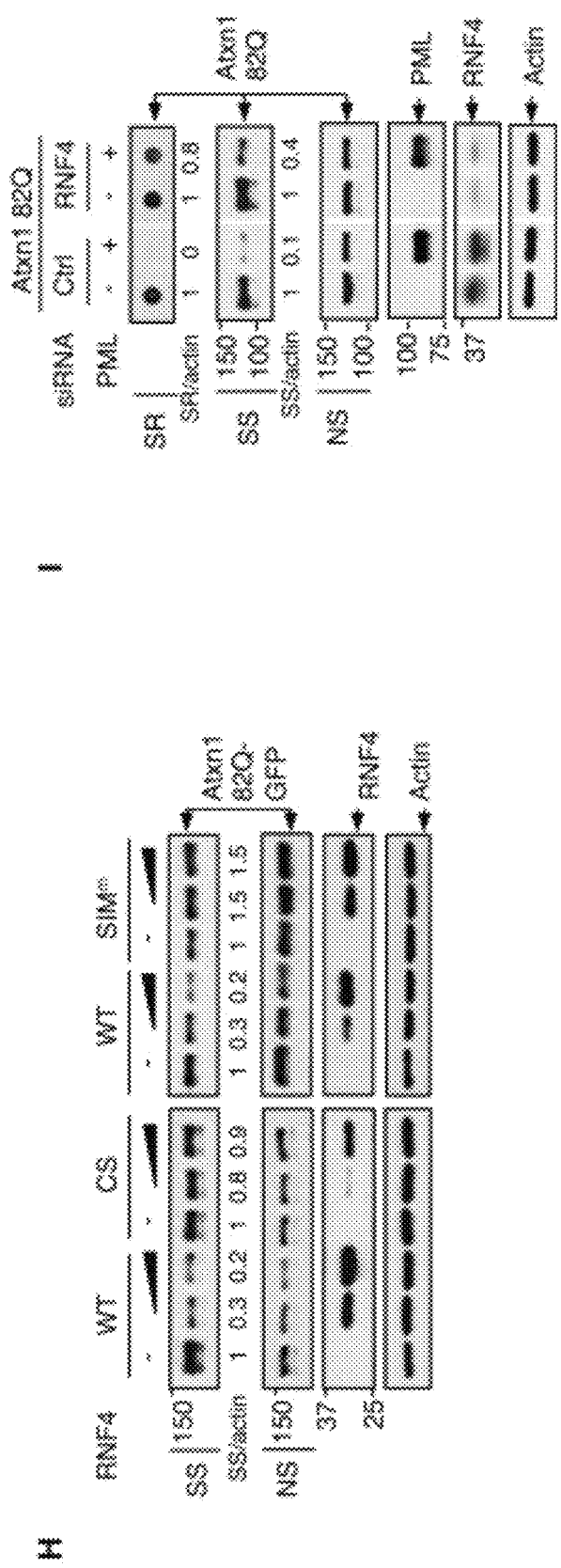
Figures 13C, 13D:
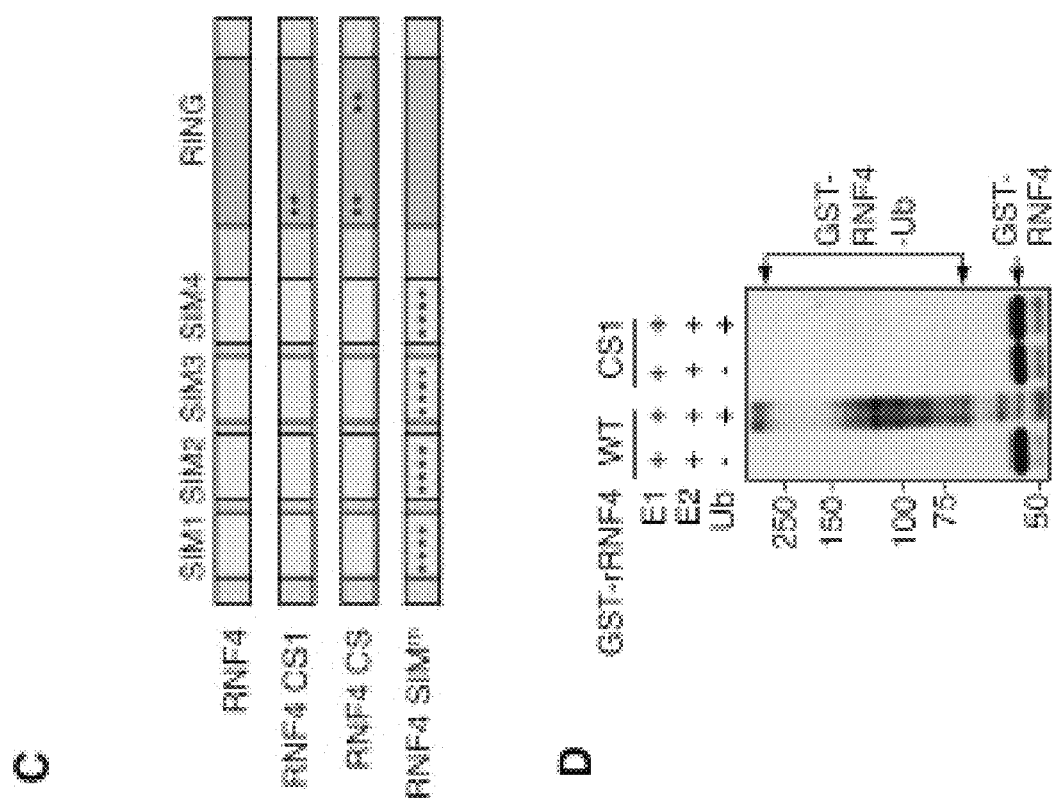

RNF4 possesses both ubiquitin ligase and SUMO-binding activities (Sun et al., 2007, EMBO J, 26: 4102-4112). To ascertain the involvement of these activities in degrading Atxn1 82Q, RNF4 mutants defective in either ubiquitin ligase (CS and CS1) or SUMO-binding (SIM$^m$) activity were generated (FIG. 13C). CS and CS1, albeit losing their ubiquitin E3 activity (FIG. 13D), were still able to co-localize with Atxn1 82Q inclusions (FIG. 6F). SIM$^m$, on the other hand, retained a substantial level of ubiquitin ligase activity (FIG. 13E), but failed to co-localize with Atxn1 82Q inclusions (FIG. 6G). Neither of the RNF4 mutant classes was capable of removing aggregated Atxn1 82Q (FIG. 6H). Collectively, these results suggest that RNF4 binds to SUMO2/3-modified misfolded proteins via its SIM region and ubiquitinates these proteins via its ligase activity.

Figures 13E, 13F:
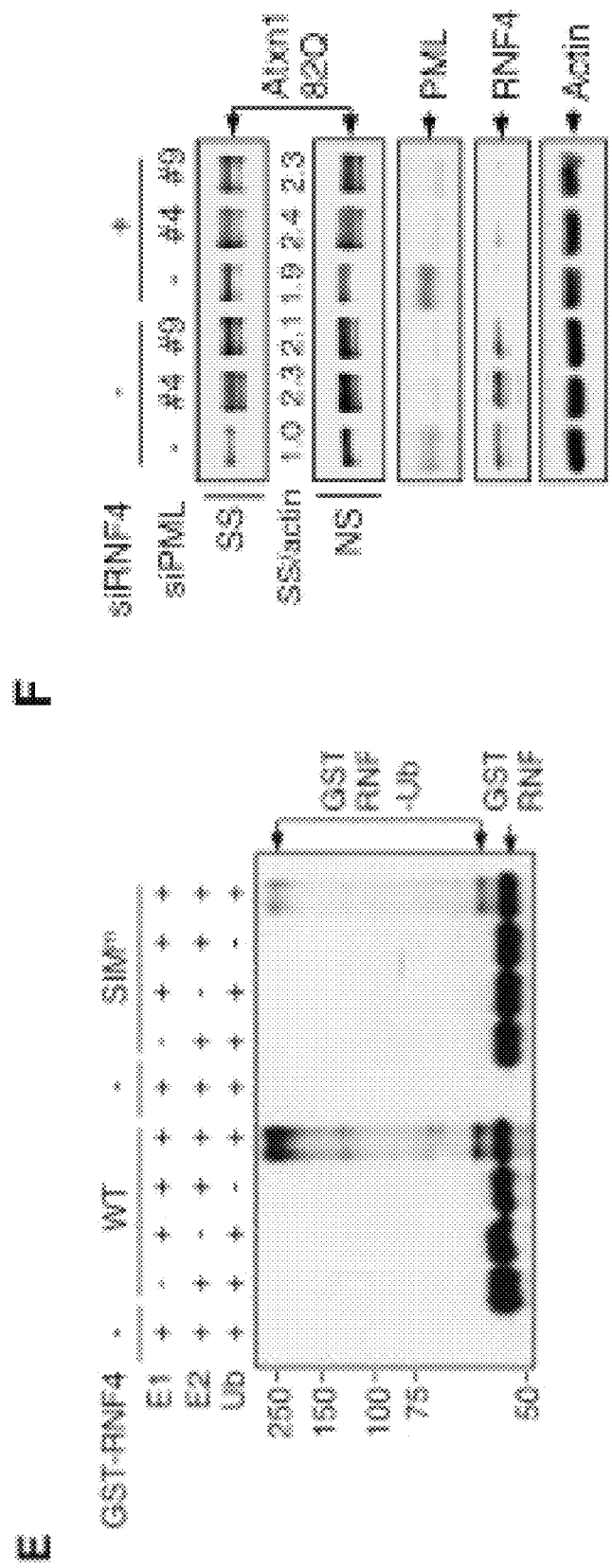

Although forced expression of PML led to effective clearance of aggregated Atxn1 82Q in control cells, this ability was greatly diminished in RNF4-depleted cells (FIG. 6I). Reciprocally, forced expression of RNF4, albeit highly effective in accelerating Atxn1 82Q degradation in control cells, failed to do so in PML-depleted cells (FIG. 5B, lanes 19-24 versus lanes 7-12; and FIG. 5C). Moreover, in PML-depleted cells, which displayed high Atxn1 82Q levels, silencing RNF4 did not further elevate the levels of Atxn1 82Q (FIG. 13F). These results indicate mutual dependence of PML and RNF4 in the degradation of Atxn1 82Q.

PML Deficiency Exacerbates Behavioral and Pathological Phenotypes in a Mouse Model of SCA1

The results described above revealed a PQC system that degrades Atxn1 82Q and likely other nuclear misfolded proteins through sequential PML-mediated SUMOylation and RNF4-mediated ubiquitination. To investigate the physiological role of this system, a mouse model of SCA1

(B05), which expresses the Atxn1 82Q transgene (Atxn1$^{tg/-}$) in the cerebellar Purkinje cells, was used. Resembling human SCA1 patients, B05 mice develop ataxia and neurological abnormalities with increasing age (Burright et al., 1995, Cell, 82: 937-948). The loss of RNF4 in mice results in embryonic lethality (Hu et al., 2010, Proc Natl Acad Sci, 107: 15087-15092), precluding the analysis of its effect on B05 mice. However, PML-knockout (PML$^{-/-}$) mice are viable and appear to develop normally (Wang et al., 1998, Science, 279: 1547-1551). B05 mice were crossbred with PML$^{-/-}$ and PML-wild-type (PML$^{+/+}$) mice and littermates of all genotypes—PML$^{+/+}$, PML$^{+/-}$, and PML$^{-/-}$, PML$^{+/+}$:Atxn1$^{tg/-}$, PML$^{+/-}$:Atxn1$^{tg/-}$ and PML$^{-/-}$:Atxn1$^{tg/-}$ were compared for both motor performance and neuropathology.

Motor performance—including balance, coordination, and endurance—was evaluated using a Rotarod apparatus with accelerating speed. To determine whether any potential behavioral defects were due to a progressively diminished capacity, as opposed to a developmental impairment, mice at different ages were examined. To rule out the influence of the long-term motor memory, only naive animals were used, each being tested for 4 consecutive days.

Figures 7A, 7B, 7C:
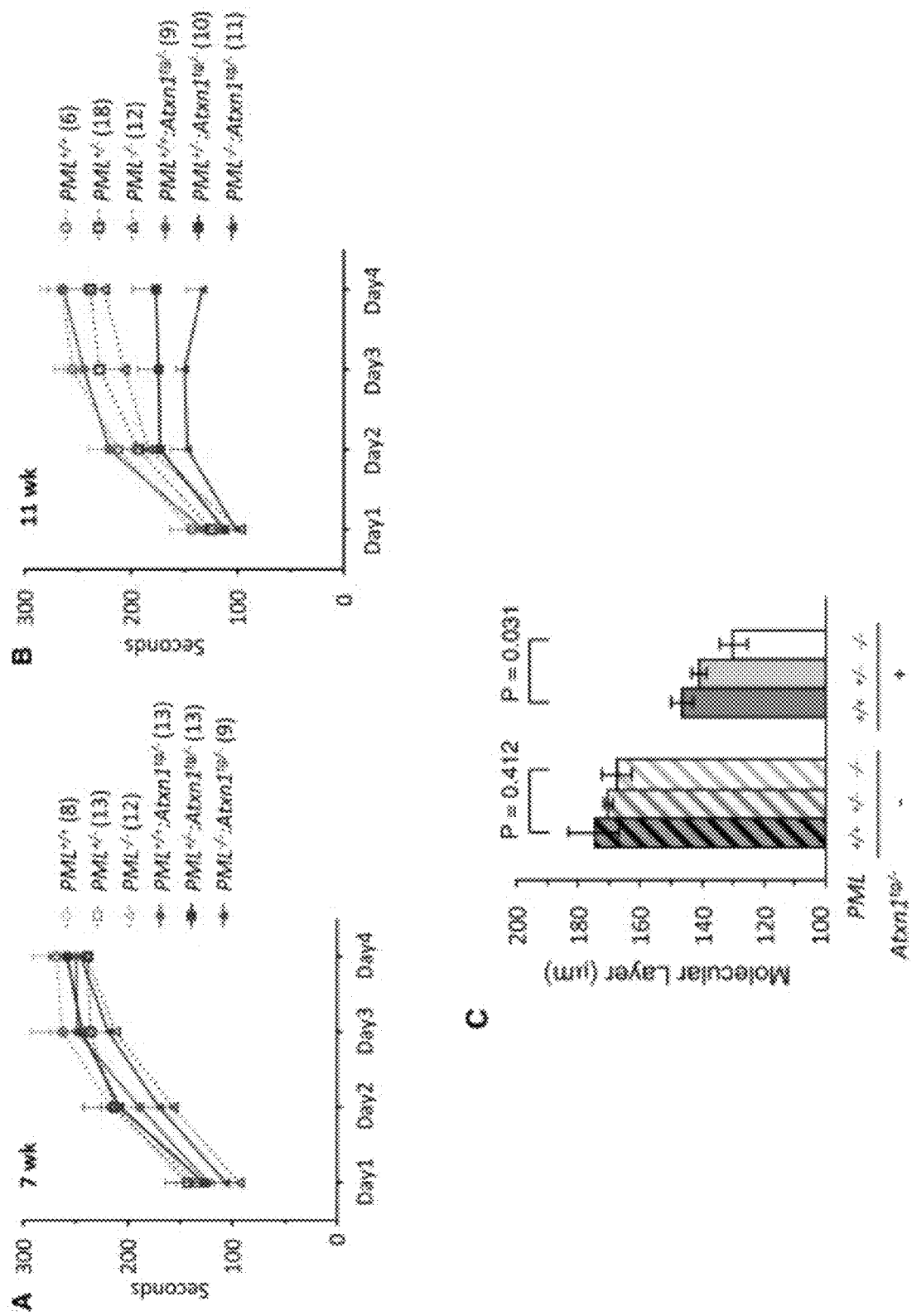
FIG. 7A through FIG. 7I, depicts the results of example experiments demonstrating that PML deficiency exacerbates behavioral and pathological phenotypes of the SCA1 mouse model.

At 7 weeks of age, all mice performed similarly on the Rotarod (FIG. 7A). Although some differences were observed among mice of distinct genotypes, they were not statistically significant (ANOVA p=0.53), suggesting that PML mice did not have pre-existing impairments in their motor functions. At 11 weeks of age, all mice lacking the Atxn1 82Q transgene (PML$^{+/+}$, PML$^{+/-}$, and PML$^{-/-}$) still showed no statistical difference in their performance (ANOVA p=0.33) (FIG. 7B), and PML$^{+/+}$ and PML$^{+/+}$:Atxn1$^{tg/-}$ also performed similarly. These observations suggest that either PML deficiency or Atxn1 82Q transgene expression alone was insufficient to cause motor defects at this age. Interestingly, PML$^{-/-}$:Atxn1$^{tg/-}$ showed severe impairments in Rotarod performance compared to either PML$^{+/+}$:Atxn1$^{tg/-}$ or PML$^{-/-}$ mice. Although these three groups of animals were comparable at the beginning of the 4 consecutive testing days, unlike the other two groups, PML$^{-/-}$:Atxn1$^{tg/-}$ mice showed minimal improvement over time. The lack of improvement of PML$^{-/-}$:Atxn1$^{tg/-}$ mice on the Rotarod was reminiscent of Atxn1$^{tg/-}$ mice at advanced stages (Clark et al., 1997, J Neurosci, 17: 7385-7395). The PML heterozygous counterparts (PML$^{+/-}$:Atxn1$^{tg/-}$ mice) displayed an intermediate impairment on the Rotarod (ANOVA p=0.0004 for the three Atxn1$^{tg/-}$ groups) (FIG. 7B). Thus, PML deficiency aggravates motor defects of the Atxn1$^{tg/-}$ mice.

Figures 7D, 7E:
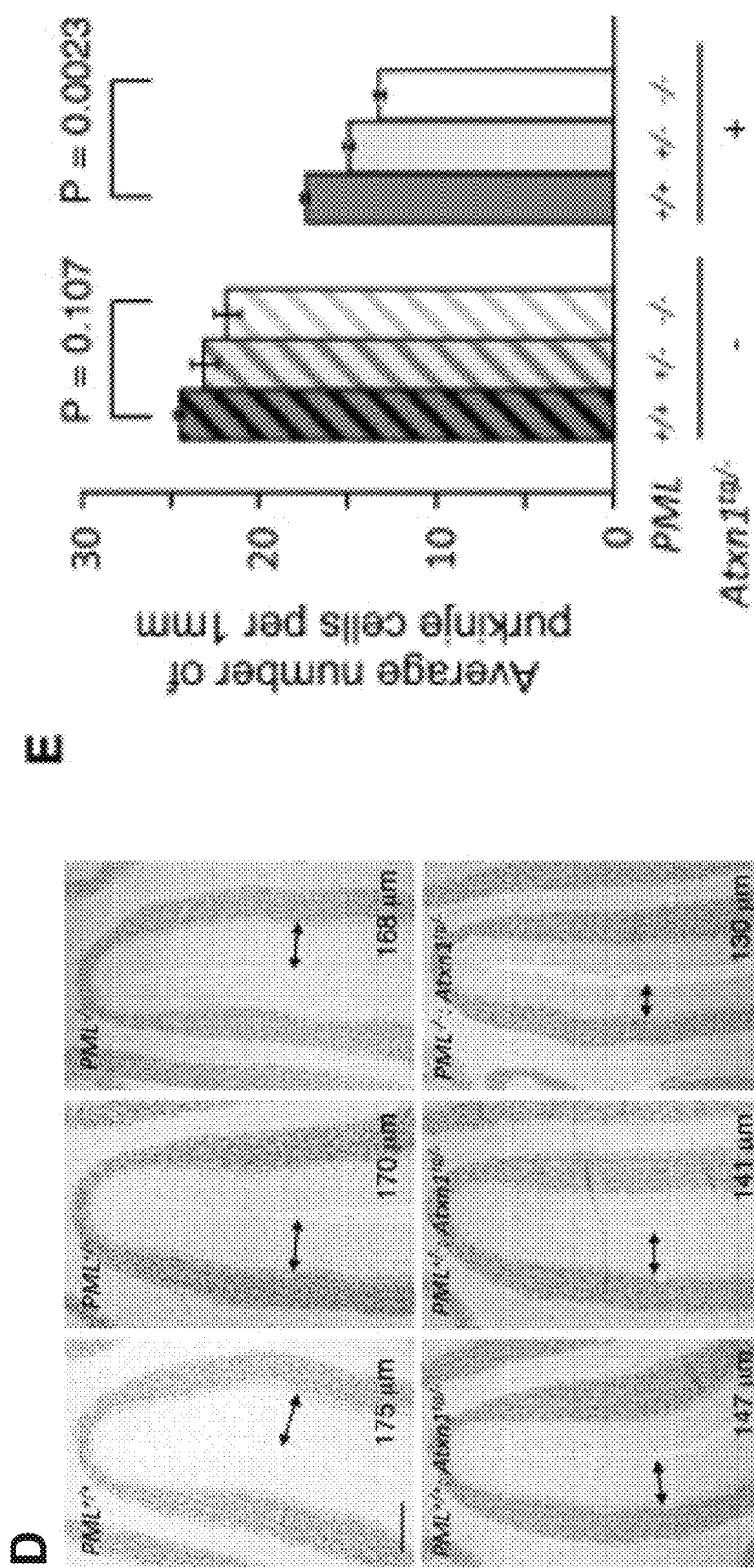

The major neuropathological phenotype of the Atxn1$^{tg/-}$ mice is the degeneration of Purkinje cells, a constituent of the top layer (the molecular layer) of the cerebellar cortex. This degeneration is manifested initially in the shrinkage of the molecular layer and the atrophy of Purkinje cell dendrites, and later in the loss of Purkinje cell bodies (Burright et al., 1995, Cell, 82: 937-948; Clark et al., 1997, J Neurosci, 17: 7385-7395). At 12 weeks of age, PML$^{+/-}$ and PML$^{-/-}$ mice showed only a slight and statistically insignificant shrinkage in the molecular layers, while PML$^{+/+}$:Atxn1$^{tg/-}$ mice exhibited a discernible shrinkage, compared to PML$^{+/+}$ mice (FIG. 7C and FIG. 7D). Because PML$^{+/+}$:Atxn1$^{tg/-}$ mice performed similarly on the Rotarod to PML$^{+/+}$ mice (FIG. 7B), neurodegeneration in PML$^{+/+}$:Atxn1$^{tg/-}$ mice might not have reached a critical threshold. This nonlinear correlation between behavioral and pathological phenotypes of the SCA1 transgenic model has been previously observed (Gehrking et al., 2011, Hum Mol Genet, 20: 2204-2212). Importantly, compared to PML$^{+/+}$:Atxn1$^{tg/-}$ mice, PML$^{+/-}$: Atxn1$^{tg/-}$ and PML$^{-/-}$:Atxn1$^{tg/-}$ mice displayed a moderate and a strong further reduction, respectively, in the thickness of molecular layer (FIG. 7C and FIG. 7D). This correlated with worsening performance of these animals on the Rotarod (FIG. 7B). Thus, PML deficiency aggravates the shrinkage of the molecular layer in Atxn1$^{tg/-}$ mice.

Figures 14A, 14B:
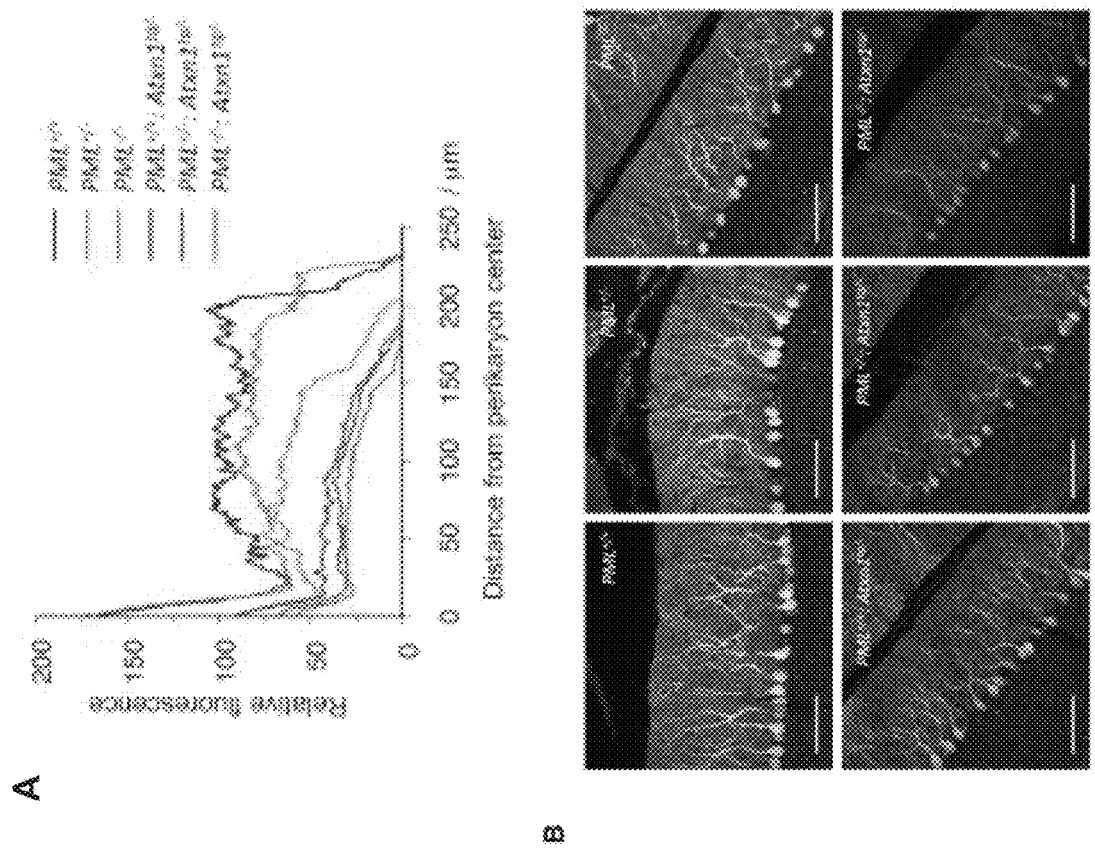
FIG. 14A through FIG. 14D, depicts the results of experiments demonstrating that PML deficiency reduces arborization of Purkinje cell dendrites but does not result in aggregates in Purkinje cells.

Dendritic arborization of Purkinje cells was also examined by immunofluorescence staining with an antibody against the Purkinje cell-specific protein calbindin. At 12 weeks of age, the fluorescence intensity of Purkinje cell dendrites in all groups containing the Atxn1 82Q transgene was reduced to very low levels that precluded precise comparison (FIG. 14A and FIG. 14B). Of note, compared to PML$^{+/+}$ littermates, PML$^{-/-}$ mice already showed a strong reduction in dendritic arborization of Purkinje cells, while PML$^{+/-}$ mice showed an intermediate reduction (FIG. 14A and FIG. 14B). These results indicate that PML itself has a role in protecting against neurodegeneration.

Figures 7F, 7G:
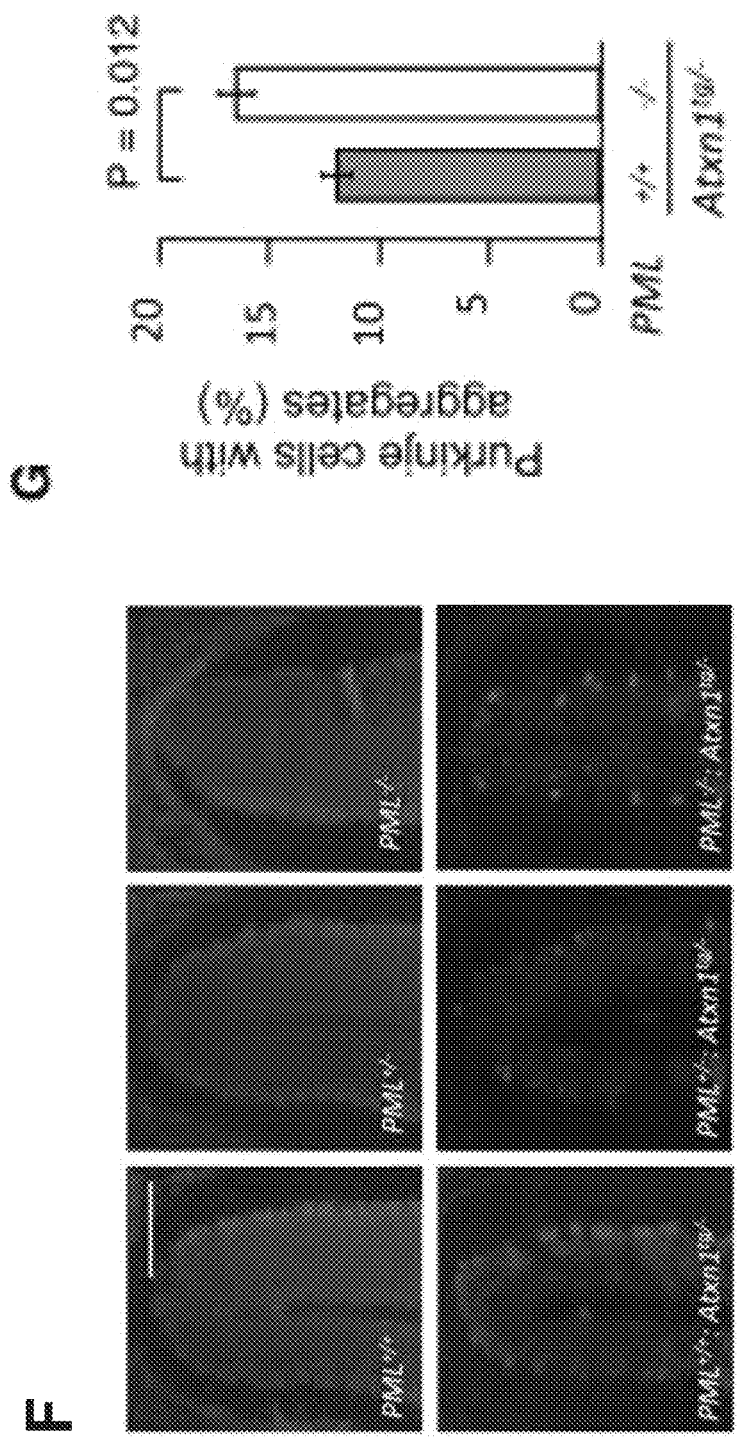
Figures 14C, 14D:
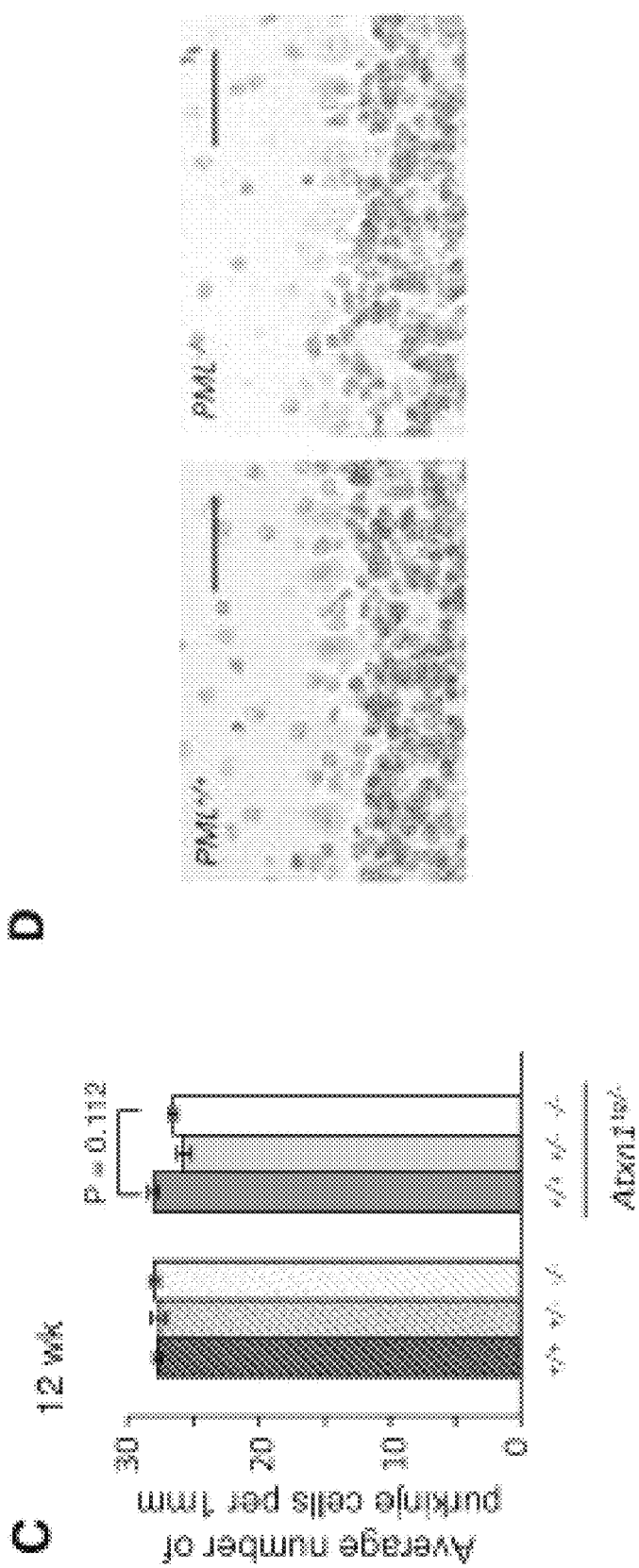

Despite the thinning of the molecular layer and the loss of Purkinje cell dendrites that were associated with PML deficiency, no significant difference in Purkinje cell population was observed among 12-week-old animals of different genotypes (FIG. 14C). At 1 year of age, PML$^{-/-}$ mice displayed only a mild (11.0%) and statistically insignificant (p=0.107) reduction in the number of Purkinje cells compared to PML$^{+/+}$ mice, while PML$^{+/+}$:Atxn1$^{tg/-}$ mice displayed a noticeable reduction (FIG. 7E and FIG. 7F). Of note, PML$^{-/-}$:Atxn1$^{tg/-}$ mice showed a significant further reduction in Purkinje cell density compared to PML$^{+/+}$:Atxn1$^{tg/-}$ mice (~24%, p=0.0023), and PML$^{+/-}$:Atxn1$^{tg/-}$ mice showed an intermediate cell loss (FIG. 7E and FIG. 7F). Again, these results demonstrate that PML deficiency worsens the neuropathological defects caused by the Atxn1 82Q transgene.

Figures 7H, 7I:
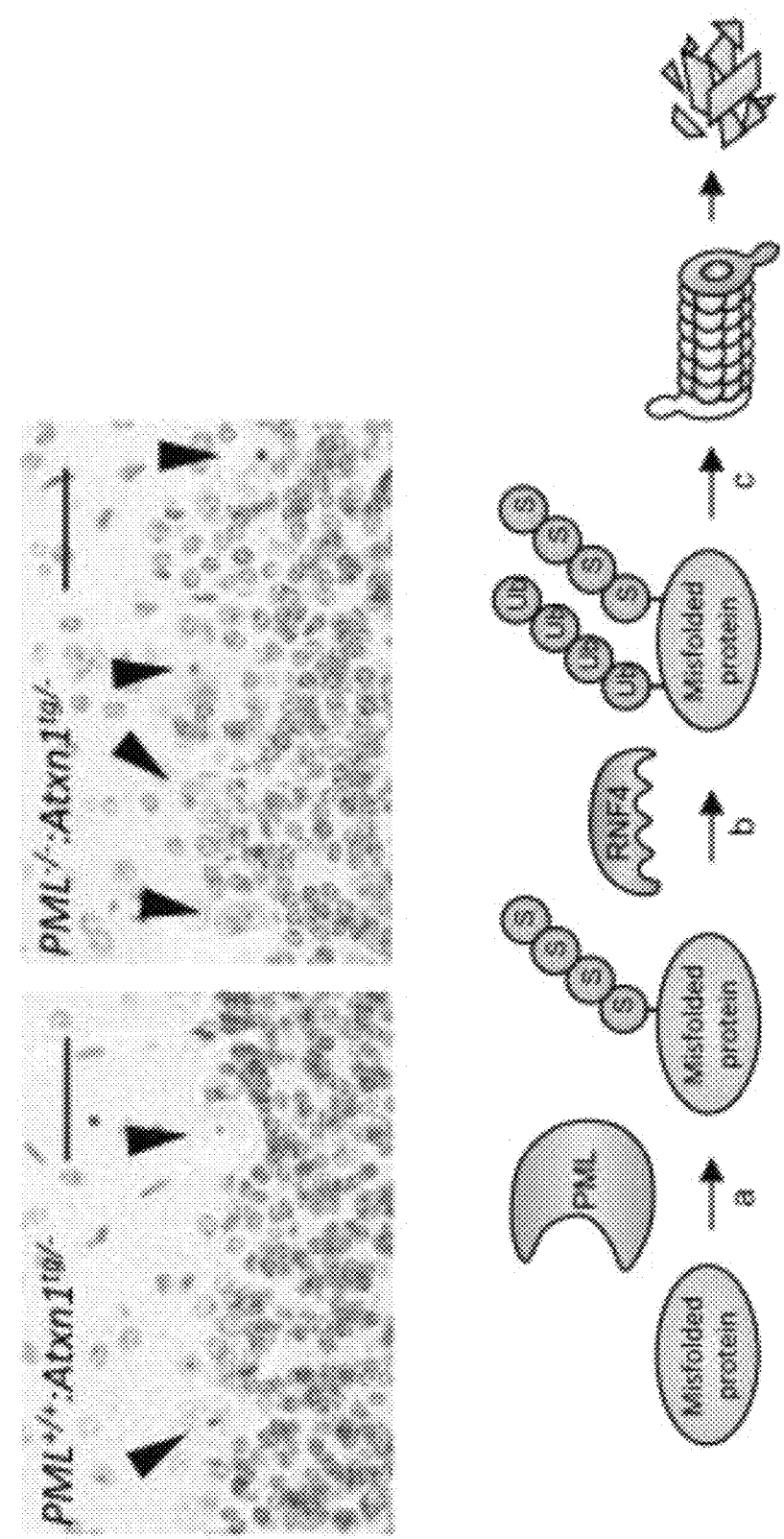

Neurodegeneration of B05 mice is accompanied by the formation of ubiquitin-positive Atxn1 82Q inclusions in Purkinje cells (Clark et al., 1997, J Neurosci, 17: 7385-7395). To determine the effect of PML on Atxn1 82Q nuclear inclusions, Purkinje cells with these inclusions were quantified in mice at 12 weeks of age. PML deficiency alone did not result in the formation of aggregates (FIG. 14D), but it significantly increase the number of aggregate-containing Purkinje cells in Atxn1 82Q transgenic mice (FIG. 7G and FIG. 7H). Collectively, these results suggest that endogenous PML plays a role in preventing accumulation of misfolded proteins in SCA1 animals and suppressing the progression of this neurodegenerative disease.

PQC System that Degrades Misfolded Proteins

Presented herein is evidence for a PQC system that degrades misfolded proteins in mammalian cell nuclei. This system comprises a recognition branch, PML, which selectively binds to misfolded proteins and marks these proteins with poly-SUMO2/3 chains, and an effector branch, RNF4, which ubiquitinates SUMOylated misfolded proteins and targets them for proteasomal degradation. This relay system likely provides a critical link between misfolded proteins and the proteasome in mammalian cells, and it may play an important role in the protection against neurodegeneration and other proteopathies (FIG. 7I).

Selective Recognition of Misfolded Proteins by PML

The exquisite selectivity of this system resides in PML, which contains at least two SRSs. SRS1, consisting of the CC region within the TRIM/RBCC motif, favors CC structures on pathogenic polyQ proteins and perhaps other misfolded proteins. SRS2, consisting of the C-terminal 63 amino acids, recognizes short peptides enriched in both aromatic (Phe, Trp, and Tyr) and positively charged (Arg and Lys) amino acids. SRS2 is similar to the bacterial Hsp100 ClpB (Schlieker et al., 2004, Nat Struct Mol Biol, 11: 607-615), except that SRS2 also favors peptides containing Leu, a residue that is often exposed in misfolded proteins and is engaged by Hsp70 (Rudiger et al., 1997, EMBO J, 16: 1501-1507). Thus, SRS2 displays a hybrid substrate specificity of ClpB and Hsp70. These observations indicate that PML can recognize structures or regions that are commonly found in misfolded proteins.

A Role for SUMOylation in Degrading Misfolded Proteins

Conjugation to SUMO is a major posttranslational modification, occurring on numerous proteins and vital to most eukaryotic life. Yet, beyond the generalization that it alters protein-protein interactions, the physiological function of SUMOylation remains elusive (Wilkinson and Henley, 2010, Biochem J, 428: 133-145). A prominent feature of the PML-RNF4 system is the involvement of SUMO2/3 modification prior to ubiquitination (FIG. 3, FIG. 4, and FIG. 11). It was observed previously that conjugation of SUMO2/3 to cellular proteins is markedly enhanced by protein-denaturing stresses (Saitoh and Hinchey, 2000, J Biol Chem, 275: 6252-6258). The evidence presented in the current study provides an explanation for this observation, and suggests that a principal physiological function of SUMO2/3 modification is likely to facilitate the degradation of misfolded proteins, acting in concert with ubiquitination.

SUMO conjugation enhances protein solubility (Panavas et al., 2009, Methods Mol Biol, 497: 303-317). Because aggregated proteins cannot be effectively degraded by the proteasome (Verhoef et al., 2002, Hum Mol Genet, 11: 2689-2700), enhancing protein solubility may be a beneficial effect conferred by PML prior to ubiquitination. Moreover, the extent of SUMOylation may enable the "triage decision" as to whether a given misfolded protein is selected for refolding or degradation. Consistent with this notion, conjugation to a single SUMO appears to be sufficient to enhance protein solubility (Panavas et al., 2009, Methods Mol Biol, 497: 303-317), and thus may facilitate refolding. In contrast, conjugation to SUMO2/3 chains is needed for effective recognition by the four tandem SIMs on RNF4 for ubiquitination and degradation (Tatham et al., 2008, Nat Cell Biol, 10: 538-546). Such chains may form after unsuccessful refolding attempts.

SUMOylation of misfolded proteins has been reported to either promote or inhibit neurodegenerative diseases (Martin et al., 2007, Nat Rev Neurosci, 8: 948-959). These seemingly contradictory observations may be reconciled by the distinct functions of SUMO1 and SUMO2/3 in the removal of misfolded proteins (FIG. 3), and by the dichotomy between the functions of SUMOylation: enhancing solubility of an abnormal protein (which may enhance its toxicity) and promoting its degradation. Thus, the outcome of elevated SUMOylation likely depends on whether it can be matched by the cellular degradative capacity.

A Potential Major PQC System

Proteins in the nucleus may harbor mutations or sustain acute and chronic damages, as proteins elsewhere do. The highly crowded environment of the nucleus likely makes it especially challenging to maintain protein quality. The ubiquitin-proteasome pathway is expected to be the main degradative system in the nucleus, where autophagy is not known to operate. Previous studies have implicated a few ubiquitin ligases, such as yeast San1 and Doa10 and mammalian UHRF-2 and E6-AP, in the degradation of nuclear misfolded proteins (Cummings et al., 1999, Neuron, 24: 879-892; Deng and Hochstrasser, 2006, Nature, 443: 827-831; Gardner et al., 2005, Cell, 120: 803-815; Iwata et al., 2009, J Biol Chem, 284: 9796-9803). Nevertheless, the predominantly nuclear localization of PML, along with the potent effect of PML and RNF4 on diverse misfolded nuclear proteins, suggests that the PML-RNF4 system is likely a major PQC system in mammalian cell nuclei.

The TRIM family of proteins is shared among metazoans, from approximately 20 members in *C. elegans* to over 70 in mice and humans (Ozato et al., 2008, Nat Rev Immunol, 8: 849-860). It was previously demonstrated that at least several other TRIM proteins also possess SUMO E3 activity (Chu and Yang, 2011, Oncogene, 30: 1108-116). Given their localization to the cytoplasm in addition to the nucleus (Ozato et al., 2008, Nat Rev Immunol, 8: 849-860), it is speculated that TRIM proteins also participate in PQC in the cytoplasm. The rapid expansion of the TRIM proteins during evolution might in part be a response to the increasing complexity of managing protein quality in cells of longer-living animals.

RNF4 is conserved among vertebrates (Sun et al., 2007, EMBO J, 26: 4102-4112). SUMO-dependent ubiquitin ligases are also present in low eukaryotic species (Sun et al., 2007, EMBO J, 26: 4102-4112), and are involved in the degradation of at least one mutant yeast transcription factor (Wang and Prelich, 2009, Mol Cell Biol, 29: 1694-1706). Thus, it is also possible that systems analogous to the PML-RNF4 system may play a role in maintaining protein quality in these organisms.

The PML-RNF4 System and Neurodegeneration

PML$^{-/-}$ mice have been extensively characterized for a variety of phenotypes including tumorigenesis (Wang et al., 1998, Science, 279: 1547-1551). The present study indicates a role for PML in protection from neurodegeneration (FIG. 7 and FIG. 14). Neurodegenerative disorders including SCAs and HD are usually late-onset diseases. Accumulating evidence suggests a progressive decline in PQC during aging (Balch et al., 2008, Science, 319: 916-919). The strong effect of the PML-RNF4 on pathogenic proteins associated with SCA1, HD, and ALS and of PML deficiency on the progression of the SCA1 mouse model, along with the accumulation of PML in neuronal inclusions in patients with various neurodegenerative diseases (Skinner et al., 1997, Nature, 389, 971-974; Takahashi et al., 2003, Neurobiol Dis, 13: 230-237), suggests that insufficiency or dysfunction of the PML-RNF4 system may have a role in these diseases. Thus, the PML-RNF4 system and analogous systems would be valuable targets in their treatment.

Example 2: TRIM Proteins can Recognize Misfolded Proteins and Promote their Degradation The tripartite motif-containing (TRIM) family consists of a large number of proteins in metazoan cells, ranging from approximately twenty in *C. elegans* to over seventy in mice and humans. These proteins share at their N-termini the characteristic TRIM or RBCC motif, which is comprised of a RING domain, one or two B-boxes (which, like the RING domain, a coordinated by zinc ions), and a coiled coil region. This is followed by C-terminal region that are much more variable among TRIM proteins and contains distinct motifs (Hatakeyama, 2011, Nat Rev Cancer, 11: 792-804; Ozato et al., 2008, Nat Rev Immunol, 8: 849-860). TRIM proteins modulate a range of cellular processes including those that protect against cancer and viral infection. Biochemically, a number of TRIM proteins exhibit ubiquitin E3 ligase activity, which is attributed to the RING domain within the TRIM/RBCC region. In addition, at least several TRIM proteins possess E3 ligases for protein conjugation to SUMO (small ubiquitin-like modifier). However, an outstanding issue has remained as to the substrates of the TRIM family of SUMO E3.

As described above, it was demonstrated that PML (promyelocytic leukemia protein; also known as TRIM19) plays a critical role in the elimination of misfolded proteins. PML was initially identified as the product of a gene involved in the t(15; 17) chromosomal translation that is associated with the majority of acute promyelocytic leukemia. It is the major structural and the namesake component of the PML nuclear bodies. It was shown that PML is able to specifically bind to and promote the degradation of a range of misfolded protein. Via distinct regions, PML can discern common features found in misfolded proteins, including peptides enriched in aromatic amino acid residues and coiled coil structures. PML then tags misfolded proteins with poly-SUMO2/3 chains through its SUMO E3 activity. This permits modified misfolded proteins to be recognized by the SUMO-targeted ubiquitin ligase (STUbL) RNF4, which ubiquitinates misfolded proteins and target them for with the consequential degradation in the proteasome. The role of PML in protein quality control is important for the protection against neurodegenerative diseases, as PML deficiency exacerbates behavioral as well as neuropathological phenotypes of a mouse model of spinocerebellar ataxia type 1 (SCA1), a progressive and lethal disease caused by the expansion of a polyglutamine (polyQ) stretch in ataxin-1. Given the existence of a large number if TRIM proteins, the results obtained using PML raises an important question as to whether other TRIM proteins, like PML, are able to recognize and degrade misfolded proteins. In the experiments presented herein, a panel of TRIM proteins is analyzed and it is observed that the ability to recognize and degrade misfolded proteins is prevalent among TRIM proteins, indicating a critical role for this family in protein quality control in metazoan cells.

The materials and methods employed in these experiments are now described.

Plasmids

FLAG-TRIM27, FLAG-TRIM32, and FLAG-TRIM5δ were made in pRK5 by PCR. Templates for PCR amplification were purchased from Open Biosystems, and the corresponding gene accession numbers are BC013580, BC003154 and CV029096, respectively. All three genes are of human origin. The following plasmids were previously described: FLAG-PML (isoform IV) (Chu and Yang, 2011, Oncogene, 30: 1108-116); Atxn1 82Q-GFP, FLAG-Atxn1 82Q, and HA-Httex1p 97QP (Guo et al., 2014, Mol Cell, 55(1): 15-30); FLAG-TRIM11 (Ishikawa et al., 2006, FEBS Lett, 580: 4784-4792); FLAG-TRIM22 (the long form) (Barr et al., 2008); HA-TRIM39 (Lee et al., 2009, Exp Cell Res, 315: 1313-1325); HA-tagged TRIM1, 2, 3, 4, 5, 6, 8, 9, 10, 11, 12, 13, 14, 18, 20, 21, 22, 23, 24, 25, 26, 27, 28, 29, 30, 31, and 32 (Reymond et al., 2001, EMBO J, 20: 2140-2151; Uchil et al., 2008, 2008, PLoS Pathog, 4: e16); and the remaining TRIM expression plasmids, expressing proteins with either an N-terminal HA-tag or C-terminal V5 tag (Versteeg et al., 2013, Immunity, 38: 384-398). For analyzing the effect of TRIM proteins on the levels of Atxn1 82Q and Httex1p 97QP, Trim11 (NM_145214.2), Trim15 (NM_033229.2), Trim28 (NM_005762.2), Trim34 (NM_021616.5), Trim39 (NM_021253.3), Trim42 (NM_152616.4), Trim43 (NM_138800.1), Trim65 (NM_173547.3), Trim67 (NM_001004342.3), Trim70 (NM_001037330.1), Trim71 (NM_001039111.2) and Trim75 (NM_001033429.2) were constructed into pcDNA 3.1(−) vector containing a 5'-HA tag. All the other Trim plasmids were obtained (Versteeg et al., 2013, Immunity, 38: 384-398).

siRNAs

SUMO2/3 siRNAs (Santa Cruz sc-37167) was a pool of three different siRNA duplexes with the sense strand sequences of 5'-CCCAUUCCUUUAUUGUACA-3' (SEQ ID NO: 157), 5'-CAGAGAAUGACCACAUCAA-3' (SEQ ID NO: 158), and 5'-CAGUUAUGUUGUCGUGUAU-3' (SEQ ID NO: 159).

TRIM27 siRNA was purchased from Qiagen, with the sense strand sequences being 5'-AACTCT-TAGGCCTAACCCAGA-3' (SEQ ID NO: 162).

Cell Culture and Transfection

HeLa cells were obtained from ATCC. PML$^{+/+}$ and PML$^{-/-}$ MEF cells were derived from the embryos of mice with the corresponding genotypes. Cells were maintained in standard culture conditions. DNA plasmids were transfected into cells using Lipofectamine 2000, and siRNAs were transfected into cells in two rounds on consecutive days using either Lipofectamine 2000 or RNAiMAX (Invitrogen), according to the manufacturer's instructions. When both DNA and siRNA were transfected, DNA was transfected a day after the second round of siRNA transfection. MG132 (Sigma) was added 24 hours after the last transfection at 7.5-10 μM (final concentration) for 4-5 hours.

Immunofluorescence

Cells cultured on coverslips were fixed with 4% paraformaldehyde for 15 minutes, permeabilized with 0.2% Triton X-100 for 15 minutes, and incubated sequentially with primary and secondary antibodies. Primary antibodies were anti-HA, anti-FLAG (mouse mAb M2, 1:2,000) (Sigma), and anti-TRIM27. Secondary antibodies were FITC-conjugated anti-mouse, anti-rabbit (Zymed), and anti-goat (Invitrogen) IgGs; Texas Red-conjugated anti-mouse and anti-rabbit IgGs (Vector labs); and Rhodamine Red-X conjugated anti-goat (Jackson ImmunoResearch Labs). Afterwards, cells were mounted with medium containing DAPI (Vector Labs), and the images were acquired with a Nikon Eclipse E800 or Olympus IX81 microscope.

Cell Lysate Fractionation, Western Blot, and Filter Retardation Assay

Samples were prepared as described (Guo et al., 2014, Mol Cell, 55(1): 15-30). Briefly, cells were lysed on ice in NP-40 lysis buffer (50 mM Tris, pH 8.8, 100 mM NaCl, 5 mM MgCl2, 0.5% NP-40, 2 mM DTT) supplemented with 250 IU/ml benzonase (Sigma), 1 mM PMSF, 1x complete protease cocktail (Roche), and 20 mM N-Ethylmaleimide (NEM; Sigma). Cell lysates were centrifuged at 13,000 rpm for 15 minutes at 4° C. The supernatant, containing NP-40-soluble (NS) proteins, was analyzed by SDS-PAGE and Western blot. The pellet was resuspended in the pellet buffer (20 mM Tris, pH 8.0, 15 mM MgCl2, 2 mM DTT) supplemented with 250 IU/ml benzonase, 1 mM PMSF, 1× complete protease cocktail, and 20 mM NEM. The pellet fraction was boiled in 2% SDS plus 50 mM DTT and was resolved by SDS-PAGE. Proteins entering the gel (SDS-soluble, SS) were detected by Western blot. For filter retardation (dot blot) assay, a portion of the boiled pellet was applied to a membrane filter with 0.2 μm pore size, and the SDS-resistant (SR) aggregates retained on the filter was analyzed by immunoblotting. Primary antibodies were: anti-HA (rabbit, Y-11, 1:500) (Santa Cruz Biotechnology); anti-FLAG (mouse, M2, 1:7,500) and anti-actin (rabbit, 1:10,000) (Sigma); anti-GFP (mouse, 1:4,000) (Clonetech); and SUMO2/3 (rabbit, 1:250, Abgent). The secondary antibodies were either conjugated to HRP (Santa Cruz Biotechnology), or labeled with IRD Fluor 800 or IRD Fluor 680 (LI-COR, Inc.). Western blots were developed using ECL reagents and analyzed using ImageJ, or scanned with the Odyssey infrared imaging system, and analyzed using Image Studio Lite (LI-COR, Inc.).

Protein Purification and In Vitro SUMOylation Assays

FLAG-TRIM27 and HA-Atxn1 82Q-FLAG were expressed in 293T cells and purified by anti-FLAG M2 beads (Sigma) as previously described (Tang et al., 2006, Nat Cell Biol, 8: 855-862; Tang et al., 2004, J Biol Chem, 279: 20369-20377) with modifications. Cells were lysed in IP-lysis buffer (50 mM Tris, pH 7.5, 150 mM NaCl, 0.5% Triton X-100, 0.5% NP-40 and 2 mM DTT) supplemented with 1 mM PMSF and 1× complete protease cocktail. For TRIM27 purification, IP-lysis buffer was also supplemented with 20 µM $ZnCl_2$. The lysates were incubated with anti-FLAG M2 beads at 4° C. for 4 hours to overnight. M2 beads were washed with IP-lysis buffers containing 0, 0.5, and 1 M KCl, and with the elution buffer (50 mM Tris, pH 7.5, 150 mM NaCl, and 2 mM DTT). The bound proteins were eluted in the elution buffer containing 0.1-0.3 mg/ml 3xFLAG peptide (Sigma).

Other components for in vitro SUMOylation reactions were purchased from Boston Biochem. In vitro SUMOylation assays were performed at 37° C. for 1.5 hours in 30 µl reaction buffer (50 mM Tris pH 7.5, 5.0 mM Mg2+-ATP, and 2.5 mM DTT) containing purified HA-Atxn1 82Q-FLAG (600 ng/200 nM), FLAG-TRIM27, SAE1/SAE2 (125 nM), Ubc9 (1 µM), His-SUMO2 (25 µM), and BSA (0.1 µg/ml). The reaction mixtures were denatured by the addition of 30 µl IP-lysis buffer containing 2% SDS and 50 mM DTT and heating at 95° C. for 10 minutes. One aliquot of the heated reaction mixes were saved for Western blot analysis, and the rest were diluted 20-fold in IP-lysis buffer without SDS. HA-Atxn1 82Q-FLAG was immunoprecipitated by anti-HA beads (Roche) and analyzed for SUMO2/3 modification using an anti-SUMO2/3 antibody.

The results of the experiments are now described.

Figures 15A, 15B:
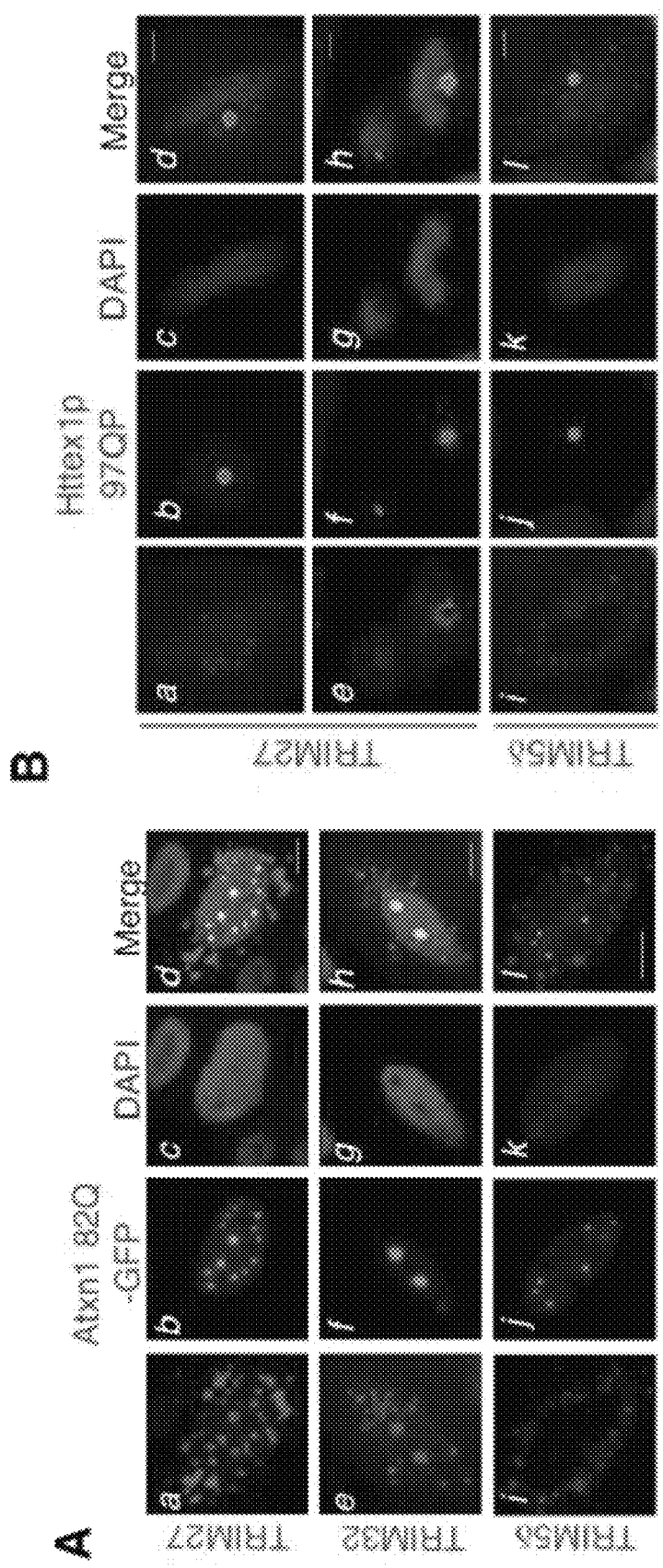
FIG. 15A through FIG. 15D, depicts the results of example experiments demonstrating the co-localization of TRIM27, TRIM32, and TRIM5δ with EGFP-Atxn1 82Q and Httex1p 97QP.

Co-Localization of TRIM27, TRIM32, and TRIM5 with Pathogenic Ataxin-1 and Huntingtin Proteins It was previously showed that PML/TRIM19 can recognize and promote the degradation of various nuclear misfolded proteins including Atxn1 82Q, a pathogenic ataxin 1 protein with a stretch of eight-two glutamine that is associated with spinocerebellar ataxia type 1 (SCA1) (Guo et al., 2014, Mol Cell, 55(1): 15-30). The TRIM family of proteins in humans and mice consists of over seventy members that can be distinguished based on structural features of the region C-terminal to the conserved TRIM/RBCC motif (Ozato et al., 2008, Nat Rev Immunol, 8: 849-860). The majority of TRIM proteins contain in this region one or more conserved domains, the most common of which include the PRY-SPRY domain (present in ~40 TRIM proteins) and multiple NHL domains (present in 4 TRIM proteins). In addition, several TRIM proteins do not contain a recognizable motif in the C-terminal region. To examine whether other human TRIM proteins, like PML, are able to recognize misfolded proteins, TRIM27 (with a PRY-SPRY domain), TRIM32 (with multiple NHL domains), and TRIM5δ (a short splicing variant of TRIM5 with no known domain) were first chosen. When expressed in HeLa cells, these three TRIM proteins displayed overlapping yet distinct cellular localization patterns: TRIM27 and TRIM32 were localized in both the cytoplasm and the nucleus, while TRIM5δ was localized only in the cytoplasm. Nevertheless, all three proteins are concentrated in the speckled bodies in their respective compartment(s) (FIG. 15A).

Figures 15C, 15D:
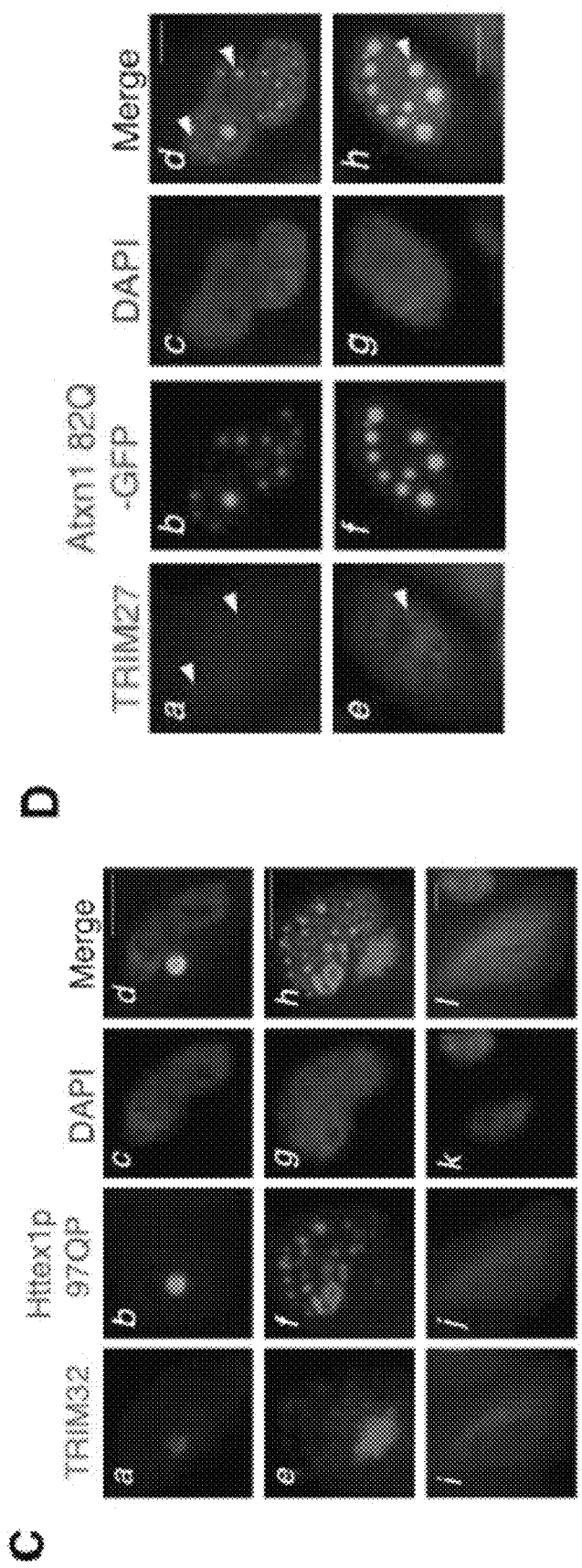

Experiments were conducted to examine the co-localization of TRIM27, TRIM32, and TRIM5δ with Atxn1 82Q, as well as with a fragment of the huntingtin protein (Htt) containing a stretch of ninety-seven glutamines (Httex1p 97Q), which is associated with HD. Atxn1 82Q, which was expressed as a fusion of enhanced green fluorescence protein (GFP), formed inclusions only in the nucleus, while HA-tagged Httex1p 97QP formed inclusions in both the nucleus and cytoplasm (Guo et al., 2014, Mol Cell, 55(1): 15-30) (FIG. 15A and FIG. 15B). Exogenous TRIM27 and TRIM32 co-localized with Atxn1 82Q-GFP inclusion in the nucleus (FIG. 15A) and with HA-Httex1p 97QP inclusions in both the nucleus and cytoplasm (FIG. 15B and FIG. 15C). Moreover, endogenous TRIM27 also co-localized with Atxn1 82QGFP inclusion (FIG. 15D). Exogenous TRIM5δ co-localized only with the cytoplasmic HA-Httex1p 97QP inclusions (FIG. 15B and FIG. 15C). Thus, despite the differences in their C-terminal sequence, TRIM27, TRIM32, and TRIM5 are able to recognize misfolded protein formed in their respective cellular compartment(s).

Figure 16A:
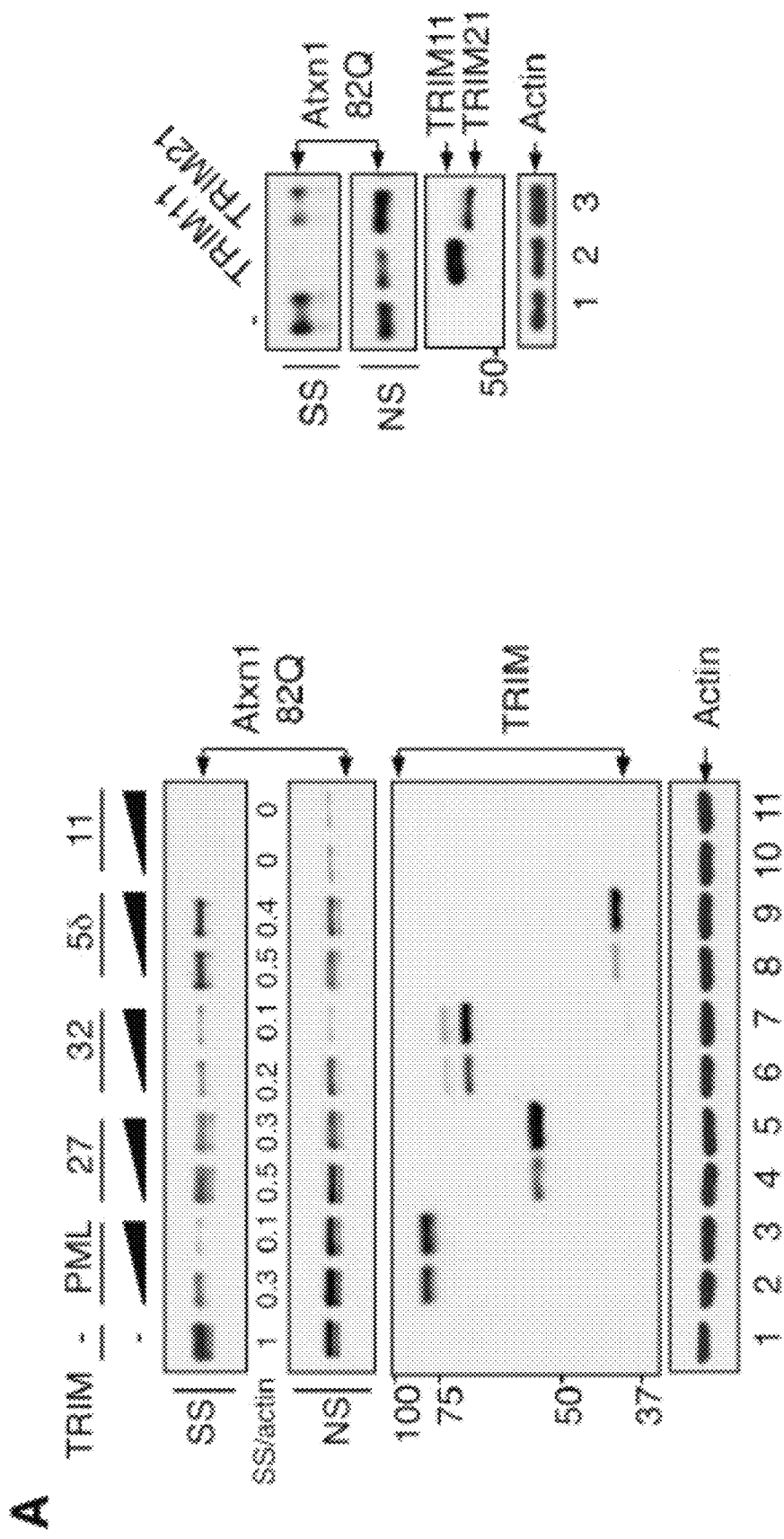
FIG. 16A through FIG. 16D, depicts the results of example experiments demonstrating the reduction of aggregated Atxn1 82Q by TRIM27, TRIM32, and TRIM5δ (FIG. 16A and FIG. 16B) Levels of Atxn1 82Q-GFP when expressed alone (-) or together with the indicated FLAG-tagged TRIM proteins in HeLa cells. The cell lysates were analyzed by Western blot. In the left panel of (FIG. 16A), the ratios of Atxn1 82Q in the SS fraction versus actin are given, and the expression of TRIM11 could be detected after a prolonged exposure.
Figures 16B, 16C, 16D:
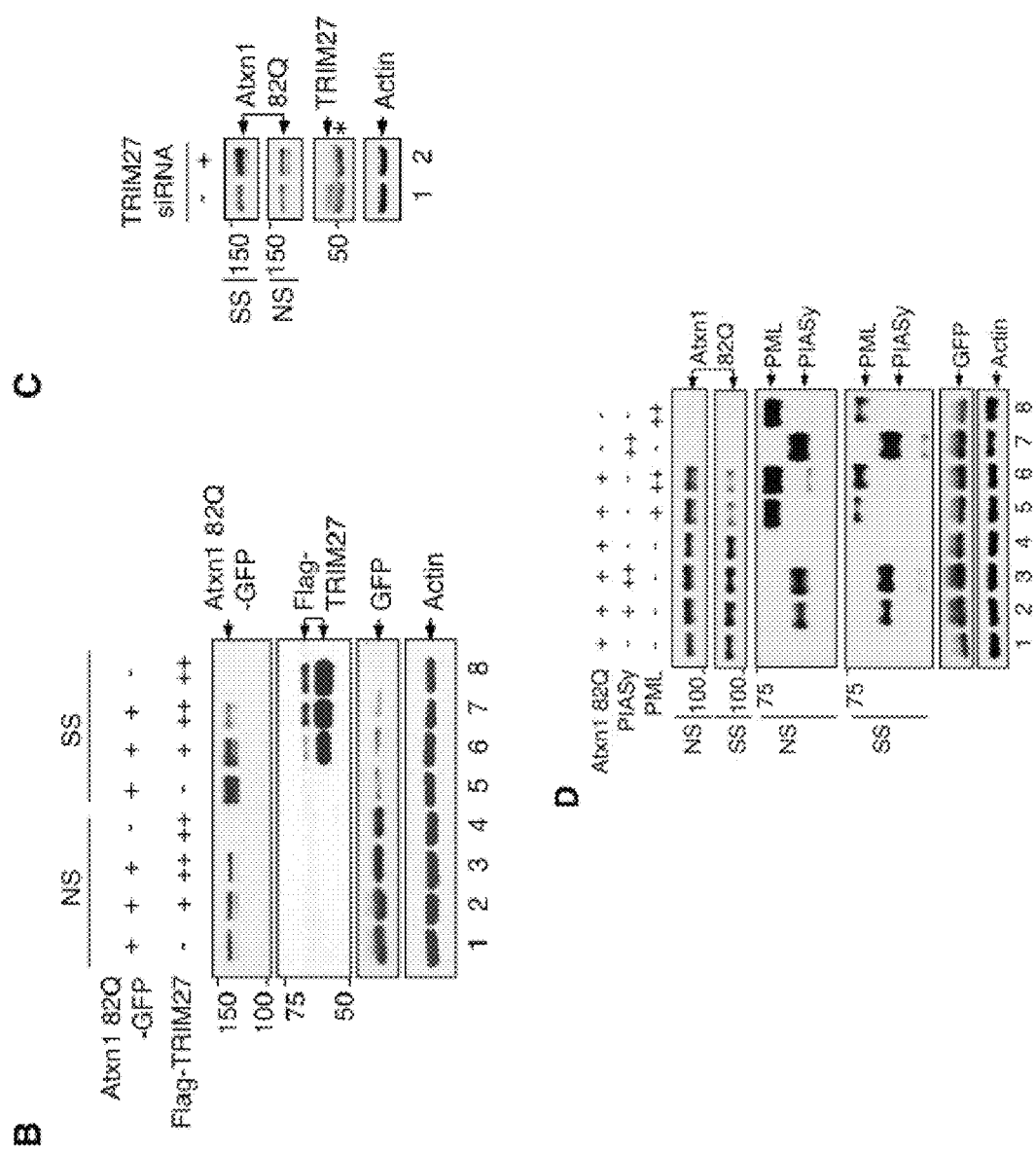

TRIM27, TRIM32, and TRIM5δ Reduce the Levels of Both Insoluble and Soluble Atxn1 82Q Proteins To examine whether these TRIM proteins are able to reduce the levels of misfolded proteins, each of them was expressed with FLAG-tagged Atxn1 82Q in HeLa cells. The levels of FLAG-Atxn1 82Q in cell lysates that were NP40-soluble (soluble or NS) and NP-40-insoluble, but SDS-soluble (aggregated or SS), were analyzed. Of note, each TRIM protein was able to reduce the levels of soluble and aggregated Atxn1 82Q protein (FIG. 16A and FIG. 16B). TRIM27 and TRIM32 also decreased the levels of Atxn1 82Q protein that were resistant to both NB-40 and SDS (SR), which were detected by a filter retardation assay and likely represented β-amyloid structure (see below).

When expressed at similar levels, all three TRIM proteins, especially TRIM32, showed stronger activity than PML in reducing the levels of soluble Atxn1 82Q (FIG. 16A). Moreover, while the activity of TRIM27 and TRIM5 was somewhat weaker than, the activity of TRIM32 in reducing aggregated Atxn1 82Q was comparable to that of PML (FIG. 16A and FIG. 16B). TRIM27 was chosen for further analysis. The expression of endogenous TRIM27 was knocked down using siRNA, which led to a significant increase in the levels of both soluble and aggregated Atnx1 82Q proteins (FIG. 16C). Together, these results suggest that similar to PML, TRIM27, TRIM32, and TRIM5 are capable of removing misfolded proteins. In contrast to these TRIM proteins, PIASy, a member of the PIAS family of SUMO E3s, was unable to reduce the levels of either soluble or aggregated Atxn1 82Q (FIG. 16D).

The Effect of TRIM27 and TRIM32 on Atxn1 82Q is Independent of PML

Figures 17A, 17B:
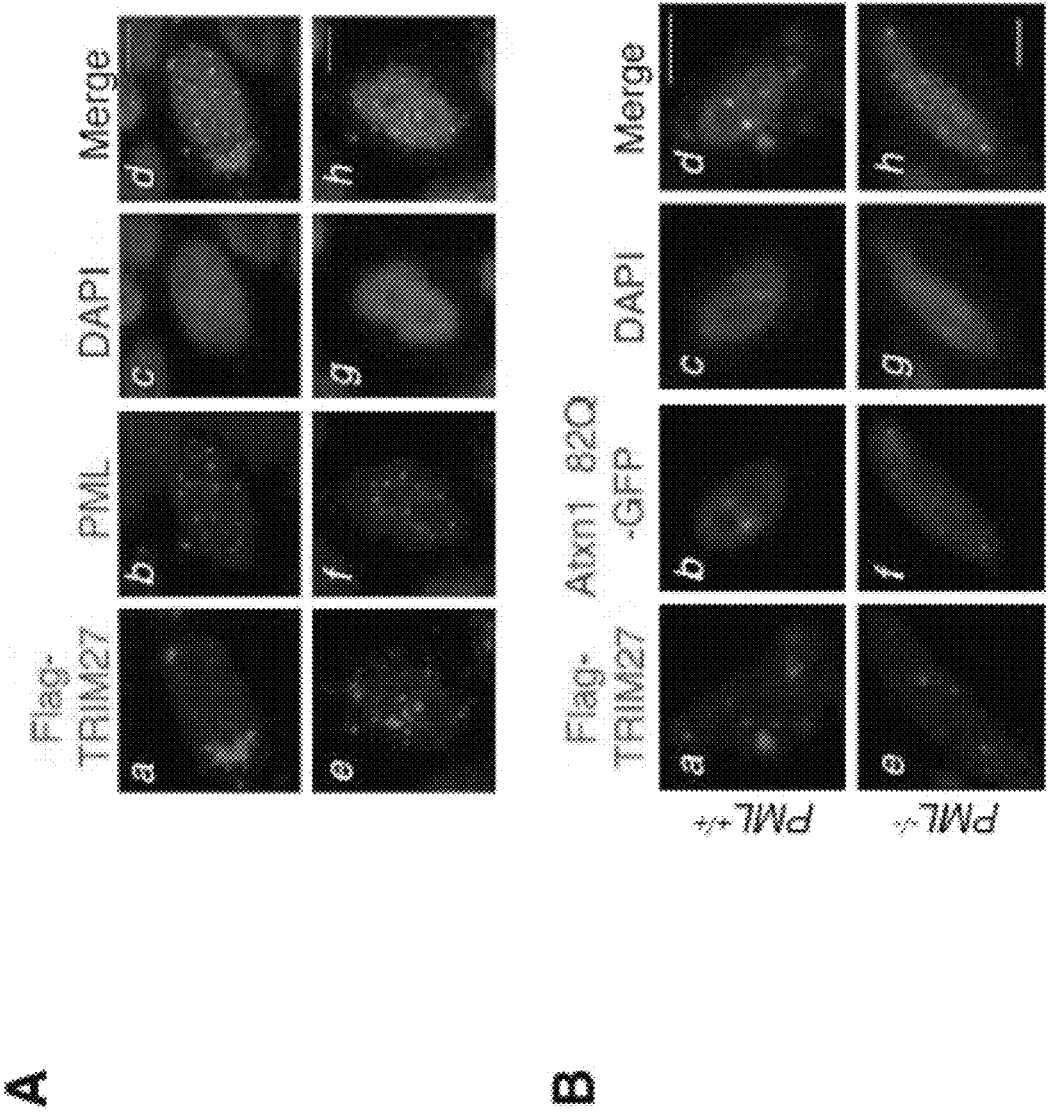
FIG. 17A through FIG. 17C, depicts the results of example experiments demonstrating that TRIM27 and TRIM32 reduce aggregated Atxn1 82Q independent of PML.
Figure 17C:
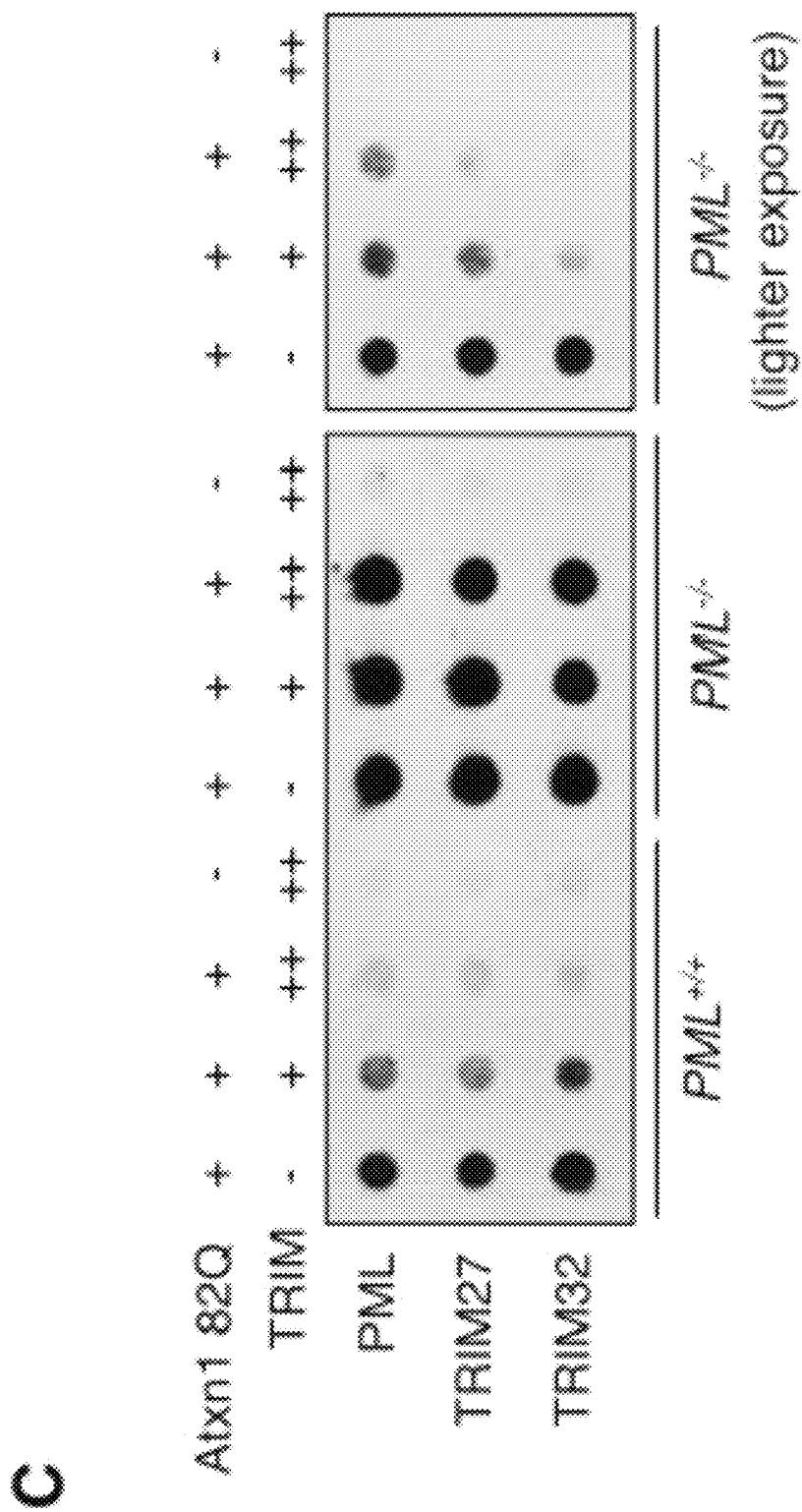

TRIM27 is partially co-localized in PML nuclear bodies (Cao et al., 1998, J Cell Sci, 111(Pt 10): 1319-1329) (FIG. 17A). To examine whether TRIM27 and the other nucleus-localized TRIM protein, TRIM32, rely on PML to degrade misfolded protein, PML-wild type ($PML^{+/+}$) and PML-deficient ($PML^{-/-}$) mouse embryonic fibroblasts (MEFs) were used. Despite the co-localization of TRIM27 with the PML nuclear bodies, TRIM27 was present in the Atxn1 82Q aggregates even in the absence of PML (FIG. 17B). The levels of SDS-insoluble Atxn1 82Q aggregates were markedly higher in PML' compared to $PML^{-/-}$ MEFs (FIG. 17C), consistent with a role for PML in removing Atxn1 82Q (Guo et al., 2014, Mol Cell, 55(1): 15-30). Re-introducing PML decreased the levels of the aggregate Atxn1 82Q. Of note, TRIM27 and TRIM32 were as effective as PML in reducing aggregated Atxn1 82Q in both PML$^{+/+}$ and PML$^{-/-}$ cells (FIG. 17C). Together, these results suggest that TRIM27 and TRIM32 can eliminate Atxn1 82Q independently of PML.

Figure 18A:
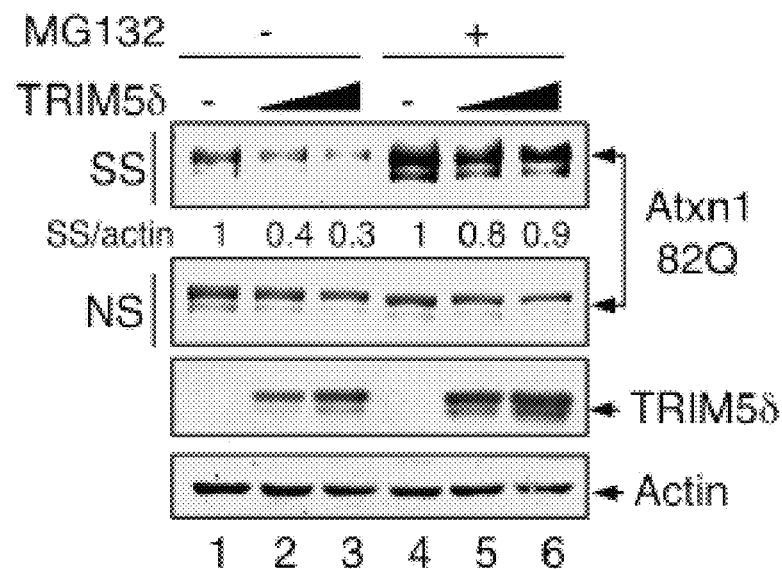
FIG. 18A through FIG. 18G, depicts the results of example experiments demonstrating that TRIM proteins depend on SUMO2/3 and the proteasome to remove insoluble Atxn1 82Q.
Figure 18B:
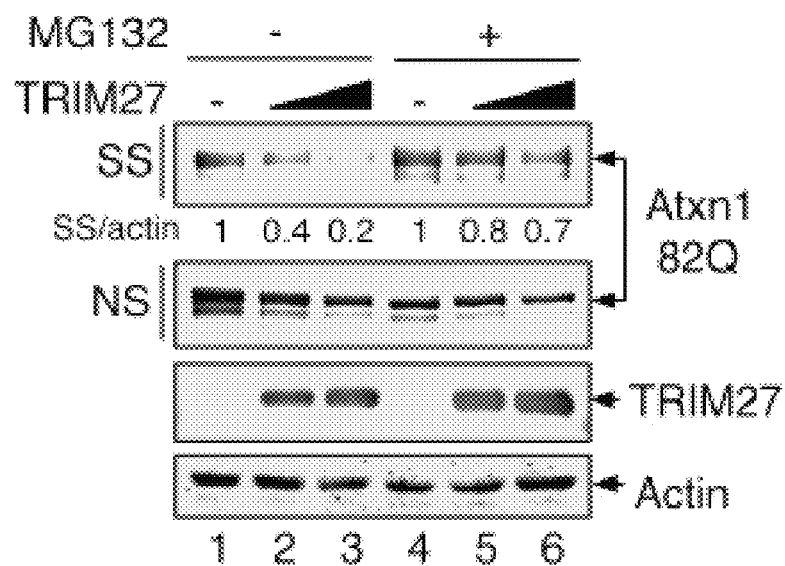
Figure 18C:
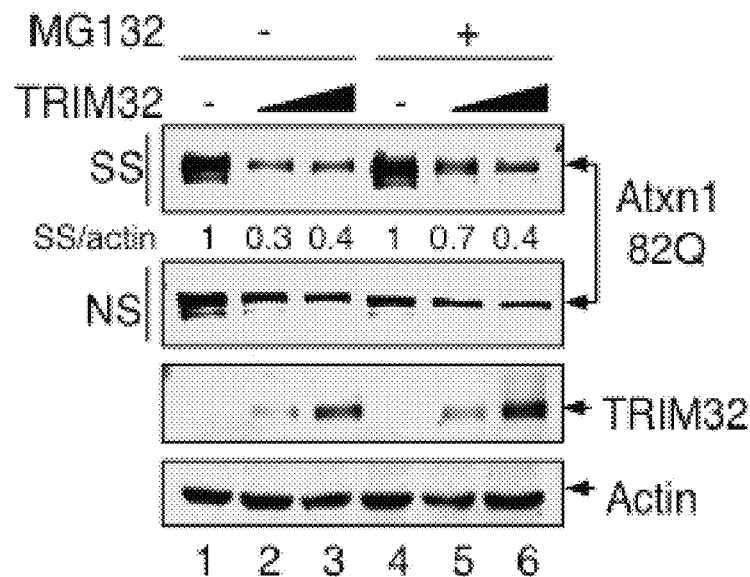
Figure 18D:
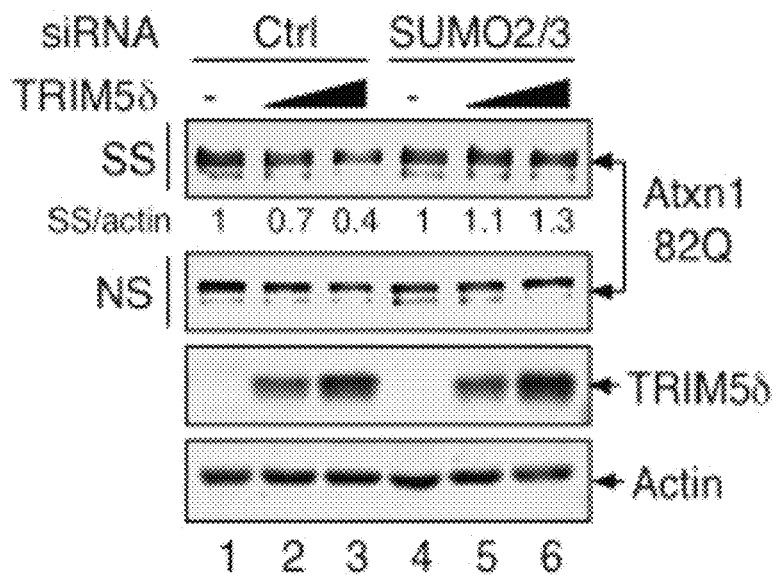
Figures 18E, 18F, 18G:
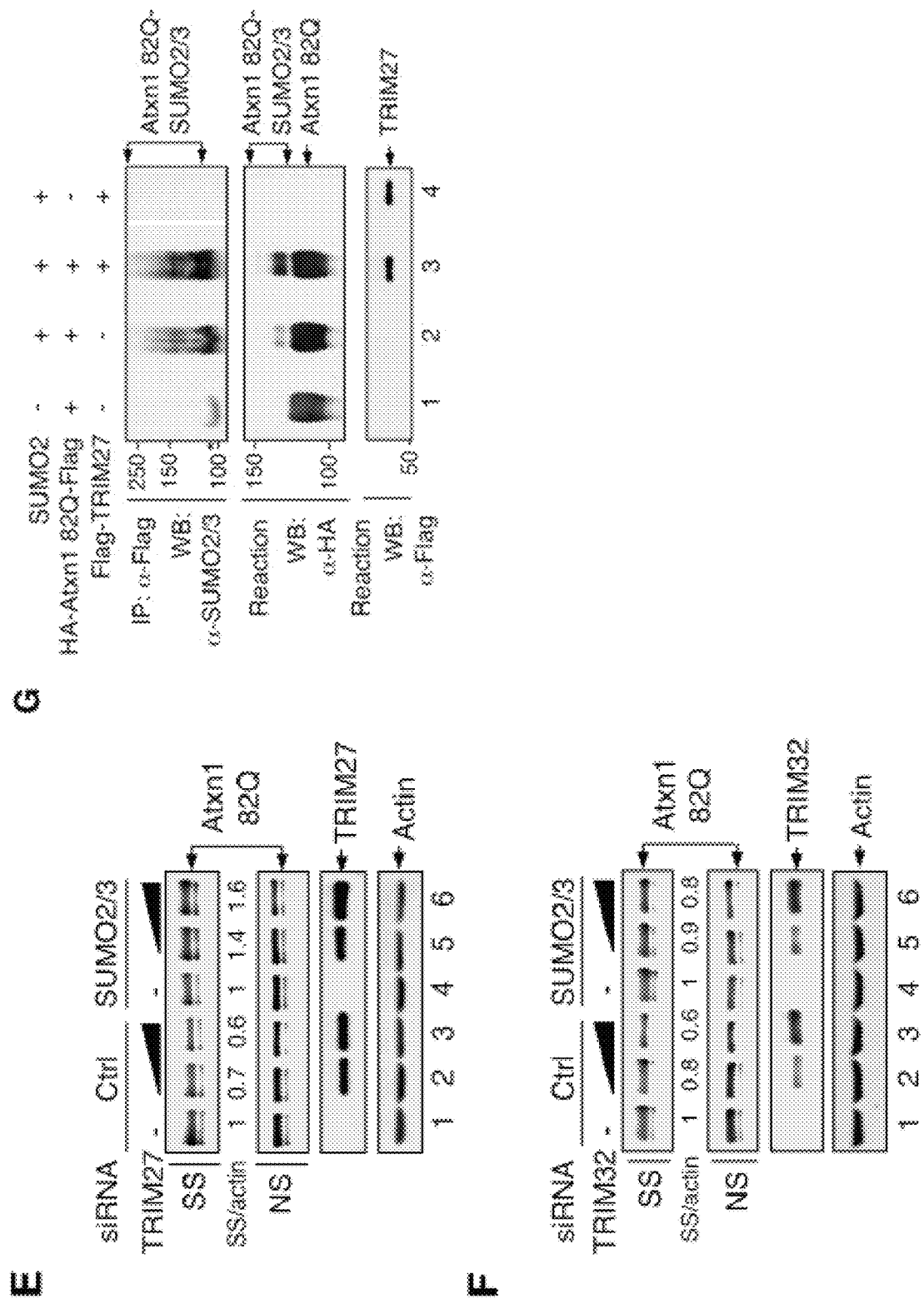
Figure 19A:
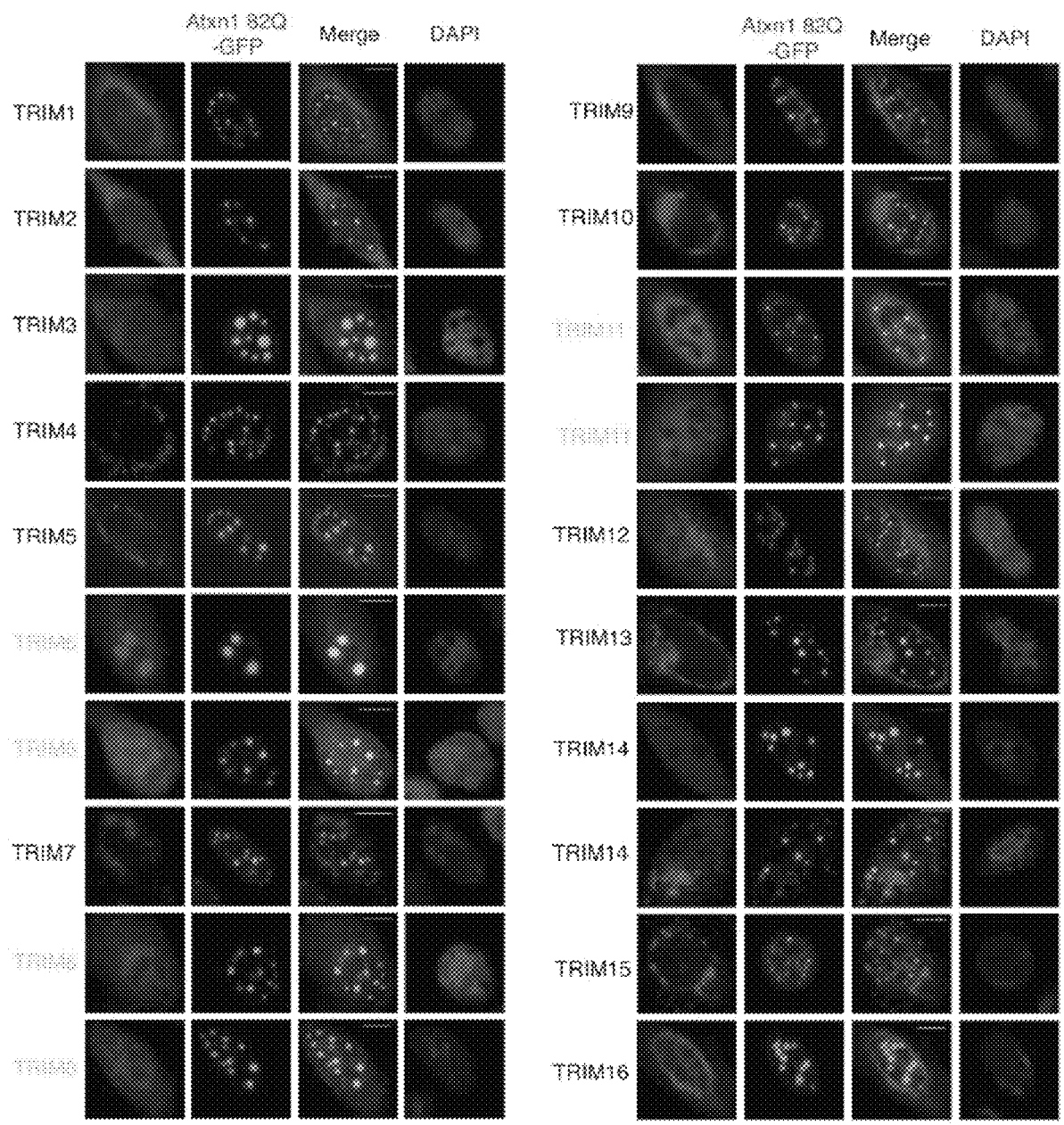
Figure 19B:
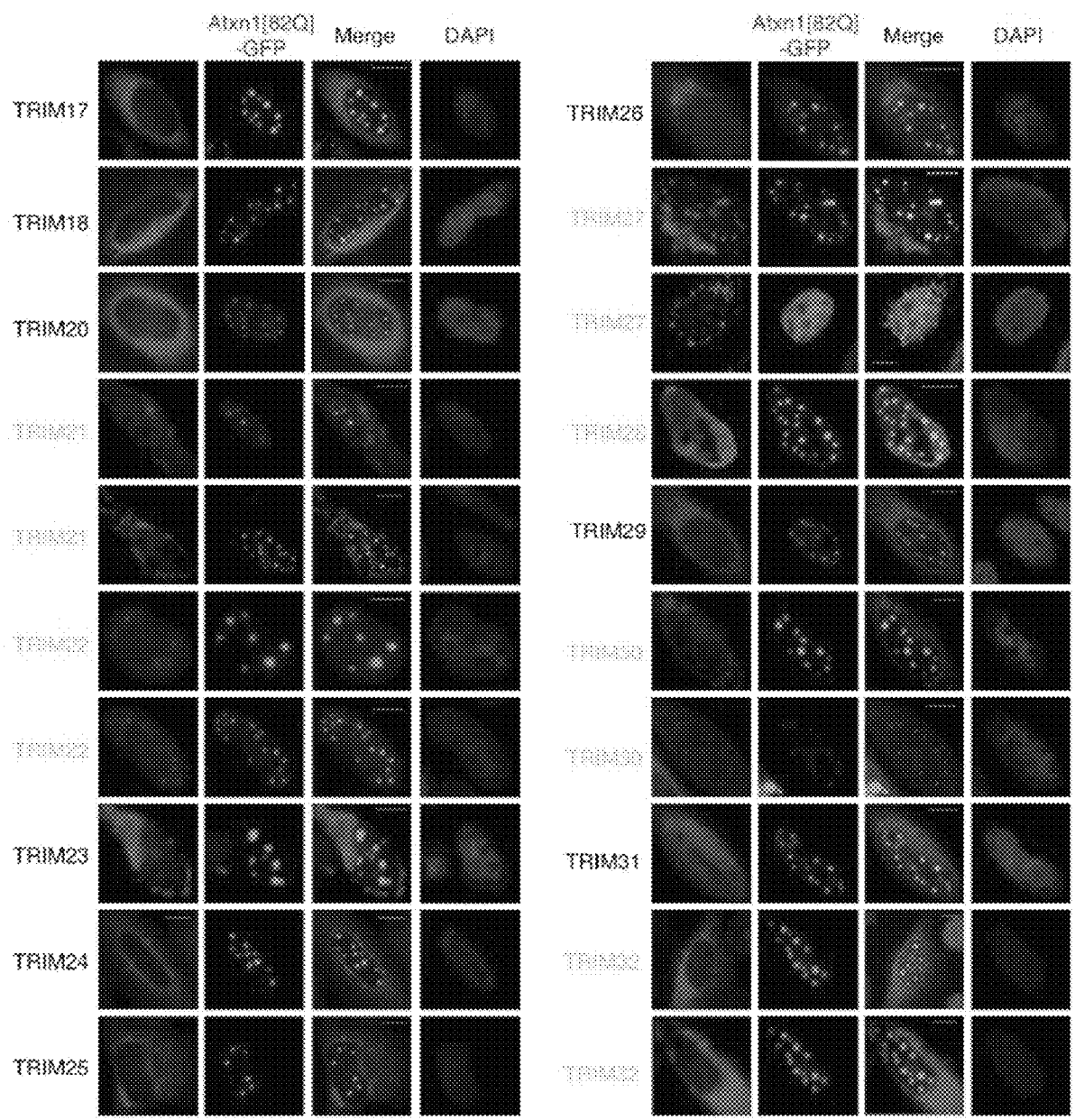
Figure 19C:
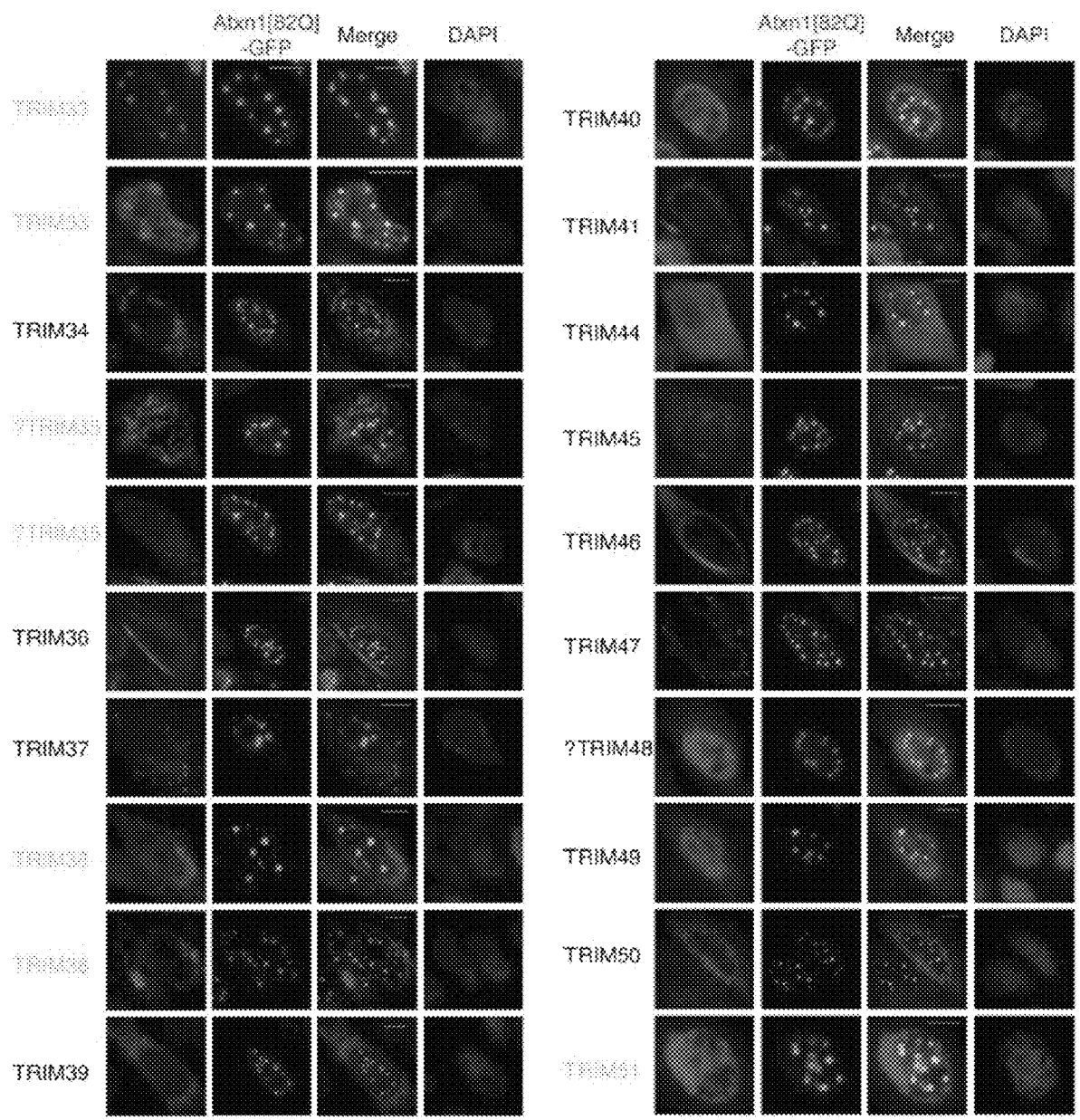
Figure 19D:
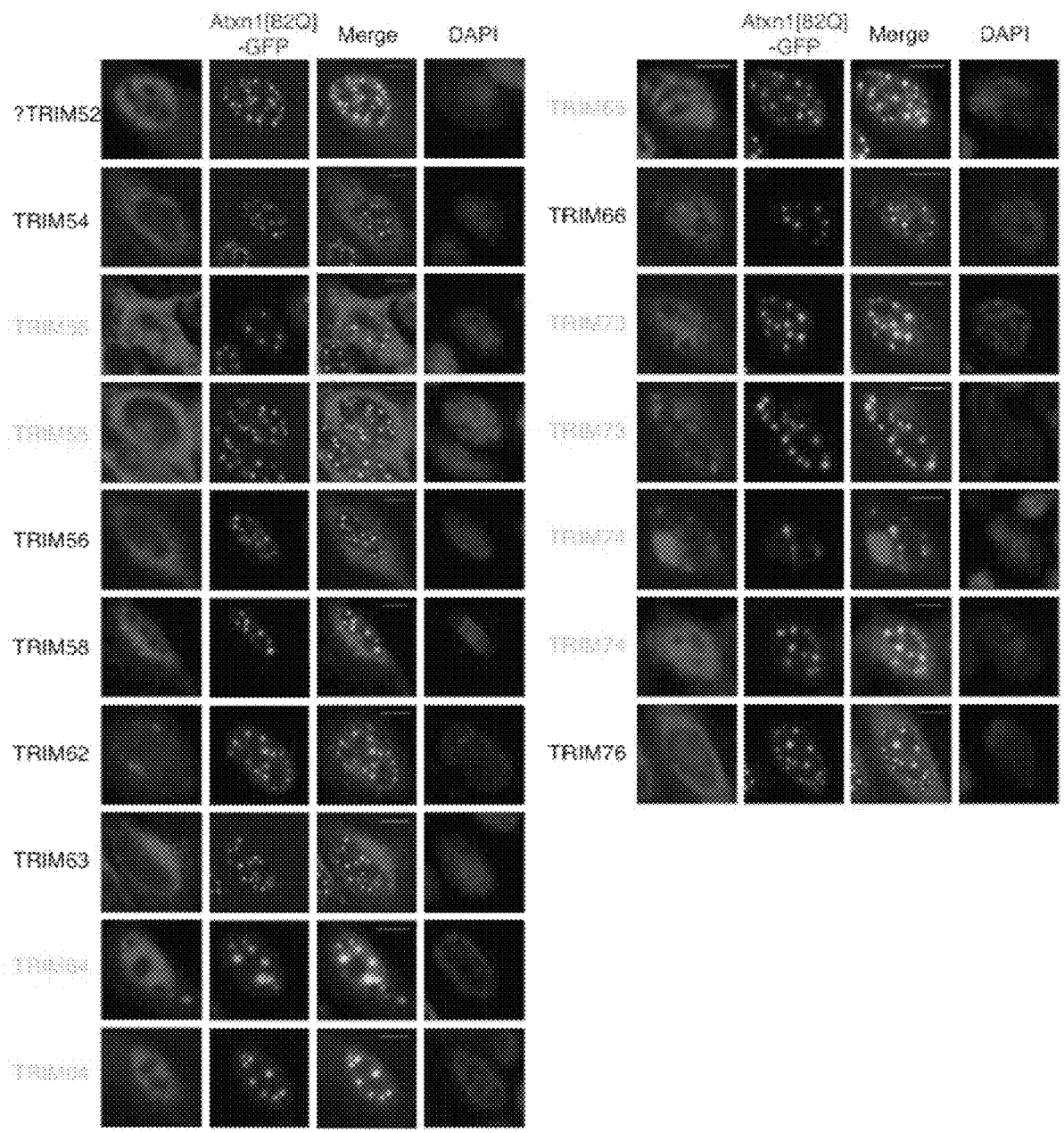

TRIM27, TRIM32, and TRIM5 Target Atxn1 82Q for Proteasomal Degradation in a SUMO2/3-Dependent Manner It was previously found that PML promotes proteasomal degradation of misfolded proteins via its SUMO E3 activity (Guo et al., 2014, Mol Cell, 55(1): 15-30). When cells were treated with the proteasome inhibitor MG132, the ability of TRIM27, TRIM32, and TRIM5 to reduce soluble and especially insoluble Atxn1 82Q protein was significantly impaired, suggesting that these three TRIM proteins also target Atxn1 82Q for proteasomal degradation (FIG. 18A-FIG. 18C). In addition, when endogenous SUMO2/3 was knocked down with siRNAs, TRIM27, TRIM32, and TRIM5δ could no longer effectively reduce the levels of Atxn1 82Q (FIG. 18D-FIG. 18F). Hence, these TRIM proteins also rely on SUMO2/3 in degrading Atxn1 82Q.

Using TRIM27 as an example, it was next examined whether TRIM proteins other than PML can act as SUMO E3 ligases for Atxn1 82Q. When incubated with SUMOylation reaction components, including SUMO E1 (SAE1/SAE2), E2 (Ubc9), SUMO2, and ATP, Atxn1 82Q was minimally conjugated to SUMO2. However, conjugation of Atxn1 82Q to SUMO2 was enhanced in a TRIM27 dose-dependent manner (FIG. 18G), suggesting that TRIM27 is a SUMO E3 for Atxn1 82Q.

Co-Localization with Misfolded Proteins is a Prevalent Property of TRIM Proteins Prompted by these observations, the remaining TRIM proteins were tested for their ability to recognize Atxn1 82Q. With the exception of two (TRIM12 and TRIM30), which are present in mice but not in humans, all the other TRIM proteins are of human origin. Each TRIM was tagged with either an HA, Flag, or V5 epitope, and was co-expressed with Atxn1 82Q-EGFP in HeLa cells.

A previous survey of a subset of TRIM proteins showed that these proteins identify with compartments in both the cytoplasm and nucleus (Reymond et al., 2001, EMBO J, 20: 2140-2151). Among the TRIM proteins tested here, eleven (TRIM42, 43, 53, 59-61, 67, 70-72, and 75) could not be detected by immunofluorescence. Among the remaining sixty-three TRIM proteins, five of them (TRIM22, 28, 33, 65, and 66) were localized exclusively in the nucleus, a localization pattern similar to PML. However, the possibility that certain isoforms of these TRIM proteins that were not tested here may be present in the cytoplasm cannot be excluded. For example, such cytoplasmic isoforms have been shown for PML. Twenty-seven TRIM proteins (TRIM1-5, 7, 9, 10, 13, 18, 20, 24, 25, 29, 34, 36, 37, 39, 45-47, 50, 54, 63, 69, and 76) were localized mainly or exclusively in the cytoplasm. Twenty-seven TRIM proteins (TRIM6, 8, 11, 12, 16, 21, 23, 27, 30-32, 35, 38, 40, 44, 48, 49, 51, 52, 55, 56, 58, 62, 64, 68, 73, and 74) were present in a substantially amount in both the nucleus and cytoplasm. A number of the TRIM proteins either formed speckled or filamentous structures in the nucleus or the cytoplasm, others were localized diffusedly, and a few of them displayed perinuclear localization. Often, a TRIM protein exhibited the combination of these localization patterns either in the same or different cells (FIG. 19 and Table 2).

Fourteen TRIM proteins (TRIM6, 8, 11, 19, 21, 22, 27, 28, 30, 32, 33, 35, 38, and 51), including PML/TRIM19, co-localized with the nuclear Atxn1 82Q inclusions in a substantial number of cells (FIG. 19 and Table 2), representing nearly 43% of the thirty-two TRIM proteins that were present either partially or exclusively in the nucleus. These TRIM proteins are from distinct subgroups with different C-terminal sequences. Six proteins (TRIM6, 11, 21, 22, 35, and 38), like TRIM27, are members of the subgroup IV, containing a SPRY motif that is often preceded by a PRY motif. TRIM8, like PML, is a member of the group V, containing no known domains. TRIM28 and TRIM33 are members of group VI, containing a PHD-BR motif. TRIM32 belongs to the subgroup VII, with a five NHL repeats. TRIM51 is considered a TRIM-like protein, lacking the two B-boxes but containing the RING domain and the coiled-coil region; it also contains a SPRY domain, like members of the subgroup IV. Together, these results show that a substantial number of TRIM proteins, despite the divergence in their C-terminus, possess the ability to recognize misfolded proteins.

Degradation of Misfolded Proteins Mediated by Other TRIM Proteins

Figure 20A:
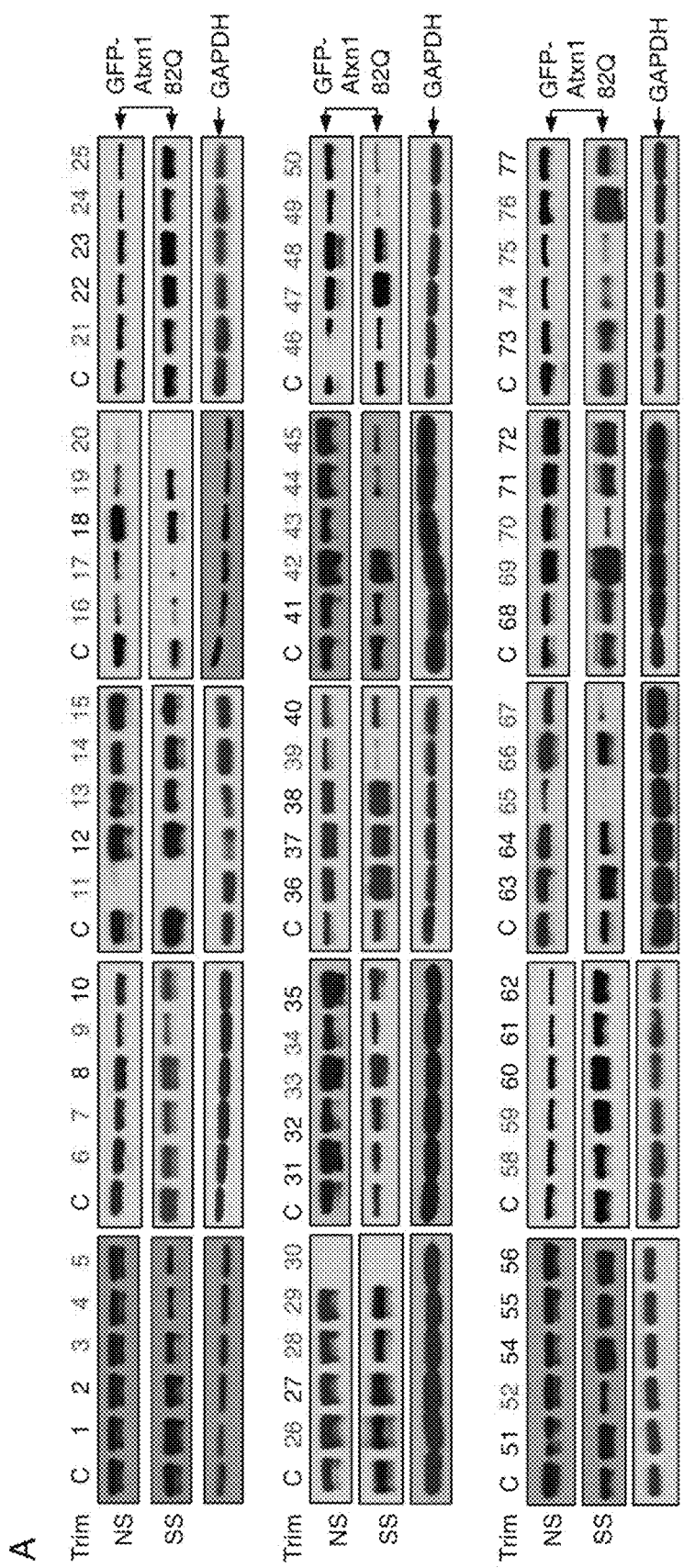
FIG. 20A and FIG. 20B, depicts the results of a systematic analysis of TRIM proteins on Atxn1 82Q and Httex1p 97QP. Atxn1 82Q-GFP (FIG. 20A) or Httex1p 97QP (FIG. 20B) was co-expressed with the indicated TRIM proteins in HeLa cells. Cell lysates were analyzed by Western blot. TRIM proteins labeled red and green are those that reduced and increased the levels of the polyQ proteins, respectively, while TRIM proteins labeled in black had no observable effect. Note that the effects of TRIM proteins can be influenced by their levels of expression, as described elsewhere herein.

To examine the role of TRIM proteins in protein quality control, all human TRIM proteins except for TRIM53 (pseudogene) and TRIM57 (same as TRIM59), as well as TRIM12 and TRIM30 (of mouse origin), were tested for the ability to degrade Atxn1 82Q. Thirty-five of the human TRIM proteins (TRIM3, 4, 5, 6, 7, 9, 11, 13-17, 19, 20, 21, 24, 25, 28, 29, 34, 39, 43-46, 49, 50, 52, 58, 59, 65, 67, 70, 74, and 75) and mouse TRIM30 were able to reduce the levels of NS and/or SS fractions of Atxn1 82Q to different extents (FIG. 20A and Table 2). Several TRIM proteins showed strong activity, including TRIM4, 5, 9, 11, 16, 17, 20, 30, 39, 43, 65, 70, 75 (FIG. 20A and Table 2), and the one with strongest activity appeared to be TRIM11 (FIG. 16A, FIG. 20A and Table 2). Of note, TRIM27 and TRIM32, which were shown above to be able to reduce Atxn1 82Q, did not display an effect in this assay. This difference was likely due to the expression levels. In the experiments described above, TRIM27 and TRIM32 were cloned into the plasmid pRK5. But in the experiments described in this section, TRIM27 and TRIM32 were cloned into pcDNA. Stronger expression from the pRK5 plasmids were consistently observed as compared to expression from the pcDNA plasmid. Therefore, even for the ones that did not display an activity to degrade Atxn1 82Q, they might do so when their expression levels were elevated. It is therefore concluded that the ability to promote degradation of Atxn1 82Q is prevalent among TRIM proteins.

Of note, a few TRIM proteins enhanced, rather than inhibited, the expression of Atxn1 82Q, including TRIM26, 33, 42, 47, 48, 66, 69, and 76. This suggests a diverse effect of different TRIM proteins on Atxn1 82Q.

Figure 20B:
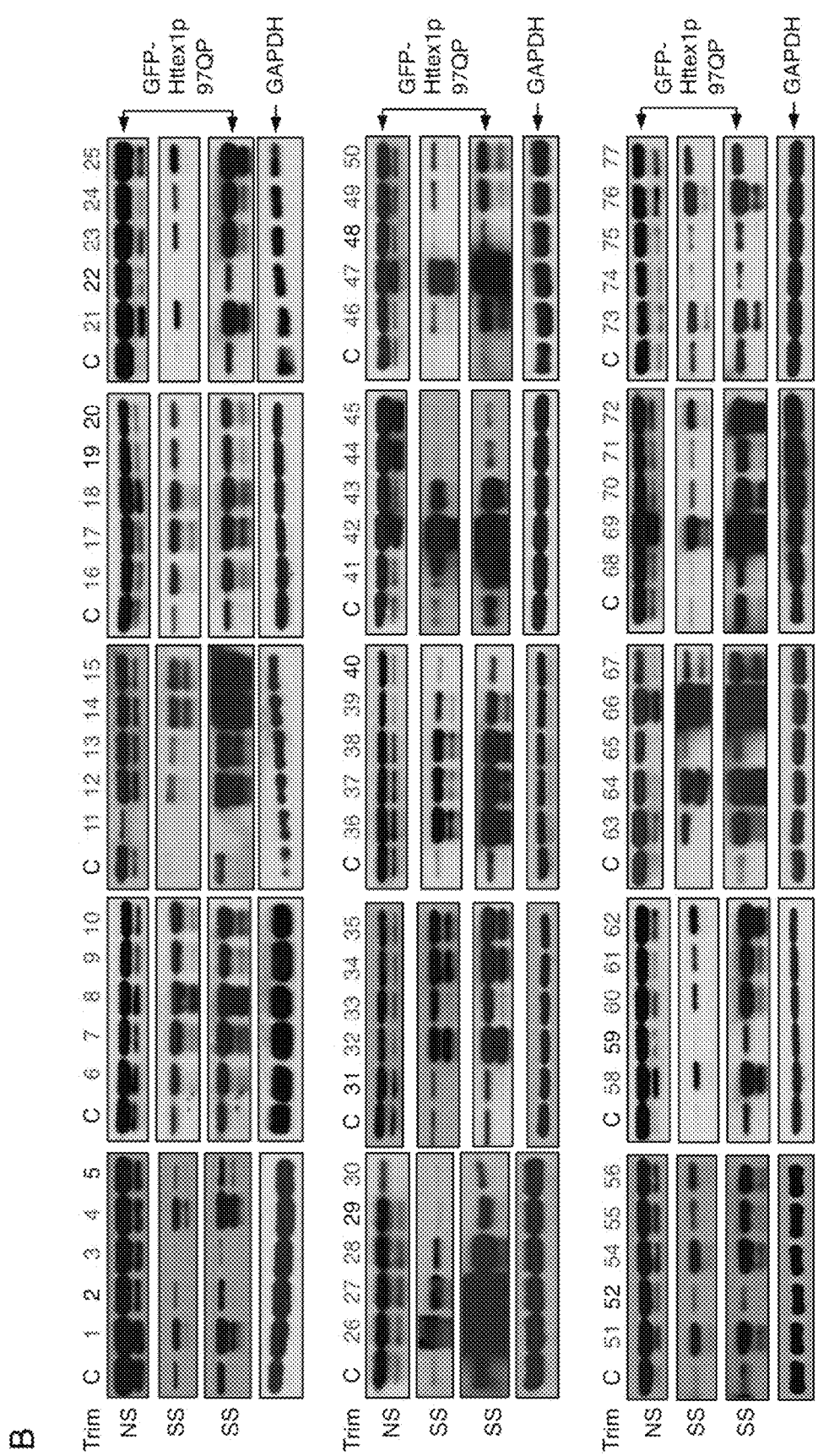

In parallel, the effect of TRIM proteins on Httex1p 97QP was also examined (FIG. 20B). Only a few TRIM proteins were able to reduce the levels of Httex1p 97QP in the NS and/or SS fractions, including TRIM3, 11, 30, 68, 74, and 75. The majority of the TRIM proteins were able to increase the levels of Httex1p 97QP, including TRIM1, 4, 6-10, 12-15, 21, 23-28, 32-39, 41-47, 49-51, 54-56, 58, 60-67, 69-73, 76, and 77. Unlike Atxn1 82Q, only a small fraction of cells expressing Httex1p 97QP contained inclusion. Consistently, the portion of Httex1p 97QP protein in the SS fraction was very low compared to the portion of Atxn1 82Q in the same fraction. Also, in the previous study, PML (cloned in the pRK5 plasmid) was able to reduce the levels of Httex1p 97QP, while here PML (cloned in pcDNA) was not. Thus, the effect of TRIM proteins on Httex1p 97QP, like their effect of Atxn1 82Q, might also be influenced by their expression levels. These results suggest different effects of TRIM proteins on different misfolded proteins, which, among others, can be influenced by their expression levels.

TRIM Proteins

Previously it has been shown that PML is able to eliminate a range of misfolded proteins presented in the nucleus of mammalian cells. The experiments presented herein systematically analyzed nearly all TRIM proteins and find that unprecedented large number of them can recognize misfolded proteins. Still, this number is likely to be an underestimate, because a single misfolded protein, Atxn1 82Q, was mainly used. At least two substrate recognition sites (SRSs) have been identified in PML, the coiled-coil region within the RBCC motif and the region comprising the last sixty amino acids. These SRSs can discern coiled-coil structures and peptides enriched in aromatic acid residues (Phe, Trp, and Tyr), respectively, which are found in some denatured proteins. TRIM proteins are most divergent in their C-terminal region (Hatakeyama, 2011, Nat Rev Cancer, 11: 792-804; Ozato et al., 2008, Nat Rev Immunol, 8: 849-860). It is likely that other TRIM proteins may process specific ability to recognized misfolded proteins of distinct structural features. Also, it is likely that many TRIM proteins that can recognize misfolded proteins in the cytoplasm. Hence, the present observations underscore the critical importance of this large family in protein quality control.

Of note, TRIM5δ was able to promote Atxn1 82Q degradation despite of its cytoplasmic localization. It is possible that TRIM5δ can recognize soluble, misfolded Atxn1 82Q in the cytoplasm before it is imported into the nucleus. Also, TRIM27 and TRIM32 show strong ability to degrade soluble Atxn1 82Q, while PML shows less activity. This might be related to the fact that, unlike PML, TRIM27 and TRIM32 are partially localized to the cytoplasm, where Atxn1 82Q protein (and virtually all the other proteins) is generated. Hence, by recognizing misfolded proteins that are destined to the nucleus, the cytoplasmic TRIM proteins may play an important role in protein quality control in the nucleus.

PML degrades misfolded proteins in a manner that is dependent on its SUMO E3 activity (Guo et al., 2014, Mol Cell, 55(1): 15-30). Likewise, TRIM5δ, TRIM27, and TRIM32 rely on SUMO to remove Atxn1 82Q. An in vitro assay also confirms the SUMO E3 activity of TRIM27 towards Atxn1 82Q. Hence, TRIM proteins might employ similar mechanism to rid cells of misfolded proteins. The most relevant SUMO proteins for degrading misfolded proteins are SUMO2/3. The poly-chains formed by SUMO2/3 facilitate the recognition by the multiple SIMs on RNF4 (Tatham et al., 2008, Nat Cell Biol, 10: 538-546). Consistent with a role in protein quality control, SUMO2/3 in unstressed cells are mainly un-conjugated forms but become conjugated to target proteins after protein damaging stresses (Golebiowski et al., 2009, Sci Signal, 2: ra24; Saitoh and Hinchey, 2000, J Biol Chem, 275: 6252-6258). Nevertheless, given the diversity among the TRIM proteins and the ubiquitin E3 ligase activity associated with some (Meroni and Diez-Roux, 2005, Bioessays, 27: 1147-1157), it is still possible that some TRIM proteins may primarily function as ubiquitin E3s for misfolded proteins.

Currently, it is unclear why some TRIM proteins can degrade misfolded proteins such as Atxn1 82Q, while others cannot. Also, among the TRIM proteins tested, TRIM11 possesses a remarkably potent activity to reduce Atxn1 82Q. It remains to be determined what may account for its activity. Some TRIM proteins can enhance the expression levels of Atxn1 82Q and especially Httex1p 97QP. This further underscores the functional diversity of these proteins. TRIM proteins can function as chaperones to prevent protein misfolding and as disaggregase to dissolve previously formed protein aggregates. These activities may in part account for the effect of TRIM proteins to stabilize Atxn1 82Q and especially Httex1p 97QP. This suggests another important usage of TRIM proteins in the therapy of diseases associated with misfolded proteins. A number of human diseases are linked closely to the degradation of mutant proteins that are partially functional. A notable example is cystic fibrosis (CF), which is caused by mutations in the gene cystic fibrosis transmembrane conductance regulator (CFTR). These mutations are degraded in the cytoplasm. Therapies are being developed to stabilize the mutant CFTR, allowing mutant CFTR to reach the member to fulfill its function. It is envisioned that using TRIM proteins may achieve such a goal in CF and other diseases associated with degradation of partially functional proteins.

TABLE 2

Summary of the effect of cellular localization of TRIM proteins and their co-localization with Atxn1 82Q.

| Name | Other common names | Domains | Species | Isoforms used in this study | Cellular localization | Pattern | Atxin1 82Q aggregates colocalizaiton |
|---|---|---|---|---|---|---|---|
| TRIM1 | MID2, FXY2, RNF60 | R B1 B2 CC COS FN3 SPRY | h | | C | diffuse, foci, filament | — |
| TRIM2 | CMT2R, RNF86 | R B2 CC FIL NHL | h | | C | diffuse, foci | — |
| TRIM3 | BERP, HAC1, RNF22, RNF97 | R B2 CC FIL NHL | h | | C | diffuse | — |
| TRIM4 | RNF87 | R B2 CC SPRY | h | | C | foci | — |
| TRIM5 | RNF88 | R B2 CC SPRY (gamma does not have SPRY) | h | γ | C | foci | — |
| TRIM6 | RNF89 | R B2 CC PRY SPRY | h | | C, N | diffuse | ** |
| TRIM7 | GNIP, RNF90 | R B2 CC PRY SPRY | h | | C | foci | — |

TABLE 2-continued

Summary of the effect of cellular localization of TRIM proteins and their co-localization with Atxn1 82Q.

| Name | Other common names | Domains | Species | Isoforms used in this study | Cellular localization | Pattern | Atxn1 82Q aggregates colocalizaiton |
|---|---|---|---|---|---|---|---|
| TRIM8 | GERP, RNF27 | R B1 B2 CC | h | | C, N | foci | *** |
| TRIM9 | RNF91, SPRING | R B1 B2 CC COS FN3 PRY SPRY | h | | C | foci, filament | — |
| TRIM10 | RNF9, HERF1, RFB30 | R B2 CC PRY SPRY | h | | C | foci, filament | — |
| TRIM11 | BIA1, RNF92 | R B2 CC PRY SPRY | h | | C, N | diffuse | *** |
| TRIM12 | 2310043C01Rik | R B2 CC | mouse only | | C, N | diffuse, foci | — |
| TRIM13 | CAR, LEU5, RFP2, DLEU5, RNF77 | R B2 CC TM | h | | Perinuclear | diffuse, foci | — |
| TRIM14 | | B2 CC PRY/SPRY | h | | C, N | foci | — |
| TRIM15 | RNF93, ZNFB7, ZNF178 | R B2 CC PRY SPRY | h | | C | foci | — |
| TRIM16 | EBBP | B2 CC PRY/SPRY | h | | C, N, perinuclear | diffuse | — |
| TRIM17 | TERF, RBCC, RNF16 | R B2 CC PRY SPRY | h | | C | diffuse | — |
| TRIM18 | MID1, FXY. RNF59 | R B1 B2 CC COS FN3 PRY SPRY | h | | C | filament | — |
| TRIM19 | PML | R B1 B2 CC | h | | N | foci | *** |
| TRIM20 | PRYRIN, MEFV | B2 CC PRY/SPRY | h | | C | diffuse, foci | — |
| TRIM21 | Ro52, SSA1, SSA/Ro, RNF81 | R B2 CC PRY SPRY | h | | C, N | diffuse, foci, filament | *** |
| TRIM22 | STAF50, GPSTAF50, RNF94 | R B2 CC SPRY | h | short and long | N | foci | *** |
| TRIM23 | ARD1, ARFD1, RNF46 | R B1 B2 CC ARF | h | | C, N, perinuclear | diffuse, foci | — |
| TRIM24 | TIF1α, TF1A, TIF1A, TIF1, PTC6, RNF82 | R B1 B2 CC PHD BR | h | | C, perinuclear | foci | — |
| TRIM25 | EFP, Z147, RNF147, ZNF147 | R CC PRY SPRY | h | | C | diffuse, foci | — |
| TRIM26 | AFP, RNF95, ZNF173 | R B2 CC PRY SPRY | h | | C | diffuse, foci | — |
| TRIM27 | RFP, RNF76 | R B2 CC PRY SPRY | h | | C, N | foci | *** |
| TRIM28 | KAP, TIF1β, TF1B, TIF1B, RNF96, PPP1R157 | R B1 B2 CC PHD BR | h | | N | diffuse | *** |
| TRIM29 | ATDC | B1 B2 CC | h | | C | filament | — |
| TRIM30 | RPT1, RGD1563970 | R B2 CC PRY/SPRY | mouse only | | C, N | diffuse, foci | *** |
| TRIM31 | RNF, HCG1, HCGI, C6orf13 | R B2 CC | h | | C, N | diffuse, foci | # |

TABLE 2-continued

Summary of the effect of cellular localization of TRIM proteins and their co-localization with Atxn1 82Q.

| Name | Other common names | Domains | Species | Isoforms used in this study | Cellular localization | Pattern | Atxn1 82Q aggregates colocalizaiton |
|---|---|---|---|---|---|---|---|
| TRIM32 | HT2A, BBS11, TATI/P, LGMD2H | R B2 CC NHL | h | | C, N | foci | ** |
| TRIM33 | TIF1γ, TF1G, TIF1G, ECTO, PTC7, RFG7 | R B1 B2 CC PHD BR | h | | N | diffuse, foci | *** |
| TRIM34 | IFP1, RNF21 | R B2 CC SPRY | h | | C | foci | — |
| TRIM35 | HLS5, MAIR | R B2 CC PRY SPRY | h | | C, N | foci | ** |
| TRIM36 | RNF98, HAPRIN, RBCC728 | R B1 B2 CC COS FN3 SPRY | h | | C | filament | — |
| TRIM37 | MUL, POB1, TEF3 | R B2 CC MATH | h | | C | foci | — |
| TRIM38 | RoRet, RNF15 | R B2 PRY SPRY | h | | C, N | foci | *** |
| TRIM39 | TFP, RNF23 | R B2 CC PRY SPRY | h | | C | foci | — |
| TRIM40 | RNF35 | R B2 CC | h | | C, N | diffuse | # |
| TRIM41 | RINCK | R CC B2 CC PRY SPRY (According to Nat imm review) | h | | C | foci | — |
| TRIM42 | T4A1, PPP1R40 | R B1 B2 CC COS FN3 | h | | N/A | N/A | N/A |
| TRIM43 | | R B2 CC SPRY | h | | N/A | N/A | N/A |
| TRIM44 | DIPB, MC7, HSA249128 | B2 CC | h | | C, N | diffuse | — |
| TRIM45 | RNF99 | R B1 B2 CC FIL NHL | h | | C | foci | — |
| TRIM46 | TRIFIC, GENEY | R B2 CC COS FN3 SPRY | h | | C | filament | — |
| TRIM47 | GOA, RNF100 | R B2 CC PRY | h | | C | foci | — |
| TRIM48 | RNF101 | R B2 SPRY | h | | C, N | diffuse | # |
| TRIM49 | RNF18, TRIM49A, TRIM49L2 | R B2 SPRY | h | | C, N | diffuse | — |
| TRIM50 | | R B2 CC PRY SPRY | h | | C | foci | — |
| TRIM51 | SPRYD5A | R B2 SPRY | h | | C, N | foci | * |
| TRIM52 | RNF102 | R B2 | h | | C, N | diffuse | # |
| TRIM53 | | R SPRY (According to Nat imm review) | h | | N/A | N/A | N/A |
| TRIM54 | MURF, RNF30, muRF3, MURF-3 | R B2 CC COS | h | | C | filament | — |
| TRIM55 | MURF-2, RNF29, muRF2 | R B2 CC COS | h | | C, N | foci, filament | *** |
| TRIM56 | RNF109 | R B2 CC | h | | C, N | diffuse, foci | — |
| TRIM58 | BIA2 | R B2 CC PRY SPRY | h | | C, N | diffuse, foci | — |
| TRIM59 | TRIM57, MRF1, TSBF1, IFT80L, RNF104 | R B2 CC TM | h | | N/A | N/A | N/A |

TABLE 2-continued

Summary of the effect of cellular localization of TRIM proteins and their co-localization with Atxn1 82Q.

| Name | Other common names | Domains | Species | Isoforms used in this study | Cellular localization | Pattern | Atxn1 82Q aggregates colocalizaiton |
|---|---|---|---|---|---|---|---|
| TRIM60 | RNF33, RNF129 | R B2 CC PRY SPRY | h | | N/A | N/A | N/A |
| TRIM61 | RNF35 | R B2 CC | h | | N/A | N/A | N/A |
| TRIM62 | DEAR1 | R B2 CC PRY SPRY | h | | C, N | foci | — |
| TRIM63 | MURF1, RF1, RNF28 | R B2 CC COS | h | | C | filament | — |
| TRIM64 | C11orf28 | R B2 CC SPRY | h | | C, N | diffuse | *** |
| TRIM65 | 4732463G12Rik | R B2 CC SPRY | h | | N | diffuse | *** |
| TRIM66 | TIF1δ, TIF1D, C11orf29, | B1 B2 CC PHD BR | h | | N | foci, diffuse | — |
| TRIM67 | TNL | R B1 B2 CC COS FN3 SPRY | h | | N/A | N/A | N/A |
| TRIM68 | GC109, RNF137, SS-56, SS56 | R B2 PRY SPRY | h | | C, N | diffuse | — |
| TRIM69 | HSD-34, HSD34, RNF36, Trif | R CC PRY SPRY | h | | C | filament | — |
| TRIM70 | | CC PRY/SPRY | h | | N/A | N/A | N/A |
| TRIM71 | LIN-41, LIN41 | R B1 B2 CC FIL NHL | h | | N/A | N/A | N/A |
| TRIM72 | MG53 | R B2 CC PRY SPRY | h | | N/A | N/A | N/A |
| TRIM73 | TRIM50B | R B2 CC | h | | C, N | foci | *** |
| TRIM74 | TRIM50C | R B2 CC | h | | C, N | foci, diffuse | ** |
| TRIM75 | | R B2 CC PRY SPRY | h | | N/A | N/A | N/A |
| TRIM76 | CMYA5, SPRYD2, C5orf10 | B CC FN3, PRY/SPRY | h | | C | diffuse | — |

— No co-localization
\# Faintly distributed around aggregates
* <5% cells
** 5-20% cells
*** >20% cells

TABLE 3

Summary of the effect of TRIM proteins on Atxn1 82Q.

| | Subfamily | Soluble WB | IS WB | Total flow | Detection WB | WB fraction Trims |
|---|---|---|---|---|---|---|
| Trim1 | I | — | — | — | Normal | S/IS |
| Trim2 | VII | — | — | — | Normal | S |
| Trim3 | VII | — | ↓ | — | Normal | S/IS |
| Trim4 | IV | — | ↓↓ | — | Normal | S/IS |
| Trim5 | IV | — | ↓↓ | — | Normal | S/IS |
| Trim6 | IV | — | ↓ | — | None | |
| Trim7 | IV | — | ↓ | — | None | |
| Trim8 | V | — | — | — | Normal | S/IS |
| Trim9 | I | ↓ | ↓↓ | ↓↓ | Low | S |
| Trim10 | IV | — | — | ↓ | | IS |
| Trim11 | IV | ↓↓↓ | ↓↓↓ | ↓↓↓ | None | |
| Trim12 | | — | — | — | Low | IS |
| Trim13 | XI | — | ↓/— | — | Normal | IS |
| Trim14 | F IV | — | ↓/— | ↓ | Normal | IS |
| Trim15 | IV | — | ↓/— | — | Normal | IS |
| Trim16 | F IV | ↓ | ↓ | — | None | |
| Trim17 | IV | — | ↓↓ | ↓ | Normal | S/IS |
| Trim18 | I | — | — | — | Normal | S |
| Trim19 | V | ↓ | — | ↓ | Normal | S/IS |
| Trim20 | F IV | ↓↓ | ↓↓↓ | ↓↓↓ | Low | S |
| Trim21 | IV | — | ↓ | ↓ | Normal | S/IS |
| Trim22 | IV | — | — | ↓ | Normal | S/IS |
| Trim23 | IX | — | — | ↓ | Low | S/IS |
| Trim24 | VI | — | ↓ | ↓↓ | None | |
| Trim25 | IV | — | — | ↓ | None | |
| Trim26 | IV | — | ↑ | ↑ | Normal | IS |
| Trim27 | IV | — | — | — | Normal | IS |
| Trim28 | VI | — | ↓ | — | Normal | S |
| Trim29 | | — | ↓ | — | Normal | IS |
| Trim30 | | — | ↓↓ | ↓↓ | Low | IS |
| Trim31 | V | — | — | ↓ | Normal | S |
| Trim32 | VII | — | — | — | Normal | IS |
| Trim33 | VI | ↑ | ↑ | — | None | |
| Trim34 | IV | — | ↓ | ↓ | Normal | IS |
| Trim35 | IV | — | — | — | Normal | IS |
| Trim36 | I | — | — | ↑ | None | |

TABLE 3-continued

Summary of the effect of TRIM proteins on Atxn1 82Q.

| | Subfamily | Soluble WB | IS WB | Total flow | Detection WB | WB fraction Trims |
|---|---|---|---|---|---|---|
| Trim37 | VIII | — | — | ↑ | None | |
| Trim38 | IV | — | — | ↑ | Low | S/IS |
| Trim39 | IV | — | — | ↓ | Normal | S/IS |
| Trim40 | V | — | — | — | Normal | S |
| Trim41 | IV | — | — | — | Normal | S/IS |
| Trim42 | III | ↑ | ↑ | ↑ | Normal | S/IS |
| Trim43 | IV | — | ↓↓ | ↓ | Normal | IS |
| Trim44 | | — | ↓ | — | Normal | S/IS |
| Trim45 | XI | — | ↓ | — | Normal | IS |
| Trim46 | I | — | ↓ | ↓ | Normal | S/IS |
| Trim47 | IV | — | ↑ | ↓ | Normal | S/IS |
| Trim48 | IV | — | — | ↓ | Low | IS |
| Trim49 | IV | ↓ | ↓↓ | ↓ | Low | S/IS |
| Trim50 | IV | — | ↓↓ | ↓ | Normal | S/IS |
| Trim51 | F IV | — | — | — | None | |
| Trim52 | V | — | ↓ | ↓ | Normal | S |
| Trim54 | II | — | — | — | none | |
| Trim55 | II | — | — | ↑ | Normal | S |
| Trim56 | V | — | — | — | None | |
| Trim58 | XI | — | — | ↑ | Normal | S/IS |
| Trim59 | XI | ↓ | ↓ | — | Normal | S/IS |
| Trim60 | IV | — | — | ↑ | None | |
| Trim61 | V | — | — | ↑ | None | |
| Trim62 | IV | — | — | — | None | |
| Trim63 | II | — | — | ↑ | Normal | |
| Trim64 | IV | — | ↑ | — | Normal | S/IS |
| Trim65 | IV | ↓ | ↓↓ | ↓ | Normal | S/IS |
| Trim66 | F IV | — | ↑ | ↑ | None | |
| Trim67 | I | — | ↓ | ↓/— | Normal | S/IS |
| Trim68 | IV | — | — | ↓ | Normal | S |
| Trim69 | IV | ↑ | ↑ | ↑ | None | |
| Trim70 | F IV | — | ↓↓ | ↓↓ | low | S/IS |
| Trim71 | VII | — | — | — | None | |
| Trim72 | IV | — | — | ↑ | Normal | S/IS |
| Trim73 | V | — | — | — | Normal | |
| Trim74 | V | — | ↓ | ↓ | Normal | |
| Trim75 | IV | — | ↓↓ | ↓ | Normal | |
| Trim76 | | — | ↑ | ↑ | Normal | S/IS |
| Trim77 | | — | — | ↑ | | |

— No Change
↓ 10-25%
↓↓ 25-50%
↓↓↓ >50%
↓/— Change <10%

TABLE 4

Summary of the effect of TRIM proteins on Httex1p 97QP

| | Subfamily | Soluble WB | IS WB | Total flow |
|---|---|---|---|---|
| Trim1 | I | — | ↑ | — |
| Trim2 | VII | — | — | — |
| Trim3 | VII | — | ↓ | — |
| Trim4 | IV | — | ↑ | — |
| Trim5 | IV | — | — | — |
| Trim6 | IV | — | ↑ | — |
| Trim7 | IV | — | ↑ | — |
| Trim8 | V | — | ↑ | — |
| Trim9 | I | — | ↑ | — |
| Trim10 | IV | — | ↑ | — |
| Trim11 | IV | ↓ | ↓ | ↓↓↓ |
| Trim12 | | — | ↑ | ↑ |
| Trim13 | XI | — | ↑ | ↑ |
| Trim14 | F IV | — | ↑↑ | ↑ |
| Trim15 | IV | — | ↑↑ | — |
| Trim16 | F IV | — | ↑ | ↓ |
| Trim17 | IV | — | ↑ | — |
| Trim18 | I | — | ↑ | — |
| Trim19 | V | — | ↑/— | ↓ |
| Trim20 | F IV | — | ↑/— | ↓ |
| Trim21 | IV | — | ↑ | ↑ |
| Trim22 | IV | — | — | — |
| Trim23 | IX | — | ↑ | ↑ |
| Trim24 | VI | — | ↑ | ↓ |
| Trim25 | IV | — | ↑ | ↑ |
| Trim26 | IV | — | ↑ | ↑ |
| Trim27 | IV | — | ↑ | ↑ |
| Trim28 | VI | — | ↑ | ↑ |
| Trim29 | | — | — | ↓ |
| Trim30 | | — | ↓ | ↓↓ |
| Trim31 | V | — | — | — |
| Trim32 | VII | — | ↑ | ↑ |
| Trim33 | VI | — | ↑ | ↑ |
| Trim34 | IV | — | ↑ | ↑ |
| Trim35 | IV | — | ↑ | ↑ |
| Trim36 | I | — | ↑ | ↑ |
| Trim37 | VIII | — | ↑ | ↑ |
| Trim38 | IV | — | ↑ | ↑ |
| Trim39 | IV | — | ↑ | — |
| Trim40 | V | — | — | ↑ |
| Trim41 | IV | — | ↑ | ↑ |

Example 3: Delivery of Recombinant TRIM11 into Mammalian Cells Promotes the Degradation of Misfolded Proteins As described above, it has been demonstrated that members of the tripartite motif-containing (TRIM) family play an important role in the recognition and degradation of misfolded proteins. Initially using PML/TRIM19 as an example, it was shown that PML can specifically bind to misfolded proteins via distinct regions that recognize structure features commonly found in misfolded proteins. PML then uses its SUMO E3 activity to tag the misfolded proteins with poly-SUMO2/3 chains. This allows misfolded proteins to be recognized by a SUMOylation-targeted ubiquitin ligase (STUbL) RNF4, with the consequential ubiquitination and proteasomal degradation of misfolded proteins. It was further shown that this PML-RNF4-mediated sequential SUMOylation and ubiquitination system plays an important role in the protection against neurodegenerative diseases.

Subsequently, the vast majority of all known human TRIM proteins were survey, and it was found that a substantially number of them are able to localize to the inclusion formed by misfolded proteins such as pathogenic ataxin 1 (Atxn1 82Q) and huntingtin (Htt 97Q) proteins. By testing representative TRIM proteins, it was shown that many TRIM proteins are also capable of degrading misfolded proteins in a SUMO-dependent manner. Of note, among the TRIM proteins that were tested, one TRIM proteins, TRIM11, exhibits a particularly strong activity to reduce misfolded proteins.

In the experiments presented herein, it was sought to develop recombinant TRIM11 as an agent for degrading intracellular misfolded proteins associated with neurodegeneration. For this, the HIV Tat-derived peptide was used, which is able to deliver proteins into mammalian cells (FIG. 22). TRIM11 was fused with the Tat-derived peptide, the fusion protein was expressed in bacteria, and the protein was purified to homogeneity using affinity resin, followed by gel filtration column. For comparison, Tat-peptide-fused SUMO2 protein was also purified in parallel.

Figures 21A, 21B, 21C:
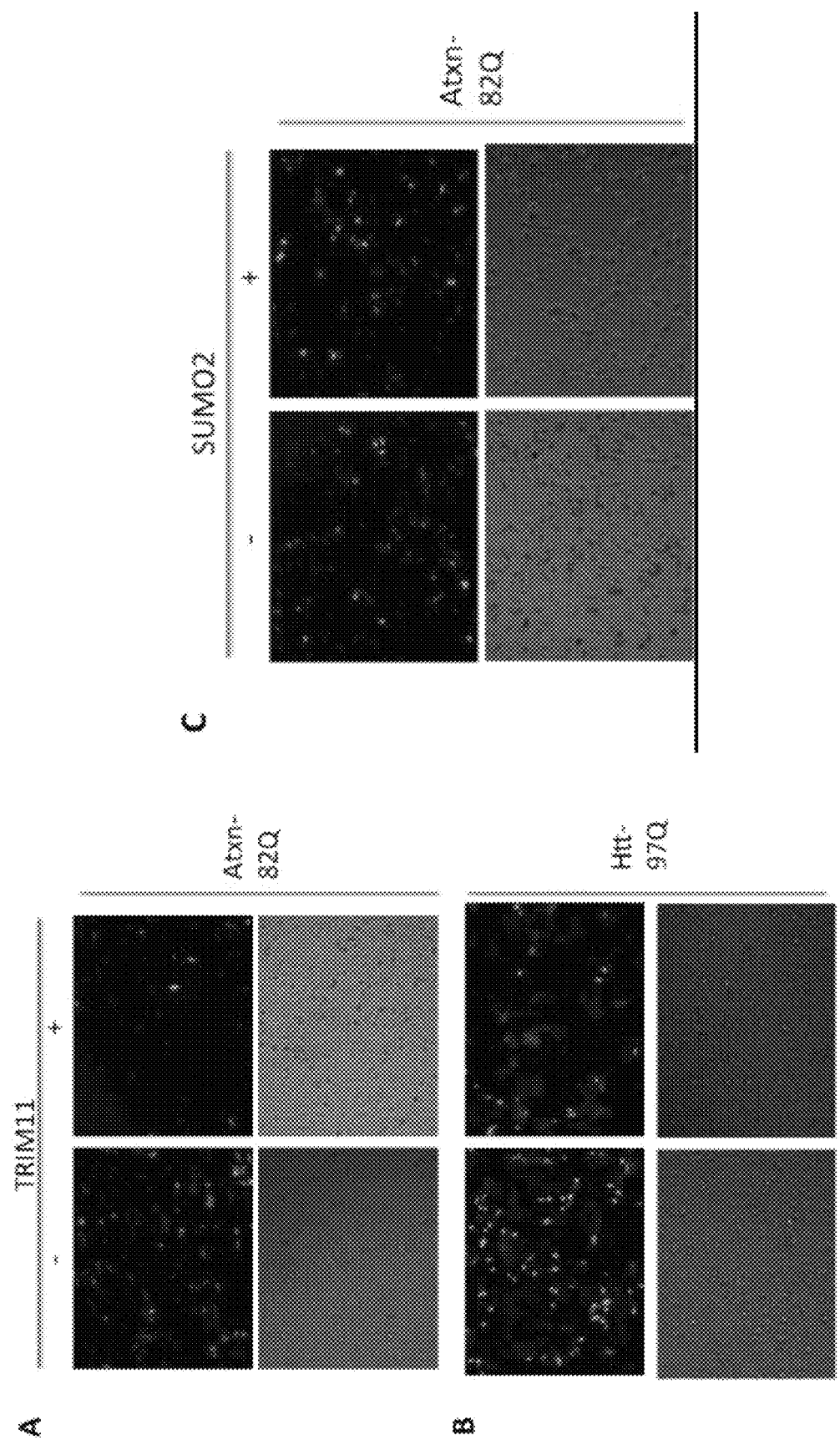
FIG. 21A through FIG. 21C, depicts the results of example experiments demonstrating that recombinant TAT-TRIM11 reduces the levels of misfolded proteins. HeLa cells were transfected with Atxn1 82Q-GFP, Atxn1 30Q, or Htt 97Q-GFP, and were subsequently incubated with recombinant TRIM11 or SUMO2 proteins.

HeLa cells were transfected with Atxn1 82Q-GFP, Atxn1 30Q, or Htt 97Q-GFP, and were subsequently incubated with recombinant TRIM11 or SUMO2 proteins. As shown in FIG. 21A, treatment of HeLa cells with TRIM11 led to strong reduction in the levels of Atxn1 82Q. It also led to strong reduction in the levels of Htt 97Q (FIG. 21B). In contrast, SUMO2 had minimal effect on the levels of Atxn1 82Q (FIG. 21C). These data suggest that delivery of TRIM11 into mammalian cells reduces the levels of misfolded proteins, providing a proof or concept evidence for targeting the TRIM-RNF4 system for the therapy of neurodegeneration and other protein-misfolding diseases.

Example 4: Localization of RNF4 to Neuronal Inclusions in SCA1 and HD Patients

RNF4 deficiency in mice results in embryonic lethality (Hu et al, 2010, PNAS 107:15087-92), precluding the analysis of its deficiency on mouse models of neurodegeneration. Previous studies showed that PML, along with SUMO and ubiquitin, co-localizes with neuronal inclusions in polyglutamine disease patients (Dorval and Fraser; 2006, J BIol Chem 281:9919-24; Martin et al., 2007, Nat Rev Neurosci 8:948-59; Skinner et al., 1997, Nature 389:971-4; Takahasi et al., 2003, Neurobiol Dis 13:230-70), suggesting the involvement of PML in these diseases. The data presented herein analyzes the localization of RNF4 in post-mortem brain tissues of human SCA1 and HD patients.

The materials and methods employed in these experiments are now described.

HD patient tissues (globus pallidus) were provided by the Harvard Brain Tissue Resource Center: AN06564, AN12127 and AN12029 (aggregates observed), and AN09048, AN19685, AN14942, AN13612 and AN17467 (no aggregates observed); SCA1 patient tissues (basis points) were obtained, National Ataxia Foundation. Immunohistochemistry and immunofluorecence were performed as previously described with modifications (Duda et al., 2000, J Neuropathol Exp Neurol 59:830-41; Emmer et al., 2011, J Biol Chem 286:35104-18). HD and SCA1 patient brains were embedded in paraffin and cut into 6 □m sections. Sections were stained for anti-RNF4 (#1: Rabbit, 11-25, 1:300, Sigma; #2: Goat, C15, 1:25, Santa Cruz), anti-Huntingtin (mouse, MAB5374, 1:500; Millipore), anti-ubiquitin (mouse, Ubi-1, MAB1510, 1:2,000; Millipore), and anti-polyQ (mouse MAB1574, 1C2, 1:1,000; Millipore) as indicated. Control rabbit antibodies were used to confirm the specificity of anti-RNF4 staining.

The results of the experiments are now described.

Figure 23:
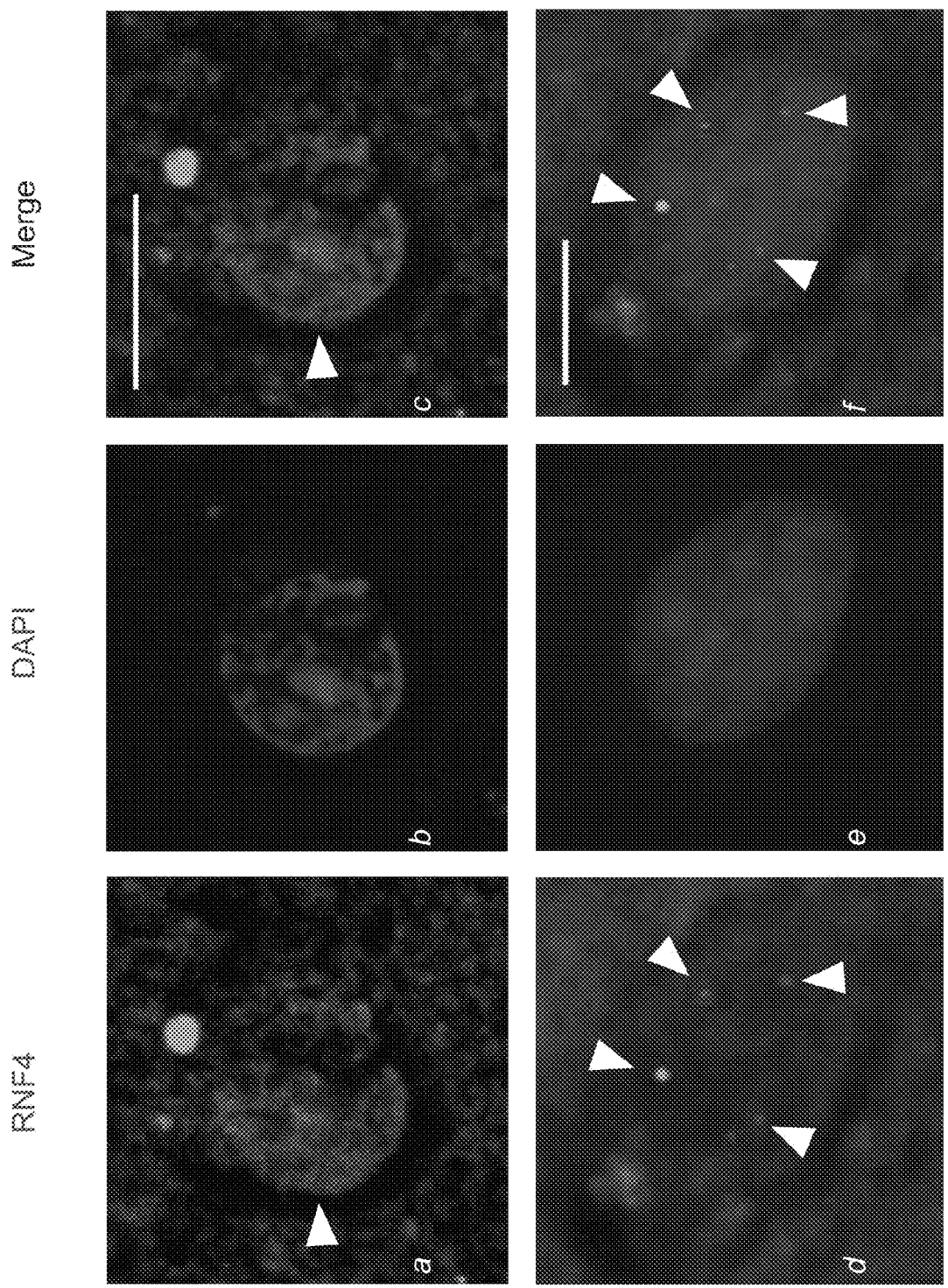
FIG. 23, comprising
Figure 24:
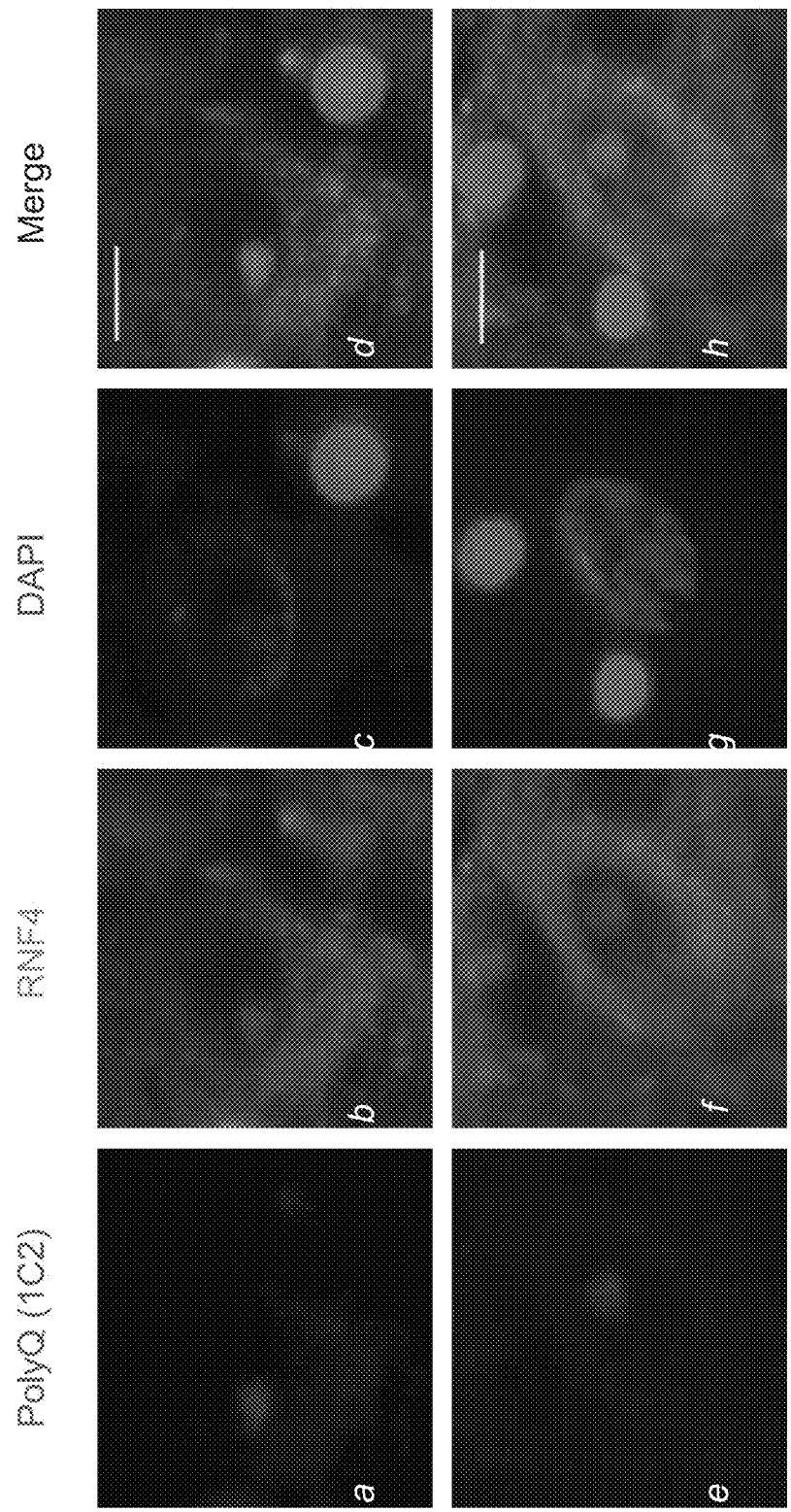
FIG. 24, comprising

When detected in patient neurons without inclusions, RNF4 tended to distribute diffusely throughout the nucleus or form nuclear foci (FIG. 23). In the two cases of SCA1 that were examined, nuclear inclusions reactive to an anti-polyQ antibody (1C2) were present. RNF4 was found in five out of sixteen and four out of seventeen 1C2-reactive nuclear inclusions, respectively (FIG. 24).

Figure 25:
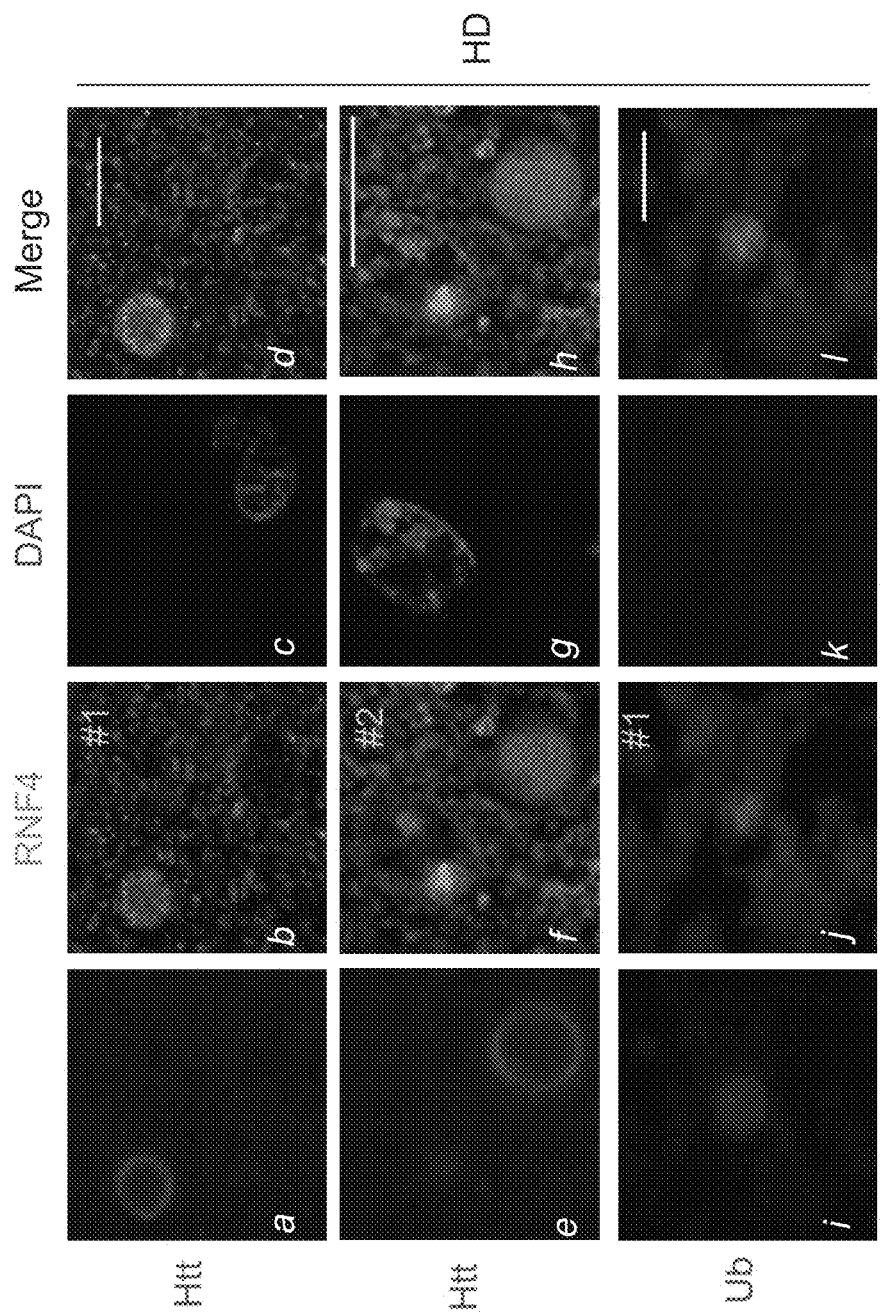
FIG. 25, comprising

Among the HD patients, cytoplasmic inclusions reactive to either anti-huntingtin or anti-ubiquitin antibody were present in the globus pallidus region in three out of eight patient samples examined. This was in agreement with previous observations that nuclear inclusions were rare in adult-onset HD cases (DiFiglia et al., 1997, Science 277: 1990-3). Nevertheless, RNF4 co-localized with approximately 20% of the inclusions in the globus pallidus region based on the results with two separate anti-RNF4 antibodies (FIG. 25 and FIG. 26). The inclusions containing RNF4 tended to show RNF4 immunoreactivity surrounded by a ring of huntingtin or ubiquitin signals (FIG. 25 and FIG. 26). The partial co-localization of RNF4 with the polyQ aggregates in SCA1 and HD patients is reminiscent of the partial co-localization of PML with polyQ aggregates (Skinner et al., 1997, Nature 389:971-4; Takahashi et al., 2003, Neurobiol Dis 13:230-7), and it may reflect the blockage of the PML/TRIM-RNF4 system in the disease-affected neurons.

Example 5: Molecular Chaperone and Protein Diaggregase Activities of TRIM Proteins The data described herein demonstrates that TRIM11 can function as a molecular chaperone and disaggregase. In one aspect, TRIM11 can prevent aggregate formation. On the other hand, TRIM11 is not only able to refold stress-induced non-amyloid aggregates (luciferase and GFP aggregates), but also disaggregate amyloid aggregates (Atxn1 82Q aggregates and alpha-Synuclein fibrils). Further, it is also shown herein that TRIM11 is also a SUMO E3 ligase that can SUMOylate Atxn1 82Q and subsequent degradation. Therefore, TRIM11 may serve as a link between protein disaggregation and degradation.

The materials and methods employed in these experiments are now described.

siRNA Transfection

Mouse TRIM11 siRNA (sc-76735) was purchased from Santa Cruz. In the first day, hippocampal neuron cells (15000 cells/well) were plated in 96 well plates with plating medium. In the second day (about 18 hours after plating), completely change the plating medium to neuronal medium. In the third day, siRNA (1 pmol) was transfected into cells by Lipofectamine RNAiMAX. The transfection methods were carried out according to the manufacturer's instructions.

Cell Culture

HCT16 cells were cultured with Mccoy 5A medium. A549 cells were cultured with RPMI1640 medium. HeLa and HEK293T cells were cultured with DMEM medium.

These culture mediums all contain 10% Fetal Bovine Serum (FBS). Primary neuron cells were obtained. Neuron cells were cultured according to previously described methods. Simply, the cells were first plated with plating medium (Combine Neurobasal medium, B27, GlutaMAX, penicillin/streptomycin and 10% FBS by the indicated dilution ratios). After 18-24 h, completely change the plating medium to neuronal medium (Combine Neurobasal medium, B27, GlutaMAX and penicillin/streptomycin by the indicated dilution ratios). Except notification, all cells were maintained at 37° C. in a humidified 5% $CO_2$ atmosphere.

Immunofluorescence

Cells plated on coverslips were fixed with 4% paraformaldehyde for 10 minutes at room temperature. Cells were further permeabilized with methanol for 10 minutes at 20° C. Cells were washed with PBS and then blocked by 2% bovine serum albumin (BSA) for 30 min at room temperature. Cells were incubated with the primary antibody overnight at 4° C., followed by incubation with a fluorescent secondary antibody for 1 hour at room temperature. Finally, the coverslips were mounted to glass slides with mounting medium containing 4',6-diamidino-2-phenylindole (DAPI) (Vector Laboratories; H-1200). For antibodies dilution, anti-HA (1:100), anti-p-a-Syn (1:100) and anti-p62 (1:200) were applied.

Antibodies

Anti-TRIM11 (ABC926) antibody was purchased from Millipore. Monoclonal anti-Flag antibody, rabbit Flag antibody and anti-Flag agarose beads were purchased from Sigma. Anti-HA affinity matrix (clone 3F10, 11815016001) was purchased from Roche. Anti-HSF1 (sc-9144) was purchased from Santa Cruz. Anti-a-Synuclein Phopho-Ser129

(825701) was purchased from Biolegend. Anti-Hsp70 (ADI-SPA-810-D) was purchased from Enzo. Anti-a-Synuclein (2642) and anti-Hsp90 (4874) was purchased from Cell signaling technology.

Protein Fractionation, Filter Retardation Assay and Immunoblotting

Cells were lysed with the lysis buffer (50 mM Tris, pH 8.8, 100 mM NaCl, 5 mM MgCl2, 0.5% IGEPAL CA-630, 1 mM DTT, 250 IU/ml benzonase (Sigma), 1 mM PMSF and 1× complete protease cocktail (Roche)) for 30 minutes on ice. The supernatant was obtained by centrifuging 13000 rpm for 15-20 minutes at 4° C. The pellet was further resuspended in the pellet buffer (20 mM Tris, pH 8.0, 15 mM MgCl2, 1 mM DTT, 250 IU/ml benzonase, 1 mM PMSF and 1× complete protease cocktail) for 30 minutes on ice, followed by directly boiling with 2% SDS buffer. Protein concentration was measured by Bradford assay (Bio-Rad Labs). All protein samples were subjected to immunoblotting by SDS-PAGE. The supernatant was considered as a soluble fraction. The pellet was considered as an insoluble fraction (SDS-soluble). The other portion was subjected to filter retardation assay. Simply, the pellet samples were filtered through a membrane with 0.2 µM pore size, so that the SDS-resistant aggregates retained on the membrane were analyzed by immunoblotting.

Protein Purification

Flag-Atxn1-82Q-HA was transfected in 293T cells and purified by anti-Flag M2 beads. For getting highly purified proteins, the beads were extensively washed with increased concentrations of NaCl.

His-Luciferase was expressed in BL21 DE3 cells purified. To generate immobilized native or denatured luciferase, native luciferase was first purified from bacterial cell lysates according to the manufacturer's instructions. Second, denatured luciferase was generated by incubating native luciferase with 8 M urea for 5 minutes In Vivo and In Vitro Sumoylation Assays For in vivo sumoylation assays, cells were transfected with the indicated plasmids. After 48 hours, cells were lysed in lysis buffer (50 mM Tris-Cl, pH 7.4, 150 mM NaCl, 0.5% Trition, 1 mM DTT, 1 mM PMSF and 1× complete protease cocktail) supplemented with 2% SDS and 50 mM DTT. Cell lysates were further boiled at 95° C. for 10 minutes. One aliquot was saved for input. The rest of cell lysates were diluted 10-fold in lysis buffer and then incubated with anti-HA beads at 4° C. overnight. The beads were extensively washed and analyzed by immunoblotting with the indicated antibodies. For in vitro sumoylation assays, His-SUMO-2 (UL-753), UbcH9 (E2-465) and SUMO E1 (E-315) were purchased from Boston Biochem.

Plasmids

Flag-TRIM11 was constructed by inserting KpnI/XbaI TRIM11 cDNA into KpnI/XbaI digested pcDNA3.1-Flag vector. Flag-TRIM11mutation (12/13EE to 12/13AA) was generated by site-directed mutation. GST-TRIM11 was constructed by inserting BglII/SalI TRIM11 cDNA into BamHI/SalI digested pGEX-1λT vector. GFP-Hsp70 and GFP-TRIM11 were constructed by inserting Hsp70 and TRIM11 cDNA into pEGFP-C1 vector. All the constructs were verified by DNA sequencing.

Luciferase Reactivation Assay

To generate aggregates, firefly luciferase (100 nM) in luciferase refolding buffer (LRB; 25 mM HEPES-KOH [pH 7.4], 150 mM KAOc, 10 mM MgAOc, 10 mM DTT) was heated at 45° C. for 8-10 minutes. Aggregated luciferase (10 nM) was incubated with the indicated concentrations of TRIM11 or other proteins at 25° C. for 90 minutes. For Hsp104/Hsp70-Hsp40 di-chaperone system, 5 mM ATP and an ATP regeration system (1 mM creatine phosphate, 0.5 uM creatine kinase) were required. For in vivo luciferase refolding assay, cells in 96 well plate were transiently transfected with wild type luciferase. After 24 hours, cells were heated at 42° C. or 45° C. for 1 hour or 30 minutes, respectively. Prior to heat shock, 20 µg/ml cycloheximide was added into culture medium. After heat shock, cells were transferred to 37° C. incubator for another 1.5 or 3 hours. Luciferase activity was measured with Promega Luciferase System.

GFP Disaggregation Assay

To generate aggregates, GFP (4.5 µM) in buffer A (20 mM Tris-HCl, pH 7.5, 100 mM KCl, 20 mM MgCl2, 5 mM DTT, 0.1 mM EDTA, 10% (v/v) glycerol) was incubated for 15 minutes at 85° C. GFP aggregates (0.45 µM) were incubated with the indicated proteins with different amounts at 25° C. for 60 minutes. Disaggregation of GFP aggregates was detected by measuring fluorescence at 510 nm upon excitation at 395 nm (Infinite M200 pro).

Reagents

Luciferase (L9506), Mg-ATP (A9187), phosphocreatine (P1937) and creatine kinase (C3755) were purchased from Sigma. KRIBB11 (385570) was purchased from Millipore. Beta-Amyloid (1-42) (RP10017) was purchased from GenScript.

The results of the experiments are now described.

PML (TRIM19) SUMOylated misfolded protein that can be recognized by RNF4 to be degraded through proteasome. However, it is unknown whether TRIM11 is also a SUMO E3 ligase. According to the structural analysis of TRIMs, two highly conserved glutamates (Glu9 and Glu10) of TRIM25 are required for its ubiquitin E3 ligase activity. Therefore mutated TRIM11 (Glu12/Glu13 to Ala12/Ala13) were generated that lacked E3 ligase activity (FIG. 27A and FIG. 27B). In vivo SUMOylation assay showed that Atxn1 82Q was efficiently SUMOylated by wild type TRIM11, as well as PML (FIG. 27A). To further confirm this, in vitro SUMOylation assay showed that purified Atxn1 82Q could be significantly SUMOylated by TRIM11. Therefore, TRIM11 was also a SUMO E3 ligase for Atxn1 82Q. In cells, TRIM11 like Hsp70 was mainly localized in the cytoplasm (FIG. 28A and FIG. 28B). Intriguingly, TRIM11 or Hsp70 could be recruited into the aggregates of Atxn1 82Q (FIG. 28C and FIG. 28D), suggesting that there might be an interaction between TRIM11 and Atxn1 82Q. To test this, pull down analysis presented that TRIM11 selectively bound to Atxn1 82Q (FIG. 29A). Importantly, TRIM11 preferentially interacted with pathologic form Atxn1 82Q, not Atxn1 30Q (FIG. 29B). Therefore it was hypothesized that TRIM11 had a potential to selectively bind to misfolded proteins. To investigate the prediction, native or denatured luciferase beads were further generated and then a pull down assay was performed. As shown in FIG. 29C, in contrast to control GST proteins, TIRM11 specifically bound to denatured luciferase, which indicated that TRIM11 was capable of binding misfolded proteins.

It has been demonstrated that Hsp70, a molecular chaperone, can suppress the expression of pathology associated Atxn1 82Q in SCA1 mice. Additionally, Hsp70 reduced the protein level of the detergent-insoluble fraction of Atxn1 82Q, which was consistent with the results presented herein (FIG. 28E). It was next investigated whether there was a similarity between TRIM11 and Hsp70 for aggregate formation. To study this, the solubilized feature of Atxn1 82Q was analyzed by detergent fractionation. As show in FIG. 28E, TRIM11, like Hsp70, reduced the detergent-insoluble fraction of Atxn1 82Q, suggesting that TRIM11 could control protein aggregation. Moreover, MG132 treatment moderately increased the insoluble Atxn1 82Q fraction (FIG. 28E), which was consistent with the previous report that the proteasome is necessary for controlling Atxn1 82Q aggregate formation. Interestingly, when Atxn1 82Q was co-expressed with wild type TRIM11 or mutant TRIM11, the mutant TRIM11 had a lower ability to reduce the detergent-insoluble fraction of Atxn1 82Q by comparing with wild type TRIM11 (FIG. 28F), suggesting that E3 ligase activity of TRIM11 was required for the reduction of Atxn1 82Q aggregates. To further test whether TRIM11 had an effect on amyloid like aggregates in cells, wild type or mutant TRIM11 was transfected into the cells and ThT staining showed that wild type and mutant TRIM11 could both down-regulate the level of amyloid like aggregates (FIG. 28G). Stable overexpression of Atxn1 82Q moderately enhanced the ThT staining (FIG. 30A). Similarly, TRIM11 could also reduce the detergent-insoluble fractions of Atxn1 82Q in stable cells (FIG. 30B). Importantly, wild type TRIM11 had a stronger ability than mutant TRIM11 could to reduce the cellular aggregates (FIGS. 30C and 30D).

Due to the similarity of Hsp70 and TRIM11, it was hypothesized that TRIM11 might function as molecular chaperone for controlling protein aggregation. Generally, chaperones have a capacity of preventing aggregation-prone misfolded proteins. This is the most primary and effective way to control protein aggregation. Therefore, the prevention function of TRIM11 in the formation of aggregate was investigated. Luciferase activity was rapidly decreased without chaperone in response to heat shock (FIG. 31A). However, incubation of TRIM11 as well as Hsp70 could efficiently protect luciferase from heat inactivation (FIG. 31A). Similarly, TRIM11 also protect GFP proteins against heat (FIG. 31C). These results suggested that TRIM11 might function as molecular chaperone like Hsp70. In cells, stable overexpression of TRIM11 was able to moderately protect luciferase against heat shock (FIG. 31C and FIG. 31D). What's more, TRIM11 could also obviously recover the heat inactivation of luciferase (FIG. 31C and FIG. 31D), which further confirmed the chaperone like function of TRIM11. Importantly, TRIM11 overexpression did not change the protein level of Hsp70 (FIG. 31E). Next, Alzheimer disease associated beta-amyloid (1-42) was used as a substrate to study the prevention function of TRIM11. As shown in FIG. 31F, TRIM11 could inhibit amyloid fiber formation by ThT analysis. Additionally, Atxn1 82Q was purified to test the process of aggregate formation. Control protein GST could not prevent Atxn1 aggregate formation, while TRIM11 efficiently blocked the formation of aggregate (FIG. 31G). Moreover, TRIM11 could also prevent amyloid like aggregate of Atxn1 82Q (FIG. 31G). It is known that p53 is prone to form aggregate in vitro. As shown in FIG. 31H, TRIM11 significantly prevented p53 from denaturation. Intriguingly, p53 could be SUMOylated by TRIM11 in vitro (FIG. 27C) and SUMOylation of p53 could block amyloid like aggregate but promoted oligomer formation. To sum up, TRIM11 may function as a molecular chaperone to prevent aggregate formation.

To determine if TRIM11 could be upregulated in response to heat shock HCT116 cells stably expressing vector or TRIM11 were used. In control stable cells, TRIM11 was increased during the recovery after heat shock (FIG. 32A). However, in TRIM11 expressing cells, exogenous TRIM11 protein could not be upregulated (FIG. 32B), meaning that the up regulation of TRIM11 induced by heat was not due to the change of protein stability. Heat-induced TRIM11 up regulation was further confirmed in HeLa cells (FIG. 32C). Because many stress can induce protein misfolding, whether TRIM11 could be induced by other stress was examined. As shown in FIGS. 30D and 30E, the protein level of TRIM11 was upregulated in response to $As_2O_3$ and $H_2O_2$ treatment. The mRNA level of TRIM11 could be induced in response to heat shock (FIG. 32F), which is similar with Hsp70. To investigate the mechanisms by which TRIM11 was induced by heat shock, A549 cells were generated which stably express HSF1, a key transcriptional factor to control heat responsive proteins. Surprisingly, overexpression of HSF1 down-regulated TRIM11 protein level with or without heat shock treatment (FIG. 32G), suggesting that HSF1 was possible not required for regulating the transcription of TRIM11.

Another key transcriptional factor, p53, can be activated during the heat shock response. p53 is also able to directly increase the transcription of TRIMs, for example TRIM21 and TRIM24. Therefore, it was investigated whether TRIM11 could be controlled by p53 in response to heat shock. As shown in FIG. 33A, TRIM11 was increased in response to heat shock in p53 wild type but not p53 null HCT116 cells. Accordingly, the mRNA level of TRIM11 only was enhanced in p53 wild type HCT116 cells (FIG. 33B), suggesting that p53 contributed to TRIM11 transcription. To further confirm the importance of p53, the protein and mRNA level of TRIM11 could not be unregulated in A549 cells stably expressing p53 shRNA (FIG. 33C). Similar phenomenon was confirmed again in p53 knockdown HCT116 cells (FIG. 33D). Together, these results strongly implied that p53 might be a key factor to upregulate TRIM11 in heat shock response. HSF1 is considered as a safeguard for cell survival following heating stress. KRIBB11, a chemical inhibitor, can be used to inhibit HSF1 activity. As shown in FIG. 33E and FIG. 33F, with KRIBB11 treatment, p53 nulls were more sensitive to heat shock, which implied that p53 also contributed to cell survival in response to heating stress.

Hsp70 may promote the dissolution of some kinds of protein aggregates. Next, it was investigated whether TRIM11 could disaggregate protein aggregates. As expected, TRIM11 resolubilized heat-inactivated luciferase from insoluble aggregates (FIG. 34A) and recovered luciferase activity in a dose-dependent manner (FIG. 34B). Also, the solubilized function of TRIM11 was further confirmed using preformed GFP aggregates as substrates (FIG. 34C and FIG. 34D). These results suggested that TRIM11 could disaggregate disordered aggregates. Next, assays were performed using Atxn1 82Q aggregates as substrates. As shown in FIG. 34E, TRIM11 could efficiently resolubilized Atxn1 82Q aggregates. Notably, Hsp70/Hsp40 di-chaperone only disaggregated amyloid like structure of Atxn1 82Q into the pellet (FIG. 34F), suggesting that TRIM11 might act in a different way. As expected, TRIM11, as well as Hsp104, significantly recovered amyloid like structure into the supernatant (FIG. 34G).

To determine which functional domain of TRIM11 was required for disaggregation activity of TRIM11 heated luciferase aggregates were used as substrates. As shown in FIG. 35B, TRIM11 could efficiently recover heat inactivation of luciferase activity, but RBC or B30.2 fragments of TRIM11 had weaker reactivation ability. Consistently, in sedimentation assay, TRIM11 had a stronger activity than its two fragments to resolubilize preformed luciferase aggregates (FIG. 35C). Further, each single domain almost lost the refolding activity by comparing with full length TRIM11 (FIG. 35D). Furthermore, full length TRIM11 very strongly interacted with Atxn1 82Q, but RBC or B30.2 did not bound to Atxn1 82Q (FIG. 36A). Similarly, single domain of TRIM11 did not bind to Atxn1 82Q (FIG. 36B). These results strongly suggested that binding to substrates might be required for TRIM11 disaggregation function.

It was next investigated whether SUMO E3 ligase activity is required for protein disaggregation. Here mutant TRIM11 was used to test its disaggregation activity. As shown in FIG. 37A, mutant TRIM11 maintained the ability to prevent luciferase from heat inactivation like wild type TRIM11. Moreover, mutant TRIM11 also had a similar potential with wild type TRIM11 to recover denatured luciferase activity (FIG. 37B). Mutant TRIM11 was still able to selectively bind to denature luciferase (FIG. 37C). All these results indicated that in vitro, TRIM11 performed its disaggregation function independently of its E3 activity. Notably, mutant TRIM11 was largely localized in the nucleus (FIG. 37D), which was different from wild type TRIM11. Further, mutant TRIM11 could also be co-localized with Atxn1 82Q.

Previous studies showed that Hsp110, Hsp70, and Hsp40, the metazoan protein disaggregase system, could not efficiently disaggregate amyloid. Therefore, it was investigated whether TRIM11 could disaggregate amyloid fiber. Here alpha-synuclein was applied as a client. Firstly, it was determined whether TRIM11 could also prevent alpha-Synuclein fiber formation. As shown in FIG. 38A, TRIM11, as well as Hsp70 and Hsp104, efficiently inhibit the formation of alpha-Synuclein amyloid fiber (FIG. 38A). Also, the inhibition was a dose-dependent manner (FIG. 38B). Indeed, electron microscopy (EM) revealed that alpha-Synuclein fibers were exhibited by control GST protein, whereas no fiber observed by TRIM11 (FIG. 38C). Next, alpha-Synuclein fibers were used to study the disaggregation of TRIM11. As shown in FIG. 38D, with TRIM11 or mutant Hsp104 treatment, solubilization of alpha-Synuclein fibers increased in a dose-dependent manner. Accordingly, fiber disassembly was obvious with TRIM11 or Hsp104 treatment by ThT fluorescence (FIG. 38E).

There are over 70 TRIM family members with common N-terminus and different C-terminus. Therefore, next whether other TRIM proteins also had similar function like TRIM11 was investigated. Therefore, TRIM21 was selected because it shares the same domains with TRIM11. In vitro pull down assay revealed that TRIM21 also preferentially bound to denatured luciferase (FIG. 39A). Similarly, TRIM21 could moderately solubilized heated luciferase aggregates (FIG. 39B) and recovered heat inactivation of luciferase (FIG. 39C). TRIM21 also was able to protect luciferase against heat inactivation (FIG. 39D). PML could degrade Atxn1 82Q aggregates through proteasome. So to investigate whether disaggregation and degradation of Atxn1 aggregates were coupled by PML, PML from was purified 293T cells (FIG. 40A). As shown in FIG. 40B, PML could recover heat inactivation of GFP fluorescence in a dose-dependent manner. However, the recover ability was weaker than TRIM11 (FIG. 40C). Several fragments of PML were also purified from 293T cells (FIG. 40D). Interestingly, one fragment (361-633) of PML might be necessary for the reactivation of heated GFP aggregates (FIG. 40E).

To better understand the role of TRIM11 in controlling formation of alpha-Synuclein aggregates, mouse primary hippocampal neurons were used as a model. Alpha-Synuclein fibrils (PEF) were generated with GST or TRIM11 in vitro (GST-PEF and TRIM11-PEF). Two weeks after PEF addition, about 30% neuron death induced by PEF aggregates (FIG. 41A). However, TRIM11-PEF has a lower toxic to neurons (FIG. 41A). Indeed, immunofluorescence revealed that there were significant alpha-Synuclein aggregates that recapitulated features of the Lewy bodies in Parkinson's disease brains, whereas there were no big aggregates following addition of TRIM11-PEF (FIG. 41B), which further showed that TRIM11 had a prevention function in formation of alpha-Synuclein fibers. Notably, in two kinds of neurons (cortical and hippocampal neurons), TRIM11 could be up-regulated in response to heat shock (FIG. 42A and FIG. 42B). Moreover, the mRNA level of TRIM11 was also increased in hippocampal neurons (FIG. 42C). It was of interest that TRIM11 was likely involved in controlling neurodegenerative disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing protein aggregates associated with a disease or disorder in a subject in need thereof, the method comprising administering to the subject a composition comprising a nucleic acid sequence encoding human TRIM11, wherein the protein aggregates are selected from the group consisting of: ataxin-1 aggregates, huntingtin aggregates, alpha-synuclein aggregates, mutant p53 aggregates and beta-amyloid aggregates.

2. The method of claim 1, wherein the disease or disorder comprises a neurodegenerative disease or disorder.

3. The method of claim 1, wherein the method comprises administering the composition to at least one neural cell of the subject.

4. The method of claim 1, wherein the composition comprises an adeno-associated viral (AAV) vector comprising a nucleic acid sequence encoding a peptide comprising human TRIM11.

5. The method of claim 4, wherein the AAV vector comprises an AAV9 vector.

6. A method comprising administering to a subject having a disease or disorder a composition comprising a nucleic acid sequence encoding human TRIM11, wherein:

a) the subject has Alzheimer's disease and wherein the method reduces the level of beta-amyloid aggregates in the subject;
b) the subject has Parkinson's disease and wherein the method reduces the level of alpha-synuclein aggregates in the subject;
c) the subject has spinocerebellar ataxia and wherein the method reduces the level of ataxin-1 aggregates in the subject;
d) the subject has Huntington's disease and wherein the method reduces the level of huntingtin aggregates in the subject; or
e) the subject has cancer associated with mutant p53 and wherein the method reduces the level of mutant p53 aggregates in the subject.

7. The method of claim 6, wherein the method comprises administering the composition to at least one neural cell of the subject.

8. The method of claim 6, wherein the composition comprises an adeno-associated viral (AAV) vector comprising a nucleic acid sequence encoding a peptide comprising human TRIM11.

9. The method of claim 8, wherein the AAV vector comprises an AAV9 vector.

* * * * *

SEQUENCE LISTING

```
<160> NUMBER OF SEQ ID NOS: 169

<210> SEQ ID NO 1
<211> LENGTH: 2208
<212> TYPE: DNA
<213> ORGANISM: Homo sapiens

<400> SEQUENCE: 1
atgggtgaaa gcccagcctc cgtggttctt aatgcctcag gaggactatt ttcactaaag      60
atggaaacac tggagtctga attgacctgt ccaatctgcc tagagttgtt tgaagacccc     120
cttctgctcc cttgtgctca cagcctctgc ttcagctgtg cccatcgcat tttggtatca     180
agctgcagct ctggtgaatc cattgaaccc attactgctt tccagtgtcc tacctgcagg     240
tatgttatct cgctgaacca ccggggcctg gatggcctca agaggaatgt gactctgcag     300
aacattattg atcgcttcca gaaggcttca gtcagtgggc ccaattcccc tagtgagagc     360
cgccgggaaa ggacttacag gcccaccact gccatgtcta gcgagcgaat tgcttgccaa     420
```

```
ttctgtgagc aggacccgcc aagggatgca gtaaaaacat gcatcacctg tgaggtctcc    480
tactgtgacc gttgcctgcg ggccacgcac cccaacaaga aacctttcac cagccaccgc    540
ctggtggaac cagtgccaga cacacatctt cgagggatca cctgcctgga ccatgagaat    600
gagaaagtga acatgtactg tgtatctgat gaccaattga tctgtgcctt atgcaaactg    660
gtgggtcgtc accgagacca tcaggtcgca tccctgaatg atcgatttga gaaactcaag    720
caaactctgg agatgaacct caccaacctg gttaagcgca cagcgaact agaaaatcaa      780
atggccaaac taatacagat ctgccagcag gttgaggtga atactgctat gcatgaggca    840
aaacttatgg aagaatgtga cgagttggta gagatcatcc agcagaggaa gcaaatgatc    900
gctgtcaaaa tcaaagagac aaaggttatg aaactgagaa agttggcaca gcaggttgct    960
aattgccgcc agtgtcttga acggtcaaca gtcctcatca accaagctga gcatatcctg    1020
aaagaaaatg accaggcacg gtttctacag tctgcaaaaa atattgctga gagggtcgct    1080
atggcaactg catcttctca agttctgatt ccagacatca ttttaatga tgcctttgaa      1140
aactttgctt tagatttttc cagagaaaag aaactgctag aggggttaga ttatttaaca    1200
gccccaaacc caccatctat ccgagaagaa ctctgtactg cctcccatga caccattaca    1260
gtccactgga tctcggatga tgagttcagc atcagctcct atgagcttca gtacaccata    1320
ttcactggcc aggctaactt catcagtaag tcatggtgta gttggggcct gtggccagag    1380
ataaggaaat gtaaggaagc agtaagctgc tcaagattgg ccggggcgcc acgaggcctg    1440
tataattcag tagacagctg gatgattgtt cccaacatta acagaaacca ttacacagtg    1500
catggactcc agagcgggac tcgctacatc ttcatcgtta aagccataaa ccaagccggc    1560
agccggaaca gtgaacctac ccgactaaaa acaaacagcc aacccttta attggatccc      1620
aaaatgactc acaagaagtt gaagatctcc aatgatggat tgcagatgga aaggatgaa      1680
agctctctaa agaagagcca cccccagag aggtttagtg gcacagggtg ctatggggca       1740
gcaggaaata tattcattga cagtggctgc cactattggg aggtggtcat gggttcctca    1800
acatggtatg caattggcat tgcctacaaa tcagctccaa agaatgaatg gattggcaag    1860
aatgcctcct catgggtctt ctctcgctgc aatagtaact tcgtggtgag acacaacaac    1920
aaggaaatgc tggtggatgt gccccacac ctgaagcgtc tgggtgtcct cctggattat      1980
gacaacaata tgctgtcttt ctatgaccca gctaactctc tccatcttca tactttttgat    2040
gtgaccttca ttcttccagt ttgtccaaca tttacaatct ggaacaaatc cctaatgatc    2100
ctgtctggct tgcctgcccc agattttatt gattaccctg agcggcagga atgcaactgc    2160
aggcctcaag aatccccta tgtttctggg atgaaaacct gtcattaa                  2208
```

<210> SEQ ID NO 2
<211> LENGTH: 735
<212> TYPE: PRT
<213> ORGANISM: Homo sapiens

<400> SEQUENCE: 2

```
Met Gly Glu Ser Pro Ala Ser Val Val Leu Asn Ala Ser Gly Gly Leu
1               5                   10                  15

Phe Ser Leu Lys Met Glu Thr Leu Glu Ser Glu Leu Thr Cys Pro Ile
            20                  25                  30

Cys Leu Glu Leu Phe Glu Asp Pro Leu Leu Leu Pro Cys Ala His Ser
        35                  40                  45

Leu Cys Phe Ser Cys Ala His Arg Ile Leu Val Ser Ser Cys Ser Ser
    50                  55                  60
```

```
Gly Glu Ser Ile Glu Pro Ile Thr Ala Phe Gln Cys Pro Thr Cys Arg
 65                  70                  75                  80

Tyr Val Ile Ser Leu Asn His Arg Gly Leu Asp Gly Leu Lys Arg Asn
                 85                  90                  95

Val Thr Leu Gln Asn Ile Ile Asp Arg Phe Gln Lys Ala Ser Val Ser
                100                 105                 110

Gly Pro Asn Ser Pro Ser Glu Ser Arg Arg Glu Arg Thr Tyr Arg Pro
                115                 120                 125

Thr Thr Ala Met Ser Ser Glu Arg Ile Ala Cys Gln Phe Cys Glu Gln
130                 135                 140

Asp Pro Pro Arg Asp Ala Val Lys Thr Cys Ile Thr Cys Glu Val Ser
145                 150                 155                 160

Tyr Cys Asp Arg Cys Leu Arg Ala Thr His Pro Asn Lys Lys Pro Phe
                165                 170                 175

Thr Ser His Arg Leu Val Glu Pro Val Pro Asp Thr His Leu Arg Gly
                180                 185                 190

Ile Thr Cys Leu Asp His Glu Asn Glu Lys Val Asn Met Tyr Cys Val
                195                 200                 205

Ser Asp Asp Gln Leu Ile Cys Ala Leu Cys Lys Leu Val Gly Arg His
210                 215                 220

Arg Asp His Gln Val Ala Ser Leu Asn Asp Arg Phe Glu Lys Leu Lys
225                 230                 235                 240

Gln Thr Leu Glu Met Asn Leu Thr Asn Leu Val Lys Arg Asn Ser Glu
                245                 250                 255

Leu Glu Asn Gln Met Ala Lys Leu Ile Gln Ile Cys Gln Gln Val Glu
                260                 265                 270

Val Asn Thr Ala Met His Glu Ala Lys Leu Met Glu Glu Cys Asp Glu
                275                 280                 285

Leu Val Glu Ile Ile Gln Gln Arg Lys Gln Met Ile Ala Val Lys Ile
                290                 295                 300

Lys Glu Thr Lys Val Met Lys Leu Arg Lys Leu Ala Gln Gln Val Ala
305                 310                 315                 320

Asn Cys Arg Gln Cys Leu Glu Arg Ser Thr Val Leu Ile Asn Gln Ala
                325                 330                 335

Glu His Ile Leu Lys Glu Asn Asp Gln Ala Arg Phe Leu Gln Ser Ala
                340                 345                 350

Lys Asn Ile Ala Glu Arg Val Ala Met Ala Thr Ala Ser Ser Gln Val
                355                 360                 365

Leu Ile Pro Asp Ile Asn Phe Asn Asp Ala Phe Glu Asn Phe Ala Leu
                370                 375                 380

Asp Phe Ser Arg Glu Lys Lys Leu Leu Glu Gly Leu Asp Tyr Leu Thr
385                 390                 395                 400

Ala Pro Asn Pro Pro Ser Ile Arg Glu Glu Leu Cys Thr Ala Ser His
                405                 410                 415

Asp Thr Ile Thr Val His Trp Ile Ser Asp Asp Glu Phe Ser Ile Ser
                420                 425                 430

Ser Tyr Glu Leu Gln Tyr Thr Ile Phe Thr Gly Gln Ala Asn Phe Ile
                435                 440                 445

Ser Lys Ser Trp Cys Ser Trp Gly Leu Trp Pro Glu Ile Arg Lys Cys
                450                 455                 460

Lys Glu Ala Val Ser Cys Ser Arg Leu Ala Gly Ala Pro Arg Gly Leu
465                 470                 475                 480
```

```
Tyr Asn Ser Val Asp Ser Trp Met Ile Val Pro Asn Ile Lys Gln Asn
                485                 490                 495

His Tyr Thr Val His Gly Leu Gln Ser Gly Thr Arg Tyr Ile Phe Ile
            500                 505                 510

Val Lys Ala Ile Asn Gln Ala Gly Ser Arg Asn Ser Glu Pro Thr Arg
            515                 520                 525

Leu Lys Thr Asn Ser Gln Pro Phe Lys Leu Asp Pro Lys Met Thr His
            530                 535                 540

Lys Lys Leu Lys Ile Ser Asn Asp Gly Leu Gln Met Glu Lys Asp Glu
545                 550                 555                 560

Ser Ser Leu Lys Lys Ser His Thr Pro Glu Arg Phe Ser Gly Thr Gly
                565                 570                 575

Cys Tyr Gly Ala Ala Gly Asn Ile Phe Ile Asp Ser Gly Cys His Tyr
            580                 585                 590

Trp Glu Val Val Met Gly Ser Ser Thr Trp Tyr Ala Ile Gly Ile Ala
            595                 600                 605

Tyr Lys Ser Ala Pro Lys Asn Glu Trp Ile Gly Lys Asn Ala Ser Ser
            610                 615                 620

Trp Val Phe Ser Arg Cys Asn Ser Asn Phe Val Val Arg His Asn Asn
625                 630                 635                 640

Lys Glu Met Leu Val Asp Val Pro Pro His Leu Lys Arg Leu Gly Val
                645                 650                 655

Leu Leu Asp Tyr Asp Asn Asn Met Leu Ser Phe Tyr Asp Pro Ala Asn
            660                 665                 670

Ser Leu His Leu His Thr Phe Asp Val Thr Phe Ile Leu Pro Val Cys
            675                 680                 685

Pro Thr Phe Thr Ile Trp Asn Lys Ser Leu Met Ile Leu Ser Gly Leu
            690                 695                 700

Pro Ala Pro Asp Phe Ile Asp Tyr Pro Glu Arg Gln Glu Cys Asn Cys
705                 710                 715                 720

Arg Pro Gln Glu Ser Pro Tyr Val Ser Gly Met Lys Thr Cys His
                725                 730                 735

<210> SEQ ID NO 3
<211> LENGTH: 2316
<212> TYPE: DNA
<213> ORGANISM: Homo sapiens

<400> SEQUENCE: 3
atgcacagga gtggccgtta tggaacgcag cagcagcgtg cagggtcaaa gacagccggc      60
cccccatgtc agtggtctag gatggccagt gaaggcacca acatcccaag tcctgtggtg     120
cgccagattg acaagcagtt tctgatttgc agtatatgcc tggaacggta caagaatccc     180
aaggttctcc cctgtctgca cactttctgc gagaggtgcc tgcagaacta cattcctgcc     240
cacagtttaa ccctctcctg cccagtgtgc cgccagacct ccatcctgcc cgagaaaggg     300
gtggccgcgc tccagaacaa tttcttcatc acaaacctga tggacgtgct gcagcgaact     360
ccaggcagca acgctgagga gtcttccatc ctggagacag tcactgctgt ggctgcggga     420
aagcctctct cttgcccaaa ccacgatggg aatgtgatgg aatttttactg ccagtcctgt     480 gagactgcca tgtgtcggga gtgcacggag ggggagcacg cagagcaccc cacagttcca     540
ctcaaggatg tggtggaaca gcacaaggcc tcgctccagg tccagctgga tgctgtcaac     600
aaaaggctcc cagaaataga ttctgctctt cagttcatct ctgaaatcat tcatcagtta     660
accaaccaaa aggccagcat cgtggatgac attcattcca cctttgatga gctccagaag     720
```

```
actttaaatg tgcgcaagag tgtgctgctt atggaattgg aggtcaacta tggcctcaaa      780
cacaaagtcc tccagtcgca gctggatact ctgctccagg ggcaggagag cattaagagc      840
tgcagcaact tcacagcgca ggccctcaac catggcacgg agaccgaggt cctactggtg      900
aagaagcaga tgagcgagaa gctgaacgag ctggccgacc aggacttccc cttgcacccg      960
cgggagaacg accagctgga tttcatcgtg aaaccgaggg gctgaagaa gtccatccac     1020 aacctcggga cgatcttaac caccaacgcc gttgcctcag agacagtggc cacgggcgag     1080
gggctgcggc agaccatcat cgggcagccc atgtccgtca ccatcaccac caaggacaaa     1140
gacggtgagc tgtgcaaaac cggcaacgcc tacctcaccg ccgaactgag cacccccgac     1200
gggagcgtgg cagacgggga gatcctggac aacaagaacg gcacctatga gttttgtac     1260 actgtccaga aggaagggga ctttaccctg tctctgagac tctatgacca gcacatccga     1320
ggcagcccgt ttaagctgaa agtgatccga tccgctgatg tgtctcccac cacagaaggc     1380
gtgaagaggc gcgttaagtc cccggggagc ggccacgtca agcagaaagc tgtgaaaaga     1440
cccgcaagca tgtacagcac tggaaaacga aaagagaatc ccatcgaaga cgatttgatc     1500
tttcgagtgg gtaccaaagg aagaaataaa ggagagttta caaatcttca gggggtagct     1560
gcatctacaa atggaaagat attaattgca gacagtaaca accaatgtgt gcagatattt     1620
tccaatgatg gccagttcaa aagtcgtttt ggcatacggg gacgctctcc ggggcagctg     1680
cagcggccca caggagtggc tgtacatccc agtggggaca taatcattgc cgattatgat     1740
aataaatggg tcagcatttt ctcctccgat gggaaattta agacaaaaat tggatcagga     1800
aagctgatgg gacccaaagg agtttctgtg gaccgcaatg ggcacattat tgttgtggac     1860
aacaaggcgt gctgcgtgtt tatcttccag ccaaacggga aaatagtcac caggtttggt     1920
agccgaggaa atggggacag gcagtttgca ggtccccatt ttgcagctgt aaatagcaat     1980
aatgagatta ttattacaga tttccataat cattctgtca aggtgtttaa tcaggaagga     2040
gaattcatgt tgaagtttgg ctcaaatgga gaaggaaatg ggcagtttaa tgctccaaca     2100
ggtgtagcag tggattcaaa tggaaacatc attgtggccg actggggaaa cagcaggatc     2160 caggttttg atgggagtgg atcattttg tcctacatta acacatctgc tgacccactc     2220
tatggccccc aaggcctggc cctaacttca gatggtcatg ttgtggttgc agactctgga     2280
aatcactgtt tcaaagtcta tcgatactta cagtaa                                2316
```

<210> SEQ ID NO 4
<211> LENGTH: 771
<212> TYPE: PRT
<213> ORGANISM: Homo sapiens

<400> SEQUENCE: 4

Met His Arg Ser Gly Arg Tyr Gly Thr Gln Gln Arg Ala Gly Ser
1               5                   10                  15

Lys Thr Ala Gly Pro Pro Cys Gln Trp Ser Arg Met Ala Ser Glu Gly
            20                  25                  30

Thr Asn Ile Pro Ser Pro Val Val Arg Gln Ile Asp Lys Gln Phe Leu
        35                  40                  45

Ile Cys Ser Ile Cys Leu Glu Arg Tyr Lys Asn Pro Lys Val Leu Pro
    50                  55                  60

Cys Leu His Thr Phe Cys Glu Arg Cys Leu Gln Asn Tyr Ile Pro Ala
65                  70                  75                  80

His Ser Leu Thr Leu Ser Cys Pro Val Cys Arg Gln Thr Ser Ile Leu

```
                 85                  90                  95
Pro Glu Lys Gly Val Ala Leu Gln Asn Asn Phe Phe Ile Thr Asn
            100                 105                 110
Leu Met Asp Val Leu Gln Arg Thr Pro Gly Ser Asn Ala Glu Glu Ser
            115                 120                 125
Ser Ile Leu Glu Thr Val Thr Ala Val Ala Ala Gly Lys Pro Leu Ser
130             135                 140
Cys Pro Asn His Asp Gly Asn Val Met Glu Phe Tyr Cys Gln Ser Cys
145                 150                 155                 160
Glu Thr Ala Met Cys Arg Glu Cys Thr Glu Gly Glu His Ala Glu His
                165                 170                 175
Pro Thr Val Pro Leu Lys Asp Val Val Glu Gln His Lys Ala Ser Leu
                180                 185                 190
Gln Val Gln Leu Asp Ala Val Asn Lys Arg Leu Pro Glu Ile Asp Ser
                195                 200                 205
Ala Leu Gln Phe Ile Ser Glu Ile Ile His Gln Leu Thr Asn Gln Lys
210                 215                 220
Ala Ser Ile Val Asp Asp Ile His Ser Thr Phe Asp Glu Leu Gln Lys
225                 230                 235                 240
Thr Leu Asn Val Arg Lys Ser Val Leu Leu Met Glu Leu Glu Val Asn
                245                 250                 255
Tyr Gly Leu Lys His Lys Val Leu Gln Ser Gln Leu Asp Thr Leu Leu
                260                 265                 270
Gln Gly Gln Glu Ser Ile Lys Ser Cys Ser Asn Phe Thr Ala Gln Ala
                275                 280                 285
Leu Asn His Gly Thr Glu Thr Glu Val Leu Leu Val Lys Lys Gln Met
            290                 295                 300
Ser Glu Lys Leu Asn Glu Leu Ala Asp Gln Asp Phe Pro Leu His Pro
305                 310                 315                 320
Arg Glu Asn Asp Gln Leu Asp Phe Ile Val Glu Thr Glu Gly Leu Lys
                325                 330                 335
Lys Ser Ile His Asn Leu Gly Thr Ile Leu Thr Thr Asn Ala Val Ala
            340                 345                 350
Ser Glu Thr Val Ala Thr Gly Glu Gly Leu Arg Gln Thr Ile Ile Gly
            355                 360                 365
Gln Pro Met Ser Val Thr Ile Thr Thr Lys Asp Lys Asp Gly Glu Leu
            370                 375                 380
Cys Lys Thr Gly Asn Ala Tyr Leu Thr Ala Glu Leu Ser Thr Pro Asp
385                 390                 395                 400
Gly Ser Val Ala Asp Gly Glu Ile Leu Asp Asn Lys Asn Gly Thr Tyr
                405                 410                 415
Glu Phe Leu Tyr Thr Val Gln Lys Glu Gly Asp Phe Thr Leu Ser Leu
                420                 425                 430
Arg Leu Tyr Asp Gln His Ile Arg Gly Ser Pro Phe Lys Leu Lys Val
                435                 440                 445
Ile Arg Ser Ala Asp Val Ser Pro Thr Thr Glu Gly Val Lys Arg Arg
            450                 455                 460
Val Lys Ser Pro Gly Ser Gly His Val Lys Gln Lys Ala Val Lys Arg
465                 470                 475                 480
Pro Ala Ser Met Tyr Ser Thr Gly Lys Arg Lys Glu Asn Pro Ile Glu
                485                 490                 495
Asp Asp Leu Ile Phe Arg Val Gly Thr Lys Gly Arg Asn Lys Gly Glu
            500                 505                 510
```

```
Phe Thr Asn Leu Gln Gly Val Ala Ala Ser Thr Asn Gly Lys Ile Leu
        515                 520                 525

Ile Ala Asp Ser Asn Asn Gln Cys Val Gln Ile Phe Ser Asn Asp Gly
    530                 535                 540

Gln Phe Lys Ser Arg Phe Gly Ile Arg Gly Arg Ser Pro Gly Gln Leu
545                 550                 555                 560

Gln Arg Pro Thr Gly Val Ala Val His Pro Ser Gly Asp Ile Ile Ile
                565                 570                 575

Ala Asp Tyr Asp Asn Lys Trp Val Ser Ile Phe Ser Ser Asp Gly Lys
            580                 585                 590

Phe Lys Thr Lys Ile Gly Ser Gly Lys Leu Met Gly Pro Lys Gly Val
        595                 600                 605

Ser Val Asp Arg Asn Gly His Ile Ile Val Val Asp Asn Lys Ala Cys
    610                 615                 620

Cys Val Phe Ile Phe Gln Pro Asn Gly Lys Ile Val Thr Arg Phe Gly
625                 630                 635                 640

Ser Arg Gly Asn Gly Asp Arg Gln Phe Ala Gly Pro His Phe Ala Ala
                645                 650                 655

Val Asn Ser Asn Asn Glu Ile Ile Ile Thr Asp Phe His Asn His Ser
            660                 665                 670

Val Lys Val Phe Asn Gln Glu Gly Glu Phe Met Leu Lys Phe Gly Ser
        675                 680                 685

Asn Gly Glu Gly Asn Gly Gln Phe Asn Ala Pro Thr Gly Val Ala Val
    690                 695                 700

Asp Ser Asn Gly Asn Ile Ile Val Ala Asp Trp Gly Asn Ser Arg Ile
705                 710                 715                 720

Gln Val Phe Asp Gly Ser Gly Ser Phe Leu Ser Tyr Ile Asn Thr Ser
                725                 730                 735

Ala Asp Pro Leu Tyr Gly Pro Gln Gly Leu Ala Leu Thr Ser Asp Gly
            740                 745                 750

His Val Val Val Ala Asp Ser Gly Asn His Cys Phe Lys Val Tyr Arg
        755                 760                 765

Tyr Leu Gln
    770

<210> SEQ ID NO 5
<211> LENGTH: 2235
<212> TYPE: DNA
<213> ORGANISM: Homo sapiens

<400> SEQUENCE: 5
atggcaaaga gggaggacag ccctggccca gaggtccagc caatggacaa gcagttcctg      60
gtatgcagca tctgcctgga tcggtaccag tgccccaagg ttcttccttg cctgcacacc     120
ttctgtgaga gatgtctcca aaactatatc cctgcccaga gcctgacgct atcctgtcca     180
gtatgccggc agacgtccat cctcccagag cagggcgtct cggcactgca gaacaacttc     240
ttcatcagca gcctcatgga ggcaatgcag caggcacctg atggggccca cgacccggag     300
gacccccacc cctcagtgt agtggctggc cgccctctct cctgcccca ccatgaaggc      360 aagacgatgg agttttactg tgaggcctgt gagacggcca tgtgtggtga gtgccgcgcc     420
ggggagcatc gtgagcatgg cacagtgctg ctgagggatg tggtggagca gcacaaggcg     480
gccctgcagc gccagctcga ggctgtgcgt ggccgattgc acagctgtc cgcagcaatt     540 gccttagtcg ggggcatcag ccagcagctg caggagcgca aggcagaggc cctggcccag     600
```

```
atcagtgcag cgttcgagga cctggagcaa gcactgcagc agcgcaagca ggctctggtc    660
agcgacctgg agaccatttg tgggccaaa cagaaggtgt tgcaaagcca gctggacaca    720
ctgcgccagg gtcaggaaca catcggcagt agctgcagct ttgcagagca ggcactgcgc    780
ctgggctcgg ccccggaggt gttgctggtg cgcaagcaca tgcgagagcg gctggctgca    840
ttggcggcac aggccttccc ggagcggcca catgagaatg cacagctgga actggtcctt    900
gaggtggacg tctgcggcg atcggtgctc aatctgggcg cactgctcac cacgagcgcc    960
actgcacacg aaacggtggc cacgggagag ggcctgcgcc aggcgctagt gggccagcct   1020
gcctcgctca ctgtcactac caaagacaag gacgggcggt ggtgcgcac aggcagcgct   1080
gagctgcgtg cagagatcac cggcccggac ggcacgcgcc ttccggtgcc agtggtggac   1140
cacaagaatg gcacatatga gctagtgtac acagcgcgca cggaaggcga gctgctcctc   1200
tcggtgctgc tctacggaca gccagtgcgc ggcagcccct tccgcgtgcg tgccctgcgt   1260
ccggggggacc tgccaccttc cccggacgat gtgaagcgcc gtgtcaagtc ccctggcggc   1320
cccggcagcc atgtgcgcca gaaggcagtg cgtaggccca gctccatgta cagcacaggc   1380
ggcaaacgaa aggacaaccc aattgaggat gagctcgtct ccgtgttgg cagtcgtgga   1440
agggagaaag gtgaattcac caatttacaa ggtgtgtccg cagccagcag cggccgcatc   1500
gtggtagcag acagcaacaa ccagtgtatt caggttttct ccaatgaggg ccagttcaag   1560
ttccgttttg gggtccgagg acgctcacct gggcagctgc agcgccccac aggtgtggca   1620
gtggacacca atggagacat aattgtggca gactatgaca ccgttgggt cagcatcttc   1680
tcccctgagg gcaagttcaa gaccaagatt ggagctggcc gcctcatggg ccccaaggga   1740
gtggccgtag accggaatgg acatatcatt gtggtcgaca caagtcttg ctgcgtcttt   1800
accttccagc ccaatggcaa actggttggc cgttttgggg gccgtgggc cactgaccgc   1860
cactttgcag ggccccattt tgtggctgtg aacaacaaga atgaaattgt agtaacggac   1920
ttccataacc attcagtgaa ggtgtacagt gccgatgag agttcctctt caagtttggc   1980
tcccatggcg agggcaatgg gcagttcaat gcccccacag gagtagctgt ggactccaat   2040
ggaaacatca ttgtggctga ctgggcaac agccgcatcc aggtattcga cagctctggc   2100
tccttcctgt cctatatcaa cacatctgca gaaccactgt atggtccaca gggcctggca   2160
ctgacctcgg atggccatgt ggtggtggct gatgctggca ccactgcttt aaagcctat   2220
cgctacctcc agtag                                                    2235
```

<210> SEQ ID NO 6
<211> LENGTH: 744
<212> TYPE: PRT
<213> ORGANISM: Homo sapiens

<400> SEQUENCE: 6

Met Ala Lys Arg Glu Asp Ser Pro Gly Pro Glu Val Gln Pro Met Asp
1               5                   10                  15

Lys Gln Phe Leu Val Cys Ser Ile Cys Leu Asp Arg Tyr Gln Cys Pro
            20                  25                  30

Lys Val Leu Pro Cys Leu His Thr Phe Cys Glu Arg Cys Leu Gln Asn
        35                  40                  45

Tyr Ile Pro Ala Gln Ser Leu Thr Leu Ser Cys Pro Val Cys Arg Gln
    50                  55                  60

Thr Ser Ile Leu Pro Glu Gln Gly Val Ser Ala Leu Gln Asn Asn Phe
65                  70                  75                  80

-continued

```
Phe Ile Ser Ser Leu Met Glu Ala Met Gln Ala Pro Asp Gly Ala
                85                  90                  95

His Asp Pro Glu Asp Pro His Pro Leu Ser Val Val Ala Gly Arg Pro
            100                 105                 110

Leu Ser Cys Pro Asn His Glu Gly Lys Thr Met Glu Phe Tyr Cys Glu
        115                 120                 125

Ala Cys Glu Thr Ala Met Cys Gly Glu Cys Arg Ala Gly Glu His Arg
    130                 135                 140

Glu His Gly Thr Val Leu Leu Arg Asp Val Val Glu Gln His Lys Ala
145                 150                 155                 160

Ala Leu Gln Arg Gln Leu Glu Ala Val Arg Gly Arg Leu Pro Gln Leu
                165                 170                 175

Ser Ala Ala Ile Ala Leu Val Gly Gly Ile Ser Gln Gln Leu Gln Glu
            180                 185                 190

Arg Lys Ala Glu Ala Leu Ala Gln Ile Ser Ala Ala Phe Glu Asp Leu
        195                 200                 205

Glu Gln Ala Leu Gln Gln Arg Lys Gln Ala Leu Val Ser Asp Leu Glu
    210                 215                 220

Thr Ile Cys Gly Ala Lys Gln Lys Val Leu Gln Ser Gln Leu Asp Thr
225                 230                 235                 240

Leu Arg Gln Gly Gln Glu His Ile Gly Ser Ser Cys Ser Phe Ala Glu
                245                 250                 255

Gln Ala Leu Arg Leu Gly Ser Ala Pro Glu Val Leu Leu Val Arg Lys
            260                 265                 270

His Met Arg Glu Arg Leu Ala Ala Leu Ala Ala Gln Ala Phe Pro Glu
        275                 280                 285

Arg Pro His Glu Asn Ala Gln Leu Glu Leu Val Leu Glu Val Asp Gly
    290                 295                 300

Leu Arg Arg Ser Val Leu Asn Leu Gly Ala Leu Leu Thr Thr Ser Ala
305                 310                 315                 320

Thr Ala His Glu Thr Val Ala Thr Gly Glu Gly Leu Arg Gln Ala Leu
                325                 330                 335

Val Gly Gln Pro Ala Ser Leu Thr Val Thr Thr Lys Asp Lys Asp Gly
            340                 345                 350

Arg Leu Val Arg Thr Gly Ser Ala Glu Leu Arg Ala Glu Ile Thr Gly
        355                 360                 365

Pro Asp Gly Thr Arg Leu Pro Val Pro Val Val Asp His Lys Asn Gly
    370                 375                 380

Thr Tyr Glu Leu Val Tyr Thr Ala Arg Thr Glu Gly Glu Leu Leu Leu
385                 390                 395                 400

Ser Val Leu Leu Tyr Gly Gln Pro Val Arg Gly Ser Pro Phe Arg Val
                405                 410                 415

Arg Ala Leu Arg Pro Gly Asp Leu Pro Ser Pro Asp Asp Val Lys
            420                 425                 430

Arg Arg Val Lys Ser Pro Gly Pro Gly Ser His Val Arg Gln Lys
        435                 440                 445

Ala Val Arg Arg Pro Ser Ser Met Tyr Ser Thr Gly Gly Lys Arg Lys
    450                 455                 460

Asp Asn Pro Ile Glu Asp Glu Leu Val Phe Arg Val Gly Ser Arg Gly
465                 470                 475                 480

Arg Glu Lys Gly Glu Phe Thr Asn Leu Gln Gly Val Ser Ala Ala Ser
                485                 490                 495
```

| | | | | | | | | | | | |
|---|---|---|---|---|---|---|---|---|---|---|---|
| Ser | Gly | Arg | Ile | Val | Val | Ala | Asp | Ser | Asn | Asn | Gln | Cys | Ile | Gln | Val |
| | | | 500 | | | | | 505 | | | | 510 | | | |

Phe Ser Asn Glu Gly Gln Phe Lys Phe Arg Phe Gly Val Arg Gly Arg
    515                  520                  525

Ser Pro Gly Gln Leu Gln Arg Pro Thr Gly Val Ala Val Asp Thr Asn
    530                  535                  540

Gly Asp Ile Ile Val Ala Asp Tyr Asp Asn Arg Trp Val Ser Ile Phe
545                550                  555                  560

Ser Pro Glu Gly Lys Phe Lys Thr Lys Ile Gly Ala Gly Arg Leu Met
                565                  570                  575

Gly Pro Lys Gly Val Ala Val Asp Arg Asn Gly His Ile Ile Val Val
    580                  585                  590

Asp Asn Lys Ser Cys Cys Val Phe Thr Phe Gln Pro Asn Gly Lys Leu
    595                  600                  605

Val Gly Arg Phe Gly Gly Arg Gly Ala Thr Asp Arg His Phe Ala Gly
    610                  615                  620

Pro His Phe Val Ala Val Asn Asn Lys Asn Glu Ile Val Val Thr Asp
625                630                  635                  640

Phe His Asn His Ser Val Lys Val Tyr Ser Ala Asp Gly Glu Phe Leu
                645                  650                  655

Phe Lys Phe Gly Ser His Gly Glu Gly Asn Gly Gln Phe Asn Ala Pro
    660                  665                  670

Thr Gly Val Ala Val Asp Ser Asn Gly Asn Ile Ile Val Ala Asp Trp
                675                  680                  685

Gly Asn Ser Arg Ile Gln Val Phe Asp Ser Ser Gly Ser Phe Leu Ser
    690                  695                  700

Tyr Ile Asn Thr Ser Ala Glu Pro Leu Tyr Gly Pro Gln Gly Leu Ala
705                710                  715                  720

Leu Thr Ser Asp Gly His Val Val Ala Asp Ala Gly Asn His Cys
                725                  730                  735

Phe Lys Ala Tyr Arg Tyr Leu Gln
    740

<210> SEQ ID NO 7
<211> LENGTH: 1503
<212> TYPE: DNA
<213> ORGANISM: Homo sapiens

<400> SEQUENCE: 7

```
atggaagctg aggacatcca ggaggagttg acctgcccca tctgcctgga ctatttccag      60
gacccggtgt ccatcgagtg cggccacaac ttctgccgcg gctgcctgca ccgcaactgg     120
gcgccgggcg gcggcccgtt ccctgcccc gaatgtcggc acccatcggc gcccgccgcg      180
ctgcgaccca actgggccct ggccaggctg actgagaaga cgcagcgccg gcgcctgggc     240
cccgtgcccc cgggcctgtg cggccgccac tgggagccgc tcggctcttc tgcgaggac     300 gaccagcggc cagtgtgcct ggtgtgcagg gagtcccagg agcaccagac tcacgccatg     360
gcacccatcg acgaggcctt cgagagctac cggacaggta actttgacat ccacgtggat     420
gaatggaaga agagactaat taggctgctc ttgtaccatt ttaagcagga ggagaaactt     480
cttaagtctc agcgtaatct cgtggccaag atgaagaaag tcatgcattt acaggatgta     540
gaagtgaaga acgccacaca gtggaaggat aagataaaga gtcagcgaat gagaatcagc     600
acggagtttt caaagctgca caacttcctg gttgaagaag aggacctgtt tcttcagaga     660
ttgaacaaag aagaagaaga gacgaagaag aagctgaatg agaacacgtt aaaactcaat     720
```

```
caaactatcg cttcattgaa gaagctcatc ttagaggtgg gggagaagag ccaggctccc    780
accctggagc tgcttcagaa tccaaaagaa gtgttgacca ggagtgagat ccaggatgtg    840
aactattctc ttgaagctgt aaaggtgaag acagtgtgcc agataccatt gatgaaggaa    900
atgctaaagc gattccaagt ggctgtaaac ctagctgaag cacacagctca tcccaaactc    960
gtcttctccc aggaagggag atacgtgaaa aatacagcat cagccagttc ttggccagtg   1020
ttttcttcag catggaacta ctttgctgga tggaggaatc ctcagaagac tgcttttgta   1080
gagagatttc agcacttacc ctgtgttctg ggaaaaaacg ttttcacctc agggaaacat   1140
tactgggaag ttgagagtag agatagtctg gaggttgctg ttggggtgtg tcggaggac    1200
gtcatgggaa ttactgatcg ttcaaaaatg tccccagatg tgggcatctg gcgatttat    1260
tggagtgctg ctggctattg gcccttgata ggcttccctg gaactcccac ccagcaagag   1320
ccagctctcc accgagtggg ggtttacctg gatcgtggga ctgggaatgt ctccttctac   1380
agcgctgtgg acggagtgca cctgcacacc tttctcttgtt cttctgtctc acgcctccgg   1440
ccattttttt ggttgagtcc attagcatct ttagtcattc caccagtgac tgataggaaa   1500
tga                                                                 1503
```

<210> SEQ ID NO 8
<211> LENGTH: 500
<212> TYPE: PRT
<213> ORGANISM: Homo sapiens

<400> SEQUENCE: 8

```
Met Glu Ala Glu Asp Ile Gln Glu Glu Leu Thr Cys Pro Ile Cys Leu
 1               5                  10                  15

Asp Tyr Phe Gln Asp Pro Val Ser Ile Glu Cys Gly His Asn Phe Cys
            20                  25                  30

Arg Gly Cys Leu His Arg Asn Trp Ala Pro Gly Gly Pro Phe Pro
        35                  40                  45

Cys Pro Glu Cys Arg His Pro Ser Ala Pro Ala Ala Leu Arg Pro Asn
    50                  55                  60

Trp Ala Leu Ala Arg Leu Thr Glu Lys Thr Gln Arg Arg Leu Gly
 65                  70                  75                  80

Pro Val Pro Pro Gly Leu Cys Gly Arg His Trp Glu Pro Leu Arg Leu
                85                  90                  95

Phe Cys Glu Asp Asp Gln Arg Pro Val Cys Leu Val Cys Arg Glu Ser
            100                 105                 110

Gln Glu His Gln Thr His Ala Met Ala Pro Ile Asp Glu Ala Phe Glu
        115                 120                 125

Ser Tyr Arg Thr Gly Asn Phe Asp Ile His Val Asp Glu Trp Lys Arg
    130                 135                 140

Arg Leu Ile Arg Leu Leu Leu Tyr His Phe Lys Gln Glu Glu Lys Leu
145                 150                 155                 160

Leu Lys Ser Gln Arg Asn Leu Val Ala Lys Met Lys Lys Val Met His
                165                 170                 175

Leu Gln Asp Val Glu Val Lys Asn Ala Thr Gln Trp Lys Asp Lys Ile
            180                 185                 190

Lys Ser Gln Arg Met Arg Ile Ser Thr Glu Phe Ser Lys Leu His Asn
        195                 200                 205

Phe Leu Val Glu Glu Glu Asp Leu Phe Leu Gln Arg Leu Asn Lys Glu
    210                 215                 220
```

```
Glu Glu Glu Thr Lys Lys Lys Leu Asn Glu Asn Thr Leu Lys Leu Asn
225                 230                 235                 240
Gln Thr Ile Ala Ser Lys Lys Leu Ile Leu Glu Val Gly Glu Lys
            245                 250                 255
Ser Gln Ala Pro Thr Leu Glu Leu Leu Gln Asn Pro Lys Glu Val Leu
            260                 265                 270
Thr Arg Ser Glu Ile Gln Asp Val Asn Tyr Ser Leu Glu Ala Val Lys
            275                 280                 285
Val Lys Thr Val Cys Gln Ile Pro Leu Met Lys Glu Met Leu Lys Arg
290                 295                 300
Phe Gln Val Ala Val Asn Leu Ala Glu Asp Thr Ala His Pro Lys Leu
305                 310                 315                 320
Val Phe Ser Gln Glu Gly Arg Tyr Val Lys Asn Thr Ala Ser Ala Ser
            325                 330                 335
Ser Trp Pro Val Phe Ser Ser Ala Trp Asn Tyr Phe Ala Gly Trp Arg
            340                 345                 350
Asn Pro Gln Lys Thr Ala Phe Val Glu Arg Phe Gln His Leu Pro Cys
            355                 360                 365
Val Leu Gly Lys Asn Val Phe Thr Ser Gly Lys His Tyr Trp Glu Val
370                 375                 380
Glu Ser Arg Asp Ser Leu Glu Val Ala Val Gly Val Cys Arg Glu Asp
385                 390                 395                 400
Val Met Gly Ile Thr Asp Arg Ser Lys Met Ser Pro Asp Val Gly Ile
            405                 410                 415
Trp Ala Ile Tyr Trp Ser Ala Ala Gly Tyr Trp Pro Leu Ile Gly Phe
            420                 425                 430
Pro Gly Thr Pro Thr Gln Gln Glu Pro Ala Leu His Arg Val Gly Val
            435                 440                 445
Tyr Leu Asp Arg Gly Thr Gly Asn Val Ser Phe Tyr Ser Ala Val Asp
            450                 455                 460
Gly Val His Leu His Thr Phe Ser Cys Ser Ser Val Ser Arg Leu Arg
465                 470                 475                 480
Pro Phe Phe Trp Leu Ser Pro Leu Ala Ser Leu Val Ile Pro Pro Val
            485                 490                 495
Thr Asp Arg Lys
            500

<210> SEQ ID NO 9
<211> LENGTH: 1482
<212> TYPE: DNA
<213> ORGANISM: Homo sapiens

<400> SEQUENCE: 9
atggcttctg gaatcctggt taatgtaaag gaggaggtga cctgcccat ctgcctggaa      60 ctcctgacac aacccctgag cctggactgc ggccacagct tctgccaagc atgcctcact     120
gcaaaccaca agaagtccat gctagacaaa ggagagagta gctgccctgt gtgccggatc     180
agttaccagc ctgagaacat acggcctaat cggcatgtag ccaacatagt ggagaagctc     240
agggaggtca gttgagccc agaggggcag aaagttgatc attgtgcacg ccatggagag     300
aaacttctac tcttctgtca ggaggacggg aaggtcattt gctggctttg tgagcggtct     360
caggagcacc gtggtcacca cacgttcctc acagaggagg ttgcccggga gtaccaagtg     420
aagctccagg cagctctgga gatgctgagg cagaagcagc aggaagctga gagttagaa      480 gctgacatca gagaagagaa agcttcctgg aagactcaaa tacagtatga caaaaccaac     540
```

```
gtcttggcag attttgagca actgagagac atcctggact gggaggagag caatgagctg    600
caaaacctgg agaaggagga ggaagacatt ctgaaaagcc ttacgaactc tgaaactgag    660
atggtgcagc agacccagtc cctgagagag ctcatctcag atctggagca tcggctgcag    720
gggtcagtga tggagctgct tcagggtgtg atggcgtca taaaaaggac ggagaacgtg    780
accttgaaga agccagaaac ttttccaaaa atcaaagga gagtgtttcg agctcctgat    840
ctgaaaggaa tgctagaagt gtttagagag ctgacagatg tccgacgcta ctgggttgat    900
gtgacagtgg ctccaaacaa catttcatgt gctgtcattt ctgaagataa agacaagtg    960 agctctccga aaccacagat aatatatggg gcacgaggga caagatacca gacatttgtg   1020
aatttcaatt attgtactgg catcctgggc tctcaaagta tcacatcagg gaaacattac   1080
tgggaggtag acgtgtccaa gaaaactgct tggatcctgg gggtatgtgc tggcttccaa   1140
cctgatgcaa tgtgtaatat tgaaaaaaat gaaaattatc aacctaaata cggctactgg   1200 gttataggt tagaggaagg agttaaatgt agtgctttcc aggatagttc cttccatact   1260
ccttctgttc ctttcattgt gcccctctct gtgattattt gtcctgatcg tgttggagtt   1320
ttcctagact atgaggcttg cactgtctca ttcttcaata tcacaaacca tggatttctc   1380
atctataagt tttctcactg ttctttttct cagcctgtat ttccatattt aaatcctaga   1440
aaatgtggag tccccatgac tctgtgctca ccaagctctt ga                      1482

<210> SEQ ID NO 10
<211> LENGTH: 493
<212> TYPE: PRT
<213> ORGANISM: Homo sapiens

<400> SEQUENCE: 10

Met Ala Ser Gly Ile Leu Val Asn Val Lys Glu Glu Val Thr Cys Pro
1               5                   10                  15

Ile Cys Leu Glu Leu Leu Thr Gln Pro Leu Ser Leu Asp Cys Gly His
                20                  25                  30

Ser Phe Cys Gln Ala Cys Leu Thr Ala Asn His Lys Lys Ser Met Leu
            35                  40                  45

Asp Lys Gly Glu Ser Ser Cys Pro Val Cys Arg Ile Ser Tyr Gln Pro
        50                  55                  60

Glu Asn Ile Arg Pro Asn Arg His Val Ala Asn Ile Val Glu Lys Leu
65                  70                  75                  80

Arg Glu Val Lys Leu Ser Pro Glu Gly Gln Lys Val Asp His Cys Ala
                85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
        115                 120                 125

Phe Leu Thr Glu Glu Val Ala Arg Glu Tyr Gln Val Lys Leu Gln Ala
    130                 135                 140

Ala Leu Glu Met Leu Arg Gln Lys Gln Gln Glu Ala Glu Glu Leu Glu
145                 150                 155                 160

Ala Asp Ile Arg Glu Glu Lys Ala Ser Trp Lys Thr Gln Ile Gln Tyr
                165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
        195                 200                 205
```

Asp Ile Leu Lys Ser Leu Thr Asn Ser Glu Thr Glu Met Val Gln Gln
    210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
                245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
        275                 280                 285

Arg Glu Leu Thr Asp Val Arg Arg Tyr Trp Val Asp Thr Val Thr Ala
    290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
                325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
        355                 360                 365

Thr Ala Trp Ile Leu Gly Val Cys Ala Gly Phe Gln Pro Asp Ala Met
    370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
                405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
        435                 440                 445

Val Ser Phe Phe Asn Ile Thr Asn His Gly Phe Leu Ile Tyr Lys Phe
    450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                485                 490

<210> SEQ ID NO 11
<211> LENGTH: 1551
<212> TYPE: DNA
<213> ORGANISM: Homo sapiens

<400> SEQUENCE: 11

| | | |
|---|---|---|
| atgtgcgggt cagagaggat tctacaggca ggaaacatct tagaaatcag ggttgggcag | 60 |
| gcaggagcca ggagagtagc tacaatgact tcaccagtac tggtggacat acgaaagag | 120 |
| gtgacctgcc ctatctgcct ggagctccta acagaacccc tgagcataga ctgtggccac | 180 |
| agcttctgcc aagcctgcat cacaccaaat ggcagggaat cagtgattgg tcaagaaggg | 240 |
| gaaagaagct gccctgtgtg ccagaccagc taccagccag gaacctgcg gcctaatcgg | 300 |
| catctggcca acatagtgag gcggctcaga gaggtagtgt gggccctgg gaagcagctg | 360 |
| aaagcagttc tttgtgcaga ccatggagaa aaactgcagc tcttctgtca ggaggatggg | 420 |
| aaggtcattt gctggctttg tgagcggtct caggagcacc gtggtcacca cacgttcctc | 480 |

-continued

```
gtggaggagg ttgcccagga gtaccaggag aagtttcagg agtctctaaa gaagctgaag      540
aacgaggagc aggaagctga gaagctaaca gcttttatca gagagaagaa aacatcctgg      600
aagaatcaga tggagcctga gagatgcagg atccagacag agtttaatca gctgcgaaat      660
atcctagaca gagtggagca acgggagctg aaaaagctgg aacaggaaga gaagaagggg      720
ctacgaatta tagaagaggc tgagaatgat ctggtccacc agacccagtc gctgcgagag      780
ctcatctcgg atctggagcg tcgatgtcag gggtcaacaa tggagctgct gcaggatgtg      840
agtgatgtca cagaaaggag tgagttctgg accctgagga agccagaagc tctccctaca      900
aagctgagaa gtatgttccg agccccagat ctgaaaagga tgctgcgagt gtgtagagag      960
ctgacagatg tccaaagcta ctgggttgac gtgaccctga atccacacac agctaattta     1020
aatcttgtcc tggctaaaaa ccggagacaa gtgaggtttg tgggagctaa agtatctgga     1080
ccttcctgtc tggaaaagca ttatgactgt agtgtcctgg gctcccagca cttctcctct     1140
ggtaagcatt actgggaggt agatgtggcc aagaagactg cctggatcct ggggtatgc      1200 agcaattcac tgggacctac attctctttc aaccattttg ctcaaaatca cagtgcttac     1260
tccaggtatc agcctcagag tggatactgg gtgattgggt tacagcataa ccatgaatat     1320
agggcctatg aggattcttc cccttccctg cttctctcca tgacagtgcc ccctcgccgt     1380
gttggggttt tcttagatta tgaggctggt actgtctcct tttataatgt cacaaaccat     1440
ggcttcccca tctacacttt ctctaaatat tactttccca ctactctttg tccatattt      1500 aatccttgca actgtgtaat tcctatgacc ctgcgtcgtc caagctcttg a              1551
```

<210> SEQ ID NO 12
<211> LENGTH: 516
<212> TYPE: PRT
<213> ORGANISM: Homo sapiens

<400> SEQUENCE: 12

```
Met Cys Gly Ser Glu Arg Ile Leu Gln Ala Gly Asn Ile Leu Glu Ile
1               5                   10                  15

Arg Val Gly Gln Ala Gly Ala Arg Arg Val Ala Thr Met Thr Ser Pro
            20                  25                  30

Val Leu Val Asp Ile Arg Glu Glu Val Thr Cys Pro Ile Cys Leu Glu
        35                  40                  45

Leu Leu Thr Glu Pro Leu Ser Ile Asp Cys Gly His Ser Phe Cys Gln
    50                  55                  60

Ala Cys Ile Thr Pro Asn Gly Arg Glu Ser Val Ile Gly Gln Glu Gly
65                  70                  75                  80

Glu Arg Ser Cys Pro Val Cys Gln Thr Ser Tyr Gln Pro Gly Asn Leu
                85                  90                  95

Arg Pro Asn Arg His Leu Ala Asn Ile Val Arg Arg Leu Arg Glu Val
            100                 105                 110

Val Leu Gly Pro Gly Lys Gln Leu Lys Ala Val Leu Cys Ala Asp His
        115                 120                 125

Gly Glu Lys Leu Gln Leu Phe Cys Gln Glu Asp Gly Lys Val Ile Cys
    130                 135                 140

Trp Leu Cys Glu Arg Ser Gln Glu His Arg Gly His His Thr Phe Leu
145                 150                 155                 160

Val Glu Glu Val Ala Gln Glu Tyr Gln Glu Lys Phe Gln Glu Ser Leu
                165                 170                 175

Lys Lys Leu Lys Asn Glu Glu Gln Glu Ala Glu Lys Leu Thr Ala Phe
            180                 185                 190
```

```
Ile Arg Glu Lys Lys Thr Ser Trp Lys Asn Gln Met Glu Pro Glu Arg
            195                 200                 205

Cys Arg Ile Gln Thr Glu Phe Asn Gln Leu Arg Asn Ile Leu Asp Arg
        210                 215                 220

Val Glu Gln Arg Glu Leu Lys Lys Leu Glu Gln Glu Lys Lys Gly
225                 230                 235                 240

Leu Arg Ile Ile Glu Glu Ala Glu Asn Asp Leu Val His Gln Thr Gln
                245                 250                 255

Ser Leu Arg Glu Leu Ile Ser Asp Leu Glu Arg Arg Cys Gln Gly Ser
            260                 265                 270

Thr Met Glu Leu Leu Gln Asp Val Ser Asp Val Thr Arg Ser Glu
        275                 280                 285

Phe Trp Thr Leu Arg Lys Pro Glu Ala Leu Pro Thr Lys Leu Arg Ser
290                 295                 300

Met Phe Arg Ala Pro Asp Leu Lys Arg Met Leu Arg Val Cys Arg Glu
305                 310                 315                 320

Leu Thr Asp Val Gln Ser Tyr Trp Val Asp Val Thr Leu Asn Pro His
                325                 330                 335

Thr Ala Asn Leu Asn Leu Val Leu Ala Lys Asn Arg Arg Gln Val Arg
            340                 345                 350

Phe Val Gly Ala Lys Val Ser Gly Pro Ser Cys Leu Glu Lys His Tyr
        355                 360                 365

Asp Cys Ser Val Leu Gly Ser Gln His Phe Ser Ser Gly Lys His Tyr
    370                 375                 380

Trp Glu Val Asp Val Ala Lys Lys Thr Ala Trp Ile Leu Gly Val Cys
385                 390                 395                 400

Ser Asn Ser Leu Gly Pro Thr Phe Ser Phe Asn His Phe Ala Gln Asn
                405                 410                 415

His Ser Ala Tyr Ser Arg Tyr Gln Pro Gln Ser Gly Tyr Trp Val Ile
            420                 425                 430

Gly Leu Gln His Asn His Glu Tyr Arg Ala Tyr Glu Asp Ser Ser Pro
        435                 440                 445

Ser Leu Leu Leu Ser Met Thr Val Pro Pro Arg Arg Val Gly Val Phe
    450                 455                 460

Leu Asp Tyr Glu Ala Gly Thr Val Ser Phe Tyr Asn Val Thr Asn His
465                 470                 475                 480

Gly Phe Pro Ile Tyr Thr Phe Ser Lys Tyr Tyr Phe Pro Thr Thr Leu
                485                 490                 495

Cys Pro Tyr Phe Asn Pro Cys Asn Cys Val Ile Pro Met Thr Leu Arg
            500                 505                 510

Arg Pro Ser Ser
        515

<210> SEQ ID NO 13
<211> LENGTH: 666
<212> TYPE: DNA
<213> ORGANISM: Homo sapiens

<400> SEQUENCE: 13
atggcggctg tgggaccgcg gaccggcccc ggaaccggcg ccgaggctct agcgctggcg      60
gcagagctgc agggcgaggc gacgtgctcc atctgcctag agctctttcg tgagccggtg     120
tccgtcgagt gcggccacag cttctgccgc gcctgcatag gcgctgctg ggagcgcccg     180 ggcgcgggt ctgttggggc cgccacccgc gcgccccct tcccactgcc ctgtccgcag      240
```

```
tgccgcgagc cgcgcgccc cagtcagctg cggcccaacc ggcagctggc ggcagtggcc      300
acgctcctgc ggcgcttcag cctgcccgcg gctgccccgg gagagcacgg gtctcaggcg      360
gccgcggccc gggcagcggc tgcccgctgc gggcagcatg gcgaacccct caagctctac      420
tgccaggacg acgacgcgcg catctgcgtg tgtgcgacc gcgcccgcga gcaccgcgag       480
cacgccgtgc tgccgctgga cgaggcggtg caggaggcca aggagctctt ggagtccagg      540
ctgagggtct tgaagaagga actggaggac tgtgaggtgt tccggtccac ggaaaagaag      600
gagagcaagg agctgctggt gagccaggca cccgcaggcc cccgtgggga cattacagag      660
gcctga                                                                 666
```

<210> SEQ ID NO 14
<211> LENGTH: 221
<212> TYPE: PRT
<213> ORGANISM: Homo sapiens

<400> SEQUENCE: 14

```
Met Ala Ala Val Gly Pro Arg Thr Gly Pro Gly Thr Gly Ala Glu Ala
1               5                   10                  15

Leu Ala Leu Ala Ala Glu Leu Gln Gly Glu Ala Thr Cys Ser Ile Cys
            20                  25                  30

Leu Glu Leu Phe Arg Glu Pro Val Ser Val Glu Cys Gly His Ser Phe
        35                  40                  45

Cys Arg Ala Cys Ile Gly Arg Cys Trp Glu Arg Pro Gly Ala Gly Ser
    50                  55                  60

Val Gly Ala Ala Thr Arg Ala Pro Pro Phe Pro Leu Pro Cys Pro Gln
65                  70                  75                  80

Cys Arg Glu Pro Ala Arg Pro Ser Gln Leu Arg Pro Asn Arg Gln Leu
                85                  90                  95

Ala Ala Val Ala Thr Leu Leu Arg Arg Phe Ser Leu Pro Ala Ala Ala
            100                 105                 110

Pro Gly Glu His Gly Ser Gln Ala Ala Ala Arg Ala Ala Ala Ala
        115                 120                 125

Arg Cys Gly Gln His Gly Glu Pro Phe Lys Leu Tyr Cys Gln Asp Asp
    130                 135                 140

Gly Arg Ala Ile Cys Val Val Cys Asp Arg Ala Arg Glu His Arg Glu
145                 150                 155                 160

His Ala Val Leu Pro Leu Asp Glu Ala Val Gln Glu Ala Lys Glu Leu
                165                 170                 175

Leu Glu Ser Arg Leu Arg Val Leu Lys Lys Glu Leu Glu Asp Cys Glu
            180                 185                 190

Val Phe Arg Ser Thr Glu Lys Lys Glu Ser Lys Glu Leu Leu Val Ser
        195                 200                 205

Gln Ala Pro Ala Gly Pro Pro Trp Asp Ile Thr Glu Ala
    210                 215                 220
```

<210> SEQ ID NO 15
<211> LENGTH: 1656
<212> TYPE: DNA
<213> ORGANISM: Homo sapiens

<400> SEQUENCE: 15

```
atggcggaga attggaagaa ctgcttcgag gaggagctca tctgccctat ctgcctgcac       60
gttttcgtgg agccagtgca gctgccgtgc aaacacaact tctgccgggg ctgcatcggc      120
```

```
gaggcgtggg ccaaggacag cggcctcgta cgctgcccag agtgcaacca ggcctacaac      180
cagaagccgg gcctggagaa gaacctgaag ctcaccaaca tcgtggagaa gttcaatgcc      240
ctgcacgtgg agaagccgcc ggcggcgctg cactgcgtgt tctgccgccg cggccccccg      300
ctgcccgcgc agaaggtctg cctgcgctgc gaggcgccct gctgccagtc ccacgtgcag      360
acgcacctgc agcagccctc caccgcccgc gggcacctcc tggtggaggc ggacgacgtg      420
cgggcctgga gctgcccgca gcacaacgcc taccgcctct accactgcga ggccgagcag      480
gtggccgtgt gccagtactg ctgctactac agcggcgcgc atcagggaca ctcggtgtgc      540
gacgtggaga tccgaaggaa tgaaatccgg aagatgctca tgaagcagca ggaccggctg      600
gaggagcgag agcaggacat tgaggaccag ctgtacaaac tcgagtcaga caagcgcctg      660
gtggaggaga aagtgaacca actgaaggag aagttcggc tgcagtacga aagctgcac       720 cagctgctgg acgaggacct gcggcagaca gtggaggtcc tagacaaggc ccaggccaag      780
ttctgcagcg agaacgcagc gcaggcgctg cacctcgggg agcgcatgca ggaggccaag      840
aagctgctgg gctccctgca gctgctcttt gataagacgg aggatgtcag cttcatgaag      900
aacaccaagt ctgtgaaaat cctgatggac aggacccaga cctgcacgag cagcagcctt      960
tcccccacta agatcggcca cctgaactcc aagctcttcc tgaacgaagt ggccaagaag     1020
gagaagcagc tgcggaaaat gctagaaggc cccttcagca cgccggtgcc cttcctgcag     1080
agtgtccccc tgtacccttg cggcgtgagc agctctgggg cggaaaagcg caagcactca     1140
acggccttcc agaggccag tttcctagag acgtcgtcgg gccctgtggg cggccagtac     1200
ggggcggcgg gcacagccag cggtgagggc cagtctgggc agccctgggt gccctgcagc     1260
tccacgcagc acttggtggc cctgccgggc ggcgcccaac cagtgcactc aagcccgtg     1320 ttcccccat cgcagtatcc caatggctcc gccgccagc agcccatgct ccccagtat       1380 ggcggccgca agattctcgt ctgttctgtg dacaactgtt actgttcttc cgtggccaac     1440
catgccggcc accagcccta ccccgctccc ggccacttc cctggacagt gccctcgcag     1500
gagtactcac acccgctccc gcccacaccc tccgtccccc agtcccttcc cagcctggcg     1560
gtcagagact ggcttgacgc ctcccagcag ccccggccacc aggatttcta cagggtgtat     1620
gggcagccgt ccaccaaaca ctacgtgacg agctaa                               1656
```

<210> SEQ ID NO 16
<211> LENGTH: 551
<212> TYPE: PRT
<213> ORGANISM: Homo sapiens

<400> SEQUENCE: 16

```
Met Ala Glu Asn Trp Lys Asn Cys Phe Glu Glu Glu Leu Ile Cys Pro
1               5                   10                  15

Ile Cys Leu His Val Phe Val Glu Pro Val Gln Leu Pro Cys Lys His
                20                  25                  30

Asn Phe Cys Arg Gly Cys Ile Gly Glu Ala Trp Ala Lys Asp Ser Gly
            35                  40                  45

Leu Val Arg Cys Pro Glu Cys Asn Gln Ala Tyr Asn Gln Lys Pro Gly
        50                  55                  60

Leu Glu Lys Asn Leu Lys Leu Thr Asn Ile Val Glu Lys Phe Asn Ala
65                  70                  75                  80

Leu His Val Glu Lys Pro Pro Ala Ala Leu His Cys Val Phe Cys Arg
                85                  90                  95

Arg Gly Pro Pro Leu Pro Ala Gln Lys Val Cys Leu Arg Cys Glu Ala
```

```
            100                 105                 110
Pro Cys Cys Gln Ser His Val Gln Thr His Leu Gln Gln Pro Ser Thr
            115                 120                 125
Ala Arg Gly His Leu Leu Val Glu Ala Asp Asp Val Arg Ala Trp Ser
            130                 135                 140
Cys Pro Gln His Asn Ala Tyr Arg Leu Tyr His Cys Glu Ala Glu Gln
145             150                 155                 160
Val Ala Val Cys Gln Tyr Cys Tyr Tyr Ser Gly Ala His Gln Gly
                165                 170                 175
His Ser Val Cys Asp Val Glu Ile Arg Arg Asn Glu Ile Arg Lys Met
                180                 185                 190
Leu Met Lys Gln Gln Asp Arg Leu Glu Glu Arg Glu Gln Asp Ile Glu
            195                 200                 205
Asp Gln Leu Tyr Lys Leu Glu Ser Asp Lys Arg Leu Val Glu Glu Lys
            210                 215                 220
Val Asn Gln Leu Lys Glu Glu Val Arg Leu Gln Tyr Glu Lys Leu His
225             230                 235                 240
Gln Leu Leu Asp Glu Asp Leu Arg Gln Thr Val Glu Val Leu Asp Lys
                245                 250                 255
Ala Gln Ala Lys Phe Cys Ser Glu Asn Ala Ala Gln Ala Leu His Leu
                260                 265                 270
Gly Glu Arg Met Gln Glu Ala Lys Lys Leu Leu Gly Ser Leu Gln Leu
            275                 280                 285
Leu Phe Asp Lys Thr Glu Asp Val Ser Phe Met Lys Asn Thr Lys Ser
            290                 295                 300
Val Lys Ile Leu Met Asp Arg Thr Gln Thr Cys Thr Ser Ser Ser Leu
305             310                 315                 320
Ser Pro Thr Lys Ile Gly His Leu Asn Ser Lys Leu Phe Leu Asn Glu
                325                 330                 335
Val Ala Lys Lys Glu Lys Gln Leu Arg Lys Met Leu Glu Gly Pro Phe
                340                 345                 350
Ser Thr Pro Val Pro Phe Leu Gln Ser Val Pro Leu Tyr Pro Cys Gly
            355                 360                 365
Val Ser Ser Gly Ala Glu Lys Arg Lys His Ser Thr Ala Phe Pro
370             375                 380
Glu Ala Ser Phe Leu Glu Thr Ser Ser Gly Pro Val Gly Gly Gln Tyr
385             390                 395                 400
Gly Ala Ala Gly Thr Ala Ser Gly Glu Gly Gln Ser Gly Gln Pro Leu
                405                 410                 415
Gly Pro Cys Ser Ser Thr Gln His Leu Val Ala Leu Pro Gly Gly Ala
                420                 425                 430
Gln Pro Val His Ser Ser Pro Val Phe Pro Pro Ser Gln Tyr Pro Asn
            435                 440                 445
Gly Ser Ala Ala Gln Gln Pro Met Leu Pro Gln Tyr Gly Gly Arg Lys
            450                 455                 460
Ile Leu Val Cys Ser Val Asp Asn Cys Tyr Cys Ser Ser Val Ala Asn
465             470                 475                 480
His Gly Gly His Gln Pro Tyr Pro Arg Ser Gly His Phe Pro Trp Thr
                485                 490                 495
Val Pro Ser Gln Glu Tyr Ser His Pro Leu Pro Pro Thr Pro Ser Val
                500                 505                 510
Pro Gln Ser Leu Pro Ser Leu Ala Val Arg Asp Trp Leu Asp Ala Ser
            515                 520                 525
```

Gln Gln Pro Gly His Gln Asp Phe Tyr Arg Val Tyr Gly Gln Pro Ser
    530                 535                 540

Thr Lys His Tyr Val Thr Ser
545                 550

<210> SEQ ID NO 17
<211> LENGTH: 2133
<212> TYPE: DNA
<213> ORGANISM: Homo sapiens

<400> SEQUENCE: 17

| | | | | | |
|---|---|---|---|---|---|
| atggaggaga | tggaagagga | gttgaaatgc | cccgtgtgcg | gctccttcta | tcgggagccc | 60 |
| atcatcctgc | cctgctctca | caatttgtgt | caggcgtgcg | cccgcaacat | cctggtgcag | 120 |
| accccagagt | ctgaatcccc | ccagagccat | cgggccgcgg | gctccggggt | ctccgactat | 180 |
| gactatctgg | acctggacaa | gatgagccta | tacagcgagg | cggacagcgg | ctatggctcc | 240 |
| tacgggggt | tcgccagcgc | ccccactacc | cgtgccaga | agtcccccaa | cggcgtccgc | 300 |
| gtgtttcccc | cggctatgcc | gccaccggcc | acccacttgt | caccggccct | ggccccggtg | 360 |
| ccccgcaact | cctgtatcac | ctgccccag | tgtcaccgca | gcctcatcct | ggatgaccgg | 420 |
| gggctccgcg | gcttccccaa | gaatcgcgta | ctggaagggg | taattgaccg | ctaccagcag | 480 |
| agcaaagccg | cggccctcaa | gtgccagctc | tgcgagaagg | cgcccaagga | agccaccgtc | 540 |
| atgtgcgaac | agtgcgatgt | cttctactgc | gatccgtgcc | gcctgcgctg | ccacccgccc | 600 |
| cgggggcccc | tagccaagca | ccgcctggtg | ccccggccc | agggtcgtgt | gagccggagg | 660 |
| ctgagcccac | gcaaggtctc | cacctgcaca | gaccacgagc | tggagaacca | cagcatgtac | 720 |
| tgcgtgcaat | gcaagatgcc | cgtgtgctac | cagtgcttgg | aggagggcaa | acactccagc | 780 |
| cacgaagtca | aggctctggg | ggccatgtgg | aaactacata | gagccagct | ctcccaggcg | 840 |
| ctgaacggac | tgtcagacag | ggccaaagaa | gccaaggagt | ttctggtaca | gctgcgcaac | 900 |
| atggtccagc | agatccagga | gaacagtgtg | gagtttgaag | cctgtctggt | ggcccaatgt | 960 |
| gatgccctca | tcgatgccct | caacagaaga | aaagcccagc | tgctggcccg | cgtcaacaag | 1020 |
| gagcatgagc | acaagctgaa | ggtggttcga | gatcagatct | ctcactgcac | agtgaaattg | 1080 |
| cgccagacca | caggtctcat | ggagtactgc | ttggaggtga | ttaaggaaaa | tgatcctagt | 1140 |
| ggttttttgc | agatttctga | cgccctcata | agaagagtgc | acctgactga | ggatcagtgg | 1200 |
| ggtaaaggca | cactcactcc | aaggatgacc | acggactttg | acttgagtct | ggacaacagc | 1260 |
| cctctgctgc | aatccatcca | ccagctggat | ttcgtgcaag | tgaaagcttc | ctctccagtc | 1320 |
| ccagcaaccc | ctatcctaca | gctggaggaa | tgttgtaccc | acaacaacag | cgctacgttg | 1380 |
| tcctggaaac | agccacctct | gtccacggtg | cccgccgatg | gatacattct | ggagctggat | 1440 |
| gatggcaacg | gtggtcaatt | ccgggaggtg | tatgtgggga | aggagacaat | gtgcactgtg | 1500 |
| gatggtcttc | acttcaacag | cacatacaac | gctcgggtca | aggccttcaa | caaaacagga | 1560 |
| gtcagcccgt | acagcaagac | cctggtcctc | caaacgtctg | aggtggcctg | gtttgctttc | 1620 |
| gaccctggct | cggcgcactc | ggacatcatc | ctctccaatg | acaacctgac | agtgacctgt | 1680 |
| agtagctatg | atgaccgggt | ggtgctaggg | aagactggct | tctccaaggg | catccactac | 1740 |
| tgggagctca | cggtagatcg | ctatgacaac | caccctgatc | ctgcctttgg | tgtggctcgc | 1800 |
| atggacgtga | tgaaggatgt | gatgttagga | aagacgaca | aagcttgggc | aatgtatgtg | 1860 |
| gacaataacc | ggagctggtt | catgcacaac | aactcgcaca | ccaacagaac | tgagggaggg | 1920 |

```
atcacaaaag gggccacaat tggggtcctc ctcgacttaa atagaaaaaa cttgacattt      1980
tttatcaacg atgaacaaca aggtcccata gcatttgata acgtggaggg cctcttcttc      2040
cctgcggtca gcctgaacag gaacgtgcag gtcacgctgc acaccgggct cccagtcccc      2100
gacttctact ccagcagagc atcaatagcc taa                                  2133
```

```
<210> SEQ ID NO 18
<211> LENGTH: 710
<212> TYPE: PRT
<213> ORGANISM: Homo sapiens

<400> SEQUENCE: 18

Met Glu Glu Met Glu Glu Leu Lys Cys Pro Val Cys Gly Ser Phe
1               5                   10                  15

Tyr Arg Glu Pro Ile Ile Leu Pro Cys Ser His Asn Leu Cys Gln Ala
            20                  25                  30

Cys Ala Arg Asn Ile Leu Val Gln Thr Pro Glu Ser Glu Ser Pro Gln
        35                  40                  45

Ser His Arg Ala Ala Gly Ser Gly Val Ser Asp Tyr Asp Tyr Leu Asp
    50                  55                  60

Leu Asp Lys Met Ser Leu Tyr Ser Glu Ala Asp Ser Gly Tyr Gly Ser
65                  70                  75                  80

Tyr Gly Gly Phe Ala Ser Ala Pro Thr Thr Pro Cys Gln Lys Ser Pro
                85                  90                  95

Asn Gly Val Arg Val Phe Pro Pro Ala Met Pro Pro Ala Thr His
            100                 105                 110

Leu Ser Pro Ala Leu Ala Pro Val Pro Arg Asn Ser Cys Ile Thr Cys
        115                 120                 125

Pro Gln Cys His Arg Ser Leu Ile Leu Asp Asp Arg Gly Leu Arg Gly
    130                 135                 140

Phe Pro Lys Asn Arg Val Leu Glu Gly Val Ile Asp Arg Tyr Gln Gln
145                 150                 155                 160

Ser Lys Ala Ala Ala Leu Lys Cys Gln Leu Cys Glu Lys Ala Pro Lys
                165                 170                 175

Glu Ala Thr Val Met Cys Glu Gln Cys Asp Val Phe Tyr Cys Asp Pro
            180                 185                 190

Cys Arg Leu Arg Cys His Pro Pro Arg Gly Pro Leu Ala Lys His Arg
        195                 200                 205

Leu Val Pro Pro Ala Gln Gly Arg Val Ser Arg Leu Ser Pro Arg
    210                 215                 220

Lys Val Ser Thr Cys Thr Asp His Glu Leu Glu Asn His Ser Met Tyr
225                 230                 235                 240

Cys Val Gln Cys Lys Met Pro Val Cys Tyr Gln Cys Leu Glu Glu Gly
                245                 250                 255

Lys His Ser Ser His Glu Val Lys Ala Leu Gly Ala Met Trp Lys Leu
            260                 265                 270

His Lys Ser Gln Leu Ser Gln Ala Leu Asn Gly Leu Ser Asp Arg Ala
        275                 280                 285

Lys Glu Ala Lys Glu Phe Leu Val Gln Leu Arg Asn Met Val Gln Gln
    290                 295                 300

Ile Gln Glu Asn Ser Val Glu Phe Glu Ala Cys Leu Val Ala Gln Cys
305                 310                 315                 320

Asp Ala Leu Ile Asp Ala Leu Asn Arg Arg Lys Ala Gln Leu Leu Ala
                325                 330                 335
```

Arg Val Asn Lys Glu His Glu His Lys Leu Lys Val Val Arg Asp Gln
            340                 345                 350

Ile Ser His Cys Thr Val Lys Leu Arg Gln Thr Thr Gly Leu Met Glu
            355                 360                 365

Tyr Cys Leu Glu Val Ile Lys Glu Asn Asp Pro Ser Gly Phe Leu Gln
370                 375                 380

Ile Ser Asp Ala Leu Ile Arg Arg Val His Leu Thr Glu Asp Gln Trp
385                 390                 395                 400

Gly Lys Gly Thr Leu Thr Pro Arg Met Thr Thr Asp Phe Asp Leu Ser
            405                 410                 415

Leu Asp Asn Ser Pro Leu Leu Gln Ser Ile His Gln Leu Asp Phe Val
            420                 425                 430

Gln Val Lys Ala Ser Ser Pro Val Pro Ala Thr Pro Ile Leu Gln Leu
            435                 440                 445

Glu Glu Cys Cys Thr His Asn Asn Ser Ala Thr Leu Ser Trp Lys Gln
            450                 455                 460

Pro Pro Leu Ser Thr Val Pro Ala Asp Gly Tyr Ile Leu Glu Leu Asp
465                 470                 475                 480

Asp Gly Asn Gly Gly Gln Phe Arg Glu Val Tyr Val Gly Lys Glu Thr
            485                 490                 495

Met Cys Thr Val Asp Gly Leu His Phe Asn Ser Thr Tyr Asn Ala Arg
            500                 505                 510

Val Lys Ala Phe Asn Lys Thr Gly Val Ser Pro Tyr Ser Lys Thr Leu
            515                 520                 525

Val Leu Gln Thr Ser Glu Val Ala Trp Phe Ala Phe Asp Pro Gly Ser
            530                 535                 540

Ala His Ser Asp Ile Ile Leu Ser Asn Asp Asn Leu Thr Val Thr Cys
545                 550                 555                 560

Ser Ser Tyr Asp Asp Arg Val Val Leu Gly Lys Thr Gly Phe Ser Lys
            565                 570                 575

Gly Ile His Tyr Trp Glu Leu Thr Val Asp Arg Tyr Asp Asn His Pro
            580                 585                 590

Asp Pro Ala Phe Gly Val Ala Arg Met Asp Val Met Lys Asp Val Met
            595                 600                 605

Leu Gly Lys Asp Asp Lys Ala Trp Ala Met Tyr Val Asp Asn Asn Arg
610                 615                 620

Ser Trp Phe Met His Asn Asn Ser His Thr Asn Arg Thr Glu Gly Gly
625                 630                 635                 640

Ile Thr Lys Gly Ala Thr Ile Gly Val Leu Leu Asp Leu Asn Arg Lys
            645                 650                 655

Asn Leu Thr Phe Phe Ile Asn Asp Glu Gln Gln Gly Pro Ile Ala Phe
            660                 665                 670

Asp Asn Val Glu Gly Leu Phe Phe Pro Ala Val Ser Leu Asn Arg Asn
            675                 680                 685

Val Gln Val Thr Leu His Thr Gly Leu Pro Val Pro Asp Phe Tyr Ser
            690                 695                 700

Ser Arg Ala Ser Ile Ala
705                 710

<210> SEQ ID NO 19
<211> LENGTH: 1446
<212> TYPE: DNA
<213> ORGANISM: Homo sapiens

<400> SEQUENCE: 19

```
atggcctctg ctgcctctgt gaccagcctg gcagatgaag tcaactgccc catctgtcag    60
ggtaccctga gggagccggt cactatcgac tgcggccaca acttctgccg ggcctgcctt   120
acccgctact gtgagatacc aggcccagac ctggaggagt cccctacttg cccactctgc   180
aaagaaccct tccgtcctgg gagcttccgg cccaactggc agctggctaa cgtggtggag   240
aacattgagc gcctccagct ggtgtccaca ctgggtttgg gagaggagga tgtctgccaa   300
gagcacggag agaagatcta cttcttctgt gaggatgatg agatgcagtt gtgcgtggtg   360
tgccgggagg ctggggagca cgctacccac accatgcgct cctggaggga tgcagcggct   420
ccctatacgg aacaaatcca taagtgtctt aaatgtctaa gaaaagagag agaggagatt   480
caagaaatcc agtcaagaga aaataaaagg atgcaagtcc tcctgactca ggtgtccacc   540
aagagacaac aggtgatttc tgagttcgca cacctgagga gtttctaga ggaacagcag   600
agcatcctct tagcacaatt ggagagccag gatggggaca tcttgaggca cgggatgaa   660
tttgatttgc tggttgctgg ggagatctgc cggtttagtg ctcttattga agaactggag   720
gagaagaatg agaggccagc aagggagctc ctgacggaca tcagaagcac tctaataaga   780
tgtgaaacca gaaagtgccg gaaaccggtg gctgtgtcgc cagagctggg ccagaggatt   840
cgggactttc cccagcaggc cctcccgctg cagagggaga tgaagatgtt tctggaaaaa   900
ctatgctttg agttggacta tgagccagct cacatttctc tagaccctca gacttcccac   960
cccaagctcc tcttgtccga ggaccaccag cgagctcagt tctcctacaa atggcagaac  1020
tcaccagaca cccccaacg ttttgaccgg gccacctgtg ttctggccca cactggcatc  1080
acaggggga gacacacgtg ggtggtgagt atagacctgg cccatggggg cagctgcacc  1140
gtgggcgtgg tgagcgagga tgtgcagcgg aaggggagc ttcggctgcg gccagaggag  1200
ggggtgtggg ctgtgaggct ggcttgggc ttcgtctcgg ctctgggctc cttccccaca  1260
cggctgaccc tgaaggagca gccccggcag gtgagggtgt ctcttgacta tgaggtgggc  1320
tgggtgacct tcaccaacgc tgtcacccga gagcccatct acaccttcac tgcctccttc  1380
actaggaagg tcattccctt ctttgggctc tggggccgag ggtccagttt ctccctgagc  1440
tcctga                                                              1446
```

<210> SEQ ID NO 20
<211> LENGTH: 481
<212> TYPE: PRT
<213> ORGANISM: Homo sapiens

<400> SEQUENCE: 20

Met Ala Ser Ala Ala Ser Val Thr Ser Leu Ala Asp Glu Val Asn Cys
1               5                   10                  15

Pro Ile Cys Gln Gly Thr Leu Arg Glu Pro Val Thr Ile Asp Cys Gly
            20                  25                  30

His Asn Phe Cys Arg Ala Cys Leu Thr Arg Tyr Cys Glu Ile Pro Gly
        35                  40                  45

Pro Asp Leu Glu Glu Ser Pro Thr Cys Pro Leu Cys Lys Glu Pro Phe
    50                  55                  60

Arg Pro Gly Ser Phe Arg Pro Asn Trp Gln Leu Ala Asn Val Val Glu
65                  70                  75                  80

Asn Ile Glu Arg Leu Gln Leu Val Ser Thr Leu Gly Leu Gly Glu Glu
                85                  90                  95

Asp Val Cys Gln Glu His Gly Glu Lys Ile Tyr Phe Phe Cys Glu Asp
            100                 105                 110

Asp Glu Met Gln Leu Cys Val Cys Arg Glu Ala Gly Glu His Ala
         115                 120                 125

Thr His Thr Met Arg Phe Leu Glu Asp Ala Ala Pro Tyr Arg Glu
     130                 135                 140

Gln Ile His Lys Cys Leu Lys Cys Leu Arg Lys Glu Arg Glu Ile
145                 150                 155                 160

Gln Glu Ile Gln Ser Arg Glu Asn Lys Arg Met Gln Val Leu Leu Thr
                 165                 170                 175

Gln Val Ser Thr Lys Arg Gln Gln Val Ile Ser Glu Phe Ala His Leu
             180                 185                 190

Arg Lys Phe Leu Glu Glu Gln Gln Ser Ile Leu Leu Ala Gln Leu Glu
         195                 200                 205

Ser Gln Asp Gly Asp Ile Leu Arg Gln Arg Asp Glu Phe Asp Leu Leu
     210                 215                 220

Val Ala Gly Glu Ile Cys Arg Phe Ser Ala Leu Ile Glu Glu Leu Glu
225                 230                 235                 240

Glu Lys Asn Glu Arg Pro Ala Arg Glu Leu Leu Thr Asp Ile Arg Ser
                 245                 250                 255

Thr Leu Ile Arg Cys Glu Thr Arg Lys Cys Arg Lys Pro Val Ala Val
             260                 265                 270

Ser Pro Glu Leu Gly Gln Arg Ile Arg Asp Phe Pro Gln Gln Ala Leu
         275                 280                 285

Pro Leu Gln Arg Glu Met Lys Met Phe Leu Glu Lys Leu Cys Phe Glu
     290                 295                 300

Leu Asp Tyr Glu Pro Ala His Ile Ser Leu Asp Pro Gln Thr Ser His
305                 310                 315                 320

Pro Lys Leu Leu Leu Ser Glu Asp His Gln Arg Ala Gln Phe Ser Tyr
                 325                 330                 335

Lys Trp Gln Asn Ser Pro Asp Asn Pro Gln Arg Phe Asp Arg Ala Thr
             340                 345                 350

Cys Val Leu Ala His Thr Gly Ile Thr Gly Arg His Thr Trp Val
         355                 360                 365

Val Ser Ile Asp Leu Ala His Gly Gly Ser Cys Thr Val Gly Val
     370                 375                 380

Ser Glu Asp Val Gln Arg Lys Gly Glu Leu Arg Leu Arg Pro Glu Glu
385                 390                 395                 400

Gly Val Trp Ala Val Arg Leu Ala Trp Gly Phe Val Ser Ala Leu Gly
                 405                 410                 415

Ser Phe Pro Thr Arg Leu Thr Leu Lys Glu Gln Pro Arg Gln Val Arg
             420                 425                 430

Val Ser Leu Asp Tyr Glu Val Gly Trp Val Thr Phe Thr Asn Ala Val
         435                 440                 445

Thr Arg Glu Pro Ile Tyr Thr Phe Thr Ala Ser Phe Thr Arg Lys Val
     450                 455                 460

Ile Pro Phe Phe Gly Leu Trp Gly Arg Gly Ser Ser Phe Ser Leu Ser
465                 470                 475                 480

Ser

<210> SEQ ID NO 21
<211> LENGTH: 1407
<212> TYPE: DNA
<213> ORGANISM: Homo sapiens

<400> SEQUENCE: 21

```
atggccgccc ccgacctgtc caccaacctc caggaggagg ccacctgcgc catctgcctc      60
gactacttca cggatccggt gatgaccgac tgcggccaca acttctgccg cgagtgcatc     120
cggcgctgct ggggccagcc cgagggcccg tacgcgtgcc ccgagtgccg cgagctgtcc     180
ccgcagagga acctgcggcc caaccgcccg cttgctaaga tggccgagat ggcgcggcgc     240
ctgcacccgc cgtcgccggt cccgcagggc gtgtgccccg cgaccgcga gccactggcc      300
gccttctgtg cgacgagct cgcctcctg tgtgcggcct cgagcgctc tggggagcac        360
tgggcgcacc gcgtgcggcc gctgcaggac gcggccgaag acctcaaggc gaagctggag     420
aagtcactgg agcatctccg gaagcagatg caggatgcgt tgctgttcca gcccaggcg      480
gatgagacct gcgtcttgtg gcagaagatg gtggagagcc agcggcagaa cgtgctgggt     540
gagttcgagc gtcttcgccg tttgctggca gaggaggagc agcagctgct gcagaggctg     600
gaggaggagg agctggaggt gctgccccgg ctgcgggagg gcgcagccca cctaggccag     660
cagagcgccc acctagctga gctcatcgcc gagctcgagg gccgctgcca gctgcctgct     720
ctggggctgc tgcaggacat caaggacgcc ctgcgcaggg tccaggatgt gaagctgcag     780
cccccagaag ttgtgcctat ggagctgagg accgtgtgca gggtcccggg actggtagag     840
acactgcgga ggtttcgagg ggacgtgacc ttggacccgg acaccgccaa ccctgagctg     900
atcctgtctg aagacaggcg gagcgtgcag cgggggacc tacggcaggc cctgccggac     960
agcccagagc gctttgaccc cggcccctgc gtgctgggcc aggagcgctt cacctcaggc    1020
cgccactact gggaggtgga ggttggggac cgcaccagct gggccctggg ggtgtgcagg    1080
gagaacgtga acaggaagga gaagggcgag ctgtccgcgg gcaacggctt ctggatcctg    1140
gtcttcctgg ggagctatta caattcctcg gaacgggcct tggctccact ccgggaccca    1200
cccaggcgcg tggggatctt tctggactac gaggctggac atctctcttt ctacagtgcc    1260
accgatgggt cactgctatt catctttccc gagatccccc tctcggggac gctgcggccc    1320
ctcttctcac ccctgtccag cagcccgacc ccgatgacta tctgccggcc gaaaggtggg    1380
tccggggaca ccctggctcc ccagtga                                         1407
```

<210> SEQ ID NO 22
<211> LENGTH: 468
<212> TYPE: PRT
<213> ORGANISM: Homo sapiens

<400> SEQUENCE: 22

```
Met Ala Ala Pro Asp Leu Ser Thr Asn Leu Gln Glu Glu Ala Thr Cys
1               5                   10                  15

Ala Ile Cys Leu Asp Tyr Phe Thr Asp Pro Val Met Thr Asp Cys Gly
            20                  25                  30

His Asn Phe Cys Arg Glu Cys Ile Arg Arg Cys Trp Gly Gln Pro Glu
        35                  40                  45

Gly Pro Tyr Ala Cys Pro Glu Cys Arg Glu Leu Ser Pro Gln Arg Asn
    50                  55                  60

Leu Arg Pro Asn Arg Pro Leu Ala Lys Met Ala Glu Met Ala Arg Arg
65                  70                  75                  80

Leu His Pro Pro Ser Pro Val Pro Gln Gly Val Cys Pro Ala His Arg
                85                  90                  95

Glu Pro Leu Ala Ala Phe Cys Gly Asp Glu Leu Arg Leu Leu Cys Ala
            100                 105                 110

Ala Cys Glu Arg Ser Gly Glu His Trp Ala His Arg Val Arg Pro Leu
```

```
                    115                 120                 125
Gln Asp Ala Ala Glu Asp Leu Lys Ala Lys Leu Glu Lys Ser Leu Glu
        130                 135                 140
His Leu Arg Lys Gln Met Gln Asp Ala Leu Leu Phe Gln Ala Gln Ala
145                 150                 155                 160
Asp Glu Thr Cys Val Leu Trp Gln Lys Met Val Glu Ser Gln Arg Gln
                165                 170                 175
Asn Val Leu Gly Glu Phe Glu Arg Leu Arg Arg Leu Leu Ala Glu Glu
            180                 185                 190
Glu Gln Gln Leu Leu Gln Arg Leu Glu Glu Glu Leu Glu Val Leu
        195                 200                 205
Pro Arg Leu Arg Glu Gly Ala Ala His Leu Gly Gln Gln Ser Ala His
210                 215                 220
Leu Ala Glu Leu Ile Ala Glu Leu Glu Gly Arg Cys Gln Leu Pro Ala
225                 230                 235                 240
Leu Gly Leu Leu Gln Asp Ile Lys Asp Ala Leu Arg Arg Val Gln Asp
                245                 250                 255
Val Lys Leu Gln Pro Pro Glu Val Val Pro Met Glu Leu Arg Thr Val
            260                 265                 270
Cys Arg Val Pro Gly Leu Val Glu Thr Leu Arg Arg Phe Arg Gly Asp
        275                 280                 285
Val Thr Leu Asp Pro Asp Thr Ala Asn Pro Glu Leu Ile Leu Ser Glu
        290                 295                 300
Asp Arg Arg Ser Val Gln Arg Gly Asp Leu Arg Gln Ala Leu Pro Asp
305                 310                 315                 320
Ser Pro Glu Arg Phe Asp Pro Gly Pro Cys Val Leu Gly Gln Glu Arg
                325                 330                 335
Phe Thr Ser Gly Arg His Tyr Trp Glu Val Glu Val Gly Asp Arg Thr
            340                 345                 350
Ser Trp Ala Leu Gly Val Cys Arg Glu Asn Val Asn Arg Lys Glu Lys
        355                 360                 365
Gly Glu Leu Ser Ala Gly Asn Gly Phe Trp Ile Leu Val Phe Leu Gly
    370                 375                 380
Ser Tyr Tyr Asn Ser Ser Glu Arg Ala Leu Ala Pro Leu Arg Asp Pro
385                 390                 395                 400
Pro Arg Arg Val Gly Ile Phe Leu Asp Tyr Glu Ala Gly His Leu Ser
                405                 410                 415
Phe Tyr Ser Ala Thr Asp Gly Ser Leu Leu Phe Ile Phe Pro Glu Ile
            420                 425                 430
Pro Phe Ser Gly Thr Leu Arg Pro Leu Phe Ser Pro Leu Ser Ser Ser
        435                 440                 445
Pro Thr Pro Met Thr Ile Cys Arg Pro Lys Gly Gly Ser Gly Asp Thr
    450                 455                 460
Leu Ala Pro Gln
465

<210> SEQ ID NO 23
<211> LENGTH: 894
<212> TYPE: DNA
<213> ORGANISM: Mus musculus

<400> SEQUENCE: 23
atggcttcac aattcatgaa gaatttaaag gaggaggtga cctgtcctgt ctgtctgaac      60
ctgatggtga aacctgtgag tgcagattgt ggtcacacct tctgccaagg ctgcatcacg     120
```

-continued

```
ttgtactttg aatccatcaa atgcgataag aaagtgttca tttgccctgt gtgccgaatt      180
agttaccagt ttagcaatct gaggcctaat cgaaatgtgg ccaacatagt agagaggctc      240
aaaatgttca agcccagccc agaagaggag cagaaagtgt taactgtgc aagacatgga       300
aagaaactcc agctcttctg taggaaggac atgatggcca tctgctggct tgtgagcga       360
tctcaggagc accgtggtca caaacagct ctcattgaag aggtggccca ggagtacaag       420
gagcagctgc aggtagttct gcaaaggctg atggcagata agaaaaaatt tgaaaactgg      480
aaagatgacc ttcagaagga tagaacttac tgggagaatc aaatacagaa agatgtgcag      540
aatgttcggt cagagtttaa acgaatgagg gatatcatgg actctgagga agaaggaa       600
ttgcagaagc tgaggcaaga gaaggaagac attctcaaca acctggcaga gtctgaaagt      660
gagcatgctc agcagagcaa gttgctagaa gacttcatct cagatgtgga acatcagtta      720
cagtgctcag acatagaaat actgcagggt gtggagaaca tcatagaacg gagtcatact      780
ttttcgatga agaagcccaa agccatcgcc agggaacaaa gaaagttccg agcccctgac      840
ctgcaaggca tgctgcaagt gctgcaagag gtcacagagg ctcatcgcta ctag            894
```

<210> SEQ ID NO 24
<211> LENGTH: 297
<212> TYPE: PRT
<213> ORGANISM: Mus musculus

<400> SEQUENCE: 24

```
Met Ala Ser Gln Phe Met Lys Asn Leu Lys Glu Glu Val Thr Cys Pro
1               5                   10                  15

Val Cys Leu Asn Leu Met Val Lys Pro Val Ser Ala Asp Cys Gly His
                20                  25                  30

Thr Phe Cys Gln Gly Cys Ile Thr Leu Tyr Phe Glu Ser Ile Lys Cys
            35                  40                  45

Asp Lys Lys Val Phe Ile Cys Pro Val Cys Arg Ile Ser Tyr Gln Phe
        50                  55                  60

Ser Asn Leu Arg Pro Asn Arg Asn Val Ala Asn Ile Val Glu Arg Leu
65                  70                  75                  80

Lys Met Phe Lys Pro Ser Pro Glu Glu Gln Lys Val Phe Asn Cys
                85                  90                  95

Ala Arg His Gly Lys Lys Leu Gln Leu Phe Cys Arg Lys Asp Met Met
            100                 105                 110

Ala Ile Cys Trp Leu Cys Glu Arg Ser Gln Glu His Arg Gly His Lys
        115                 120                 125

Thr Ala Leu Ile Glu Glu Val Ala Gln Glu Tyr Lys Glu Gln Leu Gln
    130                 135                 140

Val Val Leu Gln Arg Leu Met Ala Asp Lys Lys Phe Glu Asn Trp
145                 150                 155                 160

Lys Asp Asp Leu Gln Lys Asp Arg Thr Tyr Trp Glu Asn Gln Ile Gln
                165                 170                 175

Lys Asp Val Gln Asn Val Arg Ser Glu Phe Lys Arg Met Arg Asp Ile
            180                 185                 190

Met Asp Ser Glu Glu Lys Glu Leu Gln Lys Leu Arg Gln Glu Lys
        195                 200                 205

Glu Asp Ile Leu Asn Asn Leu Ala Glu Ser Glu Ser Glu His Ala Gln
    210                 215                 220

Gln Ser Lys Leu Leu Glu Asp Phe Ile Ser Asp Val Glu His Gln Leu
225                 230                 235                 240
```

Gln Cys Ser Asp Ile Glu Ile Leu Gln Gly Val Asn Ile Ile Glu
            245                 250                 255

Arg Ser His Thr Phe Ser Met Lys Lys Pro Lys Ala Ile Ala Arg Glu
        260                 265                 270

Gln Arg Lys Phe Arg Ala Pro Asp Leu Gln Gly Met Leu Gln Val Leu
        275                 280                 285

Gln Glu Val Thr Glu Ala His Arg Tyr
    290                 295

<210> SEQ ID NO 25
<211> LENGTH: 1224
<212> TYPE: DNA
<213> ORGANISM: Homo sapiens

<400> SEQUENCE: 25

```
atggagctgc ttgaagaaga tctcacatgc cctatttgtt gtagtctgtt tgatgatcca      60
cgggttttgc cttgctccca aacttctgc aaaaaatgct agaaggtat cttagaaggg       120
agtgtgcgga attccttgtg agaccagct ccattcaagt gtcctacatg ccgtaaggaa     180
acttcagcta ctggaattaa tagcctgcag gttaattact ccctgaaggg tattgtggaa    240
aagtataaca agatcaagat ctctcccaaa atgccagtat gcaaaggaca cttggggcag    300
cctctcaaca ttttctgcct gactgatatg cagctgattt gtgggatctg tgctactcgt   360
ggggagcaca ccaaacatgt cttctgttct attgaagatg cctatgctca ggaaagggat    420
gcctttgagt ccctcttcca gagctttgag acctggcgtc ggggagatgc tctttctcgc   480
ttggataccct tggaaactag taagaggaaa tccctacagt tactgactaa agattcagat   540
aaagtgaagg aattttttga aagttacaa cacacactgg atcaaaagaa gaatgaaatt    600
ctgtctgact tgagaccat gaaacttgct gttatgcaag catatgaccc agagatcaac    660
aaactcaaca ccatcttgca ggagcaacgg atggccttta acattgctga ggctttcaaa   720
gatgtgtcag aacccattgt atttctgcaa cagatgcagg agtttagaga gaaaatcaaa   780
gtaatcaagg aaactccttt acctccctct aatttgcctg caagcccttt aatgaagaac   840
tttgatacca gtcagtggga agacataaaa ctagtcgatg tggataaaact ttctttgcct    900
caagacactg gcacattcat tagcaagatt ccctggagct tttataagtt atttttgcta    960
atccttctgc ttggccttgt cattgtcttt ggtcctacca tgttcctaga atggtcatta    1020
tttgatgacc tggcaacttg gaaaggctgt cttttcaaact tcagttccta tctgactaaa    1080
acagccgatt tcatagaaca atcagttttt tactgggaac aggtgacaga tgggtttttc   1140
attttcaatg aaagattcaa gaattttact ttggtggtac tgaacaatgt ggcagaattt    1200
gtgtgcaaat ataaactatt ataa                                             1224
```

<210> SEQ ID NO 26
<211> LENGTH: 407
<212> TYPE: PRT
<213> ORGANISM: Homo sapiens

<400> SEQUENCE: 26

Met Glu Leu Leu Glu Glu Asp Leu Thr Cys Pro Ile Cys Cys Ser Leu
1               5                   10                  15

Phe Asp Asp Pro Arg Val Leu Pro Cys Ser His Asn Phe Cys Lys Lys
            20                  25                  30

Cys Leu Glu Gly Ile Leu Glu Gly Ser Val Arg Asn Ser Leu Trp Arg
        35                  40                  45

```
Pro Ala Pro Phe Lys Cys Pro Thr Cys Arg Lys Glu Thr Ser Ala Thr
    50                  55                  60
Gly Ile Asn Ser Leu Gln Val Asn Tyr Ser Leu Lys Gly Ile Val Glu
65                  70                  75                  80
Lys Tyr Asn Lys Ile Lys Ile Ser Pro Lys Met Pro Val Cys Lys Gly
                85                  90                  95
His Leu Gly Gln Pro Leu Asn Ile Phe Cys Leu Thr Asp Met Gln Leu
            100                 105                 110
Ile Cys Gly Ile Cys Ala Thr Arg Gly Glu His Thr Lys His Val Phe
        115                 120                 125
Cys Ser Ile Glu Asp Ala Tyr Ala Gln Glu Arg Asp Ala Phe Glu Ser
    130                 135                 140
Leu Phe Gln Ser Phe Glu Thr Trp Arg Arg Gly Asp Ala Leu Ser Arg
145                 150                 155                 160
Leu Asp Thr Leu Glu Thr Ser Lys Arg Lys Ser Leu Gln Leu Leu Thr
                165                 170                 175
Lys Asp Ser Asp Lys Val Lys Glu Phe Phe Glu Lys Leu Gln His Thr
            180                 185                 190
Leu Asp Gln Lys Lys Asn Glu Ile Leu Ser Asp Phe Glu Thr Met Lys
        195                 200                 205
Leu Ala Val Met Gln Ala Tyr Asp Pro Glu Ile Asn Lys Leu Asn Thr
    210                 215                 220
Ile Leu Gln Glu Gln Arg Met Ala Phe Asn Ile Ala Glu Ala Phe Lys
225                 230                 235                 240
Asp Val Ser Glu Pro Ile Val Phe Leu Gln Gln Met Gln Glu Phe Arg
                245                 250                 255
Glu Lys Ile Lys Val Ile Lys Glu Thr Pro Leu Pro Pro Ser Asn Leu
            260                 265                 270
Pro Ala Ser Pro Leu Met Lys Asn Phe Asp Thr Ser Gln Trp Glu Asp
        275                 280                 285
Ile Lys Leu Val Asp Val Asp Lys Leu Ser Leu Pro Gln Asp Thr Gly
    290                 295                 300
Thr Phe Ile Ser Lys Ile Pro Trp Ser Phe Tyr Lys Leu Phe Leu Leu
305                 310                 315                 320
Ile Leu Leu Leu Gly Leu Val Ile Val Phe Gly Pro Thr Met Phe Leu
                325                 330                 335
Glu Trp Ser Leu Phe Asp Asp Leu Ala Thr Trp Lys Gly Cys Leu Ser
            340                 345                 350
Asn Phe Ser Ser Tyr Leu Thr Lys Thr Ala Asp Phe Ile Glu Gln Ser
        355                 360                 365
Val Phe Tyr Trp Glu Gln Val Thr Asp Gly Phe Phe Ile Phe Asn Glu
    370                 375                 380
Arg Phe Lys Asn Phe Thr Leu Val Val Leu Asn Asn Val Ala Glu Phe
385                 390                 395                 400
Val Cys Lys Tyr Lys Leu Leu
                405

<210> SEQ ID NO 27
<211> LENGTH: 1329
<212> TYPE: DNA
<213> ORGANISM: Homo sapiens

<400> SEQUENCE: 27
atggcgggcg cggcgaccgg gagccggacc cctgggaggt cggagcttgt cgagggatgc       60
```

```
ggctggcgct gcccggagca tggcgaccgc gtggctgagc tcttctgtcg ccgctgccgc      120
cgctgcgtgt gcgcgctttg cccggtgctg ggcgcgcacc gtggccaccc tgtgggcctg      180
gcgctggagg cagcggtgca cgtgcagaaa ctcagccaag aatgtttaaa gcagctggca      240
atcaagaagc agcagcacat tgacaacata acccagatag aagatgccac cgagaagctc      300
aaggctaatg cagagtcaag taaaacctgg ctgaagggga aattcactga actcagatta      360
ctacttgacg aagaggaagc gctggccaag aaattcattg ataaaaacac gcagcttacc      420
ctccaggtgt acagggaaca agctgactct gcagagagc aacttgacat catgaatgat       480
ctctccaaca gggtctggag tatcagccag gagcccgatc ctgtccagag gcttcaggca      540
tacacggcca ccgagcagga gatgcagcag cagatgagcc tcggggagct gtgccatccc      600
gtgcccctct cctttgagcc cgtcaagagc ttctttaagg gcctcgtgga agccgtggag      660
agtacattac agacgccatt ggacattcgc cttaaggaaa gcataaactg ccagctctca      720
gacccttcca gcaccaagcc aggtaccttg ttgaaaacca gccctcacc agagcgatcg       780 ctattgctga aatacgcgcg cacgcccacg ctggatcctg acacgatgca cgcgcgcctg      840
cgcctgtccg ccgatcgcct gacggtgcgc tgcggcctgc tgggcagcct ggggcccgtg      900
cccgtgctgc ggttcgacgc gctctggcaa gtgctggctc gtgactgctt cgccaccggc      960
cgccactact gggaggttga cgtgcaggag gcgggcgccg gctggtgggt gggcgcggcc     1020
tacgcctccc ttcggcgccg cggggcctcg gccgccgccc gcctgggctg caaccgccag     1080
tcctggtgcc tcaagcgcta cgaccttgag tactgggcct tccacgacgg ccagcgcagc     1140
cgcctgcggc cccgcgacga cctcgaccgg ctcggcgtct tcctggacta cgaggccggc     1200
gtcctcgcct tctacgacgt gacgggcggc atgagccacc tgcataccct tccgcgccacg    1260 ttccaggagc cgctctaccc ggccctgcgg ctctgggagg gggccatcag catcccccgg     1320
ctgccctag                                                             1329
```

<210> SEQ ID NO 28
<211> LENGTH: 442
<212> TYPE: PRT
<213> ORGANISM: Homo sapiens

<400> SEQUENCE: 28

```
Met Ala Gly Ala Ala Thr Gly Ser Arg Thr Pro Gly Arg Ser Glu Leu
1               5                   10                  15

Val Glu Gly Cys Gly Trp Arg Cys Pro Glu His Gly Asp Arg Val Ala
            20                  25                  30

Glu Leu Phe Cys Arg Arg Cys Arg Arg Cys Val Cys Ala Leu Cys Pro
        35                  40                  45

Val Leu Gly Ala His Arg Gly His Pro Val Gly Leu Ala Leu Glu Ala
    50                  55                  60

Ala Val His Val Gln Lys Leu Ser Gln Glu Cys Leu Lys Gln Leu Ala
65                  70                  75                  80

Ile Lys Lys Gln Gln His Ile Asp Asn Ile Thr Gln Ile Glu Asp Ala
                85                  90                  95

Thr Glu Lys Leu Lys Ala Asn Ala Glu Ser Ser Lys Thr Trp Leu Lys
            100                 105                 110

Gly Lys Phe Thr Glu Leu Arg Leu Leu Leu Asp Glu Glu Ala Leu
        115                 120                 125

Ala Lys Lys Phe Ile Asp Lys Asn Thr Gln Leu Thr Leu Gln Val Tyr
    130                 135                 140
```

```
Arg Glu Gln Ala Asp Ser Cys Arg Glu Gln Leu Asp Ile Met Asn Asp
145                 150                 155                 160

Leu Ser Asn Arg Val Trp Ser Ile Ser Gln Glu Pro Asp Pro Val Gln
                165                 170                 175

Arg Leu Gln Ala Tyr Thr Ala Thr Glu Gln Glu Met Gln Gln Gln Met
            180                 185                 190

Ser Leu Gly Glu Leu Cys His Pro Val Pro Leu Ser Phe Glu Pro Val
        195                 200                 205

Lys Ser Phe Phe Lys Gly Leu Val Glu Ala Val Glu Ser Thr Leu Gln
210                 215                 220

Thr Pro Leu Asp Ile Arg Leu Lys Glu Ser Ile Asn Cys Gln Leu Ser
225                 230                 235                 240

Asp Pro Ser Ser Thr Lys Pro Gly Thr Leu Leu Lys Thr Ser Pro Ser
                245                 250                 255

Pro Glu Arg Ser Leu Leu Lys Tyr Ala Arg Thr Pro Thr Leu Asp
            260                 265                 270

Pro Asp Thr Met His Ala Arg Leu Arg Leu Ser Ala Asp Arg Leu Thr
        275                 280                 285

Val Arg Cys Gly Leu Leu Gly Ser Leu Gly Pro Val Pro Val Leu Arg
    290                 295                 300

Phe Asp Ala Leu Trp Gln Val Leu Ala Arg Asp Cys Phe Ala Thr Gly
305                 310                 315                 320

Arg His Tyr Trp Glu Val Asp Val Gln Glu Ala Gly Ala Gly Trp Trp
                325                 330                 335

Val Gly Ala Ala Tyr Ala Ser Leu Arg Arg Gly Ala Ser Ala Ala
            340                 345                 350

Ala Arg Leu Gly Cys Asn Arg Gln Ser Trp Cys Leu Lys Arg Tyr Asp
        355                 360                 365

Leu Glu Tyr Trp Ala Phe His Asp Gly Gln Arg Ser Arg Leu Arg Pro
    370                 375                 380

Arg Asp Asp Leu Asp Arg Leu Gly Val Phe Leu Asp Tyr Glu Ala Gly
385                 390                 395                 400

Val Leu Ala Phe Tyr Asp Val Thr Gly Gly Met Ser His Leu His Thr
                405                 410                 415

Phe Arg Ala Thr Phe Gln Glu Pro Leu Tyr Pro Ala Leu Arg Leu Trp
            420                 425                 430

Glu Gly Ala Ile Ser Ile Pro Arg Leu Pro
        435                 440

<210> SEQ ID NO 29
<211> LENGTH: 1398
<212> TYPE: DNA
<213> ORGANISM: Homo sapiens

<400> SEQUENCE: 29
atgcccgcaa ccccgtccct gaaggtggtc catgagctgc ctgcctgtac cctctgtgcg    60
gggccgctgg aggatgcggt gaccattccc tgtggacaca ccttctgccg gctctgcctc   120
cccgcgctct cccagatggg ggcccaatcc tcgggcaaga tcctgctctg cccgctctgc   180
caagaggagg agcaggcaga gactcccatg gcccctgtgc cctgggccc gctgggagaa   240 acttactgcg aggagcacgg cgagaagatc tacttcttct gcgagaacga tgccgagttc   300
ctctgtgtgt ctgcaggga gggtcccacg caccaggcgc acaccgtggg gttcctggac   360
gaggccattc agccctaccg ggatcgtctc aggagtcgac tggaagctct gagcacggag   420
```

```
agagatgaga ttgaggatgt aaagtgtcaa gaagaccaga agcttcaagt gctgctgact      480
cagatcgaaa gcaagaagca tcaggtggaa acagcttttg agaggctgca gcaggagctg      540
gagcagcagc gatgtctcct gctggccagg ctgagggagc tggagcagca gatttggaag      600
gagagggatg aatatatcac aaaggtctct gaggaagtca cccggcttgg agcccaggtc      660
aaggagctgg aggagaagtg tcagcagcca gcaagtgagc ttctacaaga tgtcagagtc      720
aaccagagca ggtgtgagat gaagactttt gtgagtcctg aggccatttc tcctgacctt      780
gtcaagaaga tccgtgattt ccacaggaaa atactcaccc tcccagagat gatgaggatg      840
ttctcagaaa acttggcgca tcatctggaa atagattcag gggtcatcac tctggaccct      900
cagaccgcca gccggagcct ggttctctcg gaagacagga agtcagtgag gtacacccgg      960
cagaagaaga gcctgccaga cagcccctg cgcttcgacg gcctcccggc ggttctgggc     1020
ttcccgggct ctcctccgg gcgccaccgc tggcaggttg acctgcagct gggcgacggc     1080
ggcggctgca cggtggggt ggccggggag ggggtgagga ggaagggaga gatgggactc     1140
agcgccgagg acggcgtctg ggccgtgatc atctcgcacc agcagtgctg gccagcacc     1200 tccccgggca ccgacctgcc gctgagcgag atcccgcgcg cgtgagagt cgccctggac     1260 tacgaggcgg ggcaggtgac cctccacaac gcccagaccc aggagcccat cttcaccttc     1320
actgcctctt tctccggcaa agtcttccct ttctttgccg tctggaaaaa aggttcctgc     1380
cttacgctga aaggctga                                                   1398
```

<210> SEQ ID NO 30
<211> LENGTH: 465
<212> TYPE: PRT
<213> ORGANISM: Homo sapiens

<400> SEQUENCE: 30

```
Met Pro Ala Thr Pro Ser Leu Lys Val His Glu Leu Pro Ala Cys
1               5                   10                  15

Thr Leu Cys Ala Gly Pro Leu Glu Asp Ala Val Thr Ile Pro Cys Gly
            20                  25                  30

His Thr Phe Cys Arg Leu Cys Leu Pro Ala Leu Ser Gln Met Gly Ala
        35                  40                  45

Gln Ser Ser Gly Lys Ile Leu Leu Cys Pro Leu Cys Gln Glu Glu Glu
    50                  55                  60

Gln Ala Glu Thr Pro Met Ala Pro Val Pro Leu Gly Pro Leu Gly Glu
65                  70                  75                  80

Thr Tyr Cys Glu Glu His Gly Glu Lys Ile Tyr Phe Phe Cys Glu Asn
                85                  90                  95

Asp Ala Glu Phe Leu Cys Val Phe Cys Arg Glu Gly Pro Thr His Gln
            100                 105                 110

Ala His Thr Val Gly Phe Leu Asp Glu Ala Ile Gln Pro Tyr Arg Asp
        115                 120                 125

Arg Leu Arg Ser Arg Leu Glu Ala Leu Ser Thr Glu Arg Asp Glu Ile
    130                 135                 140

Glu Asp Val Lys Cys Gln Glu Asp Gln Lys Leu Gln Val Leu Leu Thr
145                 150                 155                 160

Gln Ile Glu Ser Lys Lys His Gln Val Glu Thr Ala Phe Glu Arg Leu
                165                 170                 175

Gln Gln Glu Leu Glu Gln Gln Arg Cys Leu Leu Leu Ala Arg Leu Arg
            180                 185                 190
```

```
Glu Leu Glu Gln Gln Ile Trp Lys Glu Arg Asp Glu Tyr Ile Thr Lys
            195                 200                 205

Val Ser Glu Glu Val Thr Arg Leu Gly Ala Gln Val Lys Glu Leu Glu
        210                 215                 220

Glu Lys Cys Gln Gln Pro Ala Ser Glu Leu Leu Gln Asp Val Arg Val
225                 230                 235                 240

Asn Gln Ser Arg Cys Glu Met Lys Thr Phe Val Ser Pro Glu Ala Ile
                245                 250                 255

Ser Pro Asp Leu Val Lys Lys Ile Arg Asp Phe His Arg Lys Ile Leu
            260                 265                 270

Thr Leu Pro Glu Met Met Arg Met Phe Ser Glu Asn Leu Ala His His
        275                 280                 285

Leu Glu Ile Asp Ser Gly Val Ile Thr Leu Asp Pro Gln Thr Ala Ser
290                 295                 300

Arg Ser Leu Val Leu Ser Glu Asp Arg Lys Ser Val Arg Tyr Thr Arg
305                 310                 315                 320

Gln Lys Lys Ser Leu Pro Asp Ser Pro Leu Arg Phe Asp Gly Leu Pro
                325                 330                 335

Ala Val Leu Gly Phe Pro Gly Phe Ser Ser Gly Arg His Arg Trp Gln
            340                 345                 350

Val Asp Leu Gln Leu Gly Asp Gly Gly Cys Thr Val Gly Val Ala
        355                 360                 365

Gly Glu Gly Val Arg Arg Lys Gly Glu Met Gly Leu Ser Ala Glu Asp
            370                 375                 380

Gly Val Trp Ala Val Ile Ile Ser His Gln Gln Cys Trp Ala Ser Thr
385                 390                 395                 400

Ser Pro Gly Thr Asp Leu Pro Leu Ser Glu Ile Pro Arg Gly Val Arg
                405                 410                 415

Val Ala Leu Asp Tyr Glu Ala Gly Gln Val Thr Leu His Asn Ala Gln
            420                 425                 430

Thr Gln Glu Pro Ile Phe Thr Phe Thr Ala Ser Phe Ser Gly Lys Val
        435                 440                 445

Phe Pro Phe Phe Ala Val Trp Lys Lys Gly Ser Cys Leu Thr Leu Lys
450                 455                 460

Gly
465

<210> SEQ ID NO 31
<211> LENGTH: 1695
<212> TYPE: DNA
<213> ORGANISM: Homo sapiens

<400> SEQUENCE: 31
atggctgagt tggatctaat ggctccaggg ccactgccca gggccactgc tcagccccca      60
gcccctctca gcccagactc tgggtcaccc agcccagatt ctgggtcagc cagcccagtg     120
gaagaagagg acgtgggctc ctcggagaag cttggcaggg agacggagga acaggacagc     180
gactctgcag agcagggggga tcctgctggt gaggggaaag aggtcctgtg tgacttctgc     240
cttgatgaca ccagaagagt gaaggcagtg aagtcctgtc taacctgcat ggtgaattac     300
tgtgaagagc acttgcagcc gcatcaggtg aacatcaaac tgcaaagcca cctgctgacc     360
gagccagtga aggaccacaa ctggcgatac tgccctgccc accacagccc actgtctgcc     420
ttctgctgcc ctgatcagca gtgcatctgc caggactgtt gccaggagca cagtggccac     480
accatagtct ccctggatgc agcccgcagg gacaaggagg ctgaactcca gtgcacccag     540
```

-continued

```
ttagacttgg agcggaaact caagttgaat gaaaatgcca tctccaggct ccaggctaac      600
caaaagtctg ttctggtgtc ggtgtcagag gtcaaagcgg tggctgaaat gcagtttggg      660
gaactccttg ctgctgtgag gaaggcccag gccaatgtga tgctcttctt agaggagaag      720
gagcaagctg cgctgagcca ggccaacggt atcaaggccc acctggagta caggagtgcc      780
gagatggaga agagcaagca ggagctggag aggatggcgg ccatcagcaa cactgtccag      840
ttcttggagg agtactgcaa gtttaagaac actgaagaca tcaccttccc tagtgtttac      900
gtagggctga aggataaact ctcgggcatc cgcaaagtta tcacggaatc cactgtacac      960
ttaatccagt tgctggagaa ctataagaaa aagctccagg agttttccaa ggaagaggag     1020
tatgacatca gaactcaagt gtctgccgtt gttcagcgca aatattggac ttccaaacct     1080
gagcccagca ccagggaaca gttcctccaa tatgcgtatg acatcacgtt tgacccggac     1140
acagcacaca gtatctccg gctgcaggag gagaaccgca aggtcaccaa caccacgccc     1200
tgggagcatc cctacccgga cctccccagc aggttcctgc actggcggca ggtgctgtcc     1260
cagcagagtc tgtacctgca caggtactat tttgaggtgg agatcttcgg ggcaggcacc     1320
tatgttggcc tgacctgcaa aggcatcgac cggaaagggg aggagcgcaa cagttgcatt     1380
tccggaaaca acttctcctg gagcctccaa tggaacggga aggagttcac ggcctggtac     1440
agtgacatgg agaccccact caaagctggc cctttccgga ggctcggggt ctatatcgac     1500
ttcccgggag ggatcctttc cttctatggc gtagagtatg ataccatgac tctggttcac     1560
aagtttgcct gcaaattttc agaaccagtc tatgctgcct tctggctttc caagaaggaa     1620
aacgccatcc ggattgtaga tctgggagag gaacccgaga agccagcacc gtccttggtg     1680
gggactgctc cctag                                                       1695
```

<210> SEQ ID NO 32
<211> LENGTH: 564
<212> TYPE: PRT
<213> ORGANISM: Homo sapiens

<400> SEQUENCE: 32

```
Met Ala Glu Leu Asp Leu Met Ala Pro Gly Pro Leu Pro Arg Ala Thr
1               5                   10                  15

Ala Gln Pro Pro Ala Pro Leu Ser Pro Asp Ser Gly Ser Pro Ser Pro
                20                  25                  30

Asp Ser Gly Ser Ala Ser Pro Val Glu Glu Asp Val Gly Ser Ser
            35                  40                  45

Glu Lys Leu Gly Arg Glu Thr Glu Glu Gln Asp Ser Asp Ser Ala Glu
    50                  55                  60

Gln Gly Asp Pro Ala Gly Glu Gly Lys Glu Val Leu Cys Asp Phe Cys
65                  70                  75                  80

Leu Asp Asp Thr Arg Arg Val Lys Ala Val Lys Ser Cys Leu Thr Cys
                85                  90                  95

Met Val Asn Tyr Cys Glu Glu His Leu Gln Pro His Gln Val Asn Ile
                100                 105                 110

Lys Leu Gln Ser His Leu Leu Thr Glu Pro Val Lys Asp His Asn Trp
            115                 120                 125

Arg Tyr Cys Pro Ala His His Ser Pro Leu Ser Ala Phe Cys Cys Pro
        130                 135                 140

Asp Gln Gln Cys Ile Cys Gln Asp Cys Cys Gln Glu His Ser Gly His
145                 150                 155                 160
```

```
Thr Ile Val Ser Leu Asp Ala Ala Arg Arg Asp Lys Glu Ala Glu Leu
            165                 170                 175

Gln Cys Thr Gln Leu Asp Leu Glu Arg Lys Leu Lys Leu Asn Glu Asn
        180                 185                 190

Ala Ile Ser Arg Leu Gln Ala Asn Gln Lys Ser Val Leu Val Ser Val
            195                 200                 205

Ser Glu Val Lys Ala Val Ala Glu Met Gln Phe Gly Glu Leu Leu Ala
210                 215                 220

Ala Val Arg Lys Ala Gln Ala Asn Val Met Leu Phe Leu Glu Glu Lys
225                 230                 235                 240

Glu Gln Ala Ala Leu Ser Gln Ala Asn Gly Ile Lys Ala His Leu Glu
                245                 250                 255

Tyr Arg Ser Ala Glu Met Glu Lys Ser Lys Gln Glu Leu Glu Arg Met
            260                 265                 270

Ala Ala Ile Ser Asn Thr Val Gln Phe Leu Glu Glu Tyr Cys Lys Phe
            275                 280                 285

Lys Asn Thr Glu Asp Ile Thr Phe Pro Ser Val Tyr Val Gly Leu Lys
        290                 295                 300

Asp Lys Leu Ser Gly Ile Arg Lys Val Ile Thr Glu Ser Thr Val His
305                 310                 315                 320

Leu Ile Gln Leu Leu Glu Asn Tyr Lys Lys Lys Leu Gln Glu Phe Ser
                325                 330                 335

Lys Glu Glu Glu Tyr Asp Ile Arg Thr Gln Val Ser Ala Val Val Gln
                340                 345                 350

Arg Lys Tyr Trp Thr Ser Lys Pro Glu Pro Ser Thr Arg Glu Gln Phe
            355                 360                 365

Leu Gln Tyr Ala Tyr Asp Ile Thr Phe Asp Pro Asp Thr Ala His Lys
        370                 375                 380

Tyr Leu Arg Leu Gln Glu Glu Asn Arg Lys Val Thr Asn Thr Thr Pro
385                 390                 395                 400

Trp Glu His Pro Tyr Pro Asp Leu Pro Ser Arg Phe Leu His Trp Arg
                405                 410                 415

Gln Val Leu Ser Gln Gln Ser Leu Tyr Leu His Arg Tyr Tyr Phe Glu
                420                 425                 430

Val Glu Ile Phe Gly Ala Gly Thr Tyr Val Gly Leu Thr Cys Lys Gly
            435                 440                 445

Ile Asp Arg Lys Gly Glu Glu Arg Asn Ser Cys Ile Ser Gly Asn Asn
        450                 455                 460

Phe Ser Trp Ser Leu Gln Trp Asn Gly Lys Glu Phe Thr Ala Trp Tyr
465                 470                 475                 480

Ser Asp Met Glu Thr Pro Leu Lys Ala Gly Pro Phe Arg Arg Leu Gly
                485                 490                 495

Val Tyr Ile Asp Phe Pro Gly Gly Ile Leu Ser Phe Tyr Gly Val Glu
            500                 505                 510

Tyr Asp Thr Met Thr Leu Val His Lys Phe Ala Cys Lys Phe Ser Glu
        515                 520                 525

Pro Val Tyr Ala Ala Phe Trp Leu Ser Lys Lys Glu Asn Ala Ile Arg
530                 535                 540

Ile Val Asp Leu Gly Glu Glu Pro Glu Lys Pro Ala Pro Ser Leu Val
545                 550                 555                 560

Gly Thr Ala Pro

<210> SEQ ID NO 33
```

```
<211> LENGTH: 1434
<212> TYPE: DNA
<213> ORGANISM: Homo sapiens

<400> SEQUENCE: 33
atggaggctg tggaactcgc cagaaaactg caggaggaag ctacgtgctc catctgtctg      60
gattacttca cagaccctgt gatgaccacc tgtggccaca acttctgccg agcctgcatc     120
cagctgagct gggaaaaggc gaggggcaag aaggggaggc ggaagcggaa gggctccttc     180
ccctgccccg agtgcagaga gatgtccccg cagaggaacc tgctgcccaa ccggctgctg     240
accaaggtgg ccgagatggc gcagcagcat cctggtctgc agaagcaaga cctgtgccag     300
gagcaccacg agccctcaa gcttttctgc cagaaggacc agagccccat ctgtgtggtg      360
tgcagggagt cccgggagca ccggctgcac agggtgctgc cgccgaggac ggcagtgcag     420
gggtacaagt tgaagctgga ggaggacatg gagtaccttc gggagcagat caccaggaca     480
gggaatctgc aggccaggga ggagcagagc ttagccgagt ggcagggcaa ggtgaaggag     540
cggagagaac gcattgtgct ggagtttgag aagatgaacc tctacctggt ggaagaagag     600
cagaggctcc tccaggctct ggagacggaa gaagaggaga ctgccagcag gctccgggag     660
agcgtggcct gcctggaccg gcagggtcac tctctggagc tgctgctgct gcagctggag     720
gagcggagca cacaggggcc cctccagatg ctgcaggaca tgaaggaacc cctgagcagg     780
aagaacaacg tgagtgtgca gtgcccagag gttgcccccc caaccagacc caggactgtg     840
tgcagagttc ccggacagat tgaagtgcta agaggctttc taggatgt ggtgcctgat       900 gccacctccg cgtaccccta cctcctcctg tatgagagcc gccagaggcg ctacctcggc     960
tcttcgccgg agggcagtgg gttctgcagc aaggaccgat tgtggctta ccctgtgct     1020 gtgggccaga cggccttctc ctctgggagg cactactggg aggtgggcat gaacatcacc    1080
ggggacgcgt tgtgggccct gggtgtgtgc agggacaacg tgagccggaa agacagggtc    1140
cccaagtgcc ccgaaaacgg cttctgggtg gtgcagctgt ccaagggggac caagtactta    1200 tccaccttct ctgccctaac cccggtcatg ctgatggagc ctcccagcca catgggcatc    1260
ttcctggact cgaagccgg ggaagtgtcc ttctacagtg taagcgatgg gtcccacctg    1320
cacacctact cccaggccac cttcccaggc ccctgcagc ctttcttctg cctggggct     1380 ccgaagtctg gtcagatggt catctccaca gtgaccatgt gggtgaaagg atag          1434

<210> SEQ ID NO 34
<211> LENGTH: 477
<212> TYPE: PRT
<213> ORGANISM: Homo sapiens

<400> SEQUENCE: 34

Met Glu Ala Val Glu Leu Ala Arg Lys Leu Gln Glu Glu Ala Thr Cys
1               5                   10                  15

Ser Ile Cys Leu Asp Tyr Phe Thr Asp Pro Val Met Thr Thr Cys Gly
            20                  25                  30

His Asn Phe Cys Arg Ala Cys Ile Gln Leu Ser Trp Glu Lys Ala Arg
        35                  40                  45

Gly Lys Lys Gly Arg Arg Lys Gly Ser Phe Pro Cys Pro Glu
    50                  55                  60

Cys Arg Glu Met Ser Pro Gln Arg Asn Leu Leu Pro Asn Arg Leu Leu
65                  70                  75                  80

Thr Lys Val Ala Glu Met Ala Gln Gln His Pro Gly Leu Gln Lys Gln
                85                  90                  95
```

```
Asp Leu Cys Gln Glu His His Glu Pro Leu Lys Leu Phe Cys Gln Lys
                100                 105                 110

Asp Gln Ser Pro Ile Cys Val Val Cys Arg Glu Ser Arg Glu His Arg
            115                 120                 125

Leu His Arg Val Leu Pro Ala Glu Glu Ala Val Gln Gly Tyr Lys Leu
        130                 135                 140

Lys Leu Glu Glu Asp Met Glu Tyr Leu Arg Glu Gln Ile Thr Arg Thr
145                 150                 155                 160

Gly Asn Leu Gln Ala Arg Glu Gln Ser Leu Ala Glu Trp Gln Gly
                165                 170                 175

Lys Val Lys Glu Arg Arg Glu Arg Ile Val Leu Glu Phe Glu Lys Met
                180                 185                 190

Asn Leu Tyr Leu Val Glu Glu Gln Arg Leu Leu Gln Ala Leu Glu
            195                 200                 205

Thr Glu Glu Glu Glu Thr Ala Ser Arg Leu Arg Glu Ser Val Ala Cys
        210                 215                 220

Leu Asp Arg Gln Gly His Ser Leu Glu Leu Leu Leu Gln Leu Glu
225                 230                 235                 240

Glu Arg Ser Thr Gln Gly Pro Leu Gln Met Leu Gln Asp Met Lys Glu
                245                 250                 255

Pro Leu Ser Arg Lys Asn Asn Val Ser Val Gln Cys Pro Glu Val Ala
            260                 265                 270

Pro Pro Thr Arg Pro Arg Thr Val Cys Arg Val Pro Gly Gln Ile Glu
        275                 280                 285

Val Leu Arg Gly Phe Leu Glu Asp Val Val Pro Asp Ala Thr Ser Ala
290                 295                 300

Tyr Pro Tyr Leu Leu Leu Tyr Glu Ser Arg Gln Arg Tyr Leu Gly
305                 310                 315                 320

Ser Ser Pro Glu Gly Ser Gly Phe Cys Ser Lys Asp Arg Phe Val Ala
                325                 330                 335

Tyr Pro Cys Ala Val Gly Gln Thr Ala Phe Ser Ser Gly Arg His Tyr
            340                 345                 350

Trp Glu Val Gly Met Asn Ile Thr Gly Asp Ala Leu Trp Ala Leu Gly
        355                 360                 365

Val Cys Arg Asp Asn Val Ser Arg Lys Asp Arg Val Pro Lys Cys Pro
370                 375                 380

Glu Asn Gly Phe Trp Val Val Gln Leu Ser Lys Gly Thr Lys Tyr Leu
385                 390                 395                 400

Ser Thr Phe Ser Ala Leu Thr Pro Val Met Leu Met Glu Pro Pro Ser
                405                 410                 415

His Met Gly Ile Phe Leu Asp Phe Glu Ala Gly Glu Val Ser Phe Tyr
            420                 425                 430

Ser Val Ser Asp Gly Ser His Leu His Thr Tyr Ser Gln Ala Thr Phe
        435                 440                 445

Pro Gly Pro Leu Gln Pro Phe Phe Cys Leu Gly Ala Pro Lys Ser Gly
450                 455                 460

Gln Met Val Ile Ser Thr Val Thr Met Trp Val Lys Gly
465                 470                 475

<210> SEQ ID NO 35
<211> LENGTH: 1945
<212> TYPE: DNA
<213> ORGANISM: Homo sapiens
```

<400> SEQUENCE: 35

```
atggaaacac tggagtcaga actgacctgc cctatttgtc tggagctctt tgaggaccct      60
cttctactgc cctgcgcaca cagcctctgc ttcaactgcg cccaccgcat cctagtatca     120
cactgtgcca ccaacgagtc tgtggagtcc atcaccgcct ccagtgccc acctgccgg       180
catgtcatca ccctcagcca gcgaggtcta gacgggctca gcgcaacgt caccctacag      240
aacatcatcg acaggttcca gaaagcatca gtgagcgggc caactctcc cagcgagacc      300
cgtcgggagc gggcctttga cgccaacacc atgacctccg ccgagaaggt cctctgccag     360
tttttgtgacc aggatcctgc ccaggacgct gtgaagacct gtgtcacttg tgaagtatcc    420
tactgtgacg agtgcctgaa agccactcac ccgaataaga agcccttac aggccatcgt     480
ctgattgagc caattccgga ctctcacatc cgggggctga tgtgcttgga gcatgaggat     540
gagaaggtga atatgtactg tgtgaccgat gaccagttaa tctgtgcctt gtgtaaactg     600
gttgggcggc accgcgatca tcaggtggca gctttgagtg agcgctatga caaattgaag     660
caaaacttag agagtaacct caccaacctt attaagagga cacagaact ggagacccct     720
ttggctaaac tcatccaaac ctgtcaacat gttgaagtca atgcatcacg tcaagaagcc     780
aaattgacag aggagtgtga tcttctcatt gagatcattc agcaaagacg acagattatt    840
ggaaccaaga tcaaagaagg gaaggtgatg aggcttcgca aactggctca gcagattgca    900
aactgcaaac agtgcattga gcggtcagca tcactcatct cccaagcgga cactctctg    960
aaggagaatg atcatgcgcg tttcctacag actgctaaga atatcaccga gagagtctcc    1020
atggcaactg catcctccca ggttctaatt cctgaaatca acctcaatga cacatttgac    1080
acctttgcct tagatttttc ccgagagaag aaactgctag aatgtctgga ttaccttaca    1140
gctcccaacc ctcccacaat tagagaagag ctctgcacag cttcatatga caccatcact    1200
gtgcattgga cctccgatga tgagttcagc gtggtctcct acgagctcca gtacaccata    1260
ttcaccggac aagccaacgt cgttagtctg tgtaattcgg ctgatagctg gatgatagta    1320
cccaacatca agcagaacca ctacacggtg cacggtctgc agagcggcac caagtacatc    1380
ttcatggtca aggccatcaa ccaggcgggc agccgcagca gtgagcctgg gaagttgaag    1440
acaaacagcc aaccatttaa actggatccc aaatctgctc atcgaaaact gaaggtgtcc    1500
catgataact tgacagtaga acgtgatgag tcatcatcca agaagagtca cacacctgaa    1560
cgcttcacca gccaggggag ctatggagta gctggaaatg tgtttattga tagtggccgg    1620
cattattggg aagtggtcat aagtggaagc acatggtatg ccattggtct tgcttacaaa    1680
tcagccccga agcatgaatg gattgggaag aactctgctt cctgggcgct ctgccgctgc    1740
aacaataact gggtggtgag acacaatagc aaggaaatcc ccattgagcc tgccccccac    1800
ctccggcgcg tgggcatcct gctggactat gataacggct ctatcgcctt ttatgatgct    1860
ttgaactcca tccacctcta caccttcgac gtcgcatttg cgcagcctgt ttgccccacc    1920
ttcaccgtgt ggaacaagtg tctga                                          1945
```

<210> SEQ ID NO 36
<211> LENGTH: 667
<212> TYPE: PRT
<213> ORGANISM: Homo sapiens

<400> SEQUENCE: 36

```
Met Glu Thr Leu Glu Ser Glu Leu Thr Cys Pro Ile Cys Leu Glu Leu
1               5                   10                  15
```

-continued

```
Phe Glu Asp Pro Leu Leu Pro Cys Ala His Ser Leu Cys Phe Asn
             20              25              30

Cys Ala His Arg Ile Leu Val Ser His Cys Ala Thr Asn Glu Ser Val
         35              40              45

Glu Ser Ile Thr Ala Phe Gln Cys Pro Thr Cys Arg His Val Ile Thr
     50              55              60

Leu Ser Gln Arg Gly Leu Asp Gly Leu Lys Arg Asn Val Thr Leu Gln
 65              70              75              80

Asn Ile Ile Asp Arg Phe Gln Lys Ala Ser Val Ser Gly Pro Asn Ser
                 85              90              95

Pro Ser Glu Thr Arg Arg Glu Arg Ala Phe Asp Ala Asn Thr Met Thr
             100             105             110

Ser Ala Glu Lys Val Leu Cys Gln Phe Cys Asp Gln Asp Pro Ala Gln
             115             120             125

Asp Ala Val Lys Thr Cys Val Thr Cys Glu Val Ser Tyr Cys Asp Glu
         130             135             140

Cys Leu Lys Ala Thr His Pro Asn Lys Lys Pro Phe Thr Gly His Arg
145             150             155             160

Leu Ile Glu Pro Ile Pro Asp Ser His Ile Arg Gly Leu Met Cys Leu
                 165             170             175

Glu His Glu Asp Glu Lys Val Asn Met Tyr Cys Val Thr Asp Asp Gln
             180             185             190

Leu Ile Cys Ala Leu Cys Lys Leu Val Gly Arg His Arg Asp His Gln
         195             200             205

Val Ala Ala Leu Ser Glu Arg Tyr Asp Lys Leu Lys Gln Asn Leu Glu
 210             215             220

Ser Asn Leu Thr Asn Leu Ile Lys Arg Asn Thr Glu Leu Glu Thr Leu
225             230             235             240

Leu Ala Lys Leu Ile Gln Thr Cys Gln His Val Glu Val Asn Ala Ser
                 245             250             255

Arg Gln Glu Ala Lys Leu Thr Glu Glu Cys Asp Leu Leu Ile Glu Ile
             260             265             270

Ile Gln Gln Arg Arg Gln Ile Ile Gly Thr Lys Ile Lys Glu Gly Lys
         275             280             285

Val Met Arg Leu Arg Lys Leu Ala Gln Gln Ile Ala Asn Cys Lys Gln
 290             295             300

Cys Ile Glu Arg Ser Ala Ser Leu Ile Ser Gln Ala Glu His Ser Leu
305             310             315             320

Lys Glu Asn Asp His Ala Arg Phe Leu Gln Thr Ala Lys Asn Ile Thr
                 325             330             335

Glu Arg Val Ser Met Ala Thr Ala Ser Ser Gln Val Leu Ile Pro Glu
             340             345             350

Ile Asn Leu Asn Asp Thr Phe Asp Thr Phe Ala Leu Asp Phe Ser Arg
         355             360             365

Glu Lys Lys Leu Leu Glu Cys Leu Asp Tyr Leu Thr Ala Pro Asn Pro
 370             375             380

Pro Thr Ile Arg Glu Glu Leu Cys Thr Ala Ser Tyr Asp Thr Ile Thr
385             390             395             400

Val His Trp Thr Ser Asp Glu Phe Ser Val Ser Tyr Glu Leu
                 405             410             415

Gln Tyr Thr Ile Phe Thr Gly Gln Ala Asn Val Ser Leu Cys Asn
             420             425             430

Ser Ala Asp Ser Trp Met Ile Val Pro Asn Ile Lys Gln Asn His Tyr
```

```
                435                 440                 445
Thr Val His Gly Leu Gln Ser Gly Thr Lys Tyr Ile Phe Met Val Lys
            450                 455                 460

Ala Ile Asn Gln Ala Gly Ser Arg Ser Ser Glu Pro Gly Lys Leu Lys
465                 470                 475                 480

Thr Asn Ser Gln Pro Phe Lys Leu Asp Pro Lys Ser Ala His Arg Lys
                485                 490                 495

Leu Lys Val Ser His Asp Asn Leu Thr Val Glu Arg Asp Glu Ser Ser
            500                 505                 510

Ser Lys Lys Ser His Thr Pro Glu Arg Phe Thr Ser Gln Gly Ser Tyr
        515                 520                 525

Gly Val Ala Gly Asn Val Phe Ile Asp Ser Gly Arg His Tyr Trp Glu
    530                 535                 540

Val Val Ile Ser Gly Ser Thr Trp Tyr Ala Ile Gly Leu Ala Tyr Lys
545                 550                 555                 560

Ser Ala Pro Lys His Glu Trp Ile Gly Lys Asn Ser Ala Ser Trp Ala
                565                 570                 575

Leu Cys Arg Cys Asn Asn Asn Trp Val Val Arg His Asn Ser Lys Glu
            580                 585                 590

Ile Pro Ile Glu Pro Ala Pro His Leu Arg Arg Val Gly Ile Leu Leu
        595                 600                 605

Asp Tyr Asp Asn Gly Ser Ile Ala Phe Tyr Asp Ala Leu Asn Ser Ile
    610                 615                 620

His Leu Tyr Thr Phe Asp Val Ala Phe Ala Gln Pro Val Cys Pro Thr
625                 630                 635                 640

Phe Thr Val Trp Asn Lys Cys Leu Thr Ile Ile Thr Gly Leu Pro Ile
                645                 650                 655

Pro Asp His Leu Asp Cys Thr Glu Gln Leu Pro
            660                 665

<210> SEQ ID NO 37
<211> LENGTH: 2649
<212> TYPE: DNA
<213> ORGANISM: Homo sapiens

<400> SEQUENCE: 37
atggagcctg caccegcccg atctccgagg ccccagcagg accccgcccg gccccaggag        60
cccaccatgc ctccccccga ccccctctct gaaggccgcc agcccagccc cagccccagc       120
cctacagagc gagcccccgc ttcggaggag gagttccagt ttctgcgctg ccagcaatgc       180
caggcggaag ccaagtgccc gaagctgctg ccttgtctgc acacgctgtg ctcaggatgc       240
ctggaggcgt cgggcatgca gtgccccatc tgccaggcgc cctggcccct aggtgcagac       300
acacccgccc tggataacgt cttttttcgag agtctgcagc ggcgcctgtc ggtgtaccgg       360
cagattgtgg atgcgcaggc tgtgtgcacc cgctgcaaag agtcggccga cttctggtgc       420
tttgagtgcg agcagctcct ctgcgccaag tgcttcgagg cacaccagtg gttcctcaag       480
cacgaggccc ggcccctagc agagctgcgc aaccagtcgg tgcgtgagtt cctggacggc       540
acccgcaaga ccaacaacat cttctgctcc aaccccaacc accgccccc tacgctgacc       600 agcatctact gccgaggatg ttccaagccg ctgtgctgct cgtgcgcgct ccttgacagc       660
agccacagtg agctcaagtg cgacatcagc gcagagatcc agcagcgaca ggaggagctg       720
gacgccatga cgcaggcgct gcaggagcag gatagtgcct ttggcgcggt tcacgcgcag       780
atgcacgcgg ccgtcggcca gctgggccgc gcgcgtgccg agaccgagga gctgatccgc       840
```

```
gagcgcgtgc gccaggtggt agctcacgtg cgggctcagg agcgcgagct gctggaggct      900
gtggacgcgc ggtaccagcg cgactacgag gagatggcca gtcggctggg ccgcctggat      960
gctgtgctgc agcgcatccg cacgggcagc gcgctggtgc agaggatgaa gtgctacgcc     1020
tcggaccagg aggtgctgga catgcacggt ttcctgcgcc aggcgctctg ccgcctgcgc     1080
caggaggagc cccagagcct gcaagctgcc gtgcgcaccg atggcttcga cgagttcaag     1140
gtgcgcctgc aggacctcag ctcttgcatc acccagggga agatgcagc tgtatccaag      1200 aaagccagcc cagaggctgc cagcactccc agggaccta ttgacgttga cctgcccgag      1260
gaggcagaga gagtgaaggc ccaggttcag gccctggggc tggctgaagc ccagcctatg     1320
gctgtggtac agtcagtgcc cggggcacac cccgtgccag tgtacgcctt ctccatcaaa     1380
ggcccttcct atggagagga tgtctccaat acaacgacag cccagaagag gaagtgcagc     1440
cagacccagt gccccaggaa ggtcatcaag atggagtctg aggaggggaa ggaggcaagg     1500
ttggctcgga gctccccgga gcagcccagg cccagcacct ccaaggcagt ctcaccaccc     1560
cacctggatg gaccgcctag ccccaggagc cccgtcatag gaagtgaggt cttcctgccc     1620
aacagcaacc acgtggccag tggcgccggg gaggcagagg aacgcgttgt ggtgatcagc     1680
agctcggaag actcagatgc cgaaaactcg tcctcccgag agctggatga cagcagcagt     1740
gagtccagtg acctccagct ggaaggcccc agcaccctca gggtcctgga cgagaacctt     1800
gctgaccccc aagcagaaga cagacctctg gtttttctttg acctcaagat tgacaatgaa     1860
acccagaaga ttagccagct ggctgcggtg aaccgggaaa gcaagttccg cgtggtcatc     1920
cagcctgaag ccttcttcag catctactcc aaggccgtgt ccctggaggt ggggctgcag     1980
cacttcctca gctttctgag ctccatgcgc cgccctatct tggcctgcta caagctgtgg     2040
gggcctggcc tcccaaactt cttccgggcc ctggaggaca ttaacaggct gtgggaattc     2100
caggaggcca tctcgggctt cctggctgcc ctgcctctca tccggagcg tgtgcccggg     2160 gccagcagct tcaaactcaa gaacctggcc cagacctacc tggcgagaaa catgagcgag     2220
cgcagcgcca tggctgccgt gctggccatg cgtgacctgt gccgcctcct cgaggtctcc     2280
ccgggccccc agctggccca gcatgtctac cccttcagta gcctgcagtg ctttgcctcc     2340
ctgcagcccc tggtgcaggc agctgtgctg ccccgggctg aggcccgcct cctggcccta     2400
cacaacgtga gcttcatgga gctgctgagt gcacaccgcc gtgaccggca ggggggcctg     2460
aagaagtaca gccgctatct aagcctgcag accaccacgt tgcccctgc ccagcctgct      2520 ttcaacctgc aggctctggg cacctacttt gaaggcctgt ggagggtcc ggcgctggca     2580 cgggcagaag gagtctccac cccacttgct ggccgtggct tggcagagag gcctcccag     2640 cagagctga                                                              2649
```

<210> SEQ ID NO 38
<211> LENGTH: 882
<212> TYPE: PRT
<213> ORGANISM: Homo sapiens

<400> SEQUENCE: 38

Met Glu Pro Ala Pro Ala Arg Ser Pro Arg Pro Gln Gln Asp Pro Ala
1               5                   10                  15

Arg Pro Gln Glu Pro Thr Met Pro Pro Glu Thr Pro Ser Glu Gly
            20                  25                  30

Arg Gln Pro Ser Pro Ser Pro Ser Pro Thr Glu Arg Ala Pro Ala Ser
        35                  40                  45

-continued

```
Glu Glu Glu Phe Gln Phe Leu Arg Cys Gln Gln Cys Gln Ala Glu Ala
    50                  55                  60
Lys Cys Pro Lys Leu Leu Pro Cys Leu His Thr Leu Cys Ser Gly Cys
65                  70                  75                  80
Leu Glu Ala Ser Gly Met Gln Cys Pro Ile Cys Gln Ala Pro Trp Pro
                85                  90                  95
Leu Gly Ala Asp Thr Pro Ala Leu Asp Asn Val Phe Phe Glu Ser Leu
            100                 105                 110
Gln Arg Arg Leu Ser Val Tyr Arg Gln Ile Val Asp Ala Gln Ala Val
                115                 120                 125
Cys Thr Arg Cys Lys Glu Ser Ala Asp Phe Trp Cys Phe Glu Cys Glu
            130                 135                 140
Gln Leu Leu Cys Ala Lys Cys Phe Glu Ala His Gln Trp Phe Leu Lys
145                 150                 155                 160
His Glu Ala Arg Pro Leu Ala Glu Leu Arg Asn Gln Ser Val Arg Glu
                165                 170                 175
Phe Leu Asp Gly Thr Arg Lys Thr Asn Asn Ile Phe Cys Ser Asn Pro
            180                 185                 190
Asn His Arg Thr Pro Thr Leu Thr Ser Ile Tyr Cys Arg Gly Cys Ser
                195                 200                 205
Lys Pro Leu Cys Cys Ser Cys Ala Leu Leu Asp Ser Ser His Ser Glu
    210                 215                 220
Leu Lys Cys Asp Ile Ser Ala Glu Ile Gln Gln Arg Gln Glu Glu Leu
225                 230                 235                 240
Asp Ala Met Thr Gln Ala Leu Gln Glu Gln Asp Ser Ala Phe Gly Ala
                245                 250                 255
Val His Ala Gln Met His Ala Ala Val Gly Gln Leu Gly Arg Ala Arg
            260                 265                 270
Ala Glu Thr Glu Glu Leu Ile Arg Glu Arg Val Arg Gln Val Val Ala
                275                 280                 285
His Val Arg Ala Gln Glu Arg Glu Leu Leu Glu Ala Val Asp Ala Arg
            290                 295                 300
Tyr Gln Arg Asp Tyr Glu Glu Met Ala Ser Arg Leu Gly Arg Leu Asp
305                 310                 315                 320
Ala Val Leu Gln Arg Ile Arg Thr Gly Ser Ala Leu Val Gln Arg Met
                325                 330                 335
Lys Cys Tyr Ala Ser Asp Gln Glu Val Leu Asp Met His Gly Phe Leu
            340                 345                 350
Arg Gln Ala Leu Cys Arg Leu Arg Gln Glu Glu Pro Gln Ser Leu Gln
                355                 360                 365
Ala Ala Val Arg Thr Asp Gly Phe Asp Glu Phe Lys Val Arg Leu Gln
            370                 375                 380
Asp Leu Ser Ser Cys Ile Thr Gln Gly Lys Asp Ala Ala Val Ser Lys
385                 390                 395                 400
Lys Ala Ser Pro Glu Ala Ala Ser Thr Pro Arg Asp Pro Ile Asp Val
                405                 410                 415
Asp Leu Pro Glu Glu Ala Glu Arg Val Lys Ala Gln Val Gln Ala Leu
            420                 425                 430
Gly Leu Ala Glu Ala Gln Pro Met Ala Val Val Gln Ser Val Pro Gly
                435                 440                 445
Ala His Pro Val Pro Val Tyr Ala Phe Ser Ile Lys Gly Pro Ser Tyr
    450                 455                 460
```

```
Gly Glu Asp Val Ser Asn Thr Thr Thr Ala Gln Lys Arg Lys Cys Ser
465                 470                 475                 480

Gln Thr Gln Cys Pro Arg Lys Val Ile Lys Met Glu Ser Glu Glu Gly
            485                 490                 495

Lys Glu Ala Arg Leu Ala Arg Ser Ser Pro Glu Gln Pro Arg Pro Ser
            500                 505                 510

Thr Ser Lys Ala Val Ser Pro His Leu Asp Gly Pro Pro Ser Pro
            515                 520                 525

Arg Ser Pro Val Ile Gly Ser Glu Val Phe Leu Pro Asn Ser Asn His
            530                 535                 540

Val Ala Ser Gly Ala Gly Glu Ala Glu Arg Val Val Ile Ser
545                 550                 555                 560

Ser Ser Glu Asp Ser Asp Ala Glu Asn Ser Ser Ser Arg Glu Leu Asp
            565                 570                 575

Asp Ser Ser Glu Ser Ser Asp Leu Gln Leu Glu Gly Pro Ser Thr
            580                 585                 590

Leu Arg Val Leu Asp Glu Asn Leu Ala Asp Pro Gln Ala Glu Asp Arg
            595                 600                 605

Pro Leu Val Phe Phe Asp Leu Lys Ile Asp Asn Glu Thr Gln Lys Ile
    610                 615                 620

Ser Gln Leu Ala Ala Val Asn Arg Glu Ser Lys Phe Arg Val Val Ile
625                 630                 635                 640

Gln Pro Glu Ala Phe Phe Ser Ile Tyr Ser Lys Ala Val Ser Leu Glu
                645                 650                 655

Val Gly Leu Gln His Phe Leu Ser Phe Leu Ser Ser Met Arg Arg Pro
            660                 665                 670

Ile Leu Ala Cys Tyr Lys Leu Trp Gly Pro Gly Leu Pro Asn Phe Phe
            675                 680                 685

Arg Ala Leu Glu Asp Ile Asn Arg Leu Trp Glu Phe Gln Glu Ala Ile
            690                 695                 700

Ser Gly Phe Leu Ala Ala Leu Pro Leu Ile Arg Glu Arg Val Pro Gly
705                 710                 715                 720

Ala Ser Ser Phe Lys Leu Lys Asn Leu Ala Gln Thr Tyr Leu Ala Arg
            725                 730                 735

Asn Met Ser Glu Arg Ser Ala Met Ala Ala Val Leu Ala Met Arg Asp
            740                 745                 750

Leu Cys Arg Leu Leu Glu Val Ser Pro Gly Pro Gln Leu Ala Gln His
            755                 760                 765

Val Tyr Pro Phe Ser Ser Leu Gln Cys Phe Ala Ser Leu Gln Pro Leu
    770                 775                 780

Val Gln Ala Ala Val Leu Pro Arg Ala Glu Ala Arg Leu Leu Ala Leu
785                 790                 795                 800

His Asn Val Ser Phe Met Glu Leu Leu Ser Ala His Arg Arg Asp Arg
                805                 810                 815

Gln Gly Gly Leu Lys Lys Tyr Ser Arg Tyr Leu Ser Leu Gln Thr Thr
            820                 825                 830

Thr Leu Pro Pro Ala Gln Pro Ala Phe Asn Leu Gln Ala Leu Gly Thr
            835                 840                 845

Tyr Phe Glu Gly Leu Leu Glu Gly Pro Ala Leu Ala Arg Ala Glu Gly
            850                 855                 860

Val Ser Thr Pro Leu Ala Gly Arg Gly Leu Ala Glu Arg Ala Ser Gln
865                 870                 875                 880

Gln Ser
```

<210> SEQ ID NO 39
<211> LENGTH: 2346
<212> TYPE: DNA
<213> ORGANISM: Homo sapiens

<400> SEQUENCE: 39

| | | | | | |
|---|---|---|---|---|---|
| atggctaaga | cccctagtga | ccatctgctg | tccaccctgg | aggagctggt | gccctatgac | 60 |
| ttcgagaagt | tcaagttcaa | gctgcagaac | accagtgtgc | agaaggagca | ctccaggatc | 120 |
| ccccggagcc | agatccagag | agccaggccg | gtgaagatgg | ccactctgct | ggtcacctac | 180 |
| tatggggaag | agtacgccgt | gcagctcacc | ctgcaggtcc | tgcgggccat | caaccagcgc | 240 |
| ctgctggccg | aggagctcca | cagggcagcc | attcaggaat | attccacaca | agaaaacggc | 300 |
| acagatgatt | ccgcagcgtc | cagctccctg | ggggagaaca | agcccaggag | cctgaagact | 360 |
| ccagaccacc | ccgaggggaa | cgaggggaac | ggccctcggc | cgtacggggg | cggagctgcc | 420 |
| agcctgcggt | gcagccagcc | cgaggccggg | aggggctgt | cgaggaagcc | cctgagcaaa | 480 |
| cgcagagaga | aggcctcgga | gggcctggac | gcgcagggca | gcctcggac | ccggagcccg | 540 |
| gccctgccgg | gcgggagaag | ccccggcccc | tgcaggggcgc | tagagggggg | ccaggccgag | 600 |
| gtccggctgc | gcagaaacgc | cagctccgcg | gggaggctgc | aggggctggc | gggggggcgcc | 660 |
| ccggggcaga | aggagtgcag | gcccttcgaa | gtgtacctgc | cctcgggaaa | gatgcgacct | 720 |
| agaagccttg | aggtcaccat | ttctacaggg | gagaaggcgc | ccgcaaatcc | agaaattctc | 780 |
| ctgactctag | aggaaaagac | agctgcgaat | ctggactcgg | caacagaacc | ccgggcaagg | 840 |
| cccactccgg | atggaggggc | atctgcggac | ctgaaggaag | gccctggaaa | tccagaacat | 900 |
| tcggtcaccg | gaaggccacc | agacacggct | gcgagtcccc | gctgccacgc | ccaggaagga | 960 |
| gacccagttg | acggtacctg | tgtgcgtgat | tcctgcagct | tccccgaggc | agtttctggg | 1020 |
| cacccccagg | cctcaggcag | ccgctcacct | ggctgccccc | ggtgccagga | ctcccatgaa | 1080 |
| aggaagagcc | cgggaagcct | aagcccccag | cccctgccac | agtgtaagcg | ccacctgaag | 1140 |
| caggtccagc | tgctcttctg | tgaggatcac | gatgagccca | tctgcctcat | ctgcagtctg | 1200 |
| agtcaggagc | accaaggcca | ccgggtgcgc | cccattgagg | aggtcgccct | ggaacacaag | 1260 |
| aagaaaattc | agaagcagct | ggagcatctg | aagaagctga | gaaaatcagg | ggaggagcag | 1320 |
| cgatcctatg | ggaggagaa | ggcagtgagc | tttctgaaac | aaactgaagc | gctgaagcag | 1380 |
| cgggtgcaga | ggaagctgga | gcaggtgtac | tacttcctgg | agcagcaaga | gcatttcttt | 1440 |
| gtggcctcac | tggaggacgt | gggccagatg | gttgggcaga | tcaggaaggc | atatgacacc | 1500 |
| cgcgtatccc | aggacatcgc | cctgctcgat | gcgctgattg | ggaactgga | ggccaaggag | 1560 |
| tgccagtcag | aatgggaact | tctgcaggac | attggagaca | tcttgcacag | ggctaagaca | 1620 |
| gtgcctgtcc | ctgaaaagtg | gaccactcct | caagagataa | aacaaagat | ccaactcctc | 1680 |
| caccagaagt | cagagtttgt | ggagaagagc | acaaagtact | tctcagaaac | cctgcgttca | 1740 |
| gaaatggaaa | tgttcaatgt | tccagagctg | attggcgctc | aggcacatgc | tgttaatgtg | 1800 |
| attctggatg | cagaaaccgc | ttaccccaac | ctcatcttct | ctgatgatct | gaagagtgtt | 1860 |
| agacttggaa | caagtggga | gaggctgcct | gatggcccgc | aaagatttga | cagctgtatc | 1920 |
| attgttctgg | gctctccgag | tttcctctct | ggccgccgtt | actgggaggt | ggaggttgga | 1980 |
| gacaagacag | catggatcct | gggagcctgc | aagacatcca | taagcaggaa | agggaacatg | 2040 |
| actctgtcgc | cagagaatgg | ctactgggtg | gtgataatga | tgaaggaaaa | tgagtaccag | 2100 |

-continued

```
gcgtccagcg ttccccgac  cgcctgcta  ataaaggagc  ctcccaagcg  tgtgggcatc   2160
ttcgtggact acagagttgg aagcatctcc ttttacaatg  tgacagccag  atcccacatc   2220
tatacattcg ccagctgctc tttctctggg ccccttcaac  ctatcttcag  ccctgggaca   2280
cgtgatggag ggaagaacac agctcctctg actatctgtc  cagtgggtgg  tcagggcct    2340 gactga                                                                2346
```

<210> SEQ ID NO 40
<211> LENGTH: 781
<212> TYPE: PRT
<213> ORGANISM: Homo sapiens

<400> SEQUENCE: 40

```
Met Ala Lys Thr Pro Ser Asp His Leu Leu Ser Thr Leu Glu Glu Leu
1               5                   10                  15

Val Pro Tyr Asp Phe Glu Lys Phe Lys Phe Lys Leu Gln Asn Thr Ser
                20                  25                  30

Val Gln Lys Glu His Ser Arg Ile Pro Arg Ser Gln Ile Gln Arg Ala
            35                  40                  45

Arg Pro Val Lys Met Ala Thr Leu Leu Val Thr Tyr Tyr Gly Glu Glu
        50                  55                  60

Tyr Ala Val Gln Leu Thr Leu Gln Val Leu Arg Ala Ile Asn Gln Arg
65                  70                  75                  80

Leu Leu Ala Glu Glu Leu His Arg Ala Ala Ile Gln Glu Tyr Ser Thr
                85                  90                  95

Gln Glu Asn Gly Thr Asp Asp Ser Ala Ala Ser Ser Leu Gly Glu
                100                 105                 110

Asn Lys Pro Arg Ser Leu Lys Thr Pro Asp His Pro Glu Gly Asn Glu
            115                 120                 125

Gly Asn Gly Pro Arg Pro Tyr Gly Gly Ala Ala Ser Leu Arg Cys
        130                 135                 140

Ser Gln Pro Glu Ala Gly Arg Gly Leu Ser Arg Lys Pro Leu Ser Lys
145                 150                 155                 160

Arg Arg Glu Lys Ala Ser Glu Gly Leu Asp Ala Gln Gly Lys Pro Arg
                165                 170                 175

Thr Arg Ser Pro Ala Leu Pro Gly Gly Arg Ser Pro Gly Pro Cys Arg
            180                 185                 190

Ala Leu Glu Gly Gly Gln Ala Glu Val Arg Leu Arg Arg Asn Ala Ser
        195                 200                 205

Ser Ala Gly Arg Leu Gln Gly Leu Ala Gly Ala Pro Gly Gln Lys
    210                 215                 220

Glu Cys Arg Pro Phe Glu Val Tyr Leu Pro Ser Gly Lys Met Arg Pro
225                 230                 235                 240

Arg Ser Leu Glu Val Thr Ile Ser Thr Gly Glu Lys Ala Pro Ala Asn
                245                 250                 255

Pro Glu Ile Leu Leu Thr Leu Glu Glu Lys Thr Ala Ala Asn Leu Asp
            260                 265                 270

Ser Ala Thr Glu Pro Arg Ala Arg Pro Thr Pro Asp Gly Gly Ala Ser
        275                 280                 285

Ala Asp Leu Lys Glu Gly Pro Gly Asn Pro Glu His Ser Val Thr Gly
    290                 295                 300

Arg Pro Pro Asp Thr Ala Ala Ser Pro Arg Cys His Ala Gln Glu Gly
305                 310                 315                 320

Asp Pro Val Asp Gly Thr Cys Val Arg Asp Ser Cys Ser Phe Pro Glu
```

-continued

```
                325                 330                 335
Ala Val Ser Gly His Pro Gln Ala Ser Gly Ser Arg Ser Pro Gly Cys
            340                 345                 350
Pro Arg Cys Gln Asp Ser His Glu Arg Lys Ser Pro Gly Ser Leu Ser
            355                 360                 365
Pro Gln Pro Leu Pro Gln Cys Lys Arg His Leu Lys Gln Val Gln Leu
            370                 375                 380
Leu Phe Cys Glu Asp His Asp Glu Pro Ile Cys Leu Ile Cys Ser Leu
385                 390                 395                 400
Ser Gln Glu His Gln Gly His Arg Val Arg Pro Ile Glu Glu Val Ala
                405                 410                 415
Leu Glu His Lys Lys Ile Gln Lys Gln Leu Glu His Leu Lys Lys
                420                 425                 430
Leu Arg Lys Ser Gly Glu Glu Arg Ser Tyr Gly Glu Lys Ala
                435                 440                 445
Val Ser Phe Leu Lys Gln Thr Glu Ala Leu Lys Gln Arg Val Gln Arg
            450                 455                 460
Lys Leu Glu Gln Val Tyr Tyr Phe Leu Glu Gln Gln Glu His Phe Phe
465                 470                 475                 480
Val Ala Ser Leu Glu Asp Val Gly Gln Met Val Gly Gln Ile Arg Lys
                485                 490                 495
Ala Tyr Asp Thr Arg Val Ser Gln Asp Ile Ala Leu Leu Asp Ala Leu
            500                 505                 510
Ile Gly Glu Leu Glu Ala Lys Glu Cys Gln Ser Glu Trp Glu Leu Leu
            515                 520                 525
Gln Asp Ile Gly Asp Ile Leu His Arg Ala Lys Thr Val Pro Val Pro
            530                 535                 540
Glu Lys Trp Thr Thr Pro Gln Glu Ile Lys Gln Lys Ile Gln Leu Leu
545                 550                 555                 560
His Gln Lys Ser Glu Phe Val Glu Lys Ser Thr Lys Tyr Phe Ser Glu
                565                 570                 575
Thr Leu Arg Ser Glu Met Glu Met Phe Asn Val Pro Glu Leu Ile Gly
            580                 585                 590
Ala Gln Ala His Ala Val Asn Val Ile Leu Asp Ala Glu Thr Ala Tyr
                595                 600                 605
Pro Asn Leu Ile Phe Ser Asp Asp Leu Lys Ser Val Arg Leu Gly Asn
            610                 615                 620
Lys Trp Glu Arg Leu Pro Asp Gly Pro Gln Arg Phe Asp Ser Cys Ile
625                 630                 635                 640
Ile Val Leu Gly Ser Pro Ser Phe Leu Ser Gly Arg Arg Tyr Trp Glu
                645                 650                 655
Val Glu Val Gly Asp Lys Thr Ala Trp Ile Leu Gly Ala Cys Lys Thr
            660                 665                 670
Ser Ile Ser Arg Lys Gly Asn Met Thr Leu Ser Pro Glu Asn Gly Tyr
            675                 680                 685
Trp Val Val Ile Met Met Lys Glu Asn Glu Tyr Gln Ala Ser Ser Val
            690                 695                 700
Pro Pro Thr Arg Leu Leu Ile Lys Glu Pro Pro Lys Arg Val Gly Ile
705                 710                 715                 720
Phe Val Asp Tyr Arg Val Gly Ser Ile Ser Phe Tyr Asn Val Thr Ala
                725                 730                 735
Arg Ser His Ile Tyr Thr Phe Ala Ser Cys Ser Phe Ser Gly Pro Leu
            740                 745                 750
```

Gln Pro Ile Phe Ser Pro Gly Thr Arg Asp Gly Gly Lys Asn Thr Ala
                755                 760                 765

Pro Leu Thr Ile Cys Pro Val Gly Gly Gln Gly Pro Asp
        770                 775                 780

<210> SEQ ID NO 41
<211> LENGTH: 1428
<212> TYPE: DNA
<213> ORGANISM: Homo sapiens

<400> SEQUENCE: 41

| | |
|---|---|
| atggcttcag cagcacgctt gacaatgatg tgggaggagg tcacatgccc tatctgcctg | 60 |
| gacccttcg tggagcctgt gagcatcgag tgtggccaca gcttctgcca ggaatgcatc | 120 |
| tctcaggttg ggaaaggtgg gggcagcgtc tgtcctgtgt gccggcagcg ctttctgctc | 180 |
| aagaatctcc ggcccaatcg acagctagcc aacatggtga caaccttaa agaaatcagc | 240 |
| caggaggcca gagagggcac acaggggaa cggtgtgcag tgcatggaga gagacttcac | 300 |
| ctgttctgtg agaaagatgg gaaggccctt tgctgggtat gtgcccagtc tcggaaacac | 360 |
| cgtgaccacg ccatggtccc tcttgaggag gctgcacagg agtaccagga gaagctccag | 420 |
| gtggcattag ggaactgag aagaaagcag gagttggctg agaagttgga agtggaaatt | 480 |
| gcaataaaga gagcagactg gaagaaaaca gtggaaacac agaaatctag gattcacgca | 540 |
| gagtttgtgc agcaaaaaaa cttcctggtt gaagaagaac agaggcagct gcaggagctg | 600 |
| gagaaggatg agagggagca gctgagaatc ctgggggaga agaggccaa gctggcccag | 660 |
| cagagccagg ccctacagga gctcatctca gagctagatc gaaggtgcca cagctcagca | 720 |
| ctggaactgc tgcaggaggt gataattgtc ctggaaagga gtgagtcctg gaacctgaag | 780 |
| gacctggata ttacctctcc agaactcagg agtgtgtgcc atgtgccagg gctgaagaag | 840 |
| atgctgagga catgtgcagt ccacatcact ctggatccag acacagccaa tccgtggctg | 900 |
| atactttcag aagatcggag acaagtgagg cttggagaca cccagcagag catacctgga | 960 |
| aatgaagaga gatttgatag ttatcctatg gtcctgggtg cccagcactt tcactctgga | 1020 |
| aaacattact gggaggtaga tgtgacagga aaggaggcct gggacctggg tgtctgcaga | 1080 |
| gactctgtgc gcaggaaggg gcactttttg cttagttcca agagtggctt ctggacaatt | 1140 |
| tggttgtgga acaaacaaaa atatgaggct ggcacctacc cccagactcc cctccacctt | 1200 |
| caggtgcctc catgccaagt tgggattttc ctggactatg aggctggcat ggtctccttc | 1260 |
| tacaacatca ctgaccatgg ctccctcatc tactccttct ctgaatgtgc ctttacagga | 1320 |
| cctctgcggc ccttcttcag tcctggtttc aatgatggag gaaaaaacac agccccctcta | 1380 |
| accctctgtc cactgaatat tggatcacaa ggatccactg actattga | 1428 |

<210> SEQ ID NO 42
<211> LENGTH: 475
<212> TYPE: PRT
<213> ORGANISM: Homo sapiens

<400> SEQUENCE: 42

Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
                20                  25                  30

His Ser Phe Cys Gln Glu Cys Ile Ser Gln Val Gly Lys Gly Gly Gly
            35                  40                  45

```
Ser Val Cys Pro Val Cys Arg Gln Arg Phe Leu Leu Lys Asn Leu Arg
    50              55                  60
Pro Asn Arg Gln Leu Ala Asn Met Val Asn Asn Leu Lys Glu Ile Ser
65                  70                  75                  80
Gln Glu Ala Arg Glu Gly Thr Gln Gly Glu Arg Cys Ala Val His Gly
                85                  90                  95
Glu Arg Leu His Leu Phe Cys Glu Lys Asp Gly Lys Ala Leu Cys Trp
            100                 105                 110
Val Cys Ala Gln Ser Arg Lys His Arg Asp His Ala Met Val Pro Leu
            115                 120                 125
Glu Glu Ala Ala Gln Glu Tyr Gln Glu Lys Leu Gln Val Ala Leu Gly
130                 135                 140
Glu Leu Arg Arg Lys Gln Glu Leu Ala Glu Lys Leu Glu Val Glu Ile
145                 150                 155                 160
Ala Ile Lys Arg Ala Asp Trp Lys Lys Thr Val Glu Thr Gln Lys Ser
                165                 170                 175
Arg Ile His Ala Glu Phe Val Gln Gln Lys Asn Phe Leu Val Glu Glu
            180                 185                 190
Glu Gln Arg Gln Leu Gln Glu Leu Glu Lys Asp Glu Arg Glu Gln Leu
            195                 200                 205
Arg Ile Leu Gly Glu Lys Glu Ala Lys Leu Ala Gln Gln Ser Gln Ala
210                 215                 220
Leu Gln Glu Leu Ile Ser Glu Leu Asp Arg Arg Cys His Ser Ser Ala
225                 230                 235                 240
Leu Glu Leu Leu Gln Glu Val Ile Ile Val Leu Glu Arg Ser Glu Ser
                245                 250                 255
Trp Asn Leu Lys Asp Leu Asp Ile Thr Ser Pro Glu Leu Arg Ser Val
            260                 265                 270
Cys His Val Pro Gly Leu Lys Lys Met Leu Arg Thr Cys Ala Val His
            275                 280                 285
Ile Thr Leu Asp Pro Asp Thr Ala Asn Pro Trp Leu Ile Leu Ser Glu
290                 295                 300
Asp Arg Arg Gln Val Arg Leu Gly Asp Thr Gln Gln Ser Ile Pro Gly
305                 310                 315                 320
Asn Glu Glu Arg Phe Asp Ser Tyr Pro Met Val Leu Gly Ala Gln His
                325                 330                 335
Phe His Ser Gly Lys His Tyr Trp Glu Val Asp Val Thr Gly Lys Glu
            340                 345                 350
Ala Trp Asp Leu Gly Val Cys Arg Asp Ser Val Arg Arg Lys Gly His
            355                 360                 365
Phe Leu Leu Ser Ser Lys Ser Gly Phe Trp Thr Ile Trp Leu Trp Asn
370                 375                 380
Lys Gln Lys Tyr Glu Ala Gly Thr Tyr Pro Gln Thr Pro Leu His Leu
385                 390                 395                 400
Gln Val Pro Pro Cys Gln Val Gly Ile Phe Leu Asp Tyr Glu Ala Gly
                405                 410                 415
Met Val Ser Phe Tyr Asn Ile Thr Asp His Gly Ser Leu Ile Tyr Ser
            420                 425                 430
Phe Ser Glu Cys Ala Phe Thr Gly Pro Leu Arg Pro Phe Phe Ser Pro
            435                 440                 445
Gly Phe Asn Asp Gly Gly Lys Asn Thr Ala Pro Leu Thr Leu Cys Pro
450                 455                 460
```

-continued

Leu Asn Ile Gly Ser Gln Gly Ser Thr Asp Tyr
465                 470                 475

<210> SEQ ID NO 43
<211> LENGTH: 1497
<212> TYPE: DNA
<213> ORGANISM: Homo sapiens

<400> SEQUENCE: 43

| | | | | |
|---|---|---|---|---|
| atggatttct | cagtaaaggt | agacatagag | aaggaggtga | cctgccccat | ctgcctggag | 60 |
| ctcctgacag | aacctctgag | cctagattgt | ggccacagct | tctgccaagc | ctgcatcact | 120 |
| gcaaagatca | aggagtcagt | gatcatctca | agagggaaa | gcagctgtcc | tgtgtgtcag | 180 |
| accagattcc | agcctgggaa | cctccgacct | aatcggcatc | tggccaacat | agttgagaga | 240 |
| gtcaaagagg | tcaagatgag | cccacaggag | gggcagaaga | gagatgtctg | tgagcaccat | 300 |
| ggaaaaaaac | tccagatctt | ctgtaaggag | gatggaaaag | tcatttgctg | ggtttgtgaa | 360 |
| ctgtctcagg | aacaccaagg | tcaccaaaca | ttccgcataa | acgaggtggt | caaggaatgt | 420 |
| caggaaaagc | tgcaggtagc | cctgcagagg | ctgataaagg | aggatcaaga | ggctgagaag | 480 |
| ctggaagatg | acatcagaca | agagagaacc | gcctggaaga | attatatcca | gatcgagaga | 540 |
| cagaagattc | tgaaagggtt | caatgaaatg | agagtcatct | tggacaatga | ggagcagaga | 600 |
| gagctgcaaa | agctggagga | aggtgaggtg | aatgtgctgg | ataacctggc | agcagctaca | 660 |
| gaccagctgg | tccagcagag | gcaggatgcc | agcacgctca | tctcagatct | ccagcggagg | 720 |
| ttgagggggat | cgtcagtaga | gatgctgcag | gatgtgattg | acgtcatgaa | aggagtgaa | 780 |
| agctggacat | tgaagaagcc | aaaatctgtt | tccaagaaac | taaagagtgt | attccgagta | 840 |
| ccagatctga | gtgggatgct | gcaagttctt | aaagagctga | cagatgtcca | gtactactgg | 900 |
| gtggacgtga | tgctgaatcc | aggcagtgcc | acttcgaatg | ttgctatttc | tgtggatcag | 960 |
| agacaagtga | aaactgtacg | cacctgcaca | tttaagaatt | caaatccatg | tgatttttct | 1020 |
| gcttttggtg | tcttcggctg | ccaatatttc | tcttcgggga | atattactg | ggaagtagat | 1080 |
| gtgtctggaa | agattgcctg | gatcctgggc | gtacacagta | aaataagtag | tctgaataaa | 1140 |
| aggaagagct | ctgggtttgc | ttttgatcca | agtgtaaatt | attcaaaagt | ttactccaga | 1200 |
| tatagacctc | aatatggcta | ctgggttata | ggattacaga | atacatgtga | atataatgct | 1260 |
| tttgaggact | cctcctcttc | tgatcccaag | gttttgactc | tctttatggc | tgtgcctccc | 1320 |
| tgtcgtattg | gggttttcct | agactatgag | gcaggcattg | tctcattttt | caatgtcaca | 1380 |
| aaccacggag | cactcatcta | caagttctct | ggatgtcgct | tttctcgacc | tgcttatccg | 1440 |
| tatttcaatc | cttggaactg | cctagtcccc | atgactgtgt | gcccaccgag | ctcctga | 1497 |

<210> SEQ ID NO 44
<211> LENGTH: 498
<212> TYPE: PRT
<213> ORGANISM: Homo sapiens

<400> SEQUENCE: 44

Met Asp Phe Ser Val Lys Val Asp Ile Glu Lys Glu Val Thr Cys Pro
1               5                   10                  15

Ile Cys Leu Glu Leu Leu Thr Glu Pro Leu Ser Leu Asp Cys Gly His
                20                  25                  30

Ser Phe Cys Gln Ala Cys Ile Thr Ala Lys Ile Lys Glu Ser Val Ile
            35                  40                  45

Ile Ser Arg Gly Glu Ser Ser Cys Pro Val Cys Gln Thr Arg Phe Gln

```
            50                  55                  60
Pro Gly Asn Leu Arg Pro Asn Arg His Leu Ala Asn Ile Val Glu Arg
 65                  70                  75                  80

Val Lys Glu Val Lys Met Ser Pro Gln Glu Gly Gln Lys Arg Asp Val
                 85                  90                  95

Cys Glu His His Gly Lys Lys Leu Gln Ile Phe Cys Lys Glu Asp Gly
                100                 105                 110

Lys Val Ile Cys Trp Val Cys Glu Leu Ser Gln Glu His Gln Gly His
            115                 120                 125

Gln Thr Phe Arg Ile Asn Glu Val Val Lys Glu Cys Gln Glu Lys Leu
        130                 135                 140

Gln Val Ala Leu Gln Arg Leu Ile Lys Glu Asp Gln Glu Ala Glu Lys
145                 150                 155                 160

Leu Glu Asp Asp Ile Arg Gln Glu Arg Thr Ala Trp Lys Asn Tyr Ile
                165                 170                 175

Gln Ile Glu Arg Gln Lys Ile Leu Lys Gly Phe Asn Glu Met Arg Val
            180                 185                 190

Ile Leu Asp Asn Glu Glu Gln Arg Glu Leu Gln Lys Leu Glu Glu Gly
        195                 200                 205

Glu Val Asn Val Leu Asp Asn Leu Ala Ala Ala Thr Asp Gln Leu Val
    210                 215                 220

Gln Gln Arg Gln Asp Ala Ser Thr Leu Ile Ser Asp Leu Gln Arg Arg
225                 230                 235                 240

Leu Arg Gly Ser Ser Val Glu Met Leu Gln Asp Val Ile Asp Val Met
                245                 250                 255

Lys Arg Ser Glu Ser Trp Thr Leu Lys Lys Pro Lys Ser Val Ser Lys
            260                 265                 270

Lys Leu Lys Ser Val Phe Arg Val Pro Asp Leu Ser Gly Met Leu Gln
        275                 280                 285

Val Leu Lys Glu Leu Thr Asp Val Gln Tyr Tyr Trp Val Asp Val Met
    290                 295                 300

Leu Asn Pro Gly Ser Ala Thr Ser Asn Val Ala Ile Ser Val Asp Gln
305                 310                 315                 320

Arg Gln Val Lys Thr Val Arg Thr Cys Thr Phe Lys Asn Ser Asn Pro
                325                 330                 335

Cys Asp Phe Ser Ala Phe Gly Val Phe Gly Cys Gln Tyr Phe Ser Ser
            340                 345                 350

Gly Lys Tyr Tyr Trp Glu Val Asp Val Ser Gly Lys Ile Ala Trp Ile
        355                 360                 365

Leu Gly Val His Ser Lys Ile Ser Ser Leu Asn Lys Arg Lys Ser Ser
    370                 375                 380

Gly Phe Ala Phe Asp Pro Ser Val Asn Tyr Lys Val Tyr Ser Arg
385                 390                 395                 400

Tyr Arg Pro Gln Tyr Gly Tyr Trp Val Ile Gly Leu Gln Asn Thr Cys
                405                 410                 415

Glu Tyr Asn Ala Phe Glu Asp Ser Ser Ser Asp Pro Lys Val Leu
            420                 425                 430

Thr Leu Phe Met Ala Val Pro Pro Cys Arg Ile Gly Val Phe Leu Asp
        435                 440                 445

Tyr Glu Ala Gly Ile Val Ser Phe Phe Asn Val Thr Asn His Gly Ala
    450                 455                 460

Leu Ile Tyr Lys Phe Ser Gly Cys Arg Phe Ser Arg Pro Ala Tyr Pro
465                 470                 475                 480
```

Tyr Phe Asn Pro Trp Asn Cys Leu Val Pro Met Thr Val Cys Pro Pro
            485                 490                 495

Ser Ser

<210> SEQ ID NO 45
<211> LENGTH: 1725
<212> TYPE: DNA
<213> ORGANISM: Homo sapiens

<400> SEQUENCE: 45

| | | | | | |
|---|---|---|---|---|---|
| atggctaccc | tggttgtaaa | caagctcgga | gcgggagtag | acagtggccg | gcagggcagc | 60 |
| cgggggacag | ctgtagtgaa | ggtgctagag | tgtggagttt | gtgaagatgt | cttttctttg | 120 |
| caaggagaca | aagttccccg | tcttttgctt | tgtggccata | ccgtctgtca | tgactgtctc | 180 |
| actcgcctac | ctcttcatgg | aagagcaatc | cgttgcccat | ttgatcgaca | gtaacagac | 240 |
| ctaggtgatt | caggtgtctg | gggattgaaa | aaaaattttg | ctttattgga | gcttttggaa | 300 |
| cgactgcaga | atgggcctat | tggtcagtat | ggagctgcag | aagaatccat | tgggatatct | 360 |
| ggagagagca | tcattcgttg | tgatgaagat | gaagctcacc | ttgcctctgt | atattgcact | 420 |
| gtgtgtgcaa | ctcatttgtg | ctctgagtgt | tctcaagtta | ctcattctac | aaagacatta | 480 |
| gcaaagcaca | ggcgagttcc | tctagctgat | aaacctcatg | agaaaactat | gtgctctcag | 540 |
| caccaggtgc | atgccattga | gtttgtttgc | ttggaagaag | gttgtcaaac | tagcccactc | 600 |
| atgtgctgtg | tctgcaaaga | atatggaaaa | caccagggtc | acaagcattc | agtattggaa | 660 |
| ccagaagcta | atcagatccg | agcatcaatt | ttagatatgg | ctcactgcat | acggaccttc | 720 |
| acagaggaaa | tctcagatta | ttccagaaaa | ttagttggaa | ttgtgcagca | cattgaagga | 780 |
| ggagaacaaa | tcgtggaaga | tggaattgga | atggctcaca | cagaacatgt | accagggact | 840 |
| gcagagaatg | cccggtcatg | tattcgagct | tattttatg | atctacatga | aactctgtgt | 900 |
| cgtcaagaag | aaatggctct | aagtgttgtt | gatgctcatg | ttcgtgaaaa | attgatttgg | 960 |
| ctcaggcagc | aacaagaaga | tatgactatt | ttgttgtcag | aggtttctgc | agcctgcctc | 1020 |
| cactgtgaaa | agactttgca | gcaggatgat | tgtagagttg | tcttggcaaa | acaggaaatt | 1080 |
| acaaggttac | tggaaacatt | gcagaaacag | cagcagcagt | ttacagaagt | tgcagatcac | 1140 |
| attcagttgg | atgccagcat | ccctgtcact | tttacaaagg | ataatcgagt | tcacattgga | 1200 |
| ccaaaaatgg | aaattcgggt | cgttacgtta | ggattggatg | gtgctggaaa | aactactatc | 1260 |
| ttgtttaagt | taaaacagga | tgaattcatg | cagcccattc | caacaattgg | ttttaacgtg | 1320 |
| gaaactgtag | aatataaaaa | tctaaaattc | actatttggg | atgtaggtgg | aaaacacaaa | 1380 |
| ttaagaccat | tgtggaaaca | ttattacctc | aatactcaag | ctgttgtgtt | tgttgtagat | 1440 |
| agcagtcata | gagacagaat | tagtgaagca | cacagcgaac | ttgcaaagtt | gttaacggaa | 1500 |
| aaagaactcc | gagatgctct | gctcctgatt | tttgctaaca | acaggatgt | tgctggagca | 1560 |
| ctgtcagtag | aagaaatcac | tgaactactc | agtctccata | aattatgctg | tggccgtagc | 1620 |
| tggtatattc | agggctgtga | tgctcgaagt | ggtatgggac | tgtatgaagg | gttggactgg | 1680 |
| ctctcacggc | aacttgtagc | tgctggagta | ttggatgttg | cttga | | 1725 |

<210> SEQ ID NO 46
<211> LENGTH: 574
<212> TYPE: PRT
<213> ORGANISM: Homo sapiens

<400> SEQUENCE: 46

-continued

```
Met Ala Thr Leu Val Val Asn Lys Leu Gly Ala Gly Val Asp Ser Gly
1               5                   10                  15

Arg Gln Gly Ser Arg Gly Thr Ala Val Val Lys Val Leu Glu Cys Gly
                20                  25                  30

Val Cys Glu Asp Val Phe Ser Leu Gln Gly Asp Lys Val Pro Arg Leu
            35                  40                  45

Leu Leu Cys Gly His Thr Val Cys His Asp Cys Leu Thr Arg Leu Pro
        50                  55                  60

Leu His Gly Arg Ala Ile Arg Cys Pro Phe Asp Arg Gln Val Thr Asp
65                  70                  75                  80

Leu Gly Asp Ser Gly Val Trp Gly Leu Lys Lys Asn Phe Ala Leu Leu
                85                  90                  95

Glu Leu Leu Glu Arg Leu Gln Asn Gly Pro Ile Gly Gln Tyr Gly Ala
            100                 105                 110

Ala Glu Glu Ser Ile Gly Ile Ser Gly Glu Ser Ile Ile Arg Cys Asp
        115                 120                 125

Glu Asp Glu Ala His Leu Ala Ser Val Tyr Cys Thr Val Cys Ala Thr
        130                 135                 140

His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Val Cys Lys Glu Tyr
        195                 200                 205

Gly Lys His Gln Gly His Lys His Ser Val Leu Glu Pro Glu Ala Asn
        210                 215                 220

Gln Ile Arg Ala Ser Ile Leu Asp Met Ala His Cys Ile Arg Thr Phe
225                 230                 235                 240

Thr Glu Glu Ile Ser Asp Tyr Ser Arg Lys Leu Val Gly Ile Val Gln
                245                 250                 255

His Ile Glu Gly Gly Glu Gln Ile Val Glu Asp Gly Ile Gly Met Ala
            260                 265                 270

His Thr Glu His Val Pro Gly Thr Ala Glu Asn Ala Arg Ser Cys Ile
        275                 280                 285

Arg Ala Tyr Phe Tyr Asp Leu His Glu Thr Leu Cys Arg Gln Glu Glu
        290                 295                 300

Met Ala Leu Ser Val Val Asp Ala His Val Arg Glu Lys Leu Ile Trp
305                 310                 315                 320

Leu Arg Gln Gln Gln Glu Asp Met Thr Ile Leu Leu Ser Glu Val Ser
                325                 330                 335

Ala Ala Cys Leu His Cys Glu Lys Thr Leu Gln Gln Asp Asp Cys Arg
            340                 345                 350

Val Val Leu Ala Lys Gln Glu Ile Thr Arg Leu Leu Glu Thr Leu Gln
        355                 360                 365

Lys Gln Gln Gln Gln Phe Thr Glu Val Ala Asp His Ile Gln Leu Asp
        370                 375                 380

Ala Ser Ile Pro Val Thr Phe Thr Lys Asp Asn Arg Val His Ile Gly
385                 390                 395                 400

Pro Lys Met Glu Ile Arg Val Val Thr Leu Gly Leu Asp Gly Ala Gly
                405                 410                 415
```

| | | | | | | | | | | | | |
|---|---|---|---|---|---|---|---|---|---|---|---|---|
|Lys|Thr|Thr|Ile|Leu|Phe|Lys|Leu|Lys|Gln|Asp|Glu|Phe|Met|Gln|Pro|
| | | |420| | | |425| | | |430| | | | |

Lys Thr Thr Ile Leu Phe Lys Leu Lys Gln Asp Glu Phe Met Gln Pro
            420                 425                 430

Ile Pro Thr Ile Gly Phe Asn Val Glu Thr Val Glu Tyr Lys Asn Leu
            435                 440                 445

Lys Phe Thr Ile Trp Asp Val Gly Lys His Lys Leu Arg Pro Leu
450                 455                 460

Trp Lys His Tyr Tyr Leu Asn Thr Gln Ala Val Val Phe Val Val Asp
465             470                 475                 480

Ser Ser His Arg Asp Arg Ile Ser Glu Ala His Ser Glu Leu Ala Lys
                485                 490                 495

Leu Leu Thr Glu Lys Glu Leu Arg Asp Ala Leu Leu Ile Phe Ala
            500                 505                 510

Asn Lys Gln Asp Val Ala Gly Ala Leu Ser Val Glu Glu Ile Thr Glu
            515                 520                 525

Leu Leu Ser Leu His Lys Leu Cys Cys Gly Arg Ser Trp Tyr Ile Gln
            530                 535                 540

Gly Cys Asp Ala Arg Ser Gly Met Gly Leu Tyr Glu Gly Leu Asp Trp
545                 550                 555                 560

Leu Ser Arg Gln Leu Val Ala Ala Gly Val Leu Asp Val Ala
            565                 570

<210> SEQ ID NO 47
<211> LENGTH: 3153
<212> TYPE: DNA
<213> ORGANISM: Homo sapiens

<400> SEQUENCE: 47

```
atggaggtgg cggtggagaa ggcggtggcg gcggcggcag cggcctcggc tgcggcctcc      60
ggggggcccct cggcggcgcc gagcggggag aacgaggccg agagtcggca gggcccggac    120
tcggagcgcg gcggcgaggc ggcccggctc aacctgttgg acacttgcgc cgtgtgccac    180
cagaacatcc agagcgggc gcccaagctg ctgccctgcc tgcactcttt ctgccagcgc    240
tgcctgcccg cgccccagcg ctacctcatg ctgcccgcgc ccatgctggg ctcggccgag    300
accccgccac ccgtccctgc ccccggctcg cggtcagcg ctcgtcgcc gttcgccacc    360
caagttggag tcattcgttg cccagttgc agccaagaat gtgcagagag acacatcata    420
gataactttt ttgtgaagga cactactgag gttcccagca gtacagtaga aaagtcaaat    480
caggtatgta aagctgtga ggacaacgca gaagccaatg ggttttgtgt agagtgtgtt    540
gaatggctct gcaagacgtg tatcagagct catcagaggg taaagttcac aaaagaccac    600
actgtcagac agaaagagga agtatctcca gaggcagttg gtgtcaccag ccagcgacca    660
gtgtttgtc cttttcataa aaaggagcag ctgaagctgt actgtgagac atgtgacaaa    720
ctgacatgtc gagactgtca gttgttagaa cataaagagc atagatacca atttatagaa    780
gaagcttttc agaatcagaa agtgatcata gatacactaa tcaccaaact gatggaaaaa    840
acaaaataca taaaattcac aggaaatcag atccaaaaca gaattattga agtaaatcaa    900
aatcaaaagc aggtggaaca ggatattaaa gttgctatat ttacactgat ggtagaaata    960
aataaaaaag gaaaagctct actgcatcag ttagagagcc ttgcaaagga ccatcgcatg   1020
aaacttatgc aacaacaaca ggaagtggct ggactctcta acaattgga gcatgtcatg   1080
cattttctca atgggcagt ttccagtggc agcagtacag cattacttta tagcaaacga   1140
ctgattacat accggttacg gcacctcctt cgtgcaaggt gtgatgcatc cccagtgacc   1200
aacaacacca tccaatttca ctgtgatcct agtttctggg ctcaaaatat catcaactta   1260
```

-continued

```
ggttctttag taatcgagga taaagagagc cagccacaaa tgcctaagca gaatcctgtc    1320
gtggaacaga attcacagcc accaagtggt ttatcatcaa accagttatc caagttccca    1380
acacagatca gcctagctca attacggctc cagcatatgc agcaacaggt aatggctcag    1440
aggcaacagg tgcaacggag gccagcacct gtgggtttac caaaccctag aatgcagggg    1500
cccatccagc aaccttccat ctctcatcag caaccgcctc cacgtttgat aaactttcag    1560
aatcacagcc ccaaacccaa tggaccagtt cttcctcctc atcctcaaca actgagatat    1620
ccaccaaacc agaacatacc acgacaagca ataaagccaa accccctaca gatggctttc    1680
ttggctcaac aagccataaa acagtggcag atcagcagtg acagggaac cccatcaact     1740 accaacagca catcctctac tccttccagc ccacgattta ctagtgcagc aggatatgat    1800
ggaaaggctt ttggttcacc tatgatcgat ttgagctcac cagtgggagg gtcttataat    1860
cttccctctc ttccggatat tgactgttca agtactatta tgctggacaa tattgtgagg    1920
aaagatacta atatagatca tggccagcca agaccaccct caaacagaac ggtccagtca    1980
ccaaattcat cagtgccatc tccaggcctt gcaggacctg ttactatgac tagtgtacac    2040
cccccaatac gttcacctag tgcctccagc gttggaagcc gaggaagctc tggctcttcc    2100
agcaaaccag caggagctga ctctacacac aaagtcccag tggtcatgct ggagccaatt    2160
cgaataaaac aagaaaacag tggaccaccg gaaaattatg atttccctgt tgttatagtg    2220
aagcaagaat cagatgaaga atctaggcct caaaatgcca attatccaag aagcatactc    2280
acctccctgc tcttaaatag cagtcagagc tctacttctg aggagactgt gctaagatca    2340
gatgcccctg atagtacagg agatcaacct ggacttcacc aggacaattc ctcaaatgga    2400
aagtctgaat ggttggatcc ttcccagaag tcacctcttc atgttggaga gacaaggaaa    2460
gaggatgacc ccaatgagga ctggtgtgca gtttgtcaaa acggagggga actcctctgc    2520
tgtgaaaagt gccccaaagt attccatctt tcttgtcatg tgcccacatt gacaaatttt    2580
ccaagtggag agtggatttg cactttctgc cgagacttat ctaaaccaga agttgaatat    2640
gattgtgatg ctcccagtca caactcagaa aaaaagaaaa ctgaaggcct tgttaagtta    2700
acacctatag ataaaaggaa gtgtgagcgc ctactttat ttctttactg ccatgaaatg     2760
agcctggctt ttcaagaccc tgttcctcta actgtgcctg attattacaa aataattaaa    2820
aatccaatgg atttgtcaac catcaagaaa agactacaag aagattattc catgtactca    2880
aaacctgaag attttgtagc tgattttaga ttgatctttc aaaactgtgc tgaattcaat    2940
gagcctgatt cagaagtagc caatgctggt ataaaacttg aaaattattt tgaagaactt    3000
ctaaagaacc tctatccaga aaaaggttt cccaaaccag aattcaggaa tgaatcagaa     3060
gataataaat ttagtgatga ttcagatgat gactttgtac agccccggaa gaaacgcctc    3120
aaaagcattg aagaacgcca gttgcttaaa taa                                 3153
```

<210> SEQ ID NO 48
<211> LENGTH: 1050
<212> TYPE: PRT
<213> ORGANISM: Homo sapiens

<400> SEQUENCE: 48

Met Glu Val Ala Val Glu Lys Ala Val Ala Ala Ala Ala Ala Ala Ser
1               5                   10                  15

Ala Ala Ala Ser Gly Gly Pro Ser Ala Ala Pro Ser Gly Glu Asn Glu
            20                  25                  30

-continued

```
Ala Glu Ser Arg Gln Gly Pro Asp Ser Glu Arg Gly Gly Glu Ala Ala
            35                  40                  45

Arg Leu Asn Leu Leu Asp Thr Cys Ala Val Cys His Gln Asn Ile Gln
 50                  55                  60

Ser Arg Ala Pro Lys Leu Leu Pro Cys Leu His Ser Phe Cys Gln Arg
 65                  70                  75                  80

Cys Leu Pro Ala Pro Gln Arg Tyr Leu Met Leu Pro Ala Pro Met Leu
                 85                  90                  95

Gly Ser Ala Glu Thr Pro Pro Val Pro Ala Pro Gly Ser Pro Val
             100                 105                 110

Ser Gly Ser Ser Pro Phe Ala Thr Gln Val Gly Val Ile Arg Cys Pro
             115                 120                 125

Val Cys Ser Gln Glu Cys Ala Glu Arg His Ile Ile Asp Asn Phe Phe
             130                 135                 140

Val Lys Asp Thr Thr Glu Val Pro Ser Ser Thr Val Glu Lys Ser Asn
 145                 150                 155                 160

Gln Val Cys Thr Ser Cys Glu Asp Asn Ala Glu Ala Asn Gly Phe Cys
                 165                 170                 175

Val Glu Cys Val Glu Trp Leu Cys Lys Thr Cys Ile Arg Ala His Gln
             180                 185                 190

Arg Val Lys Phe Thr Lys Asp His Thr Val Arg Gln Lys Glu Glu Val
 195                 200                 205

Ser Pro Glu Ala Val Gly Val Thr Ser Gln Arg Pro Val Phe Cys Pro
             210                 215                 220

Phe His Lys Lys Glu Gln Leu Lys Leu Tyr Cys Glu Thr Cys Asp Lys
 225                 230                 235                 240

Leu Thr Cys Arg Asp Cys Gln Leu Leu Glu His Lys Glu His Arg Tyr
                 245                 250                 255

Gln Phe Ile Glu Glu Ala Phe Gln Asn Gln Lys Val Ile Ile Asp Thr
             260                 265                 270

Leu Ile Thr Lys Leu Met Glu Lys Thr Lys Tyr Ile Lys Phe Thr Gly
             275                 280                 285

Asn Gln Ile Gln Asn Arg Ile Ile Glu Val Asn Gln Asn Gln Lys Gln
 290                 295                 300

Val Glu Gln Asp Ile Lys Val Ala Ile Phe Thr Leu Met Val Glu Ile
 305                 310                 315                 320

Asn Lys Lys Gly Lys Ala Leu Leu His Gln Leu Glu Ser Leu Ala Lys
                 325                 330                 335

Asp His Arg Met Lys Leu Met Gln Gln Gln Glu Val Ala Gly Leu
             340                 345                 350

Ser Lys Gln Leu Glu His Val Met His Phe Ser Lys Trp Ala Val Ser
             355                 360                 365

Ser Gly Ser Ser Thr Ala Leu Leu Tyr Ser Lys Arg Leu Ile Thr Tyr
             370                 375                 380

Arg Leu Arg His Leu Leu Arg Ala Arg Cys Asp Ala Ser Pro Val Thr
 385                 390                 395                 400

Asn Asn Thr Ile Gln Phe His Cys Asp Pro Ser Phe Trp Ala Gln Asn
                 405                 410                 415

Ile Ile Asn Leu Gly Ser Leu Val Ile Glu Asp Lys Glu Ser Gln Pro
                 420                 425                 430

Gln Met Pro Lys Gln Asn Pro Val Val Glu Gln Asn Ser Gln Pro Pro
             435                 440                 445

Ser Gly Leu Ser Ser Asn Gln Leu Ser Lys Phe Pro Thr Gln Ile Ser
```

```
                450             455             460
Leu Ala Gln Leu Arg Leu Gln His Met Gln Gln Gln Val Met Ala Gln
465                     470                     475                 480
Arg Gln Gln Val Gln Arg Arg Pro Ala Pro Val Gly Leu Pro Asn Pro
                485                     490                     495
Arg Met Gln Gly Pro Ile Gln Gln Pro Ser Ile Ser His Gln Gln Pro
            500                     505                     510
Pro Pro Arg Leu Ile Asn Phe Gln Asn His Ser Pro Lys Pro Asn Gly
            515                     520                     525
Pro Val Leu Pro Pro His Pro Gln Gln Leu Arg Tyr Pro Pro Asn Gln
            530                     535                     540
Asn Ile Pro Arg Gln Ala Ile Lys Pro Asn Pro Leu Gln Met Ala Phe
545                     550                     555                 560
Leu Ala Gln Gln Ala Ile Lys Gln Trp Gln Ile Ser Ser Gly Gln Gly
                565                     570                     575
Thr Pro Ser Thr Thr Asn Ser Thr Ser Ser Thr Pro Ser Ser Pro Thr
            580                     585                     590
Ile Thr Ser Ala Ala Gly Tyr Asp Gly Lys Ala Phe Gly Ser Pro Met
            595                     600                     605
Ile Asp Leu Ser Ser Pro Val Gly Gly Ser Tyr Asn Leu Pro Ser Leu
            610                     615                     620
Pro Asp Ile Asp Cys Ser Ser Thr Ile Met Leu Asp Asn Ile Val Arg
625                     630                     635                 640
Lys Asp Thr Asn Ile Asp His Gly Gln Pro Arg Pro Ser Asn Arg
                645                     650                     655
Thr Val Gln Ser Pro Asn Ser Ser Val Pro Ser Pro Gly Leu Ala Gly
            660                     665                     670
Pro Val Thr Met Thr Ser Val His Pro Pro Ile Arg Ser Pro Ser Ala
            675                     680                     685
Ser Ser Val Gly Ser Arg Gly Ser Ser Gly Ser Ser Lys Pro Ala
            690                     695                     700
Gly Ala Asp Ser Thr His Lys Val Pro Val Val Met Leu Glu Pro Ile
705                     710                     715                 720
Arg Ile Lys Gln Glu Asn Ser Gly Pro Pro Glu Asn Tyr Asp Phe Pro
                725                     730                     735
Val Val Ile Val Lys Gln Glu Ser Asp Glu Glu Ser Arg Pro Gln Asn
                740                     745                     750
Ala Asn Tyr Pro Arg Ser Ile Leu Thr Ser Leu Leu Leu Asn Ser Ser
                755                     760                     765
Gln Ser Ser Thr Ser Glu Glu Thr Val Leu Arg Ser Asp Ala Pro Asp
            770                     775                     780
Ser Thr Gly Asp Gln Pro Gly Leu His Gln Asn Ser Ser Asn Gly
785                     790                     795                 800
Lys Ser Glu Trp Leu Asp Pro Ser Gln Lys Ser Pro Leu His Val Gly
                805                     810                     815
Glu Thr Arg Lys Glu Asp Asp Pro Asn Glu Asp Trp Cys Ala Val Cys
            820                     825                     830
Gln Asn Gly Gly Glu Leu Leu Cys Cys Glu Lys Cys Pro Lys Val Phe
            835                     840                     845
His Leu Ser Cys His Val Pro Thr Leu Thr Asn Phe Pro Ser Gly Glu
            850                     855                     860
Trp Ile Cys Thr Phe Cys Arg Asp Leu Ser Lys Pro Glu Val Glu Tyr
865                     870                     875                 880
```

```
Asp Cys Asp Ala Pro Ser His Asn Ser Glu Lys Lys Thr Glu Gly
            885                 890                 895
Leu Val Lys Leu Thr Pro Ile Asp Lys Arg Lys Cys Glu Arg Leu Leu
        900                 905                 910
Leu Phe Leu Tyr Cys His Glu Met Ser Leu Ala Phe Gln Asp Pro Val
    915                 920                 925
Pro Leu Thr Val Pro Asp Tyr Tyr Lys Ile Ile Lys Asn Pro Met Asp
930                 935                 940
Leu Ser Thr Ile Lys Lys Arg Leu Gln Glu Asp Tyr Ser Met Tyr Ser
945                 950                 955                 960
Lys Pro Glu Asp Phe Val Ala Asp Phe Arg Leu Ile Phe Gln Asn Cys
                965                 970                 975
Ala Glu Phe Asn Glu Pro Asp Ser Glu Val Ala Asn Ala Gly Ile Lys
            980                 985                 990
Leu Glu Asn Tyr Phe Glu Glu Leu Leu Lys Asn Leu Tyr Pro Glu Lys
        995                 1000                1005
Arg Phe Pro Lys Pro Glu Phe Arg Asn Glu Ser Glu Asp Asn Lys
    1010                1015                1020
Phe Ser Asp Asp Ser Asp Asp Phe Val Gln Pro Arg Lys Lys
    1025                1030                1035
Arg Leu Lys Ser Ile Glu Glu Arg Gln Leu Leu Lys
    1040                1045                1050

<210> SEQ ID NO 49
<211> LENGTH: 1893
<212> TYPE: DNA
<213> ORGANISM: Homo sapiens

<400> SEQUENCE: 49
atggcagagc tgtgccccct ggccgaggag ctgtcgtgct ccatctgcct ggagcccttc    60
aaggagccgg tcaccactcc gtgcggccac aacttctgcg gtcgtgcct gaatgagacg    120 tgggcagtcc agggctcgcc atacctgtgc ccgcagtgcc gcgccgtcta ccaggcgcga    180
ccgcagctgc acaagaacac ggtgctgtgc aacgtggtgg agcagttcct gcaggccgac    240
ctggcccggg agccacccgc cgacgtctgg acgccgcccg cccgcgcctc tgcacccagc    300
ccgaatgccc aggtggcctg cgaccactgc ctgaaggagg ccgccgtgaa gacgtgcttg    360
gtgtgcatgg cctccttctg tcaggagcac ctgcagccgc acttcgacag ccccgccttc    420
caggaccacc cgctgcagcc gcccgttcgc gacctgttgc gccgcaaatg ttcccagcac    480
aatcggctgc gggaattttt ctgccccgag cacagcgagt gcatctgcca catctgcctg    540
gtggagcata agacctgctc tcccgcgtcc ctgagccagg ccagcgccga cctggaggcc    600
accctgaggc acaaactaac tgtcatgtac agtcagatca cggggcgtc gagagcactg    660 gatgatgtga aaacaggca gcaggatgtg cggatgactg caaacagaaa ggtggagcag    720
ctacaacaag aatacacgga aatgaaggct ctcttggacg cctcagagac cacctcgaca    780
aggaagataa ggaagagga gaagagggtc aacagcaagt ttgacaccat ttatcagatt    840
ctcctcaaga gaagagtga gatccagacc ttgaaggagg agattgaaca gagcctgacc    900
aagagggatg agttcgagtt tctggagaaa gcatcaaaac tgcgaggaat ctcaacaaag    960
ccagtctaca tccccgaggt ggaactgaac acaagctga taaaaggcat ccaccagagc    1020
accatagacc tcaaaaacga gctgaagcag tgcatcgggc ggctccagga gcccaccccc    1080
agttcaggtg accctggaga gcatgaccca gcgtccacac acaaatccac acgccctgtg    1140
```

-continued

```
aagaaggtct ccaaagagga aaagaaatcc aagaaacctc ccctgtccc tgccttaccc    1200
agcaagcttc ccacgtttgg agccccggaa cagttagtgg atttaaaaca agctggcttg    1260
gaggctgcag ccaaagccac cagctcacat ccgaactcaa catctctcaa ggccaaggtg    1320
ctggagacct tcctggccaa gtccagacct gagctcctgg agtattacat taaagtcatc    1380
ctggactaca acaccgccca caacaaagtg gctctgtcag agtgctatac agtagcttct    1440
gtggctgaga tgcctcagaa ctaccggccg catccccaga ggttcacata ctgctctcag    1500
gtgctgggcc tgcactgcta caagaagggg atccactact gggaggtgga gctgcagaag    1560
aacaacttct gtggggtagg catctgctac ggaagcatga accggcaggg cccagaaagc    1620
aggctcggcc gcaacagcgc ctcctggtgc gtggagtggt caacaccaa gatctctgcc     1680
tggcacaata acgtggagaa aaccctgccc tccaccaagg ccacgcgggt gggcgtgctt    1740
ctcaactgtg accacggctt tgtcatcttc ttcgctgttg ccgacaaggt ccacctgatg    1800
tataagttca gggtggactt tactgaggct ttgtacccgg ctttctgggt attttctgct    1860
ggtgccacac tctccatctg ctcccccaag tag                                1893
```

<210> SEQ ID NO 50
<211> LENGTH: 630
<212> TYPE: PRT
<213> ORGANISM: Homo sapiens

<400> SEQUENCE: 50

```
Met Ala Glu Leu Cys Pro Leu Ala Glu Glu Leu Ser Cys Ser Ile Cys
1               5                   10                  15

Leu Glu Pro Phe Lys Glu Pro Val Thr Thr Pro Cys Gly His Asn Phe
            20                  25                  30

Cys Gly Ser Cys Leu Asn Glu Thr Trp Ala Val Gln Gly Ser Pro Tyr
        35                  40                  45

Leu Cys Pro Gln Cys Arg Ala Val Tyr Gln Ala Arg Pro Gln Leu His
    50                  55                  60

Lys Asn Thr Val Leu Cys Asn Val Val Glu Gln Phe Leu Gln Ala Asp
65                  70                  75                  80

Leu Ala Arg Glu Pro Ala Asp Val Trp Thr Pro Pro Ala Arg Ala
                85                  90                  95

Ser Ala Pro Ser Pro Asn Ala Gln Val Ala Cys Asp His Cys Leu Lys
            100                 105                 110

Glu Ala Ala Val Lys Thr Cys Leu Val Cys Met Ala Ser Phe Cys Gln
        115                 120                 125

Glu His Leu Gln Pro His Phe Asp Ser Pro Ala Phe Gln Asp His Pro
    130                 135                 140

Leu Gln Pro Pro Val Arg Asp Leu Leu Arg Arg Lys Cys Ser Gln His
145                 150                 155                 160

Asn Arg Leu Arg Glu Phe Phe Cys Pro Glu His Ser Glu Cys Ile Cys
                165                 170                 175

His Ile Cys Leu Val Glu His Lys Thr Cys Ser Pro Ala Ser Leu Ser
            180                 185                 190

Gln Ala Ser Ala Asp Leu Glu Ala Thr Leu Arg His Lys Leu Thr Val
        195                 200                 205

Met Tyr Ser Gln Ile Asn Gly Ala Ser Arg Ala Leu Asp Asp Val Arg
    210                 215                 220

Asn Arg Gln Gln Asp Val Arg Met Thr Ala Asn Arg Lys Val Glu Gln
225                 230                 235                 240
```

Leu Gln Gln Glu Tyr Thr Glu Met Lys Ala Leu Leu Asp Ala Ser Glu
            245                 250                 255

Thr Thr Ser Thr Arg Lys Ile Lys Glu Glu Lys Arg Val Asn Ser
        260                 265                 270

Lys Phe Asp Thr Ile Tyr Gln Ile Leu Leu Lys Lys Ser Glu Ile
        275                 280                 285

Gln Thr Leu Lys Glu Glu Ile Glu Gln Ser Leu Thr Lys Arg Asp Glu
        290                 295                 300

Phe Glu Phe Leu Glu Lys Ala Ser Lys Leu Arg Gly Ile Ser Thr Lys
305                 310                 315                 320

Pro Val Tyr Ile Pro Glu Val Glu Leu Asn His Lys Leu Ile Lys Gly
            325                 330                 335

Ile His Gln Ser Thr Ile Asp Leu Lys Asn Glu Leu Lys Gln Cys Ile
        340                 345                 350

Gly Arg Leu Gln Glu Pro Thr Pro Ser Ser Gly Asp Pro Gly Glu His
            355                 360                 365

Asp Pro Ala Ser Thr His Lys Ser Thr Arg Pro Val Lys Val Ser
        370                 375                 380

Lys Glu Glu Lys Lys Ser Lys Lys Pro Pro Val Pro Ala Leu Pro
385                 390                 395                 400

Ser Lys Leu Pro Thr Phe Gly Ala Pro Glu Gln Leu Val Asp Leu Lys
            405                 410                 415

Gln Ala Gly Leu Glu Ala Ala Lys Ala Thr Ser Ser His Pro Asn
        420                 425                 430

Ser Thr Ser Leu Lys Ala Lys Val Leu Glu Thr Phe Leu Ala Lys Ser
        435                 440                 445

Arg Pro Glu Leu Leu Glu Tyr Tyr Ile Lys Val Ile Leu Asp Tyr Asn
450                 455                 460

Thr Ala His Asn Lys Val Ala Leu Ser Glu Cys Tyr Thr Val Ala Ser
465                 470                 475                 480

Val Ala Glu Met Pro Gln Asn Tyr Arg Pro His Pro Gln Arg Phe Thr
            485                 490                 495

Tyr Cys Ser Gln Val Leu Gly Leu His Cys Tyr Lys Lys Gly Ile His
        500                 505                 510

Tyr Trp Glu Val Glu Leu Gln Lys Asn Asn Phe Cys Gly Val Gly Ile
        515                 520                 525

Cys Tyr Gly Ser Met Asn Arg Gln Gly Pro Glu Ser Arg Leu Gly Arg
530                 535                 540

Asn Ser Ala Ser Trp Cys Val Glu Trp Phe Asn Thr Lys Ile Ser Ala
545                 550                 555                 560

Trp His Asn Asn Val Glu Lys Thr Leu Pro Ser Thr Lys Ala Thr Arg
            565                 570                 575

Val Gly Val Leu Leu Asn Cys Asp His Gly Phe Val Ile Phe Phe Ala
        580                 585                 590

Val Ala Asp Lys Val His Leu Met Tyr Lys Phe Arg Val Asp Phe Thr
        595                 600                 605

Glu Ala Leu Tyr Pro Ala Phe Trp Val Phe Ser Ala Gly Ala Thr Leu
        610                 615                 620

Ser Ile Cys Ser Pro Lys
625                 630

<210> SEQ ID NO 51
<211> LENGTH: 1620

```
<212> TYPE: DNA
<213> ORGANISM: Homo sapiens

<400> SEQUENCE: 51
atggccacgt cagccccact acggagcctg aagaggagg tgacctgctc catctgtctt        60
gattacctgc gggaccctgt gaccattgac tgtggccacg tcttctgccg cagctgcacc      120
acagacgtcc gccccatctc agggagccgc cccgtctgcc cactctgcaa gaagcctttt      180
aagaaggaga acatccgacc cgtgtggcaa ctggccagcc tggtggagaa cattgagcgg      240
ctgaaggtgg acaagggcag gcagccggga gaggtgaccc gggagcagca ggatgcaaag      300
ttgtgcgagc gacaccgaga gaagctgcac tactactgtg aggacgacgg gaagctgctg      360
tgcgtgatgt gccgggagtc ccgggagcac aggccccaca cggccgtcct catggagaag      420
gccgcccagc cccacaggga aaaaatcctg aaccacctga gtaccctaag gagggacaga      480
gacaaaattc agggcttcca ggcaaaggga aagctgata tcctggccgc gctgaagaag       540
ctccaggacc agaggcagta cattgtggct gagtttgagc agggtcatca gttcctgagg      600
gagcgggagg aacacctgct ggaacagctg gcgaagctgg agcaggagct cacggagggc      660
agggagaagt tcaagagccg gggcgtcggg gagcttgccc ggctggccct ggtcatctcc      720
gaactggagg gcaaggcgca gcagccagct gcagagctca tgcaggacac gagagacttc      780
ctaaacaggt atccacggaa gaagttctgg gttgggaaac ccattgctcg agtggttaaa      840
aaaaagaccg gagaattctc agataaactc ctctctctgc aacgaggcct gagggaattc      900
caggggaagc tgctgagaga cttggaatat aagacagtga gcgtcaccct ggacccacag      960
tcggccagtg ggtacctgca gctgtcagag gactggaagt gcgtgaccta caccagcctg     1020
tacaagagtg cctacctgca cccccagcag tttgactgtg agcctggggt gctaggcagc     1080
aagggcttca cctgggcaa ggtctactgg gaagtggaag tggagaggga gggctggtct      1140
gaggatgaag aagaggggga tgaggaggaa gaggagaag aggaggagga ggaagaggag       1200
gccggctatg gggatggata tgacgactgg gaaacggacg aagatgagga atcgttgggc     1260
gatgaagagg aagaagagga ggaggaagag gaggaagttc tggaaagctg catggtgggg     1320
gtggctagag actctgtgaa gaggaaggga gacctctccc tgcggccaga ggatggcgtg     1380
tgggcgctgc gcctctcctc ctccggcatc tgggccaaca ccagccccga ggctgagctt     1440
ttcccagcac tgcggccccg gagagtgggc atcgccctgg attatgaagg gggcaccgtg     1500
actttcacca acgcagagtc acaggaactc atctacacct tcactgccac cttcacccgg     1560
cgcctggtcc ccttcctgtg gctcaagtgg ccaggaacac gcctcctgct aagaccctga     1620

<210> SEQ ID NO 52
<211> LENGTH: 539
<212> TYPE: PRT
<213> ORGANISM: Homo sapiens

<400> SEQUENCE: 52

Met Ala Thr Ser Ala Pro Leu Arg Ser Leu Glu Glu Val Thr Cys
1               5                   10                  15

Ser Ile Cys Leu Asp Tyr Leu Arg Asp Pro Val Thr Ile Asp Cys Gly
            20                  25                  30

His Val Phe Cys Arg Ser Cys Thr Thr Asp Val Arg Pro Ile Ser Gly
        35                  40                  45

Ser Arg Pro Val Cys Pro Leu Cys Lys Lys Pro Phe Lys Lys Glu Asn
    50                  55                  60
```

```
Ile Arg Pro Val Trp Gln Leu Ala Ser Leu Val Glu Asn Ile Glu Arg
 65                  70                  75                  80

Leu Lys Val Asp Lys Gly Arg Gln Pro Gly Glu Val Thr Arg Glu Gln
             85                  90                  95

Gln Asp Ala Lys Leu Cys Glu Arg His Arg Glu Lys Leu His Tyr Tyr
            100                 105                 110

Cys Glu Asp Asp Gly Lys Leu Leu Cys Val Met Cys Arg Glu Ser Arg
        115                 120                 125

Glu His Arg Pro His Thr Ala Val Leu Met Glu Lys Ala Ala Gln Pro
        130                 135                 140

His Arg Glu Lys Ile Leu Asn His Leu Ser Thr Leu Arg Arg Asp Arg
145                 150                 155                 160

Asp Lys Ile Gln Gly Phe Gln Ala Lys Gly Glu Ala Asp Ile Leu Ala
                165                 170                 175

Ala Leu Lys Lys Leu Gln Asp Gln Arg Gln Tyr Ile Val Ala Glu Phe
                180                 185                 190

Glu Gln Gly His Gln Phe Leu Arg Glu Arg Glu His Leu Leu Glu
            195                 200                 205

Gln Leu Ala Lys Leu Glu Gln Glu Leu Thr Glu Gly Arg Glu Lys Phe
210                 215                 220

Lys Ser Arg Gly Val Gly Glu Leu Ala Arg Leu Ala Leu Val Ile Ser
225                 230                 235                 240

Glu Leu Glu Gly Lys Ala Gln Gln Pro Ala Glu Leu Met Gln Asp
                245                 250                 255

Thr Arg Asp Phe Leu Asn Arg Tyr Pro Arg Lys Lys Phe Trp Val Gly
            260                 265                 270

Lys Pro Ile Ala Arg Val Val Lys Lys Thr Gly Glu Phe Ser Asp
        275                 280                 285

Lys Leu Leu Ser Leu Gln Arg Gly Leu Arg Glu Phe Gln Gly Lys Leu
        290                 295                 300

Leu Arg Asp Leu Glu Tyr Lys Thr Val Ser Val Thr Leu Asp Pro Gln
305                 310                 315                 320

Ser Ala Ser Gly Tyr Leu Gln Leu Ser Glu Asp Trp Lys Cys Val Thr
                325                 330                 335

Tyr Thr Ser Leu Tyr Lys Ser Ala Tyr Leu His Pro Gln Gln Phe Asp
            340                 345                 350

Cys Glu Pro Gly Val Leu Gly Ser Lys Gly Phe Thr Trp Gly Lys Val
        355                 360                 365

Tyr Trp Glu Val Glu Val Glu Arg Glu Gly Trp Ser Glu Asp Glu Glu
        370                 375                 380

Glu Gly Asp Glu Glu Glu Gly Glu Glu Glu Glu Glu Glu Glu
385                 390                 395                 400

Ala Gly Tyr Gly Asp Gly Tyr Asp Asp Trp Glu Thr Asp Glu Asp Glu
                405                 410                 415

Glu Ser Leu Gly Asp Glu Glu Glu Glu Glu Glu Glu Glu
            420                 425                 430

Val Leu Glu Ser Cys Met Val Gly Val Ala Arg Asp Ser Val Lys Arg
        435                 440                 445

Lys Gly Asp Leu Ser Leu Arg Pro Glu Asp Gly Val Trp Ala Leu Arg
        450                 455                 460

Leu Ser Ser Ser Gly Ile Trp Ala Asn Thr Ser Pro Glu Ala Glu Leu
465                 470                 475                 480

Phe Pro Ala Leu Arg Pro Arg Arg Val Gly Ile Ala Leu Asp Tyr Glu
```

```
                485              490              495
Gly Gly Thr Val Thr Phe Thr Asn Ala Glu Ser Gln Glu Leu Ile Tyr
            500              505              510

Thr Phe Thr Ala Thr Phe Thr Arg Arg Leu Val Pro Phe Leu Trp Leu
            515              520              525

Lys Trp Pro Gly Thr Arg Leu Leu Leu Arg Pro
        530              535

<210> SEQ ID NO 53
<211> LENGTH: 1542
<212> TYPE: DNA
<213> ORGANISM: Homo sapiens

<400> SEQUENCE: 53
```

| | | | | | |
|---|---|---|---|---|---|
| atggcctccg | ggagtgtggc | cgagtgcctg | cagcaggaga | ccacctgccc | cgtgtgcctg | 60 |
| cagtacttcg | cagagcccat | gatgctcgac | tgcggccata | acatctgttg | cgcgtgcctc | 120 |
| gcccgctgct | ggggcacggc | agagactaac | gtgtcgtgcc | cgcagtgccg | ggagaccttc | 180 |
| ccgcagaggc | acatgcggcc | caaccggcac | ctggccaacg | tgacccaact | ggtaaagcag | 240 |
| ctgcgcaccg | agcggccgtc | ggggcccggc | ggcgagatgg | gcgtgtgcga | gaagcaccgc | 300 |
| gagcccctga | agctgtactg | cgaggaggac | cagatgccca | tctgcgtggt | gtgcgaccgc | 360 |
| tcccgcgagc | accgcggcca | cagcgtgctg | ccgctcgagg | aggcggtgga | gggcttcaag | 420 |
| gagcaaatcc | agaaccagct | cgaccattta | aaaagagtga | agatttaaa | gaagagacgt | 480 |
| cgggcccagg | gggaacaggc | acgagctgaa | ctcttgagcc | taacccagat | ggagagggag | 540 |
| aagattgttt | gggagtttga | gcagctgtat | cactccttaa | aggagcatga | gtatcgcctc | 600 |
| ctggcccgcc | ttgaggagct | agacttggcc | atctacaata | gcatcaatgg | tgccatcacc | 660 |
| cagttctctt | gcaacatctc | ccacctcagc | agcctgatcg | ctcagctaga | agagaagcag | 720 |
| cagcagccca | ccagggagct | cctgcaggac | attggggaca | cattgagcag | ggctgaaaga | 780 |
| atcaggattc | ctgaaccttg | gatcacacct | ccagatttgc | aagagaaaat | ccacattttt | 840 |
| gcccaaaaat | gtctattctt | gacgagagt | ctaaagcagt | tcacagaaaa | aatgcagtca | 900 |
| gatatggaga | aaatccaaga | attaagagag | gctcagttat | actcagtgga | cgtgactctg | 960 |
| gacccagaca | cggcctaccc | cagcctgatc | ctctctgata | atctgcggca | agtgcggtac | 1020 |
| agttacctcc | aacaggacct | gcctgacaac | cccgagaggt | tcaatctgtt | tccctgtgtc | 1080 |
| ttgggctctc | catgcttcat | cgccgggaga | cattattggg | aggtagaggt | gggagataaa | 1140 |
| gccaagtgga | ccataggtgt | ctgtgaagac | tcagtgtgca | gaaaaggtgg | agtaacctca | 1200 |
| gccccccaga | atggattctg | ggcagtgtct | ttgtggtatg | ggaaagaata | ttgggctctt | 1260 |
| acctccccaa | tgactgccct | acccctgcgg | acccgctcc | agcgggtggg | gattttcttg | 1320 |
| gactatgatg | ctggtgaggt | ctccttctac | aacgtgacag | agaggtgtca | caccttcact | 1380 |
| ttctctcatg | ctaccttttg | tgggcctgtc | cggccctact | tcagtctgag | ttactcggga | 1440 |
| gggaaaagtg | cagctcctct | gatcatctgc | cccatgagtg | ggatagatgg | gttttctggc | 1500 |
| catgttggga | atcatggtca | ttccatggag | acctccccctt | ga | | 1542 |

```
<210> SEQ ID NO 54
<211> LENGTH: 513
<212> TYPE: PRT
<213> ORGANISM: Homo sapiens

<400> SEQUENCE: 54
```

```
Met Ala Ser Gly Ser Val Ala Glu Cys Leu Gln Gln Glu Thr Thr Cys
1               5                   10                  15
Pro Val Cys Leu Gln Tyr Phe Ala Glu Pro Met Met Leu Asp Cys Gly
            20                  25                  30
His Asn Ile Cys Cys Ala Cys Leu Ala Arg Cys Trp Gly Thr Ala Glu
        35                  40                  45
Thr Asn Val Ser Cys Pro Gln Cys Arg Glu Thr Phe Pro Gln Arg His
    50                  55                  60
Met Arg Pro Asn Arg His Leu Ala Asn Val Thr Gln Leu Val Lys Gln
65                  70                  75                  80
Leu Arg Thr Glu Arg Pro Ser Gly Pro Gly Gly Glu Met Gly Val Cys
                85                  90                  95
Glu Lys His Arg Glu Pro Leu Lys Leu Tyr Cys Glu Glu Asp Gln Met
            100                 105                 110
Pro Ile Cys Val Val Cys Asp Arg Ser Arg Glu His Arg Gly His Ser
        115                 120                 125
Val Leu Pro Leu Glu Glu Ala Val Glu Gly Phe Lys Glu Gln Ile Gln
    130                 135                 140
Asn Gln Leu Asp His Leu Lys Arg Val Lys Asp Leu Lys Lys Arg Arg
145                 150                 155                 160
Arg Ala Gln Gly Glu Gln Ala Arg Ala Glu Leu Leu Ser Leu Thr Gln
                165                 170                 175
Met Glu Arg Glu Lys Ile Val Trp Glu Phe Glu Gln Leu Tyr His Ser
            180                 185                 190
Leu Lys Glu His Glu Tyr Arg Leu Leu Ala Arg Leu Glu Glu Leu Asp
        195                 200                 205
Leu Ala Ile Tyr Asn Ser Ile Asn Gly Ala Ile Thr Gln Phe Ser Cys
    210                 215                 220
Asn Ile Ser His Leu Ser Ser Leu Ile Ala Gln Leu Glu Glu Lys Gln
225                 230                 235                 240
Gln Gln Pro Thr Arg Glu Leu Leu Gln Asp Ile Gly Asp Thr Leu Ser
                245                 250                 255
Arg Ala Glu Arg Ile Arg Ile Pro Glu Pro Trp Ile Thr Pro Pro Asp
            260                 265                 270
Leu Gln Glu Lys Ile His Ile Phe Ala Gln Lys Cys Leu Phe Leu Thr
        275                 280                 285
Glu Ser Leu Lys Gln Phe Thr Glu Lys Met Gln Ser Asp Met Glu Lys
    290                 295                 300
Ile Gln Glu Leu Arg Glu Ala Gln Leu Tyr Ser Val Asp Val Thr Leu
305                 310                 315                 320
Asp Pro Asp Thr Ala Tyr Pro Ser Leu Ile Leu Ser Asp Asn Leu Arg
                325                 330                 335
Gln Val Arg Tyr Ser Tyr Leu Gln Gln Asp Leu Pro Asp Asn Pro Glu
            340                 345                 350
Arg Phe Asn Leu Phe Pro Cys Val Leu Gly Ser Pro Cys Phe Ile Ala
        355                 360                 365
Gly Arg His Tyr Trp Glu Val Glu Val Gly Asp Lys Ala Lys Trp Thr
    370                 375                 380
Ile Gly Val Cys Glu Asp Ser Val Cys Arg Lys Gly Gly Val Thr Ser
385                 390                 395                 400
Ala Pro Gln Asn Gly Phe Trp Ala Val Ser Leu Trp Tyr Gly Lys Glu
                405                 410                 415
Tyr Trp Ala Leu Thr Ser Pro Met Thr Ala Leu Pro Leu Arg Thr Pro
```

```
              420             425             430
Leu Gln Arg Val Gly Ile Phe Leu Asp Tyr Asp Ala Gly Glu Val Ser
            435                 440                 445

Phe Tyr Asn Val Thr Glu Arg Cys His Thr Phe Ser His Ala
        450                 455                 460

Thr Phe Cys Gly Pro Val Arg Pro Tyr Phe Ser Leu Ser Tyr Ser Gly
465                 470                 475                 480

Gly Lys Ser Ala Ala Pro Leu Ile Ile Cys Pro Met Ser Gly Ile Asp
                485                 490                 495

Gly Phe Ser Gly His Val Gly Asn His Gly His Ser Met Glu Thr Ser
                500                 505                 510

Pro

<210> SEQ ID NO 55
<211> LENGTH: 2508
<212> TYPE: DNA
<213> ORGANISM: Homo sapiens

<400> SEQUENCE: 55
```

| | | | | | |
|---|---|---|---|---|---|
| atggcggcct | ccgcggcggc | agcctcggca | gcagcggcct | cggccgcctc | tggcagcccg | 60 |
| ggcccgggcg | agggctccgc | tggcggcgaa | aagcgctcca | ccgccccttc | ggccgcagcc | 120 |
| tcggcctctg | cctcagccgc | ggcgtcgtcg | cccgcggggg | gcggcgccga | ggcgctggag | 180 |
| ctgctggagc | actgcggcgt | gtgcagagag | cgcctgcgac | ccgagaggga | gccccgcctg | 240 |
| ctgccctgtt | tgcactcggc | ctgtagtgcc | tgcttagggc | ccgcggcccc | cgccgccgcc | 300 |
| aacagctcgg | gggacggcgg | ggcggcgggc | gacggcaccg | tggtggactg | tcccgtgtgc | 360 |
| aagcaacagt | gcttctccaa | agacatcgtg | gagaattatt | tcatgcgtga | tagtggcagc | 420 |
| aaggctgcca | ccgacgccca | ggatgcgaac | cagtgctgca | ctagctgtga | ggataatgcc | 480 |
| ccagccacca | gctactgtgt | ggagtgctcg | gagcctctgt | gtgagacctg | tgtagaggcg | 540 |
| caccagcggg | tgaagtacac | caaggaccat | actgtgcgct | ctactgggcc | agccaagtct | 600 |
| cgggatggtg | aacgtactgt | ctattgcaac | gtacacaagc | atgaaccccc | tgtgctgttt | 660 |
| tgtgagagct | gtgatactct | cacctgccga | gactgccagc | tcaatgccca | caaggaccac | 720 |
| cagtaccagt | tcttagagga | tgcagtgagg | aaccagcgca | agctcctggc | ctcactggtg | 780 |
| aagcgccttg | gggacaaaca | tgcaacattg | cagaagagca | ccaaggaggt | tcgcagctca | 840 |
| atccgccagg | tgtctgacgt | acagaagcgt | gtgcaagtgg | atgtcaagat | ggccatcctg | 900 |
| cagatcatga | aggagctgaa | taagcggggc | cgtgtgctgg | tcaatgatgc | ccagaaggtg | 960 |
| actgaggggc | agcaggagcg | cctggagcgg | cagcactgga | ccatgaccaa | gatccagaag | 1020 |
| caccaggagc | acattctgcg | ctttgcctct | tgggctctgg | agagtgacaa | caacacagcc | 1080 |
| cttttgcttt | ctaagaagtt | gatctacttc | cagctgcacc | gggccctcaa | gatgattgtg | 1140 |
| gatcccgtgg | agccacatgg | cgagatgaag | tttcagtggg | acctcaatgc | ctggaccaag | 1200 |
| agtgccgagg | cctttggcaa | gattgtggca | gagcgtcctg | gcactaactc | aacaggccct | 1260 |
| gcacccatgg | cccctccaag | agccccaggg | cccctgagca | agcagggctc | tggcagcagc | 1320 |
| cagcccatgg | aggtgcagga | aggctatggc | tttgggtcag | agatgatccc | tactcaagt | 1380 |
| gcagagcccc | atgtgtcagg | tgtgaaacgg | tcccgctcag | gtgagggcga | ggtgagcggc | 1440 |
| cttatgcgca | aggtgccacg | agtgagcctt | gaacgcctgg | acctggacct | cacagctgac | 1500 |
| agccagccac | ccgtcttcaa | ggtcttccca | ggcagtacca | ctgaggacta | caaccttatt | 1560 |

-continued

```
gttattgaac gtggcgctgc cgctgcagct accggccagc cagggactgc gcctgcagga    1620
acccctggtg ccccacccct ggctggcatg gccattgtca aggaggagga gacggaggct    1680
gccattggag cccctcctac tgccactgag ggccctgaga ccaaacctgt gcttatggct    1740
cttgcggagg gtcctggtgc tgagggtccc cgcctggcct cacctagtgg cagcaccagc    1800
tcagggctgg aggtggtggc tcctgagggt acctcagccc caggtggtgg cccgggaacc    1860
ctggatgaca gtgccaccat ttgccgtgtc tgccagaagc caggcgatct ggttatgtgc    1920
aaccagtgtg agttttgttt ccacctggac tgtcacctgc cggccctgca ggatgtacca    1980
ggggaggagt ggagctgctc actctgccat gtgctccctg acctgaagga ggaggatggc    2040
agcctcagcc tggatggtgc agacagcact ggcgtggtgg ccaagctctc accagccaac    2100
cagcggaaat gtgagcgtgt actgctggcc ctattctgtc acgaaccctg ccgcccctg     2160 catcagctgg ctaccgactc caccttctcc ctggaccagc ccggtggcac cctggatctg    2220
accctgatcc gtgcccgcct ccaggagaag ttgtcacctc cctacagctc cccacaggag    2280
tttgcccagg atgtgggccg catgttcaag caattcaaca gttaactga ggacaaggca     2340 gacgtgcagt ccatcatcgg cctgcagcgc ttcttcgaga cgcgcatgaa cgaggccttc    2400
ggtgacacca agttctctgc tgtgctggtg agcccccgc cgatgagcct gcctggtgct     2460
ggcctgagtt cccaggagct gtctggtggc cctggtgatg cccctga                  2508
```

<210> SEQ ID NO 56
<211> LENGTH: 835
<212> TYPE: PRT
<213> ORGANISM: Homo sapiens

<400> SEQUENCE: 56

```
Met Ala Ala Ser Ala Ala Ala Ser Ala Ala Ala Ser Ala Ala
1               5                   10                  15

Ser Gly Ser Pro Gly Pro Gly Glu Gly Ser Ala Gly Gly Glu Lys Arg
                20                  25                  30

Ser Thr Ala Pro Ser Ala Ala Ala Ser Ala Ser Ala Ala Ala
            35                  40                  45

Ser Ser Pro Ala Gly Gly Gly Ala Glu Ala Leu Glu Leu Leu Glu His
        50                  55                  60

Cys Gly Val Cys Arg Glu Arg Leu Arg Pro Glu Arg Glu Pro Arg Leu
65                  70                  75                  80

Leu Pro Cys Leu His Ser Ala Cys Ser Ala Cys Leu Gly Pro Ala Ala
                85                  90                  95

Pro Ala Ala Ala Asn Ser Ser Gly Asp Gly Gly Ala Ala Gly Asp Gly
                100                 105                 110

Thr Val Val Asp Cys Pro Val Cys Lys Gln Gln Cys Phe Ser Lys Asp
            115                 120                 125

Ile Val Glu Asn Tyr Phe Met Arg Asp Ser Gly Ser Lys Ala Ala Thr
        130                 135                 140

Asp Ala Gln Asp Ala Asn Gln Cys Cys Thr Ser Cys Glu Asp Asn Ala
145                 150                 155                 160

Pro Ala Thr Ser Tyr Cys Val Glu Cys Ser Glu Pro Leu Cys Glu Thr
                165                 170                 175

Cys Val Glu Ala His Gln Arg Val Lys Tyr Thr Lys Asp His Thr Val
            180                 185                 190

Arg Ser Thr Gly Pro Ala Lys Ser Arg Asp Gly Glu Arg Thr Val Tyr
        195                 200                 205
```

-continued

```
Cys Asn Val His Lys His Glu Pro Leu Val Leu Phe Cys Glu Ser Cys
    210                 215                 220

Asp Thr Leu Thr Cys Arg Asp Cys Gln Leu Asn Ala His Lys Asp His
225                 230                 235                 240

Gln Tyr Gln Phe Leu Glu Asp Ala Val Arg Asn Gln Arg Lys Leu Leu
                245                 250                 255

Ala Ser Leu Val Lys Arg Leu Gly Asp Lys His Ala Thr Leu Gln Lys
                260                 265                 270

Ser Thr Lys Glu Val Arg Ser Ser Ile Arg Gln Val Ser Asp Val Gln
            275                 280                 285

Lys Arg Val Gln Val Asp Val Lys Met Ala Ile Leu Gln Ile Met Lys
290                 295                 300

Glu Leu Asn Lys Arg Gly Arg Val Leu Val Asn Asp Ala Gln Lys Val
305                 310                 315                 320

Thr Glu Gly Gln Gln Glu Arg Leu Glu Arg Gln His Trp Thr Met Thr
                325                 330                 335

Lys Ile Gln Lys His Gln Glu His Ile Leu Arg Phe Ala Ser Trp Ala
                340                 345                 350

Leu Glu Ser Asp Asn Asn Thr Ala Leu Leu Leu Ser Lys Lys Leu Ile
            355                 360                 365

Tyr Phe Gln Leu His Arg Ala Leu Lys Met Ile Val Asp Pro Val Glu
370                 375                 380

Pro His Gly Glu Met Lys Phe Gln Trp Asp Leu Asn Ala Trp Thr Lys
385                 390                 395                 400

Ser Ala Glu Ala Phe Gly Lys Ile Val Ala Glu Arg Pro Gly Thr Asn
                405                 410                 415

Ser Thr Gly Pro Ala Pro Met Ala Pro Pro Arg Ala Pro Gly Pro Leu
            420                 425                 430

Ser Lys Gln Gly Ser Gly Ser Ser Gln Pro Met Glu Val Gln Glu Gly
435                 440                 445

Tyr Gly Phe Gly Ser Gly Asp Asp Pro Tyr Ser Ala Glu Pro His
                450                 455                 460

Val Ser Gly Val Lys Arg Ser Arg Ser Gly Glu Gly Glu Val Ser Gly
465                 470                 475                 480

Leu Met Arg Lys Val Pro Arg Val Ser Leu Glu Arg Leu Asp Leu Asp
                485                 490                 495

Leu Thr Ala Asp Ser Gln Pro Pro Val Phe Lys Val Phe Pro Gly Ser
            500                 505                 510

Thr Thr Glu Asp Tyr Asn Leu Ile Val Ile Glu Arg Gly Ala Ala Ala
            515                 520                 525

Ala Ala Thr Gly Gln Pro Gly Thr Ala Pro Gly Thr Pro Gly Ala
530                 535                 540

Pro Pro Leu Ala Gly Met Ala Ile Val Lys Glu Glu Thr Glu Ala
545                 550                 555                 560

Ala Ile Gly Ala Pro Pro Thr Ala Thr Glu Gly Pro Glu Thr Lys Pro
                565                 570                 575

Val Leu Met Ala Leu Ala Glu Gly Pro Gly Ala Glu Gly Pro Arg Leu
            580                 585                 590

Ala Ser Pro Ser Gly Ser Thr Ser Ser Gly Leu Glu Val Ala Pro
            595                 600                 605

Glu Gly Thr Ser Ala Pro Gly Gly Pro Gly Thr Leu Asp Asp Ser
610                 615                 620

Ala Thr Ile Cys Arg Val Cys Gln Lys Pro Gly Asp Leu Val Met Cys
```

```
                625                 630                 635                 640
Asn Gln Cys Glu Phe Cys Phe His Leu Asp Cys His Leu Pro Ala Leu
                        645                 650                 655
Gln Asp Val Pro Gly Glu Glu Trp Ser Cys Ser Leu Cys His Val Leu
                660                 665                 670
Pro Asp Leu Lys Glu Glu Asp Gly Ser Leu Ser Leu Asp Gly Ala Asp
            675                 680                 685
Ser Thr Gly Val Val Ala Lys Leu Ser Pro Ala Asn Gln Arg Lys Cys
        690                 695                 700
Glu Arg Val Leu Leu Ala Leu Phe Cys His Glu Pro Cys Arg Pro Leu
705                 710                 715                 720
His Gln Leu Ala Thr Asp Ser Thr Phe Ser Leu Asp Gln Pro Gly Gly
                        725                 730                 735
Thr Leu Asp Leu Thr Leu Ile Arg Ala Arg Leu Gln Glu Lys Leu Ser
                740                 745                 750
Pro Pro Tyr Ser Ser Pro Gln Glu Phe Ala Gln Asp Val Gly Arg Met
            755                 760                 765
Phe Lys Gln Phe Asn Lys Leu Thr Glu Asp Lys Ala Asp Val Gln Ser
        770                 775                 780
Ile Ile Gly Leu Gln Arg Phe Phe Glu Thr Arg Met Asn Glu Ala Phe
785                 790                 795                 800
Gly Asp Thr Lys Phe Ser Ala Val Leu Val Glu Pro Pro Met Ser
                        805                 810                 815
Leu Pro Gly Ala Gly Leu Ser Ser Gln Glu Leu Ser Gly Gly Pro Gly
                820                 825                 830
Asp Gly Pro
        835

<210> SEQ ID NO 57
<211> LENGTH: 1767
<212> TYPE: DNA
<213> ORGANISM: Homo sapiens

<400> SEQUENCE: 57
atggaagctg cagatgcctc caggagcaac gggtcgagcc cagaagccag ggatgcccgg     60
agcccgtcgg gccccagtgg cagcctggag aatggcacca aggctgacgg caaggatgcc    120
aagaccacca acgggcacgg cggggaggca gctgagggca gagcctgggc agcgccctg     180 aagccagggg aaggtaggag cgccctgttc gcgggcaatg agtggcggcg acccatcatc    240
cagtttgtcg agtccgggga cgacaagaac tccaactact tcagcatgga ctctatggaa    300
ggcaagaggt cgccgtacgc agggctccag ctggggggctg ccaagaagcc acccgttacc    360
tttgccgaaa aggggcgagct gcgcaagtcc attttctcgg agtcccggaa gcccacggtg    420
tccatcatgg agcccgggga gaccggcgg aacagctacc ccgggccgga cacgggcctt    480
ttttcacggt ccaagtccgg ctccgaggag gtgctgtgcg actcctgcat cggcaacaag    540
cagaaggcgg tcaagtcctg cctggtgtgc caggcctcct tctgcgagct gcatctcaag    600
ccccacctgg agggcgccgc cttccgagac caccagctgc tcgagcccat ccgggacttt    660
gaggcccgca agtgtcccgt gcatggcaag acgatggagc tcttctgcca gaccgaccag    720
acctgcatct gctacctttg catgttccag gagcacaaga tcatagcac cgtgacagtg    780 gaggaggcca aggccgagaa ggagacggag ctgtcattgc aaaaggagca gctgcagctc    840
aagatcattg agattgagga tgaagctgag aagtggcaga aggagaagga ccgcatcaag    900
```

-continued

```
agcttcacca ccaatgagaa ggccatcctg gagcagaact tccgggacct ggtgcgggac     960
ctggagaagc aaaaggagga agtgagggct gcgctggagc agcgggagca ggatgctgtg    1020
gaccaagtga aggtgatcat ggatgctctg gatgagagag ccaaggtgct gcatgaggac    1080
aagcagaccc gggagcagct gcatagcatc agcgactctg tgttgtttct gcaggaattt    1140
ggtgcattga tgagcaatta ctctctcccc ccacccctgc ccacctatca tgtcctgctg    1200
gagggggagg gcctgggaca gtcactaggc aacttcaagg acgacctgct caatgtatgc    1260
atgcgccacg ttgagaagat gtgcaaggcg gacctgagcc gtaacttcat tgagaggaac    1320
cacatggaga acggtggtga ccatcgctat gtgaacaact acacgaacag cttcgggggt    1380
gagtggagtg caccggacac catgaagaga tactccatgt acctgacacc caaaggtggg    1440
gtccggacat cataccagcc ctcgtctcct ggccgcttca ccaaggagac cacccagaag    1500
aatttcaaca atctctatgg caccaaaggt aactacacct cccgggtctg ggagtactcc    1560
tccagcattc agaactctga caatgacctg cccgtcgtcc aaggcagctc ctccttctcc    1620
ctgaaaggct atccctccct catgcggagc caaagcccca ggcccagcc ccagacttgg     1680 aaatctggca agcagactat gctgtctcac taccggccat tctacgtcaa caaaggcaac    1740
gggattgggt ccaacgaagc cccatga                                        1767
```

<210> SEQ ID NO 58
<211> LENGTH: 588
<212> TYPE: PRT
<213> ORGANISM: Homo sapiens

<400> SEQUENCE: 58

```
Met Glu Ala Ala Asp Ala Ser Arg Ser Asn Gly Ser Ser Pro Glu Ala
1               5                   10                  15

Arg Asp Ala Arg Ser Pro Ser Gly Pro Ser Gly Ser Leu Glu Asn Gly
            20                  25                  30

Thr Lys Ala Asp Gly Lys Asp Ala Lys Thr Thr Asn Gly His Gly Gly
        35                  40                  45

Glu Ala Ala Glu Gly Lys Ser Leu Gly Ser Ala Leu Lys Pro Gly Glu
    50                  55                  60

Gly Arg Ser Ala Leu Phe Ala Gly Asn Glu Trp Arg Arg Pro Ile Ile
65                  70                  75                  80

Gln Phe Val Glu Ser Gly Asp Asp Lys Asn Ser Asn Tyr Phe Ser Met
                85                  90                  95

Asp Ser Met Glu Gly Lys Arg Ser Pro Tyr Ala Gly Leu Gln Leu Gly
            100                 105                 110

Ala Ala Lys Lys Pro Pro Val Thr Phe Ala Glu Lys Gly Glu Leu Arg
        115                 120                 125

Lys Ser Ile Phe Ser Glu Ser Arg Lys Pro Thr Val Ser Ile Met Glu
    130                 135                 140

Pro Gly Glu Thr Arg Arg Asn Ser Tyr Pro Arg Ala Asp Thr Gly Leu
145                 150                 155                 160

Phe Ser Arg Ser Lys Ser Gly Ser Glu Glu Val Leu Cys Asp Ser Cys
                165                 170                 175

Ile Gly Asn Lys Gln Lys Ala Val Lys Ser Cys Leu Val Cys Gln Ala
            180                 185                 190

Ser Phe Cys Glu Leu His Leu Lys Pro His Leu Glu Gly Ala Ala Phe
        195                 200                 205

Arg Asp His Gln Leu Leu Glu Pro Ile Arg Asp Phe Glu Ala Arg Lys
    210                 215                 220
```

Cys Pro Val His Gly Lys Thr Met Glu Leu Phe Cys Gln Thr Asp Gln
225                 230                 235                 240

Thr Cys Ile Cys Tyr Leu Cys Met Phe Gln Glu His Lys Asn His Ser
            245                 250                 255

Thr Val Thr Val Glu Glu Ala Lys Ala Glu Lys Glu Thr Glu Leu Ser
        260                 265                 270

Leu Gln Lys Glu Gln Leu Gln Leu Lys Ile Ile Glu Ile Glu Asp Glu
    275                 280                 285

Ala Glu Lys Trp Gln Lys Glu Lys Asp Arg Ile Lys Ser Phe Thr Thr
290                 295                 300

Asn Glu Lys Ala Ile Leu Glu Gln Asn Phe Arg Asp Leu Val Arg Asp
305                 310                 315                 320

Leu Glu Lys Gln Lys Glu Glu Val Arg Ala Ala Leu Glu Gln Arg Glu
                325                 330                 335

Gln Asp Ala Val Asp Gln Val Lys Val Ile Met Asp Ala Leu Asp Glu
            340                 345                 350

Arg Ala Lys Val Leu His Glu Asp Lys Gln Thr Arg Glu Gln Leu His
        355                 360                 365

Ser Ile Ser Asp Ser Val Leu Phe Leu Gln Glu Phe Gly Ala Leu Met
370                 375                 380

Ser Asn Tyr Ser Leu Pro Pro Leu Pro Thr Tyr His Val Leu Leu
385                 390                 395                 400

Glu Gly Glu Gly Leu Gly Gln Ser Leu Gly Asn Phe Lys Asp Asp Leu
                405                 410                 415

Leu Asn Val Cys Met Arg His Val Glu Lys Met Cys Lys Ala Asp Leu
            420                 425                 430

Ser Arg Asn Phe Ile Glu Arg Asn His Met Glu Asn Gly Gly Asp His
        435                 440                 445

Arg Tyr Val Asn Asn Tyr Thr Asn Ser Phe Gly Gly Glu Trp Ser Ala
450                 455                 460

Pro Asp Thr Met Lys Arg Tyr Ser Met Tyr Leu Thr Pro Lys Gly Gly
465                 470                 475                 480

Val Arg Thr Ser Tyr Gln Pro Ser Ser Pro Gly Arg Phe Thr Lys Glu
                485                 490                 495

Thr Thr Gln Lys Asn Phe Asn Asn Leu Tyr Gly Thr Lys Gly Asn Tyr
            500                 505                 510

Thr Ser Arg Val Trp Glu Tyr Ser Ser Ile Gln Asn Ser Asp Asn
        515                 520                 525

Asp Leu Pro Val Val Gln Gly Ser Ser Phe Ser Leu Lys Gly Tyr
530                 535                 540

Pro Ser Leu Met Arg Ser Gln Ser Pro Lys Ala Gln Pro Gln Thr Trp
545                 550                 555                 560

Lys Ser Gly Lys Gln Thr Met Leu Ser His Tyr Arg Pro Phe Tyr Val
                565                 570                 575

Asn Lys Gly Asn Gly Ile Gly Ser Asn Glu Ala Pro
            580                 585

<210> SEQ ID NO 59
<211> LENGTH: 1491
<212> TYPE: DNA
<213> ORGANISM: Mus musculus

<400> SEQUENCE: 59
atggcctcat cagtcctgga gatgataaag gaggaagtaa cctgtcctat ctgtttggag    60

```
ctcctgaagg aacctgtgag tgctgattgt aaccacagct tctgcagagc ctgcatcaca    120
ctgaattatg agtccaacag aaacacagac gggaagggca actgccctgt atgccgagtt    180
ccttacccat ttgggaatct gaggcctaat ctacatgtgg ccaacatagt agagaggctc    240
aagggattca agtccattcc agaggaggag cagaaggtga atatctgtgc acaacatgga    300
gagaaactcc ggctcttctg taggaaggac atgatggtca tctgctggct tgtgagcga     360 tctcaggagc accgtggtca ccaaacagct ctcattgaag aggttgacca agaatacaag    420
gagaagctgc agggagctct gtggaagctg atgaaaaagg caaaaatatg tgatgaatgg    480
caggatgacc ttcaactgca gagagttgac tgggagaacc aaatacagat caatgtagaa    540
aatgttcaga gacagtttaa aggactaaga gacctcctgg actccaagga gaatgaggag    600
ctgcagaagc tgaagaaaga gaagaaagag gttatggaaa agctggaaga gtctgaaaat    660
gagctggagg atcagacaga gttggtgaga gacctcatct cagatgtgga acatcatttg    720
gagctctcaa cctagaaat gctgcagggt gcaaattgtg tcctgagaag gagtcagtcc    780
ttaagcctgc aacagcccca aactgtcccc caaaagagaa aagaacatt ccaagctcca     840 gatctgaaag gcatgctgca agtgtatcaa ggactcatgg atatccagca atactgggtt    900
catatgactc tacatgcaag gaacaatgca gtcattgcca ttaacaaaga aaaaagacaa    960
atacagtata gaagttacaa tacggttcca gtttctgaga tctaccattt gggtgtcctg   1020
ggatatccag ctctttcctc agggaagcat tactgggaag tagacatatc tagaagtgat   1080
gcctggctcc tcggattaaa tgacggaaag tgtgctcaac cccaacttca ctcaaaggaa   1140
gaaatgggca tcaaaaaaaa ccttcattct cagatcaaac aaaatgtatt gtttcagcct   1200
aaatgtggct actgggttat agggatgaag aatccgtctg tatacaaggc ctttgatgag   1260
tgttctatca cccacaattc cagtatcctg gtcatctctc tgcctgatcg tcccagtcgt   1320
gtcggagttt tcctggatcg gaaagctggc actctctcat tttatgatgt ttctaactgc   1380
ggtgctctca tctataggtt ctatgaccct gccttccctg ttgaagtcta tccatatttt   1440
aatcctatga aatgttcaga gccaatgact atatgcgggc caccctccta a            1491
```

<210> SEQ ID NO 60  
<211> LENGTH: 496  
<212> TYPE: PRT  
<213> ORGANISM: Mus musculus

<400> SEQUENCE: 60

Met Ala Ser Ser Val Leu Glu Met Ile Lys Glu Glu Val Thr Cys Pro
1               5                   10                  15

Ile Cys Leu Glu Leu Leu Lys Glu Pro Val Ser Ala Asp Cys Asn His
            20                  25                  30

Ser Phe Cys Arg Ala Cys Ile Thr Leu Asn Tyr Glu Ser Asn Arg Asn
        35                  40                  45

Thr Asp Gly Lys Gly Asn Cys Pro Val Cys Arg Val Pro Tyr Pro Phe
    50                  55                  60

Gly Asn Leu Arg Pro Asn Leu His Val Ala Asn Ile Val Glu Arg Leu
65                  70                  75                  80

Lys Gly Phe Lys Ser Ile Pro Glu Glu Glu Gln Lys Val Asn Ile Cys
                85                  90                  95

Ala Gln His Gly Glu Lys Leu Arg Leu Phe Cys Arg Lys Asp Met Met
            100                 105                 110

Val Ile Cys Trp Leu Cys Glu Arg Ser Gln Glu His Arg Gly His Gln 115                 120                 125
Thr Ala Leu Ile Glu Glu Val Asp Gln Glu Tyr Lys Glu Lys Leu Gln
                130                 135                 140

Gly Ala Leu Trp Lys Leu Met Lys Lys Ala Lys Ile Cys Asp Glu Trp
145                 150                 155                 160

Gln Asp Asp Leu Gln Leu Arg Val Asp Trp Glu Asn Gln Ile Gln
                165                 170                 175

Ile Asn Val Glu Asn Val Gln Arg Gln Phe Lys Gly Leu Arg Asp Leu
                180                 185                 190

Leu Asp Ser Lys Glu Asn Glu Glu Leu Gln Lys Leu Lys Lys Glu Lys
                195                 200                 205

Lys Glu Val Met Glu Lys Leu Glu Ser Glu Asn Glu Leu Glu Asp
            210                 215                 220

Gln Thr Glu Leu Val Arg Asp Leu Ile Ser Asp Val Glu His His Leu
225                 230                 235                 240

Glu Leu Ser Thr Leu Glu Met Leu Gln Gly Ala Asn Cys Val Leu Arg
                245                 250                 255

Arg Ser Gln Ser Leu Ser Leu Gln Gln Pro Gln Thr Val Pro Gln Lys
                260                 265                 270

Arg Lys Arg Thr Phe Gln Ala Pro Asp Leu Lys Gly Met Leu Gln Val
                275                 280                 285

Tyr Gln Gly Leu Met Asp Ile Gln Gln Tyr Trp Val His Met Thr Leu
290                 295                 300

His Ala Arg Asn Asn Ala Val Ile Ala Ile Asn Lys Glu Lys Arg Gln
305                 310                 315                 320

Ile Gln Tyr Arg Ser Tyr Asn Thr Val Pro Val Ser Glu Ile Tyr His
                325                 330                 335

Leu Gly Val Leu Gly Tyr Pro Ala Leu Ser Ser Gly Lys His Tyr Trp
                340                 345                 350

Glu Val Asp Ile Ser Arg Ser Asp Ala Trp Leu Leu Gly Leu Asn Asp
                355                 360                 365

Gly Lys Cys Ala Gln Pro Gln Leu His Ser Lys Glu Glu Met Gly Ile
                370                 375                 380

Lys Lys Asn Leu His Ser Gln Ile Lys Gln Asn Val Leu Phe Gln Pro
385                 390                 395                 400

Lys Cys Gly Tyr Trp Val Ile Gly Met Lys Asn Pro Ser Val Tyr Lys
                405                 410                 415

Ala Phe Asp Glu Cys Ser Ile Thr His Asn Ser Ser Ile Leu Val Ile
                420                 425                 430

Ser Leu Pro Asp Arg Pro Ser Arg Val Gly Val Phe Leu Asp Arg Lys
                435                 440                 445

Ala Gly Thr Leu Ser Phe Tyr Asp Val Ser Asn Cys Gly Ala Leu Ile
                450                 455                 460

Tyr Arg Phe Tyr Asp Pro Ala Phe Pro Val Glu Val Tyr Pro Tyr Phe
465                 470                 475                 480

Asn Pro Met Lys Cys Ser Glu Pro Met Thr Ile Cys Gly Pro Pro Ser
                485                 490                 495

<210> SEQ ID NO 61
<211> LENGTH: 1278
<212> TYPE: DNA
<213> ORGANISM: Homo sapiens

<400> SEQUENCE: 61

```
atggccagtg ggcagtttgt gaacaaactg caagaggaag tgatctgccc catctgcctg      60
gacattctgc agaaacctgt caccatcgac tgtgggcaca atttctgcct caaatgcatc     120
actcagattg gggaaacatc atgtggattt ttcaaatgtc ccctctgcaa aacttccgta     180
aggaagaacg caatcaggtt caactcgctg ttgcggaatc tggtggagaa atccaagct     240
ctacaagcct ctgaggtgca gtccaaaagg aaagaggcta catgcccgag gcaccaggag     300
atgttccact atttctgcga ggatgatggg aagttcctct gttttgtgtg tcgtgaatcc     360
aaggaccaca atcccataa tgtcagcttg atcgaagaag ctgcccagaa ttatcagggg      420
cagattcaag agcagatcca agtcttgcag caaaaggaga aggagacagt acaagtgaag     480
gcacaaggtg tacacagggt cgatgtcttc acggaccagg tagaacatga aagcaaagg     540
atcctcacag aatttgaact cctgcatcaa gtcctagagg aggagaagaa tttcctgcta     600
tcacggattt actggctggg tcatgaggga acggaagcgg ggaaacacta tgttgcctcc     660
actgagccac agttgaacga tctcaagaag ctcgttgatt ccctgaagac caagcagaac     720
atgccaccca ggcagctgct ggaggatatc aaagtcgtct tgtgcagaag tgaagagttt     780
cagtttctca acccaacccc tgttcctctg gaactggaga aaaaactcag tgaagcaaaa     840
tcaagacatg actccatcac agggagccta aaaaaattca agaccaact ccaggctgat      900
aggaaaaaag atgaaaacag attcttcaaa agcatgaata aaaatgacat gaagagctgg     960
ggcttgttac agaaaaataa tcataaaatg aacaaaacct cagagcccgg gtcatcttct    1020
gcaggcggca gaactacatc ggggccacca aatcaccact cttcagcccc atcccactcc    1080
ctgtttcggg cctcgtctgc tgggaaagtc acttttccag tatgtctcct ggcctcttat    1140
gatgagattt ctggtcaagg agcgagctct caggatacga agacatttga cgttgcgctg    1200
tccgaggagc tccatgcggc actgagtgag tggctgacag cgatccgggc ttggttttgt    1260
gaggttcctt caagctaa                                                  1278
```

<210> SEQ ID NO 62
<211> LENGTH: 425
<212> TYPE: PRT
<213> ORGANISM: Homo sapiens

<400> SEQUENCE: 62

Met Ala Ser Gly Gln Phe Val Asn Lys Leu Gln Glu Glu Val Ile Cys
1               5                   10                  15

Pro Ile Cys Leu Asp Ile Leu Gln Lys Pro Val Thr Ile Asp Cys Gly
            20                  25                  30

His Asn Phe Cys Leu Lys Cys Ile Thr Gln Ile Gly Glu Thr Ser Cys
        35                  40                  45

Gly Phe Phe Lys Cys Pro Leu Cys Lys Thr Ser Val Arg Lys Asn Ala
    50                  55                  60

Ile Arg Phe Asn Ser Leu Leu Arg Asn Leu Val Glu Lys Ile Gln Ala
65                  70                  75                  80

Leu Gln Ala Ser Glu Val Gln Ser Lys Arg Lys Glu Ala Thr Cys Pro
                85                  90                  95

Arg His Gln Glu Met Phe His Tyr Phe Cys Glu Asp Asp Gly Lys Phe
            100                 105                 110

Leu Cys Phe Val Cys Arg Glu Ser Lys Asp His Lys Ser His Asn Val
        115                 120                 125

Ser Leu Ile Glu Glu Ala Ala Gln Asn Tyr Gln Gly Gln Ile Gln Glu
    130                 135                 140

```
Gln Ile Gln Val Leu Gln Gln Lys Glu Lys Glu Thr Val Gln Val Lys
145                 150                 155                 160

Ala Gln Gly Val His Arg Val Asp Val Phe Thr Asp Gln Val Glu His
                165                 170                 175

Glu Lys Gln Arg Ile Leu Thr Glu Phe Glu Leu Leu His Gln Val Leu
            180                 185                 190

Glu Glu Glu Lys Asn Phe Leu Leu Ser Arg Ile Tyr Trp Leu Gly His
        195                 200                 205

Glu Gly Thr Glu Ala Gly Lys His Tyr Val Ala Ser Thr Glu Pro Gln
    210                 215                 220

Leu Asn Asp Leu Lys Lys Leu Val Asp Ser Leu Lys Thr Lys Gln Asn
225                 230                 235                 240

Met Pro Pro Arg Gln Leu Leu Glu Asp Ile Lys Val Val Leu Cys Arg
                245                 250                 255

Ser Glu Glu Phe Gln Phe Leu Asn Pro Thr Pro Val Pro Leu Glu Leu
            260                 265                 270

Glu Lys Lys Leu Ser Glu Ala Lys Ser Arg His Asp Ser Ile Thr Gly
        275                 280                 285

Ser Leu Lys Lys Phe Lys Asp Gln Leu Gln Ala Asp Arg Lys Lys Asp
    290                 295                 300

Glu Asn Arg Phe Phe Lys Ser Met Asn Lys Asn Asp Met Lys Ser Trp
305                 310                 315                 320

Gly Leu Leu Gln Lys Asn Asn His Lys Met Asn Lys Thr Ser Glu Pro
                325                 330                 335

Gly Ser Ser Ser Ala Gly Gly Arg Thr Thr Ser Gly Pro Pro Asn His
            340                 345                 350

His Ser Ser Ala Pro Ser His Ser Leu Phe Arg Ala Ser Ser Ala Gly
        355                 360                 365

Lys Val Thr Phe Pro Val Cys Leu Leu Ala Ser Tyr Asp Glu Ile Ser
    370                 375                 380

Gly Gln Gly Ala Ser Ser Gln Asp Thr Lys Thr Phe Asp Val Ala Leu
385                 390                 395                 400

Ser Glu Glu Leu His Ala Ala Leu Ser Glu Trp Leu Thr Ala Ile Arg
                405                 410                 415

Ala Trp Phe Cys Glu Val Pro Ser Ser
                420                 425

<210> SEQ ID NO 63
<211> LENGTH: 1962
<212> TYPE: DNA
<213> ORGANISM: Homo sapiens

<400> SEQUENCE: 63
atggctgcag cagcagcttc tcacctgaac ctggatgccc tccgggaagt gctagaatgc      60
cccatctgca tggagtcctt cacagaagag cagctgcgtc caagcttct gcactgtggc     120 cataccatct gccgccagtg cctggagaag ctattggcca gtagcatcaa tggtgtccgc     180 tgtcccttt gcagcaagat tacccgcata accagcttga cccagctgac agacaatctg     240
acagtgctaa agatcattga tacagctggg ctcagcgagg ctgtggggct gctcatgtgt     300
cggtcctgtg ggcggcgtct gccccggcaa ttctgccgga gctgtggttt ggtgttatgt     360
gagccctgcc gggaggcaga ccatcagcct cctggccact gtacactccc tgtcaaagaa     420
gcagctgagg agcggcgtcg ggactttgga gagaagttaa ctcgtctgcg gaacttatg     480 ggggagctgc agcggcggaa ggcagccttg gaaggtgtct ccaaggacct tcaggcaagg     540
```

```
tataaagcag ttctccagga gtatgggcat gaggagcgca gggtccagga tgagctggct    600
cgctctcgga agttcttcac aggctctttg gctgaagttg agaagtccaa tagtcaagtg    660
gtagaggagc agagttacct gcttaacatt gcagaggtgc aggctgtgtc tcgctgtgac    720
tacttcctgg ccaagatcaa gcaggcagat gtagcactac tggaggagac agctgatgag    780
gaggagccag agctcactgc cagcttgcct cgggagctca ccctgcaaga tgtggagctc    840
cttaaggtag tcatgttggg cccctccaa attggacaag ctgttaagaa gccccggaca    900
gttaacgtgg aagattcctg ggccatggag gccacagcgt ctgctgcctc tacctctgtt    960 actttttagag agatggacat gagcccggag gaagtggttg ccagccctag ggcctcacct   1020
gctaaacagc ggggtcctga ggcagcctcc aatatccagc agtgcctctt tctcaagaag   1080
atgggggcca aaggcagcac tccaggaatg ttcaatcttc cagtcagtct ctacgtgacc   1140
agtcaaggtg aagtactagt cgctgaccgt ggtaactatc gtatacaagt ctttacccgc   1200 aaaggcttt tgaaggaaat ccgccgcagc cccagtggca ttgatagctt tgtgctaagc   1260
ttccttgggg cagatctacc caacctcact cctctctcag tggcaatgaa ctgccagggg   1320
ctgattggtg tgactgacag ctatgataac tccctcaagg tataccctt ggatggccac   1380 tgcgtggcct gtcacaggag ccagctgagc aaaccatggg gtatcacagc cttgccatct   1440
ggccagtttg tagtaaccga tgtggaaggt ggaaagcttt ggtgtttcac agttgatcga   1500
ggatcagggg tggtcaaata cagctgccta tgtagtgctg tgcggcccaa atttgtcacc   1560
tgtgatgctg agggcaccgt ctacttcacc cagggcttag gcctcaatct ggagaatcgg   1620
cagaatgagc accacctgga gggtggcttt tccattggct ctgtaggccc tgatgggcag   1680
ctgggtcgcc agattagcca cttcttctcg gagaatgagg atttccgctg cattgctggc   1740
atgtgtgtgg atgctcgtgg tgatctcatc gtggctgaca gtagtcgcaa ggaaattctc   1800
catttcccta agggtgggg ctatagtgtc cttattcgag agggacttac ctgtccggtg   1860
ggcatagccc taactcctaa ggggcagctg ctggtcttgg actgttggga tcattgcatc   1920
aagatctaca gctaccatct gagaagatat tccaccccat ag                      1962
```

<210> SEQ ID NO 64
<211> LENGTH: 653
<212> TYPE: PRT
<213> ORGANISM: Homo sapiens

<400> SEQUENCE: 64

```
Met Ala Ala Ala Ala Ser His Leu Asn Leu Asp Ala Leu Arg Glu
1               5                   10                  15

Val Leu Glu Cys Pro Ile Cys Met Glu Ser Phe Thr Glu Gln Leu
                20                  25                  30

Arg Pro Lys Leu Leu His Cys Gly His Thr Ile Cys Arg Gln Cys Leu
        35                  40                  45

Glu Lys Leu Leu Ala Ser Ser Ile Asn Gly Val Arg Cys Pro Phe Cys
    50                  55                  60

Ser Lys Ile Thr Arg Ile Thr Ser Leu Thr Gln Leu Thr Asp Asn Leu
65                  70                  75                  80

Thr Val Leu Lys Ile Ile Asp Thr Ala Gly Leu Ser Glu Ala Val Gly
                85                  90                  95

Leu Leu Met Cys Arg Ser Cys Gly Arg Arg Leu Pro Arg Gln Phe Cys
                100                 105                 110

Arg Ser Cys Gly Leu Val Leu Cys Glu Pro Cys Arg Glu Ala Asp His
```

-continued

```
            115                 120                 125
Gln Pro Pro Gly His Cys Thr Leu Pro Val Lys Glu Ala Ala Glu Glu
130                 135                 140

Arg Arg Arg Asp Phe Gly Glu Lys Leu Thr Arg Leu Arg Glu Leu Met
145                 150                 155                 160

Gly Glu Leu Gln Arg Arg Lys Ala Ala Leu Glu Gly Val Ser Lys Asp
                    165                 170                 175

Leu Gln Ala Arg Tyr Lys Ala Val Leu Gln Glu Tyr Gly His Glu Glu
                180                 185                 190

Arg Arg Val Gln Asp Glu Leu Ala Arg Ser Arg Lys Phe Phe Thr Gly
                195                 200                 205

Ser Leu Ala Glu Val Glu Lys Ser Asn Ser Gln Val Val Glu Glu Gln
210                 215                 220

Ser Tyr Leu Leu Asn Ile Ala Glu Val Gln Ala Val Ser Arg Cys Asp
225                 230                 235                 240

Tyr Phe Leu Ala Lys Ile Lys Gln Ala Asp Val Ala Leu Leu Glu Glu
                245                 250                 255

Thr Ala Asp Glu Glu Pro Glu Leu Thr Ala Ser Leu Pro Arg Glu
                260                 265                 270

Leu Thr Leu Gln Asp Val Glu Leu Leu Lys Val Gly His Val Gly Pro
            275                 280                 285

Leu Gln Ile Gly Gln Ala Val Lys Lys Pro Arg Thr Val Asn Val Glu
290                 295                 300

Asp Ser Trp Ala Met Glu Ala Thr Ala Ser Ala Ser Thr Ser Val
305                 310                 315                 320

Thr Phe Arg Glu Met Asp Met Ser Pro Glu Val Val Ala Ser Pro
                325                 330                 335

Arg Ala Ser Pro Ala Lys Gln Arg Gly Pro Glu Ala Ala Ser Asn Ile
                340                 345                 350

Gln Gln Cys Leu Phe Leu Lys Lys Met Gly Ala Lys Gly Ser Thr Pro
                355                 360                 365

Gly Met Phe Asn Leu Pro Val Ser Leu Tyr Val Thr Ser Gln Gly Glu
370                 375                 380

Val Leu Val Ala Asp Arg Gly Asn Tyr Arg Ile Gln Val Phe Thr Arg
385                 390                 395                 400

Lys Gly Phe Leu Lys Glu Ile Arg Arg Ser Pro Ser Gly Ile Asp Ser
                405                 410                 415

Phe Val Leu Ser Phe Leu Gly Ala Asp Leu Pro Asn Leu Thr Pro Leu
                420                 425                 430

Ser Val Ala Met Asn Cys Gln Gly Leu Ile Gly Val Thr Asp Ser Tyr
                435                 440                 445

Asp Asn Ser Leu Lys Val Tyr Thr Leu Asp Gly His Cys Val Ala Cys
                450                 455                 460

His Arg Ser Gln Leu Ser Lys Pro Trp Gly Ile Thr Ala Leu Pro Ser
465                 470                 475                 480

Gly Gln Phe Val Val Thr Asp Val Glu Gly Gly Lys Leu Trp Cys Phe
                485                 490                 495

Thr Val Asp Arg Gly Ser Gly Val Val Lys Tyr Ser Cys Leu Cys Ser
                500                 505                 510

Ala Val Arg Pro Lys Phe Val Thr Cys Asp Ala Glu Gly Thr Val Tyr
                515                 520                 525

Phe Thr Gln Gly Leu Gly Leu Asn Leu Glu Asn Arg Gln Asn Glu His
530                 535                 540
```

```
His Leu Glu Gly Gly Phe Ser Ile Gly Ser Val Gly Pro Asp Gly Gln
545                 550                 555                 560

Leu Gly Arg Gln Ile Ser His Phe Phe Ser Glu Asn Glu Asp Phe Arg
                565                 570                 575

Cys Ile Ala Gly Met Cys Val Asp Ala Arg Gly Asp Leu Ile Val Ala
            580                 585                 590

Asp Ser Ser Arg Lys Glu Ile Leu His Phe Pro Lys Gly Gly Gly Tyr
        595                 600                 605

Ser Val Leu Ile Arg Glu Gly Leu Thr Cys Pro Val Gly Ile Ala Leu
    610                 615                 620

Thr Pro Lys Gly Gln Leu Leu Val Leu Asp Cys Trp Asp His Cys Ile
625                 630                 635                 640

Lys Ile Tyr Ser Tyr His Leu Arg Arg Tyr Ser Thr Pro
                645                 650

<210> SEQ ID NO 65
<211> LENGTH: 3384
<212> TYPE: DNA
<213> ORGANISM: Homo sapiens

<400> SEQUENCE: 65
```

| | | | | | |
|---|---|---|---|---|---|
| atggcggaaa | acaaaggcgg | cggcgaggct | gagagcggcg | gcggggggcag | cggcagcgcg | 60 |
| ccggtaactg | ccggggccgc | cgggcccgcc | gcgcaggagg | cggagccgcc | tctcaccgcg | 120 |
| gtgctggtgg | aggaggagga | ggaggaaggc | ggcagggccg | gcgctgaggg | cggcgcggcc | 180 |
| gggccccgacg | acgggggggt | ggccgcggcc | tcctcgggct | cggcccaggc | tgcttcatct | 240 |
| cctgcggcct | cagtgggcac | tggagttgcc | ggggcgcag | tatcgacgcc | ggctccagct | 300 |
| ccagcctcgc | tcccgctcc | gggtccctcg | gcagggccgc | ctcctggacc | gccagcctcg | 360 |
| ctcctggaca | cctgcgccgt | gtgtcagcag | agcttgcaga | gcggcgtga | ggcggagccc | 420 |
| aagctgctgc | cctgtcttca | ctccttctgc | ctgcgctgcc | tgcccgagcc | ggagcgccag | 480 |
| ctcagcgtgc | ccatcccggg | gggcagcaac | ggcgacatcc | agcaagttgg | tgtaatacgg | 540 |
| tgcccagtat | gccgccaaga | atgcagacag | atagaccttg | tggataatta | ttttgtgaaa | 600 |
| gacacatctg | aagctcctag | cagttctgat | gaaaaatcag | aacaggtatg | tactagttgt | 660 |
| gaagacaatg | caagtgcagt | tggcttttgt | gtagaatgtg | gagagtggct | atgtaagaca | 720 |
| tgtatcgaag | cacatcaaag | agtaaaattt | actaaagatc | acttgatcag | gaagaaagaa | 780 |
| gatgtctcag | agtctgttgg | agcatctggt | caacgccctg | ttttctgccc | tgtacacaaa | 840 |
| caagaacagt | tgaaactttt | ctgtgaaaca | tgtgatagat | tgacatgtag | agactgtcag | 900 |
| ctattggaac | acaagaacta | taggtatcag | tttttggaag | aagcttttca | aaatcagaag | 960 |
| ggtgcaattg | agaatctact | ggcgaaactt | cttgagaaga | gaattatgt | tcattttgca | 1020 |
| gctactcagg | tgcagaatag | gataaaagaa | gtaaatgaga | ctaacaaacg | agtagaacag | 1080 |
| gaaattaaag | tggccatttt | caccccttatc | aatgaaatta | taagaaagg | aaaatctctc | 1140 |
| ttacaacagc | tagagaatgt | tacaaaggaa | agacagatga | agttactaca | gcagcagaat | 1200 |
| gacatcacag | gccttttccg | gcaggtgaag | catgttatga | acttcacaaa | ttgggcaatt | 1260 |
| gcaagtggca | gcagcacagc | actactatac | agcaagcgac | tgattacttt | ccagttgcgt | 1320 |
| catattttga | agcacggtgt | tgatcctgtc | cctgctgcta | atggagcaat | acgtttccat | 1380 |
| tgtgatccca | ccttctgggc | aaagaatgta | gtcaatttag | gtaatctagt | aatagagagt | 1440 |
| aaaccagctc | ctggttatac | tcctaatgtt | gtagttgggc | aagttcctcc | agggacaaac | 1500 |

```
cacattagta aaacccctgg acagattaac ttagcacagc ttcgactcca gcacatgcaa   1560
caacaagtat atgcacagaa acatcagcag ttgcaacaga tgaggatgca gcaaccacca   1620
gcacctgtac caactacaac aacaacaaca caacagcatc ctagacaagc agcccctcag   1680
atgttacaac aacagcctcc tcgattgatc agtgtgcaaa caatgcaaag aggcaacatg   1740
aactgtggag cttttcaagc ccatcagatg agactggctc agaatgctgc cagaatacca   1800
gggataccca ggcacagcgg ccctcaatat tccatgatgc agccacacct ccaaagacaa   1860
cactcaaacc cagggcatgc tggacccttt cccgtagtat cggtacacaa caccacaatc   1920
aacccaacga gccctactac agcaactatg gcaaatgcaa accgaggtcc caccagccca   1980
tctgttacag caatagagct aatcccctca gttaccaatc cagaaaacct tccatcgctg   2040
ccagatattc cacccataca gttggaagat gctggctcaa gtagtttaga taatctacta   2100
agtagataca tctcaggcag tcacctaccc ccacagccta caagcaccat gaatccttct   2160
ccaggtccct ctgccctttc tccgggatca tcaggtttat ccaattctca cacacctgtg   2220
agacccccaa gtacttctag tactggcagt cgaggcagct gtgggtcatc aggaagaact   2280
gctgagaaga caagtcttag tttcaaatct gatcaggtga aggtcaagca agaacctggg   2340
actgaagatg aaatatgtag cttttcagga ggtgtaaaac aagaaaaaac agaggatggc   2400
aggaggagtg cttgcatgtt gagcagtcct gagagtagct tgacaccacc tctctcaacc   2460
aacctgcatc tagaaagtga attggatgca ttggcaagcc tggaaaacca tgtgaaaatt   2520
gaacctgcag atatgaatga aagctgcaaa cagtcagggc tcagcagcct tgttaatgga   2580
aagtccccaa ttcgaagcct catgcacagg tcggcaagga ttggaggaga tggcaacaat   2640
aaagatgatg acccaaatga agactggtgt gctgtctgcc aaaacggagg agatctcttg   2700
tgctgcgaaa aatgtccaaa ggtctttcat ctaacttgtc atgttccaac actacttagc   2760
tttccaagtg ggactggat atgcacattt tgtagagata ttggaaagcc agaagttgaa   2820
tatgattgtg ataatttgca acatagtaag aaggggaaaa ctgcgcaggg gttaagcccc   2880
gtggaccaaa ggaaatgtga acgtcttctg ctttacctct attgccatga attaagtatt   2940
gaattccagg agcctgttcc tgcttcgata ccaaactact ataaaattat aaagaaacca   3000
atggatttat ccaccgtgaa aaagaagctt cagaaaaaac attcccaaca ctaccaaatc   3060
ccggatgact ttgtggccga tgtccgtttg atcttcaaga actgtgaaag gtttaatgaa   3120
atgatgaaag ttgttcaagt ttatgcagac acacaagaga ttaatttgaa ggctgattca   3180
gaagtagctc aggcagggaa agcagttgca ttgtactttg aagataaact cacagagatc   3240
tactcagaca ggaccttcgc acctttgcca gagtttgagc aggaagagga tgatggtgag   3300
gtaactgagg actctgatga agactttata cagccccgca gaaaacgcct aaagtcagat   3360
gagagaccag tacatataaa gtaa                                          3384
```

<210> SEQ ID NO 66
<211> LENGTH: 1127
<212> TYPE: PRT
<213> ORGANISM: Homo sapiens

<400> SEQUENCE: 66

```
Met Ala Glu Asn Lys Gly Gly Gly Glu Ala Glu Ser Gly Gly Gly Gly
1               5                   10                  15

Ser Gly Ser Ala Pro Val Thr Ala Gly Ala Ala Gly Pro Ala Ala Gln
            20                  25                  30
```

-continued

Glu Ala Glu Pro Pro Leu Thr Ala Val Leu Val Glu Glu Glu Glu
                35                  40                  45

Glu Gly Gly Arg Ala Gly Ala Glu Gly Gly Ala Ala Gly Pro Asp Asp
 50                  55                  60

Gly Gly Val Ala Ala Ser Ser Gly Ser Ala Gln Ala Ala Ser Ser
 65                  70                  75                  80

Pro Ala Ala Ser Val Gly Thr Gly Val Ala Gly Gly Ala Val Ser Thr
                85                  90                  95

Pro Ala Pro Ala Pro Ala Ser Ala Pro Ala Gly Pro Ser Ala Gly
                100                 105                 110

Pro Pro Pro Gly Pro Pro Ala Ser Leu Leu Asp Thr Cys Ala Val Cys
                115                 120                 125

Gln Gln Ser Leu Gln Ser Arg Arg Glu Ala Glu Pro Lys Leu Leu Pro
 130                 135                 140

Cys Leu His Ser Phe Cys Leu Arg Cys Leu Pro Glu Pro Glu Arg Gln
 145                 150                 155                 160

Leu Ser Val Pro Ile Pro Gly Gly Ser Asn Gly Asp Ile Gln Gln Val
                165                 170                 175

Gly Val Ile Arg Cys Pro Val Cys Arg Gln Glu Cys Arg Gln Ile Asp
                180                 185                 190

Leu Val Asp Asn Tyr Phe Val Lys Asp Thr Ser Glu Ala Pro Ser Ser
                195                 200                 205

Ser Asp Glu Lys Ser Glu Gln Val Cys Thr Ser Cys Glu Asp Asn Ala
 210                 215                 220

Ser Ala Val Gly Phe Cys Val Glu Cys Gly Glu Trp Leu Cys Lys Thr
225                 230                 235                 240

Cys Ile Glu Ala His Gln Arg Val Lys Phe Thr Lys Asp His Leu Ile
                245                 250                 255

Arg Lys Lys Glu Asp Val Ser Glu Ser Val Gly Ala Ser Gly Gln Arg
                260                 265                 270

Pro Val Phe Cys Pro Val His Lys Gln Glu Gln Leu Lys Leu Phe Cys
                275                 280                 285

Glu Thr Cys Asp Arg Leu Thr Cys Arg Asp Cys Gln Leu Leu Glu His
                290                 295                 300

Lys Glu His Arg Tyr Gln Phe Leu Glu Glu Ala Phe Gln Asn Gln Lys
305                 310                 315                 320

Gly Ala Ile Glu Asn Leu Leu Ala Lys Leu Leu Glu Lys Lys Asn Tyr
                325                 330                 335

Val His Phe Ala Ala Thr Gln Val Gln Asn Arg Ile Lys Glu Val Asn
                340                 345                 350

Glu Thr Asn Lys Arg Val Glu Gln Glu Ile Lys Val Ala Ile Phe Thr
                355                 360                 365

Leu Ile Asn Glu Ile Asn Lys Lys Gly Lys Ser Leu Leu Gln Gln Leu
                370                 375                 380

Glu Asn Val Thr Lys Glu Arg Gln Met Lys Leu Leu Gln Gln Gln Asn
385                 390                 395                 400

Asp Ile Thr Gly Leu Ser Arg Gln Val Lys His Val Met Asn Phe Thr
                405                 410                 415

Asn Trp Ala Ile Ala Ser Gly Ser Ser Thr Ala Leu Leu Tyr Ser Lys
                420                 425                 430

Arg Leu Ile Thr Phe Gln Leu Arg His Ile Leu Lys Ala Arg Cys Asp
                435                 440                 445

Pro Val Pro Ala Ala Asn Gly Ala Ile Arg Phe His Cys Asp Pro Thr

```
              450                 455                 460
    Phe Trp Ala Lys Asn Val Val Asn Leu Gly Asn Leu Val Ile Glu Ser
    465                 470                 475                 480

Lys Pro Ala Pro Gly Tyr Thr Pro Asn Val Val Gly Gln Val Pro
                    485                 490                 495

Pro Gly Thr Asn His Ile Ser Lys Thr Pro Gly Gln Ile Asn Leu Ala
                    500                 505                 510

Gln Leu Arg Leu Gln His Met Gln Gln Val Tyr Ala Gln Lys His
                    515                 520                 525

Gln Gln Leu Gln Gln Met Arg Met Gln Gln Pro Pro Ala Pro Val Pro
    530                 535                 540

Thr Thr Thr Thr Thr Thr Gln Gln His Pro Arg Gln Ala Ala Pro Gln
    545                 550                 555                 560

Met Leu Gln Gln Gln Pro Pro Arg Leu Ile Ser Val Gln Thr Met Gln
                    565                 570                 575

Arg Gly Asn Met Asn Cys Gly Ala Phe Gln Ala His Gln Met Arg Leu
                    580                 585                 590

Ala Gln Asn Ala Ala Arg Ile Pro Gly Ile Pro Arg His Ser Gly Pro
                    595                 600                 605

Gln Tyr Ser Met Met Gln Pro His Leu Gln Arg Gln His Ser Asn Pro
                    610                 615                 620

Gly His Ala Gly Pro Phe Pro Val Val Ser Val His Asn Thr Thr Ile
    625                 630                 635                 640

Asn Pro Thr Ser Pro Thr Thr Ala Thr Met Ala Asn Ala Asn Arg Gly
                    645                 650                 655

Pro Thr Ser Pro Ser Val Thr Ala Ile Glu Leu Ile Pro Ser Val Thr
                    660                 665                 670

Asn Pro Glu Asn Leu Pro Ser Leu Pro Asp Ile Pro Pro Ile Gln Leu
                    675                 680                 685

Glu Asp Ala Gly Ser Ser Leu Asp Asn Leu Leu Ser Arg Tyr Ile
                    690                 695                 700

Ser Gly Ser His Leu Pro Pro Gln Pro Thr Ser Thr Met Asn Pro Ser
    705                 710                 715                 720

Pro Gly Pro Ser Ala Leu Ser Pro Gly Ser Ser Gly Leu Ser Asn Ser
                    725                 730                 735

His Thr Pro Val Arg Pro Pro Ser Thr Ser Ser Thr Gly Ser Arg Gly
                    740                 745                 750

Ser Cys Gly Ser Ser Gly Arg Thr Ala Glu Lys Thr Ser Leu Ser Phe
                    755                 760                 765

Lys Ser Asp Gln Val Lys Val Lys Gln Glu Pro Gly Thr Glu Asp Glu
    770                 775                 780

Ile Cys Ser Phe Ser Gly Val Lys Gln Lys Thr Glu Asp Gly
    785                 790                 795                 800

Arg Arg Ser Ala Cys Met Leu Ser Ser Pro Glu Ser Ser Leu Thr Pro
                    805                 810                 815

Pro Leu Ser Thr Asn Leu His Leu Glu Ser Glu Leu Asp Ala Leu Ala
                    820                 825                 830

Ser Leu Glu Asn His Val Lys Ile Glu Pro Ala Asp Met Asn Glu Ser
                    835                 840                 845

Cys Lys Gln Ser Gly Leu Ser Ser Leu Val Asn Gly Lys Ser Pro Ile
                    850                 855                 860

Arg Ser Leu Met His Arg Ser Ala Arg Ile Gly Gly Asp Gly Asn Asn
    865                 870                 875                 880
```

Lys Asp Asp Asp Pro Asn Glu Asp Trp Cys Ala Val Cys Gln Asn Gly
            885                 890                 895

Gly Asp Leu Leu Cys Cys Glu Lys Cys Pro Lys Val Phe His Leu Thr
        900                 905                 910

Cys His Val Pro Thr Leu Leu Ser Phe Pro Ser Gly Asp Trp Ile Cys
        915                 920                 925

Thr Phe Cys Arg Asp Ile Gly Lys Pro Glu Val Glu Tyr Asp Cys Asp
    930                 935                 940

Asn Leu Gln His Ser Lys Lys Gly Lys Thr Ala Gln Gly Leu Ser Pro
945                 950                 955                 960

Val Asp Gln Arg Lys Cys Glu Arg Leu Leu Leu Tyr Leu Tyr Cys His
                965                 970                 975

Glu Leu Ser Ile Glu Phe Gln Glu Pro Val Pro Ala Ser Ile Pro Asn
            980                 985                 990

Tyr Tyr Lys Ile Ile Lys Lys Pro Met Asp Leu Ser Thr Val Lys Lys
        995                 1000                1005

Lys Leu Gln Lys Lys His Ser Gln His Tyr Gln Ile Pro Asp Asp
    1010                1015                1020

Phe Val Ala Asp Val Arg Leu Ile Phe Lys Asn Cys Glu Arg Phe
    1025                1030                1035

Asn Glu Met Met Lys Val Val Gln Val Tyr Ala Asp Thr Gln Glu
    1040                1045                1050

Ile Asn Leu Lys Ala Asp Ser Glu Val Ala Gln Ala Gly Lys Ala
    1055                1060                1065

Val Ala Leu Tyr Phe Glu Asp Lys Leu Thr Glu Ile Tyr Ser Asp
    1070                1075                1080

Arg Thr Phe Ala Pro Leu Pro Glu Phe Glu Gln Glu Glu Asp Asp
    1085                1090                1095

Gly Glu Val Thr Glu Asp Ser Asp Glu Asp Phe Ile Gln Pro Arg
    1100                1105                1110

Arg Lys Arg Leu Lys Ser Asp Glu Arg Pro Val His Ile Lys
    1115                1120                1125

<210> SEQ ID NO 67
<211> LENGTH: 1467
<212> TYPE: DNA
<213> ORGANISM: Homo sapiens

<400> SEQUENCE: 67
atggcttcaa aaatcttgct taacgtacaa gaggaggtga cctgtcccat ctgcctggag      60
ctgttgacag aacccttgag tctagactgt ggccacagcc tctgccgagc ctgcatcact     120
gtgagcaaca aggaggcagt gaccagcatg gaggaaaaaa gcagctgtcc tgtgtgtggt     180
atcagttact catttgaaca tctacaggct aatcagcatc tggccaacat agtggagaga     240
ctcaaggagg tcaagttgag cccagacaat gggaagaaga gagatctctg tgatcatcat     300
ggagagaaac tcctactctt ctgtaaggag gataggaaag tcatttgctg gctttgtgag     360
cggtctcagg agcaccgtgg tcaccacaca gtcctcacgg aggaagtatt caaggaatgt     420
caggagaaac tccaggcagt cctcaagagg ctgaagaagg aagaggagga agctgagaag     480
ctggaagctg acatcagaga agagaaaact tcctggaagt atcaggtaca aactgagaga     540
caaaggatac aaacagaatt tgatcagctt agaagcatcc taataatga ggagcagaga     600 gagctgcaaa gattggaaga agaagaaaag aagacgctgg ataagtttgc agaggctgag     660

-continued

```
gatgagctag ttcagcagaa gcagttggtg agagagctca tctcagatgt ggagtgtcgg    720
agtcagtggt caacaatgga gctgctgcag gacatgagtg gaatcatgaa atggagtgag    780
atctggaggc tgaaaaagcc aaaaatggtt tccaagaaac tgaagactgt attccatgct    840
ccagatctga gtaggatgct gcaaatgttt agagaactga cagctgtccg gtgctactgg    900
gtggatgtca cactgaattc agtcaaccta aatttgaatc ttgtcctttc agaagatcag    960
agacaagtga tatctgtgcc aatttggcct tttcagtgtt ataattatgg tgtcttggga   1020
tcccaatatt tctcctctgg gaaacattac tgggaagtgg acgtgtccaa gaaaactgcc   1080
tggatcctgg gggtatactg tagaacatat tcccgccata tgaagtatgt tgttagaaga   1140
tgtgcaaatc gtcaaaatct ttacaccaaa tacagacctc tatttggcta ctgggttata   1200
gggttacaga ataaatgtaa gtatggtgtc tttgaagagt ctttgtcctc tgatcccgag   1260
gttttgactc tctccatggc tgtgcctccc tgccgtgttg gggttttcct cgactatgaa   1320
gcaggcattg tctcattttt caatgtcaca agccatggct ccctcattta caagttctct   1380
aaatgttgct ttctcagcc tgtttatcca tatttcaatc cttggaactg tccagctccc   1440
atgactctat gcccaccaag ctcttga                                       1467
```

<210> SEQ ID NO 68
<211> LENGTH: 488
<212> TYPE: PRT
<213> ORGANISM: Homo sapiens

<400> SEQUENCE: 68

```
Met Ala Ser Lys Ile Leu Leu Asn Val Gln Glu Glu Val Thr Cys Pro
1               5                   10                  15

Ile Cys Leu Glu Leu Leu Thr Glu Pro Leu Ser Leu Asp Cys Gly His
            20                  25                  30

Ser Leu Cys Arg Ala Cys Ile Thr Val Ser Asn Lys Glu Ala Val Thr
        35                  40                  45

Ser Met Gly Gly Lys Ser Ser Cys Pro Val Cys Gly Ile Ser Tyr Ser
    50                  55                  60

Phe Glu His Leu Gln Ala Asn Gln His Leu Ala Asn Ile Val Glu Arg
65                  70                  75                  80

Leu Lys Glu Val Lys Leu Ser Pro Asp Asn Gly Lys Lys Arg Asp Leu
                85                  90                  95

Cys Asp His His Gly Glu Lys Leu Leu Leu Phe Cys Lys Glu Asp Arg
            100                 105                 110

Lys Val Ile Cys Trp Leu Cys Glu Arg Ser Gln Glu His Arg Gly His
        115                 120                 125

His Thr Val Leu Thr Glu Glu Val Phe Lys Glu Cys Gln Glu Lys Leu
    130                 135                 140

Gln Ala Val Leu Lys Arg Leu Lys Lys Glu Glu Glu Ala Glu Lys
145                 150                 155                 160

Leu Glu Ala Asp Ile Arg Glu Glu Lys Thr Ser Trp Lys Tyr Gln Val
                165                 170                 175

Gln Thr Glu Arg Gln Arg Ile Gln Thr Glu Phe Asp Gln Leu Arg Ser
            180                 185                 190

Ile Leu Asn Asn Glu Glu Gln Arg Glu Leu Gln Arg Leu Glu Glu Glu
        195                 200                 205

Glu Lys Lys Thr Leu Asp Lys Phe Ala Glu Ala Glu Asp Glu Leu Val
    210                 215                 220

Gln Gln Lys Gln Leu Val Arg Glu Leu Ile Ser Asp Val Glu Cys Arg
```

```
                    225                 230                 235                 240
Ser Gln Trp Ser Thr Met Glu Leu Leu Gln Asp Met Ser Gly Ile Met
                245                 250                 255

Lys Trp Ser Glu Ile Trp Arg Leu Lys Lys Pro Lys Met Val Ser Lys
            260                 265                 270

Lys Leu Lys Thr Val Phe His Ala Pro Asp Leu Ser Arg Met Leu Gln
        275                 280                 285

Met Phe Arg Glu Leu Thr Ala Val Arg Cys Tyr Trp Val Asp Val Thr
    290                 295                 300

Leu Asn Ser Val Asn Leu Asn Leu Val Leu Ser Glu Asp Gln
305                 310                 315                 320

Arg Gln Val Ile Ser Val Pro Ile Trp Pro Phe Gln Cys Tyr Asn Tyr
                325                 330                 335

Gly Val Leu Gly Ser Gln Tyr Phe Ser Ser Gly Lys His Tyr Trp Glu
            340                 345                 350

Val Asp Val Ser Lys Lys Thr Ala Trp Ile Leu Gly Val Tyr Cys Arg
        355                 360                 365

Thr Tyr Ser Arg His Met Lys Tyr Val Val Arg Arg Cys Ala Asn Arg
    370                 375                 380

Gln Asn Leu Tyr Thr Lys Tyr Arg Pro Leu Phe Gly Tyr Trp Val Ile
385                 390                 395                 400

Gly Leu Gln Asn Lys Cys Lys Tyr Gly Val Phe Glu Glu Ser Leu Ser
                405                 410                 415

Ser Asp Pro Glu Val Leu Thr Leu Ser Met Ala Val Pro Pro Cys Arg
            420                 425                 430

Val Gly Val Phe Leu Asp Tyr Glu Ala Gly Ile Val Ser Phe Phe Asn
        435                 440                 445

Val Thr Ser His Gly Ser Leu Ile Tyr Lys Phe Ser Lys Cys Cys Phe
    450                 455                 460

Ser Gln Pro Val Tyr Pro Tyr Phe Asn Pro Trp Asn Cys Pro Ala Pro
465                 470                 475                 480

Met Thr Leu Cys Pro Pro Ser Ser
                485

<210> SEQ ID NO 69
<211> LENGTH: 1482
<212> TYPE: DNA
<213> ORGANISM: Homo sapiens

<400> SEQUENCE: 69
atggagcgga gtcccgacgt gtcccccggg ccttcccgct ccttcaagga ggagttgctc      60
tgcgccgtct gctacgaccc cttccgcgac gcagtcactc tgcgctgcgg ccacaacttc     120
tgccgcgggt gcgtgagccg ctgctgggag gtgcaggtgt cgcccacctg cccagtgtgc     180
aaagaccgcg cgtcacccgc cgacctgcgc accaaccaca ccctcaacaa cctggtggag     240
aagctgctgc gcgaggaggc cgagggcgcg cgctggacca gctaccgctt ctcgcgtgtc     300
tgccgcctgc accgcggaca gctcagcctc ttctgcctcg aggacaagga gctgctgtgc     360
tgctcctgcc aggccgaccc ccgacaccag gggcaccgcg tgcagccggt gaaggacact     420
gcccacgact ttcgggccaa gtgcaggaac atggagcatg cactgcggga aaggccaag      480 gccttctggg ccatgcggcg ctcctatgag gccatcgcca agcacaatca ggtggaggct     540
gcatggctga aggccggat ccggcaggag tttgataagc ttcgcgagtt cttgagagtg      600
gaggagcagg ccattctgga tgccatggcc gaggagacaa ggcagaagca acttctggcc     660
```

-continued

```
gacgagaaga tgaagcagct cacagaggag acggaggtgc tggcacatga gatcgagcgg      720
ctgcagatgg agatgaagga ggacgacgtt tcttttctca tgaaacacaa gagccgaaaa      780
cgccgactct tctgcaccat ggagccagag ccagtccagc ccggcatgct tatcgatgtc      840
tgcaagtacc tgggctccct gcagtaccgc gtctggaaga agatgcttgc atctgtggaa      900
tctgtaccct tcagctttga ccccaacacc gcagctggct ggctctccgt gtctgacgac      960
ctcaccagcg tcaccaacca tggctaccgc gtgcaggtgg agaacccgga acgcttctcc     1020
tcggcgccct gcctgctggg ctcccgtgtc ttctcacagg gctcgcacgc ctgggaggtg     1080
gcccttgggg ggctgcagag ctggagggtg ggcgtggtac gtgtgcgcca ggactcgggc     1140
gctgagggcc actcacacag ctgctaccac gacacacgct cgggcttctg gtatgtctgc     1200
cgcacgcagg gcgtggaggg ggaccactgc gtgacctcgg acccagccac gtcgcccctg     1260
gtcctggcca tcccacgccg cctgcgtgtg gagctggagt gtgaggaggg cgagctgtct     1320
ttctatgacg cggagcgcca ctgccacctg tacaccttcc acgcccgctt tggggaggtt     1380
cgcccctact tctacctggg gggtgcacgg ggcgccgggc ctccagagcc tttgcgcatc     1440
tgccccttgc acatcagtgt caaggaagaa ctggatggct ga                       1482
```

<210> SEQ ID NO 70
<211> LENGTH: 493
<212> TYPE: PRT
<213> ORGANISM: Homo sapiens

<400> SEQUENCE: 70

```
Met Glu Arg Ser Pro Asp Val Ser Pro Gly Pro Ser Arg Ser Phe Lys
1               5                   10                  15

Glu Glu Leu Leu Cys Ala Val Cys Tyr Asp Pro Phe Arg Asp Ala Val
            20                  25                  30

Thr Leu Arg Cys Gly His Asn Phe Cys Arg Gly Cys Val Ser Arg Cys
        35                  40                  45

Trp Glu Val Gln Val Ser Pro Thr Cys Pro Val Cys Lys Asp Arg Ala
    50                  55                  60

Ser Pro Ala Asp Leu Arg Thr Asn His Thr Leu Asn Asn Leu Val Glu
65                  70                  75                  80

Lys Leu Leu Arg Glu Glu Ala Glu Gly Ala Arg Trp Thr Ser Tyr Arg
                85                  90                  95

Phe Ser Arg Val Cys Arg Leu His Arg Gly Gln Leu Ser Leu Phe Cys
            100                 105                 110

Leu Glu Asp Lys Glu Leu Leu Cys Cys Ser Cys Gln Ala Asp Pro Arg
        115                 120                 125

His Gln Gly His Arg Val Gln Pro Val Lys Asp Thr Ala His Asp Phe
    130                 135                 140

Arg Ala Lys Cys Arg Asn Met Glu His Ala Leu Arg Glu Lys Ala Lys
145                 150                 155                 160

Ala Phe Trp Ala Met Arg Arg Ser Tyr Glu Ala Ile Ala Lys His Asn
                165                 170                 175

Gln Val Glu Ala Ala Trp Leu Glu Gly Arg Ile Arg Gln Glu Phe Asp
            180                 185                 190

Lys Leu Arg Glu Phe Leu Arg Val Glu Glu Gln Ala Ile Leu Asp Ala
        195                 200                 205

Met Ala Glu Glu Thr Arg Gln Lys Gln Leu Leu Ala Asp Glu Lys Met
    210                 215                 220
```

Lys Gln Leu Thr Glu Thr Glu Val Leu Ala His Glu Ile Glu Arg
225                 230                 235                 240

Leu Gln Met Glu Met Lys Glu Asp Asp Val Ser Phe Leu Met Lys His
            245                 250                 255

Lys Ser Arg Lys Arg Arg Leu Phe Cys Thr Met Glu Pro Glu Pro Val
        260                 265                 270

Gln Pro Gly Met Leu Ile Asp Val Cys Lys Tyr Leu Gly Ser Leu Gln
    275                 280                 285

Tyr Arg Val Trp Lys Lys Met Leu Ala Ser Val Glu Ser Val Pro Phe
290                 295                 300

Ser Phe Asp Pro Asn Thr Ala Ala Gly Trp Leu Ser Val Ser Asp Asp
305                 310                 315                 320

Leu Thr Ser Val Thr Asn His Gly Tyr Arg Val Gln Val Glu Asn Pro
                325                 330                 335

Glu Arg Phe Ser Ser Ala Pro Cys Leu Leu Gly Ser Arg Val Phe Ser
            340                 345                 350

Gln Gly Ser His Ala Trp Glu Val Ala Leu Gly Leu Gln Ser Trp
        355                 360                 365

Arg Val Gly Val Val Arg Val Arg Gln Asp Ser Gly Ala Glu Gly His
370                 375                 380

Ser His Ser Cys Tyr His Asp Thr Arg Ser Gly Phe Trp Tyr Val Cys
385                 390                 395                 400

Arg Thr Gln Gly Val Glu Gly Asp His Cys Val Thr Ser Asp Pro Ala
                405                 410                 415

Thr Ser Pro Leu Val Leu Ala Ile Pro Arg Arg Leu Arg Val Glu Leu
            420                 425                 430

Glu Cys Glu Glu Gly Glu Leu Ser Phe Tyr Asp Ala Glu Arg His Cys
        435                 440                 445

His Leu Tyr Thr Phe His Ala Arg Phe Gly Glu Val Arg Pro Tyr Phe
    450                 455                 460

Tyr Leu Gly Gly Ala Arg Gly Ala Gly Pro Pro Glu Pro Leu Arg Ile
465                 470                 475                 480

Cys Pro Leu His Ile Ser Val Lys Glu Glu Leu Asp Gly
                485                 490

<210> SEQ ID NO 71
<211> LENGTH: 2187
<212> TYPE: DNA
<213> ORGANISM: Homo sapiens

<400> SEQUENCE: 71
atgtcggagt ctggggagat gagtgaattt ggctacatca tggaattgat agctaaaggc    60
aaggttacca ttaagaatat cgaaagggag ctcatttgcc cagcatgcaa ggagctgttt   120
acccacccat tgattctccc ttgccaacat agtatctgtc ataaatgtgt aaaagaactc   180
ctgctgactc tcgatgattc attcaacgat gtgggatcag acaactccaa tcaaagcagt   240
cctcgacttc ggctcccctc ccctagtatg gataaaattg accgaattaa cagaccaggc   300
tggaagcgca attcattgac cccgaggaca actgttttcc cttgccctgg ctgtgagcat   360
gatgtggatc ttggagaacg aggaatcaat ggtctgtttc gaaacttcac tttgaaaact   420
attgtggaaa gatatcgtca agcagctagg gcagccacag ccattatgtg tgacctttgt   480
aaaccaccac tcaagaatc cacaaaaagc tgcatggact gtagtgcaag ttactgcaat   540
gaatgcttca aaattcatca cccttggggt actataaaag ctcaacatga gtatgttggt   600

| | |
|---|---:|
| ccaactacta acttcagacc caagatttta atgtgcccag aacatgaaac agagagaata | 660 |
| aacatgtact gtgaattatg taggaggcca gtttgccatc tgtgtaagtt gggtggtaat | 720 |
| catgccaacc accgtgtaac cactatgagc agtgcctaca aaaccttaaa ggaaaagctt | 780 |
| tcaaaggata ttgattacct tattggtaag gaaagccagg tgaagagtca aatatctgaa | 840 |
| ctaaacttgt taatgaaaga aacagagtgt aatggagaga gggctaaaga agaagcaatt | 900 |
| acacattttg aaaagctctt tgaagttctg gaagagagga aatcatctgt tttgaaagca | 960 |
| attgactcct ctaagaaact aagattagac aaatttcaga ctcaaatgga agagtaccag | 1020 |
| ggacttctag agaacaatgg acttgtggga tatgctcaag aagtgctaaa ggagacagat | 1080 |
| cagtcttgct ttgtgcagac agcaaagcag ctccacctca gaatacagaa agccacagaa | 1140 |
| tctttgaaga gctttagacc tgcagctcag acttctttg aagactatgt tgttaatacc | 1200 |
| tctaaacaaa cagaacttct tggagaatta tcctttttct ctagtggcat agacgtgcca | 1260 |
| gagatcaatg aggaacagag caaagtttat aacaatgcct tgataaattg caccatcca | 1320 |
| gaaaaggata agctgatag ctatgttctt gaatatcgga aatcaatag agatgatgaa | 1380 |
| atgtcatgga tgagataga agtgtgtgga acaagtaaaa taattcaaga cttggaaaac | 1440 |
| agtagtacct atgctttcag agtaagagct tacaaggggt caatctgtag tccttgcagc | 1500 |
| agagaattga ttcttcatac tcctccagct ccagttttca gcttcctctt tgatgaaaaa | 1560 |
| tgtggctata ataatgaaca cctcctgctg aacttgaaga gagaccgtgt agagagtaga | 1620 |
| gctggattta atcttctgct tgctgcagaa cgcatccaag tgggttatta cacaagctta | 1680 |
| gactacatca ttggagatac tggcattaca aaaggaaaac acttctgggc cttccgtgtg | 1740 |
| gaaccatatt catacctggt aaaagtggga gttgcttcta gcgataaact acaagaatgg | 1800 |
| ctccgttctc cccgggatgc agttagtcca agatatgagc aagacagtgg gcatgacagt | 1860 |
| ggaagtgagg atgcctgttt tgattcttca caaccattta ccttagttac tataggcatg | 1920 |
| cagaaatttt ttatacccaa gtcacctact tcttctaatg aacctgaaaa tagagttctc | 1980 |
| cctatgccaa caagtattgg gattttcctt gactgtgata aaggcaaagt agatttctat | 2040 |
| gatatggatc agatgaaatg cctttatgaa cgccaagtgg actgttcaca tacactgtat | 2100 |
| ccagcatttg cattaatggg cagtggagga attcagcttg aagaacccat cacagcaaaa | 2160 |
| tatctggaat accaagagga catgtag | 2187 |

<210> SEQ ID NO 72
<211> LENGTH: 728
<212> TYPE: PRT
<213> ORGANISM: Homo sapiens

<400> SEQUENCE: 72

```
Met Ser Glu Ser Gly Glu Met Ser Glu Phe Gly Tyr Ile Met Glu Leu
1               5                   10                  15

Ile Ala Lys Gly Lys Val Thr Ile Lys Asn Ile Glu Arg Glu Leu Ile
                20                  25                  30

Cys Pro Ala Cys Lys Glu Leu Phe Thr His Pro Leu Ile Leu Pro Cys
            35                  40                  45

Gln His Ser Ile Cys His Lys Cys Val Lys Glu Leu Leu Leu Thr Leu
        50                  55                  60

Asp Asp Ser Phe Asn Asp Val Gly Ser Asp Asn Ser Asn Gln Ser Ser
65                  70                  75                  80

Pro Arg Leu Arg Leu Pro Ser Pro Ser Met Asp Lys Ile Asp Arg Ile
                85                  90                  95
```

```
Asn Arg Pro Gly Trp Lys Arg Asn Ser Leu Thr Pro Arg Thr Thr Val
            100                 105                 110

Phe Pro Cys Pro Gly Cys Glu His Asp Val Asp Leu Gly Glu Arg Gly
            115                 120                 125

Ile Asn Gly Leu Phe Arg Asn Phe Thr Leu Glu Thr Ile Val Glu Arg
            130                 135                 140

Tyr Arg Gln Ala Ala Arg Ala Ala Thr Ala Ile Met Cys Asp Leu Cys
145                 150                 155                 160

Lys Pro Pro Pro Gln Glu Ser Thr Lys Ser Cys Met Asp Cys Ser Ala
            165                 170                 175

Ser Tyr Cys Asn Glu Cys Phe Lys Ile His His Pro Trp Gly Thr Ile
            180                 185                 190

Lys Ala Gln His Glu Tyr Val Gly Pro Thr Thr Asn Phe Arg Pro Lys
            195                 200                 205

Ile Leu Met Cys Pro Glu His Glu Thr Glu Arg Ile Asn Met Tyr Cys
            210                 215                 220

Glu Leu Cys Arg Arg Pro Val Cys His Leu Cys Lys Leu Gly Gly Asn
225                 230                 235                 240

His Ala Asn His Arg Val Thr Thr Met Ser Ser Ala Tyr Lys Thr Leu
            245                 250                 255

Lys Glu Lys Leu Ser Lys Asp Ile Asp Tyr Leu Ile Gly Lys Glu Ser
            260                 265                 270

Gln Val Lys Ser Gln Ile Ser Glu Leu Asn Leu Leu Met Lys Glu Thr
            275                 280                 285

Glu Cys Asn Gly Glu Arg Ala Lys Glu Ala Ile Thr His Phe Glu
            290                 295                 300

Lys Leu Phe Glu Val Leu Glu Glu Arg Lys Ser Ser Val Leu Lys Ala
305                 310                 315                 320

Ile Asp Ser Ser Lys Lys Leu Arg Leu Asp Lys Phe Gln Thr Gln Met
            325                 330                 335

Glu Glu Tyr Gln Gly Leu Leu Glu Asn Asn Gly Leu Val Gly Tyr Ala
            340                 345                 350

Gln Glu Val Leu Lys Glu Thr Asp Gln Ser Cys Phe Val Gln Thr Ala
            355                 360                 365

Lys Gln Leu His Leu Arg Ile Gln Lys Ala Thr Glu Ser Leu Lys Ser
            370                 375                 380

Phe Arg Pro Ala Ala Gln Thr Ser Phe Glu Asp Tyr Val Val Asn Thr
385                 390                 395                 400

Ser Lys Gln Thr Glu Leu Leu Gly Glu Leu Ser Phe Phe Ser Ser Gly
            405                 410                 415

Ile Asp Val Pro Glu Ile Asn Glu Glu Gln Ser Lys Val Tyr Asn Asn
            420                 425                 430

Ala Leu Ile Asn Trp His His Pro Glu Lys Asp Lys Ala Asp Ser Tyr
            435                 440                 445

Val Leu Glu Tyr Arg Lys Ile Asn Arg Asp Asp Glu Met Ser Trp Asn
            450                 455                 460

Glu Ile Glu Val Cys Gly Thr Ser Lys Ile Ile Gln Asp Leu Glu Asn
465                 470                 475                 480

Ser Ser Thr Tyr Ala Phe Arg Val Arg Ala Tyr Lys Gly Ser Ile Cys
            485                 490                 495

Ser Pro Cys Ser Arg Glu Leu Ile Leu His Thr Pro Ala Pro Val
            500                 505                 510
```

```
Phe Ser Phe Leu Phe Asp Glu Lys Cys Gly Tyr Asn Asn Glu His Leu
            515                 520                 525

Leu Leu Asn Leu Lys Arg Asp Arg Val Glu Ser Arg Ala Gly Phe Asn
    530                 535                 540

Leu Leu Leu Ala Ala Glu Arg Ile Gln Val Gly Tyr Tyr Thr Ser Leu
545                 550                 555                 560

Asp Tyr Ile Ile Gly Asp Thr Gly Ile Thr Lys Gly Lys His Phe Trp
                565                 570                 575

Ala Phe Arg Val Glu Pro Tyr Ser Tyr Leu Val Lys Val Gly Val Ala
            580                 585                 590

Ser Ser Asp Lys Leu Gln Glu Trp Leu Arg Ser Pro Arg Asp Ala Val
    595                 600                 605

Ser Pro Arg Tyr Glu Gln Asp Ser Gly His Asp Ser Gly Ser Glu Asp
610                 615                 620

Ala Cys Phe Asp Ser Ser Gln Pro Phe Thr Leu Val Thr Ile Gly Met
625                 630                 635                 640

Gln Lys Phe Phe Ile Pro Lys Ser Pro Thr Ser Ser Asn Glu Pro Glu
                645                 650                 655

Asn Arg Val Leu Pro Met Pro Thr Ser Ile Gly Ile Phe Leu Asp Cys
            660                 665                 670

Asp Lys Gly Lys Val Asp Phe Tyr Asp Met Asp Gln Met Lys Cys Leu
        675                 680                 685

Tyr Glu Arg Gln Val Asp Cys Ser His Thr Leu Tyr Pro Ala Phe Ala
            690                 695                 700

Leu Met Gly Ser Gly Gly Ile Gln Leu Glu Glu Pro Ile Thr Ala Lys
705                 710                 715                 720

Tyr Leu Glu Tyr Gln Glu Asp Met
                725
```

<210> SEQ ID NO 73
<211> LENGTH: 2895
<212> TYPE: DNA
<213> ORGANISM: Homo sapiens

<400> SEQUENCE: 73

```
atggatgaac agagcgtgga gagcattgct gaggttttcc gatgtttcat ttgtatggag    60
aaattgcggg atgcacgcct gtgtcctcat tgctccaaac tgtgttgttt cagctgtatt   120
aggcgctggc tgacagagca gagagctcaa tgtcctcatt gccgtgctcc actccagcta   180
cgagaactag taaattgtcg ttgggcagaa gaagtaacac aacagcttga tactcttcaa   240
ctctgcagtc tcaccaaaca tgaagaaat gaaaaggaca aatgtgaaaa tcaccatgaa   300
aaacttagtg tattttgctg gacttgtaag aagtgtatct gccatcagtg tgcactttgg   360
ggaggaatgc atggcggaca tactttaaa cctttggcag aaatttatga gcaacacgtc   420
actaaagtga atgaagaggt agccaaactt cgtcggcgtc tcatggaact gatcagctta   480
gttcaagaag tggaaaggaa tgtagaagct gtaagaaatg caaagatga gcgtgttcgg   540 gaaattagga atgcagtgga gatgatgatt gcacggttag acacacagct gaagaataag   600
cttataacac tgatgggtca gaagacatct ctaacccaag aaacagagct tggaatcc   660 ttacttcagg aggtggagca ccagttgcgg tcttgtagta gagtgagtt gatatctaag   720 agctcagaga tccttatgat gtttcagcaa gttcatcgga agcccatggc atcttttgtt   780
accactcctg ttccaccaga ctttaccagt gaattagtgc catcttacga ttcagctact   840
tttgttttag agaatttcag cactttgcgt cagagagcag atcctgttta cagtccacct   900
```

```
cttcaagttt caggactttg ctggaggtta aaagtttacc cagatggaaa tggagttgtg    960
cgaggttact acttatctgt gtttctggag ctctcagctg gcttgcctga aacttctaaa   1020
tatgaatatc gtgtagagat ggttcaccag tcctgtaatg atcctacaaa aaatatcatt   1080
cgagaatttg catctgactt tgaagttgga gaatgctggg gctataatag atttttccgt   1140
ttggacttac tcgcaaatga aggatacttg aatccacaaa atgatacagt gattttaagg   1200
tttcaggtac gttcaccaac tttctttcaa aaatcccggg accagcattg gtacattact   1260
cagttggaag ctgcacagac tagttatatc caacaaataa acaaccttaa agagagactt   1320
actattgagc tgtctcgaac tcagaagtca agagatttgt caccaccaga taaccatctt   1380
agcccccaaa atgatgatgc tctggagaca cgagctaaga agtctgcatg ctctgacatg   1440
cttctcgaag gtggtcctac tacagcttct gtaagagagg ccaaagagga tgaagaagat   1500
gaggagaaga ttcagaatga agattatcat cacgagcttt cagatggaga tctggatctg   1560
gatcttgttt atgaggatga agtaaatcag ctcgatggca gcagttcctc tgctagttcc   1620
acagcaacaa gtaatacaga agaaaatgat attgatgaag aaactatgtc tggagaaaat   1680
gatgtggaat ataacaacat ggaattagaa gagggagaac tcatggaaga tgcagctgct   1740
gcaggacccg caggtagtag ccatggttat gtgggttcca gtagtagaat atcaagaaga   1800
acacatttat gctccgctgc taccagtagt ttactagaca ttgatccatt aattttaata   1860
catttgttgg accttaagga ccggagcagt atagaaaatt tgtggggctt acagcctcgc   1920
ccacctgctt cacttctgca gcccacagca tcatattctc gaaaagataa agaccaaagg   1980
aagcaacagg caatgtggcg agtgccctct gatttaaaga tgctaaaaag actcaaaact   2040
caaatggccg aagttcgatg tatgaaaact gatgtaaaga atacactttc agaaataaaa   2100
agcagcagtg ctgcttctgg agacatgcag acaagccttt tttctgctga ccaggcagct   2160
ctggctgcat gtggaactga aaactctggc agattgcagg atttgggaat ggaactcctg   2220
gcaaagtcat cagttgccaa ttgttacata cgaaactcca caaataagaa gagtaattcg   2280
cccaagccag ctcgatccag tgtagcaggt agtctatcac ttcgaagagc agtggaccct   2340
ggagaaaata gtcgttcaaa gggagactgt cagactctgt ctgaaggctc cccaggaagc   2400
tctcagtctg ggagcaggca cagttctccc cgagccttga tacatggcag tatcggtgat   2460
attctgccaa aaactgaaga ccggcagtgt aaagctttgg attcagatgc tgttgtggtt   2520
gcagttttca gtggcttgcc tgcggttgag aaaaggagga aatggtcac cttggggct   2580 aatgctaaag gaggtcatct ggaaggactg cagatgactg atttggaaaa taattctgaa   2640
actggagagt tacagcctgt actacctgaa ggagcttcag ctgcccctga agaaggaatg   2700
agtagcgaca gtgacattga atgtgacact gagaatgagg agcaggaaga gcataccagt   2760
gtgggcgggt ttcacgactc cttcatggtc atgacacagc ccccggatga agatacacat   2820
tccagttttc ctgatggtga acaaataggc cctgaagatc tcagcttcaa tacagatgaa   2880
aatagtggaa ggtaa                                                    2895
```

<210> SEQ ID NO 74
<211> LENGTH: 964
<212> TYPE: PRT
<213> ORGANISM: Homo sapiens

<400> SEQUENCE: 74

Met Asp Glu Gln Ser Val Glu Ser Ile Ala Glu Val Phe Arg Cys Phe
1               5                   10                  15

-continued

```
Ile Cys Met Glu Lys Leu Arg Asp Ala Arg Leu Cys Pro His Cys Ser
            20                  25                  30
Lys Leu Cys Cys Phe Ser Cys Ile Arg Arg Trp Leu Thr Glu Gln Arg
        35                  40                  45
Ala Gln Cys Pro His Cys Arg Ala Pro Leu Gln Leu Arg Glu Leu Val
    50                  55                  60
Asn Cys Arg Trp Ala Glu Glu Val Thr Gln Gln Leu Asp Thr Leu Gln
65                  70                  75                  80
Leu Cys Ser Leu Thr Lys His Glu Glu Asn Glu Lys Asp Lys Cys Glu
                85                  90                  95
Asn His His Glu Lys Leu Ser Val Phe Cys Trp Thr Cys Lys Lys Cys
            100                 105                 110
Ile Cys His Gln Cys Ala Leu Trp Gly Gly Met His Gly Gly His Thr
        115                 120                 125
Phe Lys Pro Leu Ala Glu Ile Tyr Glu Gln His Val Thr Lys Val Asn
    130                 135                 140
Glu Glu Val Ala Lys Leu Arg Arg Arg Leu Met Glu Leu Ile Ser Leu
145                 150                 155                 160
Val Gln Glu Val Glu Arg Asn Val Glu Ala Val Arg Asn Ala Lys Asp
                165                 170                 175
Glu Arg Val Arg Glu Ile Arg Asn Ala Val Glu Met Met Ile Ala Arg
            180                 185                 190
Leu Asp Thr Gln Leu Lys Asn Lys Leu Ile Thr Leu Met Gly Gln Lys
        195                 200                 205
Thr Ser Leu Thr Gln Glu Thr Glu Leu Leu Glu Ser Leu Leu Gln Glu
    210                 215                 220
Val Glu His Gln Leu Arg Ser Cys Ser Lys Ser Glu Leu Ile Ser Lys
225                 230                 235                 240
Ser Ser Glu Ile Leu Met Met Phe Gln Gln Val His Arg Lys Pro Met
                245                 250                 255
Ala Ser Phe Val Thr Thr Pro Val Pro Pro Asp Phe Thr Ser Glu Leu
            260                 265                 270
Val Pro Ser Tyr Asp Ser Ala Thr Phe Val Leu Glu Asn Phe Ser Thr
        275                 280                 285
Leu Arg Gln Arg Ala Asp Pro Val Tyr Ser Pro Pro Leu Gln Val Ser
    290                 295                 300
Gly Leu Cys Trp Arg Leu Lys Val Tyr Pro Asp Gly Asn Gly Val Val
305                 310                 315                 320
Arg Gly Tyr Tyr Leu Ser Val Phe Leu Glu Leu Ser Ala Gly Leu Pro
                325                 330                 335
Glu Thr Ser Lys Tyr Glu Tyr Arg Val Glu Met Val His Gln Ser Cys
            340                 345                 350
Asn Asp Pro Thr Lys Asn Ile Ile Arg Glu Phe Ala Ser Asp Phe Glu
        355                 360                 365
Val Gly Glu Cys Trp Gly Tyr Asn Arg Phe Phe Arg Leu Asp Leu Leu
    370                 375                 380
Ala Asn Glu Gly Tyr Leu Asn Pro Gln Asn Asp Thr Val Ile Leu Arg
385                 390                 395                 400
Phe Gln Val Arg Ser Pro Thr Phe Phe Gln Lys Ser Arg Asp Gln His
                405                 410                 415
Trp Tyr Ile Thr Gln Leu Glu Ala Ala Gln Thr Ser Tyr Ile Gln Gln
            420                 425                 430
```

```
Ile Asn Asn Leu Lys Glu Arg Leu Thr Ile Glu Leu Ser Arg Thr Gln
            435                 440                 445

Lys Ser Arg Asp Leu Ser Pro Pro Asp Asn His Leu Ser Pro Gln Asn
450                 455                 460

Asp Asp Ala Leu Glu Thr Arg Ala Lys Lys Ser Ala Cys Ser Asp Met
465                 470                 475                 480

Leu Leu Glu Gly Gly Pro Thr Thr Ala Ser Val Arg Glu Ala Lys Glu
                485                 490                 495

Asp Glu Glu Asp Glu Glu Lys Ile Gln Asn Glu Asp Tyr His His Glu
                500                 505                 510

Leu Ser Asp Gly Asp Leu Asp Leu Asp Leu Val Tyr Glu Asp Glu Val
            515                 520                 525

Asn Gln Leu Asp Gly Ser Ser Ser Ala Ser Ser Thr Ala Thr Ser
            530                 535                 540

Asn Thr Glu Glu Asn Asp Ile Asp Glu Glu Thr Met Ser Gly Glu Asn
545                 550                 555                 560

Asp Val Glu Tyr Asn Asn Met Glu Leu Glu Glu Gly Glu Leu Met Glu
                565                 570                 575

Asp Ala Ala Ala Ala Gly Pro Ala Gly Ser Ser His Gly Tyr Val Gly
            580                 585                 590

Ser Ser Ser Arg Ile Ser Arg Arg Thr His Leu Cys Ser Ala Ala Thr
            595                 600                 605

Ser Ser Leu Leu Asp Ile Asp Pro Leu Ile Leu Ile His Leu Leu Asp
            610                 615                 620

Leu Lys Asp Arg Ser Ser Ile Glu Asn Leu Trp Gly Leu Gln Pro Arg
625                 630                 635                 640

Pro Pro Ala Ser Leu Leu Gln Pro Thr Ala Ser Tyr Ser Arg Lys Asp
                645                 650                 655

Lys Asp Gln Arg Lys Gln Ala Met Trp Arg Val Pro Ser Asp Leu
            660                 665                 670

Lys Met Leu Lys Arg Leu Lys Thr Gln Met Ala Glu Val Arg Cys Met
            675                 680                 685

Lys Thr Asp Val Lys Asn Thr Leu Ser Glu Ile Lys Ser Ser Ser Ala
690                 695                 700

Ala Ser Gly Asp Met Gln Thr Ser Leu Phe Ser Ala Asp Gln Ala Ala
705                 710                 715                 720

Leu Ala Ala Cys Gly Thr Glu Asn Ser Gly Arg Leu Gln Asp Leu Gly
                725                 730                 735

Met Glu Leu Leu Ala Lys Ser Ser Val Ala Asn Cys Tyr Ile Arg Asn
            740                 745                 750

Ser Thr Asn Lys Lys Ser Asn Ser Pro Lys Pro Ala Arg Ser Ser Val
            755                 760                 765

Ala Gly Ser Leu Ser Leu Arg Arg Ala Val Asp Pro Gly Glu Asn Ser
            770                 775                 780

Arg Ser Lys Gly Asp Cys Gln Thr Leu Ser Glu Gly Ser Pro Gly Ser
785                 790                 795                 800

Ser Gln Ser Gly Ser Arg His Ser Ser Pro Arg Ala Leu Ile His Gly
                805                 810                 815

Ser Ile Gly Asp Ile Leu Pro Lys Thr Glu Asp Arg Gln Cys Lys Ala
            820                 825                 830

Leu Asp Ser Asp Ala Val Val Ala Val Phe Ser Gly Leu Pro Ala
            835                 840                 845

Val Glu Lys Arg Arg Lys Met Val Thr Leu Gly Ala Asn Ala Lys Gly
```

```
                850              855              860
Gly His Leu Glu Gly Leu Gln Met Thr Asp Leu Glu Asn Asn Ser Glu
865              870              875              880

Thr Gly Glu Leu Gln Pro Val Leu Pro Glu Gly Ala Ser Ala Ala Pro
                885              890              895

Glu Glu Gly Met Ser Ser Asp Ser Asp Ile Glu Cys Asp Thr Glu Asn
                900              905              910

Glu Glu Gln Glu Glu His Thr Ser Val Gly Gly Phe His Asp Ser Phe
        915              920              925

Met Val Met Thr Gln Pro Pro Asp Glu Asp Thr His Ser Ser Phe Pro
        930              935              940

Asp Gly Glu Gln Ile Gly Pro Glu Asp Leu Ser Phe Asn Thr Asp Glu
945              950              955              960

Asn Ser Gly Arg

<210> SEQ ID NO 75
<211> LENGTH: 1398
<212> TYPE: DNA
<213> ORGANISM: Homo sapiens

<400> SEQUENCE: 75
atggcctcaa ccaccagcac caagaagatg atggaggaag ccacctgctc catctgcctg      60
agcctgatga cgaacccagt aagcatcaac tgtggacaca gctactgcca cttgtgtata     120
acagacttct ttaaaaaccc aagccaaaag caactgaggc aggagacatt ctgctgtccc     180
cagtgtcggg ctccatttca tatggatagc ctccgaccca caagcagct gggaagcctc      240
attgaagccc tcaaagagac ggatcaagaa atgtcatgtg aggaacacgg agagcagttc     300
cacctgttct gcgaagacga ggggcagctc atctgctggc gctgtgagcg ggcaccacag     360
cacaaaggc acaccacagc tcttgttgaa gacgtatgcc agggctacaa ggaaaagctc      420
cagaaagctg tgacaaaact gaagcaactt gaagacagat gtacggagca gaagctgtcc     480
acagcaatgc gaataactaa atggaaagag aaggtacaga ttcagagaca aaaaatccgg     540
tctgacttta agaatctcca gtgtttccta catgaggaag agaagtctta tctctggagg     600
ctggagaaag aagaacaaca gactctgagt agactgaggg actatgaggc tggtctgggg     660
ctgaagagca atgaactcaa gagccacatc tggaactgg aggaaaaatg tcagggctca      720
gcccagaaat tgctgcagaa tgtgaatgac actttgagca ggagttgggc tgtgaagctg     780
gaaacatcag aggctgtctc cttgaacttc atactatgt gcaatgtttc caagctttac      840
ttcgatgtga agaaaatgtt aaggagtcat caagttagtg tgactctgga tccagataca     900
gctcatcacg aactaattct ctctgaggat cggagacaag tgactcgtgg atacacccag     960
gagaatcagg acacatcttc caggagattt actgccttcc cctgtgtctt gggttgtgaa    1020
ggcttcacct caggaagacg ttactttgaa gtggatgttg gcgaaggaac cggatgggat    1080
ttaggagttt gtatggaaaa tgtgcagagg ggcactggca tgaagcaaga gcctcagtct    1140
ggattctgga ccctcaggct gtgcaaaaag aaaggctatg tagcacttac ttctccccca    1200
acttcccttc atctgcatga gcagcccctg cttgtgggaa ttttctgga ctatgaggcc     1260
ggagttgtat cctttatata cggaatact ggctgccaca tctttacttt cccgaaggct     1320
tccttctctg atactctccg gccctatttc caggtttatc aatattctcc tttgtttctg    1380
cctcccccag gtgactaa                                                  1398
```

<210> SEQ ID NO 76
<211> LENGTH: 465
<212> TYPE: PRT
<213> ORGANISM: Homo sapiens

<400> SEQUENCE: 76

Met Ala Ser Thr Thr Ser Thr Lys Lys Met Met Glu Glu Ala Thr Cys
1               5                   10                  15

Ser Ile Cys Leu Ser Leu Met Thr Asn Pro Val Ser Ile Asn Cys Gly
            20                  25                  30

His Ser Tyr Cys His Leu Cys Ile Thr Asp Phe Phe Lys Asn Pro Ser
        35                  40                  45

Gln Lys Gln Leu Arg Gln Glu Thr Phe Cys Pro Gln Cys Arg Ala
    50                  55                  60

Pro Phe His Met Asp Ser Leu Arg Pro Asn Lys Gln Leu Gly Ser Leu
65                  70                  75                  80

Ile Glu Ala Leu Lys Glu Thr Asp Gln Glu Met Ser Cys Glu Glu His
                85                  90                  95

Gly Glu Gln Phe His Leu Phe Cys Glu Asp Glu Gly Gln Leu Ile Cys
            100                 105                 110

Trp Arg Cys Glu Arg Ala Pro Gln His Lys Gly His Thr Thr Ala Leu
        115                 120                 125

Val Glu Asp Val Cys Gln Gly Tyr Lys Glu Lys Leu Gln Lys Ala Val
    130                 135                 140

Thr Lys Leu Lys Gln Leu Glu Asp Arg Cys Thr Gln Lys Leu Ser
145                 150                 155                 160

Thr Ala Met Arg Ile Thr Lys Trp Lys Lys Val Gln Ile Gln Arg
                165                 170                 175

Gln Lys Ile Arg Ser Asp Phe Lys Asn Leu Gln Cys Phe Leu His Glu
            180                 185                 190

Glu Glu Lys Ser Tyr Leu Trp Arg Leu Glu Lys Glu Glu Gln Gln Thr
        195                 200                 205

Leu Ser Arg Leu Arg Asp Tyr Glu Ala Gly Leu Gly Leu Lys Ser Asn
    210                 215                 220

Glu Leu Lys Ser His Ile Leu Glu Leu Glu Glu Lys Cys Gln Gly Ser
225                 230                 235                 240

Ala Gln Lys Leu Leu Gln Asn Val Asn Asp Thr Leu Ser Arg Ser Trp
                245                 250                 255

Ala Val Lys Leu Glu Thr Ser Glu Ala Val Ser Leu Glu Leu His Thr
            260                 265                 270

Met Cys Asn Val Ser Lys Leu Tyr Phe Asp Val Lys Lys Met Leu Arg
        275                 280                 285

Ser His Gln Val Ser Val Thr Leu Asp Pro Thr Ala His Glu
    290                 295                 300

Leu Ile Leu Ser Glu Asp Arg Arg Gln Val Thr Arg Gly Tyr Thr Gln
305                 310                 315                 320

Glu Asn Gln Asp Thr Ser Ser Arg Arg Phe Thr Ala Phe Pro Cys Val
                325                 330                 335

Leu Gly Cys Glu Gly Phe Thr Ser Gly Arg Arg Tyr Phe Glu Val Asp
            340                 345                 350

Val Gly Glu Gly Thr Gly Trp Asp Leu Gly Val Cys Met Glu Asn Val
        355                 360                 365

Gln Arg Gly Thr Gly Met Lys Gln Glu Pro Gln Ser Gly Phe Trp Thr
    370                 375                 380

Leu Arg Leu Cys Lys Lys Lys Gly Tyr Val Ala Leu Thr Ser Pro Pro
385                 390                 395                 400

Thr Ser Leu His Leu His Glu Gln Pro Leu Leu Val Gly Ile Phe Leu
            405                 410                 415

Asp Tyr Glu Ala Gly Val Val Ser Phe Tyr Asn Gly Asn Thr Gly Cys
        420                 425                 430

His Ile Phe Thr Phe Pro Lys Ala Ser Phe Ser Asp Thr Leu Arg Pro
        435                 440                 445

Tyr Phe Gln Val Tyr Gln Tyr Ser Pro Leu Phe Leu Pro Pro Pro Gly
    450                 455                 460

Asp
465

<210> SEQ ID NO 77
<211> LENGTH: 1557
<212> TYPE: DNA
<213> ORGANISM: Homo sapiens

<400> SEQUENCE: 77

```
atggcagaga caagtctgtt agaggctggg gcctctgcag cctctacagc tgcggctttg      60
gagaacttac aggtggaggc gagctgctct gtgtgcctgg agtatctgaa ggaacctgtc     120
atcattgagt gtgggcacaa cttctgcaaa gcttgcatca cccgctggtg ggaggaccta     180
gagagggact tccttgtcc tgtctgtcga aagacatccc gctaccgcag tctccgacct      240
aatcggcaac taggcagtat ggtggaaatt gccaagcagc tccaggccgt caagcggaag     300
atccgggatg agagcctctg ccccaacac catgaggccc tcagcctttt ctgttatgag      360
gaccaggagg ctgtatgctt gatatgtgca atttcccaca cccaccgggc ccacaccgtt     420
gtgccactgg acgatgctac acaggagtac aaggaaaaac tgcagaagtg tctggagccc     480
ctggaacaga agctgcagga gatcactcgc tgcaagtcct ctgaggagaa gagcctggt      540
gagctcaaga actagtgga agtcgccga cagcagatct tgagggagtt tgaagagctt      600
cataggcggc tggatgaaga gcagcaggtg ttgctttcac gactggaaga gaggaacag    660
gacattctgc agcgactccg agaaaatgct gctcaccttg ggacaagcg ccgggacctg     720
gcccacttgg ctgccgaggt ggagggcaag tgcttacagt caggcttcga gatgcttaag     780
gatgtcaaaa gtaccctgga aaagaatatt cctagaaagt tcggaggctc actctcaacg    840
atctgtccac gggatcataa ggctctcctt ggattagtaa aagaaatcaa cagatgtgaa    900
aaggtgaaga ccatggaggt gacttcagta tccatagagc tggaaaagaa cttcagcaat    960
tttccccgac agtactttgc cctaaggaaa atccttaaac agctaattgc ggatgtgacc   1020
ctggaccctg agacagctca tcctaaccta gtcctgtcag aggatcgtaa gagcgtcaag   1080
ttcgtggaga caagactccg ggatctccct gacacaccaa ggcgtttcac cttctaccct   1140
tgcgtcctgg ctactgaggg tttcacctca ggtcgacact actgggaggt ggaggtgggc   1200
gacaagaccc actgggcagt gggtgtatgc cgggactccg tgagccgaaa gggcgagttg   1260
actccactcc ctgagactgg ctactggcgg gtgcggctat ggaatgggga caaatatgca   1320
gccaccacca caccttttac ccctttgcac atcaaggtga aacccaagcg ggtaggcata   1380
ttcctagact atgaggccgg cacactgtct ttctacaatg tcacagaccg ctctcatatc   1440
tacaccttca ctgatacttt tactgagaaa ctttggcccc tcttctaccc aggcatccgg   1500
gctggacgga gaatgctgc accacttacc atcaggcccc caacagattg ggagtga      1557
```

<210> SEQ ID NO 78
<211> LENGTH: 518
<212> TYPE: PRT
<213> ORGANISM: Homo sapiens

<400> SEQUENCE: 78

```
Met Ala Glu Thr Ser Leu Leu Glu Ala Gly Ser Ala Ala Ser Thr
1               5                   10                  15

Ala Ala Ala Leu Glu Asn Leu Gln Val Glu Ala Ser Cys Ser Val Cys
            20                  25                  30

Leu Glu Tyr Leu Lys Glu Pro Val Ile Ile Glu Cys Gly His Asn Phe
                35                  40                  45

Cys Lys Ala Cys Ile Thr Arg Trp Trp Glu Asp Leu Glu Arg Asp Phe
50                  55                  60

Pro Cys Pro Val Cys Arg Lys Thr Ser Arg Tyr Arg Ser Leu Arg Pro
65                  70                  75                  80

Asn Arg Gln Leu Gly Ser Met Val Glu Ile Ala Lys Gln Leu Gln Ala
                85                  90                  95

Val Lys Arg Lys Ile Arg Asp Glu Ser Leu Cys Pro Gln His His Glu
                100                 105                 110

Ala Leu Ser Leu Phe Cys Tyr Glu Asp Gln Ala Val Cys Leu Ile
            115                 120                 125

Cys Ala Ile Ser His Thr His Arg Ala His Thr Val Val Pro Leu Asp
130                 135                 140

Asp Ala Thr Gln Glu Tyr Lys Glu Lys Leu Gln Lys Cys Leu Glu Pro
145                 150                 155                 160

Leu Glu Gln Lys Leu Gln Glu Ile Thr Arg Cys Lys Ser Ser Glu Glu
                165                 170                 175

Lys Lys Pro Gly Glu Leu Lys Arg Leu Val Glu Ser Arg Arg Gln Gln
                180                 185                 190

Ile Leu Arg Glu Phe Glu Glu Leu His Arg Leu Asp Glu Glu Gln
            195                 200                 205

Gln Val Leu Leu Ser Arg Leu Glu Glu Glu Gln Asp Ile Leu Gln
210                 215                 220

Arg Leu Arg Glu Asn Ala Ala His Leu Gly Asp Lys Arg Asp Leu
225                 230                 235                 240

Ala His Leu Ala Ala Glu Val Glu Gly Lys Cys Leu Gln Ser Gly Phe
            245                 250                 255

Glu Met Leu Lys Asp Val Lys Ser Thr Leu Glu Lys Asn Ile Pro Arg
                260                 265                 270

Lys Phe Gly Gly Ser Leu Ser Thr Ile Cys Pro Arg Asp His Lys Ala
            275                 280                 285

Leu Leu Gly Leu Val Lys Glu Ile Asn Arg Cys Glu Lys Val Lys Thr
            290                 295                 300

Met Glu Val Thr Ser Val Ser Ile Glu Leu Leu Lys Asn Phe Ser Asn
305                 310                 315                 320

Phe Pro Arg Gln Tyr Phe Ala Leu Arg Lys Ile Leu Lys Gln Leu Ile
                325                 330                 335

Ala Asp Val Thr Leu Asp Pro Glu Thr Ala His Pro Asn Leu Val Leu
            340                 345                 350

Ser Glu Asp Arg Lys Ser Val Lys Phe Val Glu Thr Arg Leu Arg Asp
            355                 360                 365

Leu Pro Asp Thr Pro Arg Arg Phe Thr Phe Tyr Pro Cys Val Leu Ala
        370                 375                 380
```

```
Thr Glu Gly Phe Thr Ser Gly Arg His Tyr Trp Glu Val Glu Val Gly
385                 390                 395                 400

Asp Lys Thr His Trp Ala Val Gly Val Cys Arg Asp Ser Val Ser Arg
            405                 410                 415

Lys Gly Glu Leu Thr Pro Leu Pro Glu Thr Gly Tyr Trp Arg Val Arg
        420                 425                 430

Leu Trp Asn Gly Asp Lys Tyr Ala Ala Thr Thr Pro Phe Thr Pro
        435                 440                 445

Leu His Ile Lys Val Lys Pro Lys Arg Val Gly Ile Phe Leu Asp Tyr
    450                 455                 460

Glu Ala Gly Thr Leu Ser Phe Tyr Asn Val Thr Asp Arg Ser His Ile
465                 470                 475                 480

Tyr Thr Phe Thr Asp Thr Phe Thr Glu Lys Leu Trp Pro Leu Phe Tyr
            485                 490                 495

Pro Gly Ile Arg Ala Gly Arg Lys Asn Ala Ala Pro Leu Thr Ile Arg
            500                 505                 510

Pro Pro Thr Asp Trp Glu
        515
```

```
<210> SEQ ID NO 79
<211> LENGTH: 777
<212> TYPE: DNA
<213> ORGANISM: Homo sapiens

<400> SEQUENCE: 79
atgatccctt tgcagaagga caaccaggag gagggtgtct gccccatctg ccaggagagc    60
ctgaaggagg ccgtgagcac caactgcgga catctcttct gtcgagtgtg cctgacacag   120
catgtggaga aggcctcagc ctctggggtc ttctgctgcc ccctctgccg gaagccctgt   180
tctgaggagg tgctagggac aggctatatc tgccccaacc accagaagag ggtgtgcagg   240
ttctgtgagg agagcagact tcttctatgt gtggaatgcc tggtgtcccc tgaacacatg   300
tctcatcatg aactgaccat tgaaaatgcc ctcagccact acaaggaacg actcaatcgc   360
cggagcagga agctcagaaa ggacattgca gaacttcagc ggctcaaggc tcagcaggag   420
aagaaactgc aggctctgca gtttcaggta gaccacggga accacaggct ggaggctggg   480
ccggagagcc agcaccaaac cagggaacag ctgggtgccc tccctcagca gtggctgggc   540
cagctggagc acatgccagc agaagcggcc agaatccttg acatctccag ggcagtaaca   600
cagctcagaa gcctggtcat tgatctggaa aggacggcca aggaattaga caccaacaca   660
ctgaagaatg ctggtgactt actgaacagg agtgctccac agaaattaga ggttatttat   720
ccccagttgg agaaggagt cagtgaattg cttcttcagc cccctcagaa gctctga      777
```

```
<210> SEQ ID NO 80
<211> LENGTH: 258
<212> TYPE: PRT
<213> ORGANISM: Homo sapiens

<400> SEQUENCE: 80

Met Ile Pro Leu Gln Lys Asp Asn Gln Glu Glu Gly Val Cys Pro Ile
1               5                   10                  15

Cys Gln Glu Ser Leu Lys Glu Ala Val Ser Thr Asn Cys Gly His Leu
            20                  25                  30

Phe Cys Arg Val Cys Leu Thr Gln His Val Glu Lys Ala Ser Ala Ser
        35                  40                  45

Gly Val Phe Cys Cys Pro Leu Cys Arg Lys Pro Cys Ser Glu Glu Val
```

```
                 50                  55                  60
Leu Gly Thr Gly Tyr Ile Cys Pro Asn His Gln Lys Arg Val Cys Arg
 65                  70                  75                  80

Phe Cys Glu Glu Ser Arg Leu Leu Cys Val Glu Cys Leu Val Ser
                 85                  90                  95

Pro Glu His Met Ser His His Glu Leu Thr Ile Glu Asn Ala Leu Ser
                100                 105                 110

His Tyr Lys Glu Arg Leu Asn Arg Arg Ser Arg Lys Leu Arg Lys Asp
            115                 120                 125

Ile Ala Glu Leu Gln Arg Leu Lys Ala Gln Gln Glu Lys Lys Leu Gln
        130                 135                 140

Ala Leu Gln Phe Gln Val Asp His Gly Asn His Arg Leu Glu Ala Gly
145                 150                 155                 160

Pro Glu Ser Gln His Gln Thr Arg Glu Gln Leu Gly Ala Leu Pro Gln
                165                 170                 175

Gln Trp Leu Gly Gln Leu Glu His Met Pro Ala Glu Ala Ala Arg Ile
                180                 185                 190

Leu Asp Ile Ser Arg Ala Val Thr Gln Leu Arg Ser Leu Val Ile Asp
            195                 200                 205

Leu Glu Arg Thr Ala Lys Glu Leu Asp Thr Asn Thr Leu Lys Asn Ala
        210                 215                 220

Gly Asp Leu Leu Asn Arg Ser Ala Pro Gln Lys Leu Glu Val Ile Tyr
225                 230                 235                 240

Pro Gln Leu Glu Lys Gly Val Ser Glu Leu Leu Gln Pro Pro Gln
                245                 250                 255

Lys Leu

<210> SEQ ID NO 81
<211> LENGTH: 1893
<212> TYPE: DNA
<213> ORGANISM: Homo sapiens

<400> SEQUENCE: 81
atggctgccg ttgccatgac acccaaccct gtgcagaccc ttcaggagga ggcggtgtgc    60
gccatctgcc tcgattactt cacggacccc gtgtccatcg gctgcgggca caacttctgc   120
cgagtttgtg taacccagtt gtggggtggg gaggatgagg aggacagaga tgagttagat   180
cgggaggagg aggaggagga cggagaggag gaggaagtgg aggctgtggg ggctggcgcg   240 ggtgggaca cccccatgcg ggatgaagac tacgagggtg acatggagga ggaggtcgag   300
gaggaagaag agggtgtgtt ctggaccagt ggcatgagca ggtccagctg ggacaacatg   360
gactatgtgt gggaggagga ggacgaggag gaagacctgg actactactt ggggggacatg   420 gaggaggagg acctgagggg ggaggatgag gaggacgagg aggaagtgct ggaggaggtt   480
gaggaagagg atctagaccc cgtcacccca ctgcccccgc ctccagcccc tcggaggtgc   540
ttcacatgcc ctcagtgccg aaagagcttt cctcggcgga gcttccgccc caacctgcag   600
ctggccaata tggtccaggt gattcggcag atgcacccaa ccctggtcg agggagccgc   660 gtgaccgatc agggcatctg tcccaaacac caagaagccc tgaagctctt ctgcgaggta   720
gacgaagagg ccatctgtgt ggtgtgccga gaatccagga gccacaaaca gcacagcgtg   780
gtgccattgg aggaggtggt gcaggagtac aaggccaaac tgcaggggca cgtggaacca   840
ctgaggaagc acctgaggc agtgcagaag atgaaagcca aggaggagag gcagtgaca   900 gaactgaaga gccagatgaa gtcagagctg gcagcggtgg cctcggagtt tgggcgactg   960
```

-continued

```
acacggtttc tggctgaaga gcaggcaggg ctggaacggc gtctcagaga gatgcatgaa    1020
gcccagctgg ggcgtgcggg agccgcggct agtcgccttg cagaacaggc cgcccagctc    1080
agccgcctgc tggcagaggc ccaggagcgg agccagcagg ggggtctccg gctgctccag    1140
gacatcaagg agactttcaa taggtgtgaa gaggtacagc tgcagccccc agaggtctgg    1200
tcccctgacc cgtgccaacc ccatagccat gacttcctga cagatgccat cgtgaggaaa    1260
atgagccgga tgttctgtca ggctgcgaga gtggacctga cgctggaccc tgacacgggct   1320
cacccggccc tgatgctgtc ccctgaccgc cggggggtcc gcctggcaga gcggcggcag    1380
gaggttgctg accatcccaa cgcttctcg gccgactgct cgtactggg ggcccagggc      1440
ttccgctccg gccggcacta ctgggaggta gaggtgggcg ggcggcgggg ctgggcggtg    1500
ggtgctgccc gtgaatcaac ccatcataag gaaaaggtgg gccctggggg ttcctccgtg    1560
ggcagcgggg atgccagctc ctcgcgccat caccatcgcc gccgccggct ccacctgccc    1620
cagcagcccc tgctccagcg ggaagtgtgg tgcgtgggca ccaacggcaa acgctatcag    1680
gcccagagct ccacagaaca gacgctgctg agccccagtg agaaaccaag gcgctttggt    1740
gtgtacctgg actatgaagc tgggcgcctg ggcttctaca acgcagagac tctagcccac    1800
gtgcacacct tctcggctgc cttcctgggc gagcgtgtct ttcctttctt ccgggtgctc    1860
tccaagggca cccgcatcaa gctctgccct tga                                 1893
```

<210> SEQ ID NO 82
<211> LENGTH: 630
<212> TYPE: PRT
<213> ORGANISM: Homo sapiens

<400> SEQUENCE: 82

```
Met Ala Ala Val Ala Met Thr Pro Asn Pro Val Gln Thr Leu Gln Glu
1               5                   10                  15

Glu Ala Val Cys Ala Ile Cys Leu Asp Tyr Phe Thr Asp Pro Val Ser
            20                  25                  30

Ile Gly Cys Gly His Asn Phe Cys Arg Val Cys Val Thr Gln Leu Trp
        35                  40                  45

Gly Gly Glu Asp Glu Glu Asp Arg Asp Glu Leu Asp Arg Glu Glu Glu
    50                  55                  60

Glu Glu Asp Gly Glu Glu Glu Val Glu Ala Val Gly Ala Gly Ala
65                  70                  75                  80

Gly Trp Asp Thr Pro Met Arg Asp Glu Asp Tyr Glu Gly Asp Met Glu
                85                  90                  95

Glu Glu Val Glu Glu Glu Glu Gly Val Phe Trp Thr Ser Gly Met
            100                 105                 110

Ser Arg Ser Ser Trp Asp Asn Met Asp Tyr Val Trp Glu Glu Glu Asp
        115                 120                 125

Glu Glu Glu Asp Leu Asp Tyr Tyr Leu Gly Asp Met Glu Glu Glu Asp
    130                 135                 140

Leu Arg Gly Glu Asp Glu Glu Asp Glu Glu Val Leu Glu Glu Val
145                 150                 155                 160

Glu Glu Glu Asp Leu Asp Pro Val Thr Pro Leu Pro Pro Pro Ala
                165                 170                 175

Pro Arg Arg Cys Phe Thr Cys Pro Gln Cys Arg Lys Ser Phe Pro Arg
            180                 185                 190

Arg Ser Phe Arg Pro Asn Leu Gln Leu Ala Asn Met Val Gln Val Ile
        195                 200                 205
```

```
Arg Gln Met His Pro Thr Pro Gly Arg Gly Ser Arg Val Thr Asp Gln
    210                 215                 220

Gly Ile Cys Pro Lys His Gln Glu Ala Leu Lys Leu Phe Cys Glu Val
225                 230                 235                 240

Asp Glu Glu Ala Ile Cys Val Val Cys Arg Glu Ser Arg Ser His Lys
                245                 250                 255

Gln His Ser Val Val Pro Leu Glu Glu Val Val Gln Glu Tyr Lys Ala
                260                 265                 270

Lys Leu Gln Gly His Val Glu Pro Leu Arg Lys His Leu Glu Ala Val
            275                 280                 285

Gln Lys Met Lys Ala Lys Glu Arg Arg Val Thr Glu Leu Lys Ser
290                 295                 300

Gln Met Lys Ser Glu Leu Ala Ala Val Ala Ser Glu Phe Gly Arg Leu
305                 310                 315                 320

Thr Arg Phe Leu Ala Glu Glu Gln Ala Gly Leu Glu Arg Arg Leu Arg
                325                 330                 335

Glu Met His Glu Ala Gln Leu Gly Arg Ala Gly Ala Ala Ser Arg
                340                 345                 350

Leu Ala Glu Gln Ala Ala Gln Leu Ser Arg Leu Leu Ala Glu Ala Gln
            355                 360                 365

Glu Arg Ser Gln Gln Gly Gly Leu Arg Leu Leu Gln Asp Ile Lys Glu
            370                 375                 380

Thr Phe Asn Arg Cys Glu Val Gln Leu Gln Pro Pro Glu Val Trp
385                 390                 395                 400

Ser Pro Asp Pro Cys Gln Pro His Ser His Asp Phe Leu Thr Asp Ala
                405                 410                 415

Ile Val Arg Lys Met Ser Arg Met Phe Cys Gln Ala Arg Val Asp
                420                 425                 430

Leu Thr Leu Asp Pro Asp Thr Ala His Pro Ala Leu Met Leu Ser Pro
            435                 440                 445

Asp Arg Arg Gly Val Arg Leu Ala Glu Arg Arg Gln Glu Val Ala Asp
            450                 455                 460

His Pro Lys Arg Phe Ser Ala Asp Cys Cys Val Leu Gly Ala Gln Gly
465                 470                 475                 480

Phe Arg Ser Gly Arg His Tyr Trp Glu Val Glu Val Gly Gly Arg Arg
                485                 490                 495

Gly Trp Ala Val Gly Ala Ala Arg Glu Ser Thr His His Lys Glu Lys
                500                 505                 510

Val Gly Pro Gly Gly Ser Ser Val Gly Ser Gly Asp Ala Ser Ser Ser
            515                 520                 525

Arg His His His Arg Arg Arg Leu His Leu Pro Gln Gln Pro Leu
            530                 535                 540

Leu Gln Arg Glu Val Trp Cys Val Gly Thr Asn Gly Lys Arg Tyr Gln
545                 550                 555                 560

Ala Gln Ser Ser Thr Glu Gln Thr Leu Leu Ser Pro Ser Glu Lys Pro
                565                 570                 575

Arg Arg Phe Gly Val Tyr Leu Asp Tyr Glu Ala Gly Arg Leu Gly Phe
            580                 585                 590

Tyr Asn Ala Glu Thr Leu Ala His Val His Thr Phe Ser Ala Ala Phe
            595                 600                 605

Leu Gly Glu Arg Val Phe Pro Phe Phe Arg Val Leu Ser Lys Gly Thr
610                 615                 620
```

Arg Ile Lys Leu Cys Pro
625                 630

<210> SEQ ID NO 83
<211> LENGTH: 2172
<212> TYPE: DNA
<213> ORGANISM: Homo sapiens

<400> SEQUENCE: 83

| atggaaactg | ctatgtgcgt | ttgctgtcca | tgttgtacat | ggcagagatg | ttgtcctcag | 60 |
| ttatgctcct | gtctgtgctg | caagttcatc | ttcacctcag | agcggaactg | cacctgcttc | 120 |
| ccctgccctt | acaaagatga | gcggaactgc | cagttctgcc | actgcacctg | ttctgagagc | 180 |
| cccaactgcc | attggtgttg | ctgctcttgg | gccaatgatc | ccaactgtaa | gtgctgctgc | 240 |
| acagccagca | gcaatctcaa | ctgctactac | tatgagagcc | gctgctgccg | caataccatc | 300 |
| atcactttcc | acaagggccg | cctcaggagc | atccatacct | cctccaagac | tgccctgcgc | 360 |
| actgggagca | gcgataccca | ggtggatgaa | gtaaagtcaa | taccagccaa | cagtcacctg | 420 |
| gtgaaccacc | tcaattgccc | catgtgcagc | cggctgcgcc | tgcactcatt | catgctgccc | 480 |
| tgcaaccaca | gcctgtgcga | gaagtgcctg | cggcagctgc | agaagcacgc | cgaggtcacc | 540 |
| gagaacttct | tcatcctcat | ctgcccagtg | tgcgaccgct | cgcactgcat | gccctacagc | 600 |
| aacaagatgc | agctgcccga | gaactacctg | acgggcgtc  | tcaccaagcg | ctacatgcag | 660 |
| gagcacggct | acctcaagtg | gcgctttgac | cgctcctccg | ggcccatcct | gccaggtc   | 720 |
| tgccgcaaca | gcgcatcgc  | ttacaagcgc | tgcatcacct | gccgcctcaa | cctgtgcaac | 780 |
| gactgcctca | aggccttcca | ctcggatgtg | gccatgcaag | accacgtctt | tgtggacacc | 840 |
| agcgccgagg | aacaggacga | gaagatctgc | atccacccc  | catccagccg | catcatcgag | 900 |
| tactgccgca | atgacaacaa | attgctctgc | accttctgca | agttctcttt | ccacaatggc | 960 |
| cacgacacca | ttagcctcat | cgacgcctgc | tccgagaggg | ccgcctcact | cttcagcgcc | 1020 |
| atcgccaagt | tcaaagcagt | ccgatatgaa | attgataatg | acctaatgga | attcaacatc | 1080 |
| ttaaaaaaca | gctttaaagc | tgacaaggag | gcaaagcgaa | aagagatcag | aaatggcttt | 1140 |
| ctcaagttgc | gcagcattct | tcaggagaaa | gagaagatca | tcatggagca | gatagagaat | 1200 |
| ctagaagtgt | ccaggcagaa | ggaaattgaa | aaatatgtgt | atgttacaac | catgaaagtg | 1260 |
| aacgagatgg | atggtctgat | cgcctactcc | aaggaagccc | tgaaggagac | tggccaggtg | 1320 |
| gcattcctgc | agtcagccaa | gatcctggtg | gaccagatcg | aggacggcat | ccagaccacc | 1380 |
| tacaggcctg | acccacagct | ccggctgcac | tcaataaact | acgtgccctt | ggactttgtt | 1440 |
| gagctttcca | gtgccatcca | tgagctcttc | cccacagggc | ccaagaaggt | acgctcctca | 1500 |
| ggggactccc | tgccctcccc | ctaccccgtg | cactcagaaa | caatgattgc | caggaaggtc | 1560 |
| actttcagca | cccacagcct | cggcaaccag | cacatatacc | agcgaagctc | ctccatgttg | 1620 |
| tccttcagca | cactgacaa  | gaaggccaag | gtgggtctgg | aggcctgtgg | agagcccag  | 1680 |
| tcagccaccc | ccgccaaacc | cacagacggc | ctctacacct | actggagtgc | tggagcagac | 1740 |
| agccagtctg | tacagaacag | cagcagcttc | cacaactggt | actcattcaa | cgatggctct | 1800 |
| gtgaagaccc | aggcccaat  | tgttatctac | cagactctgg | tgtacccaag | agctgccaag | 1860 |
| gtttactgga | catgtccagc | agaagacgtg | gactcttttg | agatggaatt | ctatgaagtc | 1920 |
| attacttctc | ctcctaacaa | cgtacaaatg | gagctctgtg | acaaattcg  | ggacataatg | 1980 |
| cagcaaaatc | tggagctgca | caacctgacc | cccaacacag | aatacgtgtt | taaagttaga | 2040 |

```
gccatcaatg ataatggtcc tgggcaatgg agtgatatct gcaaggtggt aacaccagat    2100
ggacatggga agaaccgagc taagtggggc ctgctgaaga atatccagtc tgccctccag    2160
aagcacttct ga                                                       2172
```

<210> SEQ ID NO 84
<211> LENGTH: 723
<212> TYPE: PRT
<213> ORGANISM: Homo sapiens

<400> SEQUENCE: 84

```
Met Glu Thr Ala Met Cys Val Cys Cys Pro Cys Cys Thr Trp Gln Arg
1               5                   10                  15

Cys Cys Pro Gln Leu Cys Ser Cys Leu Cys Cys Lys Phe Ile Phe Thr
            20                  25                  30

Ser Glu Arg Asn Cys Thr Cys Phe Pro Cys Pro Tyr Lys Asp Glu Arg
        35                  40                  45

Asn Cys Gln Phe Cys His Cys Thr Cys Ser Glu Ser Pro Asn Cys His
    50                  55                  60

Trp Cys Cys Cys Ser Trp Ala Asn Asp Pro Asn Cys Lys Cys Cys Cys
65                  70                  75                  80

Thr Ala Ser Ser Asn Leu Asn Cys Tyr Tyr Tyr Glu Ser Arg Cys Cys
                85                  90                  95

Arg Asn Thr Ile Ile Thr Phe His Lys Gly Arg Leu Arg Ser Ile His
            100                 105                 110

Thr Ser Ser Lys Thr Ala Leu Arg Thr Gly Ser Ser Asp Thr Gln Val
        115                 120                 125

Asp Glu Val Lys Ser Ile Pro Ala Asn Ser His Leu Val Asn His Leu
    130                 135                 140

Asn Cys Pro Met Cys Ser Arg Leu Arg Leu His Ser Phe Met Leu Pro
145                 150                 155                 160

Cys Asn His Ser Leu Cys Glu Lys Cys Leu Arg Gln Leu Gln Lys His
                165                 170                 175

Ala Glu Val Thr Glu Asn Phe Phe Ile Leu Ile Cys Pro Val Cys Asp
            180                 185                 190

Arg Ser His Cys Met Pro Tyr Ser Asn Lys Met Gln Leu Pro Glu Asn
        195                 200                 205

Tyr Leu His Gly Arg Leu Thr Lys Arg Tyr Met Gln Glu His Gly Tyr
    210                 215                 220

Leu Lys Trp Arg Phe Asp Arg Ser Ser Gly Pro Ile Leu Cys Gln Val
225                 230                 235                 240

Cys Arg Asn Lys Arg Ile Ala Tyr Lys Arg Cys Ile Thr Cys Arg Leu
                245                 250                 255

Asn Leu Cys Asn Asp Cys Leu Lys Ala Phe His Ser Asp Val Ala Met
            260                 265                 270

Gln Asp His Val Phe Val Asp Thr Ser Ala Glu Glu Gln Asp Glu Lys
        275                 280                 285

Ile Cys Ile His His Pro Ser Ser Arg Ile Ile Glu Tyr Cys Arg Asn
    290                 295                 300

Asp Asn Lys Leu Leu Cys Thr Phe Cys Lys Phe Ser Phe His Asn Gly
305                 310                 315                 320

His Asp Thr Ile Ser Leu Ile Asp Ala Cys Ser Glu Arg Ala Ala Ser
                325                 330                 335

Leu Phe Ser Ala Ile Ala Lys Phe Lys Ala Val Arg Tyr Glu Ile Asp
            340                 345                 350
```

Asn Asp Leu Met Glu Phe Asn Ile Leu Lys Asn Ser Phe Lys Ala Asp
            355                 360                 365

Lys Glu Ala Lys Arg Lys Glu Ile Arg Asn Gly Phe Leu Lys Leu Arg
        370                 375                 380

Ser Ile Leu Gln Glu Lys Glu Lys Ile Ile Met Glu Gln Ile Glu Asn
385                 390                 395                 400

Leu Glu Val Ser Arg Gln Lys Glu Ile Glu Lys Tyr Val Tyr Val Thr
                405                 410                 415

Thr Met Lys Val Asn Glu Met Asp Gly Leu Ile Ala Tyr Ser Lys Glu
                420                 425                 430

Ala Leu Lys Glu Thr Gly Gln Val Ala Phe Leu Gln Ser Ala Lys Ile
            435                 440                 445

Leu Val Asp Gln Ile Glu Asp Gly Ile Gln Thr Thr Tyr Arg Pro Asp
        450                 455                 460

Pro Gln Leu Arg Leu His Ser Ile Asn Tyr Val Pro Leu Asp Phe Val
465                 470                 475                 480

Glu Leu Ser Ser Ala Ile His Glu Leu Phe Pro Thr Gly Pro Lys Lys
                485                 490                 495

Val Arg Ser Ser Gly Asp Ser Leu Pro Ser Pro Tyr Pro Val His Ser
                500                 505                 510

Glu Thr Met Ile Ala Arg Lys Val Thr Phe Ser Thr His Ser Leu Gly
            515                 520                 525

Asn Gln His Ile Tyr Gln Arg Ser Ser Ser Met Leu Ser Phe Ser Asn
        530                 535                 540

Thr Asp Lys Lys Ala Lys Val Gly Leu Glu Ala Cys Gly Arg Ala Gln
545                 550                 555                 560

Ser Ala Thr Pro Ala Lys Pro Thr Asp Gly Leu Tyr Thr Tyr Trp Ser
                565                 570                 575

Ala Gly Ala Asp Ser Gln Ser Val Gln Asn Ser Ser Phe His Asn
                580                 585                 590

Trp Tyr Ser Phe Asn Asp Gly Ser Val Lys Thr Pro Gly Pro Ile Val
            595                 600                 605

Ile Tyr Gln Thr Leu Val Tyr Pro Arg Ala Ala Lys Val Tyr Trp Thr
        610                 615                 620

Cys Pro Ala Glu Asp Val Asp Ser Phe Glu Met Glu Phe Tyr Glu Val
625                 630                 635                 640

Ile Thr Ser Pro Pro Asn Asn Val Gln Met Glu Leu Cys Gly Gln Ile
                645                 650                 655

Arg Asp Ile Met Gln Gln Asn Leu Glu Leu His Asn Leu Thr Pro Asn
                660                 665                 670

Thr Glu Tyr Val Phe Lys Val Arg Ala Ile Asn Asp Asn Gly Pro Gly
            675                 680                 685

Gln Trp Ser Asp Ile Cys Lys Val Val Thr Pro Asp Gly His Gly Lys
        690                 695                 700

Asn Arg Ala Lys Trp Gly Leu Leu Lys Asn Ile Gln Ser Ala Leu Gln
705                 710                 715                 720

Lys His Phe

<210> SEQ ID NO 85
<211> LENGTH: 1341
<212> TYPE: DNA
<213> ORGANISM: Homo sapiens

<400> SEQUENCE: 85

```
atggactcag acttctcaca tgccttccag aaggaactca cctgcgtcat ctgtttgaac    60
tacctggtag accctgtcac catctgctgt gggcacagct tctgtaggcc ctgtctctgc   120
ctttcgtggg aggaagccca aagtcctgca aactgccctg catgcaggga accatcaccg   180
aaaatggact tcaaaaccaa tattcttctg aagaatttag tgaccattgc agaaaagcc    240
agtctctggc aattcctgag ctctgagaaa caaatatgtg ggacccatag caaacaaag    300
aagatgttct gtgacatgga caagagtctc ctctgcttgc tgtgctccaa ctctcaggag   360
cacggggctc acaaacacca tcccatcgaa gaggcagctg aggaacaccg ggagaaactc   420
ttaaagcaaa tgaggatttt atggaaaaag attcaagaaa tcagagaaa tctatatgag    480
gagggaagaa cagccttcct ctggaggggc aatgtggttt tacgggcaca tgatgatcagg   540
aatgagtata ggaagctgca tccggttctc cataaggaag aaaaacaaca tttagagaga   600
ctgaacaagg aataccaaga ttttttcag caactccaga gaagttgggt caaaatggat    660
caaaagagta aacacttgaa agaaatgtat caggaactaa tggaaatgtg tcataaacca   720
gatgtggagc tgctccagga tttgggagac atcgtggcaa ggagtgagtc cgtgctgctg   780
cacatgcccc agcctgtgaa tccagagctc actgcaggac ccatcactgg actggtgtac   840
aggctcaacc gcttccgagt ggaaatttcc ttccattttg aagtaaccaa tcacaatatc   900
aggctctttg aggatgtgag aagttggatg tttagacgtg gacctttgaa ttctgacaga   960
tctgactatt ttgctgcatg gggagccagg gtcttctcct ttgggaaaca ctactgggag  1020
ctggatgtgg acaactcttg tgactgggct ctgggagtct gtaacaactc ctggataagg  1080
aagaatagca caatggttaa ctctgaggac atatttcttc ttttgtgtct gaaggtggat  1140
aatcatttca atctcttgac cacctcccca gtgtttcctc actacataga gaaacctctg  1200
ggccggttg gtgtgtttct tgattttgaa agtggaagtg tgagttttt gaatgtcacc    1260
aagagttccc tcatatggag ttacccagct ggctccttaa cttttcctgt caggcctttc   1320
ttttacactg gccacagatg a                                            1341
```

<210> SEQ ID NO 86
<211> LENGTH: 446
<212> TYPE: PRT
<213> ORGANISM: Homo sapiens

<400> SEQUENCE: 86

```
Met Asp Ser Asp Phe Ser His Ala Phe Gln Lys Glu Leu Thr Cys Val
1               5                   10                  15

Ile Cys Leu Asn Tyr Leu Val Asp Pro Val Thr Ile Cys Cys Gly His
            20                  25                  30

Ser Phe Cys Arg Pro Cys Leu Cys Leu Ser Trp Glu Glu Ala Gln Ser
        35                  40                  45

Pro Ala Asn Cys Pro Ala Cys Arg Glu Pro Ser Pro Lys Met Asp Phe
    50                  55                  60

Lys Thr Asn Ile Leu Leu Lys Asn Leu Val Thr Ile Ala Arg Lys Ala
65                  70                  75                  80

Ser Leu Trp Gln Phe Leu Ser Ser Glu Lys Gln Ile Cys Gly Thr His
                85                  90                  95

Arg Gln Thr Lys Lys Met Phe Cys Asp Met Asp Lys Ser Leu Leu Cys
            100                 105                 110

Leu Leu Cys Ser Asn Ser Gln Glu His Gly Ala His Lys His His Pro
        115                 120                 125
```

Ile Glu Glu Ala Ala Glu Glu His Arg Glu Lys Leu Leu Lys Gln Met
130                 135                 140

Arg Ile Leu Trp Lys Lys Ile Gln Glu Asn Gln Arg Asn Leu Tyr Glu
145                 150                 155                 160

Glu Gly Arg Thr Ala Phe Leu Trp Arg Gly Asn Val Val Leu Arg Ala
                165                 170                 175

Gln Met Ile Arg Asn Glu Tyr Arg Lys Leu His Pro Val Leu His Lys
                180                 185                 190

Glu Glu Lys Gln His Leu Glu Arg Leu Asn Lys Glu Tyr Gln Glu Ile
                195                 200                 205

Phe Gln Gln Leu Gln Arg Ser Trp Val Lys Met Asp Gln Lys Ser Lys
210                 215                 220

His Leu Lys Glu Met Tyr Gln Glu Leu Met Glu Met Cys His Lys Pro
225                 230                 235                 240

Asp Val Glu Leu Leu Gln Asp Leu Gly Asp Ile Val Ala Arg Ser Glu
                245                 250                 255

Ser Val Leu Leu His Met Pro Gln Pro Val Asn Pro Glu Leu Thr Ala
                260                 265                 270

Gly Pro Ile Thr Gly Leu Val Tyr Arg Leu Asn Arg Phe Arg Val Glu
                275                 280                 285

Ile Ser Phe His Phe Glu Val Thr Asn His Asn Ile Arg Leu Phe Glu
290                 295                 300

Asp Val Arg Ser Trp Met Phe Arg Arg Gly Pro Leu Asn Ser Asp Arg
305                 310                 315                 320

Ser Asp Tyr Phe Ala Ala Trp Gly Ala Arg Val Phe Ser Phe Gly Lys
                325                 330                 335

His Tyr Trp Glu Leu Asp Val Asp Asn Ser Cys Asp Trp Ala Leu Gly
                340                 345                 350

Val Cys Asn Asn Ser Trp Ile Arg Lys Asn Ser Thr Met Val Asn Ser
                355                 360                 365

Glu Asp Ile Phe Leu Leu Cys Leu Lys Val Asp Asn His Phe Asn
370                 375                 380

Leu Leu Thr Thr Ser Pro Val Phe Pro His Tyr Ile Glu Lys Pro Leu
385                 390                 395                 400

Gly Arg Val Gly Val Phe Leu Asp Phe Glu Ser Gly Val Ser Phe
                405                 410                 415

Leu Asn Val Thr Lys Ser Ser Leu Ile Trp Ser Tyr Pro Ala Gly Ser
                420                 425                 430

Leu Thr Phe Pro Val Arg Pro Phe Phe Tyr Thr Gly His Arg
                435                 440                 445

<210> SEQ ID NO 87
<211> LENGTH: 1035
<212> TYPE: DNA
<213> ORGANISM: Homo sapiens

<400> SEQUENCE: 87
atggcctctg gagtgggcgc ggccttcgag gaactgcctc acgacggcac gtgtgacgag      60
tgcgagcccg acgaggctcc gggggccgag gaagtgtgcc gagaatgcgg cttctgctac     120
tgccgccgcc atgccgaggc gcacaggcag aagttcctca gtcaccatct ggccgaatac     180
gtccacggct cccaggcctg gaccccgcca gctgacggag aggggcggg gaaggaagaa     240 gcggaggtca ggtggagca ggagagggag atagaaagcg aggcagggga agagagtgag     300
tcggaggaag agagcgagtc agaggaagag agcgagacag aggaagagag tgaggatgag     360

```
agcgatgagg agagtgaaga agacagcgag gaagaaatgg aggatgagca agaaagcgag      420
gccgaagaag acaaccaaga agaagggaa tccgaggcgg agggagaaac tgaggcagaa      480
agtgaatttg acccagaaat agaaatggaa gcagagagag tggccaagag gaagtgtccg      540
gaccatgggc ttgatttgag tacctattgc caggaagata ggcagctcat ctgtgtcctg      600
tgtccagtca ttggggctca ccagggccac caactctcca ccctagacga agcctttgaa      660
gaattaagaa gcaaagactc aggtggactg aaggccgcta tgatcgaatt ggtggaaagg      720
ttgaagttca agagctcaga ccctaaagta actcgggacc aaatgaagat gtttatacag      780
caggaattta agaaagttca gaaagtgatt gctgatgagg agcagaaggc ccttcatcta      840
gtggacatcc aagaggcaat ggccacagct catgtgactg agatactggc agacatccaa      900
tcccacatgg ataggttgat gactcagatg gcccaagcca aggaacaact tgatacctct      960
aatgaatcag ctgagccaaa ggcagagggc gatgaggaag acccagtggg tgccagtgaa     1020
gaagaggaca catga                                                     1035
```

<210> SEQ ID NO 88
<211> LENGTH: 344
<212> TYPE: PRT
<213> ORGANISM: Homo sapiens

<400> SEQUENCE: 88

```
Met Ala Ser Gly Val Gly Ala Ala Phe Glu Glu Leu Pro His Asp Gly
1               5                   10                  15

Thr Cys Asp Glu Cys Glu Pro Asp Glu Ala Pro Gly Ala Glu Glu Val
            20                  25                  30

Cys Arg Glu Cys Gly Phe Cys Tyr Cys Arg Arg His Ala Glu Ala His
        35                  40                  45

Arg Gln Lys Phe Leu Ser His His Leu Ala Glu Tyr Val His Gly Ser
    50                  55                  60

Gln Ala Trp Thr Pro Pro Ala Asp Gly Glu Gly Ala Gly Lys Glu Glu
65                  70                  75                  80

Ala Glu Val Lys Val Glu Gln Glu Arg Glu Ile Glu Ser Glu Ala Gly
                85                  90                  95

Glu Glu Ser Glu Ser Glu Glu Glu Ser Glu Ser Glu Glu Glu Ser Glu
            100                 105                 110

Thr Glu Glu Glu Ser Glu Asp Glu Ser Asp Glu Glu Ser Glu Glu Asp
        115                 120                 125

Ser Glu Glu Glu Met Glu Asp Glu Gln Glu Ser Glu Ala Glu Glu Asp
    130                 135                 140

Asn Gln Glu Glu Gly Glu Ser Glu Ala Glu Gly Glu Thr Glu Ala Glu
145                 150                 155                 160

Ser Glu Phe Asp Pro Glu Ile Glu Met Glu Ala Glu Arg Val Ala Lys
                165                 170                 175

Arg Lys Cys Pro Asp His Gly Leu Asp Leu Ser Thr Tyr Cys Gln Glu
            180                 185                 190

Asp Arg Gln Leu Ile Cys Val Leu Cys Pro Val Ile Gly Ala His Gln
        195                 200                 205

Gly His Gln Leu Ser Thr Leu Asp Glu Ala Phe Glu Glu Leu Arg Ser
    210                 215                 220

Lys Asp Ser Gly Gly Leu Lys Ala Ala Met Ile Glu Leu Val Glu Arg
225                 230                 235                 240

Leu Lys Phe Lys Ser Ser Asp Pro Lys Val Thr Arg Asp Gln Met Lys
```

```
                245                 250                 255
Met Phe Ile Gln Gln Glu Phe Lys Lys Val Gln Lys Val Ile Ala Asp
            260                 265                 270

Glu Glu Gln Lys Ala Leu His Leu Val Asp Ile Gln Glu Ala Met Ala
        275                 280                 285

Thr Ala His Val Thr Glu Ile Leu Ala Asp Ile Gln Ser His Met Asp
    290                 295                 300

Arg Leu Met Thr Gln Met Ala Gln Ala Lys Glu Gln Leu Asp Thr Ser
305                 310                 315                 320

Asn Glu Ser Ala Glu Pro Lys Ala Glu Gly Asp Glu Gly Pro Ser
                325                 330                 335

Gly Ala Ser Glu Glu Glu Asp Thr
            340

<210> SEQ ID NO 89
<211> LENGTH: 1743
<212> TYPE: DNA
<213> ORGANISM: Homo sapiens

<400> SEQUENCE: 89
atgtcagaaa acagaaaacc gctgctgggc tttgtaagca aactcactag tgggactgca      60
cttgggaact caggcaagac tcactgcccc ctgtgcttgg ggcttttcaa agcccccagg     120
ctcttgcctt gtttgcatac agtttgcacc acgtgtctgg agcagctgga gcccttctca     180
gtagtggaca tccgaggggg agactctgac acaagctctg agggtcaat  attccaggaa     240 ctcaagccac gaagtctgca gtcgcagatc ggcatccttt gtcctgtatg tgatgctcag     300
gtggacctgc ccatgggtgg agtgaaggct ttaaccatag accacctggc cgtgaatgat     360
gtgatgctgg agagcctacg tggggaaggc cagggcctgg tgtgtgacct gtgcaacgac     420
agggaagtag agaagaggtg tcagacctgc aaagccaacc tctgccactt ctgctgccag     480
gctcataggc ggcagaagaa aacgacttac acaccatgg tggacctaaa agacttgaaa     540
ggctacagcc ggattgggaa gcccatcctg tgtcctgttc accctgcaga ggaactgagg     600
ctgttctgtg agttctgtga ccggcccgtg tgccaggatt gtgtggtggg ggagcatcgg     660
gaacacccct gtgacttcac cagcaatgtc atccacaagc atggggactc tgtgtgggag     720
ctcctcaaag gtactcagcc ccacgtggag gccctggagg aagccctggc tcagatccac     780
ataataaaca gtgccctcca gaagcgagtg gaggcagtgg cagctgatgt ccggacattc     840
tcggagggct acattaaggc cattgaggag catcgggaca gctgctgaa  gcagctggaa     900 gacatacggg cccagaagga aaattccctg cagctgcaga aggcccagct ggaacagtta     960
ctggcagaca tgcggactgg agtggagttc accgagcact tgctgaccag cggctcagac    1020
ttggagatcc tcatcaccaa gagggtggtg gtagaacggc tcaggaagct gaacaaagtt    1080
caatatagca cccgtcctgg agtaaatgat aagatacgct tctgtcctca ggagaaagca    1140
ggccagtgcc gtggctatga aatttatggt acgattaata ccaaagaggt tgatccagcc    1200
aaatgtgtcc tacaaggaga agacctccac agagcccggg agaaacagac ggcctctttc    1260
accctgcttt gtaaggatgc cgcaggagaa atcatgggca gggaggaga caacgttcaa    1320 gttgccgttg tccctaaaga taagaaagac agcccagtca gaacaatggt ccaggataac    1380
aaggatggga catactacat ttcctacacc cccaaggaac ctggcgtcta tactgtgtgg    1440
gtctgcatca agaacagca tgtgcagggc tcgccattca ctgtgatggt gaggagaaag    1500
caccgcccac actcaggcgt gtttcactgc tgcaccttct gctccagcgg gggccagaaa    1560
```

```
accgctcgct gcgcctgtgg aggcaccatg ccaggtgggt acctaggctg tggccatgga   1620
cacaaaggcc acccaggtca tccccactgg tcatgctgtg gaaaatttaa tgagaaatct   1680
gaatgcacat ggacaggtgg gcagagcgca ccgaggagtc tacttaggac tgtggctctc   1740
tga                                                                 1743
```

<210> SEQ ID NO 90
<211> LENGTH: 580
<212> TYPE: PRT
<213> ORGANISM: Homo sapiens

<400> SEQUENCE: 90

```
Met Ser Glu Asn Arg Lys Pro Leu Leu Gly Phe Val Ser Lys Leu Thr
1               5                   10                  15

Ser Gly Thr Ala Leu Gly Asn Ser Gly Lys Thr His Cys Pro Leu Cys
            20                  25                  30

Leu Gly Leu Phe Lys Ala Pro Arg Leu Leu Pro Cys Leu His Thr Val
        35                  40                  45

Cys Thr Thr Cys Leu Glu Gln Leu Glu Pro Phe Ser Val Val Asp Ile
    50                  55                  60

Arg Gly Gly Asp Ser Asp Thr Ser Ser Glu Gly Ser Ile Phe Gln Glu
65                  70                  75                  80

Leu Lys Pro Arg Ser Leu Gln Ser Gln Ile Gly Ile Leu Cys Pro Val
                85                  90                  95

Cys Asp Ala Gln Val Asp Leu Pro Met Gly Gly Val Lys Ala Leu Thr
            100                 105                 110

Ile Asp His Leu Ala Val Asn Asp Val Met Leu Glu Ser Leu Arg Gly
        115                 120                 125

Glu Gly Gln Gly Leu Val Cys Asp Leu Cys Asn Asp Arg Glu Val Glu
    130                 135                 140

Lys Arg Cys Gln Thr Cys Lys Ala Asn Leu Cys His Phe Cys Cys Gln
145                 150                 155                 160

Ala His Arg Arg Gln Lys Lys Thr Thr Tyr His Thr Met Val Asp Leu
                165                 170                 175

Lys Asp Leu Lys Gly Tyr Ser Arg Ile Gly Lys Pro Ile Leu Cys Pro
            180                 185                 190

Val His Pro Ala Glu Glu Leu Arg Leu Phe Cys Glu Phe Cys Asp Arg
        195                 200                 205

Pro Val Cys Gln Asp Cys Val Val Gly Glu His Arg Glu His Pro Cys
    210                 215                 220

Asp Phe Thr Ser Asn Val Ile His Lys His Gly Asp Ser Val Trp Glu
225                 230                 235                 240

Leu Leu Lys Gly Thr Gln Pro His Val Glu Ala Leu Glu Glu Ala Leu
                245                 250                 255

Ala Gln Ile His Ile Ile Asn Ser Ala Leu Gln Lys Arg Val Glu Ala
            260                 265                 270

Val Ala Ala Asp Val Arg Thr Phe Ser Glu Gly Tyr Ile Lys Ala Ile
        275                 280                 285

Glu Glu His Arg Asp Lys Leu Leu Lys Gln Leu Glu Asp Ile Arg Ala
    290                 295                 300

Gln Lys Glu Asn Ser Leu Gln Leu Gln Lys Ala Gln Leu Glu Gln Leu
305                 310                 315                 320

Leu Ala Asp Met Arg Thr Gly Val Glu Phe Thr Glu His Leu Leu Thr
                325                 330                 335
```

Ser Gly Ser Asp Leu Glu Ile Leu Ile Thr Lys Arg Val Val Glu
            340                 345                 350

Arg Leu Arg Lys Leu Asn Lys Val Gln Tyr Ser Thr Arg Pro Gly Val
            355                 360                 365

Asn Asp Lys Ile Arg Phe Cys Pro Gln Glu Lys Ala Gly Gln Cys Arg
370                 375                 380

Gly Tyr Glu Ile Tyr Gly Thr Ile Asn Thr Lys Glu Val Asp Pro Ala
385                 390                 395                 400

Lys Cys Val Leu Gln Gly Glu Asp Leu His Arg Ala Arg Glu Lys Gln
                405                 410                 415

Thr Ala Ser Phe Thr Leu Leu Cys Lys Asp Ala Ala Gly Glu Ile Met
            420                 425                 430

Gly Arg Gly Gly Asp Asn Val Gln Val Ala Val Val Pro Lys Asp Lys
            435                 440                 445

Lys Asp Ser Pro Val Arg Thr Met Val Gln Asp Asn Lys Asp Gly Thr
            450                 455                 460

Tyr Tyr Ile Ser Tyr Thr Pro Lys Glu Pro Gly Val Tyr Thr Val Trp
465                 470                 475                 480

Val Cys Ile Lys Glu Gln His Val Gln Gly Ser Pro Phe Thr Val Met
                485                 490                 495

Val Arg Arg Lys His Arg Pro His Ser Gly Val Phe His Cys Cys Thr
            500                 505                 510

Phe Cys Ser Ser Gly Gly Gln Lys Thr Ala Arg Cys Ala Cys Gly Gly
            515                 520                 525

Thr Met Pro Gly Gly Tyr Leu Gly Cys Gly His Gly His Lys Gly His
            530                 535                 540

Pro Gly His Pro His Trp Ser Cys Cys Gly Lys Phe Asn Glu Lys Ser
545                 550                 555                 560

Glu Cys Thr Trp Thr Gly Gly Gln Ser Ala Pro Arg Ser Leu Leu Arg
                565                 570                 575

Thr Val Ala Leu
            580

<210> SEQ ID NO 91
<211> LENGTH: 2280
<212> TYPE: DNA
<213> ORGANISM: Homo sapiens

<400> SEQUENCE: 91

| | | | | |
|---|---|---|---|---|
| atggcagagg | gtgaggatat | gcagaccttc | acttccatca | tggacgcact ggtccgcatc | 60 |
| agtaccagca | tgaagaacat | ggagaaggaa | ctgctgtgcc | cagtgtgtca agagatgtac | 120 |
| aagcagccac | tggtgctgcc | ctgtacccac | aacgtgtgcc | aggcctgtgc cgagaggtc | 180 |
| ttgggccagc | agggctacat | aggacatggt | ggggacccca | gctccgagcc cacctctcct | 240 |
| gcctccaccc | cttccacccg | cagccccgc | ctctcccgca | gaactctccc caagccagac | 300 |
| cgcctggacc | ggctgcttaa | gtcaggcttt | ggacatacc | ctgggaggaa gcgaggtgct | 360 |
| ttgcacccc | aagtgatcat | gttcccgtgc | ccagcctgcc | aaggtgatgt ggagcttggg | 420 |
| gagcggggtc | tggcagggct | tttccggaac | ctgaccctgg | agcgtgtggt ggagcggtac | 480 |
| cgccagagtg | tgagtgtggg | aggtgccatc | ctgtgccagt | tgtgcaagcc cccaccacta | 540 |
| gaggccacca | aggctgcac | agagtgccgc | gccaccttct | gcaatgagtg cttcaagctc | 600 |
| ttccaccct | ggggcaccca | gaaggcccag | catgagccca | ccctgcctac cctctccttc | 660 |

| | | |
|---|---|---|
| cgacccaagg gccttatgtg cccagaccac aaggaagagg tgacccacta ctgcaagaca | 720 | |
| tgccaacgcc tggtatgtca actctgccgg gtgcggcgca cccacagcgg cacaagatc | 780 | |
| acaccagtgc tcagtgccta ccaggccctc aaggacaagc tgacaaagag cctgacatac | 840 | |
| atcctgggaa accaggacac ggtacagacc cagatctgtg agctggagga ggccgtgagg | 900 | |
| cacaccgagg tgagtggtca gcaggccaag gaggaggtgt cgcagctggt gcggggctg | 960 | |
| ggggctgtgc tggaggagaa gcgggcatca ctgcttcagg ccattgaaga atgccagcag | 1020 | |
| gagcggctgg cccgtctcag cgcccagatc caggagcacc ggagcctgct ggatggctca | 1080 | |
| ggtctggtgg gctatgccca ggaagtactt aaggaaacag accagccttg ctttgtgcaa | 1140 | |
| gccgccaagc agctgcacaa caggattgcc cgagccactg aagccctcca gacattccgg | 1200 | |
| ccagctgcca gctcctcctt ccgccattgc cagctcgacg tgggacgtga gatgaagctg | 1260 | |
| ctgacagagc ttaacttcct gcgagtgcct gaggcccccg tcattgacac ccagcgcacc | 1320 | |
| tttgcctatg atcagatctt cctgtgctgg cggctgcccc cccattcacc acctgcctgg | 1380 | |
| cactataccg ttgagttccg gcgcacggat gtgcctgctc agccaggccc cacccgctgg | 1440 | |
| cagcggcggg aggaggtgag gggcaccagt gccctgcttg agaaccccga cacgggctct | 1500 | |
| gtgtatgtgc tgcgtgtccg cggctgcaac aaggccggct acggcgaata cagtgaagat | 1560 | |
| gtgcacctgc acacgccccc ggcacctgtc ctgcacttct tcctcgatag ccgctggggc | 1620 | |
| gcaagccgag agcggctggc tatcagcaag accagcgag cagtacggag tgttccaggg | 1680 | |
| ctgcccctgc tgctggctgc tgaccggctg ctgaccggct gccacctgag tgtggatgtg | 1740 | |
| gtcctgggcg acgtggctgt gacccaggc cgcagctact gggcctgcgc cgtagaccca | 1800 | |
| gcctcctact tggtcaaggt gggcgtcggg ctggagagca agcttcaaga aagtttccag | 1860 | |
| ggtgcccccg atgtgatcag ccccaggtac gacccggaca gcgggcacga cagcggtgcc | 1920 | |
| gaggatgcca cagtggaggc gtcgccaccc ttcgctttcc taaccattgg catgggcaag | 1980 | |
| atcctgctgg ggtcgggggc aagctcaaac gcagggctga cagggaggga tggccccaca | 2040 | |
| gccggctgca cagtgcccct gccacccgc ctgggcatct gcctggacta tgagcggggc | 2100 | |
| cgggtttcct tcctggatgc tgtttccttc cgtgggctct ggagtgccc cctgactgc | 2160 | |
| tcagggcctg tgtgccctgc cttttgcttc atcgggggtg gcgcagtaca gctccaggag | 2220 | |
| ccagtgggca ctaagcctga gaggaaagtc accattgggg gcttcgccaa gctggactga | 2280 | |

<210> SEQ ID NO 92
<211> LENGTH: 759
<212> TYPE: PRT
<213> ORGANISM: Homo sapiens

<400> SEQUENCE: 92

```
Met Ala Glu Gly Glu Asp Met Gln Thr Phe Thr Ser Ile Met Asp Ala
1               5                   10                  15

Leu Val Arg Ile Ser Thr Ser Met Lys Asn Met Glu Lys Glu Leu Leu
            20                  25                  30

Cys Pro Val Cys Gln Glu Met Tyr Lys Gln Pro Leu Val Leu Pro Cys
        35                  40                  45

Thr His Asn Val Cys Gln Ala Cys Ala Arg Glu Val Leu Gly Gln Gln
    50                  55                  60

Gly Tyr Ile Gly His Gly Gly Asp Pro Ser Ser Glu Pro Thr Ser Pro
65                  70                  75                  80

Ala Ser Thr Pro Ser Thr Arg Ser Pro Arg Leu Ser Arg Arg Thr Leu
                85                  90                  95
```

```
Pro Lys Pro Asp Arg Leu Asp Arg Leu Leu Lys Ser Gly Phe Gly Thr
            100                 105                 110
Tyr Pro Gly Arg Lys Arg Gly Ala Leu His Pro Gln Val Ile Met Phe
            115                 120                 125
Pro Cys Pro Ala Cys Gln Gly Asp Val Glu Leu Gly Glu Arg Gly Leu
            130                 135                 140
Ala Gly Leu Phe Arg Asn Leu Thr Leu Glu Arg Val Val Glu Arg Tyr
145                 150                 155                 160
Arg Gln Ser Val Ser Val Gly Gly Ala Ile Leu Cys Gln Leu Cys Lys
                165                 170                 175
Pro Pro Pro Leu Glu Ala Thr Lys Gly Cys Thr Glu Cys Arg Ala Thr
            180                 185                 190
Phe Cys Asn Glu Cys Phe Lys Leu Phe His Pro Trp Gly Thr Gln Lys
            195                 200                 205
Ala Gln His Glu Pro Thr Leu Pro Thr Leu Ser Phe Arg Pro Lys Gly
            210                 215                 220
Leu Met Cys Pro Asp His Lys Glu Glu Val Thr His Tyr Cys Lys Thr
225                 230                 235                 240
Cys Gln Arg Leu Val Cys Gln Leu Cys Arg Val Arg Arg Thr His Ser
                245                 250                 255
Gly His Lys Ile Thr Pro Val Leu Ser Ala Tyr Gln Ala Leu Lys Asp
            260                 265                 270
Lys Leu Thr Lys Ser Leu Thr Tyr Ile Leu Gly Asn Gln Asp Thr Val
            275                 280                 285
Gln Thr Gln Ile Cys Glu Leu Glu Glu Ala Val Arg His Thr Glu Val
            290                 295                 300
Ser Gly Gln Gln Ala Lys Glu Glu Val Ser Gln Leu Val Arg Gly Leu
305                 310                 315                 320
Gly Ala Val Leu Glu Glu Lys Arg Ala Ser Leu Leu Gln Ala Ile Glu
                325                 330                 335
Glu Cys Gln Gln Glu Arg Leu Ala Arg Leu Ser Ala Gln Ile Gln Glu
            340                 345                 350
His Arg Ser Leu Leu Asp Gly Ser Gly Leu Val Gly Tyr Ala Gln Glu
            355                 360                 365
Val Leu Lys Glu Thr Asp Gln Pro Cys Phe Val Gln Ala Ala Lys Gln
            370                 375                 380
Leu His Asn Arg Ile Ala Arg Ala Thr Glu Ala Leu Gln Thr Phe Arg
385                 390                 395                 400
Pro Ala Ala Ser Ser Phe Arg His Cys Gln Leu Asp Val Gly Arg
                405                 410                 415
Glu Met Lys Leu Leu Thr Glu Leu Asn Phe Leu Arg Val Pro Glu Ala
            420                 425                 430
Pro Val Ile Asp Thr Gln Arg Thr Phe Ala Tyr Asp Gln Ile Phe Leu
            435                 440                 445
Cys Trp Arg Leu Pro Pro His Ser Pro Pro Ala Trp His Tyr Thr Val
            450                 455                 460
Glu Phe Arg Arg Thr Asp Val Pro Ala Gln Pro Gly Pro Thr Arg Trp
465                 470                 475                 480
Gln Arg Arg Glu Glu Val Arg Gly Thr Ser Ala Leu Leu Glu Asn Pro
                485                 490                 495
Asp Thr Gly Ser Val Tyr Val Leu Arg Val Arg Gly Cys Asn Lys Ala
            500                 505                 510
```

```
Gly Tyr Gly Glu Tyr Ser Glu Asp Val His Leu His Thr Pro Pro Ala
            515                 520                 525
Pro Val Leu His Phe Phe Leu Asp Ser Arg Trp Gly Ala Ser Arg Glu
    530                 535                 540
Arg Leu Ala Ile Ser Lys Asp Gln Arg Ala Val Arg Ser Val Pro Gly
545                 550                 555                 560
Leu Pro Leu Leu Leu Ala Ala Asp Arg Leu Leu Thr Gly Cys His Leu
                565                 570                 575
Ser Val Asp Val Val Leu Gly Asp Val Ala Val Thr Gln Gly Arg Ser
            580                 585                 590
Tyr Trp Ala Cys Ala Val Asp Pro Ala Ser Tyr Leu Val Lys Val Gly
        595                 600                 605
Val Gly Leu Glu Ser Lys Leu Gln Glu Ser Phe Gln Gly Ala Pro Asp
    610                 615                 620
Val Ile Ser Pro Arg Tyr Asp Pro Asp Ser Gly His Asp Ser Gly Ala
625                 630                 635                 640
Glu Asp Ala Thr Val Glu Ala Ser Pro Pro Phe Ala Phe Leu Thr Ile
                645                 650                 655
Gly Met Gly Lys Ile Leu Leu Gly Ser Gly Ala Ser Ser Asn Ala Gly
            660                 665                 670
Leu Thr Gly Arg Asp Gly Pro Thr Ala Gly Cys Thr Val Pro Leu Pro
        675                 680                 685
Pro Arg Leu Gly Ile Cys Leu Asp Tyr Glu Arg Gly Arg Val Ser Phe
    690                 695                 700
Leu Asp Ala Val Ser Phe Arg Gly Leu Leu Glu Cys Pro Leu Asp Cys
705                 710                 715                 720
Ser Gly Pro Val Cys Pro Ala Phe Cys Phe Ile Gly Gly Ala Val
                725                 730                 735
Gln Leu Gln Glu Pro Val Gly Thr Lys Pro Glu Arg Lys Val Thr Ile
            740                 745                 750
Gly Gly Phe Ala Lys Leu Asp
            755

<210> SEQ ID NO 93
<211> LENGTH: 1917
<212> TYPE: DNA
<213> ORGANISM: Homo sapiens

<400> SEQUENCE: 93
atggacggca gtggacccct cagctgcccc atctgcctag agccactccg ggagccggtg     60
acgctgccct gcggccacaa cttctgtctc gcctgcctgg gcgcgctctg gccgcatcgt    120
ggcgcgagtg gagccggcgg acccggaggc gcggccccgc tgccgctgtg ccaggagccc    180
ttccccgacg gccttcagct ccgcaagaac cacacgctgt ccgagctgct gcagctccgc    240
cagggctcgg gccccgggtc cggccccggc ccggcccctg ccctggcccc ggagccctcg    300
gcacccagcg cgctgcccag tgtcccggag ccgtcggccc cctgcgctcc cgagccgtgg    360
cccgcgggcg aagagccagt gcgctgcgac gcgtgccccg agggcgcggc cctgccgcc    420 gcgctgtcct gcctctcctg cctcgcctcc ttttgccccg cgcacctggg cccgcacgag    480
cgcagccccg ccctccgcgg acaccgcctg gtgccgccgc tgcgccggct agaggagagc    540
ctgtgcccgc gccacctacg gccgctcgag cgctactgcc gcgcggagcg cgtgtgtctg    600
tgcgaggcct gcgccgcaca ggagcaccgc ggccacgagt ggtgccgct ggagcaggag    660 cgcgcgcttc aggaggctga gcagtccaaa gtcctgagcg ccgtggagga ccgcatggac    720
```

```
gagctgggtg ctggcattgc acagtccagg cgcacagtgg ccctcatcaa gagtgcagcc    780
gtagcagagc gggagagggt gagccggctg tttgcagatg ctgcggccgc cctgcagggc    840
ttccagaccc aggtgctggg cttcatcgag gaggggaag ctgccatgct aggccgctcc     900
cagggtgacc tgcggcgaca ggaggaacag cgcagccgcc tgagccgagc ccgccagaat    960
ctcagccagg tccctgaagc tgactcagtc agcttcctgc aggagctgct ggcactaagg   1020
ctggccctgg aggatgggtg tggccctggg cctggacccc cgaggagct cagcttcacc    1080
aaatcatccc aagctgtccg tgcagtgaga gacatgctgg ccgtggcctg cgtcaaccag   1140
tgggagcagc tgagggggcc gggtggcaac gaggatgggc cacagaagct ggactcggaa   1200
gctgatgctg agccccaaga cctcgagagt acgaacctct ggagagtga agctcccagg    1260
gactatttcc tcaagtttgc ctatattgtg gatttggaca cgacacagc agacaagttc    1320
ctgcagctgt ttggaaccaa aggtgtcaag agggtgctgt gtcctatcaa ctacccttg    1380
tcgcccaccc gcttcaccca ttgtgagcag gtgctgggcg agggtgccct ggaccgaggc   1440
acctactact gggaggtgga gattatcgag ggctgggtca gcatgggggt catggccgaa   1500
gacttctccc cacaagagcc ctacgaccgc ggccggctgg ccgcaacgc ccactcctgc    1560
tgcctgcagt ggaatggacg cagcttctcc gtctggtttc atgggctgga ggctcccctg   1620
ccccacccct tctcgcccac ggttggggtc tgcctggaat acgctgaccg tgccttggcc   1680
ttctatgctg tacgggacgg caagatgagc ctcctgcgga ggctgaaggc ctcccggccc   1740
cgccggggtg gcatcccggc ctcccccatt gacccttcc agagccgcct ggacagtcac    1800
tttgcgggc tcttcaccca cagactcaag cctgccttct tcctggagag tgtggacgcc    1860
cacttgcaga tcgggcccct caagaagtcc tgcatatccg tgctgaagag gaggtga     1917

<210> SEQ ID NO 94
<211> LENGTH: 638
<212> TYPE: PRT
<213> ORGANISM: Homo sapiens

<400> SEQUENCE: 94

Met Asp Gly Ser Gly Pro Phe Ser Cys Pro Ile Cys Leu Glu Pro Leu
1               5                   10                  15

Arg Glu Pro Val Thr Leu Pro Cys Gly His Asn Phe Cys Leu Ala Cys
                20                  25                  30

Leu Gly Ala Leu Trp Pro His Arg Gly Ala Ser Gly Ala Gly Gly Pro
            35                  40                  45

Gly Gly Ala Ala Arg Cys Pro Leu Cys Gln Glu Pro Phe Pro Asp Gly
        50                  55                  60

Leu Gln Leu Arg Lys Asn His Thr Leu Ser Glu Leu Leu Gln Leu Arg
65                  70                  75                  80

Gln Gly Ser Gly Pro Gly Ser Gly Pro Gly Pro Ala Pro Ala Leu Ala
                85                  90                  95

Pro Glu Pro Ser Ala Pro Ser Ala Leu Pro Ser Val Pro Glu Pro Ser
                100                 105                 110

Ala Pro Cys Ala Pro Glu Pro Trp Pro Ala Gly Glu Glu Pro Val Arg
            115                 120                 125

Cys Asp Ala Cys Pro Glu Gly Ala Ala Leu Pro Ala Leu Ser Cys
        130                 135                 140

Leu Ser Cys Leu Ala Ser Phe Cys Pro Ala His Leu Gly Pro His Glu
145                 150                 155                 160
```

-continued

```
Arg Ser Pro Ala Leu Arg Gly His Arg Leu Val Pro Leu Arg Arg
            165                 170                 175
Leu Glu Glu Ser Leu Cys Pro Arg His Leu Arg Pro Leu Glu Arg Tyr
        180                 185                 190
Cys Arg Ala Glu Arg Val Cys Leu Cys Glu Ala Cys Ala Ala Gln Glu
            195                 200                 205
His Arg Gly His Glu Leu Val Pro Leu Glu Gln Arg Ala Leu Gln
        210                 215                 220
Glu Ala Glu Gln Ser Lys Val Leu Ser Ala Val Glu Asp Arg Met Asp
225                 230                 235                 240
Glu Leu Gly Ala Gly Ile Ala Gln Ser Arg Arg Thr Val Ala Leu Ile
            245                 250                 255
Lys Ser Ala Ala Val Ala Glu Arg Glu Arg Val Ser Arg Leu Phe Ala
            260                 265                 270
Asp Ala Ala Ala Leu Gln Gly Phe Gln Thr Gln Val Leu Gly Phe
        275                 280                 285
Ile Glu Glu Gly Glu Ala Ala Met Leu Gly Arg Ser Gln Gly Asp Leu
    290                 295                 300
Arg Arg Gln Glu Glu Gln Arg Ser Arg Leu Ser Arg Ala Arg Gln Asn
305                 310                 315                 320
Leu Ser Gln Val Pro Glu Ala Asp Ser Val Ser Phe Leu Gln Glu Leu
                325                 330                 335
Leu Ala Leu Arg Leu Ala Leu Glu Asp Gly Cys Gly Pro Gly Pro Gly
            340                 345                 350
Pro Pro Arg Glu Leu Ser Phe Thr Lys Ser Ser Gln Ala Val Arg Ala
        355                 360                 365
Val Arg Asp Met Leu Ala Val Ala Cys Val Asn Gln Trp Glu Gln Leu
    370                 375                 380
Arg Gly Pro Gly Gly Asn Glu Asp Gly Pro Gln Lys Leu Asp Ser Glu
385                 390                 395                 400
Ala Asp Ala Glu Pro Gln Asp Leu Glu Ser Thr Asn Leu Leu Glu Ser
                405                 410                 415
Glu Ala Pro Arg Asp Tyr Phe Leu Lys Phe Ala Tyr Ile Val Asp Leu
            420                 425                 430
Asp Ser Asp Thr Ala Asp Lys Phe Leu Gln Leu Phe Gly Thr Lys Gly
            435                 440                 445
Val Lys Arg Val Leu Cys Pro Ile Asn Tyr Pro Leu Ser Pro Thr Arg
    450                 455                 460
Phe Thr His Cys Glu Gln Val Leu Gly Glu Gly Ala Leu Asp Arg Gly
465                 470                 475                 480
Thr Tyr Tyr Trp Glu Val Glu Ile Ile Glu Gly Trp Val Ser Met Gly
                485                 490                 495
Val Met Ala Glu Asp Phe Ser Pro Gln Glu Pro Tyr Asp Arg Gly Arg
            500                 505                 510
Leu Gly Arg Asn Ala His Ser Cys Cys Leu Gln Trp Asn Gly Arg Ser
        515                 520                 525
Phe Ser Val Trp Phe His Gly Leu Glu Ala Pro Leu Pro His Pro Phe
    530                 535                 540
Ser Pro Thr Val Gly Val Cys Leu Glu Tyr Ala Asp Arg Ala Leu Ala
545                 550                 555                 560
Phe Tyr Ala Val Arg Asp Gly Lys Met Ser Leu Leu Arg Arg Leu Lys
                565                 570                 575
Ala Ser Arg Pro Arg Arg Gly Gly Ile Pro Ala Ser Pro Ile Asp Pro
```

```
                580             585             590
Phe Gln Ser Arg Leu Asp Ser His Phe Ala Gly Leu Phe Thr His Arg
            595                 600                 605

Leu Lys Pro Ala Phe Phe Leu Glu Ser Val Asp Ala His Leu Gln Ile
        610                 615                 620

Gly Pro Leu Lys Lys Ser Cys Ile Ser Val Leu Lys Arg Arg
625                 630                 635

<210> SEQ ID NO 95
<211> LENGTH: 675
<212> TYPE: DNA
<213> ORGANISM: Homo sapiens

<400> SEQUENCE: 95
atgtctcgaa gaatcattgt gggaacccct caaagaaccc agcgaaacat gaattctgga      60
atctcgcaag tcttccagag ggaactcacc tgccccatct gcatgaacta cttcatagac     120
ccggtcacca tagactgtgg cacagctttt gcaggccct gtttctacct caactggcaa      180
gacatcccaa ttcttactca gtgctttgaa tgcataaaga caatacagca gagaaacctc     240
aaaactaaca ttcgattgaa gaagatggct cccttgccga aaagccag tctctggcta      300 ttcctgagct ctgaggagca aatgtgtggc attcacaggg agacaaagaa gatgttctgt     360
gaagtggaca ggagcctgct ctgtttgctg tgctccagct ctcaggagca ccggtatcac     420
agacactgtc ccgctgagtg ggctgctgag gaacactggg agaagctttt aaagaaaatg     480
cagtctttat gggaaaaagc ttgtgaaaat cagagaaacc tgaatgtgga accaccaga      540 atcagccact ggaaggcttt tggagacata ttatacagga gtgagtccgt gctgctgcac     600
atgccccagc tctgaatct agcgctcagg cagggccca tcactggact gagggacagg      660
ctcaaccaat tctga                                                       675

<210> SEQ ID NO 96
<211> LENGTH: 224
<212> TYPE: PRT
<213> ORGANISM: Homo sapiens

<400> SEQUENCE: 96

Met Ser Arg Arg Ile Ile Val Gly Thr Leu Gln Arg Thr Gln Arg Asn
1               5                   10                  15

Met Asn Ser Gly Ile Ser Gln Val Phe Gln Arg Glu Leu Thr Cys Pro
            20                  25                  30

Ile Cys Met Asn Tyr Phe Ile Asp Pro Val Thr Ile Asp Cys Gly His
        35                  40                  45

Ser Phe Cys Arg Pro Cys Phe Tyr Leu Asn Trp Gln Asp Ile Pro Ile
    50                  55                  60

Leu Thr Gln Cys Phe Glu Cys Ile Lys Thr Ile Gln Gln Arg Asn Leu
65                  70                  75                  80

Lys Thr Asn Ile Arg Leu Lys Lys Met Ala Ser Leu Ala Arg Lys Ala
                85                  90                  95

Ser Leu Trp Leu Phe Leu Ser Ser Glu Glu Gln Met Cys Gly Ile His
            100                 105                 110

Arg Glu Thr Lys Lys Met Phe Cys Glu Val Asp Arg Ser Leu Leu Cys
        115                 120                 125

Leu Leu Cys Ser Ser Ser Gln Glu His Arg Tyr His Arg His Cys Pro
    130                 135                 140

Ala Glu Trp Ala Ala Glu Glu His Trp Glu Lys Leu Leu Lys Lys Met
```

```
                145                 150                 155                 160
Gln Ser Leu Trp Glu Lys Ala Cys Glu Asn Gln Arg Asn Leu Asn Val
                165                 170                 175

Glu Thr Thr Arg Ile Ser His Trp Lys Ala Phe Gly Asp Ile Leu Tyr
            180                 185                 190

Arg Ser Glu Ser Val Leu Leu His Met Pro Gln Pro Leu Asn Leu Ala
        195                 200                 205

Leu Arg Ala Gly Pro Ile Thr Gly Leu Arg Asp Arg Leu Asn Gln Phe
    210                 215                 220

<210> SEQ ID NO 97
<211> LENGTH: 1359
<212> TYPE: DNA
<213> ORGANISM: Homo sapiens

<400> SEQUENCE: 97
atgaattctg gaatcttaca ggtctttcag ggggaactca tctgcccct  gtgcatgaac      60 tacttcatag acccggtcac catagactgt gggcacagct tttgcaggcc ttgtttctac     120
ctcaactggc aagacatccc atttcttgtc cagtgctctg aatgcacaaa gtcaaccgag     180
cagataaacc tcaaaaccaa cattcatttg aagaagatgg cttctcttgc agaaaagtc     240 agtctctggc tattcctgag ctctgaggag caaatgtgtg gcactcacag ggagacaaag     300
aagatattct gtgaagtgga caggagcctg ctctgtttgc tgtgctccag ctctcaggag     360
caccggtatc acagacaccg tcccattgag tgggctgctg aggaacaccg ggagaagctt     420
ttacagaaaa tgcagtcttt gtgggaaaaa gcttgtgaaa atcacagaaa cctgaatgtg     480
gaaaccacca gaaccagatg ctggaaggat tatgtgaatt aaggctaga  agcaattaga     540 gctgagtatc agaagatgcc tgcatttcat catgaagaag aaaaacataa tttggagatg     600
ctgaaaaaga aggggaaaga aattttcat  cgacttcatt taagtaaagc caaaatggct     660
cataggatgg agattttaag aggaatgtat gaggagctga cgaaatgtg  ccataaaca     720 gatgtggagc tacttcaggc ttttggagac atattacaca ggagtgagtc cgtgctgctg     780
cacatgcccc agcctctgaa tccagagctc agtgcagggc ccatcactgg actgagggac     840
aggctcaacc aattccgagt gcatattact ctgcatcatg aagaagccaa caatgatatc     900
tttctgtatg aaatttttgag aagcatgtgt attggatgtg accatcaaga tgtaccctat     960
ttcactgcaa cacctagaag ttttcttgca tgggtgttc  agactttcac ctcgggcaaa    1020
tattactggg aggtccatgt aggggactcc tggaattggg cttttggtgt ctgtaatatg    1080
tatcggaaag agaagaatca gaatgagaag atagatggaa aggcgggact ctttcttctt    1140
gggtgtgtta agaatgacat tcaatgcagt ctctttacca cctccccact tatgctgcaa    1200
tatatcccaa aacctaccag ccgagtagga ttattcctgg attgtgaggc taagactgtg    1260
agctttgttg atgttaatca aagctcccta atatacacca tccctaattg ctctttctca    1320
cctcctctca ggcctatctt ttgctgtatt cacttctga                           1359

<210> SEQ ID NO 98
<211> LENGTH: 452
<212> TYPE: PRT
<213> ORGANISM: Homo sapiens

<400> SEQUENCE: 98

Met Asn Ser Gly Ile Leu Gln Val Phe Gln Gly Glu Leu Ile Cys Pro
1               5                   10                  15
```

-continued

```
Leu Cys Met Asn Tyr Phe Ile Asp Pro Val Thr Ile Asp Cys Gly His
             20                  25                  30
Ser Phe Cys Arg Pro Cys Phe Tyr Leu Asn Trp Gln Asp Ile Pro Phe
             35                  40                  45
Leu Val Gln Cys Ser Glu Cys Thr Lys Ser Thr Glu Gln Ile Asn Leu
             50                  55                  60
Lys Thr Asn Ile His Leu Lys Lys Met Ala Ser Leu Ala Arg Lys Val
 65                      70                  75                  80
Ser Leu Trp Leu Phe Leu Ser Ser Glu Glu Gln Met Cys Gly Thr His
                     85                  90                  95
Arg Glu Thr Lys Lys Ile Phe Cys Glu Val Asp Arg Ser Leu Leu Cys
                 100                 105                 110
Leu Leu Cys Ser Ser Ser Gln Glu His Arg Tyr His Arg His Arg Pro
             115                 120                 125
Ile Glu Trp Ala Ala Glu Glu His Arg Glu Lys Leu Leu Gln Lys Met
             130                 135                 140
Gln Ser Leu Trp Glu Lys Ala Cys Glu Asn His Arg Asn Leu Asn Val
145                 150                 155                 160
Glu Thr Thr Arg Thr Arg Cys Trp Lys Asp Tyr Val Asn Leu Arg Leu
                 165                 170                 175
Glu Ala Ile Arg Ala Glu Tyr Gln Lys Met Pro Ala Phe His His Glu
             180                 185                 190
Glu Glu Lys His Asn Leu Glu Met Leu Lys Lys Gly Lys Glu Ile
             195                 200                 205
Phe His Arg Leu His Leu Ser Lys Ala Lys Met Ala His Arg Met Glu
             210                 215                 220
Ile Leu Arg Gly Met Tyr Glu Glu Leu Asn Glu Met Cys His Lys Pro
225                 230                 235                 240
Asp Val Glu Leu Leu Gln Ala Phe Gly Asp Ile Leu His Arg Ser Glu
                 245                 250                 255
Ser Val Leu Leu His Met Pro Gln Pro Leu Asn Pro Glu Leu Ser Ala
             260                 265                 270
Gly Pro Ile Thr Gly Leu Arg Asp Arg Leu Asn Gln Phe Arg Val His
             275                 280                 285
Ile Thr Leu His His Glu Glu Ala Asn Asn Asp Ile Phe Leu Tyr Glu
             290                 295                 300
Ile Leu Arg Ser Met Cys Ile Gly Cys Asp His Gln Asp Val Pro Tyr
305                 310                 315                 320
Phe Thr Ala Thr Pro Arg Ser Phe Leu Ala Trp Gly Val Gln Thr Phe
                 325                 330                 335
Thr Ser Gly Lys Tyr Tyr Trp Glu Val His Val Gly Asp Ser Trp Asn
             340                 345                 350
Trp Ala Phe Gly Val Cys Asn Met Tyr Arg Lys Glu Lys Asn Gln Asn
             355                 360                 365
Glu Lys Ile Asp Gly Lys Ala Gly Leu Phe Leu Leu Gly Cys Val Lys
             370                 375                 380
Asn Asp Ile Gln Cys Ser Leu Phe Thr Thr Ser Pro Leu Met Leu Gln
385                 390                 395                 400
Tyr Ile Pro Lys Pro Thr Ser Arg Val Gly Leu Phe Leu Asp Cys Glu
                 405                 410                 415
Ala Lys Thr Val Ser Phe Val Asp Val Asn Gln Ser Ser Leu Ile Tyr
             420                 425                 430
Thr Ile Pro Asn Cys Ser Phe Ser Pro Pro Leu Arg Pro Ile Phe Cys
```

Cys Ile His Phe
    450

<210> SEQ ID NO 99
<211> LENGTH: 1464
<212> TYPE: DNA
<213> ORGANISM: Homo sapiens

<400> SEQUENCE: 99

```
atggcttggc aggtgagcct gccagagctg gaggaccggc ttcagtgtcc catctgcctg      60
gaggtcttca aggagcccct gatgctgcag tgtggccact cttactgcaa gggctgcctg     120
gtttccctgt cctgccacct ggatgccgag ctgcgctgcc ccgtgtgccg gcaggcggtg     180
gacggcagca gctccctgcc caacgtctcc ctggccaggg tgatcgaagc cctgaggctc     240
cctggggacc cggagcccaa ggtctgcgtg caccaccgga acccgctcag ccttttctgc     300
gagaaggacc aggagctcat ctgtggcctc tgcggtctgc tgggctccca ccaacaccac     360
ccggtcacgc ccgtctccac cgtctacagc cgcatgaagg aggagctcgc agccctcatc     420
tctgagctga agcaggagca gaaaaaggtg gatgagctca tcgccaaact ggtgaacaac     480
cggacccgaa tcgtcaatga gtcggatgtc ttcagctggg tgatccgccg cgagttccag     540
gagctgcacc acctggtgga tgaggagaag gcccgctgcc tggaggggat aggggggtcac    600
acccgtggcc tggtggcctc cctggacatg cagctggagc aggcccaggg aacccgggag     660
cggctggccc aagccgagtg tgtgctggaa cagttcggca tgaggaccac ccacaagttc     720
atccggaagt ccactccat ggcctccaga gcagagatgc cgcaggcccg gcccttagaa      780
ggcgcattca gccccatctc cttcaagcca ggcctccacc aggctgacat caagctgacc     840
gtgtggaaaa ggctcttccg gaaagttttg ccagccccgg agcctctcaa gttggaccct     900
gccactgccc acccactcct ggagctctcc aagggcaaca cggtggtgca gtgcgggctt     960
ctggcccagc ggcgagccag ccagcctgag cgcttcgact acagcacctg cgtcctggcc    1020
agccgcggct tctcctgcgg ccgccactac tgggaggtgg tggtgggcag caagagcgac    1080
tggcgcctgg gggtcatcaa gggcacagcc agccgtaagg caagctgaa caggtccccc    1140
gagcacggcg tgtggctgat cggcctgaag gagggccggg tgtacgaagc ctttgcctgc    1200
ccccgggtac ccctgcccgt ggccggccac ccccaccgca tcgggctcta cctgcactat    1260
gagcagggcg aactcacctt cttcgatgcc gaccgccccg atgacctgcg ccgctctac     1320
accttccagg ccgacttcca gggcaagctc taccccatcc tggacacctg ctggcacgag    1380
aggggcagca actcgctgcc catggtgctg cccccgccca gcgggcctgg ccccctcagc    1440
cccgagcagc ccaccaagct gtag                                          1464
```

<210> SEQ ID NO 100
<211> LENGTH: 487
<212> TYPE: PRT
<213> ORGANISM: Homo sapiens

<400> SEQUENCE: 100

Met Ala Trp Gln Val Ser Leu Pro Glu Leu Glu Asp Arg Leu Gln Cys
1               5                   10                  15

Pro Ile Cys Leu Glu Val Phe Lys Glu Pro Leu Met Leu Gln Cys Gly
            20                  25                  30

His Ser Tyr Cys Lys Gly Cys Leu Val Ser Leu Ser Cys His Leu Asp
        35                  40                  45

-continued

```
Ala Glu Leu Arg Cys Pro Val Cys Arg Gln Ala Val Asp Gly Ser Ser
     50                  55                  60

Ser Leu Pro Asn Val Ser Leu Ala Arg Val Ile Glu Ala Leu Arg Leu
 65                  70                  75                  80

Pro Gly Asp Pro Glu Pro Lys Val Cys Val His His Arg Asn Pro Leu
                     85                  90                  95

Ser Leu Phe Cys Glu Lys Asp Gln Glu Leu Ile Cys Gly Leu Cys Gly
            100                 105                 110

Leu Leu Gly Ser His Gln His His Pro Val Thr Pro Val Ser Thr Val
            115                 120                 125

Tyr Ser Arg Met Lys Glu Leu Ala Ala Leu Ile Ser Glu Leu Lys
            130                 135                 140

Gln Glu Gln Lys Lys Val Asp Glu Leu Ile Ala Lys Leu Val Asn Asn
145                 150                 155                 160

Arg Thr Arg Ile Val Asn Glu Ser Asp Val Phe Ser Trp Val Ile Arg
                165                 170                 175

Arg Glu Phe Gln Glu Leu His His Leu Val Asp Glu Lys Ala Arg
            180                 185                 190

Cys Leu Glu Gly Ile Gly Gly His Thr Arg Gly Leu Val Ala Ser Leu
            195                 200                 205

Asp Met Gln Leu Glu Gln Ala Gln Gly Thr Arg Glu Arg Leu Ala Gln
    210                 215                 220

Ala Glu Cys Val Leu Glu Gln Phe Gly Asn Glu Asp His His Lys Phe
225                 230                 235                 240

Ile Arg Lys Phe His Ser Met Ala Ser Arg Ala Glu Met Pro Gln Ala
                245                 250                 255

Arg Pro Leu Glu Gly Ala Phe Ser Pro Ile Ser Phe Lys Pro Gly Leu
            260                 265                 270

His Gln Ala Asp Ile Lys Leu Thr Val Trp Lys Arg Leu Phe Arg Lys
            275                 280                 285

Val Leu Pro Ala Pro Glu Pro Leu Lys Leu Asp Pro Ala Thr Ala His
    290                 295                 300

Pro Leu Leu Glu Leu Ser Lys Gly Asn Thr Val Val Gln Cys Gly Leu
305                 310                 315                 320

Leu Ala Gln Arg Arg Ala Ser Gln Pro Glu Arg Phe Asp Tyr Ser Thr
                325                 330                 335

Cys Val Leu Ala Ser Arg Gly Phe Ser Cys Gly Arg His Tyr Trp Glu
            340                 345                 350

Val Val Val Gly Ser Lys Ser Asp Trp Arg Leu Gly Val Ile Lys Gly
            355                 360                 365

Thr Ala Ser Arg Lys Gly Lys Leu Asn Arg Ser Pro Glu His Gly Val
    370                 375                 380

Trp Leu Ile Gly Leu Lys Glu Gly Arg Val Tyr Glu Ala Phe Ala Cys
385                 390                 395                 400

Pro Arg Val Pro Leu Pro Val Ala Gly His Pro His Arg Ile Gly Leu
                405                 410                 415

Tyr Leu His Tyr Glu Gln Gly Glu Leu Thr Phe Phe Asp Ala Asp Arg
            420                 425                 430

Pro Asp Asp Leu Arg Pro Leu Tyr Thr Phe Gln Ala Asp Phe Gln Gly
            435                 440                 445

Lys Leu Tyr Pro Ile Leu Asp Thr Cys Trp His Glu Arg Gly Ser Asn
    450                 455                 460
```

Ser Leu Pro Met Val Leu Pro Pro Ser Pro Gly Pro Leu Ser
465                 470                 475                 480

Pro Glu Gln Pro Thr Lys Leu
            485

<210> SEQ ID NO 101
<211> LENGTH: 1359
<212> TYPE: DNA
<213> ORGANISM: Homo sapiens

<400> SEQUENCE: 101

```
atgaattctg gaatcttgca agtcttccag agggcactca cctgtcccat ctgcatgaac      60
tacttcctag acccagtcac catagactgt gggcacagct tttgccggcc ctgtttgtac     120
ctcaactggc aagacacggc agttcttgct cagtgctctg aatgcaagaa gacaacgcgg     180
cagagaaacc tcaacactga catttgtttg aagaacatgg ctttcattgc agaaaagcc     240
agcctccggc aattccttag ctctgaggag caaatatgtg ggatgcacag agagacaaag     300
aagatgttct gtgaagtgga caagagcctg ctctgtttgc cgtgctccaa ctctcaggag     360
caccggaatc acatacactg tcccattgag tgggctgctg aggaacgccg ggaggagctc     420
ctaaaaaaa tgcagtcttt atgggaaaaa gcttgtgaaa atctcagaaa tctgaacatg     480
gaaaccacaa gaaccagatg ctggaaggat tatgtgagtt taaggataga agcaatcaga     540
gctgaatatc agaagatgcc tgcatttctc catgaagaag agcaacatca cttggaaagg     600
ctgcgaaagg agggcgagga catttttcag caactcaatg aaagcaaagc cagaatggaa     660
cattccagg agcttttaag aggaatgtat gaggatctga gcaaatgtg ccataaagca     720
gatgtggagc tactccaggc ttttggagac atattacaca ggtatgagtc tctgctgctg     780
caagtgtctg agcctgtgaa tccagagctc agtgcagggc ccatcactgg actgctggac     840
agcctcagtg gattcagagt tgatttact ctgcagcctg aaagagccaa tagtcatatc     900
ttcctgtgtg agatttgag aagcatgaat gttggatgtg acctcaaga tgatcccgat     960
atcactggaa atctgaatg ttttcttgta tggggggctc aggctttcac atctggcaaa     1020
tattattggg aggttcatat gggggactct tggaattggg cttttggtgt ctgtaacaat     1080
tattggaaag agaagagaca gaatgacaag atagatggag aggagggact ctttcttctt     1140
ggatgtgtta aggaggacac tcactgcagt ctctttacca cctcccccact tgtggtgcaa     1200
tatgttccaa gacctaccag cacagtagga ttattcctgg attgtgaagg tagaaccgtg     1260
agctttgttg atgttgatca aagttccctg atatacacca tccccaattg ctccttctca     1320
cctcctctca ggcctatctt ttgctgtagt cacttctga                           1359
```

<210> SEQ ID NO 102
<211> LENGTH: 452
<212> TYPE: PRT
<213> ORGANISM: Homo sapiens

<400> SEQUENCE: 102

Met Asn Ser Gly Ile Leu Gln Val Phe Gln Arg Ala Leu Thr Cys Pro
1               5                   10                  15

Ile Cys Met Asn Tyr Phe Leu Asp Pro Val Thr Ile Asp Cys Gly His
            20                  25                  30

Ser Phe Cys Arg Pro Cys Leu Tyr Leu Asn Trp Gln Asp Thr Ala Val
        35                  40                  45

Leu Ala Gln Cys Ser Glu Cys Lys Lys Thr Thr Arg Gln Arg Asn Leu
    50                  55                  60

Asn Thr Asp Ile Cys Leu Lys Asn Met Ala Phe Ile Ala Arg Lys Ala
 65                  70                  75                  80

Ser Leu Arg Gln Phe Leu Ser Ser Glu Glu Gln Ile Cys Gly Met His
             85                  90                  95

Arg Glu Thr Lys Lys Met Phe Cys Glu Val Asp Lys Ser Leu Leu Cys
            100                 105                 110

Leu Pro Cys Ser Asn Ser Gln Glu His Arg Asn His Ile His Cys Pro
            115                 120                 125

Ile Glu Trp Ala Ala Glu Arg Glu Glu Leu Leu Lys Lys Met
130                 135                 140

Gln Ser Leu Trp Glu Lys Ala Cys Glu Asn Leu Arg Asn Leu Asn Met
145                 150                 155                 160

Glu Thr Thr Arg Thr Arg Cys Trp Lys Asp Tyr Val Ser Leu Arg Ile
                165                 170                 175

Glu Ala Ile Arg Ala Glu Tyr Gln Lys Met Pro Ala Phe Leu His Glu
                180                 185                 190

Glu Glu Gln His His Leu Glu Arg Leu Arg Lys Glu Gly Glu Asp Ile
            195                 200                 205

Phe Gln Gln Leu Asn Glu Ser Lys Ala Arg Met Glu His Ser Arg Glu
210                 215                 220

Leu Leu Arg Gly Met Tyr Glu Asp Leu Lys Gln Met Cys His Lys Ala
225                 230                 235                 240

Asp Val Glu Leu Leu Gln Ala Phe Gly Asp Ile Leu His Arg Tyr Glu
            245                 250                 255

Ser Leu Leu Leu Gln Val Ser Glu Pro Val Asn Pro Glu Leu Ser Ala
            260                 265                 270

Gly Pro Ile Thr Gly Leu Leu Asp Ser Leu Ser Gly Phe Arg Val Asp
        275                 280                 285

Phe Thr Leu Gln Pro Glu Arg Ala Asn Ser His Ile Phe Leu Cys Gly
290                 295                 300

Asp Leu Arg Ser Met Asn Val Gly Cys Asp Pro Gln Asp Asp Pro Asp
305                 310                 315                 320

Ile Thr Gly Lys Ser Glu Cys Phe Leu Val Trp Gly Ala Gln Ala Phe
                325                 330                 335

Thr Ser Gly Lys Tyr Tyr Trp Glu Val His Met Gly Asp Ser Trp Asn
            340                 345                 350

Trp Ala Phe Gly Val Cys Asn Asn Tyr Trp Lys Glu Lys Arg Gln Asn
            355                 360                 365

Asp Lys Ile Asp Gly Glu Glu Gly Leu Phe Leu Leu Gly Cys Val Lys
        370                 375                 380

Glu Asp Thr His Cys Ser Leu Phe Thr Thr Ser Pro Leu Val Val Gln
385                 390                 395                 400

Tyr Val Pro Arg Pro Thr Ser Thr Val Gly Leu Phe Leu Asp Cys Glu
                405                 410                 415

Gly Arg Thr Val Ser Phe Val Asp Val Asp Gln Ser Ser Leu Ile Tyr
            420                 425                 430

Thr Ile Pro Asn Cys Ser Phe Ser Pro Pro Leu Arg Pro Ile Phe Cys
            435                 440                 445

Cys Ser His Phe
450

<210> SEQ ID NO 103
<211> LENGTH: 894

```
<212> TYPE: DNA
<213> ORGANISM: Homo sapiens

<400> SEQUENCE: 103
atggctggtt atgccactac tcccagcccc atgcagaccc ttcaggagga agcggtgtgt      60
gccatctgct tggattactt caaggacccc gtgtccatca gctgtgggca caacttctgc     120
cgagggtgtg tgacccagct gtggagtaag gaggacgagg aggaccagaa cgaggaggaa     180
gatgaatggg aggaggagga ggacgaggaa gcggtggggg ccatggatgg atgggacggc     240
tccattcgag aggtgttgta tcgggggaat gctgacgaag agttgttcca agaccaagat     300
gacgatgaac tctggctcgg tgacagtggt ataactaatt gggacaacgt agactatatg     360
tgggacgagg aggaagaaga agaagaggaa gatcaggact attacctagg aggcttgaga     420
cctgacctga gaattgatgt ctaccgaaga agaaaatac tggaagcata cgatgaggac      480
gaagatgaag agctgtatcc tgacatccac ccgcctcctt ccttgcccct ccagggcag     540
ttcacctgcc cccagtgccg aaagagcttt acacgtcgca gctttcgtcc caacttgcag     600
ctggccaaca tggtccagat aattcgccag atgtgcccca ctccttatcg gggaaaccgg     660
agtaatgatc agggcatgtg ctttaaacac caggaagccc tgaaactctt ctgtgaggtg     720
gacaaagagg ccatctgtgt ggtgtgccga gaatccagga ccacaaaca gcacagcgtg      780
ctgcctttgg aggaggtggt gcaggagtac caggaaataa agttggaaac aactctggtg     840
ggaatacttc agatagagca agaaagcatt cacagcaagg cctataatca gtaa           894

<210> SEQ ID NO 104
<211> LENGTH: 297
<212> TYPE: PRT
<213> ORGANISM: Homo sapiens

<400> SEQUENCE: 104
```

Met Ala Gly Tyr Ala Thr Thr Pro Ser Pro Met Gln Thr Leu Gln Glu
1               5                   10                  15

Glu Ala Val Cys Ala Ile Cys Leu Asp Tyr Phe Lys Asp Pro Val Ser
                20                  25                  30

Ile Ser Cys Gly His Asn Phe Cys Arg Gly Cys Val Thr Gln Leu Trp
            35                  40                  45

Ser Lys Glu Asp Glu Glu Asp Gln Asn Glu Glu Glu Asp Glu Trp Glu
        50                  55                  60

Glu Glu Glu Asp Glu Glu Ala Val Gly Ala Met Asp Gly Trp Asp Gly
65                  70                  75                  80

Ser Ile Arg Glu Val Leu Tyr Arg Gly Asn Ala Asp Glu Glu Leu Phe
                85                  90                  95

Gln Asp Gln Asp Asp Glu Leu Trp Leu Gly Asp Ser Gly Ile Thr
            100                 105                 110

Asn Trp Asp Asn Val Asp Tyr Met Trp Asp Glu Glu Glu Glu Glu
        115                 120                 125

Glu Glu Asp Gln Asp Tyr Tyr Leu Gly Gly Leu Arg Pro Asp Leu Arg
    130                 135                 140

Ile Asp Val Tyr Arg Glu Glu Ile Leu Glu Ala Tyr Asp Glu Asp
145                 150                 155                 160

Glu Asp Glu Glu Leu Tyr Pro Asp Ile His Pro Pro Ser Leu Pro
                165                 170                 175

Leu Pro Gly Gln Phe Thr Cys Pro Gln Cys Arg Lys Ser Phe Thr Arg
            180                 185                 190

```
Arg Ser Phe Arg Pro Asn Leu Gln Leu Ala Asn Met Val Gln Ile Ile
            195                 200                 205

Arg Gln Met Cys Pro Thr Pro Tyr Arg Gly Asn Arg Ser Asn Asp Gln
        210                 215                 220

Gly Met Cys Phe Lys His Gln Glu Ala Leu Lys Leu Phe Cys Glu Val
225                 230                 235                 240

Asp Lys Glu Ala Ile Cys Val Val Cys Arg Glu Ser Arg Ser His Lys
                245                 250                 255

Gln His Ser Val Leu Pro Leu Glu Val Val Gln Glu Tyr Gln Glu
                260                 265                 270

Ile Lys Leu Glu Thr Thr Leu Val Gly Ile Leu Gln Ile Glu Gln Glu
        275                 280                 285

Ser Ile His Ser Lys Ala Tyr Asn Gln
        290                 295
```

<210> SEQ ID NO 105
<211> LENGTH: 1203
<212> TYPE: DNA
<213> ORGANISM: Homo sapiens

<400> SEQUENCE: 105

| | | | |
|---|---|---|---|
| atgaacttca cagtgggttt caagccgctg ctaggggatg cacacagcat ggacaacctg | | | 60 |
| gagaagcagc tcatctgccc catctgcctg gagatgttct ccaaaccagt ggtgatcctg | | | 120 |
| ccctgccaac acaacctgtg ccgcaaatgt gccaacgacg tcttccaggc ctcgaatcct | | | 180 |
| ctatggcagt cccggggctc caccactgtg tcttcaggag gccgtttccg ctgcccatcg | | | 240 |
| tgcaggcatg aggttgtcct ggacagacac ggtgtctacg gcctgcagcg aaacctgcta | | | 300 |
| gtggagaaca ttatcgacat ttacaagcag gagtcatcca ggccgctgca ctccaaggct | | | 360 |
| gagcagcacc tcatgtgcga ggagcatgaa gaagagaaga tcaatattta ctgcctgagc | | | 420 |
| tgtgaggtgc ccacctgctc tctctgcaag gtcttcggtg cccacaagga ctgtgaggtg | | | 480 |
| gccccactgc ccaccattta caaacgccag aagaaacagg atctcactct gttgcccagg | | | 540 |
| ctggagtgca gtggcacaaa cacaacttac tgcagccttg atctcccgag ctcaagtgat | | | 600 |
| cctcccatct tagcctcgca gaacactaag attatagata gtgagctcag cgatggcatc | | | 660 |
| gcgatgctgg tggcaggcaa tgaccgcgtg caagcagtga tcacacagat ggaggaggtg | | | 720 |
| tgccagacta tcgaggacaa tagccggagg cagaagcagt tgttaaacca gaggtttgag | | | 780 |
| agcctgtgcg cagtgctgga ggagcgcaag ggtgagctgc tgcaggcgct ggcccgggag | | | 840 |
| caagaggaga agctgcagcg cgtccgcggc ctcatccgtc agtatggcga ccacctggag | | | 900 |
| gcctcctcta agctggtgga gtctgccatc cagtccatgg aagagccaca aatggcgctg | | | 960 |
| tatctccagc aggccaagga gctgatcaat aaggtcgggg ccatgtcgaa ggtggagctg | | | 1020 |
| gcagggcggc cggagccagg ctatgagagc atggagcaat tcaccgtaag ggtggagcac | | | 1080 |
| gtggccgaaa tgctgcggac catcgacttc agccaggcg cttccgggga ggaagaggag | | | 1140 |
| gtggccccag acgagagga gggcagcgcg gggccggagg aagagcggcc ggatgggcct | | | 1200 |
| taa | | | 1203 |

<210> SEQ ID NO 106
<211> LENGTH: 400
<212> TYPE: PRT
<213> ORGANISM: Homo sapiens

<400> SEQUENCE: 106

```
Met Asn Phe Thr Val Gly Phe Lys Pro Leu Gly Asp Ala His Ser
1               5                   10                  15

Met Asp Asn Leu Glu Lys Gln Leu Ile Cys Pro Ile Cys Leu Glu Met
            20                  25                  30

Phe Ser Lys Pro Val Val Ile Leu Pro Cys Gln His Asn Leu Cys Arg
        35                  40                  45

Lys Cys Ala Asn Asp Val Phe Gln Ala Ser Asn Pro Leu Trp Gln Ser
    50                  55                  60

Arg Gly Ser Thr Thr Val Ser Ser Gly Gly Arg Phe Arg Cys Pro Ser
65                  70                  75                  80

Cys Arg His Glu Val Val Leu Asp Arg His Gly Val Tyr Gly Leu Gln
                85                  90                  95

Arg Asn Leu Leu Val Glu Asn Ile Ile Asp Ile Tyr Lys Gln Glu Ser
            100                 105                 110

Ser Arg Pro Leu His Ser Lys Ala Glu Gln His Leu Met Cys Glu Glu
        115                 120                 125

His Glu Glu Glu Lys Ile Asn Ile Tyr Cys Leu Ser Cys Glu Val Pro
    130                 135                 140

Thr Cys Ser Leu Cys Lys Val Phe Gly Ala His Lys Asp Cys Glu Val
145                 150                 155                 160

Ala Pro Leu Pro Thr Ile Tyr Lys Arg Gln Lys Lys Gln Asp Leu Thr
                165                 170                 175

Leu Leu Pro Arg Leu Glu Cys Ser Gly Thr Asn Thr Thr Tyr Cys Ser
            180                 185                 190

Leu Asp Leu Pro Ser Ser Ser Asp Pro Pro Ile Leu Ala Ser Gln Asn
        195                 200                 205

Thr Lys Ile Ile Asp Ser Glu Leu Ser Asp Gly Ile Ala Met Leu Val
    210                 215                 220

Ala Gly Asn Asp Arg Val Gln Ala Val Ile Thr Gln Met Glu Glu Val
225                 230                 235                 240

Cys Gln Thr Ile Glu Asp Asn Ser Arg Arg Lys Gln Leu Leu Asn
                245                 250                 255

Gln Arg Phe Glu Ser Leu Cys Ala Val Leu Glu Glu Arg Lys Gly Glu
            260                 265                 270

Leu Leu Gln Ala Leu Ala Arg Glu Gln Glu Lys Leu Gln Arg Val
        275                 280                 285

Arg Gly Leu Ile Arg Gln Tyr Gly Asp His Leu Glu Ala Ser Ser Lys
    290                 295                 300

Leu Val Glu Ser Ala Ile Gln Ser Met Glu Glu Pro Gln Met Ala Leu
305                 310                 315                 320

Tyr Leu Gln Gln Ala Lys Glu Leu Ile Asn Lys Val Gly Ala Met Ser
                325                 330                 335

Lys Val Glu Leu Ala Gly Arg Pro Glu Pro Gly Tyr Glu Ser Met Glu
            340                 345                 350

Gln Phe Thr Val Arg Val Glu His Val Ala Glu Met Leu Arg Thr Ile
        355                 360                 365

Asp Phe Gln Pro Gly Ala Ser Gly Glu Glu Glu Val Ala Pro Asp
    370                 375                 380

Gly Glu Glu Gly Ser Ala Gly Pro Glu Glu Arg Pro Asp Gly Pro
385                 390                 395                 400

<210> SEQ ID NO 107
<211> LENGTH: 1647
<212> TYPE: DNA
```

<213> ORGANISM: Homo sapiens

<400> SEQUENCE: 107

```
atgagcgcat ctctgaatta caaatctttt tccaaagagc agcagaccat ggataactta      60
gagaagcaac tcatctgtcc catctgctta gagatgttca cgaaacctgt ggtgattctc     120
ccttgtcagc acaacctgtg taggaaatgt gccagtgata ttttccaggc tctaacccg      180
tatttgccca agaggagg taccaccatg catcagggg ccgattccg ctgcccatcc         240
tgtagacatg aagtggtttt ggatagacat ggggtatatg acttcagag aacctgctg       300
gtggaaaata tcattgacat ctacaagcag gagtccacca ggccagaaaa gaaatccgac     360
cagcccatgt gcgaggaaca tgaagaggag cgcatcaaca tctactgtct gaactgcgaa     420
gtacccacct gctctctgtg caaggtgttt ggtgcacaca aagactgcca ggtggctccc     480
ctcactcatg tgttccagag acagaagtct gagctcagtg atggcatcgc catcctcgtg     540
ggcagcaacg atcgagtcca gggagtgatc agccagctgg aagacacctg caaaactatc     600
gaggaatgtt gcagaaaaca gaaacaagag ctttgtgaga gtttgatta cctgtatggc      660
attttggagg agaggaagaa tgaaatgacc caagtcatta cccgaaccca agaggagaaa     720
ctggaacatg tccgtgctct gatcaaaaag tattctgatc atttggagaa cgtctcaaag    780
ttggttgagt caggaattca gtttatggat gagccagaaa tggcagtgtt tctgcagaat    840
gccaaaaccc tgctaaaaaa aatctcggaa gcatcaaagg catttcagat ggagaaaata    900
gaacatggct atgagaacat gaaccacttc acagtcaacc tcaatagaga agaaaagata    960
atacgtgaaa ttgacttta cagagaagat gaagatgaag aagaagaaga aggcggagaa   1020
ggagaaaaag aaggagaagg agaagtggga ggagaagcag tagaagtgga agaggtagaa   1080
aatgttcaaa cagagtttcc aggagaagat gaaaacccag aaaaagcttc agagctctct   1140
caggtggagc tgcaggctgc ccctggggca cttccagttt cctctccaga gccacctcca   1200
gccctgccac tgctgcgga tgccctgtg acacaggggg aggttgtacc cactggctct   1260
gagcagacca cagagtctga aactccagtc cctgcagcag cagaaactgc ggatcccttg   1320
ttttacccta gttggtataa aggccaaacc cggaaagcca ccaccaaccc accttgcacc   1380
ccagggagcg aaggtctggg gcaaatagg cctccaggtt ctgaggattc gaatgtacgg   1440
aaggcagaag tggcagcagc cgcagcgagt gagagggcag ctgtgagtgg taaggaaact   1500
agtgcacctg cagctacttc tcagattgga tttgaggctc ctcccctcca gggacaggct   1560
gcagctccag cgagtggcag tggagctgat tctgagccag ctcgccatat cttctccttt   1620
tcctggttga actccctaaa tgaatga                                         1647
```

<210> SEQ ID NO 108
<211> LENGTH: 548
<212> TYPE: PRT
<213> ORGANISM: Homo sapiens

<400> SEQUENCE: 108

```
Met Ser Ala Ser Leu Asn Tyr Lys Ser Phe Ser Lys Glu Gln Gln Thr
1               5                   10                  15

Met Asp Asn Leu Glu Lys Gln Leu Ile Cys Pro Ile Cys Leu Glu Met
                20                  25                  30

Phe Thr Lys Pro Val Val Ile Leu Pro Cys Gln His Asn Leu Cys Arg
            35                  40                  45

Lys Cys Ala Ser Asp Ile Phe Gln Ala Ser Asn Pro Tyr Leu Pro Thr
        50                  55                  60
```

```
Arg Gly Gly Thr Thr Met Ala Ser Gly Gly Arg Phe Arg Cys Pro Ser
 65                  70                  75                  80

Cys Arg His Glu Val Val Leu Asp Arg His Gly Val Tyr Gly Leu Gln
                 85                  90                  95

Arg Asn Leu Leu Val Glu Asn Ile Ile Asp Ile Tyr Lys Gln Glu Ser
            100                 105                 110

Thr Arg Pro Glu Lys Lys Ser Asp Gln Pro Met Cys Glu Glu His Glu
        115                 120                 125

Glu Glu Arg Ile Asn Ile Tyr Cys Leu Asn Cys Glu Val Pro Thr Cys
    130                 135                 140

Ser Leu Cys Lys Val Phe Gly Ala His Lys Asp Cys Gln Val Ala Pro
145                 150                 155                 160

Leu Thr His Val Phe Gln Arg Gln Lys Ser Glu Leu Ser Asp Gly Ile
                165                 170                 175

Ala Ile Leu Val Gly Ser Asn Asp Arg Val Gln Gly Val Ile Ser Gln
            180                 185                 190

Leu Glu Asp Thr Cys Lys Thr Ile Glu Glu Cys Cys Arg Lys Gln Lys
        195                 200                 205

Gln Glu Leu Cys Glu Lys Phe Asp Tyr Leu Tyr Gly Ile Leu Glu Glu
    210                 215                 220

Arg Lys Asn Glu Met Thr Gln Val Ile Thr Arg Thr Gln Glu Glu Lys
225                 230                 235                 240

Leu Glu His Val Arg Ala Leu Ile Lys Lys Tyr Ser Asp His Leu Glu
                245                 250                 255

Asn Val Ser Lys Leu Val Glu Ser Gly Ile Gln Phe Met Asp Glu Pro
            260                 265                 270

Glu Met Ala Val Phe Leu Gln Asn Ala Lys Thr Leu Leu Lys Lys Ile
        275                 280                 285

Ser Glu Ala Ser Lys Ala Phe Gln Met Glu Lys Ile Glu His Gly Tyr
    290                 295                 300

Glu Asn Met Asn His Phe Thr Val Asn Leu Asn Arg Glu Glu Lys Ile
305                 310                 315                 320

Ile Arg Glu Ile Asp Phe Tyr Arg Glu Asp Glu Glu Glu Glu
                325                 330                 335

Glu Gly Gly Glu Gly Glu Lys Glu Gly Glu Gly Glu Val Gly Gly Glu
        340                 345                 350

Ala Val Glu Val Glu Glu Val Glu Asn Val Gln Thr Glu Phe Pro Gly
    355                 360                 365

Glu Asp Glu Asn Pro Glu Lys Ala Ser Glu Leu Ser Gln Val Glu Leu
        370                 375                 380

Gln Ala Ala Pro Gly Ala Leu Pro Val Ser Ser Pro Glu Pro Pro Pro
385                 390                 395                 400

Ala Leu Pro Pro Ala Ala Asp Ala Pro Val Thr Gln Gly Glu Val Val
                405                 410                 415

Pro Thr Gly Ser Glu Gln Thr Thr Glu Ser Glu Thr Pro Val Pro Ala
            420                 425                 430

Ala Ala Glu Thr Ala Asp Pro Leu Phe Tyr Pro Ser Trp Tyr Lys Gly
        435                 440                 445

Gln Thr Arg Lys Ala Thr Thr Asn Pro Pro Cys Thr Pro Gly Ser Glu
    450                 455                 460

Gly Leu Gly Gln Ile Gly Pro Pro Gly Ser Glu Asp Ser Asn Val Arg
465                 470                 475                 480
```

```
Lys Ala Glu Val Ala Ala Ala Ala Ser Glu Arg Ala Val Ser
                485                 490                 495

Gly Lys Glu Thr Ser Ala Pro Ala Ala Thr Ser Gln Ile Gly Phe Glu
            500                 505                 510

Ala Pro Pro Leu Gln Gly Gln Ala Ala Ala Pro Ala Ser Gly Ser Gly
            515                 520                 525

Ala Asp Ser Glu Pro Ala Arg His Ile Phe Ser Phe Ser Trp Leu Asn
            530                 535                 540

Ser Leu Asn Glu
545

<210> SEQ ID NO 109
<211> LENGTH: 2225
<212> TYPE: DNA
<213> ORGANISM: Homo sapiens

<400> SEQUENCE: 109
```

| | | | | |
|---|---|---|---|---|
| atggtttccc acgggtcctc gccctccctc ctggaggccc tgagcagcga cttcctggcc | | | | 60 |
| tgtaaaatct gcctggagca gctgcgggca cccaagacac tgccctgcct gcatacctac | | | | 120 |
| tgccaagact gcctggcaca gctggcggat ggcggccgcg tccgctgccc cgagtgccgc | | | | 180 |
| gagacagtgc ctgtgccgcc cgagggtgtg gcctccttca agaccaactt cttcgtcaat | | | | 240 |
| gggctgctgg aactggtgaa ggcccgggcc tgtggagacc tcgtgccgg aagccagcc | | | | 300 |
| tgtgccctgt gtccctggt gggtggcacc agcaccgggg ggccggccac ggcccggtgc | | | | 360 |
| ctggactgtg ccgatgactt gtgccaggcc tgtgccgacg gcaccgctg cacccgccag | | | | 420 |
| acccacaccc accgcgtggt ggacctggtg gctacaggg ccgggtggta tgatgaggag | | | | 480 |
| gcccgggagc gccaagcggc ccagtgtccc cagcacccg gggaggcact gcgcttcctg | | | | 540 |
| tgccagccct gctcacagtt gctgtgcaga gagtgccgcc tagaccccca cctggaccac | | | | 600 |
| ccctgcctgc ctctggctga agctgtgcgt gcccggaggc cgggcctgga gggactgctg | | | | 660 |
| gccggtgtgg acaataacct ggtggagctg aggcagcgc ggagggtgga aaggaggcg | | | | 720 |
| ctagcccggc tgcgggagca ggcggcccgg gtggggactc aggtggagga ggcggctgag | | | | 780 |
| ggcgtcctcc gggccctgct ggcccagaag caggaggtgc tggggcagct acgagcccac | | | | 840 |
| gtggaggctg ccgaagaagc tgctcgggag aggctggcgg agcttgaggg ccgggagcag | | | | 900 |
| gtggccaggg ccgcagccgc cttcgcccgc cgggtactca gctgggcg agaggccgag | | | | 960 |
| atcctctccc tggaaggggc gatcgcacag cggctcaggc agctgcaggg ctgcccctgg | | | | 1020 |
| gcaccaggcc cggccccctg cctgctccca cagctggagc tccatcctgg gctcctggac | | | | 1080 |
| aagaactgcc accttcttcg gctgtccttt gaggagcagc agcccagaa ggatggtggg | | | | 1140 |
| aaagacggag ctggtaccca gggaggtgag gagagccaga gccggaggga ggatgagccg | | | | 1200 |
| aagactgaga gacagggtgg agtccagccc caggctggag atggagccca gacccaaaa | | | | 1260 |
| gaggaaaaag cccagacaac ccgagaagag gagcccaga ccttggagga ggacagggcc | | | | 1320 |
| cagacacccc acgaggatgg aggaccccag ccccacaggg gtggcagacc caacaagaag | | | | 1380 |
| aaaaagttca aggcaggct caagtcaatt tcccgggagc ccagcccagc cctggggccg | | | | 1440 |
| aatctggacg gctctggcct cctccccaga cccatcttt actgcagttt ccccacgcg | | | | 1500 |
| atgcctggag acaagcggtc ccccggatc accgggctct gtcccttcgg tccccgggag | | | | 1560 |
| atcctggtgg cggatgagca gaaccgggca ctgaaacgct ctcccctcaa cggcgactac | | | | 1620 |
| aagggcaccg tgccggtccc tgagggctgc tccccttgca gcgtggccgc cctgcagagc | | | | 1680 |

-continued

```
gcggtggcct tctccgctag cgcacggctc tatctcatca accccaacgg cgaagtgcag     1740
tggcgcaggg ccctgagcct ctcccaggcc agccacgcgg tggcggcact gcctagcggg     1800
gaccgcgtgg ctgtcagcgt ggcgggccac gtggaggtgt acaatatgga aggcagcctg     1860
gccacccggt tcattcctgg aggcaaggcc agccggggcc tgcgggcgct ggtgtttctg     1920
accaccagcc cccaggggca tttcgtgggg tcggactggc agcagaatag tgtggtaatc     1980
tgtgatgggc tgggccaggt ggttggggag tacaaggggc caggcctgca tggctgccag     2040
ccgggctccg tgtctgtgga taagaagggc tacatctttc tgacccttcg agaagtcaac     2100
aaggtggtga tcctggaccc gaaggggtcc ctccttggag acttcctgac agcctaccac     2160
ggcctggaaa agccccgggt taccaccatg gtggatggca ggtacctggt cgtgtccctc     2220
agtaa                                                                 2225
```

<210> SEQ ID NO 110
<211> LENGTH: 755
<212> TYPE: PRT
<213> ORGANISM: Homo sapiens

<400> SEQUENCE: 110

```
Met Val Ser His Gly Ser Pro Ser Leu Leu Glu Ala Leu Ser Ser
1               5                   10                  15

Asp Phe Leu Ala Cys Lys Ile Cys Leu Glu Gln Leu Arg Ala Pro Lys
                20                  25                  30

Thr Leu Pro Cys Leu His Thr Tyr Cys Gln Asp Cys Leu Ala Gln Leu
            35                  40                  45

Ala Asp Gly Gly Arg Val Arg Cys Pro Glu Cys Arg Glu Thr Val Pro
        50                  55                  60

Val Pro Pro Glu Gly Val Ala Ser Phe Lys Thr Asn Phe Phe Val Asn
65                  70                  75                  80

Gly Leu Leu Asp Leu Val Lys Ala Arg Ala Cys Gly Asp Leu Arg Ala
                85                  90                  95

Gly Lys Pro Ala Cys Ala Leu Cys Pro Leu Val Gly Thr Ser Thr
            100                 105                 110

Gly Gly Pro Ala Thr Ala Arg Cys Leu Asp Cys Ala Asp Asp Leu Cys
        115                 120                 125

Gln Ala Cys Ala Asp Gly His Arg Cys Thr Arg Gln Thr His Thr His
    130                 135                 140

Arg Val Val Asp Leu Val Gly Tyr Arg Ala Gly Trp Tyr Asp Glu Glu
145                 150                 155                 160

Ala Arg Glu Arg Gln Ala Ala Gln Cys Pro Gln His Pro Gly Glu Ala
                165                 170                 175

Leu Arg Phe Leu Cys Gln Pro Cys Ser Gln Leu Leu Cys Arg Glu Cys
            180                 185                 190

Arg Leu Asp Pro His Leu Asp His Pro Cys Leu Pro Leu Ala Glu Ala
        195                 200                 205

Val Arg Ala Arg Arg Pro Gly Leu Glu Gly Leu Leu Ala Gly Val Asp
    210                 215                 220

Asn Asn Leu Val Glu Leu Glu Ala Ala Arg Arg Val Glu Lys Glu Ala
225                 230                 235                 240

Leu Ala Arg Leu Arg Glu Gln Ala Ala Arg Val Gly Thr Gln Val Glu
                245                 250                 255

Glu Ala Ala Glu Gly Val Leu Arg Ala Leu Leu Ala Gln Lys Gln Glu
            260                 265                 270
```

-continued

```
Val Leu Gly Gln Leu Arg Ala His Val Glu Ala Ala Glu Ala Ala
            275                 280                 285

Arg Glu Arg Leu Ala Glu Leu Glu Gly Arg Glu Gln Val Ala Arg Ala
        290                 295                 300

Ala Ala Ala Phe Ala Arg Arg Val Leu Ser Leu Gly Arg Glu Ala Glu
305                 310                 315                 320

Ile Leu Ser Leu Glu Gly Ala Ile Ala Gln Arg Leu Arg Gln Leu Gln
                325                 330                 335

Gly Cys Pro Trp Ala Pro Gly Pro Ala Pro Cys Leu Leu Pro Gln Leu
            340                 345                 350

Glu Leu His Pro Gly Leu Leu Asp Lys Asn Cys His Leu Leu Arg Leu
        355                 360                 365

Ser Phe Glu Glu Gln Gln Pro Gln Lys Asp Gly Gly Lys Asp Gly Ala
    370                 375                 380

Gly Thr Gln Gly Gly Glu Glu Ser Gln Ser Arg Arg Glu Asp Glu Pro
385                 390                 395                 400

Lys Thr Glu Arg Gln Gly Gly Val Gln Pro Gln Ala Gly Asp Gly Ala
                405                 410                 415

Gln Thr Pro Lys Glu Glu Lys Ala Gln Thr Thr Arg Glu Glu Gly Ala
            420                 425                 430

Gln Thr Leu Glu Glu Asp Arg Ala Gln Thr Pro His Glu Asp Gly Gly
        435                 440                 445

Pro Gln Pro His Arg Gly Gly Arg Pro Asn Lys Lys Lys Phe Lys
    450                 455                 460

Gly Arg Leu Lys Ser Ile Ser Arg Glu Pro Ser Pro Ala Leu Gly Pro
465                 470                 475                 480

Asn Leu Asp Gly Ser Gly Leu Leu Pro Arg Pro Ile Phe Tyr Cys Ser
                485                 490                 495

Phe Pro Thr Arg Met Pro Gly Asp Lys Arg Ser Pro Arg Ile Thr Gly
            500                 505                 510

Leu Cys Pro Phe Gly Pro Arg Glu Ile Leu Val Ala Asp Glu Gln Asn
        515                 520                 525

Arg Ala Leu Lys Arg Phe Ser Leu Asn Gly Asp Tyr Lys Gly Thr Val
    530                 535                 540

Pro Val Pro Glu Gly Cys Ser Pro Cys Ser Val Ala Ala Leu Gln Ser
545                 550                 555                 560

Ala Val Ala Phe Ser Ala Ser Ala Arg Leu Tyr Leu Ile Asn Pro Asn
                565                 570                 575

Gly Glu Val Gln Trp Arg Arg Ala Leu Ser Leu Ser Gln Ala Ser His
            580                 585                 590

Ala Val Ala Ala Leu Pro Ser Gly Asp Arg Val Ala Val Ser Val Ala
        595                 600                 605

Gly His Val Glu Val Tyr Asn Met Glu Gly Ser Leu Ala Thr Arg Phe
    610                 615                 620

Ile Pro Gly Gly Lys Ala Ser Arg Gly Leu Arg Ala Leu Val Phe Leu
625                 630                 635                 640

Thr Thr Ser Pro Gln Gly His Phe Val Gly Ser Asp Trp Gln Gln Asn
                645                 650                 655

Ser Val Val Ile Cys Asp Gly Leu Gly Gln Val Gly Glu Tyr Lys
            660                 665                 670

Gly Pro Gly Leu His Gly Cys Gln Pro Gly Ser Val Ser Val Asp Lys
        675                 680                 685

Lys Gly Tyr Ile Phe Leu Thr Leu Arg Glu Val Asn Lys Val Val Ile
```

```
                690              695              700
Leu Asp Pro Lys Gly Ser Leu Leu Gly Asp Phe Leu Thr Ala Tyr His
705                     710                 715                 720

Gly Leu Glu Lys Pro Arg Val Thr Thr Met Val Asp Gly Arg Tyr Leu
                725                 730                 735

Val Val Ser Leu Ser Asn Gly Thr Ile His Ile Phe Arg Val Arg Ser
            740                 745                 750

Pro Asp Ser
        755

<210> SEQ ID NO 111
<211> LENGTH: 1461
<212> TYPE: DNA
<213> ORGANISM: Homo sapiens

<400> SEQUENCE: 111
```

| | |
|---|---|
| atggcctggg cgccgcccgg ggagcggctg cgcgaggatg cgcggtgccc ggtgtgcctg | 60 |
| gatttcctgc aggagccggt cagcgtggac tgcggccaca gcttctgcct caggtgcatc | 120 |
| tccgagttct gcgagaagtc ggacggcgcg cagggcggcg tctacgcctg tccgcagtgc | 180 |
| cggggcccct tccggccctc gggctttcgc cccaaccggc agctggcggg cctggtggag | 240 |
| agcgtgcggc ggctggggtt gggcgcgggg cccggggcgc ggcgatgcgc gcggcacggc | 300 |
| gaggacctga ccgcttctg cgaggaggac gaggcggcgc tgtgctgggt gtgcgacgcc | 360 |
| ggccccgagc acaggacgca ccgcacggcg ccgctgcagg aggccgccgg cagctaccag | 420 |
| gtaaagctcc agatggctct ggaacttatg aggaaagagt ggaggacgc cttgactcag | 480 |
| gaggccaacg tggggaaaaa gactgtcatt tggaaggaga agtggaaat gcagaggcag | 540 |
| cgcttcagat ggagtttga gaagcatcgt ggctttctgg cccaggagga gcaacggcag | 600 |
| ctgaggcggc tggaggcgga ggagcgagcg acgctgcaga gactgcggga gagcaagagc | 660 |
| cggctggtcc agcagagcaa ggccctgaag gagctggcgg atgagctgca ggagaggtgc | 720 |
| cagcgcccgg ccctgggtct gctggagggt gtgagaggag tcctgagcag aagtaaggct | 780 |
| gtcacaaggc tggaagcaga gaacatcccc atggaactga agacagcatg ctgcatccct | 840 |
| gggaggaggg agctcttaag gaagttccaa gtggatgtaa agctggatcc cgccacggcg | 900 |
| cacccgagtc tgctcttgac cgccgacctg cgcagtgtgc aggatggaga accatggagg | 960 |
| gatgtcccca caaccctga gcgatttgac acatggccct gcatcctggg tttgcagagc | 1020 |
| ttctcatcag ggaggcatta ctgggaggtt ctggtgggag aaggagcaga gtggggttta | 1080 |
| ggggtctgtc aagacacact gccaagaaag ggggaaacca cgccatctcc tgagaatggg | 1140 |
| gtctgggccc tgtggctgct gaaagggaat gagtacatgg tccttgcctc cccatcagtg | 1200 |
| cctcttctcc aactggaaag tcctcgctgc attgggattt tcttggacta tgaagccggt | 1260 |
| gaaatttcat tctacaatgt cacagatgga tcttatatct acacattcaa ccaactcttc | 1320 |
| tctggtcttc ttcggcctta cttttttcatc tgtgatgcaa ctcctcttat cttgccaccc | 1380 |
| acaacaatag cagggtcagg aaattgggca tccagggatc atttagatcc tgcttctgat | 1440 |
| gtaagagatg atcatctcta a | 1461 |

```
<210> SEQ ID NO 112
<211> LENGTH: 486
<212> TYPE: PRT
<213> ORGANISM: Homo sapiens

<400> SEQUENCE: 112
```

-continued

```
Met Ala Trp Ala Pro Pro Gly Glu Arg Leu Arg Glu Asp Ala Arg Cys
1               5                   10                  15

Pro Val Cys Leu Asp Phe Leu Gln Glu Pro Val Ser Val Asp Cys Gly
            20                  25                  30

His Ser Phe Cys Leu Arg Cys Ile Ser Glu Phe Cys Glu Lys Ser Asp
        35                  40                  45

Gly Ala Gln Gly Gly Val Tyr Ala Cys Pro Gln Cys Arg Gly Pro Phe
    50                  55                  60

Arg Pro Ser Gly Phe Arg Pro Asn Arg Gln Leu Ala Gly Leu Val Glu
65                  70                  75                  80

Ser Val Arg Arg Leu Gly Leu Gly Ala Gly Pro Gly Ala Arg Arg Cys
                85                  90                  95

Ala Arg His Gly Glu Asp Leu Ser Arg Phe Cys Glu Glu Asp Glu Ala
            100                 105                 110

Ala Leu Cys Trp Val Cys Asp Ala Gly Pro Glu His Arg Thr His Arg
        115                 120                 125

Thr Ala Pro Leu Gln Glu Ala Ala Gly Ser Tyr Gln Val Lys Leu Gln
    130                 135                 140

Met Ala Leu Glu Leu Met Arg Lys Glu Leu Glu Asp Ala Leu Thr Gln
145                 150                 155                 160

Glu Ala Asn Val Gly Lys Lys Thr Val Ile Trp Lys Glu Lys Val Glu
                165                 170                 175

Met Gln Arg Gln Arg Phe Arg Leu Glu Phe Glu Lys His Arg Gly Phe
            180                 185                 190

Leu Ala Gln Glu Gln Arg Gln Leu Arg Arg Leu Glu Ala Glu Glu
        195                 200                 205

Arg Ala Thr Leu Gln Arg Leu Arg Glu Ser Lys Ser Arg Leu Val Gln
210                 215                 220

Gln Ser Lys Ala Leu Lys Glu Leu Ala Asp Glu Leu Gln Glu Arg Cys
225                 230                 235                 240

Gln Arg Pro Ala Leu Gly Leu Leu Glu Gly Val Arg Gly Val Leu Ser
                245                 250                 255

Arg Ser Lys Ala Val Thr Arg Leu Glu Ala Glu Asn Ile Pro Met Glu
            260                 265                 270

Leu Lys Thr Ala Cys Cys Ile Pro Gly Arg Arg Glu Leu Leu Arg Lys
        275                 280                 285

Phe Gln Val Asp Val Lys Leu Asp Pro Ala Thr Ala His Pro Ser Leu
    290                 295                 300

Leu Leu Thr Ala Asp Leu Arg Ser Val Gln Asp Gly Glu Pro Trp Arg
305                 310                 315                 320

Asp Val Pro Asn Asn Pro Glu Arg Phe Asp Thr Trp Pro Cys Ile Leu
                325                 330                 335

Gly Leu Gln Ser Phe Ser Ser Gly Arg His Tyr Trp Glu Val Leu Val
            340                 345                 350

Gly Glu Gly Ala Glu Trp Gly Leu Gly Val Cys Gln Asp Thr Leu Pro
        355                 360                 365

Arg Lys Gly Glu Thr Thr Pro Ser Pro Glu Asn Gly Val Trp Ala Leu
    370                 375                 380

Trp Leu Leu Lys Gly Asn Glu Tyr Met Val Leu Ala Ser Pro Ser Val
385                 390                 395                 400

Pro Leu Leu Gln Leu Glu Ser Pro Arg Cys Ile Gly Ile Phe Leu Asp
                405                 410                 415
```

Tyr Glu Ala Gly Glu Ile Ser Phe Tyr Asn Val Thr Asp Gly Ser Tyr
                420                 425                 430

Ile Tyr Thr Phe Asn Gln Leu Phe Ser Gly Leu Leu Arg Pro Tyr Phe
            435                 440                 445

Phe Ile Cys Asp Ala Thr Pro Leu Ile Leu Pro Pro Thr Thr Ile Ala
        450                 455                 460

Gly Ser Gly Asn Trp Ala Ser Arg Asp His Leu Asp Pro Ala Ser Asp
465                 470                 475                 480

Val Arg Asp Asp His Leu
                485

<210> SEQ ID NO 113
<211> LENGTH: 1212
<212> TYPE: DNA
<213> ORGANISM: Homo sapiens

<400> SEQUENCE: 113

```
atgcacaatt ttgaggaaga gttaacttgt cccatatgtt atagtatttt tgaagatcct    60
cgtgtactgc catgctctca tacattttgt agaaattgtt tggaaaacat tcttcaggca   120
tctggtaact tttatatatg gagaccttta cgaattccac tcaagtgccc taattgcaga   180
agtattactg aaattgctcc aactggcatt gaatctttac ctgttaattt tgcactaagg   240
gctattattg aaaagtacca gcaagaagac catccagata ttgtcacctg ccctgaacat   300
tacaggcaac cattaaatgt ttactgtcta ttagataaaa aattagtttg tggtcattgc   360
cttaccatag gtcaacatca tggtcatcct atagatgacc ttcaaagtgc ctatttgaaa   420
gaaaaggaca ctcctcaaaa actgcttgaa cagttgactg acacacactg gacagatctt   480
acccatctta ttgaaaagct gaaagaacaa aaatctcatt ctgagaaaat gatccaaggc   540
gataaggaag ctgttctcca gtattttaag gagcttaatg atacattaga acagaaaaaa   600
aaaagttttcc taacggctct ctgtgatgtt ggcaatctaa ttaatcaaga atatactcca   660
caaattgaaa gaatgaagga atacgagag cagcagcttg aattaatggc actgacaata   720
tctttacaag aagagtctcc acttaaattt cttgaaaaag ttgatgatgt acgccagcat   780
gtacagatct tgaaacaaag accacttcct gaggttcaac ccgttgaaat ttatcctcga   840
gtaagcaaaa tattgaaaga gaatggagc agaacagaaa ttggacaaat taagaacgtt   900
ctcattccca aaatgaaaat ttctccaaaa aggatgtcat gttcctggcc tggtaaggat   960
gaaaaggaag ttgaatttt aaaaatttta acattgttg tagttacatt aatttcagta  1020
atactgatgt cgatactctt tttcaaccaa cacatcataa cctttttaag tgaaatcact  1080
ttaatatggt tttctgaagc ctctctatct gtttaccaaa gtttatctaa cagtctgcat  1140
aaggtaaaga atatactgtg tcacattttc tatttgttga ggaatttgt gtggaaaata  1200
gtttcccatt ga                                                    1212
```

<210> SEQ ID NO 114
<211> LENGTH: 403
<212> TYPE: PRT
<213> ORGANISM: Homo sapiens

<400> SEQUENCE: 114

Met His Asn Phe Glu Glu Glu Leu Thr Cys Pro Ile Cys Tyr Ser Ile
1               5                   10                  15

Phe Glu Asp Pro Arg Val Leu Pro Cys Ser His Thr Phe Cys Arg Asn
            20                  25                  30

Cys Leu Glu Asn Ile Leu Gln Ala Ser Gly Asn Phe Tyr Ile Trp Arg
            35                  40                  45

Pro Leu Arg Ile Pro Leu Lys Cys Pro Asn Cys Arg Ser Ile Thr Glu
 50                  55                  60

Ile Ala Pro Thr Gly Ile Glu Ser Leu Pro Val Asn Phe Ala Leu Arg
 65                  70                  75                  80

Ala Ile Ile Glu Lys Tyr Gln Gln Glu Asp His Pro Asp Ile Val Thr
                 85                  90                  95

Cys Pro Glu His Tyr Arg Gln Pro Leu Asn Val Tyr Cys Leu Leu Asp
             100                 105                 110

Lys Lys Leu Val Cys Gly His Cys Leu Thr Ile Gly Gln His His Gly
         115                 120                 125

His Pro Ile Asp Asp Leu Gln Ser Ala Tyr Leu Lys Glu Lys Asp Thr
     130                 135                 140

Pro Gln Lys Leu Leu Glu Gln Leu Thr Asp Thr His Trp Thr Asp Leu
145                 150                 155                 160

Thr His Leu Ile Glu Lys Leu Lys Glu Gln Lys Ser His Ser Glu Lys
                 165                 170                 175

Met Ile Gln Gly Asp Lys Glu Ala Val Leu Gln Tyr Phe Lys Glu Leu
             180                 185                 190

Asn Asp Thr Leu Glu Gln Lys Lys Ser Phe Leu Thr Ala Leu Cys
         195                 200                 205

Asp Val Gly Asn Leu Ile Asn Gln Glu Tyr Thr Pro Gln Ile Glu Arg
     210                 215                 220

Met Lys Glu Ile Arg Glu Gln Leu Glu Leu Met Ala Leu Thr Ile
225                 230                 235                 240

Ser Leu Gln Glu Glu Ser Pro Leu Lys Phe Leu Glu Lys Val Asp Asp
                 245                 250                 255

Val Arg Gln His Val Gln Ile Leu Lys Gln Arg Pro Leu Pro Glu Val
             260                 265                 270

Gln Pro Val Glu Ile Tyr Pro Arg Val Ser Lys Ile Leu Lys Glu Glu
         275                 280                 285

Trp Ser Arg Thr Glu Ile Gly Gln Ile Lys Asn Val Leu Ile Pro Lys
290                 295                 300

Met Lys Ile Ser Pro Lys Arg Met Ser Cys Ser Trp Pro Gly Lys Asp
305                 310                 315                 320

Glu Lys Glu Val Glu Phe Leu Lys Ile Leu Asn Ile Val Val Thr
                 325                 330                 335

Leu Ile Ser Val Ile Leu Met Ser Ile Leu Phe Phe Asn Gln His Ile
             340                 345                 350

Ile Thr Phe Leu Ser Glu Ile Thr Leu Ile Trp Phe Ser Glu Ala Ser
         355                 360                 365

Leu Ser Val Tyr Gln Ser Leu Ser Asn Ser Leu His Lys Val Lys Asn
     370                 375                 380

Ile Leu Cys His Ile Phe Tyr Leu Leu Lys Glu Phe Val Trp Lys Ile
385                 390                 395                 400

Val Ser His

<210> SEQ ID NO 115
<211> LENGTH: 1416
<212> TYPE: DNA
<213> ORGANISM: Homo sapiens

<400> SEQUENCE: 115

| | |
|---|---:|
| atggagtttg tgacagccct ggtgaacctc aagaggagt ctagctgtcc catctgtctg | 60 |
| gagtacttga agacccagt gaccatcaac tgtgggcaca acttctgtcg ctcctgcctc | 120 |
| agtgtatcct ggaaggatct agatgatacc tttccctgtc ctgtctgccg tttttgcttt | 180 |
| ccatacaaga gcttcaggag gaaccccag ctccgtaatt tgactgaaat tgctaaacaa | 240 |
| ctccagatta ggaggagcaa gagaaagagg cagaaagaga atgccatgtg tgaaaaacac | 300 |
| aaccagtttc tgaccctctt ctgtgttaaa gatctagaga tcttatgtac acagtgcagt | 360 |
| ttctccacta acaccagaa gcactacatt tgccctatta gaaagctgc tcttatcac | 420 |
| agagaaattc tagaaggtag ccttgagccc ttgaggaata atagaacg agttgaaaaa | 480 |
| gtgataattc tgcaaggcag caaatcagtg gagctgaaaa agaaggtaga atataagagg | 540 |
| gaagaaataa attctgagtt tgagcaaata agattgtttt tacagaatga acaagagatg | 600 |
| attcttaggc agatacaaga tgaagagatg aacattttag caaaactaaa tgaaaacctt | 660 |
| gtagaacttt cagattatgt ttccacatta aaacatctac tgagggaggt agagggcaag | 720 |
| tctgtgcagt caaacctgga attactgaca caagctaaga gtatgcacca caagtatcaa | 780 |
| aacctaaaat gccctgaact cttttcattt agattaacaa aatatggttt cagtcttcct | 840 |
| cctcaatatt ctggcttgga cagaattatc aagccatttc aagtagatgt gattctagat | 900 |
| ctcaacacag cacatcctca acttcttgtc tctgaggata gaaaagctgt gcgatatgaa | 960 |
| agaaaaaaac gaaacatttg ttatgaccca aggagatttt atgtctgccc tgctgtccta | 1020 |
| ggctctcaga gatttagttc tggccgacat tactgggaag tagaagtggg aaacaaacct | 1080 |
| aaatggatat gggtgtgtg tcaagactgt cttcttagga actggcagga tcagccatca | 1140 |
| gttctgggcg gattctgggc aattgggcga tacatgaaga gtggttatgt tgcgtcaggt | 1200 |
| cctaagacaa cccagcttct gccagtagta aaacccagta aaattggtat ttttctggac | 1260 |
| tatgaattgg gtgatctttc cttttataat atgaatgata ggtctattct ctatactttt | 1320 |
| aacgattgtt tcacagaagc cgtttggcct tatttctata ctggaacaga ttccgaacct | 1380 |
| cttaaaatct gctcagtatc agattctgaa agataa | 1416 |

<210> SEQ ID NO 116
<211> LENGTH: 471
<212> TYPE: PRT
<213> ORGANISM: Homo sapiens

<400> SEQUENCE: 116

```
Met Glu Phe Val Thr Ala Leu Val Asn Leu Gln Glu Glu Ser Ser Cys
1               5                   10                  15

Pro Ile Cys Leu Glu Tyr Leu Lys Asp Pro Val Thr Ile Asn Cys Gly
            20                  25                  30

His Asn Phe Cys Arg Ser Cys Leu Ser Val Ser Trp Lys Asp Leu Asp
        35                  40                  45

Asp Thr Phe Pro Cys Pro Val Cys Arg Phe Cys Phe Pro Tyr Lys Ser
    50                  55                  60

Phe Arg Arg Asn Pro Gln Leu Arg Asn Leu Thr Glu Ile Ala Lys Gln
65                  70                  75                  80

Leu Gln Ile Arg Arg Ser Lys Arg Lys Arg Gln Lys Glu Asn Ala Met
                85                  90                  95

Cys Glu Lys His Asn Gln Phe Leu Thr Leu Phe Cys Val Lys Asp Leu
            100                 105                 110

Glu Ile Leu Cys Thr Gln Cys Ser Phe Ser Thr Lys His Gln Lys His
        115                 120                 125
```

Tyr Ile Cys Pro Ile Lys Lys Ala Ala Ser Tyr His Arg Glu Ile Leu
130                 135                 140

Glu Gly Ser Leu Glu Pro Leu Arg Asn Asn Ile Glu Arg Val Glu Lys
145                 150                 155                 160

Val Ile Ile Leu Gln Gly Ser Lys Ser Val Glu Leu Lys Lys Lys Val
                165                 170                 175

Glu Tyr Lys Arg Glu Glu Ile Asn Ser Glu Phe Glu Gln Ile Arg Leu
                180                 185                 190

Phe Leu Gln Asn Glu Gln Glu Met Ile Leu Arg Gln Ile Gln Asp Glu
            195                 200                 205

Glu Met Asn Ile Leu Ala Lys Leu Asn Glu Asn Leu Val Glu Leu Ser
210                 215                 220

Asp Tyr Val Ser Thr Leu Lys His Leu Leu Arg Glu Val Glu Gly Lys
225                 230                 235                 240

Ser Val Gln Ser Asn Leu Glu Leu Leu Thr Gln Ala Lys Ser Met His
                245                 250                 255

His Lys Tyr Gln Asn Leu Lys Cys Pro Glu Leu Phe Ser Phe Arg Leu
                260                 265                 270

Thr Lys Tyr Gly Phe Ser Leu Pro Pro Gln Tyr Ser Gly Leu Asp Arg
            275                 280                 285

Ile Ile Lys Pro Phe Gln Val Asp Val Ile Leu Asp Leu Asn Thr Ala
290                 295                 300

His Pro Gln Leu Leu Val Ser Glu Asp Arg Lys Ala Val Arg Tyr Glu
305                 310                 315                 320

Arg Lys Lys Arg Asn Ile Cys Tyr Asp Pro Arg Arg Phe Tyr Val Cys
                325                 330                 335

Pro Ala Val Leu Gly Ser Gln Arg Phe Ser Ser Gly Arg His Tyr Trp
                340                 345                 350

Glu Val Glu Val Gly Asn Lys Pro Lys Trp Ile Leu Gly Val Cys Gln
            355                 360                 365

Asp Cys Leu Leu Arg Asn Trp Gln Asp Gln Pro Ser Val Leu Gly Gly
370                 375                 380

Phe Trp Ala Ile Gly Arg Tyr Met Lys Ser Gly Tyr Val Ala Ser Gly
385                 390                 395                 400

Pro Lys Thr Thr Gln Leu Leu Pro Val Val Lys Pro Ser Lys Ile Gly
                405                 410                 415

Ile Phe Leu Asp Tyr Glu Leu Gly Asp Leu Ser Phe Tyr Asn Met Asn
                420                 425                 430

Asp Arg Ser Ile Leu Tyr Thr Phe Asn Asp Cys Phe Thr Glu Ala Val
            435                 440                 445

Trp Pro Tyr Phe Tyr Thr Gly Thr Asp Ser Glu Pro Leu Lys Ile Cys
450                 455                 460

Ser Val Ser Asp Ser Glu Arg
465                 470

<210> SEQ ID NO 117
<211> LENGTH: 630
<212> TYPE: DNA
<213> ORGANISM: Homo sapiens

<400> SEQUENCE: 117
atggaatttg ttacggccct ggctgacctc cgagcagagg ctagctgtcc catctgtctg     60
gactacttga aagacccagt gaccatcagc tgtgggcata acttctgtct ctcctgcatc    120

```
attatgtcct ggaaggatct acatgatagt ttcccctgcc ccttttgcca cttttgctgt    180
ccagaaagga aatttataag caatccccag ctgggtagtt tgactgaaat tgctaagcaa    240
ctccagataa gaagcaagaa gaggaagagg caggaagaga agcatgtgtg taagaagcat    300
aatcaggttt tgactttctt ctgtcagaaa gacctagagc ttttatgtcc aaggtgcagt    360
ttgtccactg atcaccagca tcactgtgtt tggcccataa agaaggctgc ctcctatcat    420
aggaaaaaac tggaggaata caatgcaccg tggaaggaga gagtggaact aattgaaaaa    480
gtcataacta tgcaaaccag gaaatcactg gaactgaaga aaaagatgga gtctccttct    540
gtcaccaggc tggagtgcag ttgcacgatc tcggctcact tcaacctccg cctcccggga    600
tcaagcgatt cttctgcctc tggctcctga                                    630
```

<210> SEQ ID NO 118
<211> LENGTH: 209
<212> TYPE: PRT
<213> ORGANISM: Homo sapiens

<400> SEQUENCE: 118

```
Met Glu Phe Val Thr Ala Leu Ala Asp Leu Arg Ala Glu Ala Ser Cys
1               5                   10                  15

Pro Ile Cys Leu Asp Tyr Leu Lys Asp Pro Val Thr Ile Ser Cys Gly
                20                  25                  30

His Asn Phe Cys Leu Ser Cys Ile Ile Met Ser Trp Lys Asp Leu His
            35                  40                  45

Asp Ser Phe Pro Cys Pro Phe Cys His Phe Cys Cys Pro Glu Arg Lys
        50                  55                  60

Phe Ile Ser Asn Pro Gln Leu Gly Ser Leu Thr Glu Ile Ala Lys Gln
65                  70                  75                  80

Leu Gln Ile Arg Ser Lys Lys Arg Lys Gln Glu Glu Lys His Val
                85                  90                  95

Cys Lys Lys His Asn Gln Val Leu Thr Phe Phe Cys Gln Lys Asp Leu
                100                 105                 110

Glu Leu Leu Cys Pro Arg Cys Ser Leu Ser Thr Asp His Gln His His
            115                 120                 125

Cys Val Trp Pro Ile Lys Lys Ala Ala Ser Tyr His Arg Lys Lys Leu
        130                 135                 140

Glu Glu Tyr Asn Ala Pro Trp Lys Glu Arg Val Glu Leu Ile Glu Lys
145                 150                 155                 160

Val Ile Thr Met Gln Thr Arg Lys Ser Leu Glu Leu Lys Lys Lys Met
                165                 170                 175

Glu Ser Pro Ser Val Thr Arg Leu Glu Cys Ser Cys Thr Ile Ser Ala
                180                 185                 190

His Phe Asn Leu Arg Leu Pro Gly Ser Ser Asp Ser Ser Ala Ser Gly
            195                 200                 205

Ser
```

<210> SEQ ID NO 119
<211> LENGTH: 1428
<212> TYPE: DNA
<213> ORGANISM: Homo sapiens

<400> SEQUENCE: 119

```
atggcgtgca gcctcaagga cgagctgctg tgctccatct gcctgagcat ctaccaggac    60
ccggtgagcc tgggctgcga gcattacttc tgccgccgct gcatcacgga gcactgggtg    120
```

```
cggcaggagg cgcagggcgc ccgcgactgc cccgagtgcc ggcgcacgtt cgccgagccc      180
gcgctggcgc ccagcctcaa gctggccaac atcgtggagc gctacagctc cttcccgctg      240
gacgccatcc tcaacgcgcg ccgcgccgcg cgaccctgcc aggcgcacga caaggtcaag      300
ctcttctgcc tcacggaccg cgcgcttctc tgcttcttct gcgacgagcc tgcactgcac      360
gagcagcatc aggtcaccgg catcgacgac gccttcgacg agctgcagag ggagctgaag      420
gaccaacttc aggcccttca agacagcgag cgggaacaca ccgaagcgct gcagctgctc      480
aagcgacaac tggcggagac caagtcttcc accaagagcc tgcggaccac tatcggcgag      540
gccttcgagc ggctgcaccg gctgctgcgt gaacgccaga aggccatgct agaggagctg      600
gaggcggaca cggcccgcac gctgaccgac atcgagcaga aagtccagcg ctacagccag      660
cagctgcgca aggtccagga gggagcccag atcctgcagg agcggctggc tgaaaccgac      720
cggcacacct tcctggctgg ggtggcctca ctgtccgagc ggctcaaggg aaaaatccat      780
gagaccaacc tcacatatga agactttccg acctccaagt acacaggccc cctgcagtac      840
accatctgga agtccctgtt ccaggacatc cacccagtgc cagccgccct aaccctggac      900
ccgggcacag cccaccagcg cctgatcctg tcggacgact gcaccattgt ggcttacggc      960
aacttgcacc acagccact gcaggactcg ccaaagcgct tcgatgtgga ggtgtcggtg     1020
ctgggttctg aagccttcag tagtggcgtc cactactggg aggtggtggt ggcggagaag     1080
acccagtggg tgatcgggct ggcacacgaa gccgcaagcc gcaagggcag catccagatc     1140
cagcccagcc gcggcttcta ctgcatcgtg atgcacgatg caaccagta cagcgcctgc     1200 acggagccct ggacgcggct taacgtccgg gacaagcttg acaaggtggg tgtcttcctg     1260
gactatgacc aaggcttgct catcttctac aatgctgatg acatgtcctg gctctacacc     1320
ttccgcgaga agttccctgg caagctctgc tcttacttca gccctggcca gagccacgcc     1380
aatggcaaga acgttcagcc gctgcggatc aacaccgtcc gcatctag                  1428

<210> SEQ ID NO 120
<211> LENGTH: 475
<212> TYPE: PRT
<213> ORGANISM: Homo sapiens

<400> SEQUENCE: 120

Met Ala Cys Ser Leu Lys Asp Glu Leu Leu Cys Ser Ile Cys Leu Ser
1               5                   10                  15

Ile Tyr Gln Asp Pro Val Ser Leu Gly Cys Glu His Tyr Phe Cys Arg
                20                  25                  30

Arg Cys Ile Thr Glu His Trp Val Arg Gln Glu Ala Gln Gly Ala Arg
            35                  40                  45

Asp Cys Pro Glu Cys Arg Arg Thr Phe Ala Glu Pro Ala Leu Ala Pro
        50                  55                  60

Ser Leu Lys Leu Ala Asn Ile Val Glu Arg Tyr Ser Ser Phe Pro Leu
65                  70                  75                  80

Asp Ala Ile Leu Asn Ala Arg Arg Ala Ala Arg Pro Cys Gln Ala His
                85                  90                  95

Asp Lys Val Lys Leu Phe Cys Leu Thr Asp Arg Ala Leu Leu Cys Phe
                100                 105                 110

Phe Cys Asp Glu Pro Ala Leu His Glu Gln His Gln Val Thr Gly Ile
            115                 120                 125

Asp Asp Ala Phe Asp Glu Leu Gln Arg Glu Leu Lys Asp Gln Leu Gln
        130                 135                 140
```

| | | | | | | | | | | | |
|---|---|---|---|---|---|---|---|---|---|---|---|
|Ala|Leu|Gln|Asp|Ser|Glu|Arg|Glu|His|Thr|Glu|Ala|Leu|Gln|Leu|Leu|
|145| | | | |150| | | | |155| | | | |160|

Ala Leu Gln Asp Ser Glu Arg Glu His Thr Glu Ala Leu Gln Leu Leu
145                 150                 155                 160

Lys Arg Gln Leu Ala Glu Thr Lys Ser Ser Lys Ser Leu Arg Thr
                165                 170                 175

Thr Ile Gly Glu Ala Phe Glu Arg Leu His Arg Leu Arg Glu Arg
                180                 185                 190

Gln Lys Ala Met Leu Glu Glu Leu Glu Ala Asp Thr Ala Arg Thr Leu
            195                 200                 205

Thr Asp Ile Glu Gln Lys Val Gln Arg Tyr Ser Gln Leu Arg Lys
        210                 215                 220

Val Gln Glu Gly Ala Gln Ile Leu Gln Glu Arg Leu Ala Glu Thr Asp
225                 230                 235                 240

Arg His Thr Phe Leu Ala Gly Val Ala Ser Leu Ser Glu Arg Leu Lys
                245                 250                 255

Gly Lys Ile His Glu Thr Asn Leu Thr Tyr Glu Asp Phe Pro Thr Ser
                260                 265                 270

Lys Tyr Thr Gly Pro Leu Gln Tyr Thr Ile Trp Lys Ser Leu Phe Gln
            275                 280                 285

Asp Ile His Pro Val Pro Ala Ala Leu Thr Leu Asp Pro Gly Thr Ala
        290                 295                 300

His Gln Arg Leu Ile Leu Ser Asp Asp Cys Thr Ile Val Ala Tyr Gly
305                 310                 315                 320

Asn Leu His Pro Gln Pro Leu Gln Asp Ser Pro Lys Arg Phe Asp Val
                325                 330                 335

Glu Val Ser Val Leu Gly Ser Glu Ala Phe Ser Ser Gly Val His Tyr
                340                 345                 350

Trp Glu Val Val Ala Glu Lys Thr Gln Trp Val Ile Gly Leu Ala
            355                 360                 365

His Glu Ala Ala Ser Arg Lys Gly Ser Ile Gln Ile Gln Pro Ser Arg
        370                 375                 380

Gly Phe Tyr Cys Ile Val Met His Asp Gly Asn Gln Tyr Ser Ala Cys
385                 390                 395                 400

Thr Glu Pro Trp Thr Arg Leu Asn Val Arg Asp Lys Leu Asp Lys Val
                405                 410                 415

Gly Val Phe Leu Asp Tyr Asp Gln Gly Leu Leu Ile Phe Tyr Asn Ala
                420                 425                 430

Asp Asp Met Ser Trp Leu Tyr Thr Phe Arg Glu Lys Phe Pro Gly Lys
            435                 440                 445

Leu Cys Ser Tyr Phe Ser Pro Gly Gln Ser His Ala Asn Gly Lys Asn
        450                 455                 460

Val Gln Pro Leu Arg Ile Asn Thr Val Arg Ile
465                 470                 475

<210> SEQ ID NO 121
<211> LENGTH: 1062
<212> TYPE: DNA
<213> ORGANISM: Homo sapiens

<400> SEQUENCE: 121
atggattata agtcgagcct gatccaggat gggaatccca tggagaactt ggagaagcag    60
ctgatctgcc ctatctgcct ggagatgttt accaagccag tggtcatctt gccgtgccag   120
cacaacctgt gccggaagtg tgccaatgac atcttccagg ctgcaaatcc ctactggacc   180
agccggggca gctcagtgtc catgtctgga ggccgtttcc gctgccccac ctgccgccac   240

```
gaggtgatca tggatcgtca cggagtgtac ggcctgcaga ggaacctgct ggtggagaac    300
atcatcgaca tctacaaaca ggagtgctcc agtcggccgc tgcagaaggg cagtcacccc    360
atgtgcaagg agcacgaaga tgagaaaatc aacatctact gtctcacgtg tgaggtgccc    420
acctgctcca tgtgcaaggt gtttgggatc acaaggcct gcgaggtggc cccattgcag     480
agtgtcttcc agggacaaaa gactgaactg aataactgta tctccatgct ggtggcgggg    540
aatgaccgtg tgcagaccat catcactcag ctggaggatt cccgtcgagt gaccaaggag    600
aacagtcacc aggtaaagga gagctgagc cagaagtttg acacgttgta tgccatcctg      660
gatgagaaga aaagtgagtt gctgcagcgg atcacgcagg agcaggagaa aaagcttagc    720
ttcatcgagg ccctcatcca gcagtaccag gagcagctgg acaagtccac aaagctggtg    780
gaaactgcca tccagtccct ggacgagcct gggggagcca ccttcctctt gactgccaag    840
caactcatca aaagcattgt ggaagcttcc aagggctgcc agctggggaa gacagagcag    900
ggctttgaga acatggactt ctttactttg gatttagagc acatagcaga cgccctgaga    960
gccattgact ttgggacaga tgaggaagag aagaattca ttgaagaaga agatcaggaa     1020
gaggaagagt ccacagaagg gaaggaagaa ggacaccagt aa                       1062

<210> SEQ ID NO 122
<211> LENGTH: 353
<212> TYPE: PRT
<213> ORGANISM: Homo sapiens

<400> SEQUENCE: 122

Met Asp Tyr Lys Ser Ser Leu Ile Gln Asp Gly Asn Pro Met Glu Asn
1               5                   10                  15

Leu Glu Lys Gln Leu Ile Cys Pro Ile Cys Leu Glu Met Phe Thr Lys
                20                  25                  30

Pro Val Ile Leu Pro Cys Gln His Asn Leu Cys Arg Lys Cys Ala
            35                  40                  45

Asn Asp Ile Phe Gln Ala Ala Asn Pro Tyr Trp Thr Ser Arg Gly Ser
    50                  55                  60

Ser Val Ser Met Ser Gly Gly Arg Phe Arg Cys Pro Thr Cys Arg His
65                  70                  75                  80

Glu Val Ile Met Asp Arg His Gly Val Tyr Gly Leu Gln Arg Asn Leu
                85                  90                  95

Leu Val Glu Asn Ile Ile Asp Ile Tyr Lys Gln Glu Cys Ser Ser Arg
            100                 105                 110

Pro Leu Gln Lys Gly Ser His Pro Met Cys Lys Glu His Glu Asp Glu
        115                 120                 125

Lys Ile Asn Ile Tyr Cys Leu Thr Cys Glu Val Pro Thr Cys Ser Met
    130                 135                 140

Cys Lys Val Phe Gly Ile His Lys Ala Cys Glu Val Ala Pro Leu Gln
145                 150                 155                 160

Ser Val Phe Gln Gly Gln Lys Thr Glu Leu Asn Asn Cys Ile Ser Met
                165                 170                 175

Leu Val Ala Gly Asn Asp Arg Val Gln Thr Ile Ile Thr Gln Leu Glu
            180                 185                 190

Asp Ser Arg Arg Val Thr Lys Glu Asn Ser His Gln Val Lys Glu Glu
        195                 200                 205

Leu Ser Gln Lys Phe Asp Thr Leu Tyr Ala Ile Leu Asp Glu Lys Lys
    210                 215                 220

Ser Glu Leu Leu Gln Arg Ile Thr Gln Glu Gln Glu Lys Lys Leu Ser
```

| | | | | 225 | | | | 230 | | | | 235 | | | | 240 |

Phe Ile Glu Ala Leu Ile Gln Gln Tyr Gln Glu Gln Leu Asp Lys Ser
                        245                          250                          255

Thr Lys Leu Val Glu Thr Ala Ile Gln Ser Leu Asp Glu Pro Gly Gly
                    260                           265                          270

Ala Thr Phe Leu Leu Thr Ala Lys Gln Leu Ile Lys Ser Ile Val Glu
               275                           280                          285

Ala Ser Lys Gly Cys Gln Leu Gly Lys Thr Gln Gly Phe Glu Asn
        290                         295                          300

Met Asp Phe Phe Thr Leu Asp Leu Glu His Ile Ala Asp Ala Leu Arg
305                         310                          315                      320

Ala Ile Asp Phe Gly Thr Asp Glu Glu Glu Glu Phe Ile Glu Glu
               325                           330                          335

Glu Asp Gln Glu Glu Glu Glu Ser Thr Glu Gly Lys Glu Glu Gly His
                    340                           345                          350

Gln

<210> SEQ ID NO 123
<211> LENGTH: 1350
<212> TYPE: DNA
<213> ORGANISM: Homo sapiens

<400> SEQUENCE: 123

| | |
|---|---:|
| atggattcag acgacctgca agtcttccag aatgagctca tttgctgcat ttgcgtgaac | 60 |
| tacttcatag atccggtcac cattgactgt gggcacagct tttgcaggcc ctgcctctgc | 120 |
| ctctgctcag aagaaggcag agcaccaatg cgctgcccct cgtgcagaaa aatctcagag | 180 |
| aagcccaact tcaacaccaa tgtggtactc aaaaagctgt cttccctagc cagacagacc | 240 |
| agacctcaga acatcaacag ctcagacaat atctgtgtgc tccatgagga gactaaggag | 300 |
| ctcttctgtg aggctgacaa agagattgctc tgtgggccct gctctgagtc accagagcac | 360 |
| atggctcaca gccacagccc aataggatgg gctgctgagg aatgcaggga gaaacttata | 420 |
| aaggaaatgg actatttatg ggaaatcaat caagagacaa gaaacaatct aaatcaggaa | 480 |
| actagaacat tcattcgtt aaaggactat gtgtcagtaa ggaagaggat aatcactatt | 540 |
| caatatcaaa agatgcctat atttctcgat gaggaggagc aacggcatct gcaggcactg | 600 |
| gaaagagaag cagaagagct tttccaacaa ctacaagaca gtcaagtgag aatgacccaa | 660 |
| catttagaaa ggatgaaaga catgtacaga gagctgtggg agacatgcca cgtgcctgac | 720 |
| gtggagctgc tccaggatgt gagaaatgta tcagcaagga ctgatttggc acagatgcaa | 780 |
| aagccccagc cagtgaaccc agagctcact tcatggtgca taactggagt cctagacatg | 840 |
| ctcaacaact tcagagtgga tagtgctctg agcacgaaaa tgattccttg ctatataagc | 900 |
| ctttctgagg atgtgagata tgtgatattt ggagatgacc atctcagtgc tcccacggat | 960 |
| ccccagggag tggacagctt tgctgtgtgg ggagcgcaag cattcacctc cggcaagcat | 1020 |
| tactgggagg tggatgtgac cctctcctcc aactggattc tgggagtctg tcaagattcc | 1080 |
| aggactgcag atgccaattt cgttattgat tctgatgaaa gattttttttt aatttcctca | 1140 |
| aagaggagca atcactatag tctctccacc aactctccac ctttaattca gtatgtgcaa | 1200 |
| aggcctctgg gtcaagttgg ggtgtttctg gattatgata tggatctgt gagttttttt | 1260 |
| gatgtttcta aaggttctct tatctatggt tttcctcctt cctccttctc ttcccctctg | 1320 |
| aggcctttct tttgctttgg ttgtacatga | 1350 |

<210> SEQ ID NO 124
<211> LENGTH: 449
<212> TYPE: PRT
<213> ORGANISM: Homo sapiens

<400> SEQUENCE: 124

```
Met Asp Ser Asp Asp Leu Gln Val Phe Gln Asn Glu Leu Ile Cys Cys
1               5                   10                  15

Ile Cys Val Asn Tyr Phe Ile Asp Pro Val Thr Ile Asp Cys Gly His
            20                  25                  30

Ser Phe Cys Arg Pro Cys Leu Cys Leu Cys Ser Glu Glu Gly Arg Ala
        35                  40                  45

Pro Met Arg Cys Pro Ser Cys Arg Lys Ile Ser Glu Lys Pro Asn Phe
    50                  55                  60

Asn Thr Asn Val Val Leu Lys Lys Leu Ser Ser Leu Ala Arg Gln Thr
65                  70                  75                  80

Arg Pro Gln Asn Ile Asn Ser Ser Asp Asn Ile Cys Val Leu His Glu
                85                  90                  95

Glu Thr Lys Glu Leu Phe Cys Glu Ala Asp Lys Arg Leu Leu Cys Gly
            100                 105                 110

Pro Cys Ser Glu Ser Pro Glu His Met Ala His Ser His Ser Pro Ile
        115                 120                 125

Gly Trp Ala Ala Glu Cys Arg Glu Lys Leu Ile Lys Glu Met Asp
    130                 135                 140

Tyr Leu Trp Glu Ile Asn Gln Glu Thr Arg Asn Asn Leu Asn Gln Glu
145                 150                 155                 160

Thr Arg Thr Phe His Ser Leu Lys Asp Tyr Val Ser Val Arg Lys Arg
                165                 170                 175

Ile Ile Thr Ile Gln Tyr Gln Lys Met Pro Ile Phe Leu Asp Glu Glu
            180                 185                 190

Glu Gln Arg His Leu Gln Ala Leu Glu Arg Glu Ala Glu Glu Leu Phe
        195                 200                 205

Gln Gln Leu Gln Asp Ser Gln Val Arg Met Thr Gln His Leu Glu Arg
    210                 215                 220

Met Lys Asp Met Tyr Arg Glu Leu Trp Glu Thr Cys His Val Pro Asp
225                 230                 235                 240

Val Glu Leu Leu Gln Asp Val Arg Asn Val Ser Ala Arg Thr Asp Leu
                245                 250                 255

Ala Gln Met Gln Lys Pro Gln Pro Val Asn Pro Glu Leu Thr Ser Trp
            260                 265                 270

Cys Ile Thr Gly Val Leu Asp Met Leu Asn Asn Phe Arg Val Asp Ser
        275                 280                 285

Ala Leu Ser Thr Glu Met Ile Pro Cys Tyr Ile Leu Ser Glu Asp
    290                 295                 300

Val Arg Tyr Val Ile Phe Gly Asp Asp His Leu Ser Ala Pro Thr Asp
305                 310                 315                 320

Pro Gln Gly Val Asp Ser Phe Ala Val Trp Gly Ala Gln Ala Phe Thr
                325                 330                 335

Ser Gly Lys His Tyr Trp Glu Val Asp Val Thr Leu Ser Ser Asn Trp
            340                 345                 350

Ile Leu Gly Val Cys Gln Asp Ser Arg Thr Ala Asp Ala Asn Phe Val
        355                 360                 365

Ile Asp Ser Asp Glu Arg Phe Phe Leu Ile Ser Ser Lys Arg Ser Asn
    370                 375                 380
```

```
His Tyr Ser Leu Ser Thr Asn Ser Pro Pro Leu Ile Gln Tyr Val Gln
385                 390                 395                 400

Arg Pro Leu Gly Gln Val Gly Val Phe Leu Asp Tyr Asp Asn Gly Ser
            405                 410                 415

Val Ser Phe Phe Asp Val Ser Lys Gly Ser Leu Ile Tyr Gly Phe Pro
        420                 425                 430

Pro Ser Ser Phe Ser Ser Pro Leu Arg Pro Phe Phe Cys Phe Gly Cys
            435                 440                 445

Thr
```

```
<210> SEQ ID NO 125
<211> LENGTH: 1554
<212> TYPE: DNA
<213> ORGANISM: Homo sapiens

<400> SEQUENCE: 125
atggccgcgc agctgctgga ggagaagctg acctgcgcca tctgcctggg gctctaccag      60
gacccagtga cgctgccctg cggccacaac ttctgcgggg cctgcatccg ggactggtgg     120
gaccgctgcg gaaaggcgtg ccccgagtgc cgggagccct ttcccgacgg cgccgagctg     180
cgccgcaacg tggccctcag cggcgtgctg gaggtggtgc gcgccgggcc cgcccgggat     240
cccggccccg atcccggccc cggccccgac cctgccgcgc gctgccccg ccacgggcgg      300 ccgctggagc tcttctgccg gaccgagggc cgctgtgtgt gcagcgtgtg caccgtgcgc     360
gagtgtcgcc tccacgagcg ggcgctgctg gatgccgagc gcctcaagcg cgaggcccag     420
ctgagagcca gcctggaggt tacccagcag caggccaccc aggccgaagg ccagctacta     480
gagctgcgca agcaaagcag ccagatccag aactcggcct gcatcttggc ctcctgggtc     540
tccggcaagt tcagcagcct gctacaggcc ctggaaatac agcacacgac agcactgagg     600
agcatcgagg tggccaagac gcaggcgctg gcacaggctc gagacgagga gcagcggctg     660
cgggtccatt tggaggctgt ggctcgccat ggctgcagga tccgggagct cctggagcag     720
gtggatgagc agaccttcct gcaggaatcg cagctcctcc agccccagg gcctcttggg      780 ccactgaccc ctctgcagtg ggatgaagac caacagctgg gtgacctgaa gcagttgcta     840
agccggctgt gtggcctcct cttggaagag gggagccacc tggggcacc agccaagcct      900 gtggacttag ccccgtgga ggccccaggt ccctggcac cggtcccaag cacagtttgt       960
ccactgagga ggaaactctg cagaattat cgcaatctga cctttgatcc agtcagcgcc     1020
aaccgtcact tctatctgtc gcgccaggac cagcaggtga agcactgtcg tcagtcccgg    1080
ggcccaggcg ggcccggcag ctttgagctc tggcaggtgc aatgtgccca gagcttccag    1140
gccgggcacc actactggga ggtgcgcgcg tcagaccact cggtgacact gggcgtctcc    1200
tacccgcaac tgccacggtg caggctgggg ccccacacag acaacattgg ccggggaccc    1260
tgctcctggg ggctctgcgt ccaggaggac agcctccagg cctggcacaa cggggaagcc    1320
cagcgcctcc caggggtgtc agggcggctc ctgggcatgg atttggacct ggcctcaggc    1380
tgcctcacct tctacagcct ggagcccag acccagcccc tgtacacctt ccatgccctc    1440
ttcaaccagc cctcacccc cgtcttctgg ctcctcgagg gtaggaccct gaccctgtgc    1500
catcagccag gggctgtgtt ccctctgggg ccccaggaag aggtgctcag ctga         1554
```

```
<210> SEQ ID NO 126
<211> LENGTH: 517
<212> TYPE: PRT
```

<213> ORGANISM: Homo sapiens

<400> SEQUENCE: 126

```
Met Ala Ala Gln Leu Glu Glu Lys Leu Thr Cys Ala Ile Cys Leu
1               5                   10                  15

Gly Leu Tyr Gln Asp Pro Val Thr Leu Pro Cys Gly His Asn Phe Cys
            20                  25                  30

Gly Ala Cys Ile Arg Asp Trp Trp Asp Arg Cys Gly Lys Ala Cys Pro
        35                  40                  45

Glu Cys Arg Glu Pro Phe Pro Asp Gly Ala Glu Leu Arg Arg Asn Val
    50                  55                  60

Ala Leu Ser Gly Val Leu Glu Val Val Arg Ala Gly Pro Ala Arg Asp
65                  70                  75                  80

Pro Gly Pro Asp Pro Gly Pro Gly Pro Asp Pro Ala Ala Arg Cys Pro
                85                  90                  95

Arg His Gly Arg Pro Leu Glu Leu Phe Cys Arg Thr Glu Gly Arg Cys
                100                 105                 110

Val Cys Ser Val Cys Thr Val Arg Glu Cys Arg Leu His Glu Arg Ala
            115                 120                 125

Leu Leu Asp Ala Glu Arg Leu Lys Arg Glu Ala Gln Leu Arg Ala Ser
130                 135                 140

Leu Glu Val Thr Gln Gln Ala Thr Gln Ala Glu Gly Gln Leu Leu
145                 150                 155                 160

Glu Leu Arg Lys Gln Ser Ser Gln Ile Gln Asn Ser Ala Cys Ile Leu
                165                 170                 175

Ala Ser Trp Val Ser Gly Lys Phe Ser Ser Leu Leu Gln Ala Leu Glu
            180                 185                 190

Ile Gln His Thr Thr Ala Leu Arg Ser Ile Glu Val Ala Lys Thr Gln
        195                 200                 205

Ala Leu Ala Gln Ala Arg Asp Glu Glu Gln Arg Leu Arg Val His Leu
    210                 215                 220

Glu Ala Val Ala Arg His Gly Cys Arg Ile Arg Glu Leu Leu Glu Gln
225                 230                 235                 240

Val Asp Glu Gln Thr Phe Leu Gln Glu Ser Gln Leu Leu Gln Pro Pro
                245                 250                 255

Gly Pro Leu Gly Pro Leu Thr Pro Leu Gln Trp Asp Glu Asp Gln Gln
            260                 265                 270

Leu Gly Asp Leu Lys Gln Leu Leu Ser Arg Leu Cys Gly Leu Leu Leu
        275                 280                 285

Glu Glu Gly Ser His Pro Gly Ala Pro Ala Lys Pro Val Asp Leu Ala
    290                 295                 300

Pro Val Glu Ala Pro Gly Pro Leu Ala Pro Val Pro Ser Thr Val Cys
305                 310                 315                 320

Pro Leu Arg Arg Lys Leu Trp Gln Asn Tyr Arg Asn Leu Thr Phe Asp
                325                 330                 335

Pro Val Ser Ala Asn Arg His Phe Tyr Leu Ser Arg Gln Asp Gln Gln
            340                 345                 350

Val Lys His Cys Arg Gln Ser Arg Gly Pro Gly Gly Pro Gly Ser Phe
        355                 360                 365

Glu Leu Trp Gln Val Gln Cys Ala Gln Ser Phe Gln Ala Gly His His
    370                 375                 380

Tyr Trp Glu Val Arg Ala Ser Asp His Ser Val Thr Leu Gly Val Ser
385                 390                 395                 400
```

Tyr Pro Gln Leu Pro Arg Cys Arg Leu Gly Pro His Thr Asp Asn Ile
            405                 410                 415

Gly Arg Gly Pro Cys Ser Trp Gly Leu Cys Val Gln Glu Asp Ser Leu
        420                 425                 430

Gln Ala Trp His Asn Gly Glu Ala Gln Arg Leu Pro Gly Val Ser Gly
            435                 440                 445

Arg Leu Leu Gly Met Asp Leu Asp Leu Ala Ser Gly Cys Leu Thr Phe
        450                 455                 460

Tyr Ser Leu Glu Pro Gln Thr Gln Pro Leu Tyr Thr Phe His Ala Leu
465                 470                 475                 480

Phe Asn Gln Pro Leu Thr Pro Val Phe Trp Leu Leu Glu Gly Arg Thr
                485                 490                 495

Leu Thr Leu Cys His Gln Pro Gly Ala Val Phe Pro Leu Gly Pro Gln
            500                 505                 510

Glu Glu Val Leu Ser
        515

<210> SEQ ID NO 127
<211> LENGTH: 3651
<212> TYPE: DNA
<213> ORGANISM: Homo sapiens

<400> SEQUENCE: 127

| | |
|---|---|
| atggccagga actgctctga gtgcaaggag aagagggcag cacatatcct ctgcacctac | 60 |
| tgcaatcgct ggctgtgcag ctcttgcaca gaggaacacc gacacagccc tgtccccggg | 120 |
| ggcccattct ttcctcgggc ccagaaggga tctccaggag tgaatggtgg tcccggagac | 180 |
| ttcaccttgt attgtcctct acacacacag gaagtactca agctattctg tgagacatgt | 240 |
| gatatgctca cttgccatag ctgcctagtg gtggaacaca agaacacag gtgcagacat | 300 |
| gttgaagaag ttttgcaaaa ccagaggatg cttctggaag gtgtgactac acaggtggca | 360 |
| cataagaaat ccagtctaca gacatctgca agcaaattg aggacaggat ttttgaagtg | 420 |
| aagcatcagc ataggaaggt ggaaaaccag atcaaaatgg ccaagatggt tctgatgaat | 480 |
| gagctgaaca acaggccaa tgggctaata gaggaattag aggggattac taatgagaga | 540 |
| aagcggaagc tggaacagca gttacagagc atcatggttc tcaaccgtca gtttgagcat | 600 |
| gtgcagaatt tcatcaactg gctgtctgc agcaaaacca gtgtccctt tcttttcagc | 660 |
| aaagagctga ttgtgtttca gatgcagcga ttgctggaga caagttgtaa cacagatcct | 720 |
| ggctcccctt ggagtatcag attcacctgg gagcctaact tctggaccaa gcagctagct | 780 |
| tctcttggct gcataactac tgaaggtgga caaatgtcca gggcagatgc tcctgcttat | 840 |
| ggaggcttac aggggtcatc accctttat caaagccacc agtctccagt ggctcagcaa | 900 |
| gaggctctta gccacccctc acacaagttc cagtctccag cagtgtgctc ctcatctgtg | 960 |
| tgctgctccc actgctcccc agtctcgcct tccctcaaag ccaggtccc cccacccagc | 1020 |
| atacacccag cccacagctt caggcagccc cctgagatgg tgccccagca gctggggtct | 1080 |
| ctgcagtgct ctgccctgct gcccagggag aaagagctgg cctgcagccc tcatccacca | 1140 |
| aagctgctgc agccctggct ggaaaccag cccccgtgg agcaggagag cacatcccag | 1200 |
| cggctggggc agcagctgac ttcccagccc gtgtgcattg tcccccaca ggatgttcag | 1260 |
| caaggagccc atgcccagcc caccttacag acaccctcta tccaagtcca gtttggccac | 1320 |
| caccagaagc tgaagctcag tcactttcag cagcagccac agcagcagct accacctcca | 1380 |
| ccaccacccc tcccccatcc cccacctccc ctccccctc cccacagca gccacaccca | 1440 |

| | |
|---|---|
| cctcttcctc catcccagca tctggcttct agtcagcacg agagccctcc tggccctgcc | 1500 |
| tgttctcaga acatggacat aatgcatcac aagtttgagc tggaggaaat gcagaaggac | 1560 |
| ttggagcttc ttctccaggc tcaacagccc agcctgcaac tgagtcagac caaatctcct | 1620 |
| cagcatcttc agcaaaccat tgtggggcag atcaactaca tcgtgaggca gccagcacct | 1680 |
| gtccagtccc agagccagga ggagaccctg caggctacag atgagccccc agcatctcag | 1740 |
| ggctcaaagc cggctctccc tcttgacaag aatactgctg ctgccttgcc ccaggcgtct | 1800 |
| ggggaagaaa ccctctcag tgtccccca gtggacagca ccatccagca ctcctctcca | 1860 |
| aatgtggtga gaaagcactc cacctcgctg agcatcatgg gcttttccaa cactctggag | 1920 |
| atggagttgt catctaccag gttggagagg cccctagagc cacagatcca gagtgtgagc | 1980 |
| aacctgacag ctggtgcccc ccaggcagta ccaagcctgc tgagtgctcc ccccaaaatg | 2040 |
| gtgtccagcc tgacaagtgt tcaaaaccag gccatgccca gcctgacaac cagtcaccta | 2100 |
| cagactgtgc ccagccttgt gcatagcaca ttccagtcca tgcccaacct gataagtgac | 2160 |
| tcccctcagg ctatggcaag cctggcaagt gatcaccctc aggctgggcc cagcctaatg | 2220 |
| tctggtcaca cccaggctgt gccgagtctg gcaacttgtc ctctgcagag catccctcca | 2280 |
| gtttctgaca tgcagccaga aactgggtcc agctccagtt ctggccgaac ttcagggagc | 2340 |
| ctgtgtccca gagatggggc tgatccctcc ctggagaatg ctctgtgtaa ggtaaaactg | 2400 |
| gaggagccaa ttaacctctc tgtgaagaaa cctccactgg cgccagtggt cagcacgtct | 2460 |
| acagctctgc agcagtacca gaacccaaaa gagtgtgaga atttgaaca aggagccta | 2520 |
| gagctggatg caaaagagaa ccagagcatc agagccttca atagtgagca taagattccc | 2580 |
| tatgtgcgac tggagcgact caagatctgt gctgcctcct caggagagat gcctgtgttc | 2640 |
| aaactgaagc cacagaagaa tgatcaggat gggagcttcc tgctgatcat cgagtgtggc | 2700 |
| actgagtcct ccagcatgtc cattaaggtc agccaggaca gactgtctga ggccacccag | 2760 |
| gccccaggtc tggagggaag aaaggtcact gtcacttctt tggctgggca gcggccacca | 2820 |
| gaagtggagg gcacatctcc tgaagaacac agactcattc ctcgaacccc aggagccaag | 2880 |
| aagggccccc cagccccaat agagaatgag gacttctgtg ctgtttgcct caatggcgga | 2940 |
| gagttactgt gctgtgaccg ctgccccaaa gtgttccacc tctcctgcca tgtgccagcc | 3000 |
| ttgctcagct tccagggg agagtggggtg tgtaccttgt gccgcagcct gacccagccc | 3060 |
| gagatggagt acgactgtga gaatgcctgc tataaccagc ctggaatgcg ggcatctcct | 3120 |
| ggcctaagca tgtatgacca agaagtgt gagaagctgg tattgtcctt gtgctgcaat | 3180 |
| aacctcagcc tgcccttcca tgaacctgtc agcccctgg cccggcatta ttaccagatt | 3240 |
| atcaagaggc ccatggacct gtcaatcatc cggaggaagc tgcaaaagaa ggacccagct | 3300 |
| cactatacca ccccagagga ggtggtatca gatgtgcgcc tcatgttctg gaactgtgct | 3360 |
| aagttcaatt atcctgactc cgaggttgca gaggctggcc gctgcctgga agtgttcttt | 3420 |
| gagggctggt tgaaggagat ctacccggag aaacggttg cccagccaag gcaggaggac | 3480 |
| tcagactccg aggaggtgtc tagtgagagt ggatgttcca ctcccagggg cttcccgtgg | 3540 |
| cctccctaca tgcaggaggg catccaaccc aagaggcggc gacgacatat ggagaatgaa | 3600 |
| agagcaaaaa gaatgtcatt tcgcctggcc aacagcatct ctcaggtgtg a | 3651 |

<210> SEQ ID NO 128
<211> LENGTH: 1216
<212> TYPE: PRT

<213> ORGANISM: Homo sapiens

<400> SEQUENCE: 128

```
Met Ala Arg Asn Cys Ser Glu Cys Lys Glu Lys Arg Ala Ala His Ile
1               5                   10                  15

Leu Cys Thr Tyr Cys Asn Arg Trp Leu Cys Ser Ser Cys Thr Glu Glu
            20                  25                  30

His Arg His Ser Pro Val Pro Gly Gly Pro Phe Phe Pro Arg Ala Gln
        35                  40                  45

Lys Gly Ser Pro Gly Val Asn Gly Gly Pro Gly Asp Phe Thr Leu Tyr
    50                  55                  60

Cys Pro Leu His Thr Gln Glu Val Leu Lys Leu Phe Cys Glu Thr Cys
65                  70                  75                  80

Asp Met Leu Thr Cys His Ser Cys Leu Val Val Glu His Lys Glu His
                85                  90                  95

Arg Cys Arg His Val Glu Glu Val Leu Gln Asn Gln Arg Met Leu Leu
            100                 105                 110

Glu Gly Val Thr Thr Gln Val Ala His Lys Lys Ser Ser Leu Gln Thr
        115                 120                 125

Ser Ala Lys Gln Ile Glu Asp Arg Ile Phe Glu Val Lys His Gln His
    130                 135                 140

Arg Lys Val Glu Asn Gln Ile Lys Met Ala Lys Met Val Leu Met Asn
145                 150                 155                 160

Glu Leu Asn Lys Gln Ala Asn Gly Leu Ile Glu Glu Leu Gly Ile
                165                 170                 175

Thr Asn Glu Arg Lys Arg Lys Leu Glu Gln Leu Gln Ser Ile Met
                180                 185                 190

Val Leu Asn Arg Gln Phe Glu His Val Gln Asn Phe Ile Asn Trp Ala
            195                 200                 205

Val Cys Ser Lys Thr Ser Val Pro Phe Leu Phe Ser Lys Glu Leu Ile
            210                 215                 220

Val Phe Gln Met Gln Arg Leu Leu Glu Thr Ser Cys Asn Thr Asp Pro
225                 230                 235                 240

Gly Ser Pro Trp Ser Ile Arg Phe Thr Trp Glu Pro Asn Phe Trp Thr
                245                 250                 255

Lys Gln Leu Ala Ser Leu Gly Cys Ile Thr Thr Glu Gly Gln Met
                260                 265                 270

Ser Arg Ala Asp Ala Pro Ala Tyr Gly Gly Leu Gln Gly Ser Ser Pro
        275                 280                 285

Phe Tyr Gln Ser His Gln Ser Pro Val Ala Gln Gln Glu Ala Leu Ser
    290                 295                 300

His Pro Ser His Lys Phe Gln Ser Pro Ala Val Cys Ser Ser Ser Val
305                 310                 315                 320

Cys Cys Ser His Cys Ser Pro Val Ser Pro Ser Leu Lys Gly Gln Val
                325                 330                 335

Pro Pro Pro Ser Ile His Pro Ala His Ser Phe Arg Gln Pro Pro Glu
                340                 345                 350

Met Val Pro Gln Gln Leu Gly Ser Leu Gln Cys Ser Ala Leu Leu Pro
            355                 360                 365

Arg Glu Lys Glu Leu Ala Cys Ser Pro His Pro Lys Leu Leu Gln
        370                 375                 380

Pro Trp Leu Glu Thr Gln Pro Pro Val Glu Gln Glu Ser Thr Ser Gln
385                 390                 395                 400
```

```
Arg Leu Gly Gln Gln Leu Thr Ser Gln Pro Val Cys Ile Val Pro Pro
                    405                 410                 415

Gln Asp Val Gln Gln Gly Ala His Ala Gln Pro Thr Leu Gln Thr Pro
            420                 425                 430

Ser Ile Gln Val Gln Phe Gly His His Gln Lys Leu Lys Leu Ser His
            435                 440                 445

Phe Gln Gln Gln Pro Gln Gln Leu Pro Pro Pro Pro Pro Leu
        450                 455                 460

Pro His Pro Pro Pro Leu Pro Pro Pro Gln Gln Pro His Pro
465                 470                 475                 480

Pro Leu Pro Pro Ser Gln His Leu Ala Ser Gln His Glu Ser Pro
                485                 490                 495

Pro Gly Pro Ala Cys Ser Gln Asn Met Asp Ile Met His His Lys Phe
                500                 505                 510

Glu Leu Glu Glu Met Gln Lys Asp Leu Glu Leu Leu Gln Ala Gln
            515                 520                 525

Gln Pro Ser Leu Gln Leu Ser Gln Thr Lys Ser Pro Gln His Leu Gln
            530                 535                 540

Gln Thr Ile Val Gly Gln Ile Asn Tyr Ile Val Arg Gln Pro Ala Pro
545                 550                 555                 560

Val Gln Ser Gln Ser Gln Glu Glu Thr Leu Gln Ala Thr Asp Glu Pro
                565                 570                 575

Pro Ala Ser Gln Gly Ser Lys Pro Ala Leu Pro Leu Asp Lys Asn Thr
                580                 585                 590

Ala Ala Ala Leu Pro Gln Ala Ser Gly Glu Glu Thr Pro Leu Ser Val
                595                 600                 605

Pro Pro Val Asp Ser Thr Ile Gln His Ser Ser Pro Asn Val Val Arg
610                 615                 620

Lys His Ser Thr Ser Leu Ser Ile Met Gly Phe Ser Asn Thr Leu Glu
625                 630                 635                 640

Met Glu Leu Ser Ser Thr Arg Leu Glu Arg Pro Leu Glu Pro Gln Ile
                645                 650                 655

Gln Ser Val Ser Asn Leu Thr Ala Gly Ala Pro Gln Ala Val Pro Ser
                660                 665                 670

Leu Leu Ser Ala Pro Pro Lys Met Val Ser Ser Leu Thr Ser Val Gln
                675                 680                 685

Asn Gln Ala Met Pro Ser Leu Thr Thr Ser His Leu Gln Thr Val Pro
            690                 695                 700

Ser Leu Val His Ser Thr Phe Gln Ser Met Pro Asn Leu Ile Ser Asp
705                 710                 715                 720

Ser Pro Gln Ala Met Ala Ser Leu Ala Ser Asp His Pro Gln Ala Gly
                725                 730                 735

Pro Ser Leu Met Ser Gly His Thr Gln Ala Val Pro Ser Leu Ala Thr
            740                 745                 750

Cys Pro Leu Gln Ser Ile Pro Pro Val Ser Asp Met Gln Pro Glu Thr
            755                 760                 765

Gly Ser Ser Ser Ser Gly Arg Thr Ser Gly Ser Leu Cys Pro Arg
        770                 775                 780

Asp Gly Ala Asp Pro Ser Leu Glu Asn Ala Leu Cys Lys Val Lys Leu
785                 790                 795                 800

Glu Glu Pro Ile Asn Leu Ser Val Lys Lys Pro Pro Leu Ala Pro Val
                805                 810                 815

Val Ser Thr Ser Thr Ala Leu Gln Gln Tyr Gln Asn Pro Lys Glu Cys
```

```
                820                 825                 830
Glu Asn Phe Glu Gln Gly Ala Leu Glu Leu Asp Ala Lys Glu Asn Gln
            835                 840                 845

Ser Ile Arg Ala Phe Asn Ser Glu His Lys Ile Pro Tyr Val Arg Leu
        850                 855                 860

Glu Arg Leu Lys Ile Cys Ala Ala Ser Ser Gly Glu Met Pro Val Phe
865                 870                 875                 880

Lys Leu Lys Pro Gln Lys Asn Asp Gln Asp Gly Ser Phe Leu Leu Ile
                885                 890                 895

Ile Glu Cys Gly Thr Glu Ser Ser Ser Met Ser Ile Lys Val Ser Gln
            900                 905                 910

Asp Arg Leu Ser Glu Ala Thr Gln Ala Pro Gly Leu Glu Gly Arg Lys
        915                 920                 925

Val Thr Val Thr Ser Leu Ala Gly Gln Arg Pro Glu Val Glu Gly
    930                 935                 940

Thr Ser Pro Glu Glu His Arg Leu Ile Pro Arg Thr Pro Gly Ala Lys
945                 950                 955                 960

Lys Gly Pro Pro Ala Pro Ile Glu Asn Glu Asp Phe Cys Ala Val Cys
                965                 970                 975

Leu Asn Gly Gly Glu Leu Leu Cys Cys Asp Arg Cys Pro Lys Val Phe
            980                 985                 990

His Leu Ser Cys His Val Pro Ala  Leu Leu Ser Phe Pro  Gly Gly Glu
        995                 1000                1005

Trp Val  Cys Thr Leu Cys Arg  Ser Leu Thr Gln Pro  Glu Met Glu
    1010                1015                1020

Tyr Asp  Cys Glu Asn Ala Cys  Tyr Asn Gln Pro Gly  Met Arg Ala
    1025                1030                1035

Ser Pro  Gly Leu Ser Met Tyr  Asp Gln Lys Lys Cys  Glu Lys Leu
    1040                1045                1050

Val Leu  Ser Leu Cys Cys Asn  Asn Leu Ser Leu Pro  Phe His Glu
    1055                1060                1065

Pro Val  Ser Pro Leu Ala Arg  His Tyr Tyr Gln Ile  Ile Lys Arg
    1070                1075                1080

Pro Met  Asp Leu Ser Ile Ile  Arg Arg Lys Leu Gln  Lys Lys Asp
    1085                1090                1095

Pro Ala  His Tyr Thr Thr Pro  Glu Glu Val Val Ser  Asp Val Arg
    1100                1105                1110

Leu Met  Phe Trp Asn Cys Ala  Lys Phe Asn Tyr Pro  Asp Ser Glu
    1115                1120                1125

Val Ala  Glu Ala Gly Arg Cys  Leu Glu Val Phe Phe  Glu Gly Trp
    1130                1135                1140

Leu Lys  Glu Ile Tyr Pro Glu  Lys Arg Phe Ala Gln  Pro Arg Gln
    1145                1150                1155

Glu Asp  Ser Asp Ser Glu Glu  Val Ser Ser Glu Ser  Gly Cys Ser
    1160                1165                1170

Thr Pro  Gln Gly Phe Pro Trp  Pro Pro Tyr Met Gln  Glu Gly Ile
    1175                1180                1185

Gln Pro  Lys Arg Arg Arg Arg  His Met Glu Asn Glu  Arg Ala Lys
    1190                1195                1200

Arg Met  Ser Phe Arg Leu Ala  Asn Ser Ile Ser Gln  Val
    1205                1210                1215

<210> SEQ ID NO 129
```

<211> LENGTH: 2352
<212> TYPE: DNA
<213> ORGANISM: Homo sapiens

<400> SEQUENCE: 129

| | | | | | |
|---|---|---|---|---|---|
| atggaggaag | agctgaagtg | tcccgtgtgc | ggctctctgt | ttcgggagcc | tatcatcctg | 60 |
| ccctgttccc | acaatgtctg | cctgccttgc | gctcgcacca | tcgcggtgca | gaccccggac | 120 |
| ggtgagcagc | acctgcccca | gccgctcctg | ctttcccggg | gatcggggct | gcaggcgggc | 180 |
| gccgccgccg | ctgcctctct | ggagcacgac | gctgcggctg | gcccggcctg | cggcggtgca | 240 |
| ggcgggagtg | cagctggcgg | cctcggcggc | ggtgcgggag | gtggcggaga | ccacgcggac | 300 |
| aagctcagct | tgtacagcga | gacagacagc | ggctacgggt | cctacacccc | gagcctcaag | 360 |
| tcccccaacg | gggttcgcgt | gctgcccatg | gtgcccgcac | cacccggctc | tcggctgcg | 420 |
| gcggctcggg | gtgccgcctg | ctcctcgctg | tcctcgtctt | cgagctccat | cacgtgcccg | 480 |
| cagtgccacc | gcagcgcatc | cctggaccac | cgcggcctgc | gcggcttcca | gcgcaaccgg | 540 |
| ctgctcgagg | ccatcgtgca | gcggtaccag | cagggccgcg | gggccgtgcc | ggggacgtct | 600 |
| gcagccgcgg | cggtgccat | ctgccagctg | tgcgaccgca | ccccgccaga | gccagcagcc | 660 |
| acgctctgcg | agcagtgcga | cgtcctctac | tgctctgcct | gccagctcaa | gtgccatcca | 720 |
| tcccggggac | ccttcgccaa | gcatcgcctg | gtgcagccgc | cgccgccgcc | gccgccgccc | 780 |
| gccgaggcag | cctccgggcc | cactggcacc | gcccagggcg | ccccagcgg | aggcggcggc | 840 |
| tgcaagagcc | cggaggcgc | gggggcgggg | gcgactgggg | gcagcacggc | ccgcaagttc | 900 |
| cccacgtgtc | ccgagcatga | atggagaac | tacagcatgt | actgcgtgag | ctgtcgaacc | 960 |
| ccggtgtgtt | atctgtgcct | ggaggagggc | cggcacgcca | agcacgaggt | gaagccgctg | 1020 |
| ggggccatgt | ggaagcagca | caaggcacaa | ctatctcagg | ccttaaatgg | agtttcagat | 1080 |
| aaggcaaagg | aagcaaagga | gtttctggtt | cagctaaaga | acatattgca | gcagatccag | 1140 |
| gaaaacggac | tggactacga | agcctgcctc | gttgctcagt | gtgatgccct | tgtggatgct | 1200 |
| ttaactcgtc | agaaagccaa | gctgctcacc | aaggtgacta | agagagggga | acacaagttg | 1260 |
| aagatggttt | gggaccagat | caatcactgc | acattgaagc | tgcgtcagtc | caccggactg | 1320 |
| atggagtact | gcctggaggt | gatcaaggag | aacgacccct | ccgggttctt | acagatctca | 1380 |
| gatgctctga | tcaagcgcgt | ccaggtgtct | caggagcagt | gggtcaaagg | cgccctggag | 1440 |
| ccgaaagtgt | ctgcggagtt | tgatctgact | ttggacagcg | agccgctgct | gcaggccatc | 1500 |
| caccagctgg | acttcattca | gatgaaatgt | agggtgccac | ccgtccccct | actgcagctg | 1560 |
| gagaaatgct | gcacccgtaa | caacagcgtc | acgctggcct | ggaggatgcc | acccttcacc | 1620 |
| cacagccccg | tggacggcta | catcctggag | ctggacgacg | tgccggggg | acagttccgg | 1680 |
| gaagtgtacg | tcggtaagga | ctttgtgt | accatcgacg | tcttcactt | caacagcacc | 1740 |
| tacaacgccc | gagtcaaagc | tttcaactct | tctggtgtcg | ggccttacag | taaaactgtc | 1800 |
| gtcctgcaga | catccgatgt | ggcctggttc | acatttgacc | caactctgg | gcatcgggac | 1860 |
| atcatttat | ccaatgacaa | ccagacagcc | acctgcagca | gctatgacga | ccgggtggtg | 1920 |
| ctgggcacag | ctgcgttctc | caagggcgtg | cactactggg | agctgcacgt | ggaccggtac | 1980 |
| gacaaccacc | cagaccccgc | cttcggggtg | gccagggcca | gcgtggtcaa | ggacatgatg | 2040 |
| ctgggcaagg | atgacaaggc | ctgggccatg | tatgtggaca | caaccgcag | ctggttcatg | 2100 |
| cactgcaact | cccacaccaa | caggacggaa | ggtggcgtgt | gcaggggggc | caccgtgggc | 2160 |
| gtgctgctgg | acctgaataa | gcacactctc | accttcttca | tcaacgggca | gcagcagggc | 2220 |

-continued

```
cccacagcct tcagccacgt ggacggggtc ttcatgccag ccctcagcct caaccgcaac    2280
gtgcaggtca ccctgcacac aggattggaa gtgccgacta acctggggcg gccaaagctg    2340
tcaggcaatt ag                                                        2352
```

<210> SEQ ID NO 130
<211> LENGTH: 783
<212> TYPE: PRT
<213> ORGANISM: Homo sapiens

<400> SEQUENCE: 130

```
Met Glu Glu Leu Lys Cys Pro Val Cys Gly Ser Leu Phe Arg Glu
1               5                   10                  15

Pro Ile Ile Leu Pro Cys Ser His Asn Val Cys Leu Pro Cys Ala Arg
            20                  25                  30

Thr Ile Ala Val Gln Thr Pro Asp Gly Glu Gln His Leu Pro Gln Pro
        35                  40                  45

Leu Leu Leu Ser Arg Gly Ser Gly Leu Gln Ala Gly Ala Ala Ala
    50                  55                  60

Ala Ser Leu Glu His Asp Ala Ala Ala Gly Pro Ala Cys Gly Gly Ala
65                  70                  75                  80

Gly Gly Ser Ala Ala Gly Gly Leu Gly Gly Gly Ala Gly Gly Gly Gly
                85                  90                  95

Asp His Ala Asp Lys Leu Ser Leu Tyr Ser Glu Thr Asp Ser Gly Tyr
            100                 105                 110

Gly Ser Tyr Thr Pro Ser Leu Lys Ser Pro Asn Gly Val Arg Val Leu
        115                 120                 125

Pro Met Val Pro Ala Pro Pro Gly Ser Ala Ala Ala Ala Arg Gly
    130                 135                 140

Ala Ala Cys Ser Ser Leu Ser Ser Ser Ser Ser Ile Thr Cys Pro
145                 150                 155                 160

Gln Cys His Arg Ser Ala Ser Leu Asp His Arg Gly Leu Arg Gly Phe
                165                 170                 175

Gln Arg Asn Arg Leu Leu Glu Ala Ile Val Gln Arg Tyr Gln Gln Gly
            180                 185                 190

Arg Gly Ala Val Pro Gly Thr Ser Ala Ala Ala Val Ala Ile Cys
        195                 200                 205

Gln Leu Cys Asp Arg Thr Pro Pro Glu Pro Ala Ala Thr Leu Cys Glu
    210                 215                 220

Gln Cys Asp Val Leu Tyr Cys Ser Ala Cys Gln Leu Lys Cys His Pro
225                 230                 235                 240

Ser Arg Gly Pro Phe Ala Lys His Arg Leu Val Gln Pro Pro Pro
                245                 250                 255

Pro Pro Pro Pro Ala Glu Ala Ala Ser Gly Pro Thr Gly Thr Ala Gln
            260                 265                 270

Gly Ala Pro Ser Gly Gly Gly Cys Lys Ser Pro Gly Gly Ala Gly
        275                 280                 285

Ala Gly Ala Thr Gly Gly Ser Thr Ala Arg Lys Phe Pro Thr Cys Pro
    290                 295                 300

Glu His Glu Met Glu Asn Tyr Ser Met Tyr Cys Val Ser Cys Arg Thr
305                 310                 315                 320

Pro Val Cys Tyr Leu Cys Leu Glu Gly Arg His Ala Lys His Glu
                325                 330                 335

Val Lys Pro Leu Gly Ala Met Trp Lys Gln His Lys Ala Gln Leu Ser
```

```
                340                 345                 350
Gln Ala Leu Asn Gly Val Ser Asp Lys Ala Lys Glu Ala Lys Glu Phe
            355                 360                 365
Leu Val Gln Leu Lys Asn Ile Leu Gln Gln Ile Gln Glu Asn Gly Leu
            370                 375                 380
Asp Tyr Glu Ala Cys Leu Val Ala Gln Cys Asp Ala Leu Val Asp Ala
385                 390                 395                 400
Leu Thr Arg Gln Lys Ala Lys Leu Leu Thr Lys Val Thr Lys Glu Arg
                405                 410                 415
Glu His Lys Leu Lys Met Val Trp Asp Gln Ile Asn His Cys Thr Leu
            420                 425                 430
Lys Leu Arg Gln Ser Thr Gly Leu Met Glu Tyr Cys Leu Glu Val Ile
            435                 440                 445
Lys Glu Asn Asp Pro Ser Gly Phe Leu Gln Ile Ser Asp Ala Leu Ile
            450                 455                 460
Lys Arg Val Gln Val Ser Gln Glu Gln Trp Val Lys Gly Ala Leu Glu
465                 470                 475                 480
Pro Lys Val Ser Ala Glu Phe Asp Leu Thr Leu Asp Ser Glu Pro Leu
                485                 490                 495
Leu Gln Ala Ile His Gln Leu Asp Phe Ile Gln Met Lys Cys Arg Val
            500                 505                 510
Pro Pro Val Pro Leu Leu Gln Leu Glu Lys Cys Cys Thr Arg Asn Asn
            515                 520                 525
Ser Val Thr Leu Ala Trp Arg Met Pro Pro Phe Thr His Ser Pro Val
            530                 535                 540
Asp Gly Tyr Ile Leu Glu Leu Asp Asp Gly Ala Gly Gly Gln Phe Arg
545                 550                 555                 560
Glu Val Tyr Val Gly Lys Glu Thr Leu Cys Thr Ile Asp Gly Leu His
                565                 570                 575
Phe Asn Ser Thr Tyr Asn Ala Arg Val Lys Ala Phe Asn Ser Ser Gly
            580                 585                 590
Val Gly Pro Tyr Ser Lys Thr Val Leu Gln Thr Ser Asp Val Ala
            595                 600                 605
Trp Phe Thr Phe Asp Pro Asn Ser Gly His Arg Asp Ile Ile Leu Ser
            610                 615                 620
Asn Asp Asn Gln Thr Ala Thr Cys Ser Ser Tyr Asp Asp Arg Val Val
625                 630                 635                 640
Leu Gly Thr Ala Ala Phe Ser Lys Gly Val His Tyr Trp Glu Leu His
                645                 650                 655
Val Asp Arg Tyr Asp Asn His Pro Asp Pro Ala Phe Gly Val Ala Arg
            660                 665                 670
Ala Ser Val Val Lys Asp Met Met Leu Gly Lys Asp Asp Lys Ala Trp
            675                 680                 685
Ala Met Tyr Val Asp Asn Asn Arg Ser Trp Phe Met His Cys Asn Ser
            690                 695                 700
His Thr Asn Arg Thr Glu Gly Gly Val Cys Lys Gly Ala Thr Val Gly
705                 710                 715                 720
Val Leu Leu Asp Leu Asn Lys His Thr Leu Thr Phe Phe Ile Asn Gly
                725                 730                 735
Gln Gln Gln Gly Pro Thr Ala Phe Ser His Val Asp Gly Val Phe Met
            740                 745                 750
Pro Ala Leu Ser Leu Asn Arg Asn Val Gln Val Thr Leu His Thr Gly
            755                 760                 765
```

Leu Glu Val Pro Thr Asn Leu Gly Arg Pro Lys Leu Ser Gly Asn
        770                 775                 780

<210> SEQ ID NO 131
<211> LENGTH: 1458
<212> TYPE: DNA
<213> ORGANISM: Homo sapiens

<400> SEQUENCE: 131

| | |
|---|---|
| atggatccca cagccttggt ggaagccatt gtggaagaag tggcctgtcc catctgtatg | 60 |
| accttcctga gggagcccat gagcattgac tgtggccaca gcttctgcca cagctgtctc | 120 |
| tctggactct gggagatccc aggagaatcc cagaactggg gttacacctg tcccctctgt | 180 |
| cgagctcctg tccagccaag gaacctgcgg cctaattggc agctggccaa tgttgtagaa | 240 |
| aaagtccgtc tgctaaggct acatccagga atggggctga agggtgacct gtgtgagcgc | 300 |
| catggggaaa agctgaagat gttctgcaaa gaggatgtct tgataatgtg tgaggcctgc | 360 |
| agccagtccc cagagcatga ggcccacagt gttgtgccaa tggaggatgt tgcctgggag | 420 |
| tacaagtggg aacttcatga ggccctcgaa catctgaaga agagcaaga agaggcctgg | 480 |
| aagcttgaag ttggtgaaag gaaacgaact gccacctgga gatacaggt ggaaacccga | 540 |
| aaacagagta ttgtatggga gtttgaaaaa taccagcgat tactagagaa aaagcagcca | 600 |
| ccacatcggc agctggggc agaggtagca gcagctctgg ccagcctaca gcggaggca | 660 |
| gcggagacca tgcagaaact ggagttgaac catagcgagc tcatccagca gagccaggtc | 720 |
| ctgtgtagga tgattgcaga gttgaaagag aggtcgcaga ggcctgtccg ctggatgttg | 780 |
| caggatattc aggaagtgtt aaacaggagc aaatcttgga gcttgcagca gccagaacca | 840 |
| atctccctgg agttgaagac agattgccgt gtgctggggc taagagagat cctgaagact | 900 |
| tatgcagctg atgtgcgctt ggatccagat actgcttact cccgtctcat cgtgtctgag | 960 |
| gacagaaaac gtgtgcacta tggagacacc aaccagaaac tgccagacaa tcctgagaga | 1020 |
| ttttaccgct ataatatcgt cctgggaagc cagtgcatct cctcaggccg gcactactgg | 1080 |
| gaggtggagt gggagacag gtctgagtgg ggcctgggag tatgtaagca aaatgtagac | 1140 |
| cggaaggagg tggtctactt atcccccac tatggattct gggtgataag gctgaggaag | 1200 |
| ggaaatgagt accagcagg caccgatgag tacccaatcc tgtccttgcc ggtccctcct | 1260 |
| cgccgggtgg aatcttcgt ggattatgag gcccatgaca tttcttcta caatgtgact | 1320 |
| gactgtggct cccacatctt cactttcccc cgctatccct tcctgggcg cctcctgccc | 1380 |
| tatttagtc cttgctacag cattggaacc aacaacactg ctcctctggc catctgctcc | 1440 |
| ctggatgggg aggactaa | 1458 |

<210> SEQ ID NO 132
<211> LENGTH: 485
<212> TYPE: PRT
<213> ORGANISM: Homo sapiens

<400> SEQUENCE: 132

Met Asp Pro Thr Ala Leu Val Glu Ala Ile Val Glu Glu Val Ala Cys
1               5                   10                  15

Pro Ile Cys Met Thr Phe Leu Arg Glu Pro Met Ser Ile Asp Cys Gly
                20                  25                  30

His Ser Phe Cys His Ser Cys Leu Ser Gly Leu Trp Glu Ile Pro Gly
            35                  40                  45

```
Glu Ser Gln Asn Trp Gly Tyr Thr Cys Pro Leu Cys Arg Ala Pro Val
 50                  55                  60

Gln Pro Arg Asn Leu Arg Pro Asn Trp Gln Leu Ala Asn Val Val Glu
 65                  70                  75                  80

Lys Val Arg Leu Leu Arg Leu His Pro Gly Met Gly Leu Lys Gly Asp
                 85                  90                  95

Leu Cys Glu Arg His Gly Glu Lys Leu Lys Met Phe Cys Lys Glu Asp
            100                 105                 110

Val Leu Ile Met Cys Glu Ala Cys Ser Gln Ser Pro Glu His Glu Ala
            115                 120                 125

His Ser Val Val Pro Met Glu Asp Val Ala Trp Glu Tyr Lys Trp Glu
130                 135                 140

Leu His Glu Ala Leu Glu His Leu Lys Lys Glu Gln Glu Ala Trp
145                 150                 155                 160

Lys Leu Glu Val Gly Glu Arg Lys Arg Thr Ala Thr Trp Lys Ile Gln
                165                 170                 175

Val Glu Thr Arg Lys Gln Ser Ile Val Trp Glu Phe Glu Lys Tyr Gln
            180                 185                 190

Arg Leu Leu Glu Lys Lys Gln Pro Pro His Arg Gln Leu Gly Ala Glu
            195                 200                 205

Val Ala Ala Ala Leu Ala Ser Leu Gln Arg Glu Ala Ala Glu Thr Met
210                 215                 220

Gln Lys Leu Glu Leu Asn His Ser Glu Leu Ile Gln Gln Ser Gln Val
225                 230                 235                 240

Leu Trp Arg Met Ile Ala Glu Leu Lys Glu Arg Ser Gln Arg Pro Val
                245                 250                 255

Arg Trp Met Leu Gln Asp Ile Gln Glu Val Leu Asn Arg Ser Lys Ser
            260                 265                 270

Trp Ser Leu Gln Gln Pro Glu Pro Ile Ser Leu Glu Leu Lys Thr Asp
            275                 280                 285

Cys Arg Val Leu Gly Leu Arg Glu Ile Leu Lys Thr Tyr Ala Ala Asp
290                 295                 300

Val Arg Leu Asp Pro Asp Thr Ala Tyr Ser Arg Leu Ile Val Ser Glu
305                 310                 315                 320

Asp Arg Lys Arg Val His Tyr Gly Asp Thr Asn Gln Lys Leu Pro Asp
                325                 330                 335

Asn Pro Glu Arg Phe Tyr Arg Tyr Asn Ile Val Leu Gly Ser Gln Cys
            340                 345                 350

Ile Ser Ser Gly Arg His Tyr Trp Glu Val Glu Val Gly Asp Arg Ser
            355                 360                 365

Glu Trp Gly Leu Gly Val Cys Lys Gln Asn Val Asp Arg Lys Glu Val
370                 375                 380

Val Tyr Leu Ser Pro His Tyr Gly Phe Trp Val Ile Arg Leu Arg Lys
385                 390                 395                 400

Gly Asn Glu Tyr Arg Ala Gly Thr Asp Glu Tyr Pro Ile Leu Ser Leu
                405                 410                 415

Pro Val Pro Pro Arg Arg Val Gly Ile Phe Val Asp Tyr Glu Ala His
            420                 425                 430

Asp Ile Ser Phe Tyr Asn Val Thr Asp Cys Gly Ser His Ile Phe Thr
            435                 440                 445

Phe Pro Arg Tyr Pro Phe Pro Gly Arg Leu Leu Pro Tyr Phe Ser Pro
450                 455                 460

Cys Tyr Ser Ile Gly Thr Asn Asn Thr Ala Pro Leu Ala Ile Cys Ser
```

Leu Asp Gly Glu Asp
            485

<210> SEQ ID NO 133
<211> LENGTH: 1026
<212> TYPE: DNA
<213> ORGANISM: Homo sapiens

<400> SEQUENCE: 133

| | | |
|---|---|---|
| atggaggagg agcttgccat ccaacagggt caactggaga caactctgaa ggagcttcag | 60 |
| accctgagga catgcagaa ggaagctatt gctgctcaca aggaaaacaa gctacatctg | 120 |
| cagcaacatg tgtccatgga gtttctaaag ctgcatcagt tcctgcacag caaagaaaag | 180 |
| gacattttaa ctgagctccg ggaagagggg aaagccttga atgaggagat ggagttgaat | 240 |
| ctgagccagc ttcaggagca atgtctctta gccaaggata tgttggtgag cattcaggca | 300 |
| aagacggaac aacagaactc cttcgacttt ctcaaagaca tcacaactct cttacatagc | 360 |
| ttggagcaag gaatgaaggt gctggcaacc agagagctta tttccagaaa gctgaacctg | 420 |
| ggccagtaca aggtcctat ccagtacatg gtatggaggg aaatgcagga cactctctgc | 480 |
| ccaggcctgt ctccactaac tctggaccct aaaacagctc acccaaatct ggtgctctcc | 540 |
| aaaagccaaa ccagcgtctg gcatggtgac attaagaaga taatgcctga tgatcctgag | 600 |
| aggtttgact caagtgtggc tgtactgggc tcaagaggct tcacctctgg aaagtggtac | 660 |
| tgggaagtag aagtagcaaa gaagacaaaa tggacagttg gagttgtcag agaatccatc | 720 |
| attcggaagg gcagctgtcc tctaactcct gagcaaggat tctggctttt aagactaagg | 780 |
| aaccaaactg atctaaaggc tctggatttg ccttctttca gtctgacact gactaacaac | 840 |
| ctcgacaagg tgggcatata cctggattat gaaggaggac agttgtcctt ctacaatgct | 900 |
| aaaaccatga ctcacattta cacttcagt aacactttca tggagaaact ttatccctac | 960 |
| ttctgccct gccttaatga tggtggagag aataaagaac cattgcacat cttacatcca | 1020 |
| cagtaa | 1026 |

<210> SEQ ID NO 134
<211> LENGTH: 341
<212> TYPE: PRT
<213> ORGANISM: Homo sapiens

<400> SEQUENCE: 134

Met Glu Glu Glu Leu Ala Ile Gln Gln Gly Gln Leu Glu Thr Thr Leu
1               5                   10                  15

Lys Glu Leu Gln Thr Leu Arg Asn Met Gln Lys Glu Ala Ile Ala Ala
            20                  25                  30

His Lys Glu Asn Lys Leu His Leu Gln Gln His Val Ser Met Glu Phe
        35                  40                  45

Leu Lys Leu His Gln Phe Leu His Ser Lys Glu Lys Asp Ile Leu Thr
    50                  55                  60

Glu Leu Arg Glu Glu Gly Lys Ala Leu Asn Glu Glu Met Glu Leu Asn
65                  70                  75                  80

Leu Ser Gln Leu Gln Glu Gln Cys Leu Leu Ala Lys Asp Met Leu Val
                85                  90                  95

Ser Ile Gln Ala Lys Thr Glu Gln Gln Asn Ser Phe Asp Phe Leu Lys
            100                 105                 110

Asp Ile Thr Thr Leu Leu His Ser Leu Glu Gln Gly Met Lys Val Leu

```
              115                 120                 125
Ala Thr Arg Glu Leu Ile Ser Arg Lys Leu Asn Leu Gly Gln Tyr Lys
        130                 135                 140

Gly Pro Ile Gln Tyr Met Val Trp Arg Glu Met Gln Asp Thr Leu Cys
145                 150                 155                 160

Pro Gly Leu Ser Pro Leu Thr Leu Asp Pro Lys Thr Ala His Pro Asn
                165                 170                 175

Leu Val Leu Ser Lys Ser Gln Thr Ser Val Trp His Gly Asp Ile Lys
            180                 185                 190

Lys Ile Met Pro Asp Asp Pro Glu Arg Phe Asp Ser Ser Val Ala Val
        195                 200                 205

Leu Gly Ser Arg Gly Phe Thr Ser Gly Lys Trp Tyr Trp Glu Val Glu
    210                 215                 220

Val Ala Lys Lys Thr Lys Trp Thr Val Gly Val Val Arg Glu Ser Ile
225                 230                 235                 240

Ile Arg Lys Gly Ser Cys Pro Leu Thr Pro Glu Gln Gly Phe Trp Leu
                245                 250                 255

Leu Arg Leu Arg Asn Gln Thr Asp Leu Lys Ala Leu Asp Leu Pro Ser
            260                 265                 270

Phe Ser Leu Thr Leu Thr Asn Asn Leu Asp Lys Val Gly Ile Tyr Leu
        275                 280                 285

Asp Tyr Glu Gly Gly Gln Leu Ser Phe Tyr Asn Ala Lys Thr Met Thr
    290                 295                 300

His Ile Tyr Thr Phe Ser Asn Thr Phe Met Glu Lys Leu Tyr Pro Tyr
305                 310                 315                 320

Phe Cys Pro Cys Leu Asn Asp Gly Gly Glu Asn Lys Glu Pro Leu His
                325                 330                 335

Ile Leu His Pro Gln
            340

<210> SEQ ID NO 135
<211> LENGTH: 1047
<212> TYPE: DNA
<213> ORGANISM: Homo sapiens

<400> SEQUENCE: 135
atgcagtttg gggaactcct tgctgctgtg aggaaggccc aggccaatgt gatgctcttc      60
ttagaggaga aggagcaagc tgcgctgagc caggccaacg gtatcaaggc ccacctggag     120
tacaggagtg ccgagatgga gaagagtaag caggagctgg agacgatggc ggccatcagc     180
aacactgtcc agttcttgga ggagtactgc aagtttaaga cactgaagag catcaccttc     240
cctagtgttt catagggct gaaggataaa ctctcgggca tccgcaaagt tatcacggaa     300
tccactgtac acttaatcca gttgctggag aactataaga aaaagctcca ggagttttcc     360
aaggaagagg agtatgacat cagaactcaa gtgtctgcca ttgttcagcg caaatattgg     420
acttccaaac ctgagcccag caccagggaa cagttcctcc aatatgtgca tgacatcacg     480
ttcgacccgg acacagcaca caagtatctc cggctgcagg aggagaaccg caaggtcacc     540
aacaccacgc cctgggagca tccctacccg gacctcccca gcaggttcct gcactggcgg     600
caggtgctgt cccagcagag tctgtacctg cacaggtact attttgaggt ggagatcttc     660
ggggcaggca cctatgttgg cctgacctgc aaaggcatcg accagaaagg ggaggagcgc     720
agcagttgca tttccggaaa caacttctcc tggagcctcc aatggaacgg aaggagttc      780 acggcctggt acagtgacat ggagaccca ctcaaagctg gccctttctg gaggctcggg     840
```

```
gtctatattg acttcccagg agggatcctt tccttctatg gcgtagagta tgattccatg    900
actctggttc acaagtttgc ctgcaagttt tcagaaccag tctatgctgc cttctggctt    960
tccaagaagg aaaacgccat ccggattgta gatctgggag aggaacccga gaagccagca   1020
ccgtccttgg tggggactgc tccctag                                       1047
```

<210> SEQ ID NO 136
<211> LENGTH: 348
<212> TYPE: PRT
<213> ORGANISM: Homo sapiens

<400> SEQUENCE: 136

```
Met Gln Phe Gly Glu Leu Leu Ala Ala Val Arg Lys Ala Gln Ala Asn
1               5                   10                  15

Val Met Leu Phe Leu Glu Glu Lys Glu Gln Ala Ala Leu Ser Gln Ala
            20                  25                  30

Asn Gly Ile Lys Ala His Leu Glu Tyr Arg Ser Ala Glu Met Glu Lys
        35                  40                  45

Ser Lys Gln Glu Leu Glu Thr Met Ala Ala Ile Ser Asn Thr Val Gln
    50                  55                  60

Phe Leu Glu Glu Tyr Cys Lys Phe Lys Asn Thr Glu Asp Ile Thr Phe
65                  70                  75                  80

Pro Ser Val Tyr Ile Gly Leu Lys Asp Lys Leu Ser Gly Ile Arg Lys
                85                  90                  95

Val Ile Thr Glu Ser Thr Val His Leu Ile Gln Leu Leu Glu Asn Tyr
            100                 105                 110

Lys Lys Lys Leu Gln Glu Phe Ser Lys Glu Glu Tyr Asp Ile Arg
        115                 120                 125

Thr Gln Val Ser Ala Ile Val Gln Arg Lys Tyr Trp Thr Ser Lys Pro
    130                 135                 140

Glu Pro Ser Thr Arg Glu Gln Phe Leu Gln Tyr Val His Asp Ile Thr
145                 150                 155                 160

Phe Asp Pro Asp Thr Ala His Lys Tyr Leu Arg Leu Gln Glu Glu Asn
                165                 170                 175

Arg Lys Val Thr Asn Thr Thr Pro Trp Glu His Pro Tyr Pro Asp Leu
            180                 185                 190

Pro Ser Arg Phe Leu His Trp Arg Gln Val Leu Ser Gln Gln Ser Leu
        195                 200                 205

Tyr Leu His Arg Tyr Tyr Phe Glu Val Glu Ile Phe Gly Ala Gly Thr
    210                 215                 220

Tyr Val Gly Leu Thr Cys Lys Gly Ile Asp Gln Lys Gly Glu Glu Arg
225                 230                 235                 240

Ser Ser Cys Ile Ser Gly Asn Asn Phe Ser Trp Ser Leu Gln Trp Asn
                245                 250                 255

Gly Lys Glu Phe Thr Ala Trp Tyr Ser Asp Met Glu Thr Pro Leu Lys
            260                 265                 270

Ala Gly Pro Phe Trp Arg Leu Gly Val Tyr Ile Asp Phe Pro Gly Gly
        275                 280                 285

Ile Leu Ser Phe Tyr Gly Val Tyr Asp Ser Met Thr Leu Val His
    290                 295                 300

Lys Phe Ala Cys Lys Phe Ser Glu Pro Val Tyr Ala Ala Phe Trp Leu
305                 310                 315                 320

Ser Lys Lys Glu Asn Ala Ile Arg Ile Val Asp Leu Gly Glu Glu Pro
                325                 330                 335
```

Glu Lys Pro Ala Pro Ser Leu Val Gly Thr Ala Pro
          340                 345

<210> SEQ ID NO 137
<211> LENGTH: 2607
<212> TYPE: DNA
<213> ORGANISM: Homo sapiens

<400> SEQUENCE: 137

| | | | | | |
|---|---|---|---|---|---|
| atggcttcgt | tccccgagac | cgatttccag | atctgcttgc | tgtgcaagga | gatgtgcggc | 60 |
| tcgccggcgc | cgctctcctc | caactcgtcc | gcgtcgtcgt | cctcctcgca | gacgtccacg | 120 |
| tcgtcggggg | gcggcggcgg | gggccctggg | gcggcggcgc | gccgcctaca | cgtcctgccc | 180 |
| tgcctgcacg | ccttctgccg | cccctgcctc | gaggcgcacc | ggctgccggc | ggcgggcggc | 240 |
| ggcgcggcgg | gagagccgct | caagctgcgc | tgccccgtgt | gcgaccagaa | agtagtgcta | 300 |
| gccgaggcgg | cgggtatgga | cgcgctgcct | tcgtccgcct | tcctgcttag | caacctgctc | 360 |
| gacgcggtgg | tggccactgc | cgacgagccg | ccgcccaaga | cgggcgcgc | cggcgctccg | 420 |
| gcggagcgg | gcggccacag | caaccaccgg | caccacgctc | accacgcgca | cccgcgcgcg | 480 |
| tccgcctccg | cgccgccact | cccgcaggcg | ccgcagccgc | ccgcgccttc | ccgctcggca | 540 |
| cccggcggcc | ctgccgcttc | cccgtcggcg | ctgctgctcc | gccgtcctca | cggctgcagc | 600 |
| tcgtgcgatg | agggcaacgc | agcttcttcg | cgctgcctcg | actgccagga | gcacctgtgc | 660 |
| gacaactgcg | tccgagcgca | ccagcgcgtg | cgcctcacca | aggaccacta | catcgagcgc | 720 |
| ggcccgccg | gtcccggtgc | cgcagcagcg | gcgcagcagc | tcgggctcgg | gccgccttt | 780 |
| cccggcccgc | ccttctccat | cctctcagtg | tttcccgagc | gcctcggctt | ctgccagcac | 840 |
| cacgacgacg | aggtgctgca | cctgtactgt | gacacttgct | ctgtacccat | ctgtcgtgag | 900 |
| tgcacaatgg | ccggcatggg | ggccacagc | ttcatctacc | tccaggaggc | actgcaggac | 960 |
| tcacgggcac | tcaccatcca | gctgctggca | gatgcccagc | agggacgaca | ggcaatccag | 1020 |
| ctgagcatcg | agcaggccca | gacggtggcg | gaacaggtgg | agatgaaggc | gaaggttgtg | 1080 |
| cagtcggagg | tcaaagccgt | gacggcgagg | cataagaaag | ccctggagga | acgcgagtgt | 1140 |
| gagctgctgt | ggaaggtaga | aaagatccgc | caggtgaaag | ccaagtctct | gtacctgcag | 1200 |
| gtggagaagc | tgcggcaaaa | cctcaacaag | cttgagagca | ccatcagtgc | cgtgcagcag | 1260 |
| gtcctggagg | agggtagagc | gctagacatc | ctactggccc | gagaccggat | gctggcccag | 1320 |
| gtgcaggagc | tgaagaccgt | gcggagcctc | ctgcagcccc | aggaagacga | ccgagtcatg | 1380 |
| ttcacacccc | ccgatcaggc | actgtacctt | gccatcaagt | cttttggctt | tgttagcagc | 1440 |
| ggggccttg | ccccactcac | caaggccaca | ggcgatggcc | tcaagcgtgc | cctccagggt | 1500 |
| aaggtggcct | ccttcacagt | cattggttat | gaccacgatg | gtgagccccg | cctctcagga | 1560 |
| ggcgacctga | tgtcggctgt | ggtcctgggc | cctgatggca | acctgtttgg | tgcagaggtg | 1620 |
| agtgatcagc | agaatgggac | atacgtggtg | agttaccgac | cccagctgga | gggtgagcac | 1680 |
| ctggtatctg | tgacactgtg | caaccagcac | attgagaaca | gccctttcaa | ggtggtggtc | 1740 |
| aagtcaggcc | gcagctacgt | gggcattggg | ctcccgggcc | tgagcttcgg | cagtgagggt | 1800 |
| gacagcgatg | gcaagctctg | ccgcccttgg | ggtgtgagtg | tagacaagga | gggctacatc | 1860 |
| attgtcgccg | accgcagcaa | caccgcatc | caggtgttca | gccctgcgg | cgccttccac | 1920 |
| cacaaattcg | gcaccctggg | ctcccggcct | gggcagttcg | accgaccagc | cggcgtggcc | 1980 |
| tgtgacgcct | cacgcaggat | cgtggtggct | gacaaggaca | atcatcgcat | ccagatcttc | 2040 |

```
acgttcgagg gccagttcct cctcaagttt ggtgagaaag gaaccaagaa tgggcagttc    2100
aactacccct gggatgtggc ggtgaattct gagggcaaga tcctggtctc agacacgagg    2160
aaccaccgga tccagctgtt tgggcctgat ggtgtcttcc taaacaagta tggcttcgag    2220
ggggctctct ggaagcactt tgactcccca cggggtgtgg ccttcaacca tgagggccac    2280
ttggtggtca ctgacttcaa caaccaccgg ctcctggtta ttcaccccga ctgccagtcg    2340
gcacgctttc tgggctcgga gggcacaggc aatgggcagt cctgcgccc acaaggggta    2400 gctgtggacc aggaagggcg catcattgtg gcggattcca ggaaccatcg ggtacagatg    2460
tttgaatcca acggcagctt cctgtgcaag tttggtgctc aaggcagcgg ctttgggcag    2520
atggaccgcc cttccggcat cgccatcacc cccgacggaa tgatcgttgt ggtggacttt    2580
ggcaacaatc gaatcctcgt cttctaa                                        2607
```

<210> SEQ ID NO 138
<211> LENGTH: 868
<212> TYPE: PRT
<213> ORGANISM: Homo sapiens

<400> SEQUENCE: 138

```
Met Ala Ser Phe Pro Glu Thr Asp Phe Gln Ile Cys Leu Leu Cys Lys
1               5                   10                  15

Glu Met Cys Gly Ser Pro Ala Pro Leu Ser Ser Asn Ser Ser Ala Ser
            20                  25                  30

Ser Ser Ser Ser Gln Thr Ser Thr Ser Ser Gly Gly Gly Gly Gly Gly
        35                  40                  45

Pro Gly Ala Ala Ala Arg Arg Leu His Val Leu Pro Cys Leu His Ala
    50                  55                  60

Phe Cys Arg Pro Cys Leu Glu Ala His Arg Leu Pro Ala Ala Gly Gly
65                  70                  75                  80

Gly Ala Ala Gly Glu Pro Leu Lys Leu Arg Cys Pro Val Cys Asp Gln
                85                  90                  95

Lys Val Val Leu Ala Glu Ala Ala Gly Met Asp Ala Leu Pro Ser Ser
            100                 105                 110

Ala Phe Leu Leu Ser Asn Leu Leu Asp Ala Val Val Ala Thr Ala Asp
        115                 120                 125

Glu Pro Pro Lys Asn Gly Arg Ala Gly Ala Pro Ala Gly Ala Gly
    130                 135                 140

Gly His Ser Asn His Arg His His Ala His His Ala His Pro Arg Ala
145                 150                 155                 160

Ser Ala Ser Ala Pro Pro Leu Pro Gln Ala Pro Gln Pro Pro Ala Pro
                165                 170                 175

Ser Arg Ser Ala Pro Gly Gly Pro Ala Ala Ser Pro Ser Ala Leu Leu
            180                 185                 190

Leu Arg Arg Pro His Gly Cys Ser Ser Cys Asp Glu Gly Asn Ala Ala
        195                 200                 205

Ser Ser Arg Cys Leu Asp Cys Gln Glu His Leu Cys Asp Asn Cys Val
    210                 215                 220

Arg Ala His Gln Arg Val Arg Leu Thr Lys Asp His Tyr Ile Glu Arg
225                 230                 235                 240

Gly Pro Pro Gly Pro Gly Ala Ala Ala Ala Gln Gln Leu Gly Leu
                245                 250                 255

Gly Pro Pro Phe Pro Gly Pro Pro Phe Ser Ile Leu Ser Val Phe Pro
            260                 265                 270
```

```
Glu Arg Leu Gly Phe Cys Gln His His Asp Asp Glu Val Leu His Leu
            275                 280                 285

Tyr Cys Asp Thr Cys Ser Val Pro Ile Cys Arg Glu Cys Thr Met Gly
    290                 295                 300

Arg His Gly Gly His Ser Phe Ile Tyr Leu Gln Glu Ala Leu Gln Asp
305                 310                 315                 320

Ser Arg Ala Leu Thr Ile Gln Leu Leu Ala Asp Ala Gln Gln Gly Arg
                325                 330                 335

Gln Ala Ile Gln Leu Ser Ile Glu Gln Ala Gln Thr Val Ala Glu Gln
            340                 345                 350

Val Glu Met Lys Ala Lys Val Val Gln Ser Glu Val Lys Ala Val Thr
            355                 360                 365

Ala Arg His Lys Lys Ala Leu Glu Glu Arg Glu Cys Glu Leu Leu Trp
        370                 375                 380

Lys Val Glu Lys Ile Arg Gln Val Lys Ala Lys Ser Leu Tyr Leu Gln
385                 390                 395                 400

Val Glu Lys Leu Arg Gln Asn Leu Asn Lys Leu Glu Ser Thr Ile Ser
                405                 410                 415

Ala Val Gln Gln Val Leu Glu Glu Gly Arg Ala Leu Asp Ile Leu Leu
            420                 425                 430

Ala Arg Asp Arg Met Leu Ala Gln Val Gln Glu Leu Lys Thr Val Arg
        435                 440                 445

Ser Leu Leu Gln Pro Gln Glu Asp Arg Val Met Phe Thr Pro Pro
450                 455                 460

Asp Gln Ala Leu Tyr Leu Ala Ile Lys Ser Phe Gly Phe Val Ser Ser
465                 470                 475                 480

Gly Ala Phe Ala Pro Leu Thr Lys Ala Thr Gly Asp Gly Leu Lys Arg
                485                 490                 495

Ala Leu Gln Gly Lys Val Ala Ser Phe Thr Val Ile Gly Tyr Asp His
            500                 505                 510

Asp Gly Glu Pro Arg Leu Ser Gly Gly Asp Leu Met Ser Ala Val Val
        515                 520                 525

Leu Gly Pro Asp Gly Asn Leu Phe Gly Ala Glu Val Ser Asp Gln Gln
    530                 535                 540

Asn Gly Thr Tyr Val Val Ser Tyr Arg Pro Gln Leu Glu Gly Glu His
545                 550                 555                 560

Leu Val Ser Val Thr Leu Cys Asn Gln His Ile Glu Asn Ser Pro Phe
                565                 570                 575

Lys Val Val Lys Ser Gly Arg Ser Tyr Val Gly Ile Gly Leu Pro
            580                 585                 590

Gly Leu Ser Phe Gly Ser Glu Gly Asp Ser Asp Gly Lys Leu Cys Arg
        595                 600                 605

Pro Trp Gly Val Ser Val Asp Lys Glu Gly Tyr Ile Ile Val Ala Asp
    610                 615                 620

Arg Ser Asn Asn Arg Ile Gln Val Phe Lys Pro Cys Gly Ala Phe His
625                 630                 635                 640

His Lys Phe Gly Thr Leu Gly Ser Arg Pro Gly Gln Phe Asp Arg Pro
                645                 650                 655

Ala Gly Val Ala Cys Asp Ala Ser Arg Arg Ile Val Val Ala Asp Lys
            660                 665                 670

Asp Asn His Arg Ile Gln Ile Phe Thr Phe Glu Gly Gln Phe Leu Leu
        675                 680                 685
```

```
Lys Phe Gly Glu Lys Gly Thr Lys Asn Gly Gln Phe Asn Tyr Pro Trp
    690                 695                 700
Asp Val Ala Val Asn Ser Glu Gly Lys Ile Leu Val Ser Asp Thr Arg
705                 710                 715                 720
Asn His Arg Ile Gln Leu Phe Gly Pro Asp Gly Val Phe Leu Asn Lys
                725                 730                 735
Tyr Gly Phe Glu Gly Ala Leu Trp Lys His Phe Asp Ser Pro Arg Gly
            740                 745                 750
Val Ala Phe Asn His Glu Gly His Leu Val Val Thr Asp Phe Asn Asn
        755                 760                 765
His Arg Leu Leu Val Ile His Pro Asp Cys Gln Ser Ala Arg Phe Leu
770                 775                 780
Gly Ser Glu Gly Thr Gly Asn Gly Gln Phe Leu Arg Pro Gln Gly Val
785                 790                 795                 800
Ala Val Asp Gln Glu Gly Arg Ile Ile Val Ala Asp Ser Arg Asn His
                805                 810                 815
Arg Val Gln Met Phe Glu Ser Asn Gly Ser Phe Leu Cys Lys Phe Gly
            820                 825                 830
Ala Gln Gly Ser Gly Phe Gly Gln Met Asp Arg Pro Ser Gly Ile Ala
        835                 840                 845
Ile Thr Pro Asp Gly Met Ile Val Val Asp Phe Gly Asn Asn Arg
850                 855                 860
Ile Leu Val Phe
865

<210> SEQ ID NO 139
<211> LENGTH: 1434
<212> TYPE: DNA
<213> ORGANISM: Homo sapiens

<400> SEQUENCE: 139
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc     120
gtggccgggg agccggcggc ggatggcacc gttctctgcc cctgctgcca ggcccccacg     180
cggccgcagg cactcagcac caacctgcag ctggcgcgcc tggtggaggg gctggcccag     240
gtgccgcagg ccactgcgga ggagcacctg gaccgctga gcatctactg cgagcaggac     300
cgcgcgctgg tgtgcggagt gtgcgcctca ctcggctcgc accgcggtca tcgcctcctg     360
cctgccgccg aggcccacgc acgcctcaag acacagctgc acagcagaa actgcagctg     420 caggaggcat gcatgcgcaa ggagaagagt gtggctgtgc tggagcatca gctggtggag     480
gtggaggaga cagtgcgtca gttccggggg gccgtggggg agcagctggg caagatgcgg     540
gtgttcctgg ctgcactgga gggctccttg accgcgagg cagagcgtgt acgggtgag      600 gcagggtcg ccttgcgccg ggagctgggg agcctgaact cttacctgga gcagctgcgg     660
cagatggaga aggtcctgga ggaggtggcg gacaagccgc agactgagtt cctcatgaaa     720
tactgcctgg tgaccagcag gctgcagaag atcctggcag agtctccccc acccgcccgt     780
ctggacatcc agctgccaat tatctcagat gacttcaaat tccaggtgtg gaggaagatg     840
ttccgggctc tgatgccagc gctggaggag ctgacctttg acccgagctc tgcgcacccg     900
agcctggtgg tgtcttcctc tggccgccgc gtggagtgct cggagcagaa ggcgccgccg     960 gccgggggagg acccgcgcca gttcgacaag gcggtggcgg tggtggcgca ccagcagctc    1020
tccgagggcg agcactactg ggaggtggat gttggcgaca gccgcgctg ggcgctgggc    1080
```

```
gtgatcgcgg ccgaggcccc ccgccgcggg cgcctgcacg cggtgccctc gcagggcctg    1140
tggctgctgg ggctgcgcga gggcaagatc ctggaggcac acgtggaggc caaggagccg    1200
cgcgctctgc gcagccccga gaggcggccc acgcgcattg gcctttacct gagcttcggc    1260
gacggcgtcc tctccttcta cgatgccagc gacgccgacg cgctcgtgcc gcttttgcc     1320 ttccacgagc gcctgcccag gcccgtgtac cccttcttcg acgtgtgctg cacgacaag     1380 ggcaagaatg cccagccgct gctgctcgtg ggtcccgaag cgccgaggc ctga           1434
```

<210> SEQ ID NO 140
<211> LENGTH: 477
<212> TYPE: PRT
<213> ORGANISM: Homo sapiens

<400> SEQUENCE: 140

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
```

```
                305                 310                 315                 320
Ala Gly Glu Asp Pro Arg Gln Phe Asp Lys Ala Val Ala Val Ala
                    325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Glu Ala Pro Arg
            355                 360                 365

Arg Gly Arg Leu His Ala Val Pro Ser Gln Gly Leu Trp Leu Leu Gly
            370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
                420                 425                 430

Asp Ala Leu Val Pro Leu Phe Ala Phe His Glu Arg Leu Pro Arg Pro
                435                 440                 445

Val Tyr Pro Phe Phe Asp Val Cys Trp His Asp Lys Gly Lys Asn Ala
            450                 455                 460

Gln Pro Leu Leu Leu Val Gly Pro Glu Gly Ala Glu Ala
465                 470                 475

<210> SEQ ID NO 141
<211> LENGTH: 753
<212> TYPE: DNA
<213> ORGANISM: Homo sapiens

<400> SEQUENCE: 141
atggcttggc aggtgagcct gctggagctg gaggaccggc ttcagtgtcc catctgcctg      60
gaggtcttca aggagtccct aatgctacag tgcggccact cctactgcaa gggctgcctg     120
gtttccctgt cctaccacct ggacaccaag gtgcgctgcc ccatgtgctg gcaggtggtg     180
gacggcagca gctccttgcc caacgtctcc ctggcctggg tgatcgaagc cctgaggctc     240
cctggggacc cggagcccaa ggtctgcgtg caccaccgga cccgctcag cctttttctgc    300 gagaaggacc aggagctcat ctgtggcctc tgcggtctgc tgggctccca ccaacaccac    360
ccggtcacgc ccgtctccac cgtctgcagc cgcatgaagg aggagctcgc agccctcttc    420
tctgagctga agcaggagca aagaaggtg gatgagctca tcgccaaact ggtgaaaaac    480
cggacccgaa tcgtcaatga gtcggatgtc ttcagctggg tgatccgccg cgagttccag    540
gagctgcgcc accggtgga cgaggagaag gcccgctgcc tggagggat aggggtcac    600 acccgtggcc tggtggcctc cctggacatg cagctggagc aggcccaggg aacccgggag    660
cggctggccc aagccgagtg tgtgctggaa cagttcggca atgaggacca ccatgagttc    720
atctggaagt tccactccat ggcctccagg taa                                  753

<210> SEQ ID NO 142
<211> LENGTH: 250
<212> TYPE: PRT
<213> ORGANISM: Homo sapiens

<400> SEQUENCE: 142

Met Ala Trp Gln Val Ser Leu Leu Glu Leu Glu Asp Arg Leu Gln Cys
1               5                   10                  15

Pro Ile Cys Leu Glu Val Phe Lys Glu Ser Leu Met Leu Gln Cys Gly
                20                  25                  30
```

His Ser Tyr Cys Lys Gly Cys Leu Val Ser Leu Ser Tyr His Leu Asp
        35                  40                  45

Thr Lys Val Arg Cys Pro Met Cys Trp Gln Val Val Asp Gly Ser Ser
 50                  55                  60

Ser Leu Pro Asn Val Ser Leu Ala Trp Val Ile Glu Ala Leu Arg Leu
 65                  70                  75                  80

Pro Gly Asp Pro Glu Pro Lys Val Cys Val His His Arg Asn Pro Leu
                 85                  90                  95

Ser Leu Phe Cys Glu Lys Asp Gln Glu Leu Ile Cys Gly Leu Cys Gly
             100                 105                 110

Leu Leu Gly Ser His Gln His His Pro Val Thr Pro Val Ser Thr Val
         115                 120                 125

Cys Ser Arg Met Lys Glu Glu Leu Ala Ala Leu Phe Ser Glu Leu Lys
130                 135                 140

Gln Glu Gln Lys Lys Val Asp Glu Leu Ile Ala Lys Leu Val Lys Asn
145                 150                 155                 160

Arg Thr Arg Ile Val Asn Glu Ser Asp Val Phe Ser Trp Val Ile Arg
                165                 170                 175

Arg Glu Phe Gln Glu Leu Arg His Pro Val Asp Glu Glu Lys Ala Arg
            180                 185                 190

Cys Leu Glu Gly Ile Gly Gly His Thr Arg Gly Leu Val Ala Ser Leu
        195                 200                 205

Asp Met Gln Leu Glu Gln Ala Gln Gly Thr Arg Glu Arg Leu Ala Gln
    210                 215                 220

Ala Glu Cys Val Leu Glu Gln Phe Gly Asn Glu Asp His His Glu Phe
225                 230                 235                 240

Ile Trp Lys Phe His Ser Met Ala Ser Arg
                245                 250

<210> SEQ ID NO 143
<211> LENGTH: 753
<212> TYPE: DNA
<213> ORGANISM: Homo sapiens

<400> SEQUENCE: 143
atggcttggc aggtgagcct gctggagctg gaggactggc ttcagtgtcc catctgcctg      60
gaggtcttca aggagtccct aatgctacag tgcggccact cctactgcaa gggctgcctg     120
gtttccctgt cctaccacct ggacaccaag gtgcgctgcc ccatgtgctg gcaggtggtg     180
gacggcagca gctccttgcc caacgtctcc ctggcctggg tgatcgaagc cctgaggctc     240
cctggggacc cggagcccaa ggtctgcgtg caccaccgga acccgctcag ccttttctgc     300
gagaaggacc aggagctcat ctgtggcctc tgcggtctgc tgggctccca ccaacaccac     360
ccggtcacgc ccgtctccac cgtctgcagc cgcatgaagg aggagctcgc agccctcttc     420
tctgagctga gcaggagca gaagaaggtg gatgagctca tcgccaaact ggtgaaaaac     480
cggacccgaa tcgtcaatga gtcggatgtc ttcagctggg tgatccgccg cgagttccag     540
gagctgcgcc acccggtgga cgaggagaag gcccgctgcc tggaggggat agggggtcac     600
acccgtggcc tggtggcctc cctggacatg cagctggagc aggcccaggg aacccgggag     660
cggctggccc aagccgagtg tgtgctggaa cagttcggaa atgaggacca ccatgagttc     720
atctggaagt tccactccat ggcctccagg taa                                  753

<210> SEQ ID NO 144

<211> LENGTH: 250
<212> TYPE: PRT
<213> ORGANISM: Homo sapiens

<400> SEQUENCE: 144

Met Ala Trp Gln Val Ser Leu Leu Glu Leu Glu Asp Trp Leu Gln Cys
1               5                   10                  15
Pro Ile Cys Leu Glu Val Phe Lys Glu Ser Leu Met Leu Gln Cys Gly
            20                  25                  30
His Ser Tyr Cys Lys Gly Cys Leu Val Ser Leu Ser Tyr His Leu Asp
        35                  40                  45
Thr Lys Val Arg Cys Pro Met Cys Trp Gln Val Val Asp Gly Ser Ser
    50                  55                  60
Ser Leu Pro Asn Val Ser Leu Ala Trp Val Ile Glu Ala Leu Arg Leu
65                  70                  75                  80
Pro Gly Asp Pro Glu Pro Lys Val Cys Val His Arg Asn Pro Leu
            85                  90                  95
Ser Leu Phe Cys Glu Lys Asp Gln Glu Leu Ile Cys Gly Leu Cys Gly
            100                 105                 110
Leu Leu Gly Ser His Gln His His Pro Val Thr Pro Val Ser Thr Val
        115                 120                 125
Cys Ser Arg Met Lys Glu Glu Leu Ala Ala Leu Phe Ser Glu Leu Lys
    130                 135                 140
Gln Glu Gln Lys Lys Val Asp Glu Leu Ile Ala Lys Leu Val Lys Asn
145                 150                 155                 160
Arg Thr Arg Ile Val Asn Glu Ser Asp Val Phe Ser Trp Val Ile Arg
                165                 170                 175
Arg Glu Phe Gln Glu Leu Arg His Pro Val Asp Glu Lys Ala Arg
            180                 185                 190
Cys Leu Glu Gly Ile Gly Gly His Thr Arg Gly Leu Val Ala Ser Leu
        195                 200                 205
Asp Met Gln Leu Glu Gln Ala Gln Gly Thr Arg Glu Arg Leu Ala Gln
    210                 215                 220
Ala Glu Cys Val Leu Glu Gln Phe Gly Asn Glu Asp His His Glu Phe
225                 230                 235                 240
Ile Trp Lys Phe His Ser Met Ala Ser Arg
                245                 250

<210> SEQ ID NO 145
<211> LENGTH: 1404
<212> TYPE: DNA
<213> ORGANISM: Homo sapiens

<400> SEQUENCE: 145
atggcacatg tcgaggtctt ggccagactc cagaaagaga ccaagtgccc catctgtttg      60
gacgatctga cagatcccgt caccgtcgag tgcggacaca acttctgtcg ttcctgcatc     120
aaagacttct gggcagggca gcaagccacg tcctcctgtc ctgtctgccg acaccagtgc     180
caacacagga acctcagaag caatgcccag ctgggaaaca tgattgaaac tgcccagctg     240
ctccaaggca tggagaacaa gaggcacgag agcagcacca gttgcgagag cacaaccag     300 gccctgaccc tcttctgtga ggatgacctg cagttgctct gtgaccagtg cgtggagcct     360
gagagccacg gcgccaccag ggtgctgtcc attacagagg ctgcctctct ccacaggaaa     420
caccttcagg actatagcaa gctcctgaag tgggaagtga agagattca ggggctaatg     480 agcgcactaa acaaaagaac cgtgaccctg agggagcaag cagaggcaca gaggtcacag     540

```
ctaacctctg agtgtgagaa gctcatgcgg tttctagacc aggaagagcg ggcagctttc    600
tccaggttag aagacgagga gatgaggctc gagaagagac tgcttgataa catagcagca    660
ttagaacacc acggttccag cctcagagac ctcctgagac acttgatgct gaccggagag    720
ctctccgaag ccaagatgtt gtccacggtc aaggattttt acctgaattg taggcgtcag    780
ctcatcagcc caagcatttt cccagttcag ttgagaagag tggagtacag ctttcctctc    840
cagtattcgg ccctacagaa agttatacag cattttacag acaacgtcac tctagacctg    900
aagacagccc atccaaacct gctcatttct aaggatagaa cctgcgtaac atttacaaag    960
aaaagacaac gtattcctgg ttcttcaagt tttaccaaga gccctgttgt gttgggattc    1020
ccacatttta attctgggag acacttctgg gaggtgcagg taggaaagaa gccaaagtgg    1080
gctattggca tttgcaaagc tgattcctct atcggggaaa ggcagtcccc taaccctggg    1140
gggtactgga ggattgtttg gcaggggac agcttcaacg tctcaggagc tgatccagac     1200
tctcggctga aggccgcaag agctacaagc attggtgttt cctggacta tgaactggga     1260 gaggtttctt tctatggcat gcctgagaaa tgtcacctct atactttcag ggacactttt    1320
tctggtcctg tctgccctta tttctacata gggcctcagt cagaacctct tagactctgt    1380
tctgccactg attcagaatg ctaa                                           1404

<210> SEQ ID NO 146
<211> LENGTH: 467
<212> TYPE: PRT
<213> ORGANISM: Homo sapiens

<400> SEQUENCE: 146

Met Ala His Val Glu Val Leu Ala Arg Leu Gln Lys Glu Thr Lys Cys
1               5                   10                  15

Pro Ile Cys Leu Asp Asp Leu Thr Asp Pro Val Thr Val Glu Cys Gly
            20                  25                  30

His Asn Phe Cys Arg Ser Cys Ile Lys Asp Phe Trp Ala Gly Gln Gln
        35                  40                  45

Ala Thr Ser Ser Cys Pro Val Cys Arg His Gln Cys Gln His Arg Asn
    50                  55                  60

Leu Arg Ser Asn Ala Gln Leu Gly Asn Met Ile Glu Thr Ala Gln Leu
65                  70                  75                  80

Leu Gln Gly Met Glu Asn Lys Arg His Glu Ser Ser Thr Ser Cys Glu
                85                  90                  95

Arg His Asn Gln Ala Leu Thr Leu Phe Cys Glu Asp Asp Leu Gln Leu
            100                 105                 110

Leu Cys Asp Gln Cys Val Glu Pro Glu Ser His Gly Arg His Gln Val
        115                 120                 125

Leu Ser Ile Thr Glu Ala Ala Ser Leu His Arg Lys His Leu Gln Asp
    130                 135                 140

Tyr Ser Lys Leu Leu Lys Trp Glu Val Lys Glu Ile Gln Gly Leu Met
145                 150                 155                 160

Ser Ala Leu Asn Lys Arg Thr Val Thr Leu Arg Glu Gln Ala Glu Ala
                165                 170                 175

Gln Arg Ser Gln Leu Thr Ser Glu Cys Glu Lys Leu Met Arg Phe Leu
            180                 185                 190

Asp Gln Glu Glu Arg Ala Ala Phe Ser Arg Leu Glu Asp Glu Glu Met
        195                 200                 205

Arg Leu Glu Lys Arg Leu Leu Asp Asn Ile Ala Ala Leu Glu His His
```

-continued

```
                210                 215                 220
Gly Ser Ser Leu Arg Asp Leu Arg His Leu Met Leu Thr Gly Glu
225                 230                 235                 240

Leu Ser Glu Ala Lys Met Leu Ser Thr Val Lys Asp Phe Tyr Leu Asn
            245                 250                 255

Cys Arg Arg Gln Leu Ile Ser Pro Ser Ile Phe Pro Val Gln Leu Arg
            260                 265                 270

Arg Val Glu Tyr Ser Phe Pro Leu Gln Tyr Ser Ala Leu Gln Lys Val
        275                 280                 285

Ile Gln His Phe Thr Asp Asn Val Thr Leu Asp Leu Lys Thr Ala His
    290                 295                 300

Pro Asn Leu Leu Ile Ser Lys Asp Arg Thr Cys Val Thr Phe Thr Lys
305                 310                 315                 320

Lys Arg Gln Arg Ile Pro Gly Ser Ser Ser Phe Thr Lys Ser Pro Val
                325                 330                 335

Val Leu Gly Ile Pro His Phe Asn Ser Gly Arg His Phe Trp Glu Val
            340                 345                 350

Gln Val Gly Lys Lys Pro Lys Trp Ala Ile Gly Ile Cys Lys Ala Asp
        355                 360                 365

Ser Ser Ile Gly Glu Arg Gln Ser Pro Asn Pro Trp Gly Tyr Trp Arg
    370                 375                 380

Ile Val Trp Gln Gly Asp Ser Phe Asn Val Ser Gly Ala Asp Pro Asp
385                 390                 395                 400

Ser Arg Leu Lys Ala Ala Arg Ala Thr Ser Ile Gly Val Phe Leu Asp
                405                 410                 415

Tyr Glu Leu Gly Glu Val Ser Phe Tyr Gly Met Pro Glu Lys Cys His
            420                 425                 430

Leu Tyr Thr Phe Arg Asp Thr Phe Ser Gly Pro Val Cys Pro Tyr Phe
        435                 440                 445

Tyr Ile Gly Pro Gln Ser Glu Pro Leu Arg Leu Cys Ser Ala Thr Asp
    450                 455                 460

Ser Glu Cys
465

<210> SEQ ID NO 147
<211> LENGTH: 7
<212> TYPE: PRT
<213> ORGANISM: Artificial Sequence
<220> FEATURE:
<223> OTHER INFORMATION: SV40 nuclear localization signal

<400> SEQUENCE: 147

Pro Lys Lys Lys Arg Lys Val
1               5

<210> SEQ ID NO 148
<211> LENGTH: 21
<212> TYPE: DNA
<213> ORGANISM: Artificial Sequence
<220> FEATURE:
<223> OTHER INFORMATION: PML#4

<400> SEQUENCE: 148
ctccaagatc taaaccgaga a                                          21

<210> SEQ ID NO 149
<211> LENGTH: 21
<212> TYPE: DNA
```

```
<213> ORGANISM: Artificial Sequence
<220> FEATURE:
<223> OTHER INFORMATION: PML#9

<400> SEQUENCE: 149
cacccgcaag accaacaaca t                                              21

<210> SEQ ID NO 150
<211> LENGTH: 21
<212> TYPE: DNA
<213> ORGANISM: Artificial Sequence
<220> FEATURE:
<223> OTHER INFORMATION: RNF4#5

<400> SEQUENCE: 150
ccctgtttcc taagaacgaa a                                              21

<210> SEQ ID NO 151
<211> LENGTH: 21
<212> TYPE: DNA
<213> ORGANISM: Artificial Sequence
<220> FEATURE:
<223> OTHER INFORMATION: RNF4#6

<400> SEQUENCE: 151
taggccgagc tttgcgggaa a                                              21

<210> SEQ ID NO 152
<211> LENGTH: 21
<212> TYPE: DNA
<213> ORGANISM: Artificial Sequence
<220> FEATURE:
<223> OTHER INFORMATION: RNF4#8

<400> SEQUENCE: 152
aagactgttt cgaaccaac a                                               21

<210> SEQ ID NO 153
<211> LENGTH: 19
<212> TYPE: DNA
<213> ORGANISM: Artificial Sequence
<220> FEATURE:
<223> OTHER INFORMATION: SUMO1 siRNA pooled sense strand 1

<400> SEQUENCE: 153
tcaagaaacu caaagaatc                                                 19

<210> SEQ ID NO 154
<211> LENGTH: 19
<212> TYPE: DNA
<213> ORGANISM: Artificial Sequence
<220> FEATURE:
<223> OTHER INFORMATION: SUMO1 siRNA pooled sense strand 2

<400> SEQUENCE: 154
gacagggtgt tccaatgaa                                                 19

<210> SEQ ID NO 155
<211> LENGTH: 19
<212> TYPE: DNA
<213> ORGANISM: Artificial Sequence
<220> FEATURE:
<223> OTHER INFORMATION: SUMO1 siRNA pooled sense strand 3

<400> SEQUENCE: 155
ggtttctctt tgagggtca                                                 19
```

<210> SEQ ID NO 156
<211> LENGTH: 19
<212> TYPE: DNA
<213> ORGANISM: Artificial Sequence
<220> FEATURE:
<223> OTHER INFORMATION: SUMO1 siRNA pooled sense strand 4

<400> SEQUENCE: 156
gaataaatgg gcatgccaa                                                  19

<210> SEQ ID NO 157
<211> LENGTH: 19
<212> TYPE: RNA
<213> ORGANISM: Artificial Sequence
<220> FEATURE:
<223> OTHER INFORMATION: SUMO2/3 siRNA pooled sense strand 1

<400> SEQUENCE: 157
cccauuccuu uauuguaca                                                  19

<210> SEQ ID NO 158
<211> LENGTH: 19
<212> TYPE: RNA
<213> ORGANISM: Artificial Sequence
<220> FEATURE:
<223> OTHER INFORMATION: SUMO2/3 siRNA pooled sense strand 2

<400> SEQUENCE: 158
cagagaauga ccacaucaa                                                  19

<210> SEQ ID NO 159
<211> LENGTH: 19
<212> TYPE: RNA
<213> ORGANISM: Artificial Sequence
<220> FEATURE:
<223> OTHER INFORMATION: SUMO2/3 siRNA pooled sense strand 3

<400> SEQUENCE: 159
caguuauguu gucguguau                                                  19

<210> SEQ ID NO 160
<211> LENGTH: 21
<212> TYPE: DNA
<213> ORGANISM: Artificial Sequence
<220> FEATURE:
<223> OTHER INFORMATION: antisense sequence of shRNF4

<400> SEQUENCE: 160
tggcgtttct gggagtatgg g                                               21

<210> SEQ ID NO 161
<211> LENGTH: 10
<212> TYPE: PRT
<213> ORGANISM: Artificial Sequence
<220> FEATURE:
<223> OTHER INFORMATION: antigen peptide

<400> SEQUENCE: 161

Asp Leu Thr His Asn Asp Ser Val Val Ile
1               5                   10

<210> SEQ ID NO 162
<211> LENGTH: 21
<212> TYPE: DNA
<213> ORGANISM: Artificial Sequence

```
<220> FEATURE:
<223> OTHER INFORMATION: TRIM27 siRNA sense strand

<400> SEQUENCE: 162
aactcttagg cctaacccag a                                              21

<210> SEQ ID NO 163
<211> LENGTH: 11
<212> TYPE: PRT
<213> ORGANISM: Artificial Sequence
<220> FEATURE:
<223> OTHER INFORMATION: protein transduction domain of HIV Tat

<400> SEQUENCE: 163

Tyr Gly Arg Lys Lys Arg Arg Gln Arg Arg Arg
1               5                   10

<210> SEQ ID NO 164
<211> LENGTH: 12207
<212> TYPE: DNA
<213> ORGANISM: Homo sapiens

<400> SEQUENCE: 164
atggcgagcc gcgatagcaa ccacgctggc gagagctttc tcggctccga cggggacgag      60
gaggcgaccc gggagctgga gaccgaggag gagtcggagg gcgaggagga cgagacggcg     120
gcggagtcgg aggaggagcc ggactccagg ttatcagacc aggatgaaga gggaaagatc     180
aagcaggagt atatcatatc tgacccctcc tttccatgg tgacagtcca aggggaagat      240
agtgggataa cctgggaaac caattcaagt agatcttcta ctccttgggc ttcagaagaa     300
agtcagactt ctggtgtgtg tagtcgggaa gggtcaactg tgaattctcc tcctggaaat     360 gttttccttta ttgtggatga agtgaaaaag gttcggaaaa ggactcataa gtcaaagcat     420
ggttcaccat cattacgccg gaaaggcaac agaaaaagaa attcttttga atcccaagat     480
gttccaacaa acaaaaaagg cagtcccttta acttcagcaa gccaggtact aaccacggag     540
aaagagaagt catatactgg catttatgat aaagcaagaa aaaagaagac cacttcaaat     600
acacctccga ttactggggc aatatacaaa gaacacaagc cattagtgtt aagaccagtc     660
tacataggaa cagtacaata taaaattaag atgtttaatt cggttaaaga agaattaatt     720
cctctacaat tttatggaac attgccaaag ggttatgtaa ttaaagaaat acattatagg     780
aaagggaaag atgcatccat tagtctagag ccagatttgg acaatagtgg ttctaataca     840
gtgtccaaaa cacgcaaatt agtagcccaa agcatagagg ataaagtaaa agaggttttt     900
ccaccctgga gaggcgcact ctccaaagga tcagagtccc taaccttaat gttcagtcat     960
gaagatcaaa agaaaattta tgctgattct cccctaaatg ccacatctgc attggagcac    1020
acagttccct cttattcaag tagtggcaga gcagaacaag gaatacagct caggcattca    1080
cagtcagtgc cacaacagcc agaagatgaa gcaaaaccac atgaagtgga acctccatct    1140
gtgacacccg acacacctgc aactatgttc ctgagaacaa caaggaaga atgtgagctt    1200 gcttcaccag gaactgcagc ttcagagaat gactcttcag tctcaccatc atttgctaat    1260
gaggtaaaga aggaagatgt gtattctgct caccattcca tttctctgga ggcagcgtca    1320
ccaggtctgg cagcatctac ccaggatggt ttggacccag accaagaaca gccggacctg    1380
acttcaatag aaagggcaga accagtctcc gcaaaactga cccctaccca tcccagtgtc    1440
aaaggagaga aggaggaaaa catgcttgag ccatccattt ctctttctga acctctaatg    1500
ttagaagaac cagagaaaga agaaatagaa acttccctac ccatagctat taccccctgaa    1560
```

```
cctgaagatt ctaatttagt agaagaagag atcgtagaac ttgattaccc agaaagccca   1620
ttggtttccg agaagccctt cccaccacat atgtccctg aagtggagca caaagaagaa    1680
gagcttattc taccattatt ggcagcatca tctcctgaac atgttgcttt gtctgaggaa   1740
gaaagagagg aaattgcatc tgtttctact ggttctgctt ttgtatcaga gtattcagta   1800
ccacaggatt tgaaccatga attacaggag caagaaggtg agccagttcc cccatccaat   1860
gtagaagcta tagctgaaca tgcagttttg tcagaagaag agaatgagga atttgaggct   1920
tattccccag ctgcagcccc tacatctgag agctctctct caccatccac aactgagaag   1980
acttcagaga accagtctcc actgttttca acagttacac cagaatacat ggtcctatca   2040
ggagacgagg cctcagaaag tgggtgttac acaccagact ccacatctgc ttctgaatat   2100
tcagttccat cactggcaac aaaagagtca ctgaagaaaa caattgaccg taagtccccg   2160
ttaatattga aggtgtttc tgagtacatg attccatcag aagagaagga agacactgga    2220
tcgtttactc cagctgtggc ccctgcttct gagccctctc tctcaccatc cacaaccgaa   2280
aagacttctg aatgccagtc accactgcct tctactgcca catcagaaca cgtggtccca   2340
tcagaaggag aggacctagg aagtgaacgt ttcacaccgg attcaaagtt gatctccaaa   2400
tatgcagccc cactcaatgc aacacaggaa tctcaaaaga aataatcaa tgaggcatcc    2460 caattcaaac caaaggtat ttctgagcac acagttctgt cagtagacgg caaggaggtc    2520
attggaccat cttccccaga tttggttgtt gcatctgaac actctttccc accacacaca   2580
accgagatga cttctgaatg ccaggcccca ccactttcag ccaccccatc tgaatatgtt   2640
gttctatcag acgaagaggc agtcgagttg gaacgataca caccctcttc tacatctgct   2700 tctgaattt cagtaccacc atatgcaaca ccggaggcac aggaggaaga aattgtccat    2760
agatctctaa atctaaaagg tgcatcctca cccatgaatt tatcagaaga agatcaagaa   2820
gacattggac ctttttctcc agattctgca tttgtgtcag aattctcatt tccaccgtat   2880
gcaacccagg aagcagagaa aagagaattt gagtgcgatt ctccaatatg tttaacatca   2940
ccatctgagc acactatttt gtcagatgaa gacactgaag aagcggaact gttctctcca   3000
gactcagcat cacaagtttc aatccctccc tttagaatct cagaaacaga gaaaatgaa   3060 cttgagcctg attcactatt aactgcagtg tctgcttcag gttattcctg cttttcagaa   3120
gcagatgagg aagacattgg atccacagct gctacacctg tatctgagca gttcagttca   3180
tcacagaagc aaaaagctga aactttccct ttgatgtctc cgcttgaaga cttaagtctg   3240
ccgccttcaa cagataaatc agagaaagca gaaattaagc cagagattcc aacaacctca   3300
acatctgtat ctgaatatct cattttggca cagaagcaga aaactcaagc atatttagag   3360
cctgagtctg aagcttgat tccttcacat ttaaccagtg aagtggagaa gggagaaagg    3420
gaggcaagtt catcagtagc tgcaataccct gctgctttac ctgcacaatc atctatagta   3480
aaggaagaaa ccaaacctgc atctccacat tcagttttac ctgattcagt ccctgcaatc   3540
aagaaagaac aggaacccac agcagcactc actctaaaag ctgcagatga acagatggct   3600
ttgtcaaaag tcagaaagga agaaattgtg cctgattctc aagaagctac agcacatgta   3660
tcacaggatc aaaaaatgga gcctcagcct ccaaatgttc cagagtctga gatgaaatat   3720
tcagttttgc ctgacatggt agatgagcca agaagggtg tcaagcccaa attagttcta    3780
aatgtgactt ctgaactaga acagagaaag ttgtccaaga atgagcctga agtaataaaa   3840
ccatattcac ctctaaagga aacatcttta tctggacctg aggctttatc agcagtgaaa   3900
```

```
atggagatga acatgattc caaaataaca actacaccta tagtgcttca ttcagcttcc   3960
tcaggagtgg aaaagcaagt tgaacatggt ccacctgcac tagcattttc agctttgtca   4020
gaagaaatta aaaagaaat tgaacccagt tcctcaacaa ctacagcatc tgtaactaag   4080
cttgattcaa acttaaccag agcagtaaaa gaagaaatcc caacagattc atctcttatc   4140
actcctgtag atcgtccagt cttaacaaaa gtaggaaagg gtgaattagg aagtggtttg   4200
ccaccactgg taacatctgc agatgaacat tcagttcttg cagaagaaga caaggtggca   4260
attaaaggtg cttctcccat tgaaacttca tccaaacatt tagcttggtc agaagcagag   4320
aaggaaatta aatttgattc acttccaagt gtctcctcta tagcagagca ttctgttttg   4380
tcagaagtag aagccaaaga agttaaagct gggttgccag taatcaaaac atcatcttct   4440
cagcattcag ataaatctga ggaagcaagg gtagaagaca acaagatct tttattttct   4500
acagtctgtg actctgaacg tttggtttca tcacagaaga agagcttgat gtctacctca   4560
gaggtgttag agcctgaaca tgagcttcca ctcagcctat ggggtgagat aaagaagaaa   4620
gaaactgaac ttccttcatc acaaaatgtg tcacctgcat ccaaacatat aatcccaaaa   4680
ggcaaagatg aggaaacagc aagttcatct cctgagttgg aaaatttagc atcaggttta   4740
gccccaacat tactgctcct cagtgatgat aagaacaaac cggcagtgga ggtatcttct   4800
acagctcagg gagacttccc atcagaaaaa caagatgttg ctttggcaga gctgtctttg   4860
gaacctgaga agaaagacaa gccacaccaa ccgttggaat taccaaatgc tgggtcagaa   4920
ttttctagtg atttaggtag acaaagtgga tccataggta caaaacaagc aaagtctccc   4980
ataactgaaa cagaggattc tgttttagaa aaaggcccag ctgagcttag gagcagagaa   5040
ggaaaagaag aaaatagaga gctttgtgca tcttctacga tgcctgcaat ttcagagctt   5100
tcatcattgc ttagggagga atctcagaat gaagaaatta aacctttctc tcccaagatc   5160
atcagcctag agtcgaaaga accacctgcc tctgtagctg aaggaggcaa cccagaagaa   5220
tttcagccat ttacttttc tttaaaagga ttatcagagg aggttagcca tccagccgac   5280
tttaaaaagg gaggaaatca agaaataggc ccattaccac caactggaaa tttgaaggca   5340
caagtcatgg gagatatttt agataagcta agtgaagaaa caggccaccc aaattcatcc   5400
caggtactcc agagtataac agaaccatca agattgctc cttctgacct ccttgtagaa   5460
caaaaaaaga cagaaaaagc acttcattca gatcaaactg ttaaattacc tgatgtaagc   5520
acctcttctg aagataaaca agatctgggt attaagcagt tttcacttat gagagagaat   5580
ttgcctttgg aacaatcaaa atcatttatg acaaccaagc ctgcggatgt caaagaaaca   5640
aaaatggaag aattctttat ttctccaaag gatgaaaact ggatgttggg aaagccagaa   5700
aatgtggcta gtcaacacga acagagaata gcaggatctg tgcagctgga ttcctctagc   5760
agcaatgagc tgaggccagg gcagctcaag gctgctgtgt ccagtaagga ccatacatgt   5820
gaagtgagaa agcaggtcct gccgcattct gctgaagaat tcatttgtc atcacaagaa   5880
gcagtatctg ctcttgatac ttccagtggt aatacagaga ccttatcaag taaaagttac   5940
tcttctgaag aagtaaagct ggctgaagaa ccaaagtctt tagtcctagc tggaaatgta   6000
gagagaaaca tagcagaggg gaaggagatt cattctttga tggagagtga agtttgctta   6060
ttggagaaag caaacacaga gctttcctgg ccttccaaag aagatagcca ggaaaaaatt   6120
aaactacctc ctgaaagatt cttccagaaa ccagtgtctg gcctatcagt ggaacaggtg   6180
aagtcagaaa caatctcctc ttctgtcaaa acagcccatt tcccggcaga aggtgtggaa   6240
cctgcattgg gcaatgaaaa agaagcacac aggagcacac ctcctttttcc tgaagagaag   6300
```

```
ccattggaag aatcaaaaat ggttcagtca aaggttattg atgatgctga tgagggaaag    6360
aaaccatcac ctgaagtaaa aatacccaca caaagaaaac ccatctcctc aatccatgca    6420
agagagcctc aatccccaga gtcacctgag gtgacacaaa atccacctac acaaccaaag    6480
gtggctaagc cggaccttcc tgaggaaaag ggaaagaaag gaatttcatc tttcaaatcg    6540
tggatgtcca gcttgttttt tggatcgagc actccagata caaagttgc tgaacaagaa     6600
gacttagaaa cacagccaag tccatccgta gaaaaagcag tgactgtgat agatcctgaa    6660
ggtacaattc ccaccaattt taatgtagct gagaaaccag ctgatcattc attatcagag    6720
gtaaaactta aaactgctga tgaacccaga ggtactttag taaaatctgg tgacggtcaa    6780
aacgttaaag aaaaatccat gattttatca aatgtagaag atttacaaca gccaaaattc    6840
atttctgagg tgtctaggga agattatgga aaaaagaaa tctcaggcga ttcagaggaa     6900
atgaacataa actcagtagt tacttctgct gatggtgaga accttgaaat tcaatcttat    6960
tcactaatcg gtgagaaatt ggttatggaa gaagccaaaa ctattgttcc tcctcatgtt    7020
actgatagta aaagagtcca gaagccagca atcgctcctc catctaaatg gaatatttct    7080
atttttaagg aagagccaag aagtgatcaa aaacaaaaat cactcctttc atttgatgta    7140
gtagataagg tgccacaaca gccaaaatca gcttcctcca actttgcaag taaaaatatc    7200
acaaaggaat cagagaaacc agagtcaatt attttgccag tagaagaatc aaaaggcagt    7260
ttaattgatt tcagtgaaga cagactcaag aaagaaatgc aaaatcctac ttccttgaaa    7320
atttctgaag aggaaacaaa actcaggtct gttagtccaa ctgagaagaa agataatttg    7380
gaaaacagat catataccct tggcagaaaag aaggtgctgg cagaaaaaca aaactctgtg    7440
gccccattag agcttagaga tagtaatgaa ataggggaaga cacaaattac acttggatct    7500
agatctactg aactgaaaga atcaaaagcc gatgctatgc cacagcactt ctatcaaaat    7560
gaagactaca atgaaagacc caaaatcatt gttggttctg aaaaggagaa aggtgaagaa    7620
aaagaaaatc aggtatatgt gctttcagaa ggaagaagc agcaggaaca tcagccttat    7680
tctgtgaatg tagccgagtc tatgagtaga gaatcagata tctctttagg tcattctttg    7740
ggtgaaactc aatcattttc attagttaaa gctacatcag ttactgaaaa atcagaagcc    7800
atgctcgcag aggctcaccc agaaatcaga gaagcaaagg cagtaggaac ccaaccacat    7860
cctttagaag aaagtaaagt tttggtggag aaaaccaaga cttttcctgcc ggtggctctt    7920
tcttgtcgtg atgaaataga gaaccactct ttatctcagg aaggaaatct agtattagaa    7980
aagtcaagca gagatatgcc agatcacagt gaagaaaaag aacagttcag agagtcagag    8040
ctatcgaaag gcggttcagt agatatcaca aaagaaactg tgaaacaagg atttcaagaa    8100
aaggcagtag gaacccaacc acgtccttta gaagaaagta agttttggt ggagaaaact     8160
aagactttcc tgccagtggt tctttcttgt catgatgaaa tagagaacca ctctttgtct    8220
caggaaggaa atctagtgtt agaaaagtca agcagagata tgccagatca cagtgaagaa    8280
aaagaacagt tcaaagagtc agagctatgg aaaggtggtt cagtagatat cacaaaagaa    8340
agtatgaaag aaggatttcc atctaaagaa tccgaaagga ctttagctcg tcctttttgat   8400
gaaactaaga gctcagaaac accgccatat ttgctgtcac ctgtaaaacc acaaactctt    8460
gcttcaggag cttctccaga aattaacgca gtgaagaaaa agaaatgcc acgatcagaa     8520
ttgactccag aaaggcatac agttcatact attcagacat ctaaagatga cacatccgat    8580
gtgcctaaac aatctgttct tgtttcaaag caccacttgg aggctgcgga agatacccgt    8640
```

```
gtaaaggaac cactgtcttc agcaaaaagc aactatgctc aatttatatc taatacatca    8700
gcaagcaatg ctgataaaat ggtttctaat aaagaaatgc ccaaggaacc tgaagacaca    8760
tatgcaaaag gtgaagactt tacagtgact agtaagccag ccggactttc agaagatcag    8820
aagactgcct ttagtatcat ttctgaaggc tgtgagatat tgaatattca tgctccggcc    8880
tttatttctt caatcgatca ggaagaaagt gaacaaatgc aagataaatt gaatatttg    8940 gaagagaaag cctcatttaa aaccatacca ctccctgatg atagtgaaac agttgcttgt    9000
cataaaacat taagagcag gttagaagat gaaaaagtta ccccattgaa agaaaataaa    9060
caaaaggaaa ctcataagac aaaagaagag atatccacag attcagaaac tgatttatca    9120
tttattcagc ccacaattcc cagtgaagag gattattttg aaaaatatac tttgattgat    9180
tataacatct ccccagaccc agaaaaacag aaagctccac agaaattaaa tgttgaagag    9240
aaactctcaa aggaagttac agaagaaact atctctttcc cagtaagttc agtggaaagt    9300
gcactgaaac atgaatatga cttggtgaaa ttagatgaaa gttttatgg accagaaaag    9360 ggccacaaca tattatctca tccagagacc caaagccaaa actcagctga caggaatgtt    9420
tcaaaggaca caaagagaga tgtggactca aagtcaccgg ggatgccttt atttgaagca    9480
gaggaaggag ttctatcacg aacccagata tttcctacca ctattaaagt cattgatcca    9540
gaatttctgg aggagccacc tgcacttgca tttttatata aggatctgta tgaagaagca    9600
gttggagaga aaaagaagga agaggagaca gcttctgaag gtgacagtgt gaattctgag    9660
gcatcatttc ccagcagaaa ttctgacact gatgatggaa caggaatata ttttgagaag    9720
tacatactca aagatgacat tctccatgac acatctctaa ctcaaaagga ccagggccaa    9780
ggtctggaag aaaaacgagt tggtaaggat gattcatacc aaccgatagc tgcagaaggg    9840
gaaatttggg gaaagtttgg aactatttgc agggagaaga gtctggaaga acagaaaggt    9900
gtttatgggg aaggagaatc agtagaccat gtggagaccg ttggtaacgt agcgatgcag    9960
aagaaagctc ccatcacaga ggacgtcaga gtggctaccc agaaaataag ttatgcggtt   10020
ccatttgaag acacccatca tgttctggag cgtgcagatg aagcaggcag tcacggtaat   10080
gaagtcggaa atgcaagtcc agaggtcaat ctgaatgtcc cagtacaagt gtccttcccg   10140
gaggaagaat ttgcatctgg tgcaactcat gttcaagaaa catcactaga agaacctaaa   10200
atcctggtcc cacctgagcc aagtgaagag aggctccgta atagccctgt tcaggatgag   10260
tatgaattta cagaatccct gcataatgaa gtggttcctc aagacatatt atcagaagaa   10320
ctgtcttcag aatccacacc tgaagatgtc ttatctcaag gaaaggaatc ctttgagcac   10380
atcagtgaaa atgaatttgc gagtgaggca gaacaaagta cacctgctga caaaaagag   10440 ttgggcagcg agaggaaaga agaaccaa ttatcatctg aggtagtaac tgaaaaggca   10500 caaaagagc tgaaaaagtc ccagattgac acatactgtt acacctgcaa atgtccaatt   10560
tctgccactg acaaggtgtt tggcacccac aaagaccatg aagtttcaac gcttgacaca   10620
gctataagtg ctgtaaaggt tcaattagca gaatttctag aaaatttaca agaaaagtcc   10680
ttgaggattg aagcctttgt tagtgagata gaatcctttt ttaataccat tgaggaaaac   10740
tgtagtaaaa atgagaaaag gctagaagaa cagaatgagg aaatgatgaa gaaggtttta   10800
gcacagtatg atgagaaagc ccagagcttt gaggaagtga gaagaagaa gatggagttc   10860 ctgcatgagc agatggtcca ctttctgcag agcatggaca ctgccaaaga caccctggag   10920
accatcgtga gagaagcaga ggagcttgat gaggccgtct tcctgacttc gtttgaggaa   10980
atcaatgaaa ggttgctttc tgcaatggag agcactgctt cttagagaa aatgcctgct   11040
```

-continued

```
gcgttttccc ttttcgaaca ttatgatgac agctcggcaa gaagtgacca gatgttaaaa   11100
caagtggctg ttccacagcc tcctagatta gaacctcagg aaccaaattc tgccaccagc   11160
acaacaattg cagtttactg gagcatgaac aaggaagatg tcattgattc atttcaggtt   11220
tactgcatgg aggagccaca agatgatcaa gaagtaaatg agttggtaga agaatacaga   11280
ctgacagtga aagaaagcta ctgcattttt gaagatctgg aacctgaccg atgctatcaa   11340
gtgtgggtga tggctgtgaa cttcactgga tgtagcctgc ccagtgaaag gccatctttt   11400
aggacagcac cctccacccc tgtgatccgc gctgaggact gtactgtgtg ttggaacaca   11460
gccactatcc gatggcggcc caccacccca gaggccacgg agacctacac tctggagtac   11520
tgcagacagc actctcctga gggagagggc ctcagatctt tctctggaat caaggactc    11580 cagctgaaag ttaacctcca acccaatgat aactactttt tctatgtgag ggccatcaat   11640
gcatttggga caagtgaaca gagtgaagct gctctcatct ccaccagagg aaccagattt   11700
ctcttgttga gagaaacagc tcatcctgct ctacacattt cctcaagtgg acagtgatc    11760 agctttggtg agaggagacg gctgacggaa atcccgtcag tgctgggtga ggagctgcct   11820
tcctgtggcc agcattactg ggaaaccaca gtcacagact gcccagcata tcgactcggc   11880
atctgctcca gctcggctgt gcaggcaggt gccctaggac aaggggagac ctcatggtac   11940
atgcactgct ctgagccaca gagatacaca ttttctaca gtggtattgt gagtgatgtt    12000
catgtgactg agcgtccagc cagagtgggc atcctgctgg actacaacaa ccagagactt   12060
atcttcatca acgcagagag cgagcagttg ctcttcatca tcaggcacag gtttaatgag   12120
ggtgtccacc ctgcctttgc cctggagaaa cctggaaaat gtactttgca cctggggata   12180
gagcccccgg attctgtaag gcacaag                                        12207
```

<210> SEQ ID NO 165
<211> LENGTH: 4069
<212> TYPE: PRT
<213> ORGANISM: Homo sapiens

<400> SEQUENCE: 165

```
Met Ala Ser Arg Asp Ser Asn His Ala Gly Glu Ser Phe Leu Gly Ser
1               5                   10                  15

Asp Gly Asp Glu Glu Ala Thr Arg Glu Leu Glu Thr Glu Glu Glu Ser
            20                  25                  30

Glu Gly Glu Glu Asp Glu Thr Ala Ala Glu Ser Glu Glu Pro Asp
        35                  40                  45

Ser Arg Leu Ser Asp Gln Asp Glu Gly Lys Ile Lys Gln Glu Tyr
    50                  55                  60

Ile Ile Ser Asp Pro Ser Phe Ser Met Val Thr Val Gln Arg Glu Asp
65                  70                  75                  80

Ser Gly Ile Thr Trp Glu Thr Asn Ser Ser Arg Ser Ser Thr Pro Trp
                85                  90                  95

Ala Ser Glu Glu Ser Gln Thr Ser Gly Val Cys Ser Arg Glu Gly Ser
            100                 105                 110

Thr Val Asn Ser Pro Pro Gly Asn Val Ser Phe Ile Val Asp Glu Val
        115                 120                 125

Lys Lys Val Arg Lys Arg Thr His Lys Ser Lys His Gly Ser Pro Ser
    130                 135                 140

Leu Arg Arg Lys Gly Asn Arg Lys Arg Asn Ser Phe Glu Ser Gln Asp
145                 150                 155                 160
```

```
Val Pro Thr Asn Lys Lys Gly Ser Pro Leu Thr Ser Ala Ser Gln Val
            165                 170                 175

Leu Thr Thr Glu Lys Glu Lys Ser Tyr Thr Gly Ile Tyr Asp Lys Ala
            180                 185                 190

Arg Lys Lys Lys Thr Thr Ser Asn Thr Pro Pro Ile Thr Gly Ala Ile
            195                 200                 205

Tyr Lys Glu His Lys Pro Leu Val Leu Arg Pro Val Tyr Ile Gly Thr
            210                 215                 220

Val Gln Tyr Lys Ile Lys Met Phe Asn Ser Val Lys Glu Glu Leu Ile
225                 230                 235                 240

Pro Leu Gln Phe Tyr Gly Thr Leu Pro Lys Gly Tyr Val Ile Lys Glu
            245                 250                 255

Ile His Tyr Arg Lys Gly Lys Asp Ala Ser Ile Ser Leu Glu Pro Asp
            260                 265                 270

Leu Asp Asn Ser Gly Ser Asn Thr Val Ser Lys Thr Arg Lys Leu Val
            275                 280                 285

Ala Gln Ser Ile Glu Asp Lys Val Lys Glu Val Phe Pro Pro Trp Arg
            290                 295                 300

Gly Ala Leu Ser Lys Gly Ser Glu Ser Leu Thr Leu Met Phe Ser His
305                 310                 315                 320

Glu Asp Gln Lys Lys Ile Tyr Ala Asp Ser Pro Leu Asn Ala Thr Ser
            325                 330                 335

Ala Leu Glu His Thr Val Pro Ser Tyr Ser Ser Ser Gly Arg Ala Glu
            340                 345                 350

Gln Gly Ile Gln Leu Arg His Ser Gln Ser Val Pro Gln Gln Pro Glu
            355                 360                 365

Asp Glu Ala Lys Pro His Glu Val Glu Pro Pro Ser Val Thr Pro Asp
            370                 375                 380

Thr Pro Ala Thr Met Phe Leu Arg Thr Thr Lys Glu Glu Cys Glu Leu
385                 390                 395                 400

Ala Ser Pro Gly Thr Ala Ala Ser Glu Asn Asp Ser Ser Val Ser Pro
            405                 410                 415

Ser Phe Ala Asn Glu Val Lys Lys Glu Asp Val Tyr Ser Ala His His
            420                 425                 430

Ser Ile Ser Leu Glu Ala Ala Ser Pro Gly Leu Ala Ala Ser Thr Gln
            435                 440                 445

Asp Gly Leu Asp Pro Asp Gln Glu Gln Pro Asp Leu Thr Ser Ile Glu
            450                 455                 460

Arg Ala Glu Pro Val Ser Ala Lys Leu Thr Pro Thr His Pro Ser Val
465                 470                 475                 480

Lys Gly Glu Lys Glu Glu Asn Met Leu Glu Pro Ser Ile Ser Leu Ser
            485                 490                 495

Glu Pro Leu Met Leu Glu Glu Pro Lys Glu Glu Ile Glu Thr Ser
            500                 505                 510

Leu Pro Ile Ala Ile Thr Pro Glu Pro Glu Asp Ser Asn Leu Val Glu
            515                 520                 525

Glu Glu Ile Val Glu Leu Asp Tyr Pro Glu Ser Pro Leu Val Ser Glu
            530                 535                 540

Lys Pro Phe Pro Pro His Met Ser Pro Glu Val His Lys Glu Glu
545                 550                 555                 560

Glu Leu Ile Leu Pro Leu Leu Ala Ala Ser Ser Pro Glu His Val Ala
            565                 570                 575

Leu Ser Glu Glu Glu Arg Glu Glu Ile Ala Ser Val Ser Thr Gly Ser
```

-continued

```
            580             585             590
Ala Phe Val Ser Glu Tyr Ser Val Pro Gln Asp Leu Asn His Glu Leu
            595             600             605
Gln Glu Gln Glu Gly Glu Pro Val Pro Pro Ser Asn Val Glu Ala Ile
            610             615             620
Ala Glu His Ala Val Leu Ser Glu Glu Asn Glu Glu Phe Glu Ala
625             630             635             640
Tyr Ser Pro Ala Ala Pro Thr Ser Glu Ser Ser Leu Ser Pro Ser
                    645             650             655
Thr Thr Glu Lys Thr Ser Glu Asn Gln Ser Pro Leu Phe Ser Thr Val
            660             665             670
Thr Pro Glu Tyr Met Val Leu Ser Gly Asp Glu Ala Ser Glu Ser Gly
            675             680             685
Cys Tyr Thr Pro Asp Ser Thr Ser Ala Ser Glu Tyr Ser Val Pro Ser
            690             695             700
Leu Ala Thr Lys Glu Ser Leu Lys Lys Thr Ile Asp Arg Lys Ser Pro
705             710             715             720
Leu Ile Leu Lys Gly Val Ser Glu Tyr Met Ile Pro Ser Glu Glu Lys
                    725             730             735
Glu Asp Thr Gly Ser Phe Thr Pro Ala Val Ala Pro Ala Ser Glu Pro
            740             745             750
Ser Leu Ser Pro Ser Thr Thr Glu Lys Thr Ser Glu Cys Gln Ser Pro
            755             760             765
Leu Pro Ser Thr Ala Thr Ser Glu His Val Val Pro Ser Gly Glu
            770             775             780
Asp Leu Gly Ser Glu Arg Phe Thr Pro Asp Ser Lys Leu Ile Ser Lys
785             790             795             800
Tyr Ala Ala Pro Leu Asn Ala Thr Gln Glu Ser Gln Lys Lys Ile Ile
                    805             810             815
Asn Glu Ala Ser Gln Phe Lys Pro Lys Gly Ile Ser Glu His Thr Val
            820             825             830
Leu Ser Val Asp Gly Lys Glu Val Ile Gly Pro Ser Ser Pro Asp Leu
            835             840             845
Val Val Ala Ser Glu His Ser Phe Pro Pro His Thr Thr Glu Met Thr
            850             855             860
Ser Glu Cys Gln Ala Pro Pro Leu Ser Ala Thr Pro Ser Glu Tyr Val
865             870             875             880
Val Leu Ser Asp Glu Glu Ala Val Glu Leu Glu Arg Tyr Thr Pro Ser
                    885             890             895
Ser Thr Ser Ala Ser Glu Phe Ser Val Pro Pro Tyr Ala Thr Pro Glu
            900             905             910
Ala Gln Glu Glu Glu Ile Val His Arg Ser Leu Asn Leu Lys Gly Ala
            915             920             925
Ser Ser Pro Met Asn Leu Ser Glu Glu Gln Glu Asp Ile Gly Pro
            930             935             940
Phe Ser Pro Asp Ser Ala Phe Val Ser Glu Phe Ser Phe Pro Pro Tyr
945             950             955             960
Ala Thr Gln Glu Ala Glu Lys Arg Glu Phe Glu Cys Asp Ser Pro Ile
                    965             970             975
Cys Leu Thr Ser Pro Ser Glu His Thr Ile Leu Ser Asp Glu Asp Thr
            980             985             990
Glu Glu Ala Glu Leu Phe Ser Pro  Asp Ser Ala Ser Gln  Val Ser Ile
            995             1000            1005
```

-continued

```
Pro Pro Phe Arg Ile Ser Glu Thr Glu Lys Asn Glu Leu Glu Pro
    1010                1015                1020

Asp Ser Leu Leu Thr Ala Val Ser Ala Ser Gly Tyr Ser Cys Phe
    1025                1030                1035

Ser Glu Ala Asp Glu Glu Asp Ile Gly Ser Thr Ala Ala Thr Pro
    1040                1045                1050

Val Ser Glu Gln Phe Ser Ser Gln Lys Gln Lys Ala Glu Thr
    1055                1060                1065

Phe Pro Leu Met Ser Pro Leu Glu Asp Leu Ser Leu Pro Pro Ser
    1070                1075                1080

Thr Asp Lys Ser Glu Lys Ala Glu Ile Lys Pro Glu Ile Pro Thr
    1085                1090                1095

Thr Ser Thr Ser Val Ser Glu Tyr Leu Ile Leu Ala Gln Lys Gln
    1100                1105                1110

Lys Thr Gln Ala Tyr Leu Glu Pro Glu Ser Glu Asp Leu Ile Pro
    1115                1120                1125

Ser His Leu Thr Ser Glu Val Glu Lys Gly Glu Arg Glu Ala Ser
    1130                1135                1140

Ser Ser Val Ala Ala Ile Pro Ala Ala Leu Pro Ala Gln Ser Ser
    1145                1150                1155

Ile Val Lys Glu Glu Thr Lys Pro Ala Ser Pro His Ser Val Leu
    1160                1165                1170

Pro Asp Ser Val Pro Ala Ile Lys Lys Glu Gln Glu Pro Thr Ala
    1175                1180                1185

Ala Leu Thr Leu Lys Ala Ala Asp Glu Gln Met Ala Leu Ser Lys
    1190                1195                1200

Val Arg Lys Glu Glu Ile Val Pro Asp Ser Gln Glu Ala Thr Ala
    1205                1210                1215

His Val Ser Gln Asp Gln Lys Met Glu Pro Gln Pro Pro Asn Val
    1220                1225                1230

Pro Glu Ser Glu Met Lys Tyr Ser Val Leu Pro Asp Met Val Asp
    1235                1240                1245

Glu Pro Lys Lys Gly Val Lys Pro Lys Leu Val Leu Asn Val Thr
    1250                1255                1260

Ser Glu Leu Glu Gln Arg Lys Leu Ser Lys Asn Glu Pro Glu Val
    1265                1270                1275

Ile Lys Pro Tyr Ser Pro Leu Lys Glu Thr Ser Leu Ser Gly Pro
    1280                1285                1290

Glu Ala Leu Ser Ala Val Lys Met Glu Met Lys His Asp Ser Lys
    1295                1300                1305

Ile Thr Thr Thr Pro Ile Val Leu His Ser Ala Ser Ser Gly Val
    1310                1315                1320

Glu Lys Gln Val Glu His Gly Pro Pro Ala Leu Ala Phe Ser Ala
    1325                1330                1335

Leu Ser Glu Glu Ile Lys Lys Glu Ile Glu Pro Ser Ser Ser Thr
    1340                1345                1350

Thr Thr Ala Ser Val Thr Lys Leu Asp Ser Asn Leu Thr Arg Ala
    1355                1360                1365

Val Lys Glu Glu Ile Pro Thr Asp Ser Ser Leu Ile Thr Pro Val
    1370                1375                1380

Asp Arg Pro Val Leu Thr Lys Val Gly Lys Gly Glu Leu Gly Ser
    1385                1390                1395
```

-continued

| | | | | | | | | | | |
|---|---|---|---|---|---|---|---|---|---|---|
| Gly | Leu | Pro | Pro | Leu | Val | Thr | Ser | Ala | Asp | Glu | His | Ser | Val | Leu |
| | 1400 | | | | 1405 | | | | 1410 | | | | | |
| Ala | Glu | Glu | Asp | Lys | Val | Ala | Ile | Lys | Gly | Ala | Ser | Pro | Ile | Glu |
| | 1415 | | | | 1420 | | | | 1425 | | | | | |
| Thr | Ser | Ser | Lys | His | Leu | Ala | Trp | Ser | Glu | Ala | Glu | Lys | Glu | Ile |
| | 1430 | | | | 1435 | | | | 1440 | | | | | |
| Lys | Phe | Asp | Ser | Leu | Pro | Ser | Val | Ser | Ser | Ile | Ala | Glu | His | Ser |
| | 1445 | | | | 1450 | | | | 1455 | | | | | |
| Val | Leu | Ser | Glu | Val | Glu | Ala | Lys | Glu | Val | Lys | Ala | Gly | Leu | Pro |
| | 1460 | | | | 1465 | | | | 1470 | | | | | |
| Val | Ile | Lys | Thr | Ser | Ser | Gln | His | Ser | Asp | Lys | Ser | Glu | Glu | |
| | 1475 | | | | 1480 | | | | 1485 | | | | | |
| Ala | Arg | Val | Glu | Asp | Lys | Gln | Asp | Leu | Leu | Phe | Ser | Thr | Val | Cys |
| | 1490 | | | | 1495 | | | | 1500 | | | | | |
| Asp | Ser | Glu | Arg | Leu | Val | Ser | Ser | Gln | Lys | Lys | Ser | Leu | Met | Ser |
| | 1505 | | | | 1510 | | | | 1515 | | | | | |
| Thr | Ser | Glu | Val | Leu | Glu | Pro | Glu | His | Glu | Leu | Pro | Leu | Ser | Leu |
| | 1520 | | | | 1525 | | | | 1530 | | | | | |
| Trp | Gly | Glu | Ile | Lys | Lys | Glu | Thr | Glu | Leu | Pro | Ser | Ser | Gln | |
| | 1535 | | | | 1540 | | | | 1545 | | | | | |
| Asn | Val | Ser | Pro | Ala | Ser | Lys | His | Ile | Ile | Pro | Lys | Gly | Lys | Asp |
| | 1550 | | | | 1555 | | | | 1560 | | | | | |
| Glu | Glu | Thr | Ala | Ser | Ser | Ser | Pro | Glu | Leu | Glu | Asn | Leu | Ala | Ser |
| | 1565 | | | | 1570 | | | | 1575 | | | | | |
| Gly | Leu | Ala | Pro | Thr | Leu | Leu | Leu | Ser | Asp | Asp | Lys | Asn | Lys | |
| | 1580 | | | | 1585 | | | | 1590 | | | | | |
| Pro | Ala | Val | Glu | Val | Ser | Ser | Thr | Ala | Gln | Gly | Asp | Phe | Pro | Ser |
| | 1595 | | | | 1600 | | | | 1605 | | | | | |
| Glu | Lys | Gln | Asp | Val | Ala | Leu | Ala | Glu | Leu | Ser | Leu | Glu | Pro | Glu |
| | 1610 | | | | 1615 | | | | 1620 | | | | | |
| Lys | Lys | Asp | Lys | Pro | His | Gln | Pro | Leu | Glu | Leu | Pro | Asn | Ala | Gly |
| | 1625 | | | | 1630 | | | | 1635 | | | | | |
| Ser | Glu | Phe | Ser | Ser | Asp | Leu | Gly | Arg | Gln | Ser | Gly | Ser | Ile | Gly |
| | 1640 | | | | 1645 | | | | 1650 | | | | | |
| Thr | Lys | Gln | Ala | Lys | Ser | Pro | Ile | Thr | Glu | Thr | Glu | Asp | Ser | Val |
| | 1655 | | | | 1660 | | | | 1665 | | | | | |
| Leu | Glu | Lys | Gly | Pro | Ala | Glu | Leu | Arg | Ser | Arg | Glu | Gly | Lys | Glu |
| | 1670 | | | | 1675 | | | | 1680 | | | | | |
| Glu | Asn | Arg | Glu | Leu | Cys | Ala | Ser | Ser | Thr | Met | Pro | Ala | Ile | Ser |
| | 1685 | | | | 1690 | | | | 1695 | | | | | |
| Glu | Leu | Ser | Ser | Leu | Leu | Arg | Glu | Glu | Ser | Gln | Asn | Glu | Glu | Ile |
| | 1700 | | | | 1705 | | | | 1710 | | | | | |
| Lys | Pro | Phe | Ser | Pro | Lys | Ile | Ile | Ser | Leu | Glu | Ser | Lys | Glu | Pro |
| | 1715 | | | | 1720 | | | | 1725 | | | | | |
| Pro | Ala | Ser | Val | Ala | Glu | Gly | Gly | Asn | Pro | Glu | Glu | Phe | Gln | Pro |
| | 1730 | | | | 1735 | | | | 1740 | | | | | |
| Phe | Thr | Phe | Ser | Leu | Lys | Gly | Leu | Ser | Glu | Glu | Val | Ser | His | Pro |
| | 1745 | | | | 1750 | | | | 1755 | | | | | |
| Ala | Asp | Phe | Lys | Lys | Gly | Gly | Asn | Gln | Glu | Ile | Gly | Pro | Leu | Pro |
| | 1760 | | | | 1765 | | | | 1770 | | | | | |
| Pro | Thr | Gly | Asn | Leu | Lys | Ala | Gln | Val | Met | Gly | Asp | Ile | Leu | Asp |
| | 1775 | | | | 1780 | | | | 1785 | | | | | |
| Lys | Leu | Ser | Glu | Glu | Thr | Gly | His | Pro | Asn | Ser | Ser | Gln | Val | Leu |

-continued

```
                1790                1795                1800

Gln Ser Ile Thr Glu Pro Ser Lys Ile Ala Pro Ser Asp Leu Leu
    1805                1810                1815

Val Glu Gln Lys Lys Thr Glu Lys Ala Leu His Ser Asp Gln Thr
    1820                1825                1830

Val Lys Leu Pro Asp Val Ser Thr Ser Ser Glu Asp Lys Gln Asp
    1835                1840                1845

Leu Gly Ile Lys Gln Phe Ser Leu Met Arg Glu Asn Leu Pro Leu
    1850                1855                1860

Glu Gln Ser Lys Ser Phe Met Thr Thr Lys Pro Ala Asp Val Lys
    1865                1870                1875

Glu Thr Lys Met Glu Glu Phe Phe Ile Ser Pro Lys Asp Glu Asn
    1880                1885                1890

Trp Met Leu Gly Lys Pro Glu Asn Val Ala Ser Gln His Glu Gln
    1895                1900                1905

Arg Ile Ala Gly Ser Val Gln Leu Asp Ser Ser Ser Asn Glu
    1910                1915                1920

Leu Arg Pro Gly Gln Leu Lys Ala Ala Val Ser Ser Lys Asp His
    1925                1930                1935

Thr Cys Glu Val Arg Lys Gln Val Leu Pro His Ser Ala Glu Glu
    1940                1945                1950

Ser His Leu Ser Ser Gln Glu Ala Val Ser Ala Leu Asp Thr Ser
    1955                1960                1965

Ser Gly Asn Thr Glu Thr Leu Ser Ser Lys Ser Tyr Ser Ser Glu
    1970                1975                1980

Glu Val Lys Leu Ala Glu Glu Pro Lys Ser Leu Val Leu Ala Gly
    1985                1990                1995

Asn Val Glu Arg Asn Ile Ala Glu Gly Lys Glu Ile His Ser Leu
    2000                2005                2010

Met Glu Ser Glu Ser Leu Leu Leu Glu Lys Ala Asn Thr Glu Leu
    2015                2020                2025

Ser Trp Pro Ser Lys Glu Asp Ser Gln Glu Lys Ile Lys Leu Pro
    2030                2035                2040

Pro Glu Arg Phe Phe Gln Lys Pro Val Ser Gly Leu Ser Val Glu
    2045                2050                2055

Gln Val Lys Ser Glu Thr Ile Ser Ser Ser Val Lys Thr Ala His
    2060                2065                2070

Phe Pro Ala Glu Gly Val Glu Pro Ala Leu Gly Asn Glu Lys Glu
    2075                2080                2085

Ala His Arg Ser Thr Pro Pro Phe Pro Glu Glu Lys Pro Leu Glu
    2090                2095                2100

Glu Ser Lys Met Val Gln Ser Lys Val Ile Asp Asp Ala Asp Glu
    2105                2110                2115

Gly Lys Lys Pro Ser Pro Glu Val Lys Ile Pro Thr Gln Arg Lys
    2120                2125                2130

Pro Ile Ser Ser Ile His Ala Arg Glu Pro Gln Ser Pro Glu Ser
    2135                2140                2145

Pro Glu Val Thr Gln Asn Pro Pro Thr Gln Pro Lys Val Ala Lys
    2150                2155                2160

Pro Asp Leu Pro Glu Glu Lys Gly Lys Lys Gly Ile Ser Ser Phe
    2165                2170                2175

Lys Ser Trp Met Ser Ser Leu Phe Phe Gly Ser Ser Thr Pro Asp
    2180                2185                2190
```

```
Asn Lys Val Ala Glu Gln Glu Asp Leu Glu Thr Gln Pro Ser Pro
    2195                2200                2205

Ser Val Glu Lys Ala Val Thr Val Ile Asp Pro Glu Gly Thr Ile
    2210                2215                2220

Pro Thr Asn Phe Asn Val Ala Glu Lys Pro Ala Asp His Ser Leu
    2225                2230                2235

Ser Glu Val Lys Leu Lys Thr Ala Asp Glu Pro Arg Gly Thr Leu
    2240                2245                2250

Val Lys Ser Gly Asp Gly Gln Asn Val Lys Glu Lys Ser Met Ile
    2255                2260                2265

Leu Ser Asn Val Glu Asp Leu Gln Gln Pro Lys Phe Ile Ser Glu
    2270                2275                2280

Val Ser Arg Glu Asp Tyr Gly Lys Lys Glu Ile Ser Gly Asp Ser
    2285                2290                2295

Glu Glu Met Asn Ile Asn Ser Val Val Thr Ser Ala Asp Gly Glu
    2300                2305                2310

Asn Leu Glu Ile Gln Ser Tyr Ser Leu Ile Gly Glu Lys Leu Val
    2315                2320                2325

Met Glu Glu Ala Lys Thr Ile Val Pro Pro His Val Thr Asp Ser
    2330                2335                2340

Lys Arg Val Gln Lys Pro Ala Ile Ala Pro Pro Ser Lys Trp Asn
    2345                2350                2355

Ile Ser Ile Phe Lys Glu Glu Pro Arg Ser Asp Gln Lys Gln Lys
    2360                2365                2370

Ser Leu Leu Ser Phe Asp Val Val Asp Lys Val Pro Gln Gln Pro
    2375                2380                2385

Lys Ser Ala Ser Ser Asn Phe Ala Ser Lys Asn Ile Thr Lys Glu
    2390                2395                2400

Ser Glu Lys Pro Glu Ser Ile Ile Leu Pro Val Glu Glu Ser Lys
    2405                2410                2415

Gly Ser Leu Ile Asp Phe Ser Glu Asp Arg Leu Lys Lys Glu Met
    2420                2425                2430

Gln Asn Pro Thr Ser Leu Lys Ile Ser Glu Glu Thr Lys Leu
    2435                2440                2445

Arg Ser Val Ser Pro Thr Glu Lys Lys Asp Asn Leu Glu Asn Arg
    2450                2455                2460

Ser Tyr Thr Leu Ala Glu Lys Lys Val Leu Ala Glu Lys Gln Asn
    2465                2470                2475

Ser Val Ala Pro Leu Glu Leu Arg Asp Ser Asn Glu Ile Gly Lys
    2480                2485                2490

Thr Gln Ile Thr Leu Gly Ser Arg Ser Thr Glu Leu Lys Glu Ser
    2495                2500                2505

Lys Ala Asp Ala Met Pro Gln His Phe Tyr Gln Asn Glu Asp Tyr
    2510                2515                2520

Asn Glu Arg Pro Lys Ile Ile Val Gly Ser Glu Lys Glu Lys Gly
    2525                2530                2535

Glu Glu Lys Glu Asn Gln Val Tyr Val Leu Ser Glu Gly Lys Lys
    2540                2545                2550

Gln Gln Glu His Gln Pro Tyr Ser Val Asn Val Ala Glu Ser Met
    2555                2560                2565

Ser Arg Glu Ser Asp Ile Ser Leu Gly His Ser Leu Gly Glu Thr
    2570                2575                2580
```

-continued

| | | | | | | | | | | | |
|---|---|---|---|---|---|---|---|---|---|---|---|
|Gln|Ser|Phe|Ser|Leu|Val|Lys|Ala|Thr|Ser|Val|Thr|Glu|Lys|Ser|
| |2585| | | |2590| | | |2595| | | | | |

Glu Ala Met Leu Ala Glu Ala His Pro Glu Ile Arg Glu Ala Lys
    2600            2605            2610

Ala Val Gly Thr Gln Pro His Pro Leu Glu Glu Ser Lys Val Leu
    2615            2620            2625

Val Glu Lys Thr Lys Thr Phe Leu Pro Val Ala Leu Ser Cys Arg
    2630            2635            2640

Asp Glu Ile Glu Asn His Ser Leu Ser Gln Glu Gly Asn Leu Val
    2645            2650            2655

Leu Glu Lys Ser Ser Arg Asp Met Pro Asp His Ser Glu Glu Lys
    2660            2665            2670

Glu Gln Phe Arg Glu Ser Glu Leu Ser Lys Gly Gly Ser Val Asp
    2675            2680            2685

Ile Thr Lys Glu Thr Val Lys Gln Gly Phe Gln Glu Lys Ala Val
    2690            2695            2700

Gly Thr Gln Pro Arg Pro Leu Glu Glu Ser Lys Val Leu Val Glu
    2705            2710            2715

Lys Thr Lys Thr Phe Leu Pro Val Val Leu Ser Cys His Asp Glu
    2720            2725            2730

Ile Glu Asn His Ser Leu Ser Gln Glu Gly Asn Leu Val Leu Glu
    2735            2740            2745

Lys Ser Ser Arg Asp Met Pro Asp His Ser Glu Glu Lys Glu Gln
    2750            2755            2760

Phe Lys Glu Ser Glu Leu Trp Lys Gly Gly Ser Val Asp Ile Thr
    2765            2770            2775

Lys Glu Ser Met Lys Glu Gly Phe Pro Ser Lys Glu Ser Glu Arg
    2780            2785            2790

Thr Leu Ala Arg Pro Phe Asp Glu Thr Lys Ser Ser Glu Thr Pro
    2795            2800            2805

Pro Tyr Leu Leu Ser Pro Val Lys Pro Gln Thr Leu Ala Ser Gly
    2810            2815            2820

Ala Ser Pro Glu Ile Asn Ala Val Lys Lys Lys Glu Met Pro Arg
    2825            2830            2835

Ser Glu Leu Thr Pro Glu Arg His Thr Val His Thr Ile Gln Thr
    2840            2845            2850

Ser Lys Asp Asp Thr Ser Asp Val Pro Lys Gln Ser Val Leu Val
    2855            2860            2865

Ser Lys His His Leu Glu Ala Ala Glu Asp Thr Arg Val Lys Glu
    2870            2875            2880

Pro Leu Ser Ser Ala Lys Ser Asn Tyr Ala Gln Phe Ile Ser Asn
    2885            2890            2895

Thr Ser Ala Ser Asn Ala Asp Lys Met Val Ser Asn Lys Glu Met
    2900            2905            2910

Pro Lys Glu Pro Glu Asp Thr Tyr Ala Lys Gly Glu Asp Phe Thr
    2915            2920            2925

Val Thr Ser Lys Pro Ala Gly Leu Ser Glu Asp Gln Lys Thr Ala
    2930            2935            2940

Phe Ser Ile Ile Ser Glu Gly Cys Glu Ile Leu Asn Ile His Ala
    2945            2950            2955

Pro Ala Phe Ile Ser Ser Ile Asp Gln Glu Glu Ser Glu Gln Met
    2960            2965            2970

Gln Asp Lys Leu Glu Tyr Leu Glu Glu Lys Ala Ser Phe Lys Thr

-continued

```
               2975                2980                2985

Ile Pro Leu Pro Asp Asp Ser Glu Thr Val Ala Cys His Lys Thr
    2990                2995                3000

Leu Lys Ser Arg Leu Glu Asp Glu Lys Val Thr Pro Leu Lys Glu
    3005                3010                3015

Asn Lys Gln Lys Glu Thr His Lys Thr Lys Glu Glu Ile Ser Thr
    3020                3025                3030

Asp Ser Glu Thr Asp Leu Ser Phe Ile Gln Pro Thr Ile Pro Ser
    3035                3040                3045

Glu Glu Asp Tyr Phe Glu Lys Tyr Thr Leu Ile Asp Tyr Asn Ile
    3050                3055                3060

Ser Pro Asp Pro Glu Lys Gln Lys Ala Pro Gln Lys Leu Asn Val
    3065                3070                3075

Glu Glu Lys Leu Ser Lys Glu Val Thr Glu Glu Thr Ile Ser Phe
    3080                3085                3090

Pro Val Ser Ser Val Glu Ser Ala Leu Glu His Glu Tyr Asp Leu
    3095                3100                3105

Val Lys Leu Asp Glu Ser Phe Tyr Gly Pro Glu Lys Gly His Asn
    3110                3115                3120

Ile Leu Ser His Pro Glu Thr Gln Ser Gln Asn Ser Ala Asp Arg
    3125                3130                3135

Asn Val Ser Lys Asp Thr Lys Arg Asp Val Asp Ser Lys Ser Pro
    3140                3145                3150

Gly Met Pro Leu Phe Glu Ala Glu Glu Gly Val Leu Ser Arg Thr
    3155                3160                3165

Gln Ile Phe Pro Thr Thr Ile Lys Val Ile Asp Pro Glu Phe Leu
    3170                3175                3180

Glu Glu Pro Pro Ala Leu Ala Phe Leu Tyr Lys Asp Leu Tyr Glu
    3185                3190                3195

Glu Ala Val Gly Glu Lys Lys Lys Glu Glu Thr Ala Ser Glu
    3200                3205                3210

Gly Asp Ser Val Asn Ser Glu Ala Ser Phe Pro Ser Arg Asn Ser
    3215                3220                3225

Asp Thr Asp Asp Gly Thr Gly Ile Tyr Phe Glu Lys Tyr Ile Leu
    3230                3235                3240

Lys Asp Asp Ile Leu His Asp Thr Ser Leu Thr Gln Lys Asp Gln
    3245                3250                3255

Gly Gln Gly Leu Glu Glu Lys Arg Val Gly Lys Asp Asp Ser Tyr
    3260                3265                3270

Gln Pro Ile Ala Ala Glu Gly Glu Ile Trp Gly Lys Phe Gly Thr
    3275                3280                3285

Ile Cys Arg Glu Lys Ser Leu Glu Glu Gln Lys Gly Val Tyr Gly
    3290                3295                3300

Glu Gly Glu Ser Val Asp His Val Glu Thr Val Gly Asn Val Ala
    3305                3310                3315

Met Gln Lys Lys Ala Pro Ile Thr Glu Asp Val Arg Val Ala Thr
    3320                3325                3330

Gln Lys Ile Ser Tyr Ala Val Pro Phe Glu Asp Thr His His Val
    3335                3340                3345

Leu Glu Arg Ala Asp Glu Ala Gly Ser His Gly Asn Glu Val Gly
    3350                3355                3360

Asn Ala Ser Pro Glu Val Asn Leu Asn Val Pro Val Gln Val Ser
    3365                3370                3375
```

```
Phe Pro Glu Glu Glu Phe Ala Ser Gly Ala Thr His Val Gln Glu
    3380                3385                3390

Thr Ser Leu Glu Glu Pro Lys Ile Leu Val Pro Pro Glu Pro Ser
    3395                3400                3405

Glu Glu Arg Leu Arg Asn Ser Pro Val Gln Asp Glu Tyr Glu Phe
    3410                3415                3420

Thr Glu Ser Leu His Asn Glu Val Val Pro Gln Asp Ile Leu Ser
    3425                3430                3435

Glu Glu Leu Ser Ser Glu Ser Thr Pro Glu Asp Val Leu Ser Gln
    3440                3445                3450

Gly Lys Glu Ser Phe Glu His Ile Ser Glu Asn Glu Phe Ala Ser
    3455                3460                3465

Glu Ala Glu Gln Ser Thr Pro Ala Glu Gln Lys Glu Leu Gly Ser
    3470                3475                3480

Glu Arg Lys Glu Glu Asp Gln Leu Ser Ser Glu Val Val Thr Glu
    3485                3490                3495

Lys Ala Gln Lys Glu Leu Lys Lys Ser Gln Ile Asp Thr Tyr Cys
    3500                3505                3510

Tyr Thr Cys Lys Cys Pro Ile Ser Ala Thr Asp Lys Val Phe Gly
    3515                3520                3525

Thr His Lys Asp His Glu Val Ser Thr Leu Asp Thr Ala Ile Ser
    3530                3535                3540

Ala Val Lys Val Gln Leu Ala Glu Phe Leu Glu Asn Leu Gln Glu
    3545                3550                3555

Lys Ser Leu Arg Ile Glu Ala Phe Val Ser Glu Ile Glu Ser Phe
    3560                3565                3570

Phe Asn Thr Ile Glu Glu Asn Cys Ser Lys Asn Glu Lys Arg Leu
    3575                3580                3585

Glu Glu Gln Asn Glu Glu Met Met Lys Lys Val Leu Ala Gln Tyr
    3590                3595                3600

Asp Glu Lys Ala Gln Ser Phe Glu Glu Val Lys Lys Lys Lys Met
    3605                3610                3615

Glu Phe Leu His Glu Gln Met Val His Phe Leu Gln Ser Met Asp
    3620                3625                3630

Thr Ala Lys Asp Thr Leu Glu Thr Ile Val Arg Glu Ala Glu Glu
    3635                3640                3645

Leu Asp Glu Ala Val Phe Leu Thr Ser Phe Glu Glu Ile Asn Glu
    3650                3655                3660

Arg Leu Leu Ser Ala Met Glu Ser Thr Ala Ser Leu Glu Lys Met
    3665                3670                3675

Pro Ala Ala Phe Ser Leu Phe Glu His Tyr Asp Asp Ser Ser Ala
    3680                3685                3690

Arg Ser Asp Gln Met Leu Lys Gln Val Ala Val Pro Gln Pro Pro
    3695                3700                3705

Arg Leu Glu Pro Gln Glu Pro Asn Ser Ala Thr Ser Thr Thr Ile
    3710                3715                3720

Ala Val Tyr Trp Ser Met Asn Lys Glu Asp Val Ile Asp Ser Phe
    3725                3730                3735

Gln Val Tyr Cys Met Glu Glu Pro Gln Asp Asp Gln Glu Val Asn
    3740                3745                3750

Glu Leu Val Glu Glu Tyr Arg Leu Thr Val Lys Glu Ser Tyr Cys
    3755                3760                3765
```

| Ile | Phe | Glu | Asp | Leu | Glu | Pro | Asp | Arg | Cys | Tyr | Gln | Val | Trp | Val |
|---|---|---|---|---|---|---|---|---|---|---|---|---|---|---|
| 3770 | | | | | 3775 | | | | | 3780 | | | | |

Met Ala Val Asn Phe Thr Gly Cys Ser Leu Pro Ser Glu Arg Ala
3785                    3790                    3795

Ile Phe Arg Thr Ala Pro Ser Thr Pro Val Ile Arg Ala Glu Asp
3800                    3805                    3810

Cys Thr Val Cys Trp Asn Thr Ala Thr Ile Arg Trp Arg Pro Thr
3815                    3820                    3825

Thr Pro Glu Ala Thr Glu Thr Tyr Thr Leu Glu Tyr Cys Arg Gln
3830                    3835                    3840

His Ser Pro Glu Gly Glu Gly Leu Arg Ser Phe Ser Gly Ile Lys
3845                    3850                    3855

Gly Leu Gln Leu Lys Val Asn Leu Gln Pro Asn Asp Asn Tyr Phe
3860                    3865                    3870

Phe Tyr Val Arg Ala Ile Asn Ala Phe Gly Thr Ser Glu Gln Ser
3875                    3880                    3885

Glu Ala Ala Leu Ile Ser Thr Arg Gly Thr Arg Phe Leu Leu Leu
3890                    3895                    3900

Arg Glu Thr Ala His Pro Ala Leu His Ile Ser Ser Gly Thr
3905                    3910                    3915

Val Ile Ser Phe Gly Glu Arg Arg Arg Leu Thr Glu Ile Pro Ser
3920                    3925                    3930

Val Leu Gly Glu Glu Leu Pro Ser Cys Gly Gln His Tyr Trp Glu
3935                    3940                    3945

Thr Thr Val Thr Asp Cys Pro Ala Tyr Arg Leu Gly Ile Cys Ser
3950                    3955                    3960

Ser Ser Ala Val Gln Ala Gly Ala Leu Gly Gln Gly Glu Thr Ser
3965                    3970                    3975

Trp Tyr Met His Cys Ser Glu Pro Gln Arg Tyr Thr Phe Phe Tyr
3980                    3985                    3990

Ser Gly Ile Val Ser Asp Val His Val Thr Glu Arg Pro Ala Arg
3995                    4000                    4005

Val Gly Ile Leu Leu Asp Tyr Asn Asn Gln Arg Leu Ile Phe Ile
4010                    4015                    4020

Asn Ala Glu Ser Glu Gln Leu Leu Phe Ile Ile Arg His Arg Phe
4025                    4030                    4035

Asn Glu Gly Val His Pro Ala Phe Ala Leu Glu Lys Pro Gly Lys
4040                    4045                    4050

Cys Thr Leu His Leu Gly Ile Glu Pro Pro Asp Ser Val Arg His
4055                    4060                    4065

Lys

<210> SEQ ID NO 166
<211> LENGTH: 1350
<212> TYPE: DNA
<213> ORGANISM: Homo sapiens

<400> SEQUENCE: 166

```
atggcttctg ctatcacgca gtgttctacc agtgagctca cctgctcgat ctgcacagac      60
tatttgacag accctgtcac catttgttgt gggcacagat tttgtagtcc ctgtctctgc     120
ctcttgtggg aagatacact aactcctaat tgctgccctg tgtgcaggga aatatcacag     180
caaatgtact tcaaacgcat tattttttgct gagaaacaag ttattcctac aagagaatca     240
gtcccctgcc agttatcaag ctctgccatg ctgatctgta ggagacacca ggaaatcaag     300
```

-continued

```
aacctcatct gtgaaactga taggagcctg ctgtgttttc tatgctctca atccccaagg    360
catgctactc acaaacacta tatgacaagg gaggctgatg aatactatag gaagaaactc    420
ctgattcaaa tgaagtccat ctggaaaaaa aaacagaaaa atcaaagaaa tctaaacaga    480
gagaccaaca taatcggaac atgggaagtt tttataaatt tgcggagcat gatgatcagt    540
gctgaatatc ctaaggtgtg tcaatacctc cgtgaagaag agcaaaagca cgtagagagc    600
ctggcaagag aaggcaggat aattttcag caactcaaga gaagtcaaac tagaatggct    660
aagatgggta tactcctgag agaaatgtat gagaaactga ggaaatgag ctgtaaagca    720 gatgtgaacc tgcctcagga tttgggagac gtaatgaaaa ggaatgagtt tctgaggctg    780
gccatgcctc agcctgtgaa cccacagctc agtgcatgga ccatcactgg ggtgtcagaa    840
aggcttaact tcttcagagt gtatatcacc ttggatcgta agatatgcag taatcacaag    900
cttctgttcg aagacctaag gcatttgcag tgcagccttg atgatacaga catgtcctgt    960
aatccaacaa gtacacagta tacttcttca tggggagctc agatcctcag ctctggcaaa   1020
cattactggg aggtggatgt gaaagactct tgtaattggg ttataggact tgcagagaa    1080 gcctggacaa agaggaatga catgcgactt gactctgagg gtatctttct actcctgtgt   1140
ctcaaagtgg atgaccattt cagtctcttc tctacctccc cactgttacc tcactatatt   1200
ccaaggcccc aaggctggct agggtgttc ctggattatg aatgtgggat agtgagcttt   1260
gttaatgttg cccaaagttc cctcatttgt agtttcctct cacgcatctt ctattttcct   1320
ctcagacctt tcatttgcca cggatctaaa                                     1350
```

<210> SEQ ID NO 167
<211> LENGTH: 450
<212> TYPE: PRT
<213> ORGANISM: Homo sapiens

<400> SEQUENCE: 167

```
Met Ala Ser Ala Ile Thr Gln Cys Ser Thr Ser Glu Leu Thr Cys Ser
1               5                  10                  15

Ile Cys Thr Asp Tyr Leu Thr Asp Pro Val Thr Ile Cys Cys Gly His
            20                  25                  30

Arg Phe Cys Ser Pro Cys Leu Cys Leu Leu Trp Glu Asp Thr Leu Thr
        35                  40                  45

Pro Asn Cys Cys Pro Val Cys Arg Glu Ile Ser Gln Gln Met Tyr Phe
    50                  55                  60

Lys Arg Ile Ile Phe Ala Glu Lys Gln Val Ile Pro Thr Arg Glu Ser
65                  70                  75                  80

Val Pro Cys Gln Leu Ser Ser Ser Ala Met Leu Ile Cys Arg Arg His
                85                  90                  95

Gln Glu Ile Lys Asn Leu Ile Cys Glu Thr Asp Arg Ser Leu Leu Cys
            100                 105                 110

Phe Leu Cys Ser Gln Ser Pro Arg His Ala Thr His Lys His Tyr Met
        115                 120                 125

Thr Arg Glu Ala Asp Glu Tyr Tyr Arg Lys Lys Leu Leu Ile Gln Met
    130                 135                 140

Lys Ser Ile Trp Lys Lys Lys Gln Lys Asn Gln Arg Asn Leu Asn Arg
145                 150                 155                 160

Glu Thr Asn Ile Ile Gly Thr Trp Glu Val Phe Ile Asn Leu Arg Ser
                165                 170                 175

Met Met Ile Ser Ala Glu Tyr Pro Lys Val Cys Gln Tyr Leu Arg Glu
```

```
                180             185             190
Glu Glu Gln Lys His Val Glu Ser Leu Ala Arg Glu Gly Arg Ile Ile
        195                 200                 205

Phe Gln Gln Leu Lys Arg Ser Gln Thr Arg Met Ala Lys Met Gly Ile
        210                 215                 220

Leu Leu Arg Glu Met Tyr Glu Lys Leu Lys Glu Met Ser Cys Lys Ala
225                 230                 235                 240

Asp Val Asn Leu Pro Gln Asp Leu Gly Asp Val Met Lys Arg Asn Glu
                245                 250                 255

Phe Leu Arg Leu Ala Met Pro Gln Pro Val Asn Pro Gln Leu Ser Ala
            260                 265                 270

Trp Thr Ile Thr Gly Val Ser Glu Arg Leu Asn Phe Phe Arg Val Tyr
        275                 280                 285

Ile Thr Leu Asp Arg Lys Ile Cys Ser Asn His Lys Leu Leu Phe Glu
        290                 295                 300

Asp Leu Arg His Leu Gln Cys Ser Leu Asp Asp Thr Asp Met Ser Cys
305                 310                 315                 320

Asn Pro Thr Ser Thr Gln Tyr Thr Ser Ser Trp Gly Ala Gln Ile Leu
                325                 330                 335

Ser Ser Gly Lys His Tyr Trp Glu Val Asp Val Lys Asp Ser Cys Asn
            340                 345                 350

Trp Val Ile Gly Leu Cys Arg Glu Ala Trp Thr Lys Arg Asn Asp Met
        355                 360                 365

Arg Leu Asp Ser Glu Gly Ile Phe Leu Leu Cys Leu Lys Val Asp
        370                 375                 380

Asp His Phe Ser Leu Phe Ser Thr Ser Pro Leu Leu Pro His Tyr Ile
385                 390                 395                 400

Pro Arg Pro Gln Gly Trp Leu Gly Val Phe Leu Asp Tyr Glu Cys Gly
                405                 410                 415

Ile Val Ser Phe Val Asn Val Ala Gln Ser Ser Leu Ile Cys Ser Phe
            420                 425                 430

Leu Ser Arg Ile Phe Tyr Phe Pro Leu Arg Pro Phe Ile Cys His Gly
        435                 440                 445

Ser Lys
    450

<210> SEQ ID NO 168
<211> LENGTH: 68
<212> TYPE: PRT
<213> ORGANISM: Artificial Sequence
<220> FEATURE:
<223> OTHER INFORMATION: Leader Sequence
<220> FEATURE:
<221> NAME/KEY: MISC_FEATURE
<222> LOCATION: (5)..(11)
<223> OTHER INFORMATION: 6His Tag
<220> FEATURE:
<221> NAME/KEY: MISC_FEATURE
<222> LOCATION: (40)..(51)
<223> OTHER INFORMATION: TAT peptide
<220> FEATURE:
<221> NAME/KEY: MISC_FEATURE
<222> LOCATION: (58)..(67)
<223> OTHER INFORMATION: HA tag

<400> SEQUENCE: 168

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
```

```
                 20                  25                  30
Arg Trp Gly Ser Lys Leu Gly Tyr Gly Arg Lys Lys Arg Gln Arg
             35                  40                  45
Arg Arg Gly Gly Ser Thr Met Ser Gly Tyr Pro Tyr Asp Val Pro Asp
 50                  55                  60
Tyr Ala Gly Ser
 65

<210> SEQ ID NO 169
<211> LENGTH: 536
<212> TYPE: PRT
<213> ORGANISM: Artificial Sequence
<220> FEATURE:
<223> OTHER INFORMATION: Leader sequence and TRIM11

<400> SEQUENCE: 169

Met Arg Gly Ser His His His His His His Gly Met Ala Ser Met Thr
 1               5                  10                  15
Gly Gly Gln Gln Met Gly Arg Asp Leu Tyr Asp Asp Asp Lys Asp
             20                  25                  30
Arg Trp Gly Ser Lys Leu Gly Tyr Gly Arg Lys Lys Arg Gln Arg
             35                  40                  45
Arg Arg Gly Gly Ser Thr Met Ser Gly Tyr Pro Tyr Asp Val Pro Asp
 50                  55                  60
Tyr Ala Gly Ser Met Ala Pro Asp Leu Ser Thr Asn Leu Gln Glu
 65                  70                  75                  80
Glu Ala Thr Cys Ala Ile Cys Leu Asp Tyr Phe Thr Asp Pro Val Met
                 85                  90                  95
Thr Asp Cys Gly His Asn Phe Cys Arg Glu Cys Ile Arg Arg Cys Trp
                100                 105                 110
Gly Gln Pro Glu Gly Pro Tyr Ala Cys Pro Glu Cys Arg Glu Leu Ser
            115                 120                 125
Pro Gln Arg Asn Leu Arg Pro Asn Arg Pro Leu Ala Lys Met Ala Glu
        130                 135                 140
Met Ala Arg Arg Leu His Pro Pro Ser Pro Val Pro Gln Gly Val Cys
145                 150                 155                 160
Pro Ala His Arg Glu Pro Leu Ala Ala Phe Cys Gly Asp Glu Leu Arg
                165                 170                 175
Leu Leu Cys Ala Ala Cys Glu Arg Ser Gly Glu His Trp Ala His Arg
            180                 185                 190
Val Arg Pro Leu Gln Asp Ala Ala Glu Asp Leu Lys Ala Lys Leu Glu
        195                 200                 205
Lys Ser Leu Glu His Leu Arg Lys Gln Met Gln Asp Ala Leu Leu Phe
    210                 215                 220
Gln Ala Gln Ala Asp Glu Thr Cys Val Leu Trp Gln Lys Met Val Glu
225                 230                 235                 240
Ser Gln Arg Gln Asn Val Leu Gly Glu Phe Glu Arg Leu Arg Arg Leu
                245                 250                 255
Leu Ala Glu Glu Glu Gln Gln Leu Leu Gln Arg Leu Glu Glu Glu
            260                 265                 270
Leu Glu Val Leu Pro Arg Leu Arg Glu Gly Ala Ala His Leu Gly Gln
        275                 280                 285
Gln Ser Ala His Leu Ala Glu Leu Ile Ala Glu Leu Glu Gly Arg Cys
    290                 295                 300
Gln Leu Pro Ala Leu Gly Leu Leu Gln Asp Ile Lys Asp Ala Leu Arg
```

```
305                 310                 315                 320
Arg Val Gln Asp Val Lys Leu Gln Pro Pro Glu Val Val Pro Met Glu
            325                 330                 335

Leu Arg Thr Val Cys Arg Val Pro Gly Leu Val Glu Thr Leu Arg Arg
            340                 345                 350

Phe Arg Gly Asp Val Thr Leu Asp Pro Asp Thr Ala Asn Pro Glu Leu
            355                 360                 365

Ile Leu Ser Glu Asp Arg Arg Ser Val Gln Arg Gly Asp Leu Arg Gln
        370                 375                 380

Ala Leu Pro Asp Ser Pro Glu Arg Phe Asp Pro Gly Pro Cys Val Leu
385                 390                 395                 400

Gly Gln Glu Arg Phe Thr Ser Gly Arg His Tyr Trp Glu Val Glu Val
            405                 410                 415

Gly Asp Arg Thr Ser Trp Ala Leu Gly Val Cys Arg Glu Asn Val Asn
            420                 425                 430

Arg Lys Glu Lys Gly Glu Leu Ser Ala Gly Asn Gly Phe Trp Ile Leu
            435                 440                 445

Val Phe Leu Gly Ser Tyr Tyr Asn Ser Ser Glu Arg Ala Leu Ala Pro
        450                 455                 460

Leu Arg Asp Pro Pro Arg Arg Val Gly Ile Phe Leu Asp Tyr Glu Ala
465                 470                 475                 480

Gly His Leu Ser Phe Tyr Ser Ala Thr Asp Gly Ser Leu Leu Phe Ile
            485                 490                 495

Phe Pro Glu Ile Pro Phe Ser Gly Thr Leu Arg Pro Leu Phe Ser Pro
            500                 505                 510

Leu Ser Ser Ser Pro Thr Pro Met Thr Ile Cys Arg Pro Lys Gly Gly
        515                 520                 525

Ser Gly Asp Thr Leu Ala Pro Gln
        530                 535
```